US011939597B2

(12) United States Patent
Hewitt et al.

(10) Patent No.: US 11,939,597 B2
(45) Date of Patent: Mar. 26, 2024

(54) RESTRICTIVE INVERTED TERMINAL REPEATS FOR VIRAL VECTORS

(71) Applicant: The University of North Carolina at Chapel Hill, Chapel Hill, NC (US)

(72) Inventors: Curtis Hewitt, Austin, TX (US); Richard Jude Samulski, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 18/060,799

(22) Filed: Dec. 1, 2022

(65) Prior Publication Data

US 2023/0167418 A1 Jun. 1, 2023

Related U.S. Application Data

(62) Division of application No. 16/953,109, filed on Nov. 19, 2020, now Pat. No. 11,542,478, which is a division of application No. 16/271,163, filed on Feb. 8, 2019, now Pat. No. 10,858,632, which is a division of application No. 14/922,935, filed on Oct. 26, 2015, now Pat. No. 10,233,428, which is a division of application No. 13/521,448, filed as application No. PCT/US2011/020939 on Jan. 12, 2011, now Pat. No. 9,169,494.

(60) Provisional application No. 61/294,181, filed on Jan. 12, 2010.

(51) Int. Cl.

| | |
|---|---|
| ***C12N 7/00*** | (2006.01) |
| ***C07K 14/005*** | (2006.01) |
| ***C12N 15/86*** | (2006.01) |
| ***C12N 15/864*** | (2006.01) |

(52) U.S. Cl.
CPC .............. *C12N 7/00* (2013.01); *C07K 14/005* (2013.01); *C12N 15/86* (2013.01); *C12N 15/8645* (2013.01); *C12N 2750/14122* (2013.01); *C12N 2750/14143* (2013.01); *C12N 2750/14162* (2013.01); *C12N 2750/14322* (2013.01); *C12N 2750/14352* (2013.01); *C12N 2820/60* (2013.01)

(58) Field of Classification Search
None
See application file for complete search history.

(56) References Cited

U.S. PATENT DOCUMENTS

| | | | |
|---|---|---|---|
| 6,984,517 | B1 | 1/2006 | Chiorini et al. |
| 2003/0129203 | A1 | 7/2003 | Vega et al. |
| 2004/0197895 | A1 | 10/2004 | Kotin et al. |
| 2005/0002908 | A1 | 1/2005 | Hörer et al. |

OTHER PUBLICATIONS

"European Application No. 11733293.2; Summons to Attend Oral Proceedings dated Mar. 3, 2017".
"Extended European Search Report for EP Application No. 11733293.2; dated Jan. 9, 2014; 10 Pages".
"Hewitt "Toward a recombinant adeno-associated virus origin of replication", (2009) https://cdr.lib.unc.edu/indexablecontent/uuid Retrieved Mar. 3, 2016 (152 pages)".
"International Preliminary Report on Patentability Corresponding to International Application No. PCT/US2011/020939; dated Jul. 26, 2012; 8 Pages".
"International Preliminary Report on Patentability Corresponding to International Application No. PCT/US2011/036215; dated Nov. 29, 2012; 7 Pages".
"Office Action corresponding to European Application No. 11733293.2 dated Apr. 1, 2016".
Brister, J.R. , et al., ", "Mechanism of Rep-Mediated Adeno-Associated Virus Origin Nicking", Journal of Virology, Sep. 2000, vol. 74, No. 17, p. 7762-7771".
Cathomen, T. , et al., ", "A Chimeric Protein Containing the N Terminus of the Adeno-Associated Virus Rep Protein Recognizes Its Target Site in an In Vivo Assay", Journal of Virology, Mar. 2000, vol. 74, No. 5, p. 2372-2382".
Chiorini, John A., et al., "Adeno-Associated Virus (AAV) Type 5 Rep Protein Cleaves a Unique Terminal Resolution Site Compared with Other AAV Serotypes", Journal of Virology, 73(5), 1999, 4293-4298.
Farkas, S.L. , et al., ", "A parvovirus isolated from royal python (*Python regius*) is a member of the genus *Dependovirus*", Journal of General Virology (2004), vol. 85, p. 555-561".
Goncalves , et al., ""Transfer of the full-length dystrophin-coding sequence into muscle cells by a dual high-capacity hybrid viral vector with site-specific integration ability", J Viral. 79(5):3146-3162 (2005)".
Grimm , et al., ""In Vitro and In Vivo Gene Therapy Vector Evolution via Multispecies Interbreeding and Retargeting of Adena-Associated Viruses", J. Viral. 82:5887-5911 (2008)".
Hewitt , et al., "Creating a Novel Origin of Replication through Modulating DNA-Protein Interfaces. PloS One 5(1 ):e8850".
Hewitt, F.C. , et al., ", "Reducing the Risk of Adeno-Associated Virus (AAV) Vector Mobilization with AAV Type 5 Vectors", Journal of Virology, Apr. 2009, vol. 83, No. 8, p. 3919-3929, Published Feb. 11, 2009".

(Continued)

*Primary Examiner* — Nianxiang Zou
(74) *Attorney, Agent, or Firm* — Myers Bigel, P.A.

(57) ABSTRACT

This invention relates to modified parvovirus inverted terminal repeats (ITRs) that do not functionally interact with wild-type large Rep proteins, synthetic Rep proteins that functionally interact with the modified ITRs, and methods of using the same for delivery of nucleic acids to a cell or a subject. The modifications provide a novel Rep-ITR interaction that limits vector mobilization, increasing the safety of viral vectors.

28 Claims, 65 Drawing Sheets

Specification includes a Sequence Listing.

(56) References Cited

OTHER PUBLICATIONS

Hewitt, F.C. , et al., ", "Replication Specificity of Adeno-Associated Virus Genomes", 2008 DNA Replication and Genome Integrity Meeting, Salk Institute, Jul. 20, 2008, 1 page".
Rabinowitz, J.E. , et al., ", "Cross-Packaging of a Single Adeno-Associated Virus (AAV) Type 2 Vector Genome into Multiple AAV Serotypes Enables Transduction with Broad Specificity", Journal of Virology, Jan. 2002, vol. 76, No. 2, p. 791-801".
Walker , et al., "Mutational analysis of the adeno-associated virus Rep68 protein: identification of critical residues necessary for site-specific endonuclease activity. J Virol. Apr. 1997;71 (4):2722-30".
Yoon , et al., ", "Amino-terminal domain exchange redirects origin-specific interactions of adeno-associated virus Rep78 in vitro," J. Virol. 75:3230-3239 (2001)".

```
             '                               '     +
REP5 MATFYEVIVRVPFDVEEHLPGISDSFVDWVTGQIWELPPESDLNLTLVEQ  50
REP2 MPGFYEIVIKVPSDLDGHLPGISDSFVNWVAEKEWELPPDSDMDLNLIEQ  50
     *. ***::::** *:: **********:**: : *****:**::*.*:**

                +  +   ++                       '      ' '
REP5 PQLTVADRIRRVFLYEWNKFSKQ-ESKFFVQFEKGSEYFHLHTLVETSGI  99
REP2 APLTVAEKLQRDFLTEWRRVSKAPEALFFVQFEKGESYFHMHVLVETTGV 100
       ****::::* ** **.:.**  *: ********..***:*.****:*:

      ^^  ^^  ^^   +    + +                ^ ^^  ^  ^
REP5 SSMVLGRYVSQIRAQLVKVVFQGIEPQINDWVAITKVKK--GGANKVVDS 147
REP2 KSMVLGRFLSQIREKLIQRIYRGIEPTLPNWFAVTKTRNGAGGGNKVVDE 159
     .******::****  :*::  :::**** : :*.*:**.::  **.*****.

      '       '
REP5 GYIPAYLLPKVQPELQWAWTNLDEYKLAALNLEERKRLVAQFLAESSQRS 197
REP2 CYIPNYLLPKTQPELQWAWTNMEQYLSACLNLTERKRLVAQHLTHVSQTQ 200
      *** *****.**********:::*  *.*** ********.*:. **  .

REP5 -QEAASQREFSADPVIKSKTSQKYM 222
REP2 EQNKENQNPNSDAPVIRSKTSARYM 225
      *:  .*.  *  ***:****  :**
```

*FIG. 5A*

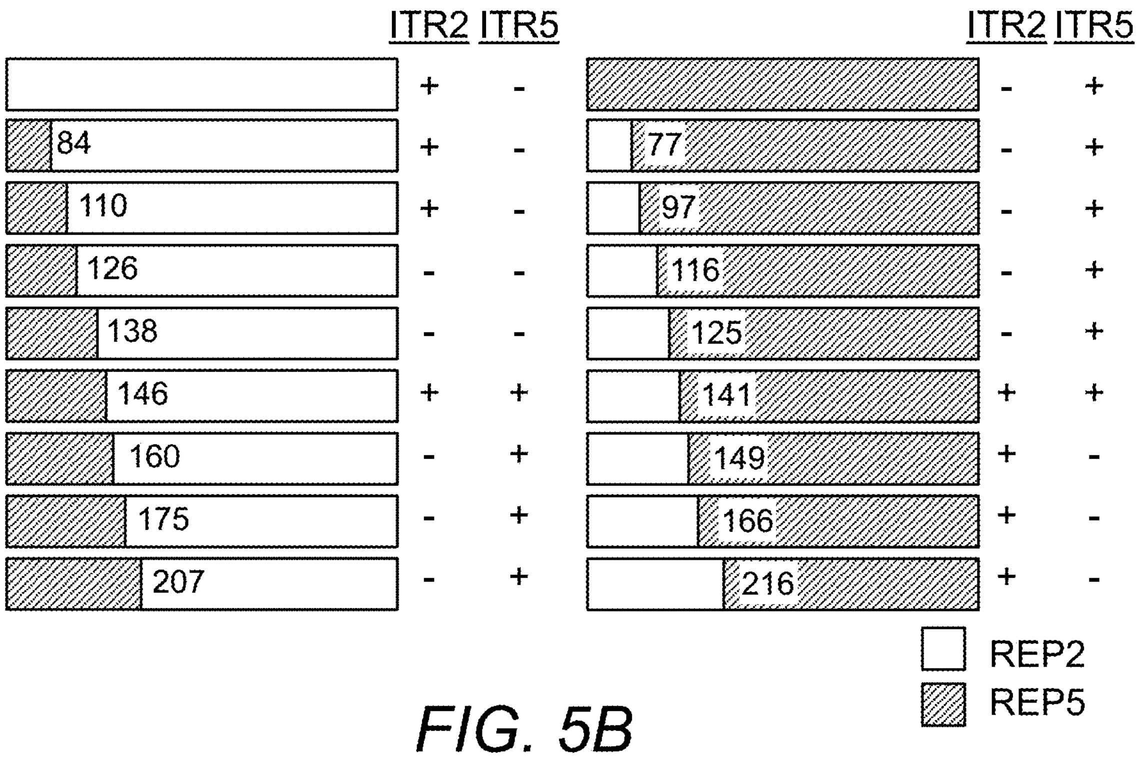

*FIG. 5B*

| | REP2 | REP5 | 25AA149 | 52AA146 |
|---|---|---|---|---|
| ITR2 | + | - | + | + |
| ITR5 | - | + | - | + |
| ITR2+5NS | + | + | + | + |
| ITR5+2NS | - | - | - | + |

AAV-1, COMPLETE SEQUENCE, GENBANK ACCESSION NO. NC_002077 AND XIAO ET AL. (1999) *J. VIROL.* 73:3994

TTGCCCACTCCCTCTCTGCGCGCTCGCTCGCTCGGTGGGGCCTGCGGACCAAAGGTCCGCAGACGGCA
GAGCTCTGCTCTGCCGGCCCCACCGAGCGAGCGAGCGCGCAGAGAGGGAGTGGGCAACTCCATCACTA
GGGGTAATCGCGAAGCGCCTCCCACGCTGCCGCGTCAGCGCTGACGTAAATTACGTCATAGGGGAGTG
GTCCTGTATTAGCTGTCACGTGAGTGCTTTTGCGACATTTTGCGACACCACGTGGCCATTTAGGGTAT
ATATGGCCGAGTGAGCGAGCAGGATCTCCATTTTGACCGCGAAATTTGAACGAGCAGCAGCCATGCCG
GGCTTCTACGAGATCGTGATCAAGGTGCCGAGCGACCTGGACGAGCACCTGCCGGGCATTTCTGACTC
GTTTGTGAGCTGGGTGGCCGAGAAGGAATGGGAGCTGCCCCCGGATTCTGACATGGATCTGAATCTGA
TTGAGCAGGCACCCCTGACCGTGGCCGAGAAGCTGCAGCGCGACTTCCTGGTCCAATGGCGCCGCGTG
AGTAAGGCCCCGGAGGCCCTCTTCTTTGTTCAGTTCGAGAAGGGCGAGTCCTACTTCCACCTCCATAT
TCTGGTGGAGACCACGGGGGTCAAATCCATGGTGCTGGGCCGCTTCCTGAGTCAGATTAGGGACAAGC
TGGTGCAGACCATCTACCGCGGGATCGAGCCGACCCTGCCCAACTGGTTCGCGGTGACCAAGACGCGT
AATGGCGCCGGAGGGGGGAACAAGGTGGTGGACGAGTGCTACATCCCCAACTACCTCCTGCCCAAGAC
TCAGCCCGAGCTGCAGTGGGCGTGGACTAACATGGAGGAGTATATAAGCGCCTGTTTGAACCTGGCCG
AGCGCAAACGGCTCGTGGCGCAGCACCTGACCCACGTCAGCCAGACCCAGGAGCAGAACAAGGAGAAT
CTGAACCCCAATTCTGACGCGCCTGTCATCCGGTCAAAAACCTCCGCGCGCTACATGGAGCTGGTCGG
GTGGCTGGTGGACCGGGGCATCACCTCCGAGAAGCAGTGGATCCAGGAGGACCAGGCCTCGTACATCT
CCTTCAACGCCGCTTCCAACTCGCGGTCCCAGATCAAGGCCGCTCTGGACAATGCCGGCAAGATCATG
GCGCTGACCAAATCCGCGCCCGACTACCTGGTAGGCCCCGCTCCGCCCGCGGACATTAAAACCAACCG
CATCTACCGCATCCTGGAGCTGAACGGCTACGAACCTGCCTACGCCGGCTCCGTCTTTCTCGGCTGGG
CCCAGAAAAGGTTCGGGAAGCGCAACACCATCTGGCTGTTTGGGCCGGCCACCACGGGCAAGACCAAC
ATCGCGGAAGCCATCGCCCACGCCGTGCCCTTCTACGGCTGCGTCAACTGGACCAATGAGAACTTTCC
CTTCAATGATTGCGTCGACAAGATGGTGATCTGGTGGGAGGAGGGCAAGATGACGGCCAAGGTCGTGG
AGTCCGCCAAGGCCATTCTCGGCGGCAGCAAGGTGCGCGTGGACCAAAAGTGCAAGTCGTCCGCCCAG
ATCGACCCCACCCCCGTGATCGTCACCTCCAACACCAACATGTGCGCCGTGATTGACGGGAACAGCAC
CACCTTCGAGCACCAGCAGCCGTTGCAGGACCGGATGTTCAAATTTGAACTCACCCGCCGTCTGGAGC
ATGACTTTGGCAAGGTGACAAAGCAGGAAGTCAAAGAGTTCTTCCGCTGGGCGCAGGATCACGTGACC
GAGGTGGCGCATGAGTTCTACGTCAGAAAGGGTGGAGCCAACAAAAGACCCGCCCCCGATGACGCGGA
TAAAAGCGAGCCCAAGCGGGCCTGCCCCTCAGTCGCGGATCCATCGACGTCAGACGCGGAAGGAGCTC
CGGTGGACTTTGCCGACAGGTACCAAAACAAATGTTCTCGTCACGCGGGCATGCTTCAGATGCTGTTT
CCCTGCAAGACATGCGAGAGAATGAATCAGAATTTCAACATTTGCTTCACGCACGGGACGAGAGACTG
TTCAGAGTGCTTCCCCGGCGTGTCAGAATCTCAACCGGTCGTCAGAAAGAGGACGTATCGGAAACTCT
GTGCCATTCATCATCTGCTGGGGCGGGCTCCCGAGATTGCTTGCTCGGCCTGCGATCTGGTCAACGTG
GACCTGGATGACTGTGTTTCTGAGCAATAAATGACTTAAACCAGGTATGGCTGCCGATGGTTATCTTC
CAGATTGGCTCGAGGACAACCTCTCTGAGGGCATTCGCGAGTGGTGGGACTTGAAACCTGGAGCCCCG
AAGCCCAAAGCCAACCAGCAAAAGCAGGACGACGGCCGGGGTCTGGTGCTTCCTGGCTACAAGTACCT
CGGACCCTTCAACGGACTCGACAAGGGGGAGCCCGTCAACGCGGCGGACGCAGCGGCCCTCGAGCACG
ACAAGGCCTACGACCAGCAGCTCAAAGCGGGTGACAATCCGTACCTGCGGTATAACCACGCCGACGCC
GAGTTTCAGGAGCGTCTGCAAGAAGATACGTCTTTTGGGGGCAACCTCGGGCGAGCAGTCTTCCAGGC
CAAGAAGCGGGTTCTCGAACCTCTCGGTCTGGTTGAGGAAGGCGCTAAGACGGCTCCTGGAAAGAAAC
GTCCGGTAGAGCAGTCGCCACAAGAGCCAGACTCCTCCTCGGGCATCGGCAAGACAGGCCAGCAGCCC
GCTAAAAAGAGACTCAATTTTGGTCAGACTGGCGACTCAGAGTCAGTCCCCGATCCACAACCTCTCGG
AGAACCTCCAGCAACCCCCGCTGCTGTGGGACCTACTACAATGGCTTCAGGCGGTGGCGCACCAATGG
CAGACAATAACGAAGGCGCCGACGGAGTGGGTAATGCCTCAGGAAATTGGCATTGCGATTCCACATGG
CTGGGCGACAGAGTCATCACCACCAGCACCCGCACCTGGGCCTTGCCCACCTACAATAACCACCTCTA
CAAGCAAATCTCCAGTGCTTCAACGGGGGCCAGCAACGACAACCACTACTTCGGCTACAGCACCCCCT
GGGGGTATTTTGATTTCAACAGATTCCACTGCCACTTTTCACCACGTGACTGGCAGCGACTCATCAAC
AACAATTGGGGATTCCGGCCCAAGAGACTCAACTTCAAACTCTTCAACATCCAAGTCAAGGAGGTCAC
GACGAATGATGGCGTCACAACCATCGCTAATAACCTTACCAGCACGGTTCAAGTCTTCTCGGACTCGG
AGTACCAGCTTCCGTACGTCCTCGGCTCTGCGCACCAGGGCTGCCTCCCTCCGTTCCCGGCGGACGTG
TTCATGATTCCGCAATACGGCTACCTGACGCTCAACAATGGCAGCCAAGCCGTGGGACGTTCATCCTT
TTACTGCCTGGAATATTTCCCTTCTCAGATGCTGAGAACGGGCAACAACTTTACCTTCAGCTACACCT
TTGAGGAAGTGCCTTTCCACAGCAGCTACGCGCACAGCCAGAGCCTGGACCGGCTGATGAATCCTCTC
ATCGACCAATACCTGTATTACCTGAACAGAACTCAAAATCAGTCCGGAAGTGCCCAAAACAAGGACTT
GCTGTTTAGCCGTGGGTCTCCAGCTGGCATGTCTGTTCAGCCCAAAAACTGGCTACCTGGACCCTGTT
ATCGGCAGCAGCGCGTTTCTAAAACAAAAACAGACAACAACAACAGCAATTTTACCTGGACTGGTGCT
TCAAAATATAACCTCAATGGGCGTGAATCCATCATCAACCCTGGCACTGCTATGGCCTCACACAAAGA
CGACGAAGACAAGTTCTTTCCCATGAGCGGTGTCATGATTTTTGGAAAAGAGAGCGCCGGAGCTTCAA
ACACTGCATTGGACAATGTCATGATTACAGACGAAGAGGAAATTAAAGCCACTAACCCTGTGGCCACC
GAAAGATTTGGGACCGTGGCAGTCAATTTCCAGAGCAGCAGCACAGACCCTGCGACCGGAGATGTGCA
TGCTATGGGAGCATTACCTGGCATGGTGTGGCAAGATAGAGACGTGTACCTGCAGGGTCCCATTTGGG
CCAAAATTCCTCACACAGATGGACACTTTCACCCGTCTCCTCTTATGGGCGGCTTTGGACTCAAGAAC
CCGCCTCCTCAGATCCTCATCAAAAACACGCCTGTTCCTGCGAATCCTCCGGCGGAGTTTTCAGCTAC
AAAGTTTGCTTCATTCATCACCCAATACTCCACAGGACAAGTGAGTGTGGAAATTGAATGGGAGCTGC
AGAAAGAAAACAGCAAGCGCTGGAATCCCGAAGTGCAGTACACATCCAATTATGCAAAATCTGCCAAC
GTTGATTTTACTGTGGACAACAATGGACTTTATACTGAGCCTCGCCCCATTGGCACCCGTTACCTTAC
CCGTCCCCTGTAATTACGTGTTAATCAATAAACCGGTTGATTCGTTTCAGTTGAACTTTGGTCTCCTG
TCCTTCTTATCTTATCGGTTACCATGGTTATAGCTTACACATTAACTGCTTGGTTGCGCTTCGCGATA
AAAGACTTACGTCATCGGGTTACCCCTAGTGATGGAGTTGCCCACTCCCTCTCTGCGCGCTCGCTCGC
TCGGTGGGGCCTGCGGACCAAAGGTCCGCAGACGGCAGAGCTCTGCTCTGCCGGCCCCACCGAGCGAG
CGAGCGCGCAGAGAGGGAGTGGGCAA

FIG. 8

AAV-2, COMPLETE SEQUENCE, GENBANK ACCESSION NO. NC_001401 AND
CHIORINI ET AL. (1999) *J. VIROL.* 73:1309

```
TTGGCCACTCCCTCTCTGCGCGCTCGCTCGCTCACTGAGGCCGGGCGACCAAAGGTCGCCCGACGCCC
GGGCTTTGCCCGGGCGGCCTCAGTGAGCGAGCGAGCGCGCAGAGAGGGAGTGGCCAACTCCATCACTA
GGGGTTCCTGGAGGGGTGGAGTCGTGACGTGAATTACGTCATAGGGTTAGGGAGGTCCTGTATTAGAG
GTCACGTGAGTGTTTTGCGACATTTTGCGACACCATGTGGTCACGCTGGGTATTTAAGCCCGAGTGAG
CACGCAGGGTCTCCATTTTGAAGCGGGAGGTTTGAACGCGCAGCCGCCATGCCGGGGTTTTACGAGAT
TGTGATTAAGGTCCCCAGCGACCTTGACGGGCATCTGCCCGGCATTTCTGACAGCTTTGTGAACTGGG
TGGCCGAGAAGGAATGGGAGTTGCCGCCAGATTCTGACATGGATCTGAATCTGATTGAGCAGGCACCC
CTGACCGTGGCCGAGAAGCTGCAGCGCGACTTTCTGACGGAATGGCGCCGTGTGAGTAAGGCCCCGGA
GGCCCTTTTCTTTGTGCAATTTGAGAAGGGAGAGAGCTACTTCCACATGCACGTGCTCGTGGAAACCA
CCGGGGTGAAATCCATGGTTTTGGGACGTTTCCTGAGTCAGATTCGCGAAAAACTGATTCAGAGAATT
TACCGCGGGATCGAGCCGACTTTGCCAAACTGGTTCGCGGTCACAAAGACCAGAAATGGCGCCGGAGG
CGGGAACAAGGTGGTGGATGAGTGCTACATCCCCAATTACTTGCTCCCCAAAACCCAGCCTGAGCTCC
AGTGGGCGTGGACTAATATGGAACAGTATTTAAGCGCCTGTTTGAATCTCACGGAGCGTAAACGGTTG
GTGGCGCAGCATCTGACGCACGTGTCGCAGACGCAGGAGCAGAACAAAGAGAATCAGAATCCCAATTC
TGATGCGCCGGTGATCAGATCAAAAACTTCAGCCAGGTACATGGAGCTGGTCGGGTGGCTCGTGGACA
AGGGGATTACCTCGGAGAAGCAGTGGATCCAGGAGGACCAGGCCTCATACATCTCCTTCAATGCGGCC
TCCAACTCGCGGTCCCAAATCAAGGCTGCCTTGGACAATGCGGGAAAGATTATGAGCCTGACTAAAAC
CGCCCCCGACTACCTGGTGGGCCAGCAGCCCGTGGAGGACATTTCCAGCAATCGGATTTATAAAATTT
TGGAACTAAACGGGTACGATCCCCAATATGCGGCTTCCGTCTTTCTGGGATGGGCCACGAAAAAGTTC
GGCAAGAGGAACACCATCTGGCTGTTTGGGCCTGCAACTACCGGGAAGACCAACATCGCGGAGGCCAT
AGCCCACACTGTGCCCTTCTACGGGTGCGTAAACTGGACCAATGAGAACTTTCCCTTCAACGACTGTG
TCGACAAGATGGTGATCTGGTGGGAGGAGGGGAAGATGACCGCCAAGGTCGTGGAGTCGGCCAAAGCC
ATTCTCGGAGGAAGCAAGGTGCGCGTGGACCAGAAATGCAAGTCCTCGGCCCAGATAGACCCGACTCC
CGTGATCGTCACCTCCAACACCAACATGTGCGCCGTGATTGACGGGAACTCAACGACCTTCGAACACC
AGCAGCCGTTGCAAGACCGGATGTTCAAATTTGAACTCACCCGCCGTCTGGATCATGACTTTGGGAAG
GTCACCAAGCAGGAAGTCAAAGACTTTTTCCGGTGGGCAAAGGATCACGTGGTTGAGGTGGAGCATGA
ATTCTACGTCAAAAAGGGTGGAGCCAAGAAAAGACCCGCCCCCAGTGACGCAGATATAAGTGAGCCCA
AACGGGTGCGCGAGTCAGTTGCGCAGCCATCGACGTCAGACGCGGAAGCTTCGATCAACTACGCAGAC
AGGTACCAAAACAAATGTTCTCGTCACGTGGGCATGAATCTGATGCTGTTTCCCTGCAGACAATGCGA
GAGAATGAATCAGAATTCAAATATCTGCTTCACTCACGGACAGAAAGACTGTTTAGAGTGCTTTCCCG
TGTCAGAATCTCAACCCGTTTCTGTCGTCAAAAAGGCGTATCAGAAACTGTGCTACATTCATCATATC
ATGGGAAAGGTGCCAGACGCTTGCACTGCCTGCGATCTGGTCAATGTGGATTTGGATGACTGCATCTT
TGAACAATAAATGATTTAAATCAGGTATGGCTGCCGATGGTTATCTTCCAGATTGGCTCGAGGACACT
CTCTCTGAAGGAATAAGACAGTGGTGGAAGCTCAAACCTGGCCCACCACCACCAAAGCCCGCAGAGCG
GCATAAGGACGACAGCAGGGGTCTTGTGCTTCCTGGGTACAAGTACCTCGGACCCTTCAACGGACTCG
ACAAGGGAGAGCCGGTCAACGAGGCAGACGCCGCGGCCCTCGAGCACGACAAAGCCTACGACCGGCAG
CTCGACAGCGGAGACAACCCGTACCTCAAGTACAACCACGCCGACGCGGAGTTTCAGGAGCGCCTTAA
AGAAGATACGTCTTTTGGGGGCAACCTCGGACGAGCAGTCTTCCAGGCGAAAAAGAGGGTTCTTGAAC
CTCTGGGCCTGGTTGAGGAACCTGTTAAGACGGCTCCGGGAAAAAAGAGGCCGGTAGAGCACTCTCCT
GTGGAGCCAGACTCCTCCTCGGGAACCGGAAAGGCGGGCCAGCAGCCTGCAAGAAAAAGATTGAATTT
TGGTCAGACTGGAGACGCAGACTCAGTACCTGACCCCCAGCCTCTCGGACAGCCACCAGCAGCCCCCT
CTGGTCTGGGAACTAATACGATGGCTACAGGCAGTGGCGCACCAATGGCAGACAATAACGAGGGCGCC
GACGGAGTGGGTAATTCCTCCGGAAATTGGCATTGCGATTCCACATGGATGGGCGACAGAGTCATCAC
CACCAGCACCCGAACCTGGGCCCTGCCCACCTACAACAACCACCTCTACAAACAAATTTCCAGCCAAT
CAGGAGCCTCGAACGACAATCACTACTTTGGCTACAGCACCCCTTGGGGGTATTTTGACTTCAACAGA
TTCCACTGCCACTTTTCACCACGTGACTGGCAAAGACTCATCAACAACAACTGGGGATTCCGACCCAA
GAGACTCAACTTCAAGCTCTTTAACATTCAAGTCAAAGAGGTCACGCAGAATGACGGTACGACGACGA
TTGCCAATAACCTTACCAGCACGGTTCAGGTGTTTACTGACTCGGAGTACCAGCTCCCGTACGTCCTC
GGCTCGGCGCATCAAGGATGCCTCCCGCCGTTCCCAGCAGACGTCTTCATGGTGCCACAGTATGGATA
CCTCACCCTGAACAACGGGAGTCAGGCAGTAGGACGCTCTTCATTTTACTGCCTGGAGTACTTTCCTT
CTCAGATGCTGCGTACCGGAAACAACTTTACCTTCAGCTACACTTTTGAGGACGTTCCTTTCCACAGC
AGCTACGCTCACAGCCAGAGTCTGGACCGTCTCATGAATCCTCTCATCGACCAGTACCTGTATTACTT
GAGCAGAACAAACACTCCAAGTGGAACCACCACGCAGTCAAGGCTTCAGTTTTCTCAGGCCGGAGCGA
GTGACATTCGGGACCAGTCTAGGAACTGGCTTCCTGGACCCTGTTACCGCCAGCAGCGAGTATCAAAG
ACATCTGCGGATAACAACAACAGTGAATACTCGTGGACTGGAGCTACCAAGTACCACCTCAATGGCAG
AGACTCTCTGGTGAATCCGGGCCCGGCCATGGCAAGCCACAAGGACGATGAAGAAAAGTTTTTTCCTC
AGAGCGGGGTTCTCATCTTTGGGAAGCAAGGCTCAGAGAAAACAAATGTGAACATTGAAAAGGTCATG
ATTACAGACGAAGAGGAAATCGGAACAACCAATCCCGTGGCTACGGAGCAGTATGGTTCTGTATCTAC
CAACCTCCAGAGAGGCAACAGACAAGCAGCTACCGCAGATGTCAACACACAAGGCGTTCTTCCAGGCA
TGGTCTGGCAGGACAGAGATGTGTACCTTCAGGGGCCCATCTGGGCAAAGATTCCACACACGGACGGA
CATTTTCACCCCTCTCCCCTCATGGGTGGATTCGGACTTAAACACCCTCCTCCACAGATTCTCATCAA
GAACACCCCGGTACCTGCGAATCCTTCGACCACCTTCAGTGCGGCAAAGTTTGCTTCCTTCATCACAC
AGTACTCCACGGGACAGGTCAGCGTGGAGATCGAGTGGGAGCTGCAGAAGGAAAACAGCAAACGCTGG
AATCCCGAAATTCAGTACACTTCCAACTACAACAAGTCTGTTAATCGTGGACTTACCGTGGATACTAA
TGGCGTGTATTCAGAGCCTCGCCCCATTGGCACCAGATACCTGACTCGTAATCTGTAATTGCTTGTTA
ATCAATAAACCGTTTAATTCGTTTCAGTTGAACTTTGGTCTCTGCGTATTTCTTTCTTATCTAGTTTC
CATGGCTACGTAGATAAGTAGCATGGCGGGTTAATCATTAACTACAAGGAACCCCTAGTGATGGAGTT
GGCCACTCCCTCTCTGCGCGCTCGCTCGCTCACTGAGGCCGGGCGACCAAAGGTCGCCCGACGCCCGG
GCTTTGCCCGGGCGGCCTCAGTGAGCGAGCGAGCGCGCAGAGAGGGAGTGGCCAA
```

FIG. 9

AAV-3A, COMPLETE SEQUENCE, GENBANK ACCESSION NO. NC_001729 AND
MURAMATSU ET AL. (1996) *VIROLOGY* 221:208

TTGGCCACTCCCTCTATGCGCACTCGCTCGCTCGGTGGGGCCTGGCGACCAAAGGTCGCCAGACGGACG
TGCTTTGCACGTCCGGCCCCACCGAGCGAGCGAGTGCGCATAGAGGGAGTGGCCAACTCCATCACTAGA
GGTATGGCAGTGACGTAACGCGAAGCGCGCGAAGCGAGACCACGCCTACCAGCTGCGTCAGCAGTCAGG
TGACCCTTTTGCGACAGTTTGCGACACCACGTGGCCGCTGAGGGTATATATTCTCGAGTGAGCGAACCA
GGAGCTCCATTTTGACCGCGAAATTTGAACGAGCAGCAGCCATGCCGGGGTTCTACGAGATTGTCCTGA
AGGTCCCGAGTGACCTGGACGAGCGCCTGCCGGGCATTTCTAACTCGTTTGTTAACTGGGTGGCCGAGA
AGGAATGGGACGTGCCGCCGGATTCTGACATGGATCCGAATCTGATTGAGCAGGCACCCCTGACCGTGG
CCGAAAAGCTTCAGCGCGAGTTCCTGGTGGAGTGGCGCCGCGTGAGTAAGGCCCCGGAGGCCCTCTTTT
TTGTCCAGTTCGAAAAGGGGGAGACCTACTTCCACCTGCACGTGCTGATTGAGACCATCGGGGTCAAAT
CCATGGTGGTCGGCCGCTACGTGAGCCAGATTAAAGAGAAGCTGGTGACCCGCATCTACCGCGGGGTCG
AGCCGCAGCTTCCGAACTGGTTCGCGGTGACCAAAACGCGAAATGGCGCCGGGGGCGGGAACAAGGTGG
TGGACGACTGCTACATCCCCAACTACCTGCTCCCCAAGACCCAGCCCGAGCTCCAGTGGGCGTGGACTA
ACATGGACCAGTATTTAAGCGCCTGTTTGAATCTCGCGGAGCGTAAACGGCTGGTGGCGCAGCATCTGA
CGCACGTGTCGCAGACGCAGGAGCAGAACAAAGAGAATCAGAACCCCAATTCTGACGCGCCGGTCATCA
GGTCAAAAACCTCAGCCAGGTACATGGAGCTGGTCGGGTGGCTGGTGGACCGCGGGATCACGTCAGAAA
AGCAATGGATTCAGGAGGACCAGGCCTCGTACATCTCCTTCAACGCCGCCTCCAACTCGCGGTCCCAGA
TCAAGGCCGCGCTGGACAATGCCTCCAAGATCATGAGCCTGACAAAGACGGCTCCGGACTACCTGGTGG
GCAGCAACCCGCCGGAGGACATTACCAAAAATCGGATCTACCAAATCCTGGAGCTGAACGGGTACGATC
CGCAGTACGCGGCCTCCGTCTTCCTGGGCTGGGCGCAAAAGAAGTTCGGGAAGAGGAACACCATCTGGC
TCTTTGGGCCGGCCACGACGGGTAAAACCAACATCGCGGAAGCCATCGCCCACGCCGTGCCCTTCTACG
GCTGCGTAAACTGGACCAATGAGAACTTTCCCTTCAACGATTGCGTCGACAAGATGGTGATCTGGTGGG
AGGAGGGCAAGATGACGGCCAAGGTCGTGGAGAGCGCCAAGGCCATTCTGGGCGGAAGCAAGGTGCGCG
TGGACCAAAAGTGCAAGTCATCGGCCCAGATCGAACCCACTCCCGTGATCGTCACCTCCAACACCAACA
TGTGCGCCGTGATTGACGGGAACAGCACCACCTTCGAGCATCAGCAGCCGCTGCAGGACCGGATGTTTG
AATTTGAACTTACCCGCCGTTTGGACCATGACTTTGGGAAGGTCACCAAACAGGAAGTAAAGGACTTTT
TCCGGTGGGCTTCCGATCACGTGACTGACGTGGCTCATGAGTTCTACGTCAGAAAGGGTGGAGCTAAGA
AACGCCCCGCCTCCAATGACGCGGATGTAAGCGAGCCAAAACGGGAGTGCACGTCACTTGCGCAGCCGA
CAACGTCAGACGCGGAAGCACCGGCGGACTACGCGGACAGGTACCAAAACAAATGTTCTCGTCACGTGG
GCATGAATCTGATGCTTTTTCCCTGTAAAACATGCGAGAGAATGAATCAAATTTCCAATGTCTGTTTTA
CGCATGGTCAAAGAGACTGTGGGGAATGCTTCCCTGGAATGTCAGAATCTCAACCCGTTTCTGTCGTCA
AAAAGAAGACTTATCAGAAACTGTGTCCAATTCATCATATCCTGGGAAGGGCACCCGAGATTGCCTGTT
CGGCCTGCGATTTGGCCAATGTGGACTTGGATGACTGTGTTTCTGAGCAATAAATGACTTAAACCAGGT
ATGGCTGCTGACGGTTATCTTCCAGATTGGCTCGAGGACAACCTTTCTGAAGGCATTCGTGAGTGGTGG
GCTCTGAAACCTGGAGTCCCTCAACCCAAAGCGAACCAACAACACCAGGACAACCGTCGGGGTCTTGTG
CTTCCGGGTTACAAATACCTCGGACCCGGTAACGGACTCGACAAAGGAGAGCCGGTCAACGAGGCGGAC
GCGGCAGCCCTCGAACACGACAAAGCTTACGACCAGCAGCTCAAGGCCGGTGACAACCCGTACCTCAAG
TACAACCACGCCGACGCCGAGTTTCAGGAGCGTCTTCAAGAAGATACGTCTTTTGGGGGCAACCTTGGC
AGAGCAGTCTTCCAGGCCAAAAAGAGGATCCTTGAGCCTCTTGGTCTGGTTGAGGAAGCAGCTAAAACG
GCTCCTGGAAAGAAGGGGGCTGTAGATCAGTCTCCTCAGGAACCGGACTCATCATCTGGTGTTGGCAAA
TCGGGCAAACAGCCTGCCAGAAAAAGACTAAATTTCGGTCAGACTGGAGACTCAGAGTCAGTCCCAGAC
CCTCAACCTCTCGGAGAACCACCAGCAGCCCCCACAAGTTTGGGATCTAATACAATGGCTTCAGGCGGT
GGCGCACCAATGGCAGACAATAACGAGGGTGCCGATGGAGTGGGTAATTCCTCAGGAAATTGGCATTGC
GATTCCCAATGGCTGGGCGACAGAGTCATCACCACCAGCACCAGAACCTGGGCCCTGCCCACTTACAAC
AACCATCTCTACAAGCAAATCTCCAGCCAATCAGGAGCTTCAAACGACAACCACTACTTTGGCTACAGC
ACCCCTTGGGGGTATTTTGACTTTAACAGATTCCACTGCCACTTCTCACCACGTGACTGGCAGCGACTC
ATTAACAACAACTGGGGATTCCGGCCCAAGAAACTCAGCTTCAAGCTCTTCAACATCCAAGTTAGAGGG
GTCACGCAGAACGATGGCACGACGACTATTGCCAATAACCTTACCAGCACGGTTCAAGTGTTTACGGAC
TCGGAGTATCAGCTCCCGTACGTGCTCGGGTCGGCGCACCAAGGCTGTCTCCCGCCGTTTCCAGCGGAC
GTCTTCATGGTCCCTCAGTATGGATACCTCACCCTGAACAACGGAAGTCAAGCGGTGGGACGCTCATCC
TTTTACTGCCTGGAGTACTTCCCTTCGCAGATGCTAAGGACTGGAAATAACTTCCAATTCAGCTATACC
TTCGAGGATGTACCTTTTCACAGCAGCTACGCTCACAGCCAGAGTTTGGATCGCTTGATGAATCCTCTT
ATTGATCAGTATCTGTACTACCTGAACAGAACGCAAGGAACAACCTCTGGAACAACCAACCAATCACGG
CTGCTTTTTAGCCAGGCTGGGCCTCAGTCTATGTCTTTGCAGGCCAGAAATTGGCTACCTGGGCCCTGC
TACCGGCAACAGAGACTTTCAAAGACTGCTAACGACAACAACAACAGTAACTTTCCTTGGACAGCGGCC
AGCAAATATCATCTCAATGGCCGCGACTCGCTGGTGAATCCAGGACCAGCTATGGCCAGTCACAAGGAC
GATGAAGAAAAATTTTTCCCTATGCACGGCAATCTAATATTTGGCAAAGAAGGGACAACGGCAAGTAAC
GCAGAATTAGATAATGTAATGATTACGGATGAAGAAGAGATTCGTACCACCAATCCTGTGGCAACAGAG
CAGTATGGAACTGTGGCAAATAACTTGCAGAGCTCAAATACAGCTCCCACGACTGGAACTGTCAATCAT
CAGGGGGCCTTACCTGGCATGGTGTGGCAAGATCGTGACGTGTACCTTCAAGGACCTATCTGGGCAAAG
ATTCCTCACACGGATGGACACTTTCATCCTTCTCCTCTGATGGGAGGCTTTGGACTGAAACATCCGCCT
CCTCAAATCATGATCAAAAATACTCCGGTACCGGCAAATCCTCCGACGACTTTCAGCCCGGCCAAGTTT
GCTTCATTTATCACTCAGTACTCCACTGGACAGGTCAGCGTGGAAATTGAGTGGGAGCTACAGAAAGAA
AACAGCAAACGTTGGAATCCAGAGATTCAGTACACTTCCAACTACAACAAGTCTGTTAATGTGGACTTT
ACTGTAGACACTAATGGTGTTTATAGTGAACCTCGCCCTATTGGAACCCGGTATCTCACACGAAACTTG
TGAATCCTGGTTAATCAATAAACCGTTTAATTCGTTTCAGTTGAACTTTGGCTCTTGTGCACTTCTTTA
TCTTTATCTTGTTTCCATGGCTACTGCGTAGATAAGCAGCGGCCTGCGGCGCTTGCGCTTCGCGGTTTA
CAACTGCTGGTTAATATTTAACTCTCGCCATACCTCTAGTGATGGAGTTGGCCACTCCCTCTATGCGCA
CTCGCTCGCTCGGTGGGGCCTGGCGACCAAAGGTCGCCAGACGGACGTGCTTTGCACGTCCGGCCCCAC
CGAGCGAGCGAGTGCGCATAGAGGGAGTGGCCAA

FIG. 10

AAV-3B, COMPLETE SEQUENCE, GENBANK ACCESSION NO. NC 001863
TGGCCACTCCCTCTATGCGCACTCGCTCGCTCGGTGGGGCCTGGCGACCAAAGGTCGCCAGACGGACGT
GCTTTGCACGTCCGGCCCCACCGAGCGAGCGAGTGCGCATAGAGGGAGTGGCCAACTCCATCACTAGAG
GTATGGCAGTGACGTAACGCGAAGCGCGCGAAGCGAGACCACGCCTACCAGCTGCGTCAGCAGTCAGGT
GACCCTTTTGCGACAGTTTGCGACACCACGTGGCCGCTGAGGGTATATATTCTCGAGTGAGCGAACCAG
GAGCTCCATTTTGACCGCGAAATTTGAACGAGCAGCAGCCATGCCGGGGTTCTACGAGATTGTCCTGAA
GGTCCCGAGTGACCTGGACGAGCACCTGCCGGGCATTTCTAACTCGTTTGTTAACTGGGTGGCCGAGAA
GGAATGGGAGCTGCCGCCGGATTCTGACATGGATCCGAATCTGATTGAGCAGGCACCCCTGACCGTGGC
CGAAAAGCTTCAGCGCGAGTTCCTGGTGGAGTGGCGCCGCGTGAGTAAGGCCCCGGAGGCCCTCTTTTT
TGTCCAGTTCGAAAAGGGGGAGACCTACTTCCACCTGCACGTGCTGATTGAGACCATCGGGGTCAAATC
CATGGTGGTCGGCCGCTACGTGAGCCAGATTAAAGAGAAGCTGGTGACCCGCATCTACCGCGGGGTCGA
GCCGCAGCTTCCGAACTGGTTCGCGGTGACCAAAACGCGAAATGGCGCCGGGGGCGGGAACAAGGTGGT
GGACGACTGCTACATCCCCAACTACCTGCTCCCCAAGACCCAGCCCGAGCTCCAGTGGGCGTGGACTAA
CATGGACCAGTATTTAAGCGCCTGTTTGAATCTCGCGGAGCGTAAACGGCTGGTGGCGCAGCATCTGAC
GCACGTGTCGCAGACGCAGGAGCAGAACAAAGAGAATCAGAACCCCAATTCTGACGCGCCGGTCATCAG
GTCAAAAACCTCAGCCAGGTACATGGAGCTGGTCGGGTGGCTGGTGGACCGCGGGATCACGTCAGAAAA
GCAATGGATTCAGGAGGACCAGGCCTCGTACATCTCCTTCAACGCCGCCTCCAACTCGCGGTCCCAGAT
CAAGGCCGCGCTGGACAATGCCTCCAAGATCATGAGCCTGACAAAGACGGCTCCGGACTACCTGGTGGG
CAGCAACCCGCCGGAGGACATTACCAAAAATCGGATCTACCAAATCCTGGAGCTGAACGGGTACGATCC
GCAGTACGCGGCCTCCGTCTTCCTGGGCTGGGCGCAAAAGAAGTTCGGGAAGAGGAACACCATCTGGCT
CTTTGGGCCGGCCACGACGGGTAAAACCAACATCGCGGAAGCCATCGCCCACGCCGTGCCCTTCTACGG
CTGCGTAAACTGGACCAATGAGAACTTTCCCTTCAACGATTGCGTCGACAAGATGGTGATCTGGTGGGA
GGAGGGCAAGATGACGGCCAAGGTCGTGGAGAGCGCCAAGGCCATTCTGGGCGGAAGCAAGGTGCGCGT
GGACCAAAAGTGCAAGTCATCGGCCCAGATCGAACCCACTCCCGTGATCGTCACCTCCAACACCAACAT
GTGCGCCGTGATTGACGGGAACAGCACCACCTTCGAGCATCAGCAGCCGCTGCAGGACCGGATGTTTAA
ATTTGAACTTACCCGCCGTTTGGACCATGACTTTGGGAAGGTCACCAAACAGGAAGTAAAGGACTTTTT
CCGGTGGGCTTCCGATCACGTGACTGACGTGGCTCATGAGTTCTACGTCAGAAAGGGTGGAGCTAAGAA
ACGCCCCGCCTCCAATGACGCGGATGTAAGCGAGCCAAAACGGCAGTGCACGTCACTTGCGCAGCCGAC
AACGTCAGACGCGGAAGCACCGGCGGACTACGCGGACAGGTACCAAAACAAATGTTCTCGTCACGTGGG
CATGAATCTGATGCTTTTTCCCTGTAAAACATGCGAGAGAATGAATCAAATTTCCAATGTCTGTTTTAC
GCATGGTCAAAGAGACTGTGGGGAATGCTTCCCTGGAATGTCAGAATCTCAACCCGTTTCTGTCGTCAA
AAAGAAGACTTATCAGAAACTGTGTCCAATTCATCATATCCTGGGAAGGGCACCCGAGATTGCCTGTTC
GGCCTGCGATTTGGCCAATGTGGACTTGGATGACTGTGTTTCTGAGCAATAAATGACTTAAACCAGGTA
TGGCTGCTGACGGTTATCTTCCAGATTGGCTCGAGGACAACCTTTCTGAAGGCATTCGTGAGTGGTGGG
CTCTGAAACCTGGAGTCCCTCAACCCAAAGCGAACCAACAACACCAGGACAACCGTCGGGGTCTTGTGC
TTCCGGGTTACAAATACCTCGGACCCGGTAACGGACTCGACAAAGGAGAGCCGGTCAACGAGGCGGACG
CGGCAGCCCTCGAACACGACAAAGCTTACGACCAGCAGCTCAAGGCCGGTGACAACCCGTACCTCAAGT
ACAACCACGCCGACGCCGAGTTTCAGGAGCGTCTTCAAGAAGATACGTCTTTTGGGGGCAACCTTGGCA
GAGCAGTCTTCCAGGCCAAAAAGAGGATCCTTGAGCCTCTTGGTCTGGTTGAGGAAGCAGCTAAAACGG
CTCCTGGAAAGAAGAGGCCTGTAGATCAGTCTCCTCAGGAACCGGACTCATCATCTGGTGTTGGCAAAT
CGGGCAAACAGCCTGCCAGAAAAAGACTAAATTTCGGTCAGACTGGCGACTCAGAGTCAGTCCCAGACC
CTCAACCTCTCGGAGAACCACCAGCAGCCCCCACAAGTTTGGGATCTAATACAATGGCTTCAGGCGGTG
GCGCACCAATGGCAGACAATAACGAGGGTGCCGATGGAGTGGGTAATTCCTCAGGAAATTGGCATTGCG
ATTCCCAATGGCTGGGCGACAGAGTCATCACCACCAGCACCAGAACCTGGGCCCTGCCCACTTACAACA
ACCATCTCTACAAGCAAATCTCCAGCCAATCAGGAGCTTCAAACGACAACCACTACTTTGGCTACAGCA
CCCCTTGGGGGTATTTTGACTTTAACAGATTCCACTGCCACTTCTCACCACGTGACTGGCAGCGACTCA
TTAACAACAACTGGGGATTCCGGCCCAAGAAACTCAGCTTCAAGCTCTTCAACATCCAAGTTAAAGAGG
TCACGCAGAACGATGGCACGACGACTATTGCCAATAACCTTACCAGCACGGTTCAAGTGTTTACGGACT
CGGAGTATCAGCTCCCGTACGTGCTCGGGTCGGCGCACCAAGGCTGTCTCCCGCCGTTTCCAGCGGACG
TCTTCATGGTCCCTCAGTATGGATACCTCACCCTGAACAACGGAAGTCAAGCGGTGGGACGCTCATCCT
TTTACTGCCTGGAGTACTTCCCTTCGCAGATGCTAAGGACTGGAAATAACTTCCAATTCAGCTATACCT
TCGAGGATGTACCTTTTCACAGCAGCTACGCTCACAGCCAGAGTTTGGATCGCTTGATGAATCCTCTTA
TTGATCAGTATCTGTACTACCTGAACAGAACGCAAGGAACAACCTCTGGAACAACCAACCAATCACGGC
TGCTTTTTAGCCAGGCTGGGCCTCAGTCTATGTCTTTGCAGGCCAGAAATTGGCTACCTGGGCCCTGCT
ACCGGCAACAGAGACTTTCAAAGACTGCTAACGACAACAACAACAGTAACTTTCCTTGGACAGCGGCCA
GCAAATATCATCTCAATGGCCGCGACTCGCTGGTGAATCCAGGACCAGCTATGGCCAGTCACAAGGACG
ATGAAGAAAAATTTTTCCCTATGCACGGCAATCTAATATTTGGCAAAGAAGGGACAACGGCAAGTAACG
CAGAATTAGATAATGTAATGATTACGGATGAAGAAGAGATTCGTACCACCAATCCTGTGGCAACAGAGC
AGTATGGAACTGTGGCAAATAACTTGCAGAGCTCAAATACAGCTCCCACGACTAGAACTGTCAATGATC
AGGGGGCCTTACCTGGCATGGTGTGGCAAGATCGTGACGTGTACCTTCAAGGACCTATCTGGGCAAAGA
TTCCTCACACGGATGGACACTTTCATCCTTCTCCTCTGATGGGAGGCTTTGGACTGAAACATCCGCCTC
CTCAAATCATGATCAAAAATACTCCGGTACCGGCAAATCCTCCGACGACTTTCAGCCCGGCCAAGTTTG
CTTCATTTATCACTCAGTACTCCACTGGACAGGTCAGCGTGGAAATTGAGTGGGAGCTACAGAAAGAAA
ACAGCAAACGTTGGAATCCAGAGATTCAGTACACTTCCAACTACAACAAGTCTGTTAATGTGGACTTTA
CTGTAGACACTAATGGTGTTTATAGTGAACCTCGCCCTATTGGAACCCGGTATCTCACACGAAACTTGT
AATCCTGGTTAATCAATAAACCGTTTAATTCGTTTCAGTTGAACTTTGGCTCTTGTGCACTTCTTATCT
TATCTTGTTTCCATGGCTACTGCGTAGATAAGCAGCGGCCTGCGGCGCTTGCGCTTCGCGGTTTACAAC
TGCTGGTTAATATTTAACTCTCGCCATACCTCTAGTGATGGAGTTGGCCACTCCCTCTATGCGCACTCG
CTCGCTCGGTGGGGCCGGACGTGCAAAGCACGTCCGTCTGGCGACCTTTGGTCGCCAGGCCCCACCGAG
CGAGCGAGTGCGCATAGAGGGAGTGGCCAA

FIG. 11

AAV-4, COMPLETE SEQUENCE, GENBANK ACCESSION NO. NC_001829 AND
CHIORINI AT AL. (1997) J. VIROL. 71:6823

TTGGCCACTCCCTCTATGCGCGCTCGCTCACTCACTCGGCCCTGGAGACCAAAGGTCTCCAGACTGCCG
GCCTCTGGCCGGCAGGGCCGAGTGAGTGAGCGAGCGCGCATAGAGGGAGTGGCCAACTCCATCATCTAG
GTTTGCCCACTGACGTCAATGTGACGTCCTAGGGTTAGGGAGGTCCCTGTATTAGCAGTCACGTGAGTG
TCGTATTTCGCGGAGCGTAGCGGAGCGCATACCAAGCTGCCACGTCACAGCCACGTGGTCCGTTTGCGA
CAGTTTGCGACACCATGTGGTCAGGAGGGTATATAACCGCGAGTGAGCCAGCGAGGAGCTCCATTTTGC
CCGCGAATTTTGAACGAGCAGCAGCCATGCCGGGGTTCTACGAGATCGTGCTGAAGGTGCCCAGCGACC
TGGACGAGCACCTGCCCGGCATTTCTGACTCTTTTGTGAGCTGGGTGGCCGAGAAGGAATGGGAGCTGC
CGCCGGATTCTGACATGGACTTGAATCTGATTGAGCAGGCACCCCTGACCGTGGCCGAAAAGCTGCAAC
GCGAGTTCCTGGTCGAGTGGCGCCGCGTGAGTAAGGCCCCGGAGGCCCTCTTCTTTGTCCAGTTCGAGA
AGGGGGACAGCTACTTCCACCTGCACATCCTGGTGGAGACCGTGGGCGTCAAATCCATGGTGGTGGGCC
GCTACGTGAGCCAGATTAAAGAGAAGCTGGTGACCCGCATCTACCGCGGGGTCGAGCCGCAGCTTCCGA
ACTGGTTCGCGGTGACCAAGACGCGTAATGGCGCCGGAGGCGGGAACAAGGTGGTGGACGACTGCTACA
TCCCCAACTACCTGCTCCCCAAGACCCAGCCCGAGCTCCAGTGGGCGTGGACTAACATGGACCAGTATA
TAAGCGCCTGTTTGAATCTCGCGGAGCGTAAACGGCTGGTGGCGCAGCATCTGACGCACGTGTCGCAGA
CGCAGGAGCAGAACAAGGAAAACCAGAACCCCAATTCTGACGCGCCGGTCATCAGGTCAAAAACCTCCG
CCAGGTACATGGAGCTGGTCGGGTGGCTGGTGGACCGCGGGATCACGTCAGAAAAGCAATGGATCCAGG
AGGACCAGGCGTCCTACATCTCCTTCAACGCCGCCTCCAACTCGCGGTCACAAATCAAGGCCGCGCTGG
ACAATGCCTCCAAAATCATGAGCCTGACAAAGACGGCTCCGGACTACCTGGTGGGCCAGAACCCGCCGG
AGGACATTTCCAGCAACCGCATCTACCGAATCCTCGAGATGAACGGGTACGATCCGCAGTACGCGGCCT
CCGTCTTCCTGGGCTGGGCGCAAAAGAAGTTCGGGAAGAGGAACACCATCTGGCTCTTTGGGCCGGCCA
CGACGGGTAAAACCAACATCGCGGAAGCCATCGCCCACGCCGTGCCCTTCTACGGCTGCGTGAACTGGA
CCAATGAGAACTTTCCGTTCAACGATTGCGTCGACAAGATGGTGATCTGGTGGGAGGAGGGCAAGATGA
CGGCCAAGGTCGTAGAGAGCGCCAAGGCCATCCTGGGCGGAAGCAAGGTGCGCGTGGACCAAAAGTGCA
AGTCATCGGCCCAGATCGACCCAACTCCCGTGATCGTCACCTCCAACACCAACATGTGCGCGGTCATCG
ACGGAAACTCGACCACCTTCGAGCACCAACAACCACTCCAGGACCGGATGTTCAAGTTCGAGCTCACCA
AGCGCCTGGAGCACGACTTTGGCAAGGTCACCAAGCAGGAAGTCAAAGACTTTTTCCGGTGGGCGTCAG
ATCACGTGACCGAGGTGACTCACGAGTTTTACGTCAGAAAGGGTGGAGCTAGAAAGAGGCCCGCCCCCA
ATGACGCAGATATAAGTGAGCCCAAGCGGGCCTGTCCGTCAGTTGCGCAGCCATCGACGTCAGACGCGG
AAGCTCCGGTGGACTACGCGGACAGGTACCAAAACAAATGTTCTCGTCACGTGGGTATGAATCTGATGC
TTTTTCCCTGCCGGCAATGCGAGAGAATGAATCAGAATGTGGACATTTGCTTCACGCACGGGGTCATGG
ACTGTGCCGAGTGCTTCCCCGTGTCAGAATCTCAACCCGTGTCTGTCGTCAGAAAGCGGACGTATCAGA
AACTGTGTCCGATTCATCACATCATGGGGAGGGCGCCCGAGGTGGCCTGCTCGGCCTGCGAACTGGCCA
ATGTGGACTTGGATGACTGTGACATGGAACAATAAATGACTCAAACCAGATATGACTGACGGTTACCTT
CCAGATTGGCTAGAGGACAACCTCTCTGAAGGCGTTCGAGAGTGGTGGGCGCTGCAACCTGGAGCCCCT
AAACCCAAGGCAAATCAACAACATCAGGACAACGCTCGGGGTCTTGTGCTTCCGGGTTACAAATACCTC
GGACCCGGCAACGGACTCGACAAGGGGGAACCCGTCAACGCAGCGGACGCGGCAGCCCTCGAGCACGAC
AAGGCCTACGACCAGCAGCTCAAGGCCGGTGACAACCCCTACCTCAAGTACAACCACGCCGACGCGGAG
TTCCAGCAGCGGCTTCAGGGCGACACATCGTTTGGGGGCAACCTCGGCAGAGCAGTCTTCCAGGCCAAA
AAGAGGGTTCTTGAACCTCTTGGTCTGGTTGAGCAAGCGGGTGAGACGGCTCCTGGAAAGAAGAGACCG
TTGATTGAATCCCCCCAGCAGCCCGACTCCTCCACGGGTATCGGCAAAAAAGGCAAGCAGCCGGCTAAA
AAGAAGCTCGTTTTCGAAGACGAAACTGGAGCAGGCGACGGACCCCCTGAGGGATCAACTTCCGGAGCC
ATGTCTGATGACAGTGAGATGCGTGCAGCAGCTGGCGGAGCTGCAGTCGAGGGCGGACAAGGTGCCGAT
GGAGTGGGTAATGCCTCGGGTGATTGGCATTGCGATTCCACCTGGTCTGAGGGCCACGTCACGACCACC
AGCACCAGAACCTGGGTCTTGCCCACCTACAACAACCACCTCTACAAGCGACTCGGAGAGAGCCTGCAG
TCCAACACCTACAACGGATTCTCCACCCCCTGGGGATACTTTGACTTCAACCGCTTCCACTGCCACTTC
TCACCACGTGACTGGCAGCGACTCATCAACAACAACTGGGGCATGCGACCCAAAGCCATGCGGGTCAAA
ATCTTCAACATCCAGGTCAAGGAGGTCACGACGTCGAACGGCGAGACAACGGTGGCTAATAACCTTACC
AGCACGGTTCAGATCTTTGCGGACTCGTCGTACGAACTGCCGTACGTGATGGATGCGGGTCAAGAGGGC
AGCCTGCCTCCTTTTCCCAACGACGTCTTTATGGTGCCCCAGTACGGCTACTGTGGACTGGTGACCGGC
AACACTTCGCAGCAACAGACTGACAGAAATGCCTTCTACTGCCTGGAGTACTTTCCTTCGCAGATGCTG
CGGACTGGCAACAACTTTGAAATTACGTACAGTTTTGAGAAGGTGCCTTTCCACTCGATGTACGCGCAC
AGCCAGAGCCTGGACCGGCTGATGAACCCTCTCATCGACCAGTACCTGTGGGGACTGCAATCGACCACC
ACCGGAACCACCCTGAATGCCGGGACTGCCACCACCAACTTTACCAAGCTGCGGCCTACCAACTTTTCC
AACTTTAAAAAGAACTGGCTGCCCGGGCCTTCAATCAAGCAGCAGGGCTTCTCAAAGACTGCCAATCAA
AACTACAAGATCCCTGCCACCGGGTCAGACAGTCTCATCAAATACGAGACGCACAGCACTCTGGACGGA
AGATGGAGTGCCCTGACCCCCGGACCTCCAATGGCCACGGCTGGACCTGCGGACAGCAAGTTCAGCAAC
AGCCAGCTCATCTTTGCGGGGCCTAAACAGAACGGCAACACGGCCACCGTACCCGGGACTCTGATCTTC
ACCTCTGAGGAGGAGCTGGCAGCCACCAACGCCACCGATACGGACATGTGGGGCAACCTACCTGGCGGT
GACCAGAGCAACAGCAACCTGCCGACCGTGGACAGACTGACAGCCTTGGGAGCCGTGCCTGGAATGGTC
TGGCAAAACAGAGACATTTACTACCAGGGTCCCATTTGGGCCAAGATTCCTCATACCGATGGACACTTT
CACCCCTCACCGCTGATTGGTGGGTTTGGGCTGAAACACCCGCCTCCTCAAATTTTTATCAAGAACACC
CCGGTACCTGCGAATCCTGCAACGACCTTCAGCTCTACTCCGGTAAACTCCTTCATTACTCAGTACAGC
ACTGGCCAGGTGTCGGTGCAGATTGACTGGGAGATCCAGAAGGAGCGGTCCAAACGCTGGAACCCCGAG
GTCCAGTTTACCTCCAACTACGGACAGCAAAACTCTCTGTTGTGGCTCCCGATGCGGCTGGAAATAC
ACTGAGCCTAGGGCTATCGGTACCCGCTACCTCACCCACCACCTGTAATAACCTGTTAATCAATAAACC
GGTTTATTCGTTTCAGTTGAACTTTGGTCTCCGTGTCCTTCTTATCTTATCTCGTTTCCATGGCTACTG
CGTACATAAGCAGCGGCCTGCGGCGCTTGCGCTTCGCGGTTTACAACTGCCGGTTAATCAGTAACTTCT
GGCAAACCAGATGATGGAGTTGGCCACATTAGCTATGCGCGCTCGCTCACTCACTCGGCCCTGGAGACC
AAAGGTCTCCAGACTGCCGGCCTCTGGCCGGCAGGGCCGAGTGAGTGAGCGAGCGCGCATAGAGGGAGT
GGCCAA

FIG. 12

AAV-5, COMPLETE SEQUENCE, GENBANK ACCESSION NO. NC_006152 AND CIORINI ET AL. (1999) *J. VIROL.* 73:1309

CTCTCCCCCCTGTCGCGTTCGCTCGCTCGCTGGCTCGTTTGGGGGGGTGGCAGCTCAAAGAGCTGCCAG
ACGACGGCCCTCTGGCCGTCGCCCCCCCAAACGAGCCAGCGAGCGAGCGAACGCGACAGGGGGGAGAGT
GCCACACTCTCAAGCAAGGAGGTTTTGTAAGCAGTGATGTCATAATGATGTAATGCTTATTGTCACGCG
ATAGTTAATGATTAACAGTCATGTGATGTGTTTTATCCAATAGGAAGAAAGCGCGCGTATGAGTTCTCG
CGAGACTTCCGGGGTATAAAAGACCGAGTGAACGAGCCCGCCGCCATTCTTTGCTCTGGACTGCTAGAG
GACCCTCGCTGCCATGGCTACCTTCTATGAAGTCATTGTTCGCGTCCCATTTGACGTGGAGGAACATCT
GCCTGGAATTTCTGACAGCTTTGTGGACTGGGTAACTGGTCAAATTTGGGAGCTGCCTCCAGAGTCAGA
TTTAAATTTGACTCTGGTTGAACAGCCTCAGTTGACGGTGGCTGATAGAATTCGCCGCGTGTTCCTGTA
CGAGTGGAACAAATTTTCCAAGCAGGAGTCCAAATTCTTTGTGCAGTTTGAAAAGGGATCTGAATATTT
TCATCTGCACACGCTTGTGGAGACCTCCGGCATCTCTTCCATGGTCCTCGGCCGCTACGTGAGTCAGAT
TCGCGCCCAGCTGGTGAAAGTGGTCTTCCAGGGAATTGAACCCCAGATCAACGACTGGGTCGCCATCAC
CAAGGTAAAGAAGGGCGGAGCCAATAAGGTGGTGGATTCTGGGTATATTCCCGCCTACCTGCTGCCGAA
GGTCCAACCGGAGCTTCAGTGGGCGTGGACAAACCTGGACGAGTATAAATTGGCCGCCCTGAATCTGGA
GGAGCGCAAACGGCTCGTCGCGCAGTTTCTGGCAGAATCCTCGCAGCGCTCGCAGGAGGCGGCTTCGCA
GCGTGAGTTCTCGGCTGACCCGGTCATCAAAAGCAAGACTTCCCAGAAATACATGGCGCTCGTCAACTG
GCTCGTGGAGCACGGCATCACTTCCGAGAAGCAGTGGATCCAGGAAAATCAGGAGAGCTACCTCTCCTT
CAACTCCACCGGCAACTCTCGGAGCCAGATCAAGGCCGCGCTCGACAACGCGACCAAAATTATGAGTCT
GACAAAAAGCGCGGTGGACTACCTCGTGGGGAGCTCCGTTCCCGAGGACATTTCAAAAAACAGAATCTG
GCAAATTTTTGAGATGAATGGCTACGACCCGGCCTACGCGGGATCCATCCTCTACGGCTGGTGTCAGCG
CTCCTTCAACAAGAGGAACACCGTCTGGCTCTACGGACCCGCCACGACCGGCAAGACCAACATCGCGGA
GGCCATCGCCCACACTGTGCCCTTTTACGGCTGCGTGAACTGGACCAATGAAAACTTTCCCTTTAATGA
CTGTGTGGACAAAATGCTCATTTGGTGGGAGGAGGGAAAGATGACCAACAAGGTGGTTGAATCCGCCAA
GGCCATCCTGGGGGGCTCAAAGGTGCGGGTCGATCAGAAATGTAAATCCTCTGTTCAAATTGATTCTAC
CCCTGTCATTGTAACTTCCAATACAAACATGTGTGTGGTGGTGGATGGGAATTCCACGACCTTTGAACA
CCAGCAGCCGCTGGAGGACCGCATGTTCAAATTTGAACTGACTAAGCGGCTCCCGCCAGATTTTGGCAA
GATTACTAAGCAGGAAGTCAAGGACTTTTTTGCTTGGGCAAAGGTCAATCAGGTGCCGGTGACTCACGA
GTTTAAAGTTCCCAGGGAATTGGCGGGAACTAAAGGGGCGGAGAAATCTCTAAAACGCCCACTGGGTGA
CGTCACCAATACTAGCTATAAAAGTCTGGAGAAGCGGGCCAGGCTCTCATTTGTTCCCGAGACGCCTCG
CAGTTCAGACGTGACTGTTGATCCCGCTCCTCTGCGACCGCTCAATTGGAATTCAAGGTATGATTGCAA
ATGTGACTATCATGCTCAATTTGACAACATTTCTAACAAATGTGATGAATGTGAATATTTGAATCGGGG
CAAAAATGGATGTATCTGTCACAATGTAACTCACTGTCAAATTTGTCATGGGATTCCCCCCTGGGAAAA
GGAAAACTTGTCAGATTTTGGGGATTTTGACGATGCCAATAAAGAACAGTAAATAAAGCGAGTAGTCAT
GTCTTTTGTTGATCACCCTCCAGATTGGTTGGAAGAAGTTGGTGAAGGTCTTCGCGAGTTTTTGGGCCT
TGAAGCGGGCCCACCGAAACCAAAACCCAATCAGCAGCATCAAGATCAAGCCCGTGGTCTTGTGCTGCC
TGGTTATAACTATCTCGGACCCGGAAACGGTCTCGATCGAGGAGAGCCTGTCAACAGGGCAGACGAGGT
CGCGCGAGAGCACGACATCTCGTACAACGAGCAGCTTGAGGCGGGAGACAACCCCTACCTCAAGTACAA
CCACGCGGACGCCGAGTTTCAGGAGAAGCTCGCCGACGACACATCCTTCGGGGGAAACCTCGGAAAGGC
AGTCTTTCAGGCCAAGAAAAGGGTTCTCGAACCTTTTGGCCTGGTTGAAGAGGGTGCTAAGACGGCCCC
TACCGGAAAGCGGATAGACGACCACTTTCCAAAAAGAAAGAAGGCTCGGACCGAAGAGGACTCCAAGCC
TTCCACCTCGTCAGACGCCGAAGCTGGACCCAGCGGATCCCAGCAGCTGCAAATCCCAGCCCAACCAGC
CTCAAGTTTGGGAGCTGATACAATGTCTGCGGGAGGTGGCGGCCCATTGGGCGACAATAACCAAGGTGC
CGATGGAGTGGGCAATGCCTCGGGAGATTGGCATTGCGATTCCACGTGGATGGGGGACAGAGTCGTCAC
CAAGTCCACCCGAACCTGGGTGCTGCCCAGCTACAACAACCACCAGTACCGAGAGATCAAAAGCGGCTC
CGTCGACGGAAGCAACGCCAACGCCTACTTTGGATACAGCACCCCCTGGGGGTACTTTGACTTTAACCG
CTTCCACAGCCACTGGAGCCCCCGAGACTGGCAAAGACTCATCAACAACTACTGGGGCTTCAGACCCCG
GTCCCTCAGAGTCAAAATCTTCAACATTCAAGTCAAAGAGGTCACGGTGCAGGACTCCACCACCACCAT
CGCCAACAACCTCACCTCCACCGTCCAAGTGTTTACGGACGACGACTACCAGCTGCCCTACGTCGTCGG
CAACGGGACCGAGGGATGCCTGCCGGCCTTCCCTCCGCAGGTCTTTACGCTGCCGCAGTACGGTTACGC
GACGCTGAACCGCGACAACACAGAAAATCCCACCGAGAGGAGCAGCTTCTTCTGCCTAGAGTACTTTCC
CAGCAAGATGCTGAGAACGGGCAACAACTTTGAGTTTACCTACAACTTTGAGGAGGTGCCCTTCCACTC
CAGCTTCGCTCCCAGTCAGAACCTCTTCAAGCTGGCCAACCCGCTGGTGGACCAGTACTTGTACCGCTT
CGTGAGCACAAATAACACTGGCGGAGTCCAGTTCAACAAGAACCTGGCCGGGAGATACGCCAACACCTA
CAAAAACTGGTTCCCGGGGCCCATGGGCCGAACCCAGGGCTGGAACCTGGGCTCCGGGGTCAACCGCGC
CAGTGTCAGCGCCTTCGCCACGACCAATAGGATGGAGCTCGAGGGCGCGAGTTACCAGGTGCCCCCGCA
GCCGAACGGCATGACCAACAACCTCCAGGGCAGCAACACCTATGCCCTGGAGAACACTATGATCTTCAA
CAGCCAGCCGGCGAACCCGGGCACCACCGCCACGTACCTCGAGGGCAACATGCTCATCACCAGCGAGAG
CGAGACGCAGCCGGTGAACCGCGTGGCGTACAACGTCGGCGGGCAGATGGCCACCAACAACCAGAGCTC
CACCACTGCCCCCGCGACCGGCACGTACAACCTCCAGGAAATCGTGCCCGGCAGCGTGTGGATGGAGAG
GGACGTGTACCTCCAAGGACCCATCTGGGCCAAGATCCCAGAGACGGGGGCGCACTTTCACCCCTCTCC
GGCCATGGGCGGATTCGGACTCAAACACCCACCGCCCATGATGCTCATCAAGAACACGCCTGTGCCCGG
AAATATCACCAGCTTCTCGGACGTGCCCGTCAGCAGCTTCATCACCCAGTACAGCACCGGGCAGGTCAC
CGTGGAGATGGAGTGGGAGCTCAAGAAGGAAAACTCCAAGAGGTGGAACCCAGAGATCCAGTACACAAA
CAACTACAACGACCCCCAGTTTGTGGACTTTGCCCCGGACAGCACCGGGGAATACAGAACCACCAGACC
TATCGGAACCCGATACCTTACCCGACCCCTTTAACCCATTCATGTCGCATACCCTCAATAAACCGTGTA
TTCGTGTCAGTAAAATACTGCCTCTTGTGGTCATTCAATGAATAACAGCTTACAACATTTACAAAACCT
CCTTGCTTGAGAGTGTGGCACTCTCCCCCCTGTCGCGTTCGCTCGCTCGCTGGCTCGTTTGGGGGGGCG
ACGGCCAGAGGGCCGTCGTCTGGCAGCTCTTTGAGCTGCCACCCCCCCAAACGAGCCAGCGAGCGAGCG
AACGCGACAGGGGGGAGAG

FIG. 13

AAV-6, COMPLETE SEQUENCE, GENBANK ACCESSION NO. NC 001862
TTGGCCACTCCCTCTCTGCGCGCTCGCTCGCTCACTGAGGCCGGGCGACCAAAGGTCGCCCGACGCCCG
GGCTTTGCCCGGGCGGCCTCAGTGAGCGAGCGAGCGCGCAGAGAGGGAGTGGCCAACTCCATCACTAGG
GGTTCCTGGAGGGGTGGAGTCGTGACGTGAATTACGTCATAGGGTTAGGGAGGTCCTGTATTAGAGGTC
ACGTGAGTGTTTTGCGACATTTTGCGACACCATGTGGTCACGCTGGGTATTTAAGCCCGAGTGAGCACG
CAGGGTCTCCATTTTGAAGCGGGAGGTTTGAACGCGCAGCGCCATGCCGGGGTTTTACGAGATTGTGAT
TAAGGTCCCCAGCGACCTTGACGAGCATCTGCCCGGCATTTCTGACAGCTTTGTGAACTGGGTGGCCGA
GAAGGAATGGGAGTTGCCGCCAGATTCTGACATGGATCTGAATCTGATTGAGCAGGCACCCCTGACCGT
GGCCGAGAAGCTGCAGCGCGACTTCCTGGTCCAGTGGCGCCGCGTGAGTAAGGCCCCGGAGGCCCTCTT
CTTTGTTCAGTTCGAGAAGGGCGAGTCCTACTTCCACCTCCATATTCTGGTGGAGACCACGGGGGTCAA
ATCCATGGTGCTGGGCCGCTTCCTGAGTCAGATTAGGGACAAGCTGGTGCAGACCATCTACCGCGGGAT
CGAGCCGACCCTGCCCAACTGGTTCGCGGTGACCAAGACGCGTAATGGCGCCGGAGGGGGGAACAAGGT
GGTGGACGAGTGCTACATCCCCAACTACCTCCTGCCCAAGACTCAGCCCGAGCTGCAGTGGGCGTGGAC
TAACATGGAGGAGTATATAAGCGCGTGTTTAAACCTGGCCGAGCGCAAACGGCTCGTGGCGCACGACCT
GACCCACGTCAGCCAGACCCAGGAGCAGAACAAGGAGAATCTGAACCCCAATTCTGACGCGCCTGTCAT
CCGGTCAAAAACCTCCGCACGCTACATGGAGCTGGTCGGGTGGCTGGTGGACCGGGGCATCACCTCCGA
GAAGCAGTGGATCCAGGAGGACCAGGCCTCGTACATCTCCTTCAACGCCGCCTCCAACTCGCGGTCCCA
GATCAAGGCCGCTCTGGACAATGCCGGCAAGATCATGGCGCTGACCAAATCCGCGCCCGACTACCTGGT
AGGCCCCGCTCCGCCCGCCGACATTAAAACCAACCGCATTTACCGCATCCTGGAGCTGAACGGCTACGA
CCCTGCCTACGCCGGCTCCGTCTTTCTCGGCTGGGCCCAGAAAAGGTTCGGAAAACGCAACACCATCTG
GCTGTTTGGGCCGGCCACCACGGGCAAGACCAACATCGCGGAAGCCATCGCCCACGCCGTGCCCTTCTA
CGGCTGCGTCAACTGGACCAATGAGAACTTTCCCTTCAACGATTGCGTCGACAAGATGGTGATCTGGTG
GGAGGAGGGCAAGATGACGGCCAAGGTCGTGGAGTCCGCCAAGGCCATTCTCGGCGGCAGCAAGGTGCG
CGTGGACCAAAAGTGCAAGTCGTCCGCCCAGATCGATCCCACCCCCGTGATCGTCACCTCCAACACCAA
CATGTGCGCCGTGATTGACGGGAACAGCACCACCTTCGAGCACCAGCAGCCGTTGCAGGACCGGATGTT
CAAATTTGAACTCACCCGCCGTCTGGAGCATGACTTTGGCAAGGTGACAAAGCAGGAAGTCAAAGAGTT
CTTCCGCTGGGCGCAGGATCACGTGACCGAGGTGGCGCATGAGTTCTACGTCAGAAAGGGTGGAGCCAA
CAAGAGACCCGCCCCCGATGACGCGGATAAAAGCGAGCCCAAGCGGGCCTGCCCCTCAGTCGCGGATCC
ATCGACGTCAGACGCGGAAGGAGCTCCGGTGGACTTTGCCGACAGGTACCAAAACAAATGTTCTCGTCA
CGCGGGCATGCTTCAGATGCTGTTTCCCTGCAAAACATGCGAGAGAATGAATCAGAATTTCAACATTTG
CTTCACGCACGGGACCAGAGACTGTTCAGAATGTTTCCCCGGCGTGTCAGAATCTCAACCGGTCGTCAG
AAAGAGGACGTATCGGAAACTCTGTGCCATTCATCATCTGCTGGGGCGGGCTCCCGAGATTGCTTGCTC
GGCCTGCGATCTGGTCAACGTGGATCTGGATGACTGTGTTTCTGAGCAATAAATGACTTAAACCAGGTA
TGGCTGCCGATGGTTATCTTCCAGATTGGCTCGAGGACAACCTCTCTGAGGGCATTCGCGAGTGGTGGG
ACTTGAAACCTGGAGCCCCGAAACCCAAAGCCAACCAGCAAAAGCAGGACGACGGCCGGGGTCTGGTGC
TTCCTGGCTACAAGTACCTCGGACCCTTCAACGGACTCGACAAGGGGGAGCCCGTCAACGCGGCGGATG
CAGCGGCCCTCGAGCACGACAAGGCCTACGACCAGCAGCTCAAAGCGGGTGACAATCCGTACCTGCGGT
ATAACCACGCCGACGCCGAGTTTCAGGAGCGTCTGCAAGAAGATACGTCTTTTGGGGGCAACCTCGGGC
GAGCAGTCTTCCAGGCCAAGAAGAGGGTTCTCGAACCTTTTGGTCTGGTTGAGGAAGGTGCTAAGACGG
CTCCTGGAAAGAAACGTCCGGTAGAGCAGTCGCCACAAGAGCCAGACTCCTCCTCGGGCATTGGCAAGA
CAGGCCAGCAGCCCGCTAAAAAGAGACTCAATTTTGGTCAGACTGGCGACTCAGAGTCAGTCCCCGACC
CACAACCTCTCGGAGAACCTCCAGCAACCCCCGCTGCTGTGGGACCTACTACAATGGCTTCAGGCGGTG
GCGCACCAATGGCAGACAATAACGAAGGCGCCGACGGAGTGGGTAATGCCTCAGGAAATTGGCATTGCG
ATTCCACATGGCTGGGCGACAGAGTCATCACCACCAGCACCCGAACATGGGCCTTGCCCACCTATAACA
ACCACCTCTACAAGCAAATCTCCAGTGCTTCAACGGGGGCCAGCAACGACAACCACTACTTCGGCTACA
GCACCCCCTGGGGGTATTTTGATTTCAACAGATTCCACTGCCATTTCTCACCACGTGACTGGCAGCGAC
TCATCAACAACAATTGGGGATTCCGGCCCAAGAGACTCAACTTCAAGCTCTTCAACATCCAAGTCAAGG
AGGTCACGACGAATGATGGCGTCACGACCATCGCTAATAACCTTACCAGCACGGTTCAAGTCTTCTCGG
ACTCGGAGTACCAGTTGCCGTACGTCCTCGGCTCTGCGCACCAGGGCTGCCTCCCTCCGTTCCCGGCGG
ACGTGTTCATGATTCCGCAGTACGGCTACCTAACGCTCAACAATGGCAGCCAGGCAGTGGGACGGTCAT
CCTTTTACTGCCTGGAATATTTCCCATCGCAGATGCTGAGAACGGGCAATAACTTTACCTTCAGCTACA
CCTTCGAGGACGTGCCTTTCCACAGCAGCTACGCGCACAGCCAGAGCCTGGACCGGCTGATGAATCCTC
TCATCGACCAGTACCTGTATTACCTGAACAGAACTCAGAATCAGTCCGGAAGTGCCCAAAACAAGGACT
TGCTGTTTAGCCGGGGGTCTCCAGCTGGCATGTCTGTTCAGCCCAAAAACTGGCTACCTGGACCCTGTT
ACCGGCAGCAGCGCGTTTCTAAAACAAAAACAGACAACAACAACAGCAACTTTACCTGGACTGGTGCTT
CAAAATATAACCTTAATGGGCGTGAATCTATAATCAACCCTGGCACTGCTATGGCCTCACACAAAGACG
ACAAAGACAAGTTCTTTCCCATGAGCGGTGTCATGATTTTTGGAAAGGAGAGCGCCGGAGCTTCAAACA
CTGCATTGGACAATGTCATGATCACAGACGAAGAGGAAATCAAAGCCACTAACCCCGTGGCCACCGAAA
GATTTGGGACTGTGGCAGTCAATCTCCAGAGCAGCAGCACAGACCCTGCGACCGGAGATGTGCATGTTA
TGGGAGCCTTACCTGGAATGGTGTGGCAAGACAGAGACGTATACCTGCAGGGTCCTATTTGGCCAAAA
TTCCTCACACGGATGGACACTTTCACCCGTCTCCTCTCATGGGCGGCTTTGGACTTAAGCACCCGCCTC
CTCAGATCCTCATCAAAAACACGCCTGTTCCTGCGAATCCTCCGGCAGAGTTTTCGGCTACAAAGTTTG
CTTCATTCATCACCCAGTATTCCACAGGACAAGTGAGCGTGGAGATTGAATGGGAGCTGCAGAAAGAAA
ACAGCAAACGCTGGAATCCCGAAGTGCAGTATACATCTAACTATGCAAAATCTGCCAACGTTGATTTCA
CTGTGGACAACAATGGACTTTATACTGAGCCTCGCCCCATTGGCACCCGTTACCTCACCCGTCCCCTGT
AATTGTGTGTTAATCAATAAACCGGTTAATTCGTGTCAGTTGAACTTTGGTCTCATGTCGTTATTATCT
TATCTGGTCACCATAGCAACCGGTTACACATTAACTGCTTAGTTGCGCTTCGCGAATACCCCTAGTGAT
GGAGTTGCCCACTCCCTCTATGCGCGCTCGCTCGCTCGGTGGGGCCGGCAGAGCAGAGCTCTGCCGTCT
GCGGACCTTTGGTCCGCAGGCCCCACCGAGCGAGCGAGCGCGCATAGAGGGAGTGGGCAA

FIG. 14

AAV-7, COMPLETE SEQUENCE, GENBANK ACCESSION NO. AF513851 AND GAO ET AL. (2002) PNAS 99:11854

TTGGCCACTCCCTCTATGCGCGCTCGCTCGCTCGGTGGGGCCTGCGGACCAAAGGTCCGCAGACGGCAG
AGCTCTGCTCTGCCGGCCCCACCGAGCGAGCGAGCGCGCATAGAGGGAGTGGCCAACTCCATCACTAGG
GGTACCGCGAAGCGCCTCCCACGCTGCCGCGTCAGCGCTGACGTAAATCACGTCATAGGGGAGTGGTCC
TGTATTAGCTGTCACGTGAGTGCTTTTGCGACATTTTGCGACACCACGTGGCCATTTGAGGTATATATG
GCCGAGTGAGCGAGCAGGATCTCCATTTTGACCGCGAAATTTGAACGAGCAGCAGCCATGCCGGGTTTC
TACGAGATCGTGATCAAGGTGCCGAGCGACCTGGACGAGCACCTGCCGGGCATTTCTGACTCGTTTGTG
AACTGGGTGGCCGAGAAGGAATGGGAGCTGCCCCCGGATTCTGACATGGATCTGAATCTGATCGAGCAG
GCACCCCTGACCGTGGCCGAGAAGCTGCAGCGCGACTTCCTGGTCCAATGGCGCCGCGTGAGTAAGGCC
CCGGAGGCCCTGTTCTTTGTTCAGTTCGAGAAGGGCGAGAGCTACTTCCACCTTCACGTTCTGGTGGAG
ACCACGGGGGTCAAGTCCATGGTGCTAGGCCGCTTCCTGAGTCAGATTCGGGAGAAGCTGGTCCAGACC
ATCTACCGCGGGGTCGAGCCCACGCTGCCCAACTGGTTCGCGGTGACCAAGACGCGTAATGGCGCCGGC
GGGGGGAACAAGGTGGTGGACGAGTGCTACATCCCCAACTACCTCCTGCCCAAGACCCAGCCCGAGCTG
CAGTGGGCGTGGACTAACATGGAGGAGTATATAAGCGCGTGTTTGAACCTGGCCGAACGCAAACGGCTC
GTGGCGCAGCACCTGACCCACGTCAGCCAGACGCAGGAGCAGAACAAGGAGAATCTGAACCCCAATTCT
GACGCGCCCGTGATCAGGTCAAAAACCTCCGCGCGCTACATGGAGCTGGTCGGGTGGCTGGTGGACCGG
GGCATCACCTCCGAGAAGCAGTGGATCCAGGAGGACCAGGCCTCGTACATCTCCTTCAACGCCGCCTCC
AACTCGCGGTCCCAGATCAAGGCCGCGCTGGACAATGCCGGCAAGATCATGGCGCTGACCAAATCCGCG
CCCGACTACCTGGTGGGCCCCTCGCTGCCCGCGGACATTAAAACCAACCGCATCTACCGCATCCTGGAG
CTGAACGGGTACGATCCTGCCTACGCCGGCTCCGTCTTTCTCGGCTGGGCCCAGAAAAAGTTCGGGAAG
CGCAACACCATCTGGCTGTTTGGGCCCGCCACCACCGGCAAGACCAACATTGCGGAAGCCATCGCCCAC
GCCGTGCCCTTCTACGGCTGCGTCAACTGGACCAATGAGAACTTTCCCTTCAACGATTGCGTCGACAAG
ATGGTGATCTGGTGGGAGGAGGGCAAGATGACGGCCAAGGTCGTGGAGTCCGCCAAGGCCATTCTCGGC
GGCAGCAAGGTGCGCGTGGACCAAAAGTGCAAGTCGTCCGCCCAGATCGACCCCACCCCCGTGATCGTC
ACCTCCAACACCAACATGTGCGCCGTGATTGACGGGAACAGCACCACCTTCGAGCACCAGCAGCCGTTG
CAGGACCGGATGTTCAAATTTGAACTCACCCGCCGTCTGGAGCACGACTTTGGCAAGGTGACGAAGCAG
GAAGTCAAAGAGTTCTTCCGCTGGGCCAGTGATCACGTGACCGAGGTGGCGCATGAGTTCTACGTCAGA
AAGGGCGGAGCCAGCAAAAGACCCGCCCCCGATGACGCGGATATAAGCGAGCCCAAGCGGGCCTGCCCC
TCAGTCGCGGATCCATCGACGTCAGACGCGGAAGGAGCTCCGGTGGACTTTGCCGACAGGTACCAAAAC
AAATGTTCTCGTCACGCGGGCATGATTCAGATGCTGTTTCCCTGCAAAACGTGCGAGAGAATGAATCAG
AATTTCAACATTTGCTTCACACACGGGGTCAGAGACTGTTTAGAGTGTTTCCCCGGCGTGTCAGAATCT
CAACCGGTCGTCAGAAAAAAGACGTATCGGAAACTCTGCGCGATTCATCATCTGCTGGGGCGGGCGCCC
GAGATTGCTTGCTCGGCCTGCGACCTGGTCAACGTGGACCTGGACGACTGCGTTTCTGAGCAATAAATG
ACTTAAACCAGGTATGGCTGCCGATGGTTATCTTCCAGATTGGCTCGAGGACAACCTCTCTGAGGGCAT
TCGCGAGTGGTGGGACCTGAAACCTGGAGCCCCGAAACCCAAAGCCAACCAGCAAAAGCAGGACAACGG
CCGGGGTCTGGTGCTTCCTGGCTACAAGTACCTCGGACCCTTCAACGGACTCGACAAGGGGGAGCCCGT
CAACGCGGCGGACGCAGCGGCCCTCGAGCACGACAAGGCCTACGACCAGCAGCTCAAAGCGGGTGACAA
TCCGTACCTGCGGTATAACCACGCCGACGCCGAGTTTCAGGAGCGTCTGCAAGAAGATACGTCATTTGG
GGGCAACCTCGGGCGAGCAGTCTTCCAGGCCAAGAAGCGGGTTCTCGAACCTCTCGGTCTGGTTGAGGA
AGGCGCTAAGACGGCTCCTGCAAAGAAGAGACCGGTAGAGCCGTCACCTCAGCGTTCCCCCGACTCCTC
CACGGGCATCGGCAAGAAAGGCCAGCAGCCCGCCAGAAAGAGACTCAATTTCGGTCAGACTGGCGACTC
AGAGTCAGTCCCCGACCCTCAACCTCTCGGAGAACCTCCAGCAGCGCCCTCTAGTGTGGGATCTGGTAC
AGTGGCTGCAGGCGGTGGCGCACCAATGGCAGACAATAACGAAGGTGCCGACGGAGTGGGTAATGCCTC
AGGAAATTGGCATTGCGATTCCACATGGCTGGGCGACAGAGTCATTACCACCAGCACCCGAACCTGGGC
CCTGCCCACCTACAACAACCACCTCTACAAGCAAATCTCCAGTGAAACTGCAGGTAGTACCAACGACAA
CACCTACTTCGGCTACAGCACCCCCTGGGGGTATTTTGACTTTAACAGATTCCACTGCCACTTCTCACC
ACGTGACTGGCAGCGACTCATCAACAACAACTGGGGATTCCGGCCCAAGAAGCTGCGGTTCAAGCTCTT
CAACATCCAGGTCAAGGAGGTCACGACGAATGACGGCGTTACGACCATCGCTAATAACCTTACCAGCAC
GATTCAGGTATTCTCGGACTCGGAATACCAGCTGCCGTACGTCCTCGGCTCTGCGCACCAGGGCTGCCT
GCCTCCGTTCCCGGCGGACGTCTTCATGATTCCTCAGTACGGCTACCTGACTCTCAACAATGGCAGTCA
GTCTGTGGGACGTTCCTCCTTCTACTGCCTGGAGTACTTCCCCTCTCAGATGCTGAGAACGGGCAACAA
CTTTGAGTTCAGCTACAGCTTCGAGGACGTGCCTTTCCACAGCAGCTACGCACACAGCCAGAGCCTGGA
CCGGCTGATGAATCCCCTCATCGACCAGTACTTGTACTACCTGGCCAGAACACAGAGTAACCCAGGAGG
CACAGCTGGCAATCGGGAACTGCAGTTTTACCAGGGCGGGCCTTCAACTATGGCCGAACAAGCCAAGAA
TTGGTTACCTGGACCTTGCTTCCGGCAACAAAGAGTCTCCAAAACGCTGGATCAAAACAACAACAGCAA
CTTTGCTTGGACTGGTGCCACCAAATATCACCTGAACGGCAGAAACTCGTTGGTTAATCCCGGCGTCGC
CATGGCAACTCACAAGGACGACGAGGACCGCTTTTTCCCATCCAGCGGAGTCCTGATTTTTGGAAAAAC
TGGAGCAACTAACAAAACTACATTGGAAAATGTGTTAATGACAAATGAAGAAGAAATTCGTCCTACTAA
TCCTGTAGCCACGGAAGAATACGGGATAGTCAGCAGCAACTTACAAGCGGCTAATACTGCAGCCCAGAC
ACAAGTTGTCAACAACCAGGGAGCCTTACCTGGCATGGTCTGGCAGAACCGGGACGTGTACCTGCAGGG
TCCCATCTGGGCCAAGATTCCTCACACGGATGGCAACTTTCACCCGTCTCCTTTGATGGGCGGCTTTGG
ACTTAAACATCCGCCTCCTCAGATCCTGATCAAGAACACTCCCGTTCCCGCTAATCCTCCGGAGGTGTT
TACTCCTGCCAAGTTTGCTTCGTTCATCACACAGTACAGCACCGGACAAGTCAGCGTGGAAATCGAGTG
GGAGCTGCAGAAGGAAAACAGCAAGCGCTGGAACCCGGAGATTCAGTACACCTCCAACTTTGAAAAGCA
GACTGGTGTGGACTTTGCCGTTGACAGCCAGGGTGTTTACTCTGAGCCTCGCCCTATTGGCACTCGTTA
CCTCACCCGTAATCTGTAATTGCATGTTAATCAATAAACCGGTTGATTCGTTTCAGTTGAACTTTGGTC
TCCTGTGCTTCTTATCTTATCGGTTTCCATAGCAACTGGTTACACATTAACTGCTTGGGTGCGCTTCAC
GATAAGAACACTGACGTCACCGCGGTACCCCTAGTGATGGAGTTGGCCACTCCCTCTATGCGCGCTCGC
TCGCTCGGTGGGGCCTGCGGACCAAAGGTCCGCAGACGGCAGAGCTCTGCTCTGCCGGCCCCACCGAGC
GAGCGAGCGCGCATAGAGGGAGTGGCCAA

FIG. 15

AAV-8, COMPLETE SEQUENCE, GENBANK ACCESSION NO. AF513852 AND GAO ET AL. (2002) PNAS 99:11854

CAGAGAGGGAGTGGCCAACTCCATCACTAGGGGTAGCGCGAAGCGCCTCCCACGCTGCCGCGTCAGC
GCTGACGTAAATTACGTCATAGGGGAGTGGTCCTGTATTAGCTGTCACGTGAGTGCTTTTGCGGCAT
TTTGCGACACCACGTGGCCATTTGAGGTATATATGGCCGAGTGAGCGAGCAGGATCTCCATTTTGAC
CGCGAAATTTGAACGAGCAGCAGCCATGCCGGGCTTCTACGAGATCGTGATCAAGGTGCCGAGCGAC
CTGGACGAGCACCTGCCGGGCATTTCTGACTCGTTTGTGAACTGGGTGGCCGAGAAGGAATGGGAGC
TGCCCCCGGATTCTGACATGGATCGGAATCTGATCGAGCAGGCACCCCTGACCGTGGCCGAGAAGCT
GCAGCGCGACTTCCTGGTCCAATGGCGCCGCGTGAGTAAGGCCCCGGAGGCCCTCTTCTTTGTTCAG
TTCGAGAAGGGCGAGAGCTACTTTCACCTGCACGTTCTGGTCGAGACCACGGGGGTCAAGTCCATGG
TGCTAGGCCGCTTCCTGAGTCAGATTCGGGAAAAGCTTGGTCCAGACCATCTACCCGCGGGGTCGAG
CCCCACCTTGCCCAACTGGTTCGCGGTGACCAAAGACGCGGTAATGGCGCCGGCGGGGGGGAACAAG
GTGGTGGACGAGTGCTACATCCCCAACTACCTCCTGCCCAAGACTCAGCCCGAGCTGCAGTGGGCGT
GGACTAACATGGAGGAGTATATAAGCGCGTGCTTGAACCTGGCCGAGCGCAAACGGCTCGTGGCGCA
GCACCTGACCCACGTCAGCCAGACGCAGGAGCAGAACAAGGAGAATCTGAACCCCAATTCTGACGCG
CCCGTGATCAGGTCAAAAACCTCCGCGCGCTATATGGAGCTGGTCGGGTGGCTGGTGGACCGGGGCA
TCACCTCCGAGAAGCAGTGGATCCAGGAGGACCAGGCCTCGTACATCTCCTTCAACGCCGCCTCCAA
CTCGCGGTCCCAGATCAAGGCCGCGCTGGACAATGCCGGCAAGATCATGGCGCTGACCAAATCCGCG
CCCGACTACCTGGTGGGGCCCTCGCTGCCCGCGGACATTACCCAGAACCGCATCTACCGCATCCTCG
CTCTCAACGGCTACGACCCTGCCTACGCCGGCTCCGTCTTTCTCGGCTGGGCTCAGAAAAAGTTCGG
GAAACGCAACACCATCTGGCTGTTTGGACCCGCCACCACCGGCAAGACCAACATTGCGGAAGCCATC
GCCCACGCCGTGCCCTTCTACGGCTGCGTCAACTGGACCAATGAGAACTTTCCCTTCAATGATTGCG
TCGACAAGATGGTGATCTGGTGGGAGGAGGGCAAGATGACGGCCAAGGTCGTGGAGTCCGCCAAGGC
CATTCTCGGCGGCAGCAAGGTGCGCGTGGACCAAAAGTGCAAGTCGTCCGCCCAGATCGACCCCACC
CCCGTGATCGTCACCTCCAACACCAACATGTGCGCCGTGATTGACGGGAACAGCACCACCTTCGAGC
ACCAGCAGCCTCTCCAGGACCGGATGTTTAAGTTCGAACTCACCCGCCGTCTGGAGCACGACTTTGG
CAAGGTGACAAAGCAGGAAGTCAAAGAGTTCTTCCGCTGGGCCAGTGATCACGTGACCGAGGTGGCG
CATGAGTTTTACGTCAGAAAGGGCGGAGCCAGCAAAAGACCCGCCCCCGATGACGCGGATAAAAGCG
AGCCCAAGCGGGCCTGCCCCTCAGTCGCGGATCCATCGACGTCAGACGCGGAAGGAGCTCCGGTGGA
CTTTGCCGACAGGTACCAAAACAAATGTTCTCGTCACGCGGGCATGCTTCAGATGCTGTTTCCCTGC
AAAACGTGCGAGAGAATGAATCAGAATTTCAACATTTGCTTCACACACGGGGTCAGAGACTGCTCAG
AGTGTTTCCCCGGCGTGTCAGAATCTCAACCGGTCGTCAGAAAGAGGACGTATCGGAAACTCTGTGC
GATTCATCATCTGCTGGGGCGGGCTCCCGAGATTGCTTGCTCGGCCTGCGATCTGGTCAACGTGGAC
CTGGATGACTGTGTTTCTGAGCAATAAATGACTTAAACCAGGTATGGCTGCCGATGGTTATCTTCCA
GATTGGCTCGAGGACAACCTCTCTGAGGGCATTCGCGAGTGGTGGGCGCTGAAACCTGGAGCCCCGA
AGCCCAAAGCCAACCAGCAAAAGCAGGACGACGGCCGGGGTCTGGTGCTTCCTGGCTACAAGTACCT
CGGACCCTTCAACGGACTCGACAAGGGGGAGCCCGTCAACGCGGCGGACGCAGCGGCCCTCGAGCAC
GACAAGGCCTACGACCAGCAGCTGCAGGCGGGTGACAATCCGTACCTGCGGTATAACCACGCCGACG
CCGAGTTTCAGGAGCGTCTGCAAGAAGATACGTCTTTTGGGGGCAACCTCGGGCGAGCAGTCTTCCA
GGCCAAGAAGCGGGTTCTCGAACCTCTCGGTCTGGTTGAGGAAGGCGCTAAGACGGCTCCTGGAAAG
AAGAGACCGGTAGAGCCATCACCCCAGCGTTCTCCAGACTCCTCTACGGGCATCGGCAAGAAAGGCC
AACAGCCCGCCAGAAAAAGACTCAATTTTGGTCAGACTGGCGACTCAGAGTCAGTTCCAGACCCTCA
ACCTCTCGGAGAACCTCCAGCAGCGCCCTCTGGTGTGGGACCTAATACAATGGCTGCAGGCGGTGGC
GCACCAATGGCAGACAATAACGAAGGCGCCGACGGAGTGGGTAGTTCCTCGGGAAATTGGCATTGCG
ATTCCACATGGCTGGGCGACAGAGTCATCACCACCAGCACCCGAACCTGGGCCCTGCCCACCTACAA
CAACCACCTCTACAAGCAAATCTCCAACGGGACATCGGGAGGAGCCACCAACGACAACACCTACTTC
GGCTACAGCACCCCCTGGGGGTATTTTGACTTTAACAGATTCCACTGCCACTTTTCACCACGTGACT
GGCAGCGACTCATCAACAACAACTGGGGATTCCGGCCCAAGAGACTCAGCTTCAAGCTCTTCAACAT
CCAGGTCAAGGAGGTCACGCAGAATGAAGGCACCAAGACCATCGCCAATAACCTCACCAGCACCATC
CAGGTGTTTACGGACTCGGAGTACCAGCTGCCGTACGTTCTCGGCTCTGCCCACCAGGGCTGCCTGC
CTCCGTTCCCGGCGGACGTGTTCATGATTCCCCAGTACGGCTACCTAACACTCAACAACGGTAGTCA
GGCCGTGGGACGCTCCTCCTTCTACTGCCTGGAATACTTTCCTTCGCAGATGCTGAGAACCGGCAAC
AACTTCCAGTTTACTTACACCTTCGAGGACGTGCCTTTCCACAGCAGCTACGCCCACAGCCAGAGCT
TGGACCGGCTGATGAATCCTCTGATTGACCAGTACCTGTACTACTTGTCTCGGACTCAAACAACAGG
AGGCACGGCAAATACGCAGACTCTGGGCTTCAGCCAAGGTGGGCCTAATACAATGGCCAATCAGGCA
AAGAACTGGCTGCCAGGACCCTGTTACCGCCAACAACGCGTCTCAACGACAACCGGGCAAAACAACA
ATAGCAACTTTGCCTGGACTGCTGGGACCAAATACCATCTGAATGGAAGAAATTCATTGGCTAATCC
TGGCATCGCTATGGCAACACACAAAGACGACGAGGAGCGTTTTTTTCCCAGTAACGGGATCCTGATT
TTTGGCAAACAAAATGCTGCCAGAGACAATGCGGATTACAGCGATGTCATGCTCACCAGCGAGGAAG
AAATCAAAACCACTAACCCTGTGGCTACAGAGGAATACGGTATCGTGGCAGATAACTTGCAGCAGCA
AAACACGGCTCCTCAAATTGGAACTGTCAACAGCCAGGGGGCCTTACCCGGTATGGTCTGGCAGAAC
CGGGACGTGTACCTGCAGGGTCCCATCTGGGCCAAGATTCCTCACACGGACGGCAACTTCCACCCGT
CTCCGCTGATGGGCGGCTTTGGCCTGAAACATCCTCCGCCTCAGATCCTGATCAAGAACACGCCTGT
ACCTGCGGATCCTCCGACCACCTTCAACCAGTCAAAGCTGAACTCTTTCATCACGCAATACAGCACC
GGACAGGTCAGCGTGGAAATTGAATGGGAGCTGCAGAAGGAAAACAGCAAGCGCTGGAACCCCGAGA
TCCAGTACACCTCCAACTACTACAAATCTACAAGTGTGGACTTTGCTGTTAATACAGAAGGCGTGTA
CTCTGAACCCCGCCCCATTGGCACCCGTTACCTCACCCGTAATCTGTAATTGCCTGTTAATCAATAA
ACCGGTTGATTCGTTTCAGTTGAACTTTGGTCTCTGCG

FIG. 16

AAV-9, GENBANK ACCESSION NO. AX753250 AND GAO ET AL. (MAY 14, 2003) EP1310571

CAGAGAGGGAGTGGCCAACTCCATCACTAGGGGTAATCGCGAAGCGCCTCCCACGCTGCCGCGTC
AGCGCTGACGTAGATTACGTCATAGGGGAGTGGTCCTGTATTAGCTGTCACGTGAGTGCTTTTGC
GACATTTTGCGACACCACATGGCCATTTGAGGTATATATGGCCGAGTGAGCGAGCAGGATCTCCA
TTTTGACCGCGAAATTTGAACGAGCAGCAGCCATGCCGGGCTTCTACGAGATTGTGATCAAGGTG
CCGAGCGACCTGGACGAGCACCTGCCGGGCATTTCTGACTCTTTTGTGAACTGGGTGGCCGAGAA
GGAATGGGAGCTGCCCCCGGATTCTGACATGGATCGGAATCTGATCGAGCAGGCACCCCTGACCG
TGGCCGAGAAGCTGCAGCGCGACTTCCTGGTCCAATGGCGCCGCGTGAGTAAGGCCCCGGAGGCC
CTCTTCTTTGTTCAGTTCGAGAAGGGCGAGAGCTACTTTCACCTGCACGTTCTGGTCGAGACCAC
GGGGGTCAAGTCCATGGTGCTAGGCCGCTTCCTGAGTCAGATTCGGGAGAAGCTGGTCCAGACCA
TCTACCGCGGGATCGAGCCGACCCTGCCCAACTGGTTCGCGGTGACCAAGACGCGTAATGGCGCC
GGCGGGGGGAACAAGGTGGTGGACGAGTGCTACATCCCCAACTACCTCCTGCCCAAGACTCAGCC
CGAGCTGCAGTGGGCGTGGACTAACATGGAGGAGTATATAAGCGCGTGCTTGAACCTGGCCGAGC
GCAAACGGCTCGTGGCGCAGCACCTGACCCACGTCAGCCAGACGCAGGAGCAGAACAAGGAGAAT
CTGAACCCCAATTCTGACGCGCCCGTGATCAGGTCAAAAACCTCCGCGCGCTACATGGAGCTGGT
CGGGTGGCTGGTGGACCGGGGCATCACCTCCGAGAAGCAGTGGATCCAGGAGGACCAGGCCTCGT
ACATCTCCTTCAACGCCGCCTCCAACTCGCGGTCCCAGATCAAGGCCGCGCTGGACAATGCCGGC
AAGATCATGGCGCTGACCAAATCCGCGCCCGACTACCTGGTAGGCCCTTCACTTCCGGTGGACAT
TACGCAGAACCGCATCTACCGCATCCTGCAGCTCAACGGCTACGACCCTGCCTACGCCGGCTCCG
TCTTTCTCGGCTGGGCACAAAAGAAGTTCGGGAAACGCAACACCATCTGGCTGTTTGGGCCGGCC
ACCACGGGAAAGACCAACATCGCAGAAGCCATTGCCCACGCCGTGCCCTTCTACGGCTGCGTCAA
CTGGACCAATGAGAACTTTCCCTTCAACGATTGCGTCGACAAGATGGTGATCTGGTGGGAGGAGG
GCAAGATGACGGCCAAGGTCGTGGAGTCCGCCAAGGCCATTCTCGGCGGCAGCAAGGTGCGCGTG
GACCAAAAGTGCAAGTCGTCCGCCCAGATCGACCCCACTCCCGTGATCGTCACCTCCAACACCAA
CATGTGCGCCGTGATTGACGGGAACAGCACCACCTTCGAGCACCAGCAGCCTCTCCAGGACCGGA
TGTTTAAGTTCGAACTCACCCGCCGTCTGGAGCACGACTTTGGCAAGGTGACAAAGCAGGAAGTC
AAAGAGTTCTTCCGCTGGGCCAGTGATCACGTGACCGAGGTGGCGCATGAGTTTTACGTCAGAAA
GGGCGGAGCCAGCAAAAGACCCGCCCCCGATGACGCGGATAAAAGCGAGCCCAAGCGGGCCTGCC
CCTCAGTCGCGGATCCATCGACGTCAGACGCGGAAGGAGCTCCGGTGGACTTTGCCGACAGGTAC
CAAAACAAATGTTCTCGTCACGCGGGCATGCTTCAGATGCTGCTTCCCTGCAAAACGTGCGAGAG
AATGAATCAGAATTTCAACATTTGCTTCACACACGGGGTCAGAGACTGCTCAGAGTGTTTCCCCG
GCGTGTCAGAATCTCAACCGGTCGTCAGAAAGAGGACGTATCGGAAACTCTGTGCGATTCATCAT
CTGCTGGGGCGGGCTCCCGAGATTGCTTGCTCGGCCTGCGATCTGGTCAACGTGGACCTGGATGA
CTGTGTTTCTGAGCAATAAATGACTTAAACCAGGTATGGCTGCCGATGGTTATCTTCCAGATTGG
CTCGAGGACAACCTCTCTGAGGGCATTCGCGAGTGGTGGGCGCTGAAACCTGGAGCCCCGAAGCC
CAAAGCCAACCAGCAAAAGCAGGACGACGGCCGGGGTCTGGTGCTTCCTGGCTACAAGTACCTCG
GACCCTTCAACGGACTCGACAAGGGGGAGCCCGTCAACGCGGCGGACGCAGCGGCCCTCGAGCAC
GGCAAGGCCTACGACCAGCAGCTGCAGGCGGGTGACAATCCGTACCTGCGGTATAACCACGCCGA
CGCCGAGTTTCAGGAGCGTCTGCAAGAAGATACGTCTTTTGGGGGCAACCTCGGGCGAGCAGTCT
TCCAGGCCAAGAAGCGGGTTCTCGAACCTCTCGGTCTGGTTGAGGAAGGCGCTAAGACGGCTCCT
GGAAAGAAGAGACCGGTAGAGCCATCACCCCAGCGTTCTCCAGACTCCTCTACGGGCATCGGCAA
GAAAGGCCAACAGCCCGCCAGAAAAAGACTCAATTTTGGTCAGACTGGCGACTCAGAGTCAGTTC
CAGACCCTCAACCTCTCGGAGAACCTCCAGCAGCGCCCTCTGGTGTGGGACCTAATACAATGGCT
GCAGGCGGTGGCGCACCAATGGCAGACAATAACGAAGGCGCCGACGGAGTGGGTAATTCCTCGGG
AAATTGGCATTGCGATTCCACATGGCTGGGGGACAGAGTCATCACCACCAGCACCCGAACCTGGG
CATTGCCCACCTACAACAACCACCTCTACAAGCAAATCTCCAATGGAACATCGGGAGGAAGCACC
AACGACAACACCTACTTTGGCTACAGCACCCCCTGGGGGTATTTTGACTTCAACAGATTCCACTG
CCACTTCTCACCACGTGACTGGCAGCGACTCATCAACAACAACTGGGGATTCCGGCCAAAGAGAC
TCAACTTCAAGCTGTTCAACATCCAGGTCAAGGAGGTTACGACGAACGAAGGCACCAAGACCATC
GCCAATAACCTTACCAGCACCGTCCAGGTCTTTACGGACTCGGAGTACCAGCTACCGTACGTCCT
AGGCTCTGCCCACCAAGGATGCCTGCCACCGTTTCCTGCAGACGTCTTCATGGTTCCTCAGTACG
GCTACCTGACGCTCAACAATGGAAGTCAAGCGTTAGGACGTTCTTCTTTCTACTGTCTGGAATAC
TTCCCTTCTCAGATGCTGAGAACCGGCAACAACTTTCAGTTCAGCTACACTTTCGAGGACGTGCC
TTTCCACAGCAGCTACGCACACAGCCAGAGTCTAGATCGACTGATGAACCCCCTCATCGACCAGT
ACCTATACTACCTGGTCAGAACACAGACAACTGGAACTGGGGGAACTCAAACTTTGGCATTCAGC
CAAGCAGGCCCTAGCTCAATGGCCAATCAGGCTAGAAACTGGGTACCCGGGCCTTGCTACCGTCA
GCAGCGCGTCTCCACAACCACCAACCAAAATAACAACAGCAACTTTGCGTGGACGGGAGCTGCTA
AATTCAAGCTGAACGGGAGAGACTCGCTAATGAATCCTGGCGTGGCTATGGCATCGCACAAAGAC
GACGAGGACCGCTTCTTTCCATCAAGTGGCGTTCTCATATTTGGCAAGCAAGGAGCCGGGAACGA
TGGAGTCGACTACAGCCAGGTGCTGATTACAGATGAGGAAGAAATTAAAGCCACCAACCCTGTAG
CCACAGAGGAATACGGAGCAGTGGCCATCAACAACCAGGCCGCTAACACGCAGGCGCAAACTGGA
CTTGTGCATAACCAGGGAGTTATTCCTGGTATGGTCTGGCAGAACCGGGACGTGTACCTGCAGGG
CCCTATTTGGGCTAAAATACCTCACACAGATGGCAACTTTCACCCGTCTCCTCTGATGGGTGGAT
TTGGACTGAAACACCCACCTCCACAGATTCTAATTAAAAATACACCAGTGCCGGCAGATCCTCCT
CTTACCTTCAATCAAGCCAAGCTGAACTCTTTCATCACGCAGTACAGCACGGGACAAGTCAGCGT
GGAAATCGAGTGGGAGCTGCAGAAAGAAAACAGCAAGCGCTGGAATCCAGAGATCCAGTATACTT
CAAACTACTACAAATCTACAAATGTGGACTTTGCTGTCAATACCAAAGGTGTTTACTCTGAGCCT
CGCCCCATTGGTACTCGTTACCTCACCCGTAATTTGTAATTGCCTGTTAATCAATAAACCGGTTA
ATTCGTTTCAGTTGAACTTTGGTCTCTGCG

FIG. 17

AAV-11, NONSTRUCTURAL PROTEIN AND CAPSID PROTEIN GENES, COMPLETE CDS, GENBANK ACCESSION NO. AY631966 AND MORI ET AL. (2004) *VIROL.* 330:375

ATGCCGGGCTTCTACGAGATCGTGATCAAGGTGCCGAGCGACCTGGACGAGCACCTGCCGGGC
ATTTCTGACTCGTTTGTGAACTGGGTGGCCGAGAAGGAATGGGAGCTGCCCCCGGATTCTGAC
ATGGATCGGAATCTGATCGAGCAGGCACCCCTGACCGTGGCCGAGAAGCTGCAGCGCGACTTC
CTGGTCCACTGGCGCCGCGTGAGTAAGGCCCCGGAGGCCCTCTTCTTTGTTCAGTTCGAGAAG
GGCGAGTCCTACTTCCACCTCCACGTTCTCGTCGAGACCACGGGGGTCAAGTCCATGGTCCTG
GGCCGCTTCCTGAGTCAGATCAGAGACAGGCTGGTGCAGACCATCTACCGCGGGGTCGAGCCC
ACGCTGCCCAACTGGTTCGCGGTGACCAAGACGCGAAATGGCGCCGGCGGGGGGAACAAGGTG
GTGGACGAGTGCTACATCCCCAACTACCTCCTGCCCAAGACCCAGCCCGAGCTGCAGTGGGCG
TGGACTAACATGGAGGAGTATATAAGCGCGTGTCTAAACCTCGCGGAGCGTAAACGGCTCGTG
GCGCAGCACCTGACCCACGTCAGCCAGACGCAGGAGCAGAACAAGGAGAATCTGAACCCGAAT
TCTGACGCGCCCGTGATCAGGTCAAAAACCTCCGCGCGCTACATGGAGCTGGTCGGGTGGCTG
GTGGACCGGGGCATCACCTCCGAGAAGCAGTGGATCCAGGAGGACCAGGCCTCGTACATCTCC
TTCAACGCCGCCTCCAACTCGCGGTCCCAGATCAAGGCCGCGCTGGACAATGCCGGAAAGATC
ATGGCGCTGACCAAATCCGCGCCCGACTACCTGGTAGGCCCGTCCTTACCCGCGGACATTAAG
GCCAACCGCATCTACCGCATCCTGGAGCTCAACGGCTACGACCCCGCCTACGCCGGCTCCGTC
TTCCTGGGCTGGGCGCAGAAAAAGTTCGGTAAACGCAACACCATCTGGCTGTTTGGCCCCGCC
ACCACCGGCAAGACCAACATCGCGGAAGCCATAGCCCACGCCGTGCCCTTCTACGGCTGCGTG
AACTGGACCAATGAGAACTTTCCCTTCAACGATTGCGTCGACAAGATGGTGATCTGGTGGGAG
GAGGGCAAGATGACCGCCAAGGTCGTGGAGTCCGCCAAGGCCATTCTGGGCGGAAGCAAGGTG
CGCGTGGACCAAAAGTGCAAGTCCTCGGCCCAGATCGACCCCACGCCCGTGATCGTCACCTCC
AACACCAACATGTGCGCCGTGATCGACGGGAACAGCACCACCTTCGAGCACCAGCAGCCGCTG
CAGGACCGCATGTTCAAGTTCGAGCTCACCCGCCGTCTGGAGCACGACTTTGGCAAGGTGACC
AAGCAGGAAGTCAAAGAGTTCTTCCGCTGGGCTCAGGATCACGTGACTGAGGTGGCGCATGAG
TTCTACGTCAGAAAGGGCGGAGCCACCAAAAGACCCGCCCCCAGTGACGCGGATATAAGCGAG
CCCAAGCGGGCCTGCCCCTCAGTTCCGGAGCCATCGACGTCAGACGCGGAAGCACCGGTGGAC
TTTGCGGACAGGTACCAAAACAAATGTTCTCGTCACGCGGGCATGCTTCAGATGCTGTTTCCC
TGCAAGACATGCGAGAGAATGAATCAGAATTTCAACGTCTGCTTCACGCACGGGGTCAGAGAC
TGCTCAGAGTGCTTCCCCGGCGCGTCAGAATCTCAACCCGTCGTCAGAAAAAAGACGTATCAG
AAACTGTGCGCGATTCATCATCTGCTGGGGCGGGCACCCGAGATTGCGTGTTCGGCCTGCGAT
CTCGTCAACGTGGACTTGGATGACTGTGTTTCTGAGCAATAAATGACTTAAACCAGGTATGGC
TGCTGACGGTTATCTTCCAGATTGGCTCGAGGACAACCTCTCTGAGGGCATTCGCGAGTGGTG
GGACCTGAAACCTGGAGCCCCGAAGCCCAAGGCCAACCAGCAGAAGCAGGACGACGGCCGGGG
TCTGGTGCTTCCTGGCTACAAGTACCTCGGACCCTTCAACGGACTCGACAAGGGGGAGCCCGT
CAACGCGGCGGACGCAGCGGCCCTCGAGCACGACAAGGCCTACGACCAGCAGCTCAAAGCGGG
TGACAATCCGTACCTGCGGTATAACCACGCCGACGCCGAGTTTCAGGAGCGTCTGCAAGAAGA
TACGTCTTTTGGGGGCAACCTCGGGCGAGCAGTCTTCCAGGCCAAGAAGAGGGTACTCGAACC
TCTGGGCCTGGTTGAAGAAGGTGCTAAAACGGCTCCTGGAAAGAAGAGACCGTTAGAGTCACC
ACAAGAGCCCGACTCCTCCTCGGGCATCGGCAAAAAAGGCAAACAACCAGCCAGAAAGAGGCT
CAACTTTGAAGAGGACACTGGAGCCGGAGACGGACCCCCTGAAGGATCAGATACCAGCGCCAT
GTCTTCAGACATTGAAATGCGTGCAGCACCGGGCGGAAATGCTGTCGATGCGGGACAAGGTTC
CGATGGAGTGGGTAATGCCTCGGGTGATTGGCATTGCGATTCCACCTGGTCTGAGGGCAAGGT
CACAACAACCTCGACCAGAACCTGGGTCTTGCCCACCTACAACAACCACTTGTACCTGCGTCT
CGGAACAACATCAAGCAGCAACACCTACAACGGATTCTCCACCCCCTGGGGATATTTTGACTT
CAACAGATTCCACTGTCACTTCTCACCACGTGACTGGCAAAGACTCATCAACAACAACTGGGG
ACTACGACCAAAAGCCATGCGCGTTAAAATCTTCAATATCCAAGTTAAGGAGGTCACAACGTC
GAACGGCGAGACTACGGTCGCTAATAACCTTACCAGCACGGTTCAGATATTTGCGGACTCGTC
GTATGAGCTCCCGTACGTGATGGACGCTGGACAAGAGGGGAGCCTGCCTCCTTTCCCCAATGA
CGTGTTCATGGTGCCTCAATATGGCTACTGTGGCATCGTGACTGGCGAGAATCAGAACCAAAC
GGACAGAAACGCTTTCTACTGCCTGGAGTATTTTCCTTCGCAAATGTTGAGAACTGGCAACAA
CTTTGAAATGGCTTACAACTTTGAGAAGGTGCCGTTCCACTCAATGTATGCTCACAGCCAGAG
CCTGGACAGACTGATGAATCCCCTCCTGGACCAGTACCTGTGGCACTTACAGTCGACTACCTC
TGGAGAGACTCTGAATCAAGGCAATGCAGCAACCACATTTGGAAAAATCAGGAGTGGAGACTT
TGCCTTTTACAGAAAGAACTGGCTGCCTGGGCCTTGTGTTAAACAGCAGAGATTCTCAAAAAC
TGCCAGTCAAAATTACAAGATTCCTGCCAGCGGGGGCAACGCTCTGTTAAAGTATGACACCCA
CTATACCTTAAACAACCGCTGGAGCAACATCGCGCCCGGACCTCCAATGGCCACAGCCGGACC
TTCGGATGGGGACTTCAGTAACGCCCAGCTTATATTCCCTGGACCATCTGTTACCGGAAATAC
AACAACTTCAGCCAACAATCTGTTGTTTACATCAGAAGAAGAAATTGCTGCCACCAACCCAAG
AGACACGGACATGTTTGGCCAGATTGCTGACAATAATCAGAATGCTACAACTGCTCCCATAAC
CGGCAACGTGACTGCTATGGGAGTGCTGCCTGGCATGGTGTGGCAAAACAGAGACATTTACTA
CCAAGGGCCAATTTGGGCCAAGATCCCACACGCGGACGGACATTTTCATCCTTCACCGCTGAT
TGGTGGGTTTGGACTGAAACACCCGCCTCCCCAGATATTCATCAAGAACACTCCCGTACCTGC
CAATCCTGCGACAACCTTCACTGCAGCCAGAGTGGACTCTTTCATCACACAATACAGCACCGG
CCAGGTCGCTGTTCAGATTGAATGGGAAATTGAAAAGGAACGCTCCAAACGCTGGAATCCTGA
AGTGCAGTTTACTTCAAACTATGGGAACCAGTCTTCTATGTTGTGGGCTCCTGATACAACTGG
GAAGTATACAGAGCCGCGGGTTATTGGCTCTCGTTATTTGACTAATCATTTGTAA

*FIG. 18*

AAV-13, NONSTRUCTURAL PROTEIN AND CAPSID PROTEIN GENES, COMPLETE CDS, GENBANK ACCESSION NO. EU285562 AND SCHMIDT ET AL. (2008) *J. VIROL.* 82:8911

CCGCGAGTGAGCGAACCAGGAGCTCCATTTTGCCCGCGAATTTTGAACGAGCAGCAGCCATGC
CGGGATTCTACGAGATTGTCCTGAAGGTGCCCAGCGACCTGGACGAGCACCTGCCTGGCATTT
CTGACTCTTTTGTAAACTGGGTGGCGGAGAAGGAATGGGAGCTGCCGCCGGATTCTGACATGG
ATCTGAATCTGATTGAGCAGGCACCCCTAACCGTGGCCGAAAAGCTGCAACGCGAATTCCTGG
TCGAGTGGCGCCGCGTGAGTAAGGCCCCGGAGGCCCTCTTCTTTGTTCAGTTCGAGAAGGGGG
ACAGCTACTTCCACCTACACATTCTGGTGGAGACCGTGGGCGTGAAATCCATGGTGGTGGGCC
GCTACGTGAGCCAGATTAAAGAGAAGCTGGTGACCCGCATCTACCGCGGGGTCGAGCCGCAGC
TTCCGAACTGGTTCGCGGTGACCAAGACGCGTAATGGCGCCGGAGGCGGGAACAAGGTGGTGG
ACGACTGCTACATCCCCAACTACCTGCTCCCCAAGACCCAGCCCGAGCTCCAGTGGGCGTGGA
CTAATATGGACCAGTATTTAAGCGCCTGTTTGAATCTCGCGGAGCGTAAACGGCTGGTGGCGC
AGCATCTGACGCACGTGTCGCAGACGCAGGAGCAGAACAAAGAGAACCAGAATCCCAATTCTG
ACGCGCCGGTGATCAGATCAAAAACCTCCGCGAGGTACATGGAGCTGGTCGGGTGGCTGGTGG
ACCGCGGGATCACGTCAGAAAAGCAATGGATCCAGGAGGACCAGGCCTCTTACATCTCCTTCA
ACGCCGCCTCCAACTCGCGGTCACAAATCAAGGCCGCACTGGACAATGCCTCCAAATTTATGA
GCCTGACAAAAACGGCTCCGGACTACCTGGTGGGAAACAACCCGCCGGAGGACATTACCAGCA
ACCGGATCTACAAAATCCTCGAGATGAACGGGTACGATCCGCAGTACGCGGCCTCCGTCTTCC
TGGGCTGGGCGCAAAAGAAGTTCGGGAAGAGGAACACCATCTGGCTCTTTGGCCGGCCACGA
CGGGTAAAACCAACATCGCTGAAGCTATCGCCCACGCCGTGCCCTTTTACGGCTGCGTGAACT
GGACCAATGAGAACTTTCCGTTCAACGATTGCGTCGACAAGATGGTGATCTGGTGGGAGGAGG
GCAAGATGACGGCCAAGGTCGTGGAGTCCGCCAAGGCCATTCTGGGCGGAAGCAAGGTGCGCG
TGGACCAAAAGTGCAAGTCATCGGCCCAGATCGACCCAACTCCCGTCATCGTCACCTCCAACA
CCAACATGTGCGCGGTCATCGACGGAAATTCCACCACCTTCGAGCACCAACAACCACTCCAAG
ACCGGATGTTCAAGTTCGAGCTCACCAAGCGCCTGGAGCACGACTTTGGCAAGGTCACCAAGC
AGGAAGTCAAGGACTTTTTCCGGTGGGCGTCAGATCACGTGACTGAGGTGTCTCACGAGTTTT
ACGTCAGAAAGGGTGGAGCTAGAAAGAGGCCCGCCCCCAATGACGCAGATATAAGTGAGCCCA
AGCGGGCCTGTCCGTCAGTTGCGCAGCCATCGACGTCAGACGCGGAAGCTCCGGTGGACTACG
CGGACAGGTACCAAAACAAATGTTCTCGTCACGTGGGCATGAATCTGATGCTTTTTCCCTGCC
GGCAATGCGAGAGAATGAATCAGAATGTGGACATTTGCTTCACGCACGGGGTCATGGACTGTG
CCGAGTGCTTCCCCGTGTCAGAATCTCAACCCGTGTCTGTCGTCAGAAAGCGGACATATCAGA
AACTGTGTCCGATTCATCACATCATGGGGAGGGCGCCCGAGGTGGCTTGTTCGGCCTGCGATC
TGGCCAATGTGGACTTGGATGACTGTGACATGGAGCAATAAATGACTCAAACCAGATATGACT
GACGGTTACCTTCCAGATTGGCTAGAGGACAACCTCTCTGAAGGCGTTCGAGAGTGGTGGGCG
CTGCAACCTGGAGCCCCTAAACCCAAGGCAAATCAACAACATCAGGACAACGCTCGGGGTCTT
GTGCTTCCGGGTTACAAATACCTCGGACCCGGCAACGGACTTGACAAGGGGGAACCCGTCAAC
GCAGCGGACGCGGCAGCCCTCGAACACGACAAGGCCTACGACCAGCAGCTCAAGGCCGGTGAC
AACCCCTACCTCAAGTACAACCACGCCGACGCCGAGTTTCAGGAGCGTCTTCAAGAAGATACG
TCTTTTGGGGGCAACCTCGGACGAGCAGTCTTCCAGGCCAAAAAGAGGATCCTTGAGCCTCTG
GGTCTGGTTGAGGAAGCGGCTAAGACGGCTCCTGGAAAAAAGAGACCTGTAGAGCAATCTCCA
GCAGAACCGGACTCCTCTTCGGGCATCGGCAAATCAGGCCAGCAGCCCGCTAGAAAAAGACTG
AATTTTGGTCAGACTGGCGACACAGAGTCAGTCCCAGACCCTCAACCACTCGGACAACCTCCC
GCAGCCCCCTCTGGTGTGGGATCTACTACAATGGCTTCAGGCGGTGGCGCACCAATGGCAGAC
AATAACGAGGGTGCCGATGGAGTGGGTAATTCCTCAGGAAATTGGCATTGCGATTCCCAATGG
CTGGGCGACAGAGTCATCACCACCAGCACCCGCACCTGGGCCCTGCCCACCTACAACAATCAC
CTCTACAAGCAAATCTCCAGCCAATCAGGAGCCACCAACGACAACCACTACTTTGGCTACAGC
ACCCCCTGGGGGTATTTTGACTTCAACAGATTCCACTGCCACTTTTCACCACGTGACTGGCAA
AGACTCATCAACAACAACTGGGGATTCCGACCCAAGAGACTCAACTTCAAGCTCTTTAACATT
CAAGTCAAAGAGGTCACGCAGAATGACGGTACGACGACGATTGCCAATAACCTTACCAGCACG
GTTCAGGTGTTTACTGACTCCGAGTACCAGCTCCCGTACGTCCTCGGCTCGGCGCATCAGGGA
TGCCTCCCGCCGTTCCCAGCAGACGTCTTCATGGTCCCACAGTATGGATACCTCACCCTGAAC
AACGGGAGTCAGGCGGTAGGACGCTCTTCCTTTTACTGCCTGGAGTACTTTCCTTCTCAGATG
CTGCGTACTGGAAACAACTTTCAGTTTAGCTACACTTTTGAAGACGTGCCTTTCCACAGCAGC
TACGCTCACAGCCAAAGTCTGGACCGTCTCATGAATCCTCTGATCGACCAGTACCTGTACTAT
CTGAACAGGACACAAACAGCCAGTGGAACTCAGCAGTCTCGGCTACTGTTTAGCCAAGCTGGA
CCCACCAGTATGTCTCTTCAAGCTAAAAACTGGCTGCCTGGACCTTGCTACAGACAGCAGCGT
CTGTCAAAGCAGGCAAACGACAACAACAACAGCAACTTTCCCTGGACTGGTGCCACCAAATAT
CATCTGAATGGCCGGGACTCATTGGTGAACCCGGGCCCTGCTATGGCCAGTCACAAGGATGAC
AAAGAAAAGTTTTTCCCCATGCATGGAACCCTGATATTTGGTAAAGAAGGAACAAATGCCAAC
AACGCGGATTTGGAAAATGTCATGATTACAGATGAAGAAGAAATCCGCACCACCAATCCCGTG
GCTACGGAGCAGTACGGGACTGTGTCAAATAATTTGCAAAACTCAAACGCTGGTCCAACTACT
GGAACTGTCAATCACCAAGGAGCGTTACCTGGTATGGTGTGGCAGGATCGAGACGTGTACCTG
CAGGGACCCATTTGGGCCAAGATTCCTCACACCGATGGACACTTTCATCCTTCTCCACTGATG
GGAGGTTTTGGGCTCAAACACCCGCCTCCTCAGATCATGATCAAAAACACTCCCGTTCCAGCC
AATCCTCCCACAAACTTTAGTGCGGCAAAGTTTGCTTCCTTCATCACACAGTACTCCACGGGG
CAGGTCAGCGTGGAGATCGAGTGGGAGCTGCAGAAGGAGAACAGCAAACGCTGGAATCCCGAA
ATTCAGTACACTTCCAACTACAACAAATCTGTTAATGTGGACTTTACTGTGGACACTAATGGT
GTGTATTCAGAGCCTCGCCCCATTGGCACCAGATACCTGACTCGTAATCTGTAATTGCTTGTT
AATCAATAAACCGGTTAATTCG

FIG. 19

B19 PARVOVIRUS, COMPLETE SEQUENCE, GENBANK ACCESSION NO. NC_000883 AND SHADE ET AL. (1986) *J. VIROL.* 58:921

CCAAATCAGATGCCGCCGGTCGCCGCCGGTAGGCGGGACTTCCGGTACAAGATGGCGGACAATTACGTCATTT
CCTGTGACGTCATTTCCTGTGACGTCACTTCCGGTGGGCGGGACTTCCGGAATTAGGGTTGGCTCTGGGCCAG
CTTGCTTGGGGTTGCCTTGACACTAAGACAAGCGGCGCGCCGCTTGTCTTAGTGGCACGTCAACCCCAAGCGC
TGGCCCAGAGCCAACCCTAATTCCGGAAGTCCCGCCCACCGGAAGTGACGTCACAGGAAATGACGTCACAGGA
AATGACGTAATTGTCCGCCATCTTGTACCGGAAGTCCCGCCTACCGGCGGCGACCGGCGGCATCTGATTTGGT
GTCTTCTTTTAAATTTTAGCGGGCTTTTTTCCCGCCTTATGCAAATGGGCAGCCATTTTAAGTGTTTCACTAT
AATTTTATTGGTCAGTTTTGTAACGGTTAAAATGGGCGGAGCGTAGGCGGGGACTACAGTATATATAGCACGG
CACTGCCGCAGCTCTTTCTTTCTGGGCTGCTTTTTCCTGGACTTTCTTGCTGTTTTTTGTGAGCTAACTAACA
GGTATTTATACTACTTGTTAACATACTAACATGGAGCTATTTAGAGGGGTGCTTCAAGTTTCTTCTAATGTTC
TGGACTGTGCTAACGATAACTGGTGGTGCTCTTTACTGGATTTAGACACTTCTGACTGGGAACCACTAACTCA
TACTAACAGACTAATGGCAATATACTTAAGCAGTGTGGCTTCTAAGCTTGACTTTACCGGGGGCCACTAGCG
GGGTGCTTGTACTTTTTTCAAGTAGAATGTAACAAATTTGAAGAAGGCTATCATATTCATGTGGTTATTGGGG
GGCCAGGGTTAAACCCCAGAAACCTCACAGTGTGTGTAGAGGGGTTATTTAATAATGTACTTTATCACCTTGT
AACTGAAAATGTAAAGCTAAAATTTTTGCCAGGAATGACTACAAAAGGCAAATACTTTAGAGATGGAGAGCAG
TTTATAGAAAACTATTTAATGAAAAAAATACCTTTAAATGTTGTATGGTGTGTTACTAATATTGATGGATATA
TAGATACCTGTATTTCTGCTACTTTTAGAAGGGGAGCTTGCCATGCCAAGAAACCCCGCATTACCACAGCCAT
AAATGACACTAGTAGTGATGCTGGGGAGTCTAGCGGCACAGGGGCAGAGGTTGTGCCAATTAATGGGAAGGGA
ACTAAGGCTAGCATAAAGTTTCAAACTATGGTAAACTGGTTGTGTGAAAACAGAGTGTTTACAGAGGATAAGT
GGAAACTAGTTGACTTTAACCAGTACACTTTACTAAGCAGTAGTCACAGTGGAAGTTTTCAAATTCAAAGTGC
ACTAAAACTAGCAATTTATAAAGCAACTAATTTAGTGCCTACAAGCACATTTCTATTGCATACAGACTTTGAG
CAGGTTATGTGTATTAAAGACAATAAAATTGTTAAATTGTTACTTTGTCAAAACTATGACCCCCTATTAGTGG
GGCAGCATGTGTTAAAGTGGATTGATAAAAAATGTGGCAAGAAAAATACACTGTGGTTTTATGGCCGCCAAG
TACAGGAAAAACAAACTTGGCAATGGCCATTGCTAAAAGTGTTCCAGTATATGGCATGGTTAACTGGAATAAT
GAAAACTTTCCATTTAATGATGTAGCAGGGAAAAGCTTGGTGGTCTGGGATGAAGGTATTATTAAGTCTACAA
TTGTAGAAGCTGCAAAAGCCATTTTAGGCGGGCAACCCACCAGGGTAGATCAAAAAATGCGTGGAAGTGTAGC
TGTGCCTGGAGTACCTGTGGTTATAACCAGCAATGGTGACATTACTTTTGTTGTAAGCGGGAACACTACAACA
ACTGTACATGCTAAAGCCTTAAAAGAGCGAATGGTAAAGTTAAACTTTACTGTAAGATGCAGCCCTGACATGG
GGTTACTAACAGAGGCTGATGTACAACAGTGGCTTACATGGTGTAATGCACAAAGCTGGGACCACTATGAAAA
CTGGGCAATAAACTACACTTTTGATTTCCCTGGAATTAATGCAGATGCCCTCCACCCAGACCTCCAAACCACC
CCAATTGTCACAGACACCAGTATCAGCAGCAGTGGTGGTGAAAGCTCTGAAGAACTCAGTGAAAGCAGCTTTT
TTAACCTCATCACCCCAGGCGCCTGGAACACTGAAACCCCGCGCTCTAGTACGCCCATCCCCGGGACCAGTTC
AGGAGAATCATTTGTCGGAAGCTCAGTTTCCTCCGAAGTTGTAGCTGCATCGTGGGAAGAAGCCTTCTACACA
CCTTTGGCAGACCAGTTTCGTGAACTGTTAGTTGGGGTTGATTATGTGTGGGACGGTGTAAGGGGTTTACCTG
TGTGTTGTGTGCAACATATTAACAATAGTGGGGGAGGCTTGGGACTTTGTCCCCATTGCATTAATGTAGGGGC
TTGGTATAATGGATGGAAATTTCGAGAATTTACCCCAGATTTGGTGCGGTGTAGCTGCCATGTGGGAGCTTCT
AATCCCTTTTCTGTGCTAACCTGCAAAAAATGTGCTTACCTGTCTGGATTGCAAAGCTTTGTAGATTATGAGT
AAAGAAAGTGGCAAATGGTGGGAAAGTGATGATAAATTTGCTAAAGCTGTGTATCAGCAATTTGTGGAATTTT
ATGAAAAGGTTACTGGAACAGACTTAGAGCTTATTCAAATATTAAAAGATCACTATAATATTTCTTTAGATAA
TCCCCTAGAAAACCCATCCTCTCTGTTTGACTTAGTTGCTCGTATTAAAAATAACCTTAAAAACTCTCCAGAC
TTATATAGTCATCATTTTCAAAGTCATGGACAGTTATCTGACCACCCCCATGCCTTATCATCCAGTAGCAGTC
ATGCAGAACCTAGAGGAGAAAATGCAGTATTATCTAGTGAAGACTTACACAAGCCTGGGCAAGTTAGCGTACA
ACTACCCGGTACTAACTATGTTGGGCCTGGCAATGAGCTACAAGCTGGGCCCCCGCAAAGTGCTGTTGACAGT
GCTGCAAGGATTCATGACTTTAGGTATAGCCAACTGGCTAAGTTGGGAATAAATCCATATACTCATTGGACTG
TAGCAGATGAAGAGCTTTTAAAAAATATAAAAAATGAAACTGGGTTTCAAGCACAAGTAGTAAAAGACTACTT
TACTTTAAAAGGTGCAGCTGCCCCTGTGGCCCATTTTCAAGGAAGTTTGCCGGAAGTTCCCGCTTACAACGCC
TCAGAAAAATACCCAAGCATGACTTCAGTTAATTCTGCAGAAGCCAGCACTGGTGCAGGAGGGGGTGGCAGTA
ATCCTGTCAAAAGCATGTGGAGTGAGGGGGCCACTTTTAGTGCCAACTCTGTAACTTGTACATTTTCCAGACA
GTTTTTAATTCCTTATGACCCAGAGCACCATTATAAGGTGTTTTCTCCCGCAGCAAGCAGCTGCCACAATGCC
AGTGGAAAGGAGGCAAAGGTTTGCACAATTAGTCCCATAATGGGATACTCAACCCCATGGAGATATTTAGATT
TTAATGCTTTAAATTTATTTTTTTCACCTTTAGAGTTTCAGCACTTAATTGAAAATTATGGAAGTATAGCTCC
TGATGCTTTAACTGTAACCATATCAGAAATTGCTGTTAAGGATGTTACAGACAAAACTGGAGGGGGGGTACAG
GTTACTGACAGCACTACAGGGCGCCTATCCATGTTAGTAGACCATGAATACAAGTACCCATATGTGTTAGGAC
AAGGTCAGGATACTTTAGCCCCAGAACTTCCTATTTGGGTATACTTTCCCCCTCAATATGCTTACTTAACAGT
AGGAGATGTTAACACACAAGGAATCTCTGGAGACAGCAAAAAATTAGCAAGTGAAGAATCAGCATTTTATGTT
TTGGAACACAGTTCTTTTCAGCTTTTAGGTACAGGAGGTACAGCAACTATGTCTTATAAGTTTCCTCCAGTGC
CCCCAGAAAATTTAGAGGGCTGCAGTCAACACTTTTATGAAATGTACAATCCCTTATACGGATCCCGCTTAGG
GGTTCCTGACACATTAGGAGGTGACCCAAAATTTAGATCTTTAACACATGAAGACCATGCAATTCAGCCCCAA
AACTTCATGCCAGGGCCACTAGTAAACTCAGTGTCTACAAAGGAGGGAGACAGCTCTAATACTGGAGCTGGAA
AAGCCTTAACAGGCCTTAGCACAGGCACCTCTCAAAACACTAGAATATCCTTACGCCCTGGGCCAGTGTCACA
GCCATACCACCACTGGGACACAGATAAATATGTTCCAGGAATAAATGCCATTTCTCATGGTCAGACCACTTAT
GGTAACGCTGAAGACAAAGAGTATCAGCAAGGAGTGGGTAGATTTCCAAATGAAAAAGAACAGCTAAAACAGT
TACAGGGTTTAAACATGCACACCTATTTCCCCAATAAAGGAACCCAGCAATATACAGATCAAATTGAGCGCCC
CCTAATGGTGGGTTCTGTATGGAACAGAAGAGCCCTTCACTATGAAAGCCAGCTGTGGAGTAAAATTCCAAAT
TTAGATGACAGTTTTAAAACTCAGTTTGCAGCCTTAGGAGGATGGGGTTTGCATCAGCCACCTCCTCAAATAT
TTTTAAAAATATTACCACAAAGTGGGCCAATTGGAGGTATTAAATCAATGGGAATTACTACCTTAGTTCAGTA
TGCCGTGGGAATTATGACAGTAACTATGACATTTAAATTGGGGCCCCGTAAAGCTACGGGACGGTGGAATCCT
CAACCTGGAGTATATCCCCCGCACGCAGCAGGTCATTTACCATATGTACTATGACCCCACAGCTACAGATG
CAAAACAACACCACAGGCATGGATACGAAAAGCCTGAAGAATTGTGGACAGCCAAAAGCCGTGTGCACCCATT
GTAAACACTCCCCACCGTGCCCTCAGCCAGGATGCGTAACTAAACGCCCACCAGTACCACCCAGACTGTACCT
GCCCCCTCCTGTACCTATAAGACAGCCTAACACAAAAGATATAGACAATGTAGAATTTAAGTACTTAACCAGA
TATGAACAACATGTTATTAGAATGTTAAGATTGTGTAATATGTATCAAAATTTAGAAAAATAAACATTTGTTG
TGGTTAAAAAATTATGTTGTTGCGCTTTAAAAATTTAAAAGAAGACACCAAATCAGATGCCGCCGGTCGCCGC
CGGTAGGCGGGACTTCCGGTACAAGATGGCGGACAATTACGTCATTTCCTGTGACGTCATTTCCTGTGACGTC
ACTTCCGGTGGGCGGGACTTCCGGAATTAGGGTTGGCTCTGGGCCAGCGCTTGGGGTTGACGTGCCACTAAGA
CAAGCGGCGCGCCGCTTGTCTTAGTGTCAAGGCAACCCCAAGCAAGCTGGCCCAGAGCCAACCCTAATTCCGG
AAGTCCCGCCCACCGGAAGTGACGTCACAGGAAATGACGTCACAGGAAATGACGTAATTGTCCGCCATCTTGT
ACCGGAAGTCCCGCCTACCGGCGGCGACCGGCGGCATCTGATTTGG

*FIG. 20*

MINUTE VIRUS FROM MOUSE (MVM), COMPLETE SEQUENCE, GENBANK ACCESSION NO. NC 001510

ATTTTTAGAACTGACCAACCATGTTCACGTAAGTGACGTGATGACGCGCGCTGCGCGCGCGCCTTC
GGACGTCACACGTCACTTACGTTTCACATGGTTGGTCAGTTCTAAAAATGATAAGCGGTTCAGGGA
GTTTAAACCAAGGCGCGAAAAGGAAGTGGGCGTGGTTTAAAGTATATAAGCAACTACTGAAGTCAG
TTACTTATCTTTTCTTTCATTCTGTGAGTCGAGACGCACAGAAAGAGAGTAACCAACTAACCATGG
CTGGAAATGCTTACTCTGATGAAGTTTTGGGAGCAACCAACTGGTTAAAGGAAAAAAGTAACCAGG
AAGTGTTCTCATTTGTTTTTAAAAATGAAAATGTTCAACTGAATGGAAAAGATATCGGATGGAATA
GTTACAAAAAAGAGCTGCAGGAGGACGAGCTGAAATCTTTACAACGAGGAGCGGAAACTACTTGGG
ACCAAAGCGAGGACATGGAATGGGAAACCACAGTGGATGAAATGACCAAAAAGCAAGTATTCATTT
TTGATTCTTTGGTTAAAAAATGTTTATTTGAAGTGCTTAACACAAAGAATATATTTCCTGGTGATG
TTAATTGGTTTGTGCAACATGAATGGGGAAAAGACCAAGGCTGGCACTGCCATGTACTAATTGGAG
GAAAGGACTTTAGTCAAGCTCAAGGGAAATGGTGGAGAAGGCAACTAAATGTTTACTGGAGCAGAT
GGTTGGTAACAGCCTGTAATGTGCAACTAACACCAGCTGAAAGAATTAAACTAAGAGAAATAGCAG
AAGACAATGAGTGGGTTACTCTACTTACTTATAAGCATAAGCAAACCAAAAAAGACTATACCAAGT
GTGTTCTTTTTGGAAACATGATTGCTTACTATTTTTTAACTAAAAAGAAAATAAGCACTAGTCCAC
CAAGAGACGGAGGCTATTTTCTTAGCAGTGACTCTGGCTGGAAAACTAACTTTTTAAAAGAAGGCG
AGCGCCATCTAGTGAGCAAACTATACACTGATGACATGCGGCCAGAAACGGTTGAAACCACAGTAA
CCACTGCGCAGGAAACTAAGCGCGGCAGAATTCAAACTAAAAAAGAAGTTTCTATTAAAACTACAC
TTAAAGAGCTGGTGCATAAAAGAGTAACCTCACCAGAGGACTGGATGATGATGCAGCCAGACAGTT
ACATTGAAATGATGGCTCAACCAGGTGGAGAAAACCTGCTGAAAAATACGCTAGAGATTTGTACAC
TAACTCTAGCCAGAACCAAAACAGCATTTGACTTAATTTTAGAAAAAGCTGAAACCAGCAAACTAA
CCAACTTTTCACTGCCTGACACAAGAACCTGCAGAATTTTTGCTTTTCATGGCTGGAACTATGTTA
AAGTTTGCCATGCTATTTGCTGTGTTTTAAACAGACAAGGAGGCAAAAGAAATACTGTTTTATTTC
ATGGACCAGCCAGCACAGGCAAATCTATTATTGCACAAGCCATAGCACAAGCAGTTGGCAATGTTG
GTTGCTATAATGCAGCCAATGTAAACTTTCCATTTAATGACTGTACCAACAAGAACTTGATTTGGG
TAGAAGAAGCTGGTAACTTTGGACAGCAAGTAAACCAGTTTAAAGCCATTTGCTCTGGTCAAACTA
TTCGCATTGATCAAAAAGGAAAAGGCAGCAAACAGATTGAACCAACACCAGTCATCATGACCACAA
ATGAGAACATTACAGTGGTCAGAATAGGCTGCGAAGAAAGACCAGAACACACTCAACCAATCAGAG
ACAGAATGCTTAACATTCATCTAACACATACCTTGCCTGGTGACTTTGGTTTGGTTGACAAAAATG
AATGGCCCATGATTTGTGCTTGGTTGGTAAAGAATGGTTACCAATCTACCATGGCAAGCTACTGTG
CTAAATGGGGCAAAGTTCCTGATTGGTCAGAAAACTGGGCGGAGCCAAAGGTGCCAACTCCTATAA
ATTTACTAGGTTCGGCACGCTCACCATTCACGACACCGAAAAGTACGCCTCTCAGCCAGAACTATG
CACTAACTCCACTTGCATCGGATCTCGAGGACCTGGCTTTAGAGCCTTGGAGCACACCAAATACTC
CTGTTGCGGGCACTGCAGAAACCCAGAACACTGGGGAAGCTGGTTCCAAAGCCTGCCAAGATGGTC
AACTGAGCCCAACTTGGTCAGAGATCGAGGAGGATTTGAGAGCGTGCTTCGGTGCGGAACCGTTGA
AGAAAGACTTCAGCGAGCCGCTGAACTTGGACTAAGGTACGATGGCGCCTCCAGCTAAAAGAGCTA
AAAGAGGTAAGGGTTTAAGGGATGGTTGGTTGGTGGGGTATTAATGTTTAATTACCTGTTTTACAG
GCCTGAAATCACTTGGTTTTAGGTTGGGTGCCTCCTGGCTACAAGTACCTGGGACCAGGGAACAGC
CTTGACCAAGGAGAACCAACCAATCCATCTGACGCCGCTGCCAAAGAGCACGACGAGGCCTATGAT
CAATACATCAAATCTGGAAAAAATCCTTACCTGTACTTCTCTGCTGCTGATCAACGCTTTATTGAC
CAAACCAAGGACGCCAAAGACTGGGGAGGCAAGGTTGGTCACTACTTTTTTAGAACCAAGCGCGCT
TTTGCACCTAAGCTTGCTACTGACTCTGAACCTGGAACTTCTGGTGTAAGCAGAGCTGGTAAACGC
ACTAGACCACCTGCTTACATTTTTATTAACCAAGCCAGAGCTAAAAAAAAACTTACTTCTTCTGCT
GCACAGCAAAGCAGTCAAACCATGAGTGATGGCACCAGCCAACCTGACAGCGGAAACGCTGTCCAC
TCAGCTGCAAGAGTTGAACGAGCAGCTGACGGCCCTGGAGGCTCTGGGGGTGGGGGCTCTGGCGGG
GGTGGGGTTGGTGTTTCTACTGGGTCTTATGATAATCAAACGCATTATAGATTCTTGGGTGACGGC
TGGGTAGAAATTACTGCACTAGCAACTAGACTAGTACATTTAAACATGCCTAAATCAGAAAACTAT
TGCAGAATCAGAGTTCACAATACAACAGACACATCAGTCAAAGGCAACATGGCAAAAGATGATGCT
CATGAGCAAATTTGGACACCATGGAGCTTGGTGGATGCTAATGCTTGGGGAGTTTGGCTCCAGCCA
AGTGACTGGCAATACATTTGCAACACCATGAGCCAGCTTAACTTGGTATCACTTGATCAAGAAATA
TTCAATGTAGTGCTGAAAACTGTTACAGAGCAAGACTTAGGAGGTCAAGCTATAAAAATATACAAC
AATGACCTTACAGCTTGCATGATGGTTGCAGTAGACTCAAACAACATTTTGCCATACACACCTGCA
GCAAACTCAATGGAAACACTTGGTTTCTACCCCTGGAAACCAACCATAGCATCACCATACAGGTAC
TATTTTTGCGTTGACAGAGATCTTTCAGTGACCTACGAAAATCAAGAAGGCACAGTTGAACATAAT
GTGATGGGAACACCAAAAGGAATGAATTCTCAATTTTTTACCATTGAGAACACACAACAAATCACA
TTGCTCAGAACAGGGGACGAATTTGCCACAGGTACTTACTACTTTGACACAAATTCAGTTAAACTC
ACACACACGTGGCAAACCAACCGTCAACTTGGACAGCCTCCACTGCTGTCAACCTTTCCTGAAGCT
GACACTGATGCAGGTACACTTACTGCTCAAGGGAGCAGACATGGAACAACACAAATGGGGGTTAAC
TGGGTGAGTGAAGCAATCAGAACCAGACCTGCTCAAGTAGGATTTTGTCAACCACACAATGACTTT
GAAGCCAGCAGAGCTGGACCATTTGCTGCCCCAAAAGTTCCAGCAGATATTACTCAAGGAGTAGAC
AAAGAAGCCAATGGCAGTGTTAGATACAGTTATGGCAAACAGCATGGTGAAAATTGGGCTTCACAT
GGACCAGCACCAGAGCGCTACACATGGGATGAAACAAGCTTTGGTTCAGGTAGAGACACCAAAGAT
GGTTTTATTCAATCAGCACCACTAGTTGTTCCACCACCACTAAATGGCATTCTTACAAATGCAAAC
CCTATTGGGACTAAAAATGACATTCATTTTTCAAATGTTTTTAACAGCTATGGTCCACTAACTGCA
TTTTCACACCCAAGTCCTGTATACCCTCAAGGACAAATATGGGACAAAGAACTAGATCTTGAACAC
AAACCTAGACTTCACATAACTGCTCCATTTGTTTGTAAAAACAATGCACCTGGACAAATGTTGGTT
AGATTAGGACCAAACCTAACTGACCAATATGATCCAAACGGAGCCACACTTTCTAGAATTGTTACA
TACGGTACATTTTTCTGGAAAGGAAAACTAACCATGAGAGCAAAACTTAGAGCTAACACCACTTGG
AACCCAGTGTACCAAGTAAGTGCTGAAGACAATGGCAACTCATACATGAGTGTAACTAAATGGTTA
CCAACTGCTACTGGAAACATGCAGTCTGTGCCGCTTATAACAAGACCTGTTGCTAGAAATACTTAC
TAACTAACCATGCTTTTTCTTTCTGTACTTCATATATTATTAAGACTAATAAAGATACAACATAGA
AATATAATATTACGTATAGATTTAAGAAATAGAATAATATGGTACTTAGTAACTGTTAAAAATAAT
AGAACCTTTGGAATAACAAGATAGTTAGTTGGTTAATGTTAGATAGAATAAGAAGATCATGTATAA
TGAATAAAAGGGTGGAAGGGTGGTTGGTAGGTTAATGTTAGATAGAATAAGAAGATCATGTATAAT
GAATAAAAGGGTGGAAGGGTGGTTGGTAGGTATTCCCTTAGACTTGATGTTAAGGACCAAAAAAAT
AATAAAACTTTTTTAAAACTCAACCAAGACTACTGTCTATTCAGTGAACCAACTGAACCATTAGTA
TTACTATGTTTTTAGGGTGGGAGGGTGGGAGATACATGTGTTCGCTATGAGCGAACTGGTACTGGT
TGGTTGCTCTGCTCAACCAACCAGACCGGCAAAGCCGGTCTGGTTGGTTGAGCGCAACCAACCAGT
ACCAGTTCGCTCATAGCGAACACATGTATCTCCCACCCTCCCACCCTAAAAACATAGTAATACTAA
T

FIG. 21

GOOSE PARVOVIRUS, COMPLETE SEQUENCE, GENBANK ACCESSION NO. NC_001701
CTCATTGGAGGGTTCGTTCGTTCGAACCAGCCAATCAGGGGAGGGGGAAGTGACGCAAGTTCCGG
TCACATGCTTCCGGTGACGCACATCCGGTGACGTAGTTCCGGTCACGTGCTTCCTGTCACGTGTT
TCCGGTCACGTGACTTCCGGTCATGTGACTTCCGGTGACGTGTTTCCGGCTGTTAGGTTGACCAC
GCGCATGCCGCGCGGTCAGCCCAATAGTTAAGCCGGAAACACGTCACCGGAAGTCACATGACCGG
AAGTCACGTGACCGGAAACACGTGACAGGAAGCACGTGACCGGAACTACGTCACCGGATGTGCGT
CACCGGAAGCATGTGACCGGAACTTGCGTCACTTCCCCCTCCCCTGATTGGCTGGTTCGAACGAA
CGAACCCTCCAATGAGACTCAAGGACAAGAGGATATTTTGCGCGCCAGGAAGTGACGTGCAATGC
CACCCTATATAAGCCAGGAAACTTCCGGTTTAGTTCATTCGTTACTCTGCTCTCAGAGAGAACGG
ACCTCAGGTCGGAGAGATGGCACTTTCTAGGCCTCTTCAGATTTCTTCTGATAAATTCTATGAAG
TTATTATTAGATTATCATCGGATATTGATCAAGATGTCCCCGGTCTGTCTCTTAACTTTGTAGAA
TGGCTTTCTACCGGAGTTTGGGAGCCCACGGGCATCTGGAACATGGAGCATGTGAATCTACCGAT
GGTGACCTTGGCAGAGAAGATCAAGAACATTTTCATACAAAGATGGAATCAGTTCAACCAGGACG
AAACGGACTTCTTCTTTCAACTGGAAGAAGGCAGTGAGTACATTCATCTTCATTGCTGTATTGCC
CAGGGCAATGTACGGTCTTTTGTTCTCGGGAGATATATGTCTCAGATAAAAGACTCTATCATAAG
AGATGTATATGAAGGGAAACAAATCAAGATCCCCGATTGGTTTGCTATTACTAAAACCAAGAGGG
GAGGACAGAATAAGACCGTGACTGCAGCATACATACTGCATTACCTTATTCCTAAAAAGCAACCT
GAACTGCAATGGGCCTTTACCAATATGCCTTTATTCACTGCTGCTGCTCTTTGTCTGCAAAAGCG
GCAAGAATTGCTGGATGCATTTCAAGAAAGTGATTTGGCTGCCCCTTTACCTGATCCTCAAGCAT
CAACTGTGGCACCGCTTATTTCCAACAGAGCGGCAAAGAACTATAGCAACCTTGTTGATTGGCTC
ATTGAAATGGGGATAACATCTGAGAAGCAATGGCTCACTGAGAACCGAGAGAGCTACAGAAGCTT
TCAAGCAACTTCTTCAAATAATAGACAAGTGAAAGCTGCACTGGAAAATGCCCGTGCTGAAATGT
TATTGACAAAGACTGCAACTGATTACCTGATAGGAAAAGACCCTGTCCTGGATATAACTAAGAAT
AGGGTCTATCAAATTCTGAAAATGAATAACTACAACCCTCAATACATAGGAAGTATCCTGTGCGG
CTGGGTGAAGAGAGAGTTCAACAAAAGAAACGCCATATGGCTCTACGGACCTGCCACCACCGGGA
AGACCAACATTGCAGAAGCTATTGCCCATGCTGTACCCTTCTATGGCTGTGTTAACTGGACTAAT
GAGAACTTTCCTTTTAATGATTGTGTTGATAAAATGCTGATTTGGTGGGAGGAGGGAAAAATGAC
TAATAAGGTTGTTGAATCTGCAAAAGCAATTTTGGGAGGGTCTGCTGTCCGGGTAGACCAGAAAT
GTAAAGGATCTGTTTGTATTGAACCTACTCCTGTAATTATTACTAGTAATACTGATATGTGTATG
ATTGTTGATGGCAACTCTACTACAATGGAACATAGAATACCATTAGAGGAGCGTATGTTTCAAAT
TGTCCTATCACATAAATTGGAGCCTTCTTTTGGAAAAATTTCTAAAAAAGAAGTCAGAGAATTTT
TCAAATGGGCCAATGACAATCTAGTTCCTGTTGTGTCTGAGTTCAAAGTCCGAACTAATGAACAA
ACCAACTTGCCAGAGCCCGTTCCTGAACGAGCGAACGAGCCGGAGGAGCCTCCTAAGATCTGGGC
TCCTCCTACTAGGGAGGAGTTAGAAGAGCTTTTAAGAGCCAGCCCAGAATTGTTCTCATCAGTCG
CTCCAATTCCTGTGACTCCTCAGAACTCCCCTGAGCCTAAGAGAAGCAGGAACAATTACCAGGTA
CGCTGCGCTTTGCATACTTATGACAATTCTATGGATGTATTTGAATGTATGGAATGTGAGAAAGC
AAACTTTCCTGAATTTCAACCTCTGGGAGAAAATTATTGTGATGAACATGGGTGGTATGATTGTG
CTATATGTAAAGAGTTGAAAAATGAACTTGCAGAAATTGAGCATGTGTTTGAGCTTGATGATGCT
GAAAATGAACAATAAAGATGACTCAAAGCAGATATGTCTACTTTTTTAGATTCTTTTGAAGAGTG
GTATGAGACTGCAGCCGCCTCGTGGCGGAATCTGAAAGCTGGAGCCCCTCAGCCAAAACCAAACC
AGCAGTCTCAGTCTGTGTCTCCAGACAGAGAACCCGAACGAAAAGATAATAATCGGGGCTTTGTA
CTTCCTGGCTATAAGTATCTTGGGCCTGGTAACGGCCTGGATAAAGGCCCACCTGTCAATAAGGC
GGACAGCGTCGCGCTTGAACACGACAAGGCCTATGACCAGCAGCTTAAAGCGGGAGACAACCCAT
ATATAAAATTCAATCACGCTGACCAGGACTTTATAGATAGCCTCCAAGACGACCAGTCATTCGGA
GGTAATCTTGGAAAGGCTGTATTTCAGGCCAAAAAACGTATCTTAGAGCCATTTGGCCTAGTAGA
AGATCCTGTCAACACGGCACCTGCAAAAAAAAATACAGGGAAGCTTACTGACCATTACCCGGTAG
TTAAGAAGCCTAAACTTACCGAGGAAGTCAGTGCGGGAGGTGGTAGCAGTGCCGTACAAGACGGA
GGAGCCACCGCGGAGGGCACCGAACCTGTGGCAGCATCTGAAATGGCAGAGGGAGGAGGCGGAGC
TATGGGCGACTCTTCAGGGGGTGCCGATGGAGTGGGTAATGCCTCGGGAAATTGGCATTGCGATT
CCCAATGGATGGGAAACACAGTCATCACAAAGACCACCAGAACCTGGGTCCTGCCAAGCTACAAC
AACCACATCTACAAAGCAATTACCAGCGGAACCTCTCAAGATGCAAATGTCCAGTATGCAGGATA
CAGTACCCCCTGGGGGTACTTTGATTTCAACCGCTTCCACTGCCACTTCTCCCCTAGAGACTGGC
AGAGACTTATCAACAACCATTGGGGAATCAGACCCAAGTCTCTTAAATTCAAGATCTTCAATGTC
CAAGTCAAAGAAGTCACAACGCAGGATCAGACAAAGACCATTGCAAACAATCTCACCTCAACAAT
TCAAGTCTTTACGGATGATGAGCATCAACTCCCGTATGTCCTGGGCTCGGCTACGGAAGGCACCA
TGCCGCCGTTCCCGTCGGATGTCTATGCCCTGCCGCAGTACGGGTACTGCACAATGCACACCAAC
CAGAATGGAGCACGGTTCAATGACCGTAGTGCATTCTACTGCTTAGAGTACTTCCCTAGTCAGAT
GCTAAGAACAGGCAACAACTTTGAGTTCACATTTGACTTTGAAGAAGTTCCTTTCCATAGCATGT
TCGCTCATTCACAGGACTTAGACAGGCTGATGAACCCCCTAGTGGATCAATACCTCTGGAATTTC
AATGAGGTAGACAGCAGCAGAAATGCTCAATTTAAAAAGGCTGTGAAAGGGGCTTATGGCACCAT
GGGCCGCAATTGGCTGCCAGGACCTAAATTCCTGGATCAAAGAGTTAGGGCCTACACAGGAGGAA
CAGACAACTATGCAAACTGGAACATCTGGAGTAATGGAACAAGGTGAATTTGAAAGACAGACAG
TATCTCCTACAACCCGGACCTGTGTCAGCTACTTACACAGAAGGGGAGGCTTCCAGCCTTCCAGC
TCAAAATATTTTAGGGATAGCTAAAGATCCATACAGATCAGGCAGCACTACAGCAGGAATAAGTG
ACATTATGGTCACGGAAGAACAAGAAGTAGCACCTACAAATGGAGTAGGGTGGAAACCATATGGT
AGGACTGTAACGAATGAACAAAACACTACTACAGCTCCTACAAGTTCAGATCTGGATGTTCTTGG
AGCTTTACCAGGAATGGTTTGGCAGAACAGGGATATATATCTGCAGGGACCTATTGGGGCAAAAA
TACCGAAGACTGATGGTAAATTCCATCCTTCTCCGAATCTCGGAGGATTTGGCCTGCACAATCCA
CCACCGCAGGTGTTCATCAAGAATACACCAGTGCCTGCAGACCCTCCAGTAGAATACGTGCACCA
GAAGTGGAATTCCTACATAACCCAGTACTCTACGGGCCAGTGTACAGTAGAGATGGTGTGGGAGC
TGAGAAAAGAGAATTCAAAGAGATGGAACCCAGAAATCCAGTTCACCAGTAATTTCAGTAACAGA
ACAAGCATAATGTTTGCACCTAATGAAACTGGTGGATATGTAGAAGATAGATTGATTGGAACCAG
ATATCTAACTCAAAATCTGTAAATTCTGTGTAAAAATTCAAATAAAGCACTTCCTGGCGCGCAAA
ATATCCTCTTGTCCTTGAGTCTCATTGGAGGGTTCGTTCGTTCGAACCAGCCAATCAGGGGAGGG
GGAAGTGACGCAAGTTCCGGTCACATGCTTCCGGTGACGCACATCCGGTGACGTAGTTCCGGTCA
CGTGCTTCCTGTCACGTGTTTCCGGTCACGTGACTTCCGGTCATGTGACTTCCGGTGACGTGTTT
CCGGCTTAACTATTGGGCTGACCGCGCGCATGCGCGTGGTCAACCTAACAGCCGGAAACACGTCA
CCGGAAGTCACATGACCGGAAGTCACGTGACCGGAAACACGTGACAGGAAGCACGTGACCGGAAC
TACGTCACCGGATGTGCGTCACCGGAAGCATGTGACCGGAACTTGCGTCACTTCCCCCTCCCCTG
ATTGGCTGGTTCGAACGAACGAACCCTCCAATGAGA

FIG. 22

SNAKE PARVOVIRUS 1, COMPLETE GENOME, GENBANK ACCESSION NO. NC_006148 AND FARKAS ET AL. (2004) J. GEN. VIROL. 85:555

CGCCCCACCCCTAGTGATCGCGCGCGCTCTCTCTTGGGGCCTGACGGCCGAAGGCCGTCAGCT
GCCGAGCTTCGCTCGGCAGGCCCCAAGAGAGAGCGCGCGCGATCACTAGGGGTGGGGCGAGTG
CCCTGCTCAACGGGTTTTTTGGTGGGCGGAGCAATGACGTCAGCGGACATGTCTGGACATGTC
TTTGAGCAAGTCCATATAAGGAGTTCCGCCGGATATGCAAATGAGCAATCGCGCAAAGCATTT
TGGGTAGTCACCATGAATAAAAAGGACAGCAAGAAAGATGACGCCCCATAATTTTAATAGGAA
TTTTAACCATGGCGTTTTACGAGGTTGTGTTTCGTTTGCCAAGAGACAATAACAACTTGTTGG
ATGAAGATAGATATCAGCCAGAGTTGAAAGAAGAAGATGACTGGCCTGAGGAATATTTAACCA
GTGAAGATGCCAGCTTTATCGGACTAGCGTATGCTGTGCTAAGTGAAATTCGGAGATTCTTTG
GAAAGGAACTACAATGGTTTGCCCAGGTTGAATGGTGTCCTACTGCTGGTTACCACATGCATG
TTTTGTTGAACCATCCTAAGCTGAGTAACCAGACTTATGGAAGAAAGGTCAATGAACTGGCTT
GCCGTATAGTCGATACCTTTGGCCTAATTAATCCAGAAGAAGTCATCAGTACCCATTATGTTA
AAAGCAACTATGGACATAAAAAGGTGAGAGTCATTCACCTAGAGTCTTATTTGAAGAACTACT
TTTTCAGAAAGACTTTAGCTCCTCCCAATTATACCGAGGAAGGAGACTATAAAAGAGAGGAAG
AAGTCGTGCTGTGGGCATTTACGAATATCGTCGCTTGGAAGCCATTCGTGCGGAATCTCATCA
AGAGATCGGAGCTAGCGACTGTTCCTAAGCAACCAGAGAATCCGGCGGGAGACGGACCGGCAC
CTCGAGTGACTGCAGGAACCCGCCATTTTATGGAAACCATCGACTGGTTGGTGAAACATGGAA
TTACTACAGAACGAGAATTCTGCCACGCCAACCGCCCCTTTGTACCTGTCTATGCTGGCTTCTA
CTTCGGGTGCTGGGCAGATTAAAAGAGCGCTGGACCAGGCGAAACACATGATGACCAGCACCA
TGTCAGCAGAGGATTACCTGACAACAGAAGAGGATGTGATCGAACCACCTACTGAAAATAGAA
TCTACAAGATTATGAAACTGAATCGCTATGATCCAGAACTAGCAGCTGCTCTCTTCTACGGCT
GGACCTGCAAGAACTTTGGCAAGAGAAACACCATCTGGCTGTATGGTCCAGCTACTACCGGCA
AAACCATCATCGCTCAAGCTATTGCACATGCTGTTAAACTGTTTGCTGGTGTTAATTGGACTA
ATGAAAACTTTCCCTTCTGTAACTGTCCAGGGAAACTGCTTATCTGGTGGGAGGAGGGCAAGA
TGACAAACAAAATGGTGGAGACGGCTAAATGTATACTGGGGGGATCTGCTGTACCTGTAGACA
TCAAAGGCAAACCCGCTGAAATGTGTCCTCAAACACCCTGTATTATTACTAGCAATACTAACA
TGTGTCAAGTATATGATGGTAATAGTTCTAGCTTTGAGCACCAAGAACCCCTAGAGGAACGCA
TGTTTATGTTCAGACTTAATACTAAACTGCCATCGACCTTTGGCAAGATCACAGAAGAGGAAG
TCAAACAGTTTATTACCTGGGGGAGGAGCTTAAAGGTTCAAGTTCCACATCAGTTCAGAGTGC
CTACCACAGGAGAGTATAAAAGGCCAGCCCCCGAGGCGAAAGCTCATTCTTCGGATGAGCCGC
CAAAAGAGAAGGTCGCGCGTATTGATGACTCTCTAACCAGGTATGTTAACAATATTGATGAGT
CAGCTACCAGTAGAGAAATGTTTCTAGAGATTGCTAATACTAATCAATGTATGTTGCATCATT
GCTTTTCTTGTACCGAATGTTATCCTGAATTGCTTGATGACATGGACAAGGAACAATAAACTT
ACTGATAACAGATATGGATTTTCTCGATGATTTCTTTGCAGATAAATATAAAGAGACTGTTAA
CGAACTCGGTAAACCGGTCAATCCTAAACCTGTAAAACACATTAGCGAAGCTCACTCGCAACC
TGGCAGCAGGAGGGGCTTTGTGGTGCCTGGGTATCGGTATCTTGGGCCTGGTAATAGCTTGGA
CCGTGGAAAGCCCGTTAACAAAGCAGACGAGGCTGCTAAAAAGCACGATCAAGAATACGATCA
ACAGCTTAAAGCGGGAGACAATCCCTACATAAAATATAATCACGCGGACGAACAGTTCCAGAA
AGACCTACAAGGTGATACCAGTCTAGCCGGCAACGCGGCTAACGCTCTATTTCAAGGCAAAAA
GACTCTACTAGCGCCCCTTGGCCTAGTAGAGACCCCTGTCGGCAAAACGTCTGAAAAGCACAA
ATTAGACGAATACTATCCTAAAGCTAAAAAGGCCAAACAAGGCTTGCAGATACCAGCTCCACC
TAAAGGCGGAGAAGAAGAAGCTACATCGTCACAATCTGGAGGGAGCCCAGCAGGTTCCGATAC
TAGCGGCACATCTGTCATGGCTACAGGAGGAGGCGGTCCGATGGCAGACGATAACCAGGGCGC
CGAGGGAGTGGGTAATTCCTCAGGTGATTGGCATTGCGATACCAAGTGGATGGGAGACCACGT
CATTACAAAGTCAACCAGAACTTGGGTGCTCCCCACTTACGGGAATCATCTCTACGGGCCTAT
CAACTTTGACGGCACCACAGGTTCGGGTGCTAATGCAGCCTATGCAGGATACAAGACTCCCTG
GGGGTACTTTGACTTCAATCGATTCCATTGCCACTTCTCCCCCCGAGACTGGCAAAGACTCAT
CAACAACCACACAGGCATCAGGCCGAAAGGACTCAAAATCAAAGTCTTTAACGTCCAAGTCAA
AGAAGTTACAACACAAGATTCAACGAAAACAATTGCCAACAATCTCACCAGCACCGTACAGAT
CTTTGCGGACGAGAACTACGACTTACCATATGTATTAGGCAGTGCTACACAAGGCACATTTCC
TCCATTTCCCAATGATGTATTTATGTTACCACAATATGCTTATTGTACACTTCAAGGAAATTC
GGGGAAATTTGTAGATAGAAGTGCCTTTTATTGTTTAGAATATTTTCCTTCACAAATGCTGAG
AACAGGAAACAATTTTGAGTTCCAGTTTAAATTTGAAGAAGTTCCCTTTCATTCTGGATGGGC
ACAGAGTCAAAGCCTAGACAGATTGATGAATCCGTTGCTTGATCAATATCTGATAGGAGACTA
TGGAACAGATGCATCAGGAAACCTTATTTATCACAGAGCTGGTCCAAATGATTTGAATGAATT
CTACAAGAATTGGGCACCTGCACCCTATGAATGTATCCAGAATATTAACAGCAGTGATAATAC
CAAGAATGCTAATTCTATAAATGGTTCAAATTCTACCAACAAATGGGGACTACAAGGAAGACA
AGCATGGGATGCTCCAGGATTTGTTCAAGCTAGTACCTATGAAGGTGCAGCAGCAGGACAATC
TCTTCTTAATGGCGTACTTACTTTCGATAAAAGTTCAGCTACTACTTCATCTCCAGCTGCTAC
TGCAGTAAACAGAACAATTGAAGACGAAATACAGGGTACCAATAATTTTGGTAATGCTAGAAA
TAACATTGTTGCTATCAATCAACAAACGAAAGGAACAAATCCAACAACAGGTAGTACATCTCA
ATTTGAGACAATGCCAGGTATGGTGTGGTCTAATAGAGACATTTACTTACAGGGGCCTATTTG
GGCTAAAATTCCAAATACAGATGGACATTTTCATCCTTCTCCCAGAATGGGTGGTTTTGGATT
AAAACATCCTCCGCCTATGATTCTGATCAAAAATACACCAGTTCCTGCTGATCCTCCAACTAC
CTTCAATCCAATGCCACAGACTAGTTTCATTACTGAATACAGTACAGGACAAGTAACTGTTGA
AATGTTGTGGGAGGTACAGAAAGAATCCTCCAAAAGATGGAATCCAGAAGTACAGTTTACTTC
CAATTTTGGAACTTCAGATCCAGCTGTTGATGGAATACCGTTTGGAATTAATAATTTGGGTAC
TTATGTTGAATCTAGACCTATTGGAACTCGTTATATTTCTAAACACTTGTAAATAATAAAAAT
TGTCAAATTTGCACTAAGAATTGTTGTCACGTGGTTGTTTACATGCTTGCTAAAACACGCCCA
CCAAAAAACCCGTTGAGCAGGGCACTCGCCCCACCCCTAGTGATCGCGCGCGCTCTCTCTTGG
GGCCTGCCGAGCGAAGCTCGGCAGCTGACGGCCTTCGGCCGTCAGGCCCCAAGAGAGAGCGCG
CGCGATCACTAGGGGTGGGGCG

FIG. 23

CHIMERIC ITRS

ITR2
1 AGGAACCCCT AGTGATGGAG TTGGCCACTC CCTCTCTGCG CGCTCGCTCG CTCACTGAGG GCGGGCGACC AAAGGTCGCC CGAGCCCGGC CCTTTGGGCC
101 GGGCCCCTCA GTGAGCGAGC GAGCGCGCAG AGAGGGAGTG GCCAACTCCA TCACTAGGGG TTCCT
ITR5
1 TACAAAACCT CCTTGCTTGA GAGTGTGGCA CTCTCCCCCC TGTCGCGTTC GCTCGCTCGC TGGCTCGTTT GGGGGGGCGA CGGCCCAAAG GGCCGTCGTC
101 TGGCAGCTCT TTGAGCTGCC ACCCCCCCAA ACGAGCCAGC GAGCGAGCGA ACGCGACAGG GGGGAGAGTG CCACACTCTC AAGCAAGGAG GTTTTGTA
ITR5+2SNS
1 AGGAACCCCT AGTGATGGAG TTGGCCACTC CCTCCCCCCT GTCGCGTTCG CGCGCTCGCT CGCTCACTGA GGGCGGGCGA CCAAAGGTCG CCCGAGCCCG
101 GCCCTTTGGG CCGGGCCCCT CAGTGAGCGA GCGAGCGCGC GAACGCGACA GGGGGGAGGG AGTGGCCAAC TCCATCACTA GGGGTTCCT
ITR2+5SNS
1 TACAAAACCT CCTTGCTTGA GAGTGTGGCA CTCTCCCCCC TGTCGCGTTC GCGCGCTCGC TCGCTCACTG AGGGCGGGCG ACCAAAGGTC GCCCGAGCCC
101 GGCCCTTTGG GCCGGGCCCC TCAGTGAGCG AGCGAGCGCG CGAACGCGAC AGGGGGGAGA GTGCCACACT CTCAAGCAAG GAGGTTTTGT A
ITR5+2NS
1 AGGAACCCCT AGTGATGGAG TTGGCCACTC CCTCCCCCCT GTCGCGTTCG CTCGCTCGCT GGCTCGTTTG GGGGGGCGAC GGCCCAAAGG GCCGTCGTCT
101 GGCAGCTCTT TGAGCTGCCA CCCCCCCAAA CGAGCCAGCG AGCGAGCGAA CGCGACAGGG GGGAGGGAGT GGCCAACTCC ATCACTAGGG GTTCCT
ITR2+5NS
1 TACAAAACCT CCTTGCTTGA GAGTGTGGCA CTCTCTCTGC GCGCTCGCTC GCTCACTGAG GGCGGGCGAC CAAAGGTCGC CCGACGCCCG GCCCTTTGGG
101 CCGGGCGGCC CTCAGTGAGC GAGCGAGCGC GCAGAGAGAG TGCCACACTC TCAAGCAAGG AGGTTTTGTA
ITR2 - TA
1 AGGAACCCCT AGTGATGGAG TGGCCCTCCC TCTCTGCGCG CTCGCTCGCT CACTGAGGGC GGGCGACCAA AGGTCGCCCG ACGCCCGGCC CTTTGGGCCG
101 GGCGGCCCTC AGTGAGCGAG CGAGCGCGCA GAGAGGGAGG GCCACTCCAT CACTAGGGGT TCCT
ITR5 + TA
1 TACAAAACCT CCTTGCTTGA GAGTGTTGGA CACTCTCCCC CCTGTCGCGT TCGCTCGCTC GCTGGCTCGT TTGGGGGGGC GACGGCCCAA AGGGCCGTCG
101 TCTGGCAGCT CTTTGAGCTG CCACCCCCCC AAACGAGCCA GCGAGCGAGC GAACGCGACA GGGGGGAGAG TGTCCAACAC TCTCAAGCAA GGAGGTTTTG
201 TA
ITR2 -GC
1 AGGAACCCCT AGTATGGAGT TGGCCACTCC ATTCTGCGCG CTCGCTCGCT CACTGAGGGC GGGCGACCAA AGGTCGCCCG AGCCCGGCCC TTTGGGCCGG
101 GCCCCTCAGT GAGCGAGCGA GCGCGCAGAA TGGAGTGGCC AACTCCATAC TAGGGGTTCC T

FIG. 24

ITR5 +GC

1 TACAAAACCT CCTTGCTTGG AGAGTGTGGC ACTCTCCCCC CCTGTCGCGT TCGCTCGCTC GCTGGCTCGT TTGGGGGGGC GACGGCCCAA AGGGCCGTCG

101 TCTGGCAGCT CTTTGAGCTG CCACCCCCCC AAACGAGCCA GCGAGCGAGC GAACGCGACA GGGGGGGAGA GTGCCACACT CTCCAAGCAA GGAGGTTTTG

201 TA

ITR2 ~2nt

1 AGGAACCCCT AGTGCTGGAG TTGGCCACTC CCGCGCGCTC GCTCGCTCAC TGAGGGCGGG CGACCAAAGG TCGCCCGAGC CCGGCCCTTT GGGCCGGGCC

101 CCTCAGTGAG CGAGCGAGCG CGCGGGAGTG GCCAACTCCA GCACTAGGGG TTCCT

ITR2 5nt

1 AGGAACCCCT AGTGGAGTTG GCCACTCCTC TGCGCGCTCG CTCGCTCACT GAGGGCGGGC GACCAAAGGT CGCCCGAGCC CGGCCCTTTG GGCCGGGCCC

101 CTCAGTGAGC GAGCGAGCGC GCAGAGGAGT GGCCAACTCC ACTAGGGGTT CCT

ITR2+7

1 AGGAACCCCT AGTGATGGAG TTGGCCACTC CCTCCACGCG TTCTGCGCGC TCGCTCGCTC ACTGAGGGCG GGCGACCAAA GGTCGCCCGA CGCCCGGCCC

101 TTTGGGCCGG GCGGCCCTCA GTGAGCGAGC GAGCGCGCAG AACGCGTGGA GGGAGTGGCC AACTCCATCA CTAGGGGTTC CT

ITR2 9nt

1 AGGAACCCCT AGTGGATGGA GTTGGCCACT CCCTCCTCTG CGCGCTCGCT CGCTCACTGA GGGCGGGCGA CCAAAGGTCG CCCGAGCCCG GCCCTTTGGG

101 CCGGGCCCCT CAGTGAGCGA GCGAGCGCGC AGAGGAGTGG CCAACTCCAC TAGGGGTTCC T

ITR2 10nt

1 AGGAACCCCT AGTGATGGAG TTGGCCACTC CCTCCACGCG TTCTGCGCGC TCGCTCGCTC ACTGAGGGCG GGCGACCAAA GGTCGCCCGA CGCCCGGCCC

101 TTTGGGCCGG GCGGCCCTCA GTGAGCGAGC GAGCGCGCAG AACGCGTGGA GGGAGTGGCC AACTCCATCA CTAGGGGTTC CT

ITR2 11nt

1 AGGAACCCCT AGTCGTGATG GAGTTGGCCA CTCCCTCACG TCTGCGCGCT CGCTCGCTCA CTGAGGGCGG GCGACCAAAG GTCGCCCGAG CCCGGCCCTT

101 TGGGCCGGGC CCCTCAGTGA GCGAGCGAGC GCGCAGACGT GAGGGAGTGG CCAACTCCAT CACGACTAGG GGTTCCT

ITR2 15nt

1 AGGAACCCCT AGTGATGGAG TTGGCCACTC CCTCCCCCCT GTCGCGTTCG CGCGCTCGCT CGCTCACTGA GGGCGGGCGA CCAAAGGTCG CCCGAGCCCG

101 GCCCTTTGGG CCGGGCCCCT CAGTGAGCGA GCGAGCGCGC AGAGAGGGAG TGGCCAACTC CATCACTAGG GGTTCCT

ITR5 3nt

1 TACAAAACCT CCTTGCTTGA GAGTGTGGCA CTCTTCTGCT CGCTCGCTGG CTCGTTTGGG GGGGCGACGG CCCAAAGGGC CGTCGTCTGG CAGCTCTTTG

101 AGCTGCCACC CCCCCAAACG AGCCAGCGAG CGAGCAGAGA GAGTGCCACA CTCTCAAGCA AGGAGGTTTT GTA

FIG. 24 (cont.)

ITR5 6nt
1 TACAAAACCT CCTTGCTTAG AGTGTGGCAC TCTCCCCCTG TCGCGTTCGC TCGCTCGCTG GCTCGTTTGG GGGGGCGACG GCCCAAAGGG CCGTCGTCTG
101 GCAGCTCTTT GAGCTGCCAC CCCCCCAAAC GAGCCAGCGA GCGAGCGAAC GCGACAGGGG GAGAGTGCCA CACTCTAAGC AAGGAGGTTT TGTA

ITR5 9bp NS
1 TACAAAACCT CCTTGCTTGA GAGAGTGTGG CACTCTCTCC CCCCTGTCGC GTTCGCTCGC TCGCTGGCTC GTTTGGGGGG GCGACGGCCC AAAGGGCCGT
101 CGTCTGGCAG CTCTTTGAGC TGCCACCCCC CCAAACGAGC CAGCGAGCGA GCGAACGCGA CAGGGGGGAG AGAGTGCCAC ACTCTCTCAA GCAAGGAGGT
201 TTTGTA

ITR5 21nt
1 TACAAAACCT CCTTGCTTGA GAGTGTGGCA CTCTACGCGT CCCCCCTGTC GCGTTCGCTC GCTCGCTGGC TCGTTTGGGG GGGCGACGGC CCAAAGGGCC
101 GTCGTCTGGC AGCTCTTTGA GCTGCCACCC CCCCAAACGA GCCAGCGAGC GAGCGAACGC GACAGGGGGC GCGTGGAGAG TGCCACACTC TCAAGCAAGG
201 AGGTTTTGTA

ITR5 30nt
1 TACAAAACCT CCTTGCTTGA GAGTGTGGCA CTCTCACGCG TAGATCTAGA CCCCCTGTCG CGTTCGCTCG CTCGCTGGCT CGTTTGGGGG GGCGACGGCC
101 CAAAGGGCCG TCGTCTGGCA GCTCTTTGAG CTGCCACCCC CCCAAACGAG CCAGCGAGCG AGCGAACGCG ACAGGGGGTC TAGATCTACG GTGAGAGTGC
201 CACACTCTCA AGCAAGGAGG TTTTGTA

ITR5 GAGY
1 TACAAAACCT CCTTGCTTGA GAGTGTGGCA CTCTCCCCGC TCGCTCGCTC GCTCGCTCGC TGGCTCGTTT GGGGGGGCGA CGGCCCAAAG GGCCGTCGTC
101 TGGCAGCTCT TTGAGCTGCC ACCCCCCCAA ACGAGCCAGC GAGCGAGCGA GCGAGCGAGC GGGGAGAGTG CCACACTCTC AAGCAAGGAG GTTTTGTA

ITR5 No GAGY
1 TACAAAACCT CCTTGCTTGA GAGTGTGGCA CTCTCCCCAG CTAAGATGCA GCTCGCTCGC TGGCTCGTTT GGGGGGGCGA CGGCCCAAAG GGCCGTCGTC
101 TGGCAGCTCT TTGAGCTGCC ACCCCCCCAA ACGAGCCAGC GAGCGAGCTG CATCTTAGCT GGGGAGAGTG CCACACTCTC AAGCAAGGAG GTTTTGTA

ITR2 +8nt GAGY
1 AGGAACCCCT AGTGATGGAG TTGGCCACTC CCTCTCTGCT CGCTCGCGCG CTCGCTCGCT CACTGAGGGC GGGCGACCAA AGGTCGCCCG AGCCCGGCCC
101 TTTGGGCCGG GCCCCTCAGT GAGCGAGCGA GCGCGCGAGC GAGCAGAGAG GGAGTGGCCA ACTCCATCAC TAGGGGTTCC T

ITR5 SPACER RBE
1 TACAAAACCT CCTTGCTTGA GAGTGTGGCA CTCTCCCCCC TGTCGCGTTC GCTCAGCTAA GATGCAGTTT GGGGGGGCGA CGGCCCAAAG GGCCGTCGTC
101 TGGCAGCTCT TTGAGCTGCC ACCCCCCCAA ACTGCATCTT AGCTGAGCGA ACGCGACAGG GGGGAGAGTG CCACACTCTC AAGCAAGGAG GTTTTGTA

ITR2 +8-8 SPACER RBE
1 AGGAACCCCT AGTGATGGAG TTGGCCACTC CCTCTCTGCT CGCTCGCGCG CTCAAGATGC ACTGAGGGCG GGCGACCAAA GGTCGCCCGA GCCCGGCCCT
101 TTGGGCCGGG CCCCTCAGTT GCATCTTGAG CGCGCGAGCG AGCAGAGAGG GAGTGGCCAA CTCCATCACT AGGGGTTCCT

FIG. 24 (cont.

ITR5 WITH ITR2 HAIRPINS

1 TACAAAACCT CCTTGCTTGA GAGTGTGGCA CTCTCCCCCC TGTCGCGTTC GCTCGCTCGC TGGCTCGTTT GGGGGGGCGG GCGACCAAAG GTCGCCCGAG
101 CCCGGCCCTT TGGGCCGGGC CCCCCCCAAA CGAGCCAGCG AGCGAGCGAA CGCGACAGGG GGGAGAGTGC CACACTCTCA AGCAAGGAGG TTTTGTA

ITR2 NO HAIRPINS

1 AGGAACCCCT AGTGATGGAG TTGGCCACTC CCTCTCTGCG CGCTCGCTCG CTCACTGAGG CGGCCCTTTG GGCCGCCTCA GTGAGCGAGC GAGCGCGCAG
101 AGAGGGAGTG GCCAACTCCA TCACTAGGGG TTCCT

ITR2 T1

1 AGGAACCCCT AGTGATGGAG TTGGGGTCTG CGCGCGCTCG CTCGCTCACT GAGGGCGGGC GACCAAAGGT CGCCCGAGCC CGGCCCTTTG GGCCGGGCCC
101 CTCAGTGAGC GAGCGAGCGC GCGCAGACCC CAACTCCATC ACTAGGGGTT CCT

ITR2 T2

1 AGGAACCCCT AGTGATGGAG TTGGGACTCC CTCTCTGCGC GCTCGCTCGC TCACTGAGGG CGGGCGACCA AAGGTCGCCC GAGCCCGGCC CTTTGGGCCG
101 GGCCCCTCAG TGAGCGAGCG AGCGCGCAGA GAGGGAGTCC CCAACTCCAT CACTAGGGGT TCCT

ITR2 T2 #2

1 AGGAACCCCT AGTGATGGAG TTGGGGTTAA CTCTGCGCGC TCGCTCGCTC ACTGAGGGCG GGCGACCAAA GGTCGCCCGA GCCCGGCCCT TTGGGCCGGG
101 CCCCTCAGTG AGCGAGCGAG CGCGCAGAGT TAACCCCAAC TCCATCACTA GGGGTTCCT

ITR2 T3

1 AGGAACCCCT AGTGATGGAG TTGGTCCCTC TCTGCGCGCT CGCTCGCTCA CTGAGGGCGG GCGACCAAAG GTCGCCCGAG CCCGGCCCTT TGGGCCGGGC
101 CCCTCAGTGA GCGAGCGAGC GCGCAGAGAG GGACCAACTC CATCACTAGG GGTTCCT

ITR2 T4

1 AGGAACCCCT AGTGATGGAG TTGGGGTTAA CCCCTCTGCG CGCTCGCTCG CTCACTGAGG GCGGGCGACC AAAGGTCGCC CGAGCCCGGC CCTTTGGGCC
101 GGGCCCCTCA GTGAGCGAGC GAGCGCGCAG AGGGGTTAAC CCCAACTCCA TCACTAGGGG TTCCT

ITR5+3nt SPACER & ITR5 NS

1 AGGAACCCCT AGTGATGGAG TTGGCCACTC CCTCTTCGCT CGCTCGCTGG CTCGTTTGGG GGGGCGACGG CCCAAAGGGC CGTCGTCTGG CAGCTCTTTG
101 AGCTGCCACC CCCCCAAACG AGCCAGCGAG CGAGCGAAGA GGGAGTGGCC AACTCCATCA CTAGGGGTTC CT

ITR2 pHpa8

1 AGGAACCCCT AGTGATGGAG TTGGGGTTAA CCCCACTCCC TCTCTGCGCG CTCGCTCGCT CACTGAGGGC GGGCGACCAA AGGTCGCCCG AGCCCGGCCC
101 TTTGGGCCGG GCCCCTCAGT GAGCGAGCGA GCGCGCAGAG AGGGAGTGGG GTTAACCCCA ACTCCATCAC TAGGGGTTCCT

FIG. 24 (cont.)

CHIMERIC REP PROTEINS

REP52AA73

```
  1 MATFYEVIVR VPFDVEEHLP GISDSFVDWV TGQIWELPPE SDLNLTLVEQ PQLTVADRIR RVFLYEWNKF SKAPEALFFV QFEKGESYFH MHVLVETTGV
101 KSMVLGRFLS QIREKLIQRI YRGIEPTLPN WFAVTKTRNG AGGGNKVVDE CYIPNYLLPK TQPELQWAWT NMEQYLSACL NLTERKRLVA QHLTHVSQTQ
201 EQNKENQNPN SDAPVIRSKT SARYMELVGW LVDKGITSEK QWIQEDQASY ISFNAASNSR SQIKAALDNA GKIMSLTKTA PDYLVGQQPV EDISSNRIYK
301 ILELNGYDPQ YAASVFLGWA TKKFGKRNTI WLFGPATTGK TNIAEAIAHT VPFYGCVNWT NENFPFNDCV DKMVIWWEEG KMTAKVVESA KAILGGSKVR
401 VDQKCKSSAQ IDPTPVIVTS NTNMCAVIDG NSTTFEHQQP LQDRMFKFEL TRRLDHDFGK VTKQEVKDFF RWAKDHVVEV EHEFYVKKGG AKKRPAPSDA
501 DISEPKRVRE SVAQPSTSDA EASINYADRY QNKCSRHVGM NLMLFPCRQC ERMNQNSNIC FTHGQKDCLE CFPVSESQPV SVVKKAYQKL CYIHHIMGKV
601 PDACTACDLV NVDLDDCIFE Q*
```

REP52AA84

```
  1 MATFYEVIVR VPFDVEEHLP GISDSFVDWV TGQIWELPPE SDLNLTLVEQ PQLTVADRIR RVFLYEWNKF SKQESKFFVQ FEKG ESYFH MHVLVETTGV
101 KSMVLGRFLS QIREKLIQRI YRGIEPTLPN WFAVTKTRNG AGGGNKVVDE CYIPNYLLPK TQPELQWAWT NMEQYLSACL NLTERKRLVA QHLTHVSQTQ
201 EQNKENQNPN SDAPVIRSKT SARYMELVGW LVDKGITSEK QWIQEDQASY ISFNAASNSR SQIKAALDNA GKIMSLTKTA PDYLVGQQPV EDISSNRIYK
301 ILELNGYDPQ YAASVFLGWA TKKFGKRNTI WLFGPATTGK TNIAEAIAHT VPFYGCVNWT NENFPFNDCV DKMVIWWEEG KMTAKVVESA KAILGGSKVR
401 VDQKCKSSAQ IDPTPVIVTS NTNMCAVIDG NSTTFEHQQP LQDRMFKFEL TRRLDHDFGK VTKQEVKDFF RWAKDHVVEV EHEFYVKKGG AKKRPAPSDA
501 DISEPKRVRE SVAQPSTSDA EASINYADRY QNKCSRHVGM NLMLFPCRQC ERMNQNSNIC FTHGQKDCLE CFPVSESQPV SVVKKAYQKL CYIHHIMGKV
601 PDACTACDLV NVDLDDCIFE Q*
```

REP52AA110

```
  1 MATFYEVIVR VPFDVEEHLP GISDSFVDWV TGQIWELPPE SDLNLTLVEQ PQLTVADRIR RVFLYEWNKF SKQESKFFVQ FEKGSEYFHL HTLVETSGIS
101 SMVLGRYVSQ IREKLIQRIY RGIEPTLPNW FAVTKTRNGA GGGNKVVDEC YIPNYLLPKT QPELQWAWTN MEQYLSACLN LTERKRLVAQ HLTHVSQTQE
201 QNKENQNPNS DAPVIRSKTS ARYMELVGWL VDKGITSEKQ WIQEDQASYI SFNAASNSRS QIKAALDNAG KIMSLTKTAP DYLVGQQPVE DISSNRIYKI
301 LELNGYDPQY AASVFLGWAT KKFGKRNTIW LFGPATTGKT NIAEAIAHTV PFYGCVNWTN ENFPFNDCVD KMVIWWEEGK MTAKVVESAK AILGGSKVRV
401 DQKCKSSAQI DPTPVIVTSN TNMCAVIDGN STTFEHQQPL QDRMFKFELT RRLDHDFGKV TKQEVKDFFR WAKDHVVEVE HEFYVKKGGA KKRPAPSDAD
501 ISEPKRVRES VAQPSTSDAE ASINYADRYQ NKCSRHVGMN LMLFPCRQCE RMNQNSNICF THGQKDCLEC FPVSESQPVS VVKKAYQKLC YIHHIMGKVP
601 DACTACDLVN VDLDDCIFEQ *
```

REP52AA126

```
  1 MATFYEVIVR VPFDVEEHLP GISDSFVDWV TGQIWELPPE SDLNLTLVEQ PQLTVADRIR RVFLYEWNKF SKQESKFFVQ FEKGSEYFHL HTLVETSGIS
101 SMVLGRYVSQ IRAQLVKVVF QGIEPTLPNW FAVTKTRNGA GGGNKVVDEC YIPNYLLPKT QPELQWAWTN MEQYLSACLN LTERKRLVAQ HLTHVSQTQE
201 QNKENQNPNS DAPVIRSKTS ARYMELVGWL VDKGITSEKQ WIQEDQASYI SFNAASNSRS QIKAALDNAG KIMSLTKTAP DYLVGQQPVE DISSNRIYKI
301 LELNGYDPQY AASVFLGWAT KKFGKRNTIW LFGPATTGKT NIAEAIAHTV PFYGCVNWTN ENFPFNDCVD KMVIWWEEGK MTAKVVESAK AILGGSKVRV
401 DQKCKSSAQI DPTPVIVTSN TNMCAVIDGN STTFEHQQPL QDRMFKFELT RRLDHDFGKV TKQEVKDFFR WAKDHVVEVE HEFYVKKGGA KKRPAPSDAD
501 ISEPKRVRES VAQPSTSDAE ASINYADRYQ NKCSRHVGMN LMLFPCRQCE RMNQNSNICF THGQKDCLEC FPVSESQPVS VVKKAYQKLC YIHHIMGKVP
601 DACTACDLVN VDLDDCIFEQ *
```

FIG. 25

REP52AA138

```
  1 MATFYEVIVR VPFDVEEHLP GISDSFVDWV TGQIWELPPE SDLNLTLVEQ PQLTVADRIR RVFLYEWNKF SKQESKFFVQ FEKGSEYFHL HTLVETSGIS
101 SMVLGRYVSQ IRAQLVKVVF QGIEPQINDW VAITKVKKGG GNKVVDECYI PNYLLPKTQP ELQWAWTNME QYLSACLNLT ERKRLVAQHL THVSQTQEQN
201 KENQNPNSDA PVIRSKTSAR YMELVGWLVD KGITSEKQWI QEDQASYISF NAASNSRSQI KAALDNAGKI MSLTKTAPDY LVGQQPVEDI SSNRIYKILE
301 LNGYDPQYAA SVFLGWATKK FGKRNTIWLF GPATTGKTNI AEAIAHTVPF YGCVNWTNEN FPFNDCVDKM VIWWEEGKMT AKVVESAKAI LGGSKVRVDQ
401 KCKSSAQIDP TPVIVTSNTN MCAVIDGNST TFEHQQPLQD RMFKFELTRR LDHDFGKVTK QEVKDFFRWA KDHVVEVEHE FYVKKGGAKK RPAPSDADIS
501 EPKRVRESVA QPSTSDAEAS INYADRYQNK CSRHVGMNLM LFPCRQCERM NQNSNICFTH GQKDCLECFP VSESQPVSVV KKAYQKLCYI HHIMGKVPDA
601 CTACDLVNVD LDDCIFEQ*
```

REP52AA160

```
  1 MATFYEVIVR VPFDVEEHLP GISDSFVDWV TGQIWELPPE SDLNLTLVEQ PQLTVADRIR RVFLYEWNKF SKQESKFFVQ FEKGSEYFHL HTLVETSGIS
101 SMVLGRYVSQ IRAQLVKVVF QGIEPQINDW VAITKVKKGG ANKVVDSGYI PAYLLPKVQP ELQWAWTNME QYLSACLNLT ERKRLVAQHL THVSQTQEQN
201 KENQNPNSDA PVIRSKTARY MELVGWLVDK GITSEKQWIQ EDQASYISFN AASNSRSQIK AALDNAGKIM SLTKTAPDYL VGQQPVEDIS SNRIYKILEL
301 NGYDPQYAAS VFLGWATKKF GKRNTIWLFG PATTGKTNIA EAIAHTVPFY GCVNWTNENF PFNDCVDKMV IWWEEGKMTA KVVESAKAIL GGSKVRVDQK
401 CKSSAQIDPT PVIVTSNTNM CAVIDGNSTT FEHQQPLQDR MFKFELTRRL DHDFGKVTKQ EVKDFFRWAK DHVVEVEHEF YVKKGGAKKR PAPSDADISE
501 PKRVRESVAQ PSTSDAEASI NYADRYQNKC SRHVGMNLML FPCRQCERMN QNSNICFTHG QKDCLECFPV SESQPVSVVK KAYQKLCYIH HIMGKVPDAC
601 TACDLVNVDL DDCIFEQ*
```

REP52AA175

```
  1 MATFYEVIVR VPFDVEEHLP GISDSFVDWV TGQIWELPPE SDLNLTLVEQ PQLTVADRIR RVFLYEWNKF SKQESKFFVQ FEKGSEYFHL HTLVETSGIS
101 SMVLGRYVSQ IRAQLVKVVF QGIEPQINDW VAITKVKKGG ANKVVDSGYI PAYLLPKVQP ELQWAWTNLD EYKLACLNLT ERKRLVAQHL THVSQTQEQN
201 KENQNPNDAP VIRSKTARYM ELVGWLVDKG ITSEKQWIQE DQASYISFNA ASNSRSQIKA ALDNAGKIMS LTKTAPDYLV GQQPVEDISS NRIYKILELN
301 GYDPQYAASV FLGWATKKFG KRNTIWLFGP ATTGKTNIAE AIAHTVPFYG CVNWTNENFP FNDCVDKMVI WWEEGKMTAK VVESAKAILG GSKVRVDQKC
401 KSSAQIDPTP VIVTSNTNMC AVIDGNSTTF EHQQPLQDRM FKFELTRRLD HDFGKVTKQE VKDFFRWAKD HVVEVEHEFY VKKGGAKKRP APSDADISEP
501 KRVRESVAQP STSDAEASIN YADRYQNKCS RHVGMNLMLF PCRQCERMNQ NSNICFTHGQ KDCLECFPVS ESQPVSVVKK AYQKLCYIHH IMGKVPDACT
601 ACDLVNVDLD DCIFEQ*
```

REP52AA187

```
  1 MATFYEVIVR VPFDVEEHLP GISDSFVDWV TGQIWELPPE SDLNLTLVEQ PQLTVADRIR RVFLYEWNKF SKQESKFFVQ FEKGSEYFHL HTLVETSGIS
101 SMVLGRYVSQ IRAQLVKVVF QGIEPQINDW VAITKVKKGG ANKVVDSGYI PAYLLPKVQP ELQWAWTNLD EYKLAALNLE ERKRRKRLVA QHLTHVSQTQ
201 EQNKENQNPN SDAPVIRSKT SARYMELVGW LVDKGITSEK QWIQEDQASY ISFNAASNSR SQIKAALDNA GKIMSLTKTA PDYLVGQQPV EDISSNRIYK
301 ILELNGYDPQ YAASVFLGWA TKKFGKRNTI WLFGPATTGK TNIAEAIAHT VPFYGCVNWT NENFPFNDCV DKMVIWWEEG KMTAKVVESA KAILGGSKVR
401 VDQKCKSSAQ IDPTPVIVTS NTNMCAVIDG NSTTFEHQQP LQDRMFKFEL TRRLDHDFGK VTKQEVKDFF RWAKDHVVEV EHEFYVKKGG AKKRPAPSDA
501 DISEPKRVRE SVAQPSTSDA EASINYADRY QNKCSRHVGM NLMLFPCRQC ERMNQNSNIC FTHGQKDCLE CFPVSESQPV SVVKKAYQKL CYIHHIMGKV
601 PDACTACDLV NVDLDDCIFE Q*
```

*FIG. 25 (cont.)*

REP52AA207

1 MATFYEVIVR VPFDVEEHLP GISDSFVDWV TGQIWELPPE SDLNLTLVEQ PQLTVADRIR RVFLYEWNKF SKQESKFFVQ FEKGSEYFHL HTLVETSGIS
101 SMVLGRYVSQ IRAQLVKVVF QGIEPQINDW VAITKVKKGG ANKVVDSGYI PAYLLPKVQP ELQWAWTNLD EYKLAALNLE ERKRLVAQFL AESSQRSEQN
201 KENQNPNSDA PVIRSKSARY MELVGWLVDK GITSEKQWIQ EDQASYISFN AASNSRSQIK AALDNAGKIM SLTKTAPDYL VGQQPVEDIS SNRIYKILEL
301 NGYDPQYAAS VFLGWATKKF GKRNTIWLFG PATTGKTNIA EAIAHTVPFY GCVNWTNENF PFNDCVDKMV IWWEEGKMTA KVVESAKAIL GGSKVRVDQK
401 CKSSAQIDPT PVIVTSNTNM CAVIDGNSTT FEHQQPLQDR MFKFELTRRL DHDFGKVTKQ EVKDFFRWAK DHVVEVEHEF YVKKGGAKKR PAPSDADISE
501 PKRVRESVAQ PSTSDAEASI NYADRYQNKC SRHVGMNLML FPCRQCERMN QNSNICFTHG QKDCLECFPV SESQPVSVVK KAYQKLCYIH HIMGKVPDAC
601 TACDLVNVDL DDCIFEQ*

REP25AA73

1 MPGFYEIVIK VPSDLDGHLP GISDSFVNWV AEKEWELPPD SDMDLNLIEQ APLTVAEKLQ RDFLTEWRRV SKQESKFFVQ FEKGSEYFHL HTLVETSGIS
101 SMVLGRYVSQ IRAQLVKVVF QGIEPQINDW VAITKVKKGG ANKVVDSGYI PAYLLPKVQP ELQWAWTNLD EYKLAALNLE ERKRLVAQFL AESSQRSQEA
201 ASQREFSADP VIKSKTSQKY MALVNWLVEH GITSEKQWIQ ENQESYLSFN STGNSRSQIK AALDNATKIM SLTKSAVDYL VGSSVPEDIS KNRIWQIFEM
301 NGYDPAYAGS ILYGWCQRSF NKRNTVWLYG PATTGKTNIA EAIAHTVPFY GCVNWTNENF PFNDCVDKML IWWEEGKMTN KVVESAKAIL GGSKVRVDQK
401 CKSSVQIDST PVIVTSNTNM CVVVDGNSTT FEHQQPLEDR MFKFELTKRL PPDFGKITKQ EVKDFFAWAK VNQVPVTHEF KVPRELAGTK GAEKSLKRPL
501 GDVTNTSYKS LEKRARLSFV PETPRSSDVT VDPAPLRPLN WNSRYDCKCD YHAQFDNISN KCDECEYLNR GKNGCICHNV THCQICHGIP PWEKENLSDF
601 GDFDDANKEQ *

REP25AA77

1 MPGFYEIVIK VPSDLDGHLP GISDSFVNWV AEKEWELPPD SDMDLNLIEQ APLTVAEKLQ RDFLTEWRRV SKAPEALFFV QFEKGSEYFH LHTLVETSGI
101 SSMVLGRYVS QIRAQLVKVV FQGIEPQIND WVAITKVKKG GANKVVDSGY IPAYLLPKVQ PELQWAWTNL DEYKLAALNL EERKRLVAQF LAESSQRSQE
201 AASQREFSAD PVIKSKTSQK YMALVNWLVE HGITSEKQWI QENQESYLSF NSTGNSRSQI KAALDNATKI MSLTKSAVDY LVGSSVPEDI SKNRIWQIFE
301 MNGYDPAYAG SILYGWCQRS FNKRNTVWLY GPATTGKTNI AEAIAHTVPF YGCVNWTNEN FPFNDCVDKM LIWWEEGKMT NKVVESAKAI LGGSKVRVDQ
401 KCKSSVQIDS TPVIVTSNTN MCVVVDGNST TFEHQQPLED RMFKFELTKR LPPDFGKITK QEVKDFFAWA KVNQVPVTHE FKVPRELAGT KGAEKSLKRP
501 LGDVTNTSYK SLEKRARLSF VPETPRSSDV TVDPAPLRPL NWNSRYDCKC DYHAQFDNIS NKCDECEYLN RGKNGCICHN VTHCQICHGI PPWEKENLSD
601 FGDFDDANKE Q*

REP25AA97

1 MPGFYEIVIK VPSDLDGHLP GISDSFVNWV AEKEWELPPD SDMDLNLIEQ APLTVAEKLQ RDFLTEWRRV SKAPEALFFV QFEKGESYFH MHVLVETSGI
101 SSMVLGRYVS QIRAQLVKVV FQGIEPQIND WVAITKVKKG GANKVVDSGY IPAYLLPKVQ PELQWAWTNL DEYKLAALNL EERKRLVAQF LAESSQRSQE
201 AASQREFSAD PVIKSKTSQK YMALVNWLVE HGITSEKQWI QENQESYLSF NSTGNSRSQI KAALDNATKI MSLTKSAVDY LVGSSVPEDI SKNRIWQIFE
301 MNGYDPAYAG SILYGWCQRS FNKRNTVWLY GPATTGKTNI AEAIAHTVPF YGCVNWTNEN FPFNDCVDKM LIWWEEGKMT NKVVESAKAI LGGSKVRVDQ
401 KCKSSVQIDS TPVIVTSNTN MCVVVDGNST TFEHQQPLED RMFKFELTKR LPPDFGKITK QEVKDFFAWA KVNQVPVTHE FKVPRELAGT KGAEKSLKRP
501 LGDVTNTSYK SLEKRARLSF VPETPRSSDV TVDPAPLRPL NWNSRYDCKC DYHAQFDNIS NKCDECEYLN RGKNGCICHN VTHCQICHGI PPWEKENLSD
601 FGDFDDANKE Q*

FIG. 25 (cont.)

REP25AA116

```
  1 MPGFYEIVIK VPSDLDGHLP GISDSFVNWV AEKEWELPPD SDMDLNLIEQ APLTVAEKLQ RDFLTEWRRV SKAPEALFFV QFEKGESYFH MHVLVETTGV
101 KSMVLGRFLS QIREKLVKVV FQGIEPQIND WVAITKVKKG GANKVVDSGY IPAYLLPKVQ PELQWAWTNL DEYKLAALNL EERKRLVAQF LAESSQRSQE
201 AASQREFSAD PVIKSKTSQK YMALVNWLVE HGITSEKQWI QENQESYLSF NSTGNSRSQI KAALDNATKI MSLTKSAVDY LVGSSVPEDI SKNRIWQIFE
301 MNGYDPAYAG SILYGWCQRS FNKRNTVWLY GPATTGKTNI AEAIAHTVPF YGCVNWTNEN FPFNDCVDKM LIWWEEGKMT NKVVESAKAI LGGSKVRVDQ
401 KCKSSVQIDS TPVIVTSNTN MCVVVDGNST TFEHQQPLED RMFKFELTKR LPPDFGKITK QEVKDFFAWA KVNQVPVTHE FKVPRELAGT KGAEKSLKRP
501 LGDVTNTSYK SLEKRARLSF VPETPRSSDV TVDPAPLRPL NWNSRYDCKC DYHAQFDNIS NKCDECEYLN RGKNGCICHN VTHCQICHGI PPWEKENLSD
601 FGDFDDANKE Q*
```

REP25AA125

```
  1 MPGFYEIVIK VPSDLDGHLP GISDSFVNWV AEKEWELPPD SDMDLNLIEQ APLTVAEKLQ RDFLTEWRRV SKAPEALFFV QFEKGESYFH MHVLVETTGV
101 KSMVLGRFLS QIREKLIQRI YRGIEPQIND WVAITKVKKG GANKVVDSGY IPAYLLPKVQ PELQWAWTNL DEYKLAALNL EERKRLVAQF LAESSQRSQE
201 AASQREFSAD PVIKSKTSQK YMALVNWLVE HGITSEKQWI QENQESYLSF NSTGNSRSQI KAALDNATKI MSLTKSAVDY LVGSSVPEDI SKNRIWQIFE
301 MNGYDPAYAG SILYGWCQRS FNKRNTVWLY GPATTGKTNI AEAIAHTVPF YGCVNWTNEN FPFNDCVDKM LIWWEEGKMT NKVVESAKAI LGGSKVRVDQ
401 KCKSSVQIDS TPVIVTSNTN MCVVVDGNST TFEHQQPLED RMFKFELTKR LPPDFGKITK QEVKDFFAWA KVNQVPVTHE FKVPRELAGT KGAEKSLKRP
501 LGDVTNTSYK SLEKRARLSF VPETPRSSDV TVDPAPLRPL NWNSRYDCKC DYHAQFDNIS NKCDECEYLN RGKNGCICHN VTHCQICHGI PPWEKENLSD
601 FGDFDDANKE Q*
```

REP25AA141

```
  1 MPGFYEIVIK VPSDLDGHLP GISDSFVNWV AEKEWELPPD SDMDLNLIEQ APLTVAEKLQ RDFLTEWRRV SKAPEALFFV QFEKGESYFH MHVLVETTGV
101 KSMVLGRFLS QIREKLIQRI YRGIEPTLPN WFAVTKTRNG AGGANKVVDS GYIPAYLLPK VQPELQWAWT NLDEYKLAAL NLEERKRLVA QFLAESSQRS
201 QEAASQREFS ADPVIKSKTS QKYMALVNWL VEHGITSEKQ WIQENQESYL SFNSTGNSRS QIKAALDNAT KIMSLTKSAV DYLVGSSVPE DISKNRIWQI
301 FEMNGYDPAY AGSILYGWCQ RSFNKRNTVW LYGPATTGKT NIAEAIAHTV PFYGCVNWTN ENFPFNDCVD KMLIWWEEGK MTNKVVESAK AILGGSKVRV
401 DQKCKSSVQI DSTPVIVTSN TNMCVVVDGN STTFEHQQPL EDRMFKFELT KRLPPDFGKI TKQEVKDFFA WAKVNQVPVT HEFKVPRELA GTKGAEKSLK
501 RPLGDVTNTS YKSLEKRARL SFVPETPRSS DVTVDPAPLR PLNWNSRYDC KCDYHAQFDN ISNKCDECEY LNRGKNGCIC HNVTHCQICH GIPPWEKENL
601 SDFGDFDDAN KEQ*
```

REP25AA149

```
  1 MPGFYEIVIK VPSDLDGHLP GISDSFVNWV AEKEWELPPD SDMDLNLIEQ APLTVAEKLQ RDFLTEWRRV SKAPEALFFV QFEKGESYFH MHVLVETTGV
101 KSMVLGRFLS QIREKLIQRI YRGIEPTLPN WFAVTKTRNG AGGGNKVVDS GYIPAYLLPK VQPELQWAWT NLDEYKLAAL NLEERKRLVA QFLAESSQRS
201 QEAASQREFS ADPVIKSKTS QKYMALVNWL VEHGITSEKQ WIQENQESYL SFNSTGNSRS QIKAALDNAT KIMSLTKSAV DYLVGSSVPE DISKNRIWQI
301 FEMNGYDPAY AGSILYGWCQ RSFNKRNTVW LYGPATTGKT NIAEAIAHTV PFYGCVNWTN ENFPFNDCVD KMLIWWEEGK MTNKVVESAK AILGGSKVRV
401 DQKCKSSVQI DSTPVIVTSN TNMCVVVDGN STTFEHQQPL EDRMFKFELT KRLPPDFGKI TKQEVKDFFA WAKVNQVPVT HEFKVPRELA GTKGAEKSLK
501 RPLGDVTNTS YKSLEKRARL SFVPETPRSS DVTVDPAPLR PLNWNSRYDC KCDYHAQFDN ISNKCDECEY LNRGKNGCIC HNVTHCQICH GIPPWEKENL
601 SDFGDFDDAN KEQ*
```

FIG. 25 (cont.)

REP25AA166

```
  1 MPGFYEIVIK VPSDLDGHLP GISDSFVNWV AEKEWELPPD SDMDLNLIEQ APLTVAEKLQ RDFLTEWRRV SKAPEALFFV QFEKGESYFH MHVLVETTGV
101 KSMVLGRFLS QIREKLIQRI YRGIEPTLPN WFAVTKTRNG AGGGNKVVDE CYIPNYLLPK TQPELQWAWT NLDEYKLAAL NLEERKRLVA QFLAESSQRS
201 QEAASQREFS ADPVIKSKTS QKYMALVNWL VEHGITSEKQ WIQENQESYL SFNSTGNSRS QIKAALDNAT KIMSLTKSAV DYLVGSSVPE DISKNRIWQI
301 FEMNGYDPAY AGSILYGWCQ RSFNKRNTVW LYGPATTGKT NIAEAIAHTV PFYGCVNWTN ENFPFNDCVD KMLIWWEEGK MTNKVVESAK AILGGSKVRV
401 DQKCKSSVQI DSTPVIVTSN TNMCVVVDGN STTFEHQQPL EDRMFKFELT KRLPPDFGKI TKQEVKDFFA WAKVNQVPVT HEFKVPRELA GTKGAEKSLK
501 RPLGDVTNTS YKSLEKRARL SFVPETPRSS DVTVDPAPLR PLNWNSRYDC KCDYHAQFDN ISNKCDECEY LNRGKNGCIC HNVTHCQICH GIPPWEKENL
601 SDFGDFDDAN KEQ*
```

REP25AA187

```
  1 MPGFYEIVIK VPSDLDGHLP GISDSFVNWV AEKEWELPPD SDMDLNLIEQ APLTVAEKLQ RDFLTEWRRV SKAPEALFFV QFEKGESYFH MHVLVETTGV
101 KSMVLGRFLS QIREKLIQRI YRGIEPTLPN WFAVTKTRNG AGGGNKVVDE CYIPNYLLPK TQPELQWAWT NMEQYLSACL NLTERKRLVA QFLAESSQRS
201 QEAASQREFS ADPVIKSKTS QKYMALVNWL VEHGITSEKQ WIQENQESYL SFNSTGNSRS QIKAALDNAT KIMSLTKSAV DYLVGSSVPE DISKNRIWQI
301 FEMNGYDPAY AGSILYGWCQ RSFNKRNTVW LYGPATTGKT NIAEAIAHTV PFYGCVNWTN ENFPFNDCVD KMLIWWEEGK MTNKVVESAK AILGGSKVRV
401 DQKCKSSVQI DSTPVIVTSN TNMCVVVDGN STTFEHQQPL EDRMFKFELT KRLPPDFGKI TKQEVKDFFA WAKVNQVPVT HEFKVPRELA GTKGAEKSLK
501 RPLGDVTNTS YKSLEKRARL SFVPETPRSS DVTVDPAPLR PLNWNSRYDC KCDYHAQFDN ISNKCDECEY LNRGKNGCIC HNVTHCQICH GIPPWEKENL
601 SDFGDFDDAN KEQ*
```

REP25AA216

```
  1 MPGFYEIVIK VPSDLDGHLP GISDSFVNWV AEKEWELPPD SDMDLNLIEQ APLTVAEKLQ RDFLTEWRRV SKAPEALFFV QFEKGESYFH MHVLVETTGV
101 KSMVLGRFLS QIREKLIQRI YRGIEPTLPN WFAVTKTRNG AGGGNKVVDE CYIPNYLLPK TQPELQWAWT NMEQYLSACL NLTERKRLVA QHLTHVSQTQ
201 EQNKENQNPN SDAPVIKSKT SQKYMALVNW LVEHGITSEK QWIQENQESY LSFNSTGNSR SQIKAALDNA TKIMSLTKSA VDYLVGSSVP EDISKNRIWQ
301 IFEMNGYDPA YAGSILYGWC QRSFNKRNTV WLYGPATTGK TNIAEAIAHT VPFYGCVNWT NENFPFNDCV DKMLIWWEEG KMTNKVVESA KAILGGSKVR
401 VDQKCKSSVQ IDSTPVIVTS NTNMCVVVDG NSTTFEHQQP LEDRMFKFEL TKRLPPDFGK ITKQEVKDFF AWAKVNQVPV THEFKVPREL AGTKGAEKSL
501 KRPLGDVTNT SYKSLEKRAR LSFVPETPRS SDVTVDPAPL RPLNWNSRYD CKCDYHAQFD NISNKCDECE YLNRGKNGCI CHNVTHCQIC HGIPPWEKEN
601 LSDFGDFDDA NKEQ*
```

REP525AA110-148

```
  1 MATFYEVIVR VPFDVEEHLP GISDSFVDWV TGQIWELPPE SDLNLTLVEQ PQLTVADRIR RVFLYEWNKF SKQESKFFVQ FEKGSEYFHL HTLVETSGIS
101 SMVLGRYVSQ IREKLIQRIY RGIEPTLPNW FAVTKTRNGA GGGNKVVDSG YIPAYLLPKV QPELQWAWTN LDEYKLAALN LEERKRLVAQ FLAESSQRSQ
201 EAASQREFSA DPVIKSKTSQ KYMALVNWLV EHGITSEKQW IQENQESYLS FNSTGNSRSQ IKAALDNATK IMSLTKSAVD YLVGSSVPED ISKNRIWQIF
301 EMNGYDPAYA GSILYGWCQR SFNKRNTVWL YGPATTGKTN IAEAIAHTVP FYGCVNWTNE NFPFNDCVDK MLIWWEEGKM TNKVVESAKA ILGGSKVRVD
401 QKCKSSVQID STPVIVTSNT NMCVVVDGNS TTFEHQQPLE DRMFKFELTK RLPPDFGKIT KQEVKDFFAW AKVNQVPVTH EFKVPRELAG TKGAEKSLKR
501 PLGDVTNTSY KSLEKRARLS FVPETPRSSD VTVDPAPLRP LNWNSRYDCK CDYHAQFDNI SNKCDECEYL NRGKNGCICH NVTHCQICHG IPPWEKENLS
601 DFGDFDDANK EQ*
```

FIG. 25 (cont.)

REP525AA146-187

```
  1 MATFYEVIVR VPFDVEEHLP GISDSFVDWV TGQIWELPPE SDLNLTLVEQ PQLTVADRIR RVFLYEWNKF SKQESKFFVQ FEKGSEYFHL HTLVETSGIS
101 SMVLGRYVSQ IRAQLVKVVF QGIEPQINDW VAITKVKKGG ANKVVDECYI PNYLLPKTQP ELQWAWTNME QYLSACLNLT ERKRLVAQFL AESSQRSQEA
201 ASQREFSADP VIKSKTSQKY MALVNWLVEH GITSEKQWIQ ENQESYLSFN STGNSRSQIK AALDNATKIM SLTKSAVDYL VGSSVPEDIS KNRIWQIFEM
301 NGYDPAYAGS ILYGWCQRSF NKRNTVWLYG PATTGKTNIA EAIAHTVPFY GCVNWTNENF PFNDCVDKML IWWEEGKMTN KVVESAKAIL GGSKVRVDQK
401 CKSSVQIDST PVIVTSNTNM CVVVDGNSTT FEHQQPLEDR MFKFELTKRL PPDFGKITKQ EVKDFFAWAK VNQVPVTHEF KVPRELAGTK GAEKSLKRPL
501 GDVTNTSYKS LEKRARLSFV PETPRSSDVT VDPAPLRPLN WNSRYDCKCD YHAQFDNISN KCDECEYLNR GKNGCICHNV THCQICHGIP PWEKENLSDF
601 GDFDDANKEQ *
```

REP525AA110-187

```
  1 MATFYEVIVR VPFDVEEHLP GISDSFVDWV TGQIWELPPE SDLNLTLVEQ PQLTVADRIR RVFLYEWNKF SKQESKFFVQ FEKGSEYFHL HTLVETSGIS
101 SMVLGRYVSQ IREKLIQRIY RGIEPTLPNW FAVTKTRNGA GGGNKVVDEC YIPNYLLPKT QPELQWAWTN MEQYLSACLN LTERKRLVAQ FLAESSQRSQ
201 EAASQREFSA DPVIKSKTSQ KYMALVNWLV EHGITSEKQW IQENQESYLS FNSTGNSRSQ IKAALDNATK IMSLTKSAVD YLVGSSVPED ISKNRIWQIF
301 EMNGYDPAYA GSILYGWCQR SFNKRNTVWL YGPATTGKTN IAEAIAHTVP FYGCVNWTNE NFPFNDCVDK MLIWWEEGKM TNKVVESAKA ILGGSKVRVD
401 QKCKSSVQID STPVIVTSNT NMCVVVDGNS TTFEHQQPLE DRMFKFELTK RLPPDFGKIT KQEVKDFFAW AKVNQVPVTH EFKVPRELAG TKGAEKSLKR
501 PLGDVTNTSY KSLEKRARLS FVPETPRSSD VTVDPAPLRP LNWNSRYDCK CDYHAQFDNI SNKCDECEYL NRGKNGCICH NVTHCQICHG IPPWEKENLS
601 DFGDFDDANK EQ*
```

REP252AA97-146

```
  1 MPGFYEIVIK VPSDLDGHLP GISDSFVNWV AEKEWELPPD SDMDLNLIEQ APLTVAEKLQ RDFLTEWRRV SKAPEALFFV QFEKGESYFH MHVLVETSGI
101 SSMVLGRYVS QIRAQLVKVV FQGIEPQIND WVAITKVKKG GANKVVDECY IPNYLLPKTQ PELQWAWTNM EQYLSACLNL TERKRLVAQH LTHVSQTQEQ
201 NKENQNPNSD APVIRSKTSA RYMELVGWLV DKGITSEKQW IQEDQASYIS FNAASNSRSQ IKAALDNAGK IMSLTKTAPD YLVGQQPVED ISSNRIYKIL
301 ELNGYDPQYA ASVFLGWATK KFGKRNTIWL FGPATTGKTN IAEAIAHTVP FYGCVNWTNE NFPFNDCVDK MVIWWEEGKM TAKVVESAKA ILGGSKVRVD
401 QKCKSSAQID PTPVIVTSNT NMCAVIDGNS TTFEHQQPLQ DRMFKFELTR RLDHDFGKVT KQEVKDFFRW AKDHVVEVEH EFYVKKGGAK KRPAPSDADI
501 SEPKRVRESV AQPSTSDAEA SINYADRYQN KCSRHVGMNL MLFPCRQCER MNQNSNICFT HGQKDCLECF PVSESQPVSV VKKAYQKLCY IHHIMGKVPD
601 ACTACDLVNV DLDDCIFEQ*
```

REP252AA149-187

```
  1 MPGFYEIVIK VPSDLDGHLP GISDSFVNWV AEKEWELPPD SDMDLNLIEQ APLTVAEKLQ RDFLTEWRRV SKAPEALFFV QFEKGESYFH MHVLVETTGV
101 KSMVLGRFLS QIREKLIQRI YRGIEPTLPN WFAVTKTRNG AGGGNKVVDS GYIPAYLLPK VQPELQWAWT NLDEYKLAAL NLEERKRRKR LVAQHLTHVS
201 QTQEQNKENQ NPNSDAPVIR SKTSARYMEL VGWLVDKGIT SEKQWIQEDQ ASYISFNAAS NSRSQIKAAL DNAGKIMSLT KTAPDYLVGQ QPVEDISSNR
301 IYKILELNGY DPQYAASVFL GWATKKFGKR NTIWLFGPAT TGKTNIAEAI AHTVPFYGCV NWTNENFPFN DCVDKMVIWW EEGKMTAKVV ESAKAILGGS
401 KVRVDQKCKS SAQIDPTPVI VTSNTNMCAV IDGNSTTFEH QQPLQDRMFK FELTRRLDHD FGKVTKQEVK DFFRWAKDHV VEVEHEFYVK KGGAKKRPAP
501 SDADISEPKR VRESVAQPST SDAEASINYA DRYQNKCSRH VGMNLMLFPC RQCERMNQNS NICFTHGQKD CLECFPVSES QPVSVVKKAY QKLCYIHHIM
601 GKVPDACTAC DLVNVDLDDC IFEQ*
```

FIG. 25 (cont.)

REP252AA97-187

```
  1 MPGFYEIVIK VPSDLDGHLP GISDSFVNWV AEKEWELPPD SDMDLNLIEQ APLTVAEKLQ RDFLTEWRRV SKAPEALFFV QFEKGESYFH MHVLVETSGI
101 SSMVLGRYVS QIRAQLVKVV FQGIEPQIND WVAITKVKKG GANKVVDSGY IPAYLLPKVQ PELQWAWTNL DEYKLAALNL EERKRRKRLV AQHLTHVSQT
201 QEQNKENQNP NSDAPVIRSK TSARYMELVG WLVDKGITSE KQWIQEDQAS YISFNAASNS RSQIKAALDN AGKIMSLTKT APDYLVGQQP VEDISSNRIY
301 KILELNGYDP QYAASVFLGW ATKKFGKRNT IWLFGPATTG KTNIAEAIAH TVPFYGCVNW TNENFPFNDC VDKMVIWWEE GKMTAKVVES AKAILGGSKV
401 RVDQKCKSSA QIDPTPVIVT SNTNMCAVID GNSTTFEHQQ PLQDRMFKFE LTRRLDHDFG KVTKQEVKDF FRWAKDHVVE VEHEFYVKKG GAKKRPAPSD
501 ADISEPKRVR ESVAQPSTSD AEASINYADR YQNKCSRHVG MNLMLFPCRQ CERMNQNSNI CFTHGQKDCL ECFPVSESQP VSVVKKAYQK LCYIHHIMGK
601 VPDACTACDL VNVDLDDCIF EQ*
```

*FIG. 25 (cont.)*

REP52AA146

```
   1 ATGGCTACCT TCTATGAAGT CATTGTTCGC GTCCCATTTG ACGTGGAGGA ACATCTGCCT GGAATTTCTG ACAGCTTTGT GGACTGGGTA ACTGGTCAAA
 101 TTTGGGAGCT GCCTCCAGAG TCAGATTTAA ATTTGACTCT GGTTGAACAG CCTCAGTTGA CGGTGGCTGA TAGAATTCGC CGCGTGTTCC TGTACGAGTG
 201 GAACAAATTT TCCAAGCAGG AGTCCAAATT CTTTGTGCAG TTTGAAAAGG GATCTGAATA TTTTCATCTG CACACGCTTG TGGAGACCTC CGGCATCTCT
 301 TCCATGGTCC TCGGCCGCTA CGTGAGTCAG ATTCGCGCCC AGCTGGTGAA AGTGGTCTTC CAGGGAATTG AACCCCAGAT CAACGACTGG GTCGCCATCA
 401 CCAAGGTAAA GAAGGGCGGA GCCAATAAGG TGGTGGATGA GTGCTACATC CCCAATTACT TGCTCCCCAA AACCCAGCCT GAGCTCCAGT GGGCGTGGAC
 501 TAATATGGAA CAGTATTTAA GCGCCTGTTT GAATCTCACG GAGCGTAAAC GGTTGGTGGC GCAGCATCTG ACGCACGTGT CGCAGACGCA GGAGCAGAAC
 601 AAAGAGAATC AGAATCCCAA TTCTGATGCG CCGGTGATCA GATCAAAAAC TTCAGCCAGG TACATGGAGC TGGTCGGGTG GCTCGTGGAC AAGGGGATTA
 701 CCTCGGAGAA GCAGTGGATC CAGGAGGACC AGGCCTCATA CATCTCCTTC AATGCGGCCT CCAACTCGCG GTCCCAAATC AAGGCTGCCT TGGACAATGC
 801 GGGAAAGATT ATGAGCCTGA CTAAAACCGC CCCCGACTAC CTGGTGGGCC AGCAGCCCGT GGAGGACATT TCCAGCAATC GGATTTATAA AATTTTGGAA
 901 CTAAACGGGT ACGATCCCCA ATATGCGGCT TCCGTCTTTC TGGGATGGGC CACGAAAAAG TTCGGCAAGA GGAACACCAT CTGGCTGTTT GGGCCTGCAA
1001 CTACCGGGAA GACCAACATC GCGGAGGCCA TAGCCCACAC TGTGCCCTTC TACGGGTGCG TAAACTGGAC CAATGAGAAC TTTCCCTTCA ACGACTGTGT
1101 CGACAAGATG GTGATCTGGT GGGAGGAGGG GAAGATGACC GCCAAGGTCG TGGAGTCGGC CAAAGCCATT CTCGGAGGAA GCAAGGTGCG CGTGGACCAG
1201 AAATGCAAGT CCTCGGCCCA GATAGACCCG ACTCCCGTGA TCGTCACCTC CAACACCAAC ATGTGCGCCG TGATTGACGG GAACTCAACG ACCTTCGAAC
1301 ACCAGCAGCC GTTGCAAGAC CGGATGTTCA AATTTGAACT CACCCGCCGT CTGGATCATG ACTTTGGGAA GGTCACCAAG CAGGAAGTCA AAGACTTTTT
1401 CCGGTGGGCA AAGGATCACG TGGTTGAGGT GGAGCATGAA TTCTACGTCA AAAAGGGTGG AGCCAAGAAA AGACCCGCCC CCAGTGACGC AGATATAAGT
1501 GAGCCCAAAC GGGTGCGCGA GTCAGTTGCG CAGCCATCGA CGTCAGACGC GGAAGCTTCG ATCAACTACG CAGACAGGTA CCAAAACAAA TGTTCTCGTC
1601 ACGTGGGCAT GAATCTGATG CTGTTTCCCT GCAGACAATG CGAGAGAATG AATCAGAATT CAAATATCTG CTTCACTCAC GGACAGAAAG ACTGTTTAGA
1701 GTGCTTTCCC GTGTCAGAAT CTCAACCCGT TTCTGTCGTC AAAAAGGCGT ATCAGAAACT GTGCTACATT CATCATATCA TGGGAAAGGT GCCAGACGCT
1801 TGCACTGCCT GCGATCTGGT CAATGTGGAT TTGGATGACT GCATCTTTGA ACAATAA

  1 MATFYEVIVR VPFDVEEHLP GISDSFVDWV TGQIWELPPE SDLNLTLVEQ PQLTVADRIR RVFLYEWNKF SKQESKFFVQ FEKGSEYFHL HTLVETSGIS
101 SMVLGRYVSQ IRAQLVKVVF QGIEPQINDW VAITKVKKGG ANKVVDECYI PNYLLPKTQP ELQWAWTNME QYLSACLNLT ERKRLVAQHL THVSQTQEQN
201 KENQNPNSDA PVIRSKTSAR YMELVGWLVD KGITSEKQWI QEDQASYISF NAASNSRSQI KAALDNAGKI MSLTKTAPDY LVGQQPVEDI SSNRIYKILE
301 LNGYDPQYAA SVFLGWATKK FGKRNTIWLF GPATTGKTNI AEAIAHTVPF YGCVNWTNEN FPFNDCVDKM VIWWEEGKMT AKVVESAKAI LGGSKVRVDQ
401 KCKSSAQIDP TPVIVTSNTN MCAVIDGNST TFEHQQPLQD RMFKFELTRR LDHDFGKVTK QEVKDFFRWA KDHVVEVEHE FYVKKGGAKK RPAPSDADIS
501 EPKRVRESVA QPSTSDAEAS INYADRYQNK CSRHVGMNLM LFPCRQCERM NQNSNICFTH GQKDCLECFP VSESQPVSVV KKAYQKLCYI HHIMGKVPDA
601 CTACDLVNVD LDDCIFEQ*
```

*FIG. 26*

REP52AA147

```
   1 ATGGCTACCT TCTATGAAGT CATTGTTCGC GTCCCATTTG ACGTGGAGGA ACATCTGCCT GGAATTTCTG ACAGCTTTGT GGACTGGGTA ACTGGTCAAA
 101 TTTGGGAGCT GCCTCCAGAG TCAGATTTAA ATTTGACTCT GGTTGAACAG CCTCAGTTGA CGGTGGCTGA TAGAATTCGC CGCGTGTTCC TGTACGAGTG
 201 GAACAAATTT TCCAAGCAGG AGTCCAAATT CTTTGTGCAG TTTGAAAAGG GATCTGAATA TTTTCATCTG CACACGCTTG TGGAGACCTC CGGCATCTCT
 301 TCCATGGTCC TCGGCCGCTA CGTGAGTCAG ATTCGCGCCC AGCTGGTGAA AGTGGTCTTC CAGGGAATTG AACCCCAGAT CAACGACTGG GTCGCCATCA
 401 CCAAGGTAAA GAAGGGCGGA GCCAATAAGG TGGTGGATTC TTGCTACATC CCCAATTACT TGCTCCCCAA AACCCAGCCT GAGCTCCAGT GGGCGTGGAC
 501 TAATATGGAA CAGTATTTAA GCGCCTGTTT GAATCTCACG GAGCGTAAAC GGTTGGTGGC GCAGCATCTG ACGCACGTGT CGCAGACGCA GGAGCAGAAC
 601 AAAGAGAATC AGAATCCCAA TTCTGATGCG CCGGTGATCA GATCAAAAAC TTCAGCCAGG TACATGGAGC TGGTCGGGTG GCTCGTGGAC AAGGGGATTA
 701 CCTCGGAGAA GCAGTGGATC CAGGAGGACC AGGCCTCATA CATCTCCTTC AATGCGGCCT CCAACTCGCG GTCCCAAATC AAGGCTGCCT TGGACAATGC
 801 GGGAAAGATT ATGAGCCTGA CTAAAACCGC CCCCGACTAC CTGGTGGGCC AGCAGCCCGT GGAGGACATT TCCAGCAATC GGATTTATAA AATTTTGGAA
 901 CTAAACGGGT ACGATCCCCA ATATGCGGCT TCCGTCTTTC TGGGATGGGC CACGAAAAAG TTCGGCAAGA GGAACACCAT CTGGCTGTTT GGGCCTGCAA
1001 CTACCGGGAA GACCAACATC GCGGAGGCCA TAGCCCACAC TGTGCCCTTC TACGGGTGCG TAAACTGGAC CAATGAGAAC TTTCCCTTCA ACGACTGTGT
1101 CGACAAGATG GTGATCTGGT GGGAGGAGGG GAAGATGACC GCCAAGGTCG TGGAGTCGGC CAAAGCCATT CTCGGAGGAA GCAAGGTGCG CGTGGACCAG
1201 AAATGCAAGT CCTCGGCCCA GATAGACCCG ACTCCCGTGA TCGTCACCTC CAACACCAAC ATGTGCGCCG TGATTGACGG GAACTCAACG ACCTTCGAAC
1301 ACCAGCAGCC GTTGCAAGAC CGGATGTTCA AATTTGAACT CACCCGCCGT CTGGATCATG ACTTTGGGAA GGTCACCAAG CAGGAAGTCA AAGACTTTTT
1401 CCGGTGGGCA AAGGATCACG TGGTTGAGGT GGAGCATGAA TTCTACGTCA AAAAGGGTGG AGCCAAGAAA AGACCCGCCC CCAGTGACGC AGATATAAGT
1501 GAGCCCAAAC GGGTGCGCGA GTCAGTTGCG CAGCCATCGA CGTCAGACGC GGAAGCTTCG ATCAACTACG CAGACAGGTA CCAAAACAAA TGTTCTCGTC
1601 ACGTGGGCAT GAATCTGATG CTGTTTCCCT GCAGACAATG CGAGAGAATG AATCAGAATT CAAATATCTG CTTCACTCAC GGACAGAAAG ACTGTTTAGA
1701 GTGCTTTCCC GTGTCAGAAT CTCAACCCGT TTCTGTCGTC AAAAAGGCGT ATCAGAAACT GTGCTACATT CATCATATCA TGGGAAAGGT GCCAGACGCT
1801 TGCACTGCCT GCGATCTGGT CAATGTGGAT TTGGATGACT GCATCTTTGA ACAATAA

   1 MATFYEVIVR VPFDVEEHLP GISDSFVDWV TGQIWELPPE SDLNLTLVEQ PQLTVADRIR RVFLYEWNKF SKQESKFFVQ FEKGSEYFHL HTLVETSGIS
 101 SMVLGRYVSQ IRAQLVKVVF QGIEPQINDW VAITKVKKGG ANKVVDSCYI PNYLLPKTQP ELQWAWTNME QYLSACLNLT ERKRLVAQHL THVSQTQEQN
 201 KENQNPNSDA PVIRSKTSAR YMELVGWLVD KGITSEKQWI QEDQASYISF NAASNSRSQI KAALDNAGKI MSLTKTAPDY LVGQQPVEDI SSNRIYKILE
 301 LNGYDPQYAA SVFLGWATKK FGKRNTIWLF GPATTGKTNI AEAIAHTVPF YGCVNWTNEN FPFNDCVDKM VIWWEEGKMT AKVVESAKAI LGGSKVRVDQ
 401 KCKSSAQIDP TPVIVTSNTN MCAVIDGNST TFEHQQPLQD RMFKFELTRR LDHDFGKVTK QEVKDFFRWA KDHVVEVEHE FYVKKGGAKK RPAPSDADIS
 501 EPKRVRESVA QPSTSDAEAS INYADRYQNK CSRHVGMNLM LFPCRQCERM NQNSNICFTH GQKDCLECFP VSESQPVSVV KKAYQKLCYI HHIMGKVPDA
 601 CTACDLVNVD LDDCIFEQ*
```

FIG. 27

REP 52AA151

```
   1 ATGGCTACCT TCTATGAAGT CATTGTTCGC GTCCCATTTG ACGTGGAGGA ACATCTGCCT GGAATTTCTG ACAGCTTTGT GGACTGGGTA ACTGGTCAAA
 101 TTTGGGAGCT GCCTCCAGAG TCAGATTTAA ATTTGACTCT GGTTGAACAG CCTCAGTTGA CGGTGGCTGA TAGAATTCGC CGCGTGTTCC TGTACGAGTG
 201 GAACAAATTT TCCAAGCAGG AGTCCAAATT CTTTGTGCAG TTTGAAAAGG GATCTGAATA TTTTCATCTG CACACGCTTG TGGAGACCTC CGGCATCTCT
 301 TCCATGGTCC TCGGCCGCTA CGTGAGTCAG ATTCGCGCCC AGCTGGTGAA AGTGGTCTTC CAGGGAATTG AACCCCAGAT CAACGACTGG GTCGCCATCA
 401 CCAAGGTAAA GAAGGGCGGA GCCAATAAGG TGGTGGATTC TGGGTATATT CCCAATTACT TGCTCCCCAA AACCCAGCCT GAGCTCCAGT GGGCGTGGAC
 501 TAATATGGAA CAGTATTTAA GCGCCTGTTT GAATCTCACG GAGCGTAAAC GGTTGGTGGC GCAGCATCTG ACGCACGTGT CGCAGACGCA GGAGCAGAAC
 601 AAAGAGAATC AGAATCCCAA TTCTGATGCG CCGGTGATCA GATCAAAAAC TTCAGCCAGG TACATGGAGC TGGTCGGGTG GCTCGTGGAC AAGGGGATTA
 701 CCTCGGAGAA GCAGTGGATC CAGGAGGACC AGGCCTCATA CATCTCCTTC AATGCGGCCT CCAACTCGCG GTCCCAAATC AAGGCTGCCT TGGACAATGC
 801 GGGAAAGATT ATGAGCCTGA CTAAAACCGC CCCCGACTAC CTGGTGGGCC AGCAGCCCGT GGAGGACATT TCCAGCAATC GGATTTATAA AATTTTGGAA
 901 CTAAACGGGT ACGATCCCCA ATATGCGGCT TCCGTCTTTC TGGGATGGGC CACGAAAAAG TTCGGCAAGA GGAACACCAT CTGGCTGTTT GGGCCTGCAA
1001 CTACCGGGAA GACCAACATC GCGGAGGCCA TAGCCCACAC TGTGCCCTTC TACGGGTGCG TAAACTGGAC CAATGAGAAC TTTCCCTTCA ACGACTGTGT
1101 CGACAAGATG GTGATCTGGT GGGAGGAGGG GAAGATGACC GCCAAGGTCG TGGAGTCGGC CAAAGCCATT CTCGGAGGAA GCAAGGTGCG CGTGGACCAG
1201 AAATGCAAGT CCTCGGCCCA GATAGACCCG ACTCCCGTGA TCGTCACCTC CAACACCAAC ATGTGCGCCG TGATTGACGG GAACTCAACG ACCTTCGAAC
1301 ACCAGCAGCC GTTGCAAGAC CGGATGTTCA AATTTGAACT CACCCGCCGT CTGGATCATG ACTTTGGGAA GGTCACCAAG CAGGAAGTCA AAGACTTTTT
1401 CCGGTGGGCA AAGGATCACG TGGTTGAGGT GGAGCATGAA TTCTACGTCA AAAAGGGTGG AGCCAAGAAA AGACCCGCCC CCAGTGACGC AGATATAAGT
1501 GAGCCCAAAC GGGTGCGCGA GTCAGTTGCG CAGCCATCGA CGTCAGACGC GGAAGCTTCG ATCAACTACG CAGACAGGTA CCAAAACAAA TGTTCTCGTC
1601 ACGTGGGCAT GAATCTGATG CTGTTTCCCT GCAGACAATG CGAGAGAATG AATCAGAATT CAAATATCTG CTTCACTCAC GGACAGAAAG ACTGTTTAGA
1701 GTGCTTTCCC GTGTCAGAAT CTCAACCCGT TTCTGTCGTC AAAAAGGCGT ATCAGAAACT GTGCTACATT CATCATATCA TGGGAAAGGT GCCAGACGCT
1801 TGCACTGCCT GCGATCTGGT CAATGTGGAT TTGGATGACT GCATCTTTGA ACAATAA

   1 MATFYEVIVR VPFDVEEHLP GISDSFVDWV TGQIWELPPE SDLNLTLVEQ PQLTVADRIR RVFLYEWNKF SKQESKFFVQ FEKGSEYFHL HTLVETSGIS
 101 SMVLGRYVSQ IRAQLVKVVF QGIEPQINDW VAITKVKKGG ANKVVDSGYI PNYLLPKTQP ELQWAWTNME QYLSACLNLT ERKRLVAQHL THVSQTQEQN
 201 KENQNPNSDA PVIRSKTSAR YMELVGWLVD KGITSEKQWI QEDQASYISF NAASNSRSQI KAALDNAGKI MSLTKTAPDY LVGQQPVEDI SSNRIYKILE
 301 LNGYDPQYAA SVFLGWATKK FGKRNTIWLF GPATTGKTNI AEAIAHTVPF YGCVNWTNEN FPFNDCVDKM VIWWEEGKMT AKVVESAKAI LGGSKVRVDQ
 401 KCKSSAQIDP TPVIVTSNTN MCAVIDGNST TFEHQQPLQD RMFKFELTRR LDHDFGKVTK QEVKDFFRWA KDHVVEVEHE FYVKKGGAKK RPAPSDADIS
 501 EPKRVRESVA QPSTSDAEAS INYADRYQNK CSRHVGMNLM LFPCRQCERM NQNSNICFTH GQKDCLECFP VSESQPVSVV KKAYQKLCYI HHIMGKVPDA
 601 CTACDLVNVD LDDCIFEQ*
```

*FIG. 28*

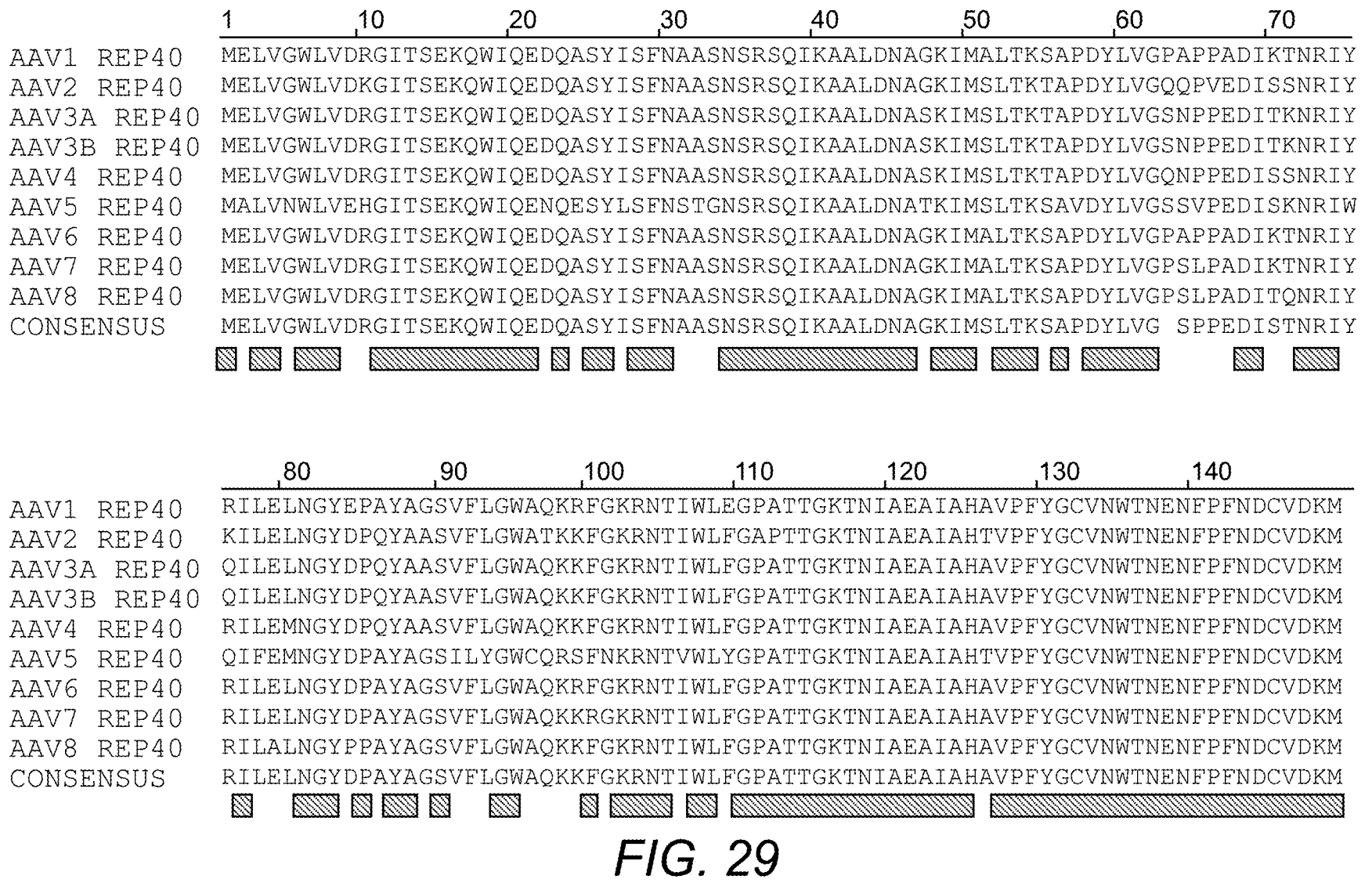

| | 1 10 20 30 40 50 60 70 |
|---|---|
| AAV1 REP40 | MELVGWLVDRGITSEKQWIQEDQASYISFNAASNSRSQIKAALDNAGKIMALTKSAPDYLVGPAPPADIKTNRIY |
| AAV2 REP40 | MELVGWLVDKGITSEKQWIQEDQASYISFNAASNSRSQIKAALDNAGKIMSLTKTAPDYLVGQQPVEDISSNRIY |
| AAV3A REP40 | MELVGWLVDRGITSEKQWIQEDQASYISFNAASNSRSQIKAALDNASKIMSLTKTAPDYLVGSNPPEDITKNRIY |
| AAV3B REP40 | MELVGWLVDRGITSEKQWIQEDQASYISFNAASNSRSQIKAALDNASKIMSLTKTAPDYLVGSNPPEDITKNRIY |
| AAV4 REP40 | MELVGWLVDRGITSEKQWIQEDQASYISFNAASNSRSQIKAALDNASKIMSLTKTAPDYLVGQNPPEDISSNRIY |
| AAV5 REP40 | MALVNWLVEHGITSEKQWIQENQESYLSFNSTGNSRSQIKAALDNATKIMSLTKSAVDYLVGSSVPEDISKNRIW |
| AAV6 REP40 | MELVGWLVDRGITSEKQWIQEDQASYISFNAASNSRSQIKAALDNAGKIMALTKSAPDYLVGPAPPADIKTNRIY |
| AAV7 REP40 | MELVGWLVDRGITSEKQWIQEDQASYISFNAASNSRSQIKAALDNAGKIMALTKSAPDYLVGPSLPADIKTNRIY |
| AAV8 REP40 | MELVGWLVDRGITSEKQWIQEDQASYISFNAASNSRSQIKAALDNAGKIMALTKSAPDYLVGPSLPADITQNRIY |
| CONSENSUS | MELVGWLVDRGITSEKQWIQEDQASYISFNAASNSRSQIKAALDNAGKIMSLTKSAPDYLVG SPPEDISTNRIY |

| | 80 90 100 110 120 130 140 |
|---|---|
| AAV1 REP40 | RILELNGYEPAYAGSVFLGWAQKRFGKRNTIWLEGPATTGKTNIAEAIAHAVPFYGCVNWTNENFPFNDCVDKM |
| AAV2 REP40 | KILELNGYDPQYAASVFLGWATKKFGKRNTIWLFGAPTTGKTNIAEAIAHTVPFYGCVNWTNENFPFNDCVDKM |
| AAV3A REP40 | QILELNGYDPQYAASVFLGWAQKKFGKRNTIWLFGPATTGKTNIAEAIAHAVPFYGCVNWTNENFPFNDCVDKM |
| AAV3B REP40 | QILELNGYDPQYAASVFLGWAQKKFGKRNTIWLFGPATTGKTNIAEAIAHAVPFYGCVNWTNENFPFNDCVDKM |
| AAV4 REP40 | RILEMNGYDPQYAASVFLGWAQKKFGKRNTIWLFGPATTGKTNIAEAIAHAVPFYGCVNWTNENFPFNDCVDKM |
| AAV5 REP40 | QIFEMNGYDPAYAGSILYGWCQRSFNKRNTVWLYGPATTGKTNIAEAIAHTVPFYGCVNWTNENFPFNDCVDKM |
| AAV6 REP40 | RILELNGYDPAYAGSVFLGWAQKRFGKRNTIWLFGPATTGKTNIAEAIAHAVPFYGCVNWTNENFPFNDCVDKM |
| AAV7 REP40 | RILELNGYDPAYAGSVFLGWAQKKRGKRNTIWLFGPATTGKTNIAEAIAHAVPFYGCVNWTNENFPFNDCVDKM |
| AAV8 REP40 | RILALNGYPPAYAGSVFLGWAQKKFGKRNTIWLFGPATTGKTNIAEAIAHAVPFYGCVNWTNENFPFNDCVDKM |
| CONSENSUS | RILELNGYDPAYAGSVFLGWAQKKFGKRNTIWLFGPATTGKTNIAEAIAHAVPFYGCVNWTNENFPFNDCVDKM |

FIG. 29

```
             150       160       170       180       190       200       210       220
AAV1 REP40   VIWWEEGKMTAKVVESAKAILGGSKVRVDQKCKSSAQIDPTPVIVTSNTNMCAVIDGNSTTFEHQQPLQDRMFKF
AAV2 REP40   VIWWEEGKMTAKVVESAKAILGGSKVRVDQKCKSSAQIDPTPVIVTSNTNMCAVIDGNSTTFEHQQPLQDRMFKF
AAV3A REP40  VIWWEEGKMTAKVVESAKAILGGSKVRVDQKCKSSAQIEPTPVIVTSNTNMCAVIDGNSTTFEHQQPLQDRMFEF
AAV3B REP40  VIWWEEGKMTAKVVESAKAILGGSKVRVDQKCKSSAQIEPTPVIVTSNTNMCAVIDGNSTTFEHQQPLQDRMFKF
AAV4 REP40   VIWWEEGKMTAKVVESAKAILGGSKVRVDQKCKSSAQIDPTPVIVTSNTNMCAVIDGNSTTFEHQQPLQDRMFKF
AAV5 REP40   LIWWEEGKMTNKVVESAKAILGGSKVRVDQKCKSSVQIDSTPVIVTSNTNMCVVVDGNSTTFEHQQPLEDRMFKF
AAV6 REP40   VIWWEEGKMTAKVVESAKAILGGSKVRVDQKCKSSAQIDPTPVIVTSNTNMCAVIDGNSTTFEHQQPLQDRMFKF
AAV7 REP40   VIWWEEGKMTAKVVESAKAILGGSKVRVDQKCKSSAQIDPTPVIVTSNTNMCAVIDGNSTTFEHQQPLQDRMFKF
AAV8 REP40   VIWWEEGKMTAKVVESAKAILGGSKVRVDQKCKSSAQIDPTPVIVTSNTNMCAVIDGNSTTFEHQQPLQDRMFKF
CONSENSUS    VIWWEEGKMTAKVVESAKAILGGSKVRVDQKCKSSAQIDPTPVIVTSNTNMCAVIDGNSTTFEHQQPLQDRMFKF

                 230       240       250       260       270       280       290
AAV1 REP40   ELTRRLEHDFGKVTKQEVKEFFRWAQDHVTEVAHEFYVR------KGGAN--KRPAPDDADKSEP-----KRACP
AAV2 REP40   ELTRRLDHDFGKVTKQEVKDFFRWAKDHVVEVEHEFYVK------KGGAK--KRPAPSDADISEP-----KRVRE
AAV3A REP40  ELTRRLDHDFGKVTKQEVKDFFRWASDHVTDVAHEFYVR------KGGAK--KRPASNDADVSEP-----KRECT
AAV3B REP40  ELTRRLDHDFGKVTKQEVKDFFRWASDHVTDVAHEFYVR------KGGAK--KRPASNDADVSEP-----KRQCT
AAV4 REP40   ELTKRLEHDFGKVTKQEVKDFFRWASDHVTEVTHEFYVR------KGGAR--KRPAPNDADISEP-----KRACP
AAV5 REP40   ELTKRLPPDFGKITKQEVKDFFAWAKVNQVPVTHEFKVPRELAGTKGAEKSLKRPLGDVTNTSYKSLEKRARLSF
AAV6 REP40   ELTRRLEHDFGKVTKQEVKEFFRWAQDHVTEVAHEFYVR------KGGAN--KRPAPDDADKSEP-----KRACP
AAV7 REP40   ELTRRLEHDFGKVTKQEVKEFFRWASDHVTEVAHEFYVR------KGGAS--KRPAPDDADISEP-----KRACP
AAV8 REP40   ELTRRLEHDFGKVTKQEVKEFFRWASDHVTEVAHEFYVR------KGGAS--KRPAPDDADKSEP-----KRACP
CONSENSUS    ELTRRLEHDFGKVTKQEVKDFFRWASDHVTEVAHEFYVR------KGGAK--KRPAPDDADISEP-----KRACP
```

FIG. 29 (cont.)

| | 300 310 329 | |
|---|---|---|
| AAV1 REP40 | SVADPSTSDAEGAPVDFADLARGQPL---- | (SEQ ID NO:84) |
| AAV2 REP40 | SVAQPSTSDAE-ASINYADLARGHSL---- | (SEQ ID NO:85) |
| AAV3A REP40 | SLAQPTTSDAE-APADYADLARGQPF---- | (SEQ ID NO:86) |
| AAV3B REP40 | SLAQPTTSDAE-APADYADLARGQPF---- | (SEQ ID NO:87) |
| AAV4 REP40 | SVAQPSTSDAE-APVDYADLARGQPL---- | (SEQ ID NO:88) |
| AAV5 REP40 | VPETPRSSDVTVDPAPLRPLNWNSLVGPSW | (SEQ ID NO:89) |
| AAV6 REP40 | SVADPSTSDAEGAPVDFADLARGQPL---- | (SEQ ID NO:90) |
| AAV7 REP40 | SVADPSTSDAEGAPVDFADLARGQPL---- | (SEQ ID NO:91) |
| AAV8 REP40 | SVADPSTSDAEGAPVDFADLARGQPL---- | (SEQ ID NO:92) |
| CONSENSUS | SVA PSTSDAE APVDFADLARGQPL | (SEQ ID NO:93) |

FIG. 29 (cont.)

| | 1 10 20 30 40 50 60 70 |
|---|---|
| AAV1 REP52 | MELVGWLVDRGITSEKQWIQEDQASYISFNAASNSRSQIKAALDNAGKIMALTKSAPDYLVGPAPPADIKTNRI |
| AAV2 REP52 | MELVGWLVDKGITSEKQWIQEDQASYISFNAASNSRSQIKAALDNAGKIMSLTKTAPDYLVGQQPVEDISSNRI |
| AAV3A REP52 | MELVGWLVDRGITSEKQWIQEDQASYISFNAASNSRSQIKAALDNASKIMSLTKTAPDYLVGSNPPEDITKNRI |
| AAV3B REP52 | MELVGWLVDRGITSEKQWIQEDQASYISFNAASNSRSQIKAALDNASKIMSLTKTAPDYLVGSNPPEDITKNRI |
| AAV4 REP52 | MELVGWLVDRGITSEKQWIQEDQASYISFNAASNSRSQIKAALDNASKIMSLTKTAPDYLVGQNPPEDISSNRI |
| AAV5 REP52 | MALVNWLVEHGITSEKQWIQENQESYLSFNSTGNSRSQIKAALDNATKIMSLTKSAVDYLVGSSVPEDISKNRI |
| AAV6 REP52 | MELVGWLVDRGITSEKQWIQEDQASYISFNAASNSRSQIKAALDNAGKIMALTKSAPDYLVGPAPPADIKTNRI |
| AAV7 REP52 | MELVGWLVDRGITSEKQWIQEDQASYISFNAASNSRSQIKAALDNAGKIMALTKSAPDYLVGPSLPADIKTNRI |
| AAV8 REP52 | MELVGWLVDRGITSEKQWIQEDQASYISFNAASNSRSQIKAALDNAGKIMALTKSAPDYLVGPSLPADITQNRI |
| CONSENSUS | MELVGWLVDRGITSEKQWIQEDQASYISFNAASNSRSQIKAALDNAGKIMSLTKSAPDYLVG SPPEDISTNRI |

FIG. 30

| | 80 90 100 110 120 130 140 |
|---|---|
| AAV1 REP52 | YRILELNGYEPAYAGSVFLGWAQKRFGKRNTIWLFGPATTGKTNIAEAIAHAVPFYGCVNWTNENFPFNDCVDKM |
| AAV2 REP52 | YKILELNGYDPQYAASVFLGWATKKFGKRNTIWLFGPATTGKTNIAEAIAHTVPFYGCVNWTNENFPFNDCVDKM |
| AAV3A REP52 | YQILELNGYDPQYAASVFLGWAQKKFGKRNTIWLFGPATTGKTNIAEAIAHAVPFYGCVNWTNENFPFNDCVDKM |
| AAV3B REP52 | YQILELNGYDPQYAASVFLGWAQKKFGKRNTIWLFGPATTGKTNIAEAIAHAVPFYGCVNWTNENFPFNDCVDKM |
| AAV4 REP52 | YRILEMNGYDPQYAASVFLGWAQKKFGKRNTIWLFGPATTGKTNIAEAIAHAVPFYGCVNWTNENFPFNDCVDKM |
| AAV5 REP52 | WQIFEMNGYDPAYAGSILYGWCQRSFNKRNTVWLYGPATTGKTNIAEAIAHTVPFYGCVNWTNENFPFNDCVDKM |
| AAV6 REP52 | YRILELNGYDPAYAGSVFLGWAQKRFGKRNTIWLFGPATTGKTNIAEAIAHAVPFYGCVNWTNENFPFNDCVDKM |
| AAV7 REP52 | YRILELNGYDPAYAGSVFLGWAQKKFGKRNTIWLFGPATTGKTNIAEAIAHAVPFYGCVNWTNENFPFNDCVDKM |
| AAV8 REP52 | YRILALNGYDPAYAGSVFLGWAQKKFGKRNTIWLFGPATTGKTNIAEAIAHAVPFYGCVNWTNENFPFNDCVDKM |
| CONSENSUS | YRILELNGYDPAYAGSVFLGWAQKKFGKRNTIWLFGPATTGKTNIAEAIAHAVPFYGCVNWTNENFPFNDCVDKM |

| | 150 160 170 180 190 200 210 220 |
|---|---|
| AAV1 REP52 | VIWWEEGKMTAKVVESAKAILGGSKVRVDQKCKSSAQIDPTPVIVTSNTNMCAVIDGNSTTFEHQQPLQDRMFKF |
| AAV2 REP52 | VIWWEEGKMTAKVVESAKAILGGSKVRVDQKCKSSAQIDPTPVIVTSNTNMCAVIDGNSTTFEHQQPLQDRMFKF |
| AAV3A REP52 | VIWWEEGKMTAKVVESAKAILGGSKVRVDQKCKSSAQIEPTPVIVTSNTNMCAVIDGNSTTFEHQQPLQDRMFEF |
| AAV3B REP52 | VIWWEEGKMTAKVVESAKAILGGSKVRVDQKCKSSAQIEPTPVIVTSNTNMCAVIDGNSTTFEHQQPLQDRMFKF |
| AAV4 REP52 | VIWWEEGKMTAKVVESAKAILGGSKVRVDQKCKSSAQIDPTPVIVTSNTNMCAVIDGNSTTFEHQQPLQDRMFKF |
| AAV5 REP52 | LIWWEEGKMTNKVVESAKAILGGSKVRVDQKCKSSVQIDSTPVIVTSNTNMCVVVDGNSTTFEHQQPLEDRMFKF |
| AAV6 REP52 | VIWWEEGKMTAKVVESAKAILGGSKVRVDQKCKSSAQIDPTPVIVTSNTNMCAVIDGNSTTFEHQQPLQDRMFKF |
| AAV7 REP52 | VIWWEEGKMTAKVVESAKAILGGSKVRVDQKCKSSAQIDPTPVIVTSNTNMCAVIDGNSTTFEHQQPLQDRMFKF |
| AAV8 REP52 | VIWWEEGKMTAKVVESAKAILGGSKVRVDQKCKSSAQIDPTPVIVTSNTNMCAVIDGNSTTFEHQQPLQDRMFKF |
| CONSENSUS | VIWWEEGKMTAKVVESAKAILGGSKVRVDQKCKSSAQIDPTPVIVTSNTNMCAVIDGNSTTFEHQQPLQDRMFKF |

FIG. 30 (cont.)

```
                 230       240       250       260       270       280       290
AAV1 REP52   ELTRRLEHDFGKVTKQEVKEFFRWAQDHVTEVAHEFYVR------KGGAN--KRPAPDDADKSEP---KRA----
AAV2 REP52   ELTRRLDHDFGKVTKQEVKDFFRWAKDHVVEVEHEFYVK======KGGAK--KRPAPSDADISEP---KRV----
AAV3A REP52  ELTRRLDHDFGKVTKQEVKDFFRWASDHVTDVAHEFYVR------KGGAK--KRPASNDADVSEP---KRE----
AAV3B REP52  ELTRRLDHDFGKVTKQEVKDFFRWASDHVTDVAHEFYVR------KGGAK--KRPASNDADVSEP---KRQ----
AAV4 REP52   ELTKRLEHDFGKVTKQEVKDFFRWASDHVTEVTHEFYVR------KGGAR--KRPAPNDADISEP---KRA----
AAV5 REP52   ELTKRLPPDFGKITKQEVKDFFAWAKVNQVPVTHEFKVPRELAGTKGAEKSLKRPLGDVTNTSYKSLEKRARLSF
AAV6 REP52   ELTRRLEHDFGKVTKQEVKEFFRWAQDHVTEVAHEFYVR------KGGAN--KRPAPDDADKSEP---KAR----
AAV7 REP52   ELTRRLEHDFGKVTKQEVKEFFRWASDHVTEVAHEFYVR------KGGAS--KRPAPDDADISEP---KRA----
AAV8 REP52   ELTRRLEHDFGKVTKQEVKEFFRWASDHVTEVAHEFYVR------KGGAS--KRPAPDDADKSEP---KRA----
CONSENSUS    ELTRRLEHDFGKVTKQEVKDFFRWASDHVTEVAHEFYVR      KGGAK  KRPAPDDADISEP   KRA

               300       310       320       330       340       350       360
AAV1 REP52   ---CPSVADPSTSDAEGAPVDFADRYQNKCSRHAGMLQMLFPCKTCERMNQNFNICFTHGTRDCSECFPG
AAV2 REP52   ---RESVAQPSTSDAE-ASINYADRYQNKCSRHVGMNLMLFPCRQCERMNQNSNICFTHGQKDCLECFPV
AAV3A REP52  ---CTSLAQPTTSDAE-APADYADRYQNKCSRHVGMNLMLFPCKTCERMNQISNVCFTHGQRDCGECFPG
AAV3B REP52  ---CTSLAQPTTSDAE-APADYADRYQNKCSRHVGMNLMLFPCKTCERMNQISNVCFTHGQRDCGECFPG
AAV4 REP52   ---CPSVAQPSTSDAE-APVDYADRYQNKCSRHVGMNLMLFPCRQCERMNQNVDICFTHGVMDCAECFPV
AAV5 REP52   VPETPRSSDVTVDPAPLRPLNWNSRYDCKCDYHAQFDNISNKCDECEYLNRGKNGCICHNVTHCQICHGI
AAV6 REP52   ---CPSVADPSTSDAEGAPVDFADRYQNKCSRHAGMLQMLFPCKTCERMNQNFNICFTHGTRDCSECFPG
AAV7 REP52   ---CPSVADPSTSDAEGAPVDFADRYQNKCSFHAGMIQMLFPCKTCERMNQNFNICFTHGVRDCLECFPG
AAV8 REP52   ---CPSVADPSTSDAEGAPVDFADRYQNKCSRHAGMLQMLFPCKTCERMNQNFNICFTHGVRDCSECFPG
CONSENSUS       CPSVADPSTSDAE APVDFADRYQNKCSRHAGM QMLFPCKTCERMNQN NICFTHG RDC ECFPG
```

FIG. 30 (cont.)

```
             370       380       390       400       410       420
AAV1 REP52   VSESQ--PVVRKRTYRKLCAIHHLLGRAPEIACSACDLVNVDLDDCVSEQ- (SEQ ID NO:94)
AAV2 REP52   S-ESQPVSVVKK-AYQKLCYIHHIMGKVPD-ACTACDLVNVDLDDCIFEQ- (SEQ ID NO:96)
AAV3A REP52  MSESQPVSVVKKKTYQKLCPIHHILGRAPEIACSACDLANVDLDDCVSEQ- (SEQ ID NO:97)
AAV3B REP52  MSESQPVSVVKKKTYQKLCPIHHILGRAPEIACSACDLANVDLDDCVSEQ- (SEQ ID NO:98)
AAV4 REP52   S-ESQPVSVVRKRTYQKLCPIHHIMGRAPEVACSACELANVDLDDCDMEQ- (SEQ ID NO:99)
AAV5 REP52   P-------------------PWEK--ENLS------DFG--DFDDANKEQ- (SEQ ID NO:100)
AAV6 REP52   VSESQ--PVVRKRTYRKLCAIHHLLGRAPEIACSACDLVNVDLDDCVSEQ- (SEQ ID NO:101)
AAV7 REP52   VSESQ--PVVRKKTYRKLCAIHHLLGRAPEIACSACDLVNVDLDDCVSEQ- (SEQ ID D NO:95)
AAV8 REP52   VSESQ--PVVRKRTYRKLCAIHHLLGRAPEIACSACDLVNVDLDDCVSEQ- (SEQ ID NO:102)
CONSENSUS    VSESQ   VVRKRTY KLC IHHILGRAPEIACSACDLVNVDLDDCVSEQ  (SEQ ID NO:103)
```

FIG. 30 (cont.)

```
             1        10        20        30        40        50        60        70
AAV1 REP68   MPGFYEIVIKVPSDLDEHLPGISDSFVSWVAEKEWELPPDSDMDLNLIEQAPLTVAEKLQRDFLVQWRRVSKAP
AAV2 REP68   MPGFYEIVIKVPSDLDEHLPGISDSFVNWVAEKEWELPPDSDMDLNLIEQAPLTVAEKLQRDFLTEWRRVSKAP
AAV3A REP68  MPGFYEIVLKVPSDLDERLPGISNSFVNWVAEKEWDVPPDSDMDPNLIEQAPLTVAEKLQREFLVEWRRVSKAP
AAV3B REP68  MPGFYEIVLKVPSDLDEHLPGISNSFVNWVAEKEWELPPDSDMDPNLIEQAPLTVAEKLQREFLVEWRRVSKAP
AAV4 REP68   MPGFYEIVLKVPSDLDEHLPGISDSFVSWVAEKEWELPPDSDMDLNLIEQAPLTVAEKLQREFLVEWRRVSKAP
AAV5 REP68   MATFYEVIVRVPFDVEEHLPGISDSFVDWVTGQIWELPPESDLNLTLVEQPQLTVADRIRRVFLYEWNKFSKQ-
AAV6 REP68   MPGFYEIVIKVPSDLDEHLPGISDSFVNWVAEKEWELPPDSDMDLNLIEQAPLTVAEKLQRDFLVQWRRVSKAP
AAV7 REP68   MPGFYEIVIKVPSDLDEHLPGISDSFVNWVAEKEWELPPDSDMDLNLIEQAPLTVAEKLQRDFLVQWRRVSKAP
AAV8 REP68   MPGFYEIVIKVPSDLDEHLPGISDSFVNWVAEKEWELPPDSDMDRNLIEQAPLTVAEKLQRDFLVQWRRVSKAP
```

FIG. 31

```
            80        90        100       110       120       130       140
AAV1  REP68 FALFFVQFEKGESYFHLHILVETTGVKSMVLGRFLSQIRDKLVQTIYRG-IEPTLPNWFAVTKTRNGAGGG-NKV
AAV2  REP68 EALFFVQFEKGESYFHMHVLVETTGVKSMVLGRFLSQIREKLIQRIYRG-IEPTLPNWFAVTKTRNGAGGG-NKV
AAV3A REP68 EALFFVQFEKGETYFHLHVLIETIGVKSMVVGRYVSQIKEKLVTRIYRG-VEPQLPNWFAVTKTRNGAGGG-NKV
AAV3B REP68 EALFFVQFEKGETYFHLHVLIETIGVKSMVVGRYVSQIKEKLVTRIYRG-VEPQLPNWFAVTKTRNGAGGG-NKV
AAV4  REP68 EALFFVQFEKGDSYFHLHILVETVGVKSMVVGRYVSQIKEKLVTRIYRG-VEPQLPNWFAVTKTRNGAGGG-NKV
AAV5  REP68 ESKFFVQFEKGSEYFHLHTLVETSGISSMVLGRYVSQIRAQLVKVVFQG-IEPQINDWVAITKVKK---GGANKV
AAV6  REP68 EALFFVQFEKGESYFHLHILVETTGVKSMVLGRFLSQIRDKLVQTIYRG-IEPTLPNWFAVTKTRNGAGGG-NKV
AAV7  REP68 EALFFVQFEKGESYFHLHVLVETTGVKSMVLGRFLSQIREKLVQTIYRG-VEPTLPNWFAVTKTRNGAGGG-NKV
AAV8  REP68 EALFFVQFELGESYFHLHVLVETTGVKSMVLGRFLSQIREKLGPDHLPAGSSPTLPNWFAVTKDAVMAPAGGNKV

            150       160       170       180       190       200       210       220
AAV1  REP68 VDECYIPNYLLPKTQPELQWAWTNMEEYISACLNLAERKRLVAQHLTHVSQTQEQNKENLNPNSDAPVIRSKTSA
AAV2  REP68 VDECYIPNYLLPKTQPELQWAWTNMEQYLSACLNLTERKRLVAQHLTHVSQTQEQNKENQNPNSDAPVIRSKTSA
AAV3A REP68 VDDCYIPNYLLPKTQPELQWAWTNMDQYLSACLNLAERKRLVAQHLTHVSQTQEQNKENQNPNSDAPVIRSKTSA
AAV3B REP68 VDDCYIPNYLLPKTQPELQWAWTNMDQYLSACLNLAERKRLVAQHLTHVSQTQEQNKENQNPNSDAPVIRSKTSA
AAV4  REP68 VDDCYIPNYLLPKTQPELQWAWTNMDQYISACLNLAERKRLVAQHLTHVSQTQEQNKENQNPNSDAPVIRSKTSA
AAV5  REP68 VDSGYIPAYLLPKVQPELQWAWTNLDEYKLAALNLEERKRLVAQFLAESSQRS-QEAASQREFSADPVIKSKTSQ
AAV6  REP68 VDECYIPNYLLPKTQPELQWAWTNMEEYISACLNLAERKRLVAHDLTHVSQTQEQNKENLNPNSDAPVIRSKTSA
AAV7  REP68 VDECYIPNYLLPKTQPELQWAWTNMEEYISACLNLAERKRLVAQHLTHVSQTQEQNKENLNPNSDAPVIRSKTSA
AAV8  REP68 VDECYIPNYLLPKTQPELQWAWTNMEEYISACLNLAERKRLVAQHLTHVSQTQEQNKENLNPNSDAPVIRSKTSA
```

FIG. 31 (cont.)

```
                  230       240       250       260       270       280       290
AAV1  REP68  RYMELVGWLVDRGITSEKQWIQEDQASYISFNAASNSRSQIKAALDNAGKIMALTKSAPDYLVGPAPPADIKTNR
AAV2  REP68  RYMELVGWLVDKGITSEKQWIQEDQASYISFNAASNSRSQIKAALDNAGKIMSLTKTAPDYLVGQQPVEDISSNR
AAV3A REP68  RYMELVGWLVDRGITSEKQWIQEDQASYISFNAASNSRSQIKAALDNASKIMSLTKTAPDYLVGSNPPEDITKNR
AAV3B REP68  RYMELVGWLVDRGITSEKQWIQEDQASYISFNAASNSRSQIKAALDNASKIMSLTKTAPDYLVGSNPPEDITKNR
AAV4  REP68  RYMELVGWLVDRGITSEKQWIQEDQASYISFNAASNSRSQIKAALDNASKIMSLTKTAPDYLVGQNPPEDISSNR
AAV5  REP68  KYMALVNWLVEHGITSEKQWIQENQESYLSFNSTGNSRSQIKAALDNATKIMSLTKSAVDYLVGSSVPEDISKNR
AAV6  REP68  RYMELVGWLVDRGITSEKQWIQEDQASYISFNAASNSRSQIKAALDNAGKIMALTKSAPDYLVGPAPPADIKTNR
AAV7  REP68  RYM LVGWLVDRGITSEKQWIQEDQASYISFNAASNSRSQIKAALDNAGKIMALTKSAPDYLVGPSLPADIKTNR
AAV8  REP68  RYMELVGWLVDRGITSEKQWIQEDQASYISFNAASNSRSQIKAALDNAGKIMALTKSAPDYLVGPSLPADITQNR

             300       310       320       330       340       350       360       370
AAV1  REP68  IYRILELNGYEPAYAGSVFLGWAQKRFGKRNTIWLFGPATTGKTNIAEAIAHAVPFYGCVNWTNENFPFNDCVDK
AAV2  REP68  IYKILELNGYDPQYAASVFLGWATKKFGKRNTIWLFGPATTGKTNIAEAIAHTVPFYGCVNWTNENFPFNDCVDK
AAV3A REP68  IYQILELNGYDPQYAASVFLGWAQKKFGKRNTIWLFGPATTGKTNIAEAIAHAVPFYGCVNWTNENFPFNDCVDK
AAV3B REP68  IYQILELNGYDPQYAASVFLGWAQKKFGKRNTIWLFGPATTGKTNIAEAIAHAVPFYGCVNWTNENFPFNDCVDK
AAV4  REP68  IYRILEMNGYDPQYAASVFLGWAQKKFGKRNTIWLFGPATTGKTNIAEAIAHAVPFYGCVNWTNENFPFNDCVDK
AAV5  REP68  IWQIFEMNGYDPAYAGSILYGWCQRSFNKRNTVWLYGPATTGKTNIAEAIAHTVPFYGCVNWTNENFPFNDCVDK
AAV6  REP68  IYRILELNGYDPAYAGSVFLGWAQKRFGKRNTIWLFGPATTGKTNIAEAIAHAVPFYGCVNWTNENFPFNDCVDK
AAV7  REP68  IYRILELNGYDPAYAGSVFLGWAQKKFGKRNTIWLFGPATTGKTNIAEAIAHAVPFYGCVNWTNENFPFNDCVDK
AAV8  REP68  IYRILALNGYDPAYAGSVFLGWAQKKFGKRNTIWLFGPATTGKTNIAEAIAHAVPFYGCVNWTNENFPFNDCVDK
```

FIG. 31 (cont.)

```
             380       390       400       410       420       430       440
AAV1 REP68   MVIWWEEGKMTAKVVESAKAILGGSKVRVDQKCKSSAQIDPTPVIVTSNTNMCAVIDGNSTTFEHQQPLQDRMFK
AAV2 REP68   MVIWWEEGKMTAKVVESAKAILGGSKVRVDQKCKSSAQIDPTPVIVTSNTNMCAVIDGNSTTFEHQQPLQDRMFK
AAV3A REP68  MVIWWEEGKMTAKVVESAKAILGGSKVRVDQKCKSSAQIEPTPVIVTSNTNMCAVIDGNSTTFEHQQPLQDRMFE
AAV3B REP68  MVIWWEEGKMTAKVVESAKAILGGSKVRVDQKCKSSAQIEPTPVIVTSNTNMCAVIDGNSTTFEHQQPLQDRMFK
AAV4 REP68   MVIWWEEGKMTAKVVESAKAILGGSKVRVDQKCKSSAQIDPTPVIVTSNTNMCAVIDGNSTTFEHQQPLQDRMFK
AAV5 REP68   MLIWWEEGKMTNKVVESAKAILGGSKVRVDQKCKSSVQIDSTPVIVTSNTNMCVVVDGNSTTFEHQQPLEDRMFK
AAV6 REP68   MVIWWEEGKMTAKVVESAKAILGGSKVRVDQKCKSSAQIDPTPVIVTSNTNMCAVIDGNSTTFEHQQPLQDRMFK
AAV7 REP68   MVIWWEEGKMTAKVVESAKAILGGSKVRVDQKCKSSAQIDPTPVIVTSNTNMCAVIDGNSTTFEHQQPLQDRMFK
AAV8 REP68   MVIWWEEGKMTAKVVESAKAILGGSKVRVDQKCKSSAQIDPTPVIVTSNTNMCAVIDGNSTTFEHQQPLQDRMFK

             450       460       470       480       490       500       510
AAV1 REP68   FELTRRLEHDFGKVTKQEVKEFFRWAQDHVTEVAHEFYVR------KGGAN--KRPAPDDADKSEP----
AAV2 REP68   FELTRRLDHDFGKVTKQEVKDFFRWAKDHVVEVEHEFYVK------KGGAK--KRPAPSDADISEP----
AAV3A REP68  FELTRRLDHDFGKVTKQEVKDFFRWASDHVTDVAHEFYVR------KGGAK--KRPASNDADVSEP----
AAV3B REP68  FELTRRLDHDFGKVTKQEVKDFFRWASDHVTDVAHEFYVR------KGGAK--KRPASNDADVSEP----
AAV4 REP68   FELTKRLEHDFGKVTKQEVKDFFRWASDHVTEVTHEFYVR------KGGAR--KRPAPNDADISEP----
AAV5 REP68   FELTKRLPPDFGKITKQEVKDFFAWAKVNQVPVTHEFKVPRELAGTKGAEKSLKRPLGDVTNTSYKSLEK
AAV6 REP68   FELTRRLEHDFGKVTKQEVKEFFRWAQDHVTEVAHEFYVR------KGGAN--KRPAPDDADKSEP----
AAV7 REP68   FELTRRLEHDFGKVTKQEVKEFFRWASDHVTEVAHEFYVR------KGGAS--KRPAPDDADISEP----
AAV8 REP68   FELTRRLEHDFGKVTKQEVKEFFRWASDHVTEVAHEFYVR------KGGAS--KRPAPDDADKSEP----
```

FIG. 31 (cont.)

```
              520       530       540            555
AAV1  REP68   -KRACPSVADPSTSDAEGAPVDFADLARGQPL----   (SEQ ID NO:104)
AAV2  REP68   -KRVRESVAQPSTSDAE-ASINYADLARGHSL----   (SEQ ID NO:105)
AAV3A REP68   -KRECTSLAQPTTSDAE-APADYADLARGQPF----   (SEQ ID NO:106)
AAV3B REP68   -KRQCTSLAQPTTSDAE-APADYADLARGQPF----   (SEQ ID NO:107)
AAV4  REP68   -KRACPSVAQPSTSDAE-APVDYADLARGQPL----   (SEQ ID NO:108)
AAV5  REP68   RARLSFVPETPRSSDVTVDPAPLRPLNWNSLVGRSW   (SEQ ID NO:109)
AAV6  REP68   -KRACPSVADPSTSDAEGAPVDFADLARGQPL----   (SEQ ID NO:110)
AAV7  REP68   -KRACPSVADPSTSDAEGAPVDFADLARGQPL----   (SEQ ID NO:111)
AAV8  REP68   -KRACPSVADPSTSDAEGAPVDFADLARGQPL----   (SEQ ID NO:112)
```

FIG. 31 (cont.)

```
              1        10        20        30        40        50        60        70
AAV1  REP78   MPGFYEIVIKVPSDLDEHLPGISDSFVSWVAEKEWELPPDSDMDLNLIEQAPLTVAEKLQRDFLVQWRRVSKAP
AAV2  REP78   MPGFYEIVIKVPSDLDEHLPGISDSFVNWVAEKEWELPPDSDMDLNLIEQAPLTVAEKLQRDFLTEWRRVSKAP
AAV3A REP78   MPGFYEIVLKVPSDLDERLPGISNSFVNWVAEKEWDVPPDSDMDPNLIEQAPLTVAEKLQREFLVEWRRVSKAP
AAV3B REP78   MPGFYEIVLKVPSDLDEHLPGISNSFVNWVAEKEWELPPDSDMDPNLIEQAPLTVAEKLQREFLVEWRRVSKAP
AAV4  REP78   MPGFYEIVLKVPSDLDEHLPGISDSFVSWVAEKEWELPPDSDMDLNLIEQAPLTVAEKLQREFLVEWRRVSKAP
AAV5  REP78   MATFYEVIVRVPFDVEEHLPGISDSFVDWVTGQIWELPPESDLNLTLVEQPQLTVADRIRRVFLYEWNKFSKQ-
AAV6  REP78   MPGFYEIVIKVPSDLDEHLPGISDSFVNWVAEKEWELPPDSDMDLNLIEQAPLTVAEKLQRDFLVQWRRVSKAP
AAV7  REP78   MPGFYEIVIKVPSDLDEHLPGISDSFVNWVAEKEWELPPDSDMDLNLIEQAPLTVAEKLQRDFLVQWRRVSKAP
AAV8  REP78   MPGFYEIVIKVPSDLDEHLPGISDSFVNWVAEKEWELPPDSDMDRNLIEQAPLTVAEKLQRDFLVQWRRVSKAP
CONSENSUS     MPGFYEIVIKVPSDLDEHLPGISDSFVNWVAEKEWELPPDSDMDLNLIEQAPLTVAEKLQRDFLVEWRRVSKAP
```

FIG. 32

```
                80        90        100       110       120       130       140
AAV1  REP78  EALFFVQFEKGESYFHLHILVETTGVKSMVLGRFLSQIRDKLVQTIYRG-IEPTLPNWFAVTKTRNGAGGG-NKV
AAV2  REP78  EALFFVQFEKGESYFHMHVLVETTGVKSMVLGRFLSQIREKLIQRIYRG-IEPTLPNWFAVTKTRNGAGGG-NKV
AAV3A REP78  EALFFVQFEKGETYFHLHVLIETTGVKSMVVGRYVSQIKEKLVTRIYRG-VEPQLPNWFAVTKTRNGAGGG-NKV
AAV3B REP78  EALFFVQFEKGETYFHLHVLIETTGVKSMVVGRYVSQIKEKLVTRIYRG-VEPQLPNWFAVTKTRNGAGGG-NKV
AAV4  REP78  EALFFVQFEKGDSYFHLHILVETVGVKSMVVGRYVSQIKEKLVTRIYRG-VEPQLPNWFAVTKTRNGAGGG-NKV
AAV5  REP78  ESKFFVQFEKGSEYFHLHILVETSGISSMVLGRYVSQIRAQLVKVVFQG-IEPQINDWVAITKVKK---GGANKV
AAV6  REP78  EALFFVQFEKGESYFHLHILVETTGVKSMVLGRFLSQIRDKLVQTIYRG-IEPTLPNWFAVTKTRNGAGGG-NKV
AAV7  REP78  EALFFVQFEKGESYFHLHVLVETTGVKSMVLGRFLSQIREKLVQTIYRG-VEPTLPNWFAVTKTRNGAGGG-NKV
AAV8  REP78  EALFFVQFEKGESYFHLHVLVETTGVKSMVLGRFLSQIREKLGPDHLPAGSSPTLPNWFAVTKDAVMAPAGGNKV
CONSENSUS    EALFFVQFEKGESYFHLHVLVETTGVKSMVLGRFLSQIREKLV   IYRG IEPTLPNWFAVTKTRNGAGGG NKV

             150       160       170       180       190       200       210       220
AAV1  REP78  VDECYIPNYLLPKTQPELQWAWTNMEEYISACLNLAERKRLVAQHLTHVSQTQEQNKENLNPNSDAPVIRSKTSA
AAV2  REP78  VDECYIPNYLLPKTQPELQWAWTNMEQYISACLNLTERKRLVAQHLTHVSQTQEQNKENQNPNSDAPVIRSKTSA
AAV3A REP78  VDDCYIPNYLLPKTQPELQWAWTNMDQYISACLNLAERKRLVAQHLTHVSQTQEQNKENQNPNSDAPVIRSKTSA
AAV3B REP78  VDDCYIPNYLLPKTQPELQWAWTNMDQYISACLNLAERKRLVAQHLTHVSQTQEQNKENQNPNSDAPVIRSKTSA
AAV4  REP78  VDDCYIPNYLLPKTQPELQWAWTNMDQYISACLNLAERKRLVAQHLTHVSQTQEQNKENQNPNSDAPVIRSKTSA
AAV5  REP78  VDSCYIPAYLLPKVQPELQWAWTNLDEYKLAALNLEERKRLVAQFLAESSQRS-QEAASQREFSADPVIKSKTSQ
AAV6  REP78  VDECYIPNYLLPKTQPELQWAWTNMEEYISACLNLAERKRLVAHDLTHVSQTQEQNKENLNPNSDAPVIRSKTSA
AAV7  REP78  VDECYIPNYLLPKTQPELQWAWTNMEEYISACLNLAERKRLVAQHLTHVSQTQEQNKENLNPNSDAPVIRSKTSA
AAV8  REP78  VDECYIPNYLLPKTQPELQWAWTNMEEYISACLNLAERKRLVAQHLTHVSQTQEQNKENLNPNSDAPVIRSKTSA
CONSENSUS    VDECYIPNYLLPKTQPELQWAWTNMEEYISACLNLAERKRLVAQHLTHVSQTQEQNKENQNPNSDAPVIRSKTSA
```

FIG. 32 (cont.)

```
             230       240       250       260       270       280       290
AAV1 REP78   RYMELVGWLVDRGITSEKQWIQEDQASYISFNAASNSRSQIKAALDNAGKIMALTKSAPDYLVGPAPPADIKTNR
AAV2 REP78   RYMELVGWLVDKGITSEKQWIQEDQASYISFNAASNSRSQIKAALDNAGKIMSLTKTAPDYLVGQQPVEDISSNR
AAV3A REP78  RYMELVGWLVDRGITSEKQWIQEDQASYISFNAASNSRSQIKAALDNASKIMSLTKTAPDYLVGSNPPEDITKNR
AAV3B REP78  RYMELVGWLVDRGITSEKQWIQEDQASYISFNAASNSRSQIKAALDNASKIMSLTKTAPDYLVGSNPPEDITKNR
AAV4 REP78   RYMELVGWLVDRGITSEKQWIQEDQASYISFNAASNSRSQIKAALDNASKIMSLTKTAPDYLVGSNPPEDISSNR
AAV5 REP78   KYMALVNWLVEHGITSEKQWIQENQESYLSFNSTGNSRSQIKAALDNATKIMSLTKSAVDYLVGSSVPEDISKNR
AAV6 REP78   RYMELVGWLVDRGITSEKQWIQEDQASYISFNAASNSRSQIKAALDNAGKIMALTKSAPDYLVGPAPPADIKTNR
AAV7 REP78   RYMELVGWLVDRGITSEKQWIQEDQASYISFNAASNSRSQIKAALDNAGKIMALTKSAPDYLVGPSLPADIKTNR
AAV8 REP78   RYMELVGWLVDRGITSEKQWIQEDQASYISFNAASNSRSQIKAALDNAGKIMALTKSAPDYLVGPSLPADITQNR
CONSENSUS    RYMELVGWLVDRGITSEKQWIQEDQASYISFNAASNSRSQIKAALDNAGKIMSLTKSAPDYLVG SPPEDISTNR

             300       310       320       330       340       350       360       370
AAV1 REP78   IYRILELNGYEPAYAGSVFLGWAQKRFGKRNTIWLFGPATTGKTNIAEAIAHAVPFYGCVNWTNENFPFNDCVDK
AAV2 REP78   IYKILELNGYDPQYAASVFLGWATKKFGKRNTIWLFGPATTGKTNIAEAIAHTVPFYGCVNWTNENFPFNDCVDK
AAV3A REP78  IYQILELNGYDPQYAASVFLGWAQKKFGKRNTIWLFGPATTGKTNIAEAIAHAVPFYGCVNWTNENFPFNDCVDK
AAV3B REP78  IYQILELNGYDPQYAASVFLGWAQKKFGKRNTIWLFGPATTGKTNIAEAIAHAVPFYGCVNWTNENFPFNDCVDK
AAV4 REP78   IYRILEMNGYDPQYAASVFLGWAQKKFGKRNTIWLFGPATTGKTNIAEAIAHAVPFYGCVNWTNENFPFNDCVDK
AAV5 REP78   IWQIFEMNGYDPAYAGSILYGWCQRSFNKRNTVWLYGPATTGKTNIAEAIAHTVPFYGCVNWTNENFPFNDCVDK
AAV6 REP78   IYRILELNGYDPAYAGSVFLGWAQKRFGKRNTIWLFGPATTGKTNIAEAIAHAVPFYGCVNWTNENFPFNDCVDK
AAV7 REP78   IYRILELNGYDPAYAGSVFLGWAQKKFGKRNTIWLFGPATTGKTNIAEAIAHAVPFYGCVNWTNENFPFNDCVDK
AAV8 REP78   IYRILALNGYDPAYAGSVFLGWAQKKFGKRNTIWLFGPATTGKTNIAEAIAHAVPFYGCVNWTNENFPFNDCVDK
CONSENSUS    IYRILELNGYDPAYAGSVFLGWAQKKFGKRNTIWLFGPATTGKTNIAEAIAHAVPFYGCVNWTNENFPFNDCVDK
```

FIG. 32 (cont.)

```
                 380       390       400       410       420       430       440
AAV1 REP78   MVIWWEEGKMTAKVVESAKAILGGSKVRVDQKCKSSAQIDPTPVIVTSNTNMCAVIDGNSTTFEHQQPLQDRMFK
AAV2 REP78   MVIWWEEGKMTAKVVESAKAILGGSKVRVDQKCKSSAQIDPTPVIVTSNTNMCAVIDGNSTTFEHQQPLQDRMFK
AAV3A REP78  MVIWWEEGKMTAKVVESAKAILGGSKVRVDQKCKSSAQIEPTPVIVTSNTNMCAVIDGNSTTFEHQQPLQDRMFE
AAV3B REP78  MVIWWEEGKMTAKVVESAKAILGGSKVRVDQKCKSSAQIEPTPVIVTSNTNMCAVIDGNSTTFEHQQPLQDRMFK
AAV4 REP78   MVIWWEEGKMTAKVVESAKAILGGSKVRVDQKCKSSAQIDPTPVIVTSNTNMCAVIDGNSTTFEHQQPLQDRMFK
AAV5 REP78   MLIWWEEGKMTNKVVESAKAILGGSKVRVDQKCKSSVQIDSTPVIVTSNTNMCVVVDGNSTTFEHQQPLEDRMFK
AAV6 REP78   MVIWWEEGKMTAKVVESAKAILGGSKVRVDQKCKSSAQIDPTPVIVTSNTNMCAVIDGNSTTFEHQQPLQDRMFK
AAV7 REP78   MVIWWEEGKMTAKVVESAKAILGGSKVRVDQKCKSSAQIDPTPVIVTSNTNMCAVIDGNSTTFEHQQPLQDRMFK
AAV8 REP78   MVIWWEEGKMTAKVVESAKAILGGSKVRVDQKCKSSAQIDPTPVIVTSNTNMCAVIDGNSTTFEHQQPLQDRMFK
CONSENSUS    MVIWWEEGKMTAKVVESAKAILGGSKVRVDQKCKSSAQIDPTPVIVTSNTNMCAVIDGNSTTFEHQQPLQDRMFK

             450       460       470       480       490       500       510       520
AAV1 REP78   FELTRRLEHDFGKVTKQEVKEFFRWAQDHVTEVAHEFYVR------KGGAN--KRPAPDDADKSEP---KRA---
AAV2 REP78   FELTRRLDHDFGKVTKQEVKDFFRWAKDHVVEVEHEFYVK------KGGAK--KRPAPSDADISEP---KRV---
AAV3A REP78  FELTRRLDHDFGKVTKQEVKDFFRWASDHVTDVAHEFYVR------KGGAK--KRPASNDADVSEP---KRE---
AAV3B REP78  FELTRRLDHDFGKVTKQEVKDFFRWASDHVTDVAHEFYVR------KGGAK--KRPASNDADVSEP---KRQ===
AAV4 REP78   FELTKRLEHDFGKVTKQEVKDFFRWASDHVTEVTHEFYVR------KGGAR--KRPAPNDADISEP---KRA---
AAV5 REP78   FELTKRLPPDFGKITKQEVKDFFAWAKVNQVPVTHEFKVPRELAGTKGAEKSLKRPLGDVTNTSYKSLEKRARLS
AAV6 REP78   FELTRRLEHDFGKVTKQEVKEFFRWAQDHVTEVAHEFYVR------KGGAN--KRPAPDDADKSEP---KRA---
AAV7 REP78   FELTRRLEHDFGKVTKQEVKEFFRWASDHVTEVAHEFYVR------KGGAS--KRPAPDDADISEP---KRA---
AAV8 REP78   FELTRRLEHDFGKVTKQEVKEFFRWASDHVTEVAHEFYVR------KGGAS--KRPAPDDADKSEP---KRA---
CONSENSUS    FELTRRLEHDFGKVTKQEVKDFFRWASDHVTEVAHEFYVR      KGGAK  KRPAPDDADISEP   KRA
```

FIG. 32 (cont.)

```
              530       540       550       560       570       580       590
AAV1 REP78   ----CPSVADPSTSDAEGAPVDFADRYQNKCSRHAGMLQMLFPCKTCERMNQNFNICFTHGTRDCSECFPGVSES
AAV2 REP78   ----RESVAQPSTSDAE-ASINYADRYQNKCSRHVGMNLMLFPCRQCERMNQNSNICFTHGQKDCLECFPVS-ES
AAV3A REP78  ----CTSLAQPTTSDAE-APADYADRYQNKCSRHVGMNLMLFPCKTCERMNQISNVCFTHGQRDCGECFPGMSES
AAV3B REP78  ----CTSLAQPTTSDAE-APADYADRYQNKCSRHVGMNLMLFPCKTCERMNQISNVCFTHGQRDCGECFPGMSES
AAV4 REP78   ----CPSVAQPSTSDAE-APVDYADRYQNKCSRHVGMNLMLFPCRQCERMNQNVDICFTHGVMDCAECFPVS-ES
AAV5 REP78   FVPETPRSSDVTVDPAPLRPLNWNSRYDCKCDYHAQFDNISNKCDECEYLNRGKNGCICHNVTHCQICHGIPPWE
AAV6 REP78   ----CPSVADPSTSDAEGAPVDFADRYQNKCSRHAGMLQMLFPCKTCERMNQNFNICFTHGTRDCSECFPGVSES
AAV7 REP78   ----CPSVADPSTSDAEGAPVDFADRYQNKCSRHAGMLQMLFPCKTCERMNQNFNICFTHGVRDCLECFPGVSES
AAV8 REP78   ----CPSVADPSTSDAEGAPVDFADRYQNKCSRHAGMLQMLFPCKTCERMNQNFNICFTHGVRDCSECFPGVSES
CONSENSUS        CPSVADPSTSDAE APVDFADRYQNKCSRHAGM QMLFPCKTCERMNQN NICFTHG RDC ECFPGVSES

             600       610       620       630       646
AAV1 REP78   Q--PVVRKRTYRKLCAIHHLLGRAPEIACSACDLVNVDLDDCVSEQ-  (SEQ ID NO:113)
AAV2 REP78   QPVSVVKK-AYQKLCYIHHIMGKVPD-ACTACDLVNVDLDDCIFEQ-  (SEQ ID NO:114)
AAV3A REP78  QPVSVVKKKTYQKLCPIHHILGRAPEIACSACDLANVDLDDCVSEQ-  (SEQ ID NO:115)
AAV3B REP78  QPVSVVKKKTYQKLCPIHHILGRAPEIACSACDLANVDLDDCVSEQ-  (SEQ ID NO:116)
AAV4 REP78   QPVSVVRKRTYQKLCPIHHIMGRAPEVACSACELANVDLDDCDMEQ-  (SEQ ID NO:117)
AAV5 REP78   K-----------------------E--NLSD---FGDFDDANKEQ-  (SEQ ID NO:118)
AAV6 REP78   Q--PVVRKRTYRKLCAIHHLLGRAPEIACSACDLVNVDLDDCVSEQ-  (SEQ ID NO:119)
AAV7 REP78   Q--PVVRKKTYRKLCAIHHLLGRAPEIACSACDLVNVDLDDCVSEQ-  (SEQ ID NO:120)
AAV8 REP78   Q--PVVRKRTYRKLCAIHHLLGRAPEIACSACDLVNVDLDDCVSEQ-  (SEQ ID NO:121)
CONSENSUS    Q   VVRKRTY KLC IHHILGRAPEIACSACDLVNVDLDDCVSEQ   (SEQ ID NO:122)
```

FIG. 32 (cont.)

```
SNAKE ITR
 1 CGCCCCACCC CTAGTGATCG CGCGCGCTCT CTCTTGGGGC CTGACGGCCG AAGGCCGTCA GCTGCCGAGC TTCGCTCGGC AGGCCCCAAG
91 AGAGAGCGCG CGCGATCACT AGGGGTGGGG CG
```

FIG. 33

SNAKE ITR EGFP VECTOR PLASMID (pSnTR-eGFP)
GTGGCACTTTTCGGGGAAATGTGCGCGGAACCCCTATTTGTTTATTTTTCTAAATACATTCAAATATGTATCCGCTC
ATGAGACAATAACCCTGATAAATGCTTCAATAATATTGAAAAAGGAAGAGTATGAGTATTCAACATTTCCGTGTCGC
CCTTATTCCCTTTTTTGCGGCATTTTGCCTTCCTGTTTTTGCTCACCCAGAAACGCTGGTGAAAGTAAAAGATGCTG
AAGATCAGTTGGGTGCACGAGTGGGTTACATCGAACTGGATCTCAACAGCGGTAAGATCCTTGAGAGTTTTCGCCCC
GAAGAACGTTTTCCAATGATGAGCACTTTTAAAGTTCTGCTATGTGGCGCGGTATTATCCCGTATTGACGCCGGGCA
AGAGCAACTCGGTCGCCGCATACACTATTCTCAGAATGACTTGGTTGAGTACTCACCAGTCACAGAAAAGCATCTTA
CGGATGGCATGACAGTAAGAGAATTATGCAGTGCTGCCATAACCATGAGTGATAACACTGCGGCCAACTTACTTCTG
ACAACGATCGGAGGACCGAAGGAGCTAACCGCTTTTTTGCACAACATGGGGGATCATGTAACTCGCCTTGATCGTTG
GGAACCGGAGCTGAATGAAGCCATACCAAACGACGAGCGTGACACCACGATGCCTGTAGCAATGGCAACAACGTTGC
GCAAACTATTAACTGGCGAACTACTTACTCTAGCTTCCCGGCAACAATTAATAGACTGGATGGAGGCGGATAAAGTT
GCAGGACCACTTCTGCGCTCGGCCCTTCCGGCTGGCTGGTTTATTGCTGATAAATCTGGAGCCGGTGAGCGTGGGTC
TCGCGGTATCATTGCAGCACTGGGGCCAGATGGTAAGCCCTCCCGTATCGTAGTTATCTACACGACGGGGAGTCAGG
CAACTATGGATGAACGAAATAGACAGATCGCTGAGATAGGTGCCTCACTGATTAAGCATTGGTAACTGTCAGACCAA
GTTTACTCATATATACTTTAGATTGATTTAAAACTTCATTTTTAATTTAAAAGGATCTAGGTGAAGATCCTTTTTGA
TAATCTCATGACCAAAATCCCTTAACGTGAGTTTTCGTTCCACTGAGCGTCAGACCCCGTAGAAAAGATCAAAGGAT
CTTCTTGAGATCCTTTTTTTCTGCGCGTAATCTGCTGCTTGCAAACAAAAAAACCACCGCTACCAGCGGTGGTTTGT
TTGCCGGATCAAGAGCTACCAACTCTTTTTCCGAAGGTAACTGGCTTCAGCAGAGCGCAGATACCAAATACTGTCCT
TCTAGTGTAGCCGTAGTTAGGCCACCACTTCAAGAACTCTGTAGCACCGCCTACATACCTCGCTCTGCTAATCCTGT
TACCAGTGGCTGCTGCCAGTGGCGATAAGTCGTGTCTTACCGGGTTGGACTCAAGACGATAGTTACCGGATAAGGCG
CAGCGGTCGGGCTGAACGGGGGGTTCGTGCACACAGCCCAGCTTGGAGCGAACGACCTACACCGAACTGAGATACCT
ACAGCGTGAGCTATGAGAAAGCGCCACGCTTCCCGAAGGGAGAAAGGCGGACAGGTATCCGGTAAGCGGCAGGGTCG
GAACAGGAGAGCGCACGAGGGAGCTTCCAGGGGGAAACGCCTGGTATCTTTATAGTCCTGTCGGGTTTCGCCACCTC
TGACTTGAGCGTCGATTTTTGTGATGCTCGTCAGGGGGGCGGAGCCTATGGAAAAACGCCAGCAACGCGGCCTTTTT
ACGGTTCCTGGCCTTTTGCTGGCCTTTTGCTCACATGTTCTTTCCTGCGTTATCCCCTGATTCTGTGGATAACCGTA
TTACCGCCTTTGAGTGAGCTGATACCGCTCGCCGCAGCCGAACGACCGAGCGCAGCGAGTCAGTGAGCGAGGAAGCG
GAAGAGCGCCCAATACGCAAACCGCCTCTCCCCGCGCGTTGGCCGATTCATTAATGCAGCTGGCACGACAGGTTTCC
CGACTGGAAAGCGGGCAGTGAGCGCAACGCAATTAATGTGAGTTAGCTCACTCATTAGGCACCCCAGGCTTTACACT
TTATGCTTCCGGCTCGTATGTTGTGTGGAATTGTGAGCGGATAACAATTTCACACAGGAAACAGCTATGACCATGAT
TACGCCAAGCGCGCAATTAACCCTCACTAAAGGGAACAAAAGCTGGGTACCGGGCCCCCCCTCGAGGTCGACGGTAT
CGATAAGCTTGATCGCCCCACCCCTAGTGATCGCGCGCGCTCTCTCTTGGGGCCTGACGGCCGAAGGCCGTCAGCTG
CCGAGCTTCGCTCGGCAGGCCCCAAGAGAGAGCGCGCGATCACTAGGGGTGGGGCGAGTGCCCTGCTCAACGGGT
TTTTTGGTGGGCGGAGCAATGACGTCAGCGGACATGTCTGGACATGTCTTTGAGCAAGTCCATATAAGGAGTTCCGC
CGGATATGCAAATGAGCAATCGCGCAAAGCATTTTGGGTAGTCACCATGAATAAAAAGGACAGCAAGAAAGATGACG
CCCCATAATTTTAATAGGAATTTTAACCATGTTCTTTCCTGCGTTATCCCCTGATTCTGTGGATAACCGTATTACCG
CCTTTGAGTGAGCTGATACCGCTCGCCGCAGCCGAACGACCGAGCGCAGCGAGTCAGTGAGCGAGGAAGCGGAAGAG
CGCCCAATACGCAAACCGCCTCTCCCCGCGCGTTGGCCGATTCATTAATGCAGCTGGCACGACAGGTTTCCCGACTG
GAAAGCGGGCAGTGAGCGCAACGCAATTAATGTGAGTTAGCTCACTCATTAGGCACCCCAGGCTTTACACTTTATGC
TTCCGGCTCGTATGTTGTGTGGAATTGTGAGCGGATAACAATTTCACACAGGAAACAGCTATGACCATGATTACGAA
TTGTTGTTGTTAACTTGTTTATTGCAGCTTATAATGGTTACAAATAAAGCAATAGCATCACAAATTTCACAAATAAA
GCATTTTTTTCACTGCATTCTAGTTGTGGTTTGTCCAAACTCATCAATGTATCTTATCATGTCTGGATCCCCGCGGC
CGCTTTACTTGTACAGCTCGTCCATGCCGAGAGTGATCCCGGCGGCGGTCACGAACTCCAGCAGGACCATGTGATCG
CGCTTCTCGTTGGGGTCTTTGCTCAGGGCGGACTGGGTGCTCAGGTAGTGGTTGTCGGGCAGCAGCACGGGGCCGTC
GCCGATGGGGGTGTTCTGCTGGTAGTGGTCGGCGAGCTGCACGCTGCCGTCCTCGATGTTGTGGCGGATCTTGAAGT
TCACCTTGATGCCGTTCTTCTGCTTGTCGGCCATGATATAGACGTTGTGGCTGTTGTAGTTGTACTCCAGCTTGTGC
CCCAGGATGTTGCCGTCCTCCTTGAAGTCGATGCCCTTCAGCTCGATGCGGTTCACCAGGGTGTCGCCCTCGAACTT
CACCTCGGCGCGGGTCTTGTAGTTGCCGTCGTCCTTGAAGAAGATGGTGCGCTCCTGGACGTAGCCTTCGGGCATGG
CGGACTTGAAGAAGTCGTGCTGCTTCATGTGGTCGGGGTAGCGGCTGAAGCACTGCACGCCGTAGGTCAGGGTGGTC
ACGAGGGTGGGCCAGGGCACGGGCAGCTTGCCGGTGGTGCAGATGAACTTCAGGGTCAGCTTGCCGTAGGTGGCATC
GCCCTCGCCCTCGCCGGACACGCTGAACTTGTGGCCGTTTACGTCGCCGTCCAGCTCGACCAGGATGGGCACCACCC
CGGTGAACAGCTCCTCGCCCTTGCTCACCATGGTGGCGACCGGTGGATCCCGGGCCGCGGGTACAATTCCGCAGCTT
TTAGAGCAGAAGTAACACTTCCGTACAGGCCTAGAAGTAAAGGCAACATCCACTGAGGAGCAGTTCTTTGATTTGCA
CCACCACCGGATCCGGGACCTGAAATAAAAGACAAAAAGACTAAACTTACCAGTTAACTTTCTGGTTTTTCAGTTCC
TCGAGTACCGGATCCTCTAGAGTCCGGAGGCTGGATCGGTCCCGGTGTCTTCTATGGAGGTCAAAACAGCGTGGATG
GCGTCTCCAGGCGATCTGACGGTTCACTAAACGAGCTCTGCTTATATAGACCTCCCACCGTACACGCCTACCGCCCA
TTTGCGTCAATGGGGCGGAGTTGTTACGACATTTTGGAAAGTCCCGTTGATTTTGGTGCCAAAACAAACTCCCATTG
ACGTCAATGGGGTGGAGACTTGGAAATCCCCGTGAGTCAAACCGCTATCCACGCCCATTGATGTACTGCCAAAACCG
CATCACCATGGTAATAGCGATGACTAATACGTAGATGTACTGCCAAGTAGGAAAGTCCCATAAGGTCATGTACTGGG
CATAATGCCAGGCGGGCCATTTACCGTCATTGACGTCAATAGGGGGCGTACTTGGCATATGATACACTTGATGTACT
GCCAAGTGGGCAGTTTACCGTAAATACTCCACCCATTGACGTCAATGGAAAGTCCCTATTGGCGTTACTATTGACGT
CAATGGGCGGGGGTCGTTGGGCGGTCAGCCAGGCGGGCCATTTACCGTAAGTTATGTAACGGGTACCCGGGGATCCT
CTAGAGTCGACCTGCAGTAAACAGAACAATTGAAGACGAAATACAGGGTACCAATAATTTTGGTAATGCTAGAAATA
ACATTGTTGCTATCAATCAACAAACGAAAGGAACAAATCCAACAACAGGTAGTACATCTCAATTTGAGACAATGCCA
GGTATGGTGTGGTCTAATAGAGACATTTACTTACAGGGGCCTATTTGGGCTAAAATTCCAAATACAGATGGACATTT
TCATCCTTCTCCCAGAATGGGTGGTTTTGGATTAAAACATCCTCCGCCTATGATTCTGATCAAAAATACACCAGTTC
CTGCTGATCCTCCAACTACCTTCAATCCAATGCCACAGACTAGTTTCATTACTGAATACAGTACAGGACAAGTAACT
GTTGAAATGTTGTGGGAGGTACAGAAAGAATCCTCCAAAAGATGGAATCCAGAAGTACAGTTTACTTCCAATTTTGG
AACTTCAGATCCAGCTGTTGATGGAATACCGTTTGGAATTAATAATTTGGGTACTTATGTTGAATCTAGACCTATTG
GAACTCGTTATATTTCTAAACACTTGTAAATAATAAAAATTGTCAAATTTGCACTAAGAATTGTTGTCACGTGGTTG
TTTACATGCTTGCTAAAACACGCCCACCAAAAAACCCGTTGAGCAGGGCACTCGCCCCACCCCTAGTGATCGCGCGC
GCTCTCTCTTGGGGCCTGCCGAGCGAAGCTCGGCAGCTGACGGCCTTCGGCCGTCAGGCCCCAAGAGAGAGCGCGCG
CGATCACTAGGGGTGGGGCGGGGGGATCCACTAGTTCTAGAGCGGCCGCCACCGCGGTGGAGCTCCAATTCGCCCTA
TAGTGAGTCGTATTACGCGCGCTCACTGGCCGTCGTTTTACAACGTCGTGACTGGGAAAACCCTGGCGTTACCCAAC
TTAATCGCCTTGCAGCACATCCCCCTTTCGCCAGCTGGCGTAATAGCGAAGAGGCCCGCACCGATCGCCCTTCCCAA
CAGTTGCGCAGCCTGAATGGCGAATGGGACGCGCCCTGTAGCGGCGCATTAAGCGCGGCGGGTGTGGTGGTTACGCG
CAGCGTGACCGCTACACTTGCCAGCGCCCTAGCGCCCGCTCCTTTCGCTTTCTTCCCTTCCTTTCTCGCCACGTTCG
CCGGCTTTCCCCGTCAAGCTCTAAATCGGGGGCTCCCTTTAGGGTTCCGATTTAGTGCTTTACGGCACCTCGACCCC
AAAAAACTTGATTAGGGTGATGGTTCACGTAGTGGGCCATCGCCCTGATAGACGGTTTTTCGCCCTTTGACGTTGGA
GTCCACGTTCTTTAATAGTGGACTCTTGTTCCAAACTGGAACAACACTCAACCCTATCTCGGTCTATTCTTTTGATT
TATAAGGGATTTTGCCGATTTCGGCCTATTGGTTAAAAAATGAGCTGATTTAACAAAAATTTAACGCGAATTTTAAC
AAAATATTAACGCTTACAATTTAG

FIG. 34

SNAKE REPCAP2 PLASMID (PSNREPCAP2)
TCGCGCGTTTCGGTGATGACGGTGAAAACCTCTGACACATGCAGCTCCCGGAGACGGTCACAGCTTGTCTGTAAGCG
GATGCCGGGAGCAGACAAGCCCGTCAGGGCGCGTCAGCGGGTGTTGGCGGGTGTCGGGGCTGGCTTAACTATGCGGC
ATCAGAGCAGATTGTACTGAGAGTGCACCATATGCGGTGTGAAATACCGCACAGATGCGTAAGGAGAAAATACCGCA
TCAGGAAATTGTAAACGTTAATATTTTGTTAAAATTCGCGTTAAATTTTTGTTAAATCAGCTCATTTTTTAACCAAT
AGGCCGAAATCGGCAAAATCCCTTATAAATCAAAAGAATAGACCGAGATAGGGTTGAGTGTTGTTCCAGTTTGGAAC
AAGAGTCCACTATTAAAGAACGTGGACTCCAACGTCAAAGGGCGAAAAACCGTCTATCAGGGCGATGGCCCACTACG
TGAACCATCACCCTAATCAAGTTTTTTGGGGTCGAGGTGCCGTAAAGCACTAAATCGGAACCCTAAAGGGAGCCCCC
GATTTAGAGCTTGACGGGGAAAGCCGGCGAACGTGGCGAGGAAGGAAGGGAAGAAAGCGAAAGGAGCGGGCGCTAGG
GCGCTGGCAAGTGTAGCGGTCACGCTGCGCGTAACCACCACACCCGCCGCGCTTAATGCGCCGCTACAGGGCGCGTC
GCGCCATTCGCCATTCAGGCTGCGCAACTGTTGGGAAGGGCGATCGGTGCGGGCCTCTTCGCTATTACGCCAGCTGG
CGAAAGGGGGATGTGCTGCAAGGCGATTAAGTTGGGTAACGCCAGGGTTTTCCCAGTCACGACGTTGTAAAACGACG
GCCAGTGAATTGTAATACGACTCACTATAGGGCGAATTCGAGCTCGCAGCGGACATGTCTGGACATGTCTTTGAGCA
AGTCCATATAAGGAGTTCCGCCGGATATGCAAATGAGCAATCGCGCAAAGCATTTTGGGTAGTCACCATGAATAAAA
AGGACAGCAAGAAAGATGACGCCCCATAATTTTAATAGGAATTTTAACCATGGCGTTTTACGAGGTTGTGTTTCGTT
TGCCAAGAGACAATAACAACTTGTTGGATGAAGATAGATATCAGCCAGAGTTGAAAGAAGAAGATGACTGGCCTGAG
GAATATTTAACCAGTGAAGATGCCAGCTTTATCGGACTAGCGTATGCTGTGCTAAGTGAAATTCGGAGATTCTTTGG
AAAGGAACTACAATGGTTTGCCCAGGTTGAATGGTGTCCTACTGCTGGTTACCACATGCATGTTTTGTTGAACCATC
CTAAGCTGAGTAACCAGACTTATGGAAGAAAGGTCAATGAACTGGCTTGCCGTATAGTCGATACCTTTGGCCTAATT
AATCCAGAAGAAGTCATCAGTACCCATTATGTTAAAAGCAACTATGGACATAAAAAGGTGAGAGTCATTCACCTAGA
GTCTTATTTGAAGAACTACTTTTTCAGAAAGACTTTAGCTCCTCCCAATTATACCGAGGAAGGAGACTATAAAAGAG
AGGAAGAAGTCGTGCTGTGGGCATTTACGAATATCGTCGCTTGGAAGCCATTCGTGCGGAATCTCATCAAGAGATCG
GAGCTAGCGACTGTTCCTAAGCAACCAGAGAATCCGGCGGGAGACGGACCGGCACCTCGAGTGACTGCAGGAACCCG
CCATTTTATGGAAACCATCGACTGGTTGGTGAAACATGGAATTACTACAGAACGAGAATTCTGCCACGCCAACCGCC
CTTTGTACCTGTCTATGCTGGCTTCTACTTCGGGTGCTGGGCAGATTAAAAGAGCGCTGGACCAGGCGAAACACATG
ATGACCAGCACCATGTCAGCAGAGGATTACCTGACAACAGAAGAGGATGTGATCGAACCACCTACTGAAAATAGAAT
CTACAAGATTATGAAACTGAATCGCTATGATCCAGAACTAGCAGCTGCTCTCTTCTACGGCTGGACCTGCAAGAACT
TTGGCAAGAGAAACACCATCTGGCTGTATGGTCCAGCTACTACCGGCAAAACCATCATCGCTCAAGCTATTGCACAT
GCTGTTAAACTGTTTGCTGGTGTTAATTGGACTAATGAAAACTTTCCCTTCTGTAACTGTCCAGGGAAACTGCTTAT
CTGGTGGGAGGAGGGCAAGATGACAAACAAAATGGTGGAGACGGCTAAATGTATACTGGGGGGATCTGCTGTACCTG
TAGACATCAAAGGCAAACCCGCTGAAATGTGTCCTCAAACACCCTGTATTATTACTAGCAATACTAACATGTGTCAA
GTATATGATGGTAATAGTTCTAGCTTTGAGCACCAAGAACCCCTAGAGGAACGCATGTTTATGTTCAGACTTAATAC
TAAACTGCCATCGACCTTTGGCAAGATCACAGAAGAGGAAGTCAAACAGTTTATTACCTGGGGGAGGAGCTTAAAGG
TTCAAGTTCCACATCAGTTCAGAGTGCCTACCACAGGAGAGTATAAAAGGCCAGCCCCCGAGGCGAAAGCTCATTCT
TCGGATGAGCCGCCAAAAGAGAAGGTCGCGCGTATTGATGACTCTCTAACCAGGTATGTTAACAATATTGATGAGTC
AGCTACCAGTAGAGAAATGTTTCTAGAGATTGCTAATACTAATCAATGTATGTTGCATCATTGCTTTTCTTGTACCG
AATGTTATCCTGAATTGCTTGATGACATGGACAAGGAACAATAAACTTACTGATAACAGATATGGCTGCCGATGGTT
ATCTTCCAGATTGGCTCGAGGACACTCTCTCTGAAGGAATAAGACAGTGGTGGAAGCTCAAACCTGGCCCACCACCA
CCAAAGCCCGCAGAGCGGCATAAGGACGACAGCAGGGGTCTTGTGCTTCCTGGGTACAAGTACCTCGGACCCTTCAA
CGGACTCGACAAGGGAGAGCCGGTCAACGAGGCAGACGCCGCGGCCCTCGAGCACGACAAAGCCTACGACCGGCAGC
TCGACAGCGGAGACAACCCGTACCTCAAGTACAACCACGCCGACGCGGAGTTTCAGGAGCGCCTTAAAGAAGATACG
TCTTTTGGGGGCAACCTCGGACGAGCAGTCTTCCAGGCGAAAAAGAGGGTTCTTGAACCTCTGGGCCTGGTTGAGGA
ACCTGTTAAGACGGCTCCGGGAAAAAAGAGGCCGGTAGAGCACTCTCCTGTGGAGCCAGACTCCTCCTCGGGAACCG
GAAAGGCGGGCCAGCAGCCTGCAAGAAAAAGATTGAATTTTGGTCAGACTGGAGACGCAGACTCAGTACCTGACCCC
CAGCCTCTCGGACAGCCACCAGCAGCCCCCTCTGGTCTGGGAACTAATACGATGGCTACAGGCAGTGGCGCACCAAT
GGCAGACAATAACGAGGGCGCCGACGGAGTGGGTAATTCCTCGGGAAATTGGCATTGCGATTCCACATGGATGGGCG
ACAGAGTCATCACCACCAGCACCCGAACCTGGGCCCTGCCCACCTACAACAACCACCTCTACAAACAAATTTCCAGC
CAATCAGGAGCCTCGAACGACAATCACTACTTTGGCTACAGCACCCCTTGGGGGTATTTTGACTTCAACAGATTCCA
CTGCCACTTTTCACCACGTGACTGGCAAAGACTCATCAACAACAACTGGGGATTCCGACCCAAGAGACTCAACTTCA
AGCTCTTTAACATTCAAGTCAAAGAGGTCACGCAGAATGACGGTACGACGACGATTGCCAATAACCTTACCAGCACG
GTTCAGGTGTTTACTGACTCGGAGTACCAGCTCCCGTACGTCCTCGGCTCGGCGCATCAAGGATGCCTCCCGCCGTT
CCCAGCAGACGTCTTCATGGTGCCACAGTATGGATACCTCACCCTGAACAACGGGAGTCAGGCAGTAGGACGCTCTT
CATTTTACTGCCTGGAGTACTTTCCTTCTCAGATGCTGCGTACCGGAAACAACTTTACCTTCAGCTACACTTTTGAG
GACGTTCCTTTCCACAGCAGCTACGCTCACAGCCAGAGTCTGGACCGTCTCATGAATCCTCTCATCGACCAGTACCT
GTATTACTTGAGCAGAACAAACACTCCAAGTGGAACCACCACGCAGTCAAGGCTTCAGTTTTCTCAGGCCGGAGCGA
GTGACATTCGGGACCAGTCTAGGAACTGGCTTCCTGGACCCTGTTACCGCCAGCAGCGAGTATCAAAGACATCTGCG
GATAACAACAACAGTGAATACTCGTGGACTGGAGCTACCAAGTACCACCTCAATGGCAGAGACTCTCTGGTGAATCC
GGGCCCGGCCATGGCAAGCCACAAGGACGATGAAGAAAAGTTTTTTCCTCAGAGCGGGGTTCTCATCTTTGGGAAGC
AAGGCTCAGAGAAAACAAATGTGGACATTGAAAAGGTCATGATTACAGACGAAGAGGAAATCAGGACAACCAATCCC
GTGGCTACGGAGCAGTATGGTTCTGTATCTACCAACCTCCAGAGAGGCAACAGACAAGCAGCTACCGCAGATGTCAA
CACACAAGGCGTTCTTCCAGGCATGGTCTGGCAGGACAGAGATGTGTACCTTCAGGGGCCCATCTGGGCAAAGATTC
CACACACGGACGGACATTTTCACCCCTCTCCCCTCATGGGTGGATTCGGACTTAAACACCCTCCTCCACAGATTCTC

FIG. 35

ATCAAGAACACCCCGGTACCTGCGAATCCTTCGACCACCTTCAGTGCGGCAAAGTTTGCTTCCTTCATCACACAGTA
CTCCACGGGACAGGTCAGCGTGGAGATCGAGTGGGAGCTGCAGAAGGAAAACAGCAAACGCTGGAATCCCGAAATTC
AGTACACTTCCAACTACAACAAGTCTGTTAATGTGGACTTTACTGTGGACACTAATGGCGTGTATTCAGAGCCTCGC
CCCATTGGCACCAGATACCTGACTCGTAATCTGTAATTGCTTGTTAATCAATAAACCGTTTAATTCGTTTCAGTTGA
ACTTTGGTGTCGCGGCCGCTCGATAAGCTTTTGTTCCCTTTAGTGAGGGTTAATTCCGAGCTTGGCGTAATCATGGT
CATAGCTGTTTCCTGTGTGAAATTGTTATCCGCTCACAATTCCACACAACATACGAGCCGGAAGCATAAAGTGTAAA
GCCTGGGGTGCCTAATGAGTGAGCTAACTCACATTAATTGCGTTGCGCTCACTGCCCGCTTTCCAGTCGGGAAACCT
GTCGTGCCAGCTGCATTAATGAATCGGCCAACGCGCGGGGAGAGGCGGTTTGCGTATTGGGCGCTCTTCCGCTTCCT
CGCTCACTGACTCGCTGCGCTCGGTCGTTCGGCTGCGGCGAGCGGTATCAGCTCACTCAAAGGCGGTAATACGGTTA
TCCACAGAATCAGGGGATAACGCAGGAAAGAACATGTGAGCAAAAGGCCAGCAAAAGGCCAGGAACCGTAAAAAGGC
CGCGTTGCTGGCGTTTTTCCATAGGCTCCGCCCCCCTGACGAGCATCACAAAAATCGACGCTCAAGTCAGAGGTGGC
GAAACCCGACAGGACTATAAAGATACCAGGCGTTTCCCCCTGGAAGCTCCCTCGTGCGCTCTCCTGTTCCGACCCTG
CCGCTTACCGGATACCTGTCCGCCTTTCTCCCTTCGGGAAGCGTGGCGCTTTCTCATAGCTCACGCTGTAGGTATCT
CAGTTCGGTGTAGGTCGTTCGCTCCAAGCTGGGCTGTGTGCACGAACCCCCCGTTCAGCCCGACCGCTGCGCCTTAT
CCGGTAACTATCGTCTTGAGTCCAACCCGGTAAGACACGACTTATCGCCACTGGCAGCAGCCACTGGTAACAGGATT
AGCAGAGCGAGGTATGTAGGCGGTGCTACAGAGTTCTTGAAGTGGTGGCCTAACTACGGCTACACTAGAAGGACAGT
ATTTGGTATCTGCGCTCTGCTGAAGCCAGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGGTCATGAGATTATCAAAAAG
GATCTTCACCTAGATCCTTTTAAATTAAAAATGAAGTTTTAAATCAATCTAAAGTATATATGAGTAAACTTGGTCTG
ACAGTTACCAATGCTTAATCAGTGAGGCACCTATCTCAGCGATCTGTCTATTTCGTTCATCCATAGTTGCCTGACTC
CCCGTCGTGTAGATAACTACGATACGGGAGGGCTTACCATCTGGCCCCAGTGCTGCAATGATACCGCGAGACCCACG
CTCACCGGCTCCAGATTTATCAGCAATAAACCAGCCAGCCGGAAGGGCCGAGCGCAGAAGTGGTCCTGCAACTTTAT
CCGCCTCCATCCAGTCTATTAATTGTTGCCGGGAAGCTAGAGTAAGTAGTTCGCCAGTTAATAGTTTGCGCAACGTT
GTTGCCATTGCTACAGGCATCGTGGTGTCACGCTCGTCGTTTGGTATGGCTTCATTCAGCTCCGGTTCCCAACGATC
AAGGCGAGTTACATGATCCCCCATGTTGTGCAAAAAAGCGGTTAGCTCCTTCGGTCCTCCGATCGTTGTCAGAAGTA
AGTTGGCCGCAGTGTTATCACTCATGGTTATGGCAGCACTGCATAATTCTCTTACTGTCATGCCATCCGTAAGATGC
TTTTCTGTGACTGGTGAGTACTCAACCAAGTCATTCTGAGAATAGTGTATGCGGCGACCGAGTTGCTCTTGCCCGGC
GTCAATACGGGATAATACCGCGCCACATAGCAGAACTTTAAAAGTGCTCATCATTGGAAAACGTTCTTCGGGGCGAA
AACTCTCAAGGATCTTACCGCTGTTGAGATCCAGTTCGATGTAACCCACTCGTGCACCCAACTGATCTTCAGCATCT
TTTACTTTCACCAGCGTTTCTGGGTGAGCAAAAACAGGAAGGCAAAATGCCGCAAAAAAGGGAATAAGGGCGACACG
GAAATGTTGAATACTCATACTCTTCCTTTTTCAATATTATTGAAGCATTTATCAGGGTTATTGTCTCATGAGCGGAT
ACATATTTGAATGTATTTAGAAAAATAAACAAATAGGGGTTCCGCGCACATTTCCCCGAAAAGTGCCACCTGACGTC
TAAGAAACCATTATTATCATGACATTAACCTATAAAAATAGGCGTATCACGAGGCCCTTTCGTC

FIG. 35 (cont.)

SEQUENCE LISTING

```
Sequence total quantity: 155
SEQ ID NO: 1            moltype = DNA  length = 4718
FEATURE                 Location/Qualifiers
source                  1..4718
                        mol_type = genomic DNA
                        organism = Adeno-associated virus 1
SEQUENCE: 1
ttgcccactc cctctctgcg cgctcgctcg ctcggtgggg cctgcggacc aaaggtccgc  60
agacggcaga gctctgctct gccggcccca ccgagcgagc gagcgcgcag agagggagtg  120
ggcaactcca tcactagggg taatcgcgaa gcgcctccca cgctgccgcg tcagcgctga  180
cgtaaattac gtcatagggg agtggtcctg tattagctgt cacgtgagtg cttttgcgac  240
attttgcgac accacgtggc catttagggt atatatggcc gagtgagcga gcaggatctc  300
cattttgacc gcgaaatttg aacgagcagc agccatgccg ggcttctacg agatcgtgat  360
caaggtgccg agcgacctgg acgagcacct gccgggcatt tctgactcgt ttgtgagctg  420
ggtggccgag aaggaatggg agctgccccc ggattctgac atggatctga atctgattga  480
gcaggcaccc ctgaccgtgg ccgagaagct gcagcgcgac ttcctggtcc aatggcgccg  540
cgtgagtaag gccccggagg ccctcttctt tgttcagttc gagaagggcg agtcctactt  600
ccacctccat attctggtgg agaccacggg ggtcaaatcc atggtgctgg gccgcttcct  660
gagtcagatt agggacaagc tggtgcagac catctaccgc gggatcgagc cgaccctgcc  720
caactggttc gcggtgacca agacgcgtaa tggcgccgga ggggggaaca aggtggtgga  780
cgagtgctac atccccaact acctcctgcc caagactcag cccgagctgc agtgggcgtg  840
gactaacatg gaggagtata taagcgcctg tttgaacctg gccgagcgca aacggctcgt  900
ggcgcagcac ctgacccacg tcagccagac ccaggagcag aacaaggaga atctgaaccc  960
caattctgac gcgcctgtca tccggtcaaa aacctccgcg cgctacatgg agctggtcgg  1020
gtggctggtg gaccggggca tcacctccga gaagcagtgg atccaggagg accaggcctc  1080
gtacatctcc ttcaacgccg cttccaactc gcggtcccag atcaaggccg ctctggacaa  1140
tgccggcaag atcatggcgc tgaccaaatc cgcgcccgac tacctggtag gccccgctcc  1200
gcccgcggac attaaaacca accgcatcta ccgcatcctg gagctgaacg gctacgaacc  1260
tgcctacgcc ggctccgtct ttctcggctg ggcccagaaa aggttcggga agcgcaacac  1320
catctggctg tttgggccgg ccaccacggg caagaccaac atcgcggaag ccatcgccca  1380
cgccgtgccc ttctacggct gcgtcaactg gaccaatgag aactttccct tcaatgattg  1440
cgtcgacaag atggtgatct ggtgggagga gggcaagatg acggccaagg tcgtggagtc  1500
cgccaaggcc attctcggcg gcagcaaggt gcgcgtggac caaaagtgca agtcgtccgc  1560
ccagatcgac cccacccccg tgatcgtcac ctccaacacc aacatgtgcg ccgtgattga  1620
cgggaacagc accaccttcg agcaccagca gccgttgcag gaccggatgt tcaaatttga  1680
actcacccgc cgtctggagc atgactttgg caaggtgaca aagcaggaag tcaaagagtt  1740
cttccgctgg gcgcaggatc acgtgaccga ggtggcgcat gagttctacg tcagaaaggg  1800
tggagccaac aaaagacccg cccccgatga cgcggataaa agcgagccca agcgggcctg  1860
cccctcagtc gcggatccat cgacgtcaga cgcggaagga gctccggtgg actttgccga  1920
caggtaccaa aacaaatgtt ctcgtcacgc gggcatgctt cagatgctgt ttccctgcaa  1980
gacatgcgag agaatgaatc agaatttcaa catttgcttc acgcacggga cgagagactg  2040
ttcagagtgc ttccccggcg tgtcagaatc tcaaccggtc gtcagaaaga ggacgtatcg  2100
gaaactctgt gccattcatc atctgctggg gcgggctccc gagattgctt gctcggcctg  2160
cgatctggtc aacgtggacc tggatgactg tgtttctgag caataaatga cttaaaccag  2220
gtatggctgc cgatggttat cttccagatt ggctcgagga caacctctct gagggcattc  2280
gcgagtggtg ggacttgaaa cctggagccc cgaagcccaa agccaaccag caaaagcagg  2340
```

-continued

```
acgacggccg gggtctggtg cttcctggct acaagtacct cggacccttc aacggactcg  2400
acaaggggga gcccgtcaac gcggcggacg cagcggccct cgagcacgac aaggcctacg  2460
accagcagct caaagcgggt gacaatccgt acctgcggta taaccacgcc gacgccgagt  2520
ttcaggagcg tctgcaagaa gatacgtctt ttgggggcaa cctcgggcga gcagtcttcc  2580
aggccaagaa gcgggttctc gaacctctcg gtctggttga ggaaggcgct aagacggctc  2640
ctggaaagaa acgtccggta gagcagtcgc cacaagagcc agactcctcc tcgggcatcg  2700
gcaagacagg ccagcagccc gctaaaaaga gactcaattt tggtcagact ggcgactcag  2760
agtcagtccc cgatccacaa cctctcggag aacctccagc aacccccgct gctgtgggac  2820
ctactacaat ggcttcaggc ggtggcgcac caatggcaga caataacgaa ggcgccgacg  2880
gagtgggtaa tgcctcagga aattggcatt gcgattccac atggctgggc gacagagtca  2940
tcaccaccag cacccgcacc tgggccttgc ccacctacaa taaccacctc tacaagcaaa  3000
tctccagtgc ttcaacgggg gccagcaacg acaaccacta cttcggctac agcacccct   3060
gggggtattt tgatttcaac agattccact gccacttttc accacgtgac tggcagcgac  3120
tcatcaacaa caattgggga ttccggccca agagactcaa cttcaaactc ttcaacatcc  3180
aagtcaagga ggtcacgacg aatgatggcg tcacaaccat cgctaataac cttaccagca  3240
cggttcaagt cttctcggac tcggagtacc agcttccgta cgtcctcggc tctgcgcacc  3300
agggctgcct ccctccgttc ccggcggacg tgttcatgat tccgcaatac ggctacctga  3360
cgctcaacaa tggcagccaa gccgtgggac gttcatcctt ttactgcctg gaatatttcc  3420
cttctcagat gctgagaacg ggcaacaact ttaccttcag ctacaccttt gaggaagtgc  3480
ctttccacag cagctacgcg cacagccaga gcctggaccg gctgatgaat cctctcatcg  3540
accaatacct gtattacctg aacagaactc aaaatcagtc cggaagtgcc caaaacaagg  3600
acttgctgtt tagccgtggg tctccagctg gcatgtctgt tcagcccaaa aactggctac  3660
ctggaccctg ttatcggcag cagcgcgttt ctaaaacaaa aacagacaac aacaacagca  3720
attttacctg gactggtgct tcaaaatata acctcaatgg gcgtgaatcc atcatcaacc  3780
ctggcactgc tatggcctca cacaaagacg acgaagacaa gttctttccc atgagcggtg  3840
tcatgatttt tggaaaagag agcgccggag cttcaaacac tgcattggac aatgtcatga  3900
ttacagacga agaggaaatt aaagccacta accctgtggc caccgaaaga tttgggaccg  3960
tggcagtcaa tttccagagc agcagcacag accctgcgac cggagatgtg catgctatgg  4020
gagcattacc tggcatggtg tggcaagata gagacgtgta cctgcagggt cccatttggg  4080
ccaaaattcc tcacacagat ggacactttc acccgtctcc tcttatgggc ggctttggac  4140
tcaagaaccc gcctcctcag atcctcatca aaaacacgcc tgttcctgcg aatcctccgg  4200
cggagttttc agctacaaag tttgcttcat tcatcaccca atactccaca ggacaagtga  4260
gtgtggaaat tgaatgggag ctgcagaaag aaaacagcaa gcgctggaat cccgaagtgc  4320
agtacacatc caattatgca aaatctgcca acgttgattt tactgtggac aacaatggac  4380
tttatactga gcctcgcccc attggcaccc gttaccttac ccgtcccctg taattacgtg  4440
ttaatcaata aaccggttga ttcgtttcag ttgaactttg gtctcctgtc cttcttatct  4500
tatcggttac catggttata gcttacacat taactgcttg gttgcgcttc gcgataaaag  4560
acttacgtca tcgggttacc cctagtgatg gagttgccca ctccctctct gcgcgctcgc  4620
tcgctcggtg gggcctgcgg accaaaggtc cgcagacggc agagctctgc tctgccggcc  4680
ccaccgagcg agcgagcgcg cagagaggga gtgggcaa                          4718

SEQ ID NO: 2              moltype = DNA  length = 4679
FEATURE                   Location/Qualifiers
source                    1..4679
                          mol_type = genomic DNA
                          organism = Adeno-associated virus 2
SEQUENCE: 2
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctggagg ggtggagtcg tgacgtgaat tacgtcatag  180
ggttagggag gtcctgtatt agaggtcacg tgagtgtttt gcgacatttt gcgacaccat  240
gtggtcacgc tgggtattta agcccgagtg agcacgcagg gtctccattt tgaagcggga  300
ggtttgaacg cgcagccgcc atgccggggt tttacgagat tgtgattaag gtccccagcg  360
accttgacga gcatctgccc ggcatttctg acagctttgt gaactgggtg gccgagaagg  420
aatgggagtt gccgccagat tctgacatgg atctgaatct gattgagcag gcacccctga  480
ccgtggccga gaagctgcag cgcgactttc tgacggaatg gcgccgtgtg agtaaggccc  540
cggaggccct tttctttgtg caatttgaga agggagagag ctacttccac atgcacgtgc  600
tcgtggaaac caccggggtg aaatccatgg ttttgggacg tttcctgagt cagattcgcg  660
aaaaactgat tcagagaatt taccgcggga tcgagccgac tttgccaaac tggttcgcgg  720
tcacaaagac cagaaatggc gccggaggcg ggaacaaggt ggtggatgag tgctacatcc  780
ccaattactt gctccccaaa acccagcctg agctccagtg ggcgtggact aatatggaac  840
agtatttaag cgcctgtttg aatctcacgg agcgtaaacg gttggtggcg cagcatctga  900
cgcacgtgtc gcagacgcag gagcagaaca aagagaatca gaatcccaat tctgatgcgc  960
cggtgatcag atcaaaaact tcagccaggt acatggagct ggtcgggtgg ctcgtggaca  1020
aggggattac ctcggagaag cagtggatcc aggaggacca ggcctcatac atctccttca  1080
atgcggcctc caactcgcgg tcccaaatca aggctgcctt ggacaatgcg ggaaagatta  1140
tgagcctgac taaaaccgcc cccgactacc tggtgggcca gcagcccgtg gaggacattt  1200
ccagcaatcg gatttataaa attttggaac taaacgggta cgatccccaa tatgcggctt  1260
ccgtctttct gggatgggcc acgaaaaagt tcggcaagag gaacaccatc tggctgtttg  1320
ggcctgcaac taccgggaag accaacatcg cggaggccat agcccacact gtgcccttct  1380
acgggtgcgt aaactggacc aatgagaact ttcccttcaa cgactgtgtc gacaagatgg  1440
tgatctggtg ggaggagggg aagatgaccg ccaaggtcgt ggagtcggcc aaagccattc  1500
tcggaggaag caaggtgcgc gtggaccaga aatgcaagtc ctcggcccag atagacccga  1560
ctcccgtgat cgtcacctcc aacaccaaca tgtgcgccgt gattgacggg aactcaacga  1620
ccttcgaaca ccagcagccg ttgcaagacc ggatgttcaa atttgaactc acccgccgtc  1680
tggatcatga ctttgggaag gtcaccaagc aggaagtcaa agacttttc cggtgggcaa   1740
aggatcacgt ggttgaggtg gagcatgaat tctacgtcaa aaagggtgga gccaagaaaa  1800
gacccgcccc cagtgacgca gatataagtg agcccaaacg ggtgcgcgag tcagttgcgc  1860
agccatcgac gtcagacgcg gaagcttcga tcaactacgc agacaggtac caaaacaaat  1920
```

```
gttctcgtca cgtgggcatg aatctgatgc tgtttccctg cagacaatgc gagagaatga  1980
atcagaattc aaatatctgc ttcactcacg gacagaaaga ctgtttagag tgctttcccg  2040
tgtcagaatc tcaacccgtt tctgtcgtca aaaaggcgta tcagaaactg tgctacattc  2100
atcatatcat gggaaaggtg ccagacgctt gcactgcctg cgatctggtc aatgtggatt  2160
tggatgactg catctttgaa caataaatga tttaaatcag gtatggctgc cgatggttat  2220
cttccagatt ggctcgagga cactctctct gaaggaataa gacagtggtg gaagctcaaa  2280
cctggcccac caccaccaaa gcccgcagag cggcataagg acgacagcag gggtcttgtg  2340
cttcctgggt acaagtacct cggacccttc aacggactcg acaagggaga gccggtcaac  2400
gaggcagacg ccgcggccct cgagcacgac aaagcctacg accggcagct cgacagcgga  2460
gacaacccgt acctcaagta caaccacgcc gacgcggagt ttcaggagcg ccttaaagaa  2520
gatacgtctt ttgggggcaa cctcggacga gcagtcttcc aggcgaaaaa gagggttctt  2580
gaacctctgg gcctggttga ggaacctgtt aagacggctc cgggaaaaaa gaggccggta  2640
gagcactctc ctgtggagcc agactcctcc tcgggaaccg gaaaggcggg ccagcagcct  2700
gcaagaaaaa gattgaattt tggtcagact ggagacgcag actcagtacc tgacccccag  2760
cctctcggac agccaccagc agccccctct ggtctgggaa ctaatacgat ggctacaggc  2820
agtggcgcac caatggcaga caataacgag ggcgccgacg gagtgggtaa ttcctcggga  2880
aattggcatt gcgattccac atggatgggc gacagagtca tcaccaccag cacccgaacc  2940
tgggccctgc ccacctacaa caaccacctc tacaaacaaa tttccagcca atcaggagcc  3000
tcgaacgaca atcactactt tggctacagc accccttggg ggtattttga cttcaacaga  3060
ttccactgcc acttttcacc acgtgactgg caaagactca tcaacaacaa ctggggattc  3120
cgacccaaga gactcaactt caagctcttt aacattcaag tcaaagaggt cacgcagaat  3180
gacggtacga cgacgattgc caataacctt accagcacgg ttcaggtgtt tactgactcg  3240
gagtaccagc tcccgtacgt cctcggctcg gcgcatcaag gatgcctccc gccgttccca  3300
gcagacgtct tcatggtgcc acagtatgga tacctcaccc tgaacaacgg gagtcaggca  3360
gtaggacgct cttcatttta ctgcctggag tactttcctt ctcagatgct gcgtaccgga  3420
aacaacttta ccttcagcta cacttttgag gacgttcctt tccacagcag ctacgctcac  3480
agccagagtc tggaccgtct catgaatcct ctcatcgacc agtacctgta ttacttgagc  3540
agaacaaaca ctccaagtgg aaccaccacg cagtcaaggc ttcagttttc tcaggccgga  3600
gcgagtgaca ttcgggacca gtctaggaac tggcttcctg gaccctgtta ccgccagcag  3660
cgagtatcaa agacatctgc ggataacaac aacagtgaat actcgtggac tggagctacc  3720
aagtaccacc tcaatggcag agactctctg gtgaatccgg gcccggccat ggcaagccac  3780
aaggacgatg aagaaaagtt ttttcctcag agcggggttc tcatctttgg gaagcaaggc  3840
tcagagaaaa caaatgtgga cattgaaaag gtcatgatta cagacgaaga ggaaatcagg  3900
acaaccaatc ccgtggctac ggagcagtat ggttctgtat ctaccaacct ccagagaggc  3960
aacagacaag cagctaccgc agatgtcaac acacaaggcg ttcttccagg catggtctgg  4020
caggacagag atgtgtacct tcaggggccc atctgggcaa agattccaca cacggacgga  4080
cattttcacc cctctcccct catgggtgga ttcggactta aacaccctcc tccacagatt  4140
ctcatcaaga acaccccggt acctgcgaat ccttcgacca ccttcagtgc ggcaaagttt  4200
gcttccttca tcacacagta ctccacggga caggtcagcg tggagatcga gtgggagctg  4260
cagaaggaaa acagcaaacg ctggaatccc gaaattcagt acacttccaa ctacaacaag  4320
tctgttaatg tggactttac tgtggacact aatggcgtgt attcagagcc tcgccccatt  4380
ggcaccagat acctgactcg taatctgtaa ttgcttgtta atcaataaac cgtttaattc  4440
gtttcagttg aactttggtc tctgcgtatt tctttcttat ctagtttcca tggctacgta  4500
gataagtagc atggcgggtt aatcattaac tacaaggaac ccctagtgat ggagttggcc  4560
actccctctc tgcgcgctcg ctcgctcact gaggccgggc gaccaaaggt cgcccgacgc  4620
ccgggctttg cccgggcggc ctcagtgagc gagcgagcgc gcagagaggg agtggccaa   4679

SEQ ID NO: 3           moltype = DNA  length = 4726
FEATURE                Location/Qualifiers
source                 1..4726
                       mol_type = genomic DNA
                       organism = Adeno-associated virus 3A
SEQUENCE: 3
ttggccactc cctctatgcg cactcgctcg ctcggtgggg cctggcgacc aaaggtcgcc  60
agacggacgt gctttgcacg tccggcccca ccgagcgagc gagtgcgcat agagggagtg  120
gccaactcca tcactagagg tatggcagtg acgtaacgcg aagcgcgcga agcgagacca  180
cgcctaccag ctgcgtcagc agtcaggtga cccttttgcg acagtttgcg acaccacgtg  240
gccgctgagg gtatatattc tcgagtgagc gaaccaggag ctccattttg accgcgaaat  300
ttgaacgagc agcagccatg ccggggttct acgagattgt cctgaaggtc ccgagtgacc  360
tggacgagcg cctgccgggc atttctaact cgtttgttaa ctgggtggcc gagaaggaat  420
gggacgtgcc gccggattct gacatggatc cgaatctgat tgagcaggca cccctgaccg  480
tggccgaaaa gcttcagcgc gagttcctgg tggagtggcg ccgcgtgagt aaggccccgg  540
aggccctctt ttttgtccag ttcgaaaagg gggagaccta cttccacctg cacgtgctga  600
ttgagaccat cggggtcaaa tccatggtgg tcggccgcta cgtgagccag attaaagaga  660
agctggtgac ccgcatctac cgcggggtcg agccgcagct tccgaactgg ttcgcggtga  720
ccaaaacgcg aaatggcgcc gggggcggga acaaggtggt ggacgactgc tacatcccca  780
actacctgct ccccaagacc cagcccgagc tccagtgggc gtggactaac atggaccagt  840
atttaagcgc ctgtttgaat ctcgcggagc gtaaacggct ggtggcgcag catctgacgc  900
acgtgtcgca gacgcaggag cagaacaaag agaatcagaa ccccaattct gacgcgccgg  960
tcatcaggtc aaaaacctca gccaggtaca tggagctggt cgggtggctg gtggaccgcg  1020
ggatcacgtc agaaaagcaa tggattcagg aggaccaggc ctcgtacatc tccttcaacg  1080
ccgcctccaa ctcgcggtcc cagatcaagg ccgcgctgga caatgcctcc aagatcatga  1140
gcctgacaaa gacggctccg gactacctgg tgggcagcaa cccgccggag gacattacca  1200
aaaatcggat ctaccaaatc ctggagctga acgggtacga tccgcagtac gcggcctccg  1260
tcttcctggg ctgggcgcaa aagaagttcg ggaagaggaa caccatctgg ctctttgggc  1320
cggccacgac gggtaaaacc aacatcgcgg aagccatcgc ccacgccgtg cccttctacg  1380
gctgcgtaaa ctggaccaat gagaactttc ccttcaacga ttgcgtcgac aagatggtga  1440
tctggtggga ggagggcaag atgacggcca aggtcgtgga gagcgccaag gccattctgg  1500
gcggaagcaa ggtgcgcgtg gaccaaaagt gcaagtcatc ggcccagatc gaacccactc  1560
```

```
ccgtgatcgt cacctccaac accaacatgt gcgccgtgat tgacgggaac agcaccacct  1620
tcgagcatca gcagccgctg caggaccgga tgtttgaatt tgaacttacc cgccgtttgg  1680
accatgactt tgggaaggtc accaaacagg aagtaaagga ctttttccgg tgggcttccg  1740
atcacgtgac tgacgtggct catgagttct acgtcagaaa gggtggagct aagaaacgcc  1800
ccgcctccaa tgacgcggat gtaagcgagc caaaacggga gtgcacgtca cttgcgcagc  1860
cgacaacgtc agacgcggaa gcaccggcgg actacgcgga caggtaccaa aacaaatgtt  1920
ctcgtcacgt gggcatgaat ctgatgcttt ttccctgtaa aacatgcgag agaatgaatc  1980
aaatttccaa tgtctgtttt acgcatggtc aaagagactg tggggaatgc ttccctggaa  2040
tgtcagaatc tcaacccgtt tctgtcgtca aaaagaagac ttatcagaaa ctgtgtccaa  2100
ttcatcatat cctgggaagg gcacccgaga ttgcctgttc ggcctgcgat ttggccaatg  2160
tggacttgga tgactgtgtt tctgagcaat aaatgactta aaccaggtat ggctgctgac  2220
ggttatcttc cagattggct cgaggacaac ctttctgaag gcattcgtga gtggtgggct  2280
ctgaaacctg gagtccctca acccaaagcg aaccaacaac accaggacaa ccgtcggggt  2340
cttgtgcttc cgggttacaa atacctcgga cccggtaacg gactcgacaa aggagagccg  2400
gtcaacgagg cggacgcggc agccctcgaa cacgacaaag cttacgacca gcagctcaag  2460
gccggtgaca acccgtacct caagtacaac cacgccgacg ccgagtttca ggagcgtctt  2520
caagaagata cgtcttttgg gggcaacctt ggcagagcag tcttccaggc caaaaagagg  2580
atccttgagc ctcttggtct ggttgaggaa gcagctaaaa cggctcctgg aaagaagggg  2640
gctgtagatc agtctcctca ggaaccggac tcatcatctg gtgttggcaa atcgggcaaa  2700
cagcctgcca gaaaaagact aaatttcggt cagactggag actcagagtc agtcccagac  2760
cctcaacctc tcggagaacc accagcagcc cccacaagtt tgggatctaa tacaatggct  2820
tcaggcggtg gcgcaccaat ggcagacaat aacgagggtg ccgatggagt gggtaattcc  2880
tcaggaaatt ggcattgcga ttcccaatgg ctgggcgaca gagtcatcac caccagcacc  2940
agaacctggg ccctgcccac ttacaacaac catctctaca agcaaatctc cagccaatca  3000
ggagcttcaa acgacaacca ctactttggc tacagcaccc cttgggggta ttttgacttt  3060
aacagattcc actgccactt ctcaccacgt gactggcagc gactcattaa caacaactgg  3120
ggattccggc ccaagaaact cagcttcaag ctcttcaaca tccaagttag aggggtcacg  3180
cagaacgatg gcacgacgac tattgccaat aaccttacca gcacggttca agtgtttacg  3240
gactcggagt atcagctccc gtacgtgctc gggtcggcgc accaaggctg tctcccgccg  3300
tttccagcgg acgtcttcat ggtccctcag tatggatacc tcaccctgaa caacggaagt  3360
caagcggtgg gacgctcatc ctttactgc ctggagtact tcccttcgca gatgctaagg  3420
actggaaata acttccaatt cagctatacc ttcgaggatg taccttttca cagcagctac  3480
gctcacagcc agagtttgga tcgcttgatg aatcctctta ttgatcagta tctgtactac  3540
ctgaacagaa cgcaaggaac aacctctgga acaaccaacc aatcacggct gctttttagc  3600
caggctgggc ctcagtctat gtctttgcag gccagaaatt ggctacctgg gccctgctac  3660
cggcaacaga gactttcaaa gactgctaac gacaacaaca acagtaactt tccttggaca  3720
gcggccagca aatatcatct caatggccgc gactcgctgg tgaatccagg accagctatg  3780
gccagtcaca aggacgatga agaaaaattt ttccctatgc acggcaatct aatatttggc  3840
aaagaaggga caacggcaag taacgcagaa ttagataatg taatgattac ggatgaagaa  3900
gagattcgta ccaccaatcc tgtggcaaca gagcagtatg gaactgtggc aaataacttg  3960
cagagctcaa atacagctcc cacgactgga actgtcaatc atcagggggc cttacctggc  4020
atggtgtggc aagatcgtga cgtgtacctt caaggaccta tctgggcaaa gattcctcac  4080
acggatggac actttcatcc ttctcctctg atgggaggct ttggactgaa acatccgcct  4140
cctcaaatca tgatcaaaaa tactccggta ccggcaaatc ctccgacgac tttcagcccg  4200
gccaagtttg cttcatttat cactcagtac tccactggac aggtcagcgt ggaaattgag  4260
tgggagctac agaaagaaaa cagcaaacgt tggaatccag agattcagta cacttccaac  4320
tacaacaagt ctgttaatgt ggactttact gtagacacta atggtgttta tagtgaacct  4380
cgccctattg gaacccggta tctcacacga aacttgtgaa tcctggttaa tcaataaacc  4440
gtttaattcg tttcagttga actttggctc ttgtgcactt ctttatcttt atcttgtttc  4500
catggctact gcgtagataa gcagcggcct gcggcgcttg cgcttcgcgg tttacaactg  4560
ctggttaata tttaactctc gccatacctc tagtgatgga gttggccact ccctctatgc  4620
gcactcgctc gctcggtggg gcctggcgac caaaggtcgc cagacggacg tgctttgcac  4680
gtccggcccc accgagcgag cgagtgcgca tagagggagt ggccaa                4726
```

```
SEQ ID NO: 4            moltype = DNA  length = 4722
FEATURE                 Location/Qualifiers
source                  1..4722
                        mol_type = genomic DNA
                        organism = Adeno-associated virus 3B
SEQUENCE: 4
tggccactcc ctctatgcgc actcgctcgc tcggtggggc ctggcgacca aaggtcgcca  60
gacggacgtg ctttgcacgt ccggccccac cgagcgagcg agtgcgcata gagggagtgg  120
ccaactccat cactagaggt atggcagtga cgtaacgcga agcgcgcgaa gcgagaccac  180
gcctaccagc tgcgtcagca gtcaggtgac ccttttgcga cagtttgcga caccacgtgg  240
ccgctgaggg tatatattct cgagtgagcg aaccaggagc tccattttga ccgcgaaatt  300
tgaacgagca gcagccatgc cggggttcta cgagattgtc ctgaaggtcc cgagtgacct  360
ggacgagcac ctgccgggca tttctaactc gtttgttaac tgggtggccg agaaggaatg  420
ggagctgccg ccggattctg acatggatcc gaatctgatt gagcaggcac ccctgaccgt  480
ggccgaaaag cttcagcgcg agttcctggt ggagtggcgc cgcgtgagta aggcccccga  540
ggccctcttt tttgtccagt tcgaaaaggg ggagacctac ttccacctgc acgtgctgat  600
tgagaccatc ggggtcaaat ccatggtggt cggccgctac gtgagccaga ttaaagagaa  660
gctggtgacc cgcatctacc gcggggtcga gccgcagctt ccgaactggt tcgcggtgac  720
caaaacgcga aatggcgccg gggcgggaa caaggtggtg gacgactgct acatccccaa  780
ctacctgctc cccaagaccc agcccgagct ccagtgggcg tggactaaca tggaccagta  840
tttaagcgcc tgtttgaatc tcgcggagcg taaacggctg gtggcgcagc atctgacgca  900
cgtgtcgcag acgcaggagc agaacaaaga gaatcagaac cccaattctg acgcgccggt  960
catcaggtca aaaacctcag ccaggtacat ggagctggtc gggtggctgg tggaccgcgg  1020
gatcacgtca gaaaagcaat ggattcagga ggaccaggcc tcgtacatct ccttcaacgc  1080
cgcctccaac tcgcggtccc agatcaaggc cgcgctggac aatgcctcca agatcatgag  1140
```

-continued

```
cctgacaaag acggctccgg actacctggt gggcagcaac ccgccggagg acattaccaa  1200
aaatcggatc taccaaatcc tggagctgaa cgggtacgat ccgcagtacg cggcctccgt  1260
cttcctgggc tgggcgcaaa agaagttcgg gaagaggaac accatctggc tctttgggcc  1320
ggccacgacg ggtaaaacca acatcgcgga agccatcgcc cacgccgtgc ccttctacgg  1380
ctgcgtaaac tggaccaatg agaactttcc cttcaacgat tgcgtcgaca agatggtgat  1440
ctggtgggag gagggcaaga tgacggccaa ggtcgtggag agcgccaagg ccattctggg  1500
cggaagcaag gtgcgcgtgg accaaaagtg caagtcatcg gcccagatcg aacccactcc  1560
cgtgatcgtc acctccaaca ccaacatgtg cgccgtgatt gacgggaaca gcaccacctt  1620
cgagcatcag cagccgctgc aggaccggat gtttaaattt gaacttaccc gccgtttgga  1680
ccatgacttt gggaaggtca ccaaacagga agtaaaggac tttttccggt gggcttccga  1740
tcacgtgact gacgtggctc atgagttcta cgtcagaaag ggtggagcta agaaacgccc  1800
cgcctccaat gacgcggatg taagcgagcc aaaacggcag tgcacgtcac ttgcgcagcc  1860
gacaacgtca gacgcggaag caccggcgga ctacgcggac aggtaccaaa acaaatgttc  1920
tcgtcacgtg ggcatgaatc tgatgctttt tccctgtaaa acatgcgaga gaatgaatca  1980
aatttccaat gtctgtttta cgcatggtca aagagactgt ggggaatgct tccctggaat  2040
gtcagaatct caacccgttt ctgtcgtcaa aaagaagact tatcagaaac tgtgtccaat  2100
tcatcatatc ctgggaaggg cacccgagat tgcctgttcg gcctgcgatt tggccaatgt  2160
ggacttggat gactgtgttt ctgagcaata aatgacttaa accaggtatg gctgctgacg  2220
gttatcttcc agattggctc gaggacaacc tttctgaagg cattcgtgag tggtgggctc  2280
tgaaacctgg agtccctcaa cccaaagcga accaacaaca ccaggacaac cgtcggggtc  2340
ttgtgcttcc gggttacaaa tacctcggac ccggtaacgg actcgacaaa ggagagccgg  2400
tcaacgaggc ggacgcggca gccctcgaac acgacaaagc ttacgaccag cagctcaagg  2460
ccggtgacaa cccgtacctc aagtacaacc acgccgacgc cgagtttcag gagcgtcttc  2520
aagaagatac gtcttttggg ggcaaccttg gcagagcagt cttccaggcc aaaaagagga  2580
tccttgagcc tcttggtctg gttgaggaag cagctaaaac ggctcctgga aagaagaggc  2640
ctgtagatca gtctcctcag gaaccggact catcatctgg tgttggcaaa tcgggcaaac  2700
agcctgccag aaaaagacta aatttcggtc agactggcga ctcagagtca gtcccagacc  2760
ctcaacctct cggagaacca ccagcagccc ccacaagttt gggatctaat acaatggctt  2820
caggcggtgg cgcaccaatg gcagacaata acgagggtgc cgatggagtg ggtaattcct  2880
caggaaattg gcattgcgat tcccaatggc tgggcgacag agtcatcacc accagcacca  2940
gaacctgggc cctgcccact tacaacaacc atctctacaa gcaaatctcc agccaatcag  3000
gagcttcaaa cgacaaccac tactttggct acagcacccc ttgggggtat tttgacttta  3060
acagattcca ctgccacttc tcaccacgtg actggcagcg actcattaac aacaactggg  3120
gattccggcc caagaaactc agcttcaagc tcttcaacat ccaagttaaa gaggtcacgc  3180
agaacgatgg cacgacgact attgccaata accttaccag cacggttcaa gtgtttacgg  3240
actcggagta tcagctcccg tacgtgctcg ggtcggcgca ccaaggctgt ctcccgccgt  3300
ttccagcgga cgtcttcatg gtccctcagt atggatacct caccctgaac aacggaagtc  3360
aagcggtggg acgctcatcc ttttactgcc tggagtactt cccttcgcag atgctaagga  3420
ctggaaataa cttccaattc agctatacct tcgaggatgt accttttcac agcagctacg  3480
ctcacagcca gagtttggat cgcttgatga atcctcttat tgatcagtat ctgtactacc  3540
tgaacagaac gcaaggaaca acctctggaa caaccaacca atcacggctg ctttttagcc  3600
aggctgggcc tcagtctatg tctttgcagg ccagaaattg gctacctggg ccctgctacc  3660
ggcaacagag actttcaaag actgctaacg acaacaacaa cagtaacttt ccttggacag  3720
cggccagcaa atatcatctc aatggccgcg actcgctggt gaatccagga ccagctatgg  3780
ccagtcacaa ggacgatgaa gaaaaatttt tccctatgca cggcaatcta atatttggca  3840
aagaagggac aacggcaagt aacgcagaat tagataatgt aatgattacg gatgaagaag  3900
agattcgtac caccaatcct gtggcaacag agcagtatgg aactgtggca aataacttgc  3960
agagctcaaa tacagctccc acgactagaa ctgtcaatga tcaggggggcc ttacctggca  4020
tggtgtggca agatcgtgac gtgtaccttc aaggacctat ctgggcaaag attcctcaca  4080
cggatggaca ctttcatcct tctcctctga tgggaggctt tggactgaaa catccgcctc  4140
ctcaaatcat gatcaaaaat actccggtac cggcaaatcc tccgacgact ttcagcccgg  4200
ccaagtttgc ttcatttatc actcagtact ccactggaca ggtcagcgtg gaaattgagt  4260
gggagctaca gaaagaaaac agcaaacgtt ggaatccaga gattcagtac acttccaact  4320
acaacaagtc tgttaatgtg gactttactg tagacactaa tggtgtttat agtgaacctc  4380
gccctattgg aacccggtat ctcacacgaa acttgtaatc ctggttaatc aataaaccgt  4440
ttaattcgtt tcagttgaac tttggctctt gtgcacttct tatcttatct tgtttccatg  4500
gctactgcgt agataagcag cggcctgcgg cgcttgcgct tcgcggttta caactgctgg  4560
ttaatattta actctcgcca tacctctagt gatggagttg gccactccct ctatgcgcac  4620
tcgctcgctc ggtggggccg gacgtgcaaa gcacgtccgt ctggcgacct ttggtcgcca  4680
ggccccaccg agcgagcgag tgcgcataga gggagtggcc aa                      4722

SEQ ID NO: 5           moltype = DNA  length = 4767
FEATURE                Location/Qualifiers
source                 1..4767
                       mol_type = genomic DNA
                       organism = Adeno-associated virus 4
SEQUENCE: 5
ttggccactc cctctatgcg cgctcgctca ctcactcggc cctggagacc aaaggtctcc  60
agactgccgg cctctggccg gcagggccga gtgagtgagc gagcgcgcat agagggagtg  120
gccaactcca tcatctaggt ttgcccactg acgtcaatgt gacgtcctag ggttagggag  180
gtccctgtat tagcagtcac gtgagtgtcg tatttcgcgg agcgtagcgg agcgcatacc  240
aagctgccac gtcacagcca cgtggtccgt ttgcgacagt ttgcgacacc atgtggtcag  300
gagggtatat aaccgcgagt gagccagcga ggagctccat tttgcccgcg aattttgaac  360
gagcagcagc catgccgggg ttctacgaga tcgtgctgaa ggtgcccagc gacctggacg  420
agcacctgcc cggcatttct gactcttttg tgagctgggt ggccgagaag gaatgggagc  480
tgccgccgga ttctgacatg gacttgaatc tgattgagca ggcacccctg accgtggccg  540
aaaagctgca acgcgagttc ctggtcgagt ggcgccgcgt gagtaaggcc ccggaggccc  600
tcttctttgt ccagttcgag aagggggaca gctacttcca cctgcacatc ctggtggaga  660
ccgtgggcgt caaatccatg gtggtgggcc gctacgtgag ccagattaaa gagaagctgg  720
```

-continued

```
tgacccgcat ctaccgcggg gtcgagccgc agcttccgaa ctggttcgcg gtgaccaaga  780
cgcgtaatgg cgcccggaggc gggaacaagg tggtggacga ctgctacatc cccaactacc  840
tgctccccaa gacccagccc gagctccagt gggcgtggac taacatggac cagtatataa  900
gcgcctgttt gaatctcgcg gagcgtaaac ggctggtggc gcagcatctg acgcacgtgt  960
cgcagacgca ggagcagaac aaggaaaacc agaaccccaa ttctgacgcg ccggtcatca  1020
ggtcaaaaac ctccgccagg tacatggagc tggtcgggtg gctggtggac cgcgggatca  1080
cgtcagaaaa gcaatggatc caggaggacc aggcgtccta catctccttc aacgccgcct  1140
ccaactcgcg gtcacaaatc aaggccgcgc tggacaatgc ctccaaaatc atgagcctga  1200
caaagacggc tccggactac ctggtgggcc agaacccgcc ggaggacatt tccagcaacc  1260
gcatctaccg aatcctcgag atgaacgggt acgatccgca gtacgcggcc tccgtcttcc  1320
tgggctgggc gcaaaagaag ttcgggaaga ggaacaccat ctggctcttt gggccggcca  1380
cgacgggtaa aaccaacatc gcggaagcca tcgcccacgc cgtgcccttc tacggctgcg  1440
tgaactggac caatgagaac tttccgttca acgattgcgt cgacaagatg gtgatctggt  1500
gggaggaggg caagatgacg gccaaggtcg tagagagcgc caaggccatc ctgggcggaa  1560
gcaaggtgcg cgtggaccaa aagtgcaagt catcggccca gatcgaccca actcccgtga  1620
tcgtcacctc caacaccaac atgtgcgcgg tcatcgacgg aaactcgacc accttcgagc  1680
accaacaacc actccaggac cggatgttca agttcgagct caccaagcgc ctggagcacg  1740
actttggcaa ggtcaccaag caggaagtca aagacttttt ccggtgggcg tcagatcacg  1800
tgaccgaggt gactcacgag ttttacgtca gaaagggtgg agctagaaag aggcccgccc  1860
ccaatgacgc agatataagt gagcccaagc gggcctgtcc gtcagttgcg cagccatcga  1920
cgtcagacgc ggaagctccg gtggactacg cggacaggta ccaaaacaaa tgttctcgtc  1980
acgtgggtat gaatctgatg ctttttccct gccggcaatg cgagagaatg aatcagaatg  2040
tggacatttg cttcacgcac ggggtcatgg actgtgccga gtgcttcccc gtgtcagaat  2100
ctcaacccgt gtctgtcgtc agaaagcgga cgtatcagaa actgtgtccg attcatcaca  2160
tcatggggag ggcgcccgag gtggcctgct cggcctgcga actggccaat gtggacttgg  2220
atgactgtga catggaacaa taaatgactc aaaccagata tgactgacgg ttaccttcca  2280
gattggctag aggacaacct ctctgaaggc gttcgagagt ggtgggcgct gcaacctgga  2340
gcccctaaac ccaaggcaaa tcaacaacat caggacaacg ctcggggtct tgtgcttccg  2400
ggttacaaat acctcggacc cggcaacgga ctcgacaagg gggaacccgt caacgcagcg  2460
gacgcggcag ccctcgagca cgacaaggcc tacgaccagc agctcaaggc cggtgacaac  2520
ccctacctca agtacaacca cgccgacgcg gagttccagc agcggcttca gggcgacaca  2580
tcgtttgggg gcaacctcgg cagagcagtc ttccaggcca aaaagagggt tcttgaacct  2640
cttggtctgg ttgagcaagc gggtgagacg gctcctggaa agaagagacc gttgattgaa  2700
tccccccagc agcccgactc ctccacgggt atcggcaaaa aaggcaagca gccggctaaa  2760
aagaagctcg ttttcgaaga cgaaactgga gcaggcgacg gaccccctga gggatcaact  2820
tccggagcca tgtctgatga cagtgagatg cgtgcagcag ctggcggagc tgcagtcgag  2880
ggcggacaag gtgccgatgg agtgggtaat gcctcgggtg attggcattg cgattccacc  2940
tggtctgagg gccacgtcac gaccaccagc accagaacct gggtcttgcc cacctacaac  3000
aaccacctct acaagcgact cggagagagc ctgcagtcca acacctacaa cggattctcc  3060
accccctggg gatactttga cttcaaccgc ttccactgcc acttctcacc acgtgactgg  3120
cagcgactca tcaacaacaa ctggggcatg cgacccaaag ccatgcgggt caaaatcttc  3180
aacatccagg tcaaggaggt cacgacgtcg aacggcgaga caacggtggc taataacctt  3240
accagcacgg ttcagatctt tgcggactcg tcgtacgaac tgccgtacgt gatggatgcg  3300
ggtcaagagg gcagcctgcc tccttttccc aacgacgtct ttatggtgcc ccagtacggc  3360
tactgtggac tggtgaccgg caacacttcg cagcaacaga ctgacagaaa tgccttctac  3420
tgcctggagt actttccttc gcagatgctg cggactggca acaactttga aattacgtac  3480
agttttgaga aggtgccttt ccactcgatg tacgcgcaca gccagagcct ggaccggctg  3540
atgaaccctc tcatcgacca gtacctgtgg ggactgcaat cgaccaccac cggaaccacc  3600
ctgaatgccg ggactgccac caccaacttt accaagctgc ggcctaccaa cttttccaac  3660
tttaaaaaga actggctgcc cgggccttca atcaagcagc agggcttctc aaagactgcc  3720
aatcaaaact acaagatccc tgccaccggg tcagacagtc tcatcaaata cgagacgcac  3780
agcactctgg acggaagatg gagtgccctg acccccggac ctccaatggc cacggctgga  3840
cctgcggaca gcaagttcag caacagccag ctcatctttg cggggcctaa acagaacggc  3900
aacacggcca ccgtacccgg gactctgatc ttcacctctg aggaggagct ggcagccacc  3960
aacgccaccg atacggacat gtggggcaac ctacctggcg gtgaccagag caacagcaac  4020
ctgccgaccg tggacagact gacagccttg ggagccgtgc ctggaatggt ctggcaaaac  4080
agagacattt actaccaggg tcccatttgg gccaagattc ctcataccga tggacacttt  4140
cacccctcac cgctgattgg tgggtttggg ctgaaacacc cgcctcctca aatttttatc  4200
aagaacaccc cggtacctgc gaatcctgca acgaccttca gctctactcc ggtaaactcc  4260
ttcattactc agtacagcac tggccaggtg tcggtgcaga ttgactggga gatccagaag  4320
gagcggtcca aacgctggaa ccccgaggtc cagtttacct ccaactacgg acagcaaaac  4380
tctctgttgt gggctcccga tgcggctggg aaatacactg agcctagggc tatcggtacc  4440
cgctacctca cccaccacct gtaataacct gttaatcaat aaaccggttt attcgtttca  4500
gttgaacttt ggtctccgtg tccttcttat cttatctcgt ttccatggct actgcgtaca  4560
taagcagcgg cctgcggcgc ttgcgcttcg cggtttacaa ctgccggtta atcagtaact  4620
tctggcaaac cagatgatgg agttggccac attagctatg cgcgctcgct cactcactcg  4680
gccctggaga ccaaaggtct ccagactgcc ggcctctggc cggcagggcc gagtgagtga  4740
gcgagcgcgc atagagggag tggccaa                                     4767

SEQ ID NO: 6            moltype = DNA  length = 4642
FEATURE                 Location/Qualifiers
source                  1..4642
                        mol_type = genomic DNA
                        organism = Adeno-associated virus 5
SEQUENCE: 6
ctctcccccc tgtcgcgttc gctcgctcgc tggctcgttt ggggggggtgg cagctcaaag  60
agctgccaga cgacggccct ctggccgtcg cccccccaaa cgagccagcg agcgagcgaa  120
cgcgacaggg gggagagtgc cacactctca agcaaggggg ttttgtaagc agtgatgtca  180
taatgatgta atgcttattg tcacgcgata gttaatgatt aacagtcatg tgatgtgttt  240
```

-continued

```
tatccaatag gaagaaagcg cgcgtatgag ttctcgcgag acttccgggg tataaaagac  300
cgagtgaacg agcccgccgc cattctttgc tctggactgc tagaggaccc tcgctgccat  360
ggctaccttc tatgaagtca ttgttcgcgt cccatttgac gtggaggaac atctgcctgg  420
aatttctgac agctttgtgg actgggtaac tggtcaaatt tgggagctgc ctccagagtc  480
agatttaaat ttgactctgg ttgaacagcc tcagttgacg gtggctgata gaattcgccg  540
cgtgttcctg tacgagtgga acaaattttc caagcaggag tccaaattct ttgtgcagtt  600
tgaaaaggga tctgaatatt ttcatctgca cacgcttgtg gagacctccg gcatctcttc  660
catggtcctc ggccgctacg tgagtcagat tcgcgcccag ctggtgaaag tggtcttcca  720
gggaattgaa ccccagatca acgactgggt cgccatcacc aaggtaaaga agggcggagc  780
caataaggtg gtggattctg ggtatattcc cgcctacctg ctgccgaagg tccaaccgga  840
gcttcagtgg gcgtggacaa acctggacga gtataaattg gccgccctga atctggagga  900
gcgcaaacgg ctcgtcgcgc agtttctggc agaatcctcg cagcgctcgc aggaggcggc  960
ttcgcagcgt gagttctcgg ctgacccggt catcaaaagc aagacttccc agaaatacat  1020
ggcgctcgtc aactggctcg tggagcacgg catcacttcc gagaagcagt ggatccagga  1080
aaatcaggag agctacctct ccttcaactc caccggcaac tctcggagcc agatcaaggc  1140
cgcgctcgac aacgcgacca aaattatgag tctgacaaaa agcgcggtgg actacctcgt  1200
ggggagctcc gttcccgagg acatttcaaa aaacagaatc tggcaaattt ttgagatgaa  1260
tggctacgac ccggcctacg cgggatccat cctctacggc tggtgtcagc gctccttcaa  1320
caagaggaac accgtctggc tctacggacc cgccacgacc ggcaagacca acatcgcgga  1380
ggccatcgcc cacactgtgc ccttttacgg ctgcgtgaac tggaccaatg aaaactttcc  1440
ctttaatgac tgtgtggaca aaatgctcat ttggtgggag gagggaaaga tgaccaacaa  1500
ggtggttgaa tccgccaagg ccatcctggg gggctcaaag gtgcgggtcg atcagaaatg  1560
taaatcctct gttcaaattg attctacccc tgtcattgta acttccaata caaacatgtg  1620
tgtggtggtg gatgggaatt ccacgacctt tgaacaccag cagccgctgg aggaccgcat  1680
gttcaaattt gaactgacta agcggctccc gccagatttt ggcaagatta ctaagcagga  1740
agtcaaggac tttttttgctt gggcaaaggt caatcaggtg ccggtgactc acgagtttaa  1800
agttcccagg gaattggcgg gaactaaagg ggcggagaaa tctctaaaac gcccactggg  1860
tgacgtcacc aatactagct ataaaagtct ggagaagcgg gccaggctct catttgttcc  1920
cgagacgcct cgcagttcag acgtgactgt tgatcccgct cctctgcgac cgctcaattg  1980
gaattcaagg tatgattgca aatgtgacta tcatgctcaa tttgacaaca tttctaacaa  2040
atgtgatgaa tgtgaatatt tgaatcgggg caaaaatgga tgtatctgtc acaatgtaac  2100
tcactgtcaa atttgtcatg ggattccccc ctgggaaaag gaaaacttgt cagattttgg  2160
ggattttgac gatgccaata aagaacagta aataaagcga gtagtcatgt cttttgttga  2220
tcaccctcca gattggttgg aagaagttgg tgaaggtctt cgcgagtttt tgggccttga  2280
agcgggccca ccgaaaccaa aacccaatca gcagcatcaa gatcaagccc gtggtcttgt  2340
gctgcctggt tataactatc tcggacccgg aaacggtctc gatcgaggag agcctgtcaa  2400
cagggcagac gaggtcgcgc gagagcacga catctcgtac aacgagcagc ttgaggcggg  2460
agacaacccc tacctcaagt acaaccacgc ggacgccgag tttcaggaga agctcgccga  2520
cgacacatcc ttcgggggaa acctcggaaa ggcagtcttt caggccaaga aaagggttct  2580
cgaacctttt ggcctggttg aagagggtgc taagacggcc cctaccggaa agcggataga  2640
cgaccacttt ccaaaaagaa agaaggctcg gaccgaagag gactccaagc cttccacctc  2700
gtcagacgcc gaagctggac ccagcggatc ccagcagctg caaatcccag cccaaccagc  2760
ctcaagtttg ggagctgata caatgtctgc gggaggtggc ggcccattgg gcgacaataa  2820
ccaaggtgcc gatggagtgg gcaatgcctc gggagattgg cattgcgatt ccacgtggat  2880
gggggacaga gtcgtcacca agtccacccg aacctgggtg ctgcccagct acaacaacca  2940
ccagtaccga gagatcaaaa gcggctccgt cgacggaagc aacgccaacg cctactttgg  3000
atacagcacc ccctgggggt actttgactt taaccgcttc cacagccact ggagccccccg  3060
agactggcaa agactcatca acaactactg gggcttcaga ccccggtccc tcagagtcaa  3120
aatcttcaac attcaagtca aagaggtcac ggtgcaggac tccaccacca ccatcgccaa  3180
caacctcacc tccaccgtcc aagtgtttac ggacgacgac taccagctgc cctacgtcgt  3240
cggcaacggg accgagggat gcctgccggc cttccctccg caggtcttta cgctgccgca  3300
gtacggttac gcgacgctga accgcgacaa cacagaaaat cccaccgaga ggagcagctt  3360
cttctgccta gagtactttc ccagcaagat gctgagaacg ggcaacaact ttgagtttac  3420
ctacaacttt gaggaggtgc ccttccactc cagcttcgct cccagtcaga acctgttcaa  3480
gctggccaac ccgctggtgg accagtactt gtaccgcttc gtgagcacaa ataacactgg  3540
cggagtccag ttcaacaaga acctggccgg gagatacgcc aacacctaca aaaactggtt  3600
cccggggccc atgggccgaa cccagggctg gaacctgggc tccggggtca accgcgccag  3660
tgtcagcgcc ttcgccacga ccaataggat ggagctcgag ggcgcgagtt accaggtgcc  3720
cccgcagccg aacggcatga ccaacaacct ccagggcagc aacacctatg ccctggagaa  3780
cactatgatc ttcaacagcc agccggcgaa cccgggcacc accgccacgt acctcgaggg  3840
caacatgctc atcaccagcg agagcgagac gcagccggtg aaccgcgtgg cgtacaacgt  3900
cggcgggcag atggccacca acaaccagag ctccaccact gcccccgcga ccggcacgta  3960
caacctccag gaaatcgtgc ccggcagcgt gtggatggag agggacgtgt acctccaagg  4020
acccatctgg gccaagatcc cagagacggg ggcgcacttt caccccctctc cggccatggg  4080
cggattcgga ctcaaacacc caccgcccat gatgctcatc aagaacacgc ctgtgcccgg  4140
aaatatcacc agcttctcgg acgtgcccgt cagcagcttc atcacccagt acagcaccgg  4200
gcaggtcacc gtggagatgg agtgggagct caagaaggaa aactccaaga ggtggaaccc  4260
agagatccag tacacaaaca actacaacga cccccagttt gtggactttg ccccggacag  4320
caccggggaa tacagaacca ccagacctat cggaacccga taccttaccc gacccccttta  4380
acccattcat gtcgcatacc ctcaataaac cgtgtattcg tgtcagtaaa atactgcctc  4440
ttgtggtcat tcaatgaata acagcttaca acatctacaa aacctccttg cttgagagtg  4500
tggcactctc ccccctgtcg cgttcgctcg ctcgctggct cgtttggggg ggtggcagct  4560
caaagagctg ccagacgacg gccctctggc cgtcgccccc ccaaacgagc cagcgagcga  4620
gcgaacgcga caggggggag ag                                           4642
```

-continued

SEQ ID NO: 7 moltype = DNA length = 4683
FEATURE Location/Qualifiers
source 1..4683
mol_type = genomic DNA
organism = Adeno-associated virus 6
SEQUENCE: 7
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctggagg ggtggagtcg tgacgtgaat tacgtcatag 180
ggttagggag gtcctgtatt agaggtcacg tgagtgtttt gcgacatttt gcgacaccat 240
gtggtcacgc tgggtattta agcccgagtg agcacgcagg gtctccattt tgaagcggga 300
ggtttgaacg cgcagcgcca tgccggggtt ttacgagatt gtgattaagg tccccagcga 360
ccttgacgag catctgcccg gcatttctga cagctttgtg aactgggtgg ccgagaagga 420
atgggagttg ccgccagatt ctgacatgga tctgaatctg attgagcagg cacccctgac 480
cgtggccgag aagctgcagc gcgacttcct ggtccagtgg cgccgcgtga gtaaggcccc 540
ggaggccctc ttctttgttc agttcgagaa gggcgagtcc tacttccacc tccatattct 600
ggtggagacc acgggggtca aatccatggt gctgggccgc ttcctgagtc agattaggga 660
caagctggtg cagaccatct accgcgggat cgagccgacc ctgcccaact ggttcgcggt 720
gaccaagacg cgtaatggcg ccggaggggg gaacaaggtg gtggacgagt gctacatccc 780
caactacctc ctgcccaaga ctcagcccga gctgcagtgg gcgtggacta acatggagga 840
gtatataagc gcgtgtttaa acctggccga gcgcaaacgg ctcgtggcgc acgacctgac 900
ccacgtcagc cagacccagg agcagaacaa ggagaatctg aaccccaatt ctgacgcgcc 960
tgtcatccgg tcaaaaacct ccgcacgcta catggagctg gtcgggtggc tggtggaccg 1020
gggcatcacc tccgagaagc agtggatcca ggaggaccag gcctcgtaca tctccttcaa 1080
cgccgcctcc aactcgcggt cccagatcaa ggccgctctg gacaatgccg gcaagatcat 1140
ggcgctgacc aaatccgcgc ccgactacct ggtaggcccc gctccgcccg ccgacattaa 1200
aaccaaccgc atttaccgca tcctggagct gaacggctac gaccctgcct acgccggctc 1260
cgtctttctc ggctgggccc agaaaaggtt cggaaaacgc aacaccatct ggctgtttgg 1320
gccggccacc acgggcaaga ccaacatcgc ggaagccatc gcccacgccg tgcccttcta 1380
cggctgcgtc aactggacca atgagaactt tcccttcaac gattgcgtcg acaagatggt 1440
gatctggtgg gaggagggca agatgacggc caaggtcgtg gagtccgcca aggccattct 1500
cggcggcagc aaggtgcgcg tggaccaaaa gtgcaagtcg tccgcccaga tcgatcccac 1560
ccccgtgatc gtcacctcca acaccaacat gtgcgccgtg attgacggga acagcaccac 1620
cttcgagcac cagcagccgt tgcaggaccg gatgttcaaa tttgaactca cccgccgtct 1680
ggagcatgac tttggcaagg tgacaaagca ggaagtcaaa gagttcttcc gctgggcgca 1740
ggatcacgtg accgaggtgg cgcatgagtt ctacgtcaga aagggtggag ccaacaagag 1800
acccgccccc gatgacgcgg ataaaagcga gcccaagcgg gcctgcccct cagtcgcgga 1860
tccatcgacg tcagacgcgg aaggagctcc ggtggacttt gccgacaggt accaaaacaa 1920
atgttctcgt cacgcgggca tgcttcagat gctgtttccc tgcaaaacat gcgagagaat 1980
gaatcagaat ttcaacattt gcttcacgca cgggaccaga gactgttcag aatgtttccc 2040
cggcgtgtca gaatctcaac cggtcgtcag aaagaggacg tatcggaaac tctgtgccat 2100
tcatcatctg ctggggcggg ctcccgagat tgcttgctcg gcctgcgatc tggtcaacgt 2160
ggatctggat gactgtgttt ctgagcaata aatgacttaa accaggtatg gctgccgatg 2220
gttatcttcc agattggctc gaggacaacc tctctgaggg cattcgcgag tggtgggact 2280
tgaaacctgg agccccgaaa cccaaagcca accagcaaaa gcaggacgac ggccggggtc 2340
tggtgcttcc tggctacaag tacctcggac ccttcaacgg actcgacaag ggggagcccg 2400
tcaacgcggc ggatgcagcg gccctcgagc acgacaaggc ctacgaccag cagctcaaag 2460
cgggtgacaa tccgtacctg cggtataacc acgccgacgc cgagtttcag gagcgtctgc 2520
aagaagatac gtcttttggg ggcaacctcg ggcgagcagt cttccaggcc aagaagaggg 2580
ttctcgaacc ttttggtctg gttgaggaag gtgctaagac ggctcctgga aagaaacgtc 2640
cggtagagca gtcgccacaa gagccagact cctcctcggg cattggcaag acaggccagc 2700
agcccgctaa aaagagactc aattttggtc agactggcga ctcagagtca gtccccgacc 2760
cacaacctct cggagaacct ccagcaaccc ccgctgctgt gggacctact acaatggctt 2820
caggcggtgg cgcaccaatg gcagacaata acgaaggcgc cgacggagtg ggtaatgcct 2880
caggaaattg gcattgcgat tccacatggc tgggcgacag agtcatcacc accagcaccc 2940
gaacatgggc cttgcccacc tataacaacc acctctacaa gcaaatctcc agtgcttcaa 3000
cgggggccag caacgacaac cactacttcg gctacagcac cccctggggg tattttgatt 3060
tcaacagatt ccactgccat ttctcaccac gtgactggca gcgactcatc aacaacaatt 3120
ggggattccg gcccaagaga ctcaacttca agctcttcaa catccaagtc aaggaggtca 3180
cgacgaatga tggcgtcacg accatcgcta ataaccttac cagcacggtt caagtcttct 3240
cggactcgga gtaccagttg ccgtacgtcc tcggctctgc gcaccagggc tgcctccctc 3300
cgttcccggc ggacgtgttc atgattccgc agtacggcta cctaacgctc aacaatggca 3360
gccaggcagt gggacggtca tccttttact gcctggaata tttcccatcg cagatgctga 3420
gaacgggcaa taactttacc ttcagctaca ccttcgagga cgtgcctttc cacagcagct 3480
acgcgcacag ccagagcctg gaccggctga tgaatcctct catcgaccag tacctgtatt 3540
acctgaacag aactcagaat cagtccggaa gtgcccaaaa caaggacttg ctgtttagcc 3600
gggggtctcc agctggcatg tctgttcagc ccaaaaactg gctacctgga ccctgttacc 3660
ggcagcagcg cgtttctaaa acaaaaacag acaacaacaa cagcaacttt acctggactg 3720
gtgcttcaaa atataacctt aatgggcgtg aatctataat caaccctggc actgctatgg 3780
cctcacacaa agacgacaaa gacaagttct ttcccatgag cggtgtcatg atttttggaa 3840
aggagagcgc cggagcttca aacactgcat tggacaatgt catgatcaca gacgaagagg 3900
aaatcaaagc cactaacccc gtggccaccg aaagatttgg gactgtggca gtcaatctcc 3960
agagcagcag cacagaccct gcgaccggag atgtgcatgt tatgggagcc ttacctggaa 4020
tggtgtggca agacagagac gtatacctgc agggtcctat ttgggccaaa attcctcaca 4080
cggatggaca ctttcacccg tctcctctca tgggcggctt tggacttaag cacccgcctc 4140
ctcagatcct catcaaaaac acgcctgttc ctgcgaatcc tccggcagag ttttcggcta 4200
caaagtttgc ttcattcatc acccagtatt ccacaggaca agtgagcgtg gagattgaat 4260
gggagctgca gaaagaaaac agcaaacgct ggaatcccga agtgcagtat acatctaact 4320

-continued

```
atgcaaaatc tgccaacgtt gatttcactg tggacaacaa tggactttat actgagcctc  4380
gccccattgg cacccgttac ctcacccgtc ccctgtaatt gtgtgttaat caataaaccg  4440
gttaattcgt gtcagttgaa ctttggtctc atgtcgttat tatcttatct ggtcaccata  4500
gcaaccggtt acacattaac tgcttagttg cgcttcgcga atacccctag tgatggagtt  4560
gcccactccc tctatgcgcg ctcgctcgct cggtggggcc ggcagagcag agctctgccg  4620
tctgcggacc tttggtccgc aggccccacc gagcgagcga gcgcgcatag agggagtggg  4680
caa                                                                4683

SEQ ID NO: 8            moltype = DNA  length = 4721
FEATURE                 Location/Qualifiers
source                  1..4721
                        mol_type = genomic DNA
                        organism = Adeno-associated virus 7
SEQUENCE: 8
ttggccactc cctctatgcg cgctcgctcg ctcggtgggg cctgcggacc aaaggtccgc  60
agacggcaga gctctgctct gccggcccca ccgagcgagc gagcgcgcat agagggagtg  120
gccaactcca tcactagggg taccgcgaag cgcctcccac gctgccgcgt cagcgctgac  180
gtaaatcacg tcatagggga gtggtcctgt attagctgtc acgtgagtgc ttttgcgaca  240
ttttgcgaca ccacgtggcc atttgaggta tatatggccg agtgagcgag caggatctcc  300
attttgaccg cgaaatttga acgagcagca gccatgccgg gtttctacga gatcgtgatc  360
aaggtgccga gcgacctgga cgagcacctg ccgggcattt ctgactcgtt tgtgaactgg  420
gtggccgaga aggaatggga gctgcccccg gattctgaca tggatctgaa tctgatcgag  480
caggcacccc tgaccgtggc cgagaagctg cagcgcgact tcctggtcca atggcgccgc  540
gtgagtaagg ccccggaggc cctgttcttt gttcagttcg agaagggcga gagctacttc  600
caccttcacg ttctggtgga gaccacgggg gtcaagtcca tggtgctagg ccgcttcctg  660
agtcagattc gggagaagct ggtccagacc atctaccgcg gggtcgagcc cacgctgccc  720
aactggttcg cggtgaccaa gacgcgtaat ggcgccggcg gggggaacaa ggtggtggac  780
gagtgctaca tccccaacta cctcctgccc aagacccagc ccgagctgca gtgggcgtgg  840
actaacatgg aggagtatat aagcgcgtgt ttgaacctgg ccgaacgcaa acggctcgtg  900
gcgcagcacc tgacccacgt cagccagacg caggagcaga acaaggagaa tctgaacccc  960
aattctgacg cgcccgtgat caggtcaaaa acctccgcgc gctacatgga gctggtcggg  1020
tggctggtgg accggggcat cacctccgag aagcagtgga tccaggagga ccaggcctcg  1080
tacatctcct tcaacgccgc ctccaactcg cggtcccaga tcaaggccgc gctggacaat  1140
gccggcaaga tcatggcgct gaccaaatcc gcgcccgact acctggtggg gccctcgctg  1200
cccgcggaca ttaaaaccaa ccgcatctac cgcatcctgg agctgaacgg gtacgatcct  1260
gcctacgccg gctccgtctt tctcggctgg gcccagaaaa agttcgggaa gcgcaacacc  1320
atctggctgt ttgggcccgc caccaccggc aagaccaaca ttgcggaagc catcgcccac  1380
gccgtgccct tctacggctg cgtcaactgg accaatgaga actttccctt caacgattgc  1440
gtcgacaaga tggtgatctg gtgggaggag ggcaagatga cggccaaggt cgtggagtcc  1500
gccaaggcca ttctcggcgg cagcaaggtg cgcgtggacc aaaagtgcaa gtcgtccgcc  1560
cagatcgacc ccacccccgt gatcgtcacc tccaacacca acatgtgcgc cgtgattgac  1620
gggaacagca ccaccttcga gcaccagcag ccgttgcagg accggatgtt caaatttgaa  1680
ctcacccgcc gtctggagca cgactttggc aaggtgacga agcaggaagt caaagagttc  1740
ttccgctggg ccagtgatca cgtgaccgag gtggcgcatg agttctacgt cagaaagggc  1800
ggagccagca aaagacccgc ccccgatgac gcggatataa gcgagcccaa gcgggcctgc  1860
ccctcagtcg cggatccatc gacgtcagac gcggaaggag ctccggtgga ctttgccgac  1920
aggtaccaaa acaaatgttc tcgtcacgcg ggcatgattc agatgctgtt tccctgcaaa  1980
acgtgcgaga gaatgaatca gaatttcaac atttgcttca cacacggggt cagagactgt  2040
ttagagtgtt tccccggcgt gtcagaatct caaccggtcg tcagaaaaaa gacgtatcgg  2100
aaactctgcg cgattcatca tctgctgggg cgggcgcccg agattgcttg ctcggcctgc  2160
gacctggtca acgtggacct ggacgactgc gtttctgagc aataaatgac ttaaaccagg  2220
tatggctgcc gatggttatc ttccagattg gctcgaggac aacctctctg agggcattcg  2280
cgagtggtgg gacctgaaac ctggagcccc gaaacccaaa gccaaccagc aaaagcagga  2340
caacggccgg ggtctggtgc ttcctggcta caagtacctc ggacccttca acggactcga  2400
caagggggag cccgtcaacg cggcggacgc agcggccctc gagcacgaca aggcctacga  2460
ccagcagctc aaagcgggtg acaatccgta cctgcggtat aaccacgccg acgccgagtt  2520
tcaggagcgt ctgcaagaag atacgtcatt tgggggcaac ctcgggcgag cagtcttcca  2580
ggccaagaag cgggttctcg aacctctcgg tctggttgag gaaggcgcta agacggctcc  2640
tgcaaagaag agaccggtag agccgtcacc tcagcgttcc cccgactcct ccacgggcat  2700
cggcaagaaa ggccagcagc ccgccagaaa gagactcaat ttcggtcaga ctggcgactc  2760
agagtcagtc cccgaccctc aacctctcgg agaacctcca gcagcgccct ctagtgtggg  2820
atctggtaca gtggctgcag gcggtggcgc accaatggca gacaataacg aaggtgccga  2880
cggagtgggt aatgcctcag gaaattggca ttgcgattcc acatggctgg gcgacagagt  2940
cattaccacc agcacccgaa cctgggccct gcccacctac aacaaccacc tctacaagca  3000
aatctccagt gaaactgcag gtagtaccaa cgacaacacc tacttcggct acagcacccc  3060
ctgggggtat tttgacttta acagattcca ctgccacttc tcaccacgtg actggcagcg  3120
actcatcaac aacaactggg gattccggcc caagaagctg cggttcaagc tcttcaacat  3180
ccaggtcaag gaggtcacga cgaatgacgg cgttacgacc atcgctaata accttaccag  3240
cacgattcag gtattctcgg actcggaata ccagctgccg tacgtcctcg gctctgcgca  3300
ccagggctgc ctgcctccgt tcccggcgga cgtcttcatg attcctcagt acggctacct  3360
gactctcaac aatggcagtc agtctgtggg acgttcctcc ttctactgcc tggagtactt  3420
cccctctcag atgctgagaa cgggcaacaa ctttgagttc agctacagct tcgaggacgt  3480
gcctttccac agcagctacg cacacagcca gagcctggac cggctgatga atcccctcat  3540
cgaccagtac ttgtactacc tggccagaac acagagtaac ccaggaggca cagctggcaa  3600
tcgggaactg cagttttacc agggcgggcc ttcaactatg gccgaacaag ccaagaattg  3660
gttacctgga ccttgcttcc ggcaacaaag agtctccaaa acgctggatc aaaacaacaa  3720
cagcaacttt gcttggactg gtgccaccaa atatcacctg aacggcagaa actcgttggt  3780
taatcccggc gtcgccatgg caactcacaa ggacgacgag gaccgctttt tcccatccag  3840
cggagtcctg atttttggaa aaactggagc aactaacaaa actacattgg aaaatgtgtt  3900
```

```
aatgacaaat gaagaagaaa ttcgtcctac taatcctgta gccacggaag aatacgggat  3960
agtcagcagc aacttacaag cggctaatac tgcagcccag acacaagttg tcaacaacca  4020
gggagcctta cctggcatgg tctggcagaa ccgggacgtg tacctgcagg gtcccatctg  4080
ggccaagatt cctcacacgg atggcaactt tcacccgtct cctttgatgg gcggctttgg  4140
acttaaacat ccgcctcctc agatcctgat caagaacact cccgttcccg ctaatcctcc  4200
ggaggtgttt actcctgcca agtttgcttc gttcatcaca cagtacagca ccggacaagt  4260
cagcgtggaa atcgagtggg agctgcagaa ggaaaacagc aagcgctgga acccggagat  4320
tcagtacacc tccaactttg aaaagcagac tggtgtggac tttgccgttg acagccaggg  4380
tgtttactct gagcctcgcc ctattggcac tcgttacctc acccgtaatc tgtaattgca  4440
tgttaatcaa taaaccggtt gattcgtttc agttgaactt tggtctcctg tgcttcttat  4500
cttatcggtt tccatagcaa ctggttacac attaactgct tgggtgcgct tcacgataag  4560
aacactgacg tcaccgcggt acccctagtg atggagttgg ccactccctc tatgcgcgct  4620
cgctcgctcg gtggggcctg cggaccaaag gtccgcagac ggcagagctc tgctctgccg  4680
gccccaccga gcgagcgagc gcgcatagag ggagtggcca a                        4721

SEQ ID NO: 9           moltype = DNA  length = 4393
FEATURE                Location/Qualifiers
source                 1..4393
                       mol_type = genomic DNA
                       organism = Adeno-associated virus 8
SEQUENCE: 9
cagagaggga gtggccaact ccatcactag gggtagcgcg aagcgcctcc cacgctgccg  60
cgtcagcgct gacgtaaatt acgtcatagg ggagtggtcc tgtattagct gtcacgtgag  120
tgcttttgcg gcattttgcg acaccacgtg gccatttgag gtatatatgg ccgagtgagc  180
gagcaggatc tccattttga ccgcgaaatt tgaacgagca gcagccatgc cgggcttcta  240
cgagatcgtg atcaaggtgc cgagcgacct ggacgagcac ctgccgggca tttctgactc  300
gtttgtgaac tgggtggccg agaaggaatg ggagctgccc ccggattctg acatggatcg  360
gaatctgatc gagcaggcac ccctgaccgt ggccgagaag ctgcagcgcg acttcctggt  420
ccaatggcgc cgcgtgagta aggccccgga ggccctcttc tttgttcagt tcgagaaggg  480
cgagagctac tttcacctgc acgttctggt cgagaccacg gggtcaagt  ccatggtgct  540
aggccgcttc ctgagtcaga ttcgggaaaa gcttggtcca gaccatctac ccgcggggtc  600
gagccccacc ttgcccaact ggttcgcggt gaccaaagac gcggtaatgg cgccggcggg  660
ggggaacaag gtggtggacg agtgctacat ccccaactac ctcctgccca agactcagcc  720
cgagctgcag tgggcgtgga ctaacatgga ggagtatata agcgcgtgct tgaacctggc  780
cgagcgcaaa cggctcgtgg cgcagcacct gacccacgtc agccagacgc aggagcagaa  840
caaggagaat ctgaacccca attctgacgc gcccgtgatc aggtcaaaaa cctccgcgcg  900
ctatatggag ctggtcgggt ggctggtgga ccggggcatc acctccgaga agcagtggat  960
ccaggaggac caggcctcgt acatctcctt caacgccgcc tccaactcgc ggtcccagat  1020
caaggccgcg ctggacaatg ccggcaagat catggcgctg accaaatccg cgcccgacta  1080
cctggtgggg ccctcgctgc ccgcggacat tacccagaac cgcatctacc gcatcctcgc  1140
tctcaacggc tacgaccctg cctacgccgg ctccgtcttt ctcggctggg ctcagaaaaa  1200
gttcgggaaa cgcaacacca tctggctgtt tggacccgcc accaccggca agaccaacat  1260
tgcggaagcc atcgcccacg ccgtgccctt ctacggctgc gtcaactgga ccaatgagaa  1320
ctttcccttc aatgattgcg tcgacaagat ggtgatctgg tgggaggagg gcaagatgac  1380
ggccaaggtc gtggagtccg ccaaggccat tctcggcggc agcaaggtgc gcgtggacca  1440
aaagtgcaag tcgtccgccc agatcgaccc caccccgtg  atcgtcacct ccaacaccaa  1500
catgtgcgcc gtgattgacg ggaacagcac caccttcgag caccagcagc ctctccagga  1560
ccggatgttt aagttcgaac tcacccgccg tctggagcac gactttggca aggtgacaaa  1620
gcaggaagtc aaagagttct tccgctgggc cagtgatcac gtgaccgagg tggcgcatga  1680
gttttacgtc agaaagggcg gagccagcaa aagacccgcc cccgatgacg cggataaaag  1740
cgagcccaag cgggcctgcc cctcagtcgc ggatccatcg acgtcagacg cggaaggagc  1800
tccggtggac tttgccgaca ggtaccaaaa caaatgttct cgtcacgcgg gcatgcttca  1860
gatgctgttt ccctgcaaaa cgtgcgagag aatgaatcag aatttcaaca tttgcttcac  1920
acacggggtc agagactgct cagagtgttt ccccggcgtg tcagaatctc aaccggtcgt  1980
cagaaagagg acgtatcgga aactctgtgc gattcatcat ctgctggggc gggctcccga  2040
gattgcttgc tcggcctgcg atctggtcaa cgtggacctg gatgactgtg tttctgagca  2100
ataaatgact taaaccaggt atggctgccg atggttatct tccagattgg ctcgaggaca  2160
acctctctga gggcattcgc gagtggtggg cgctgaaacc tggagccccg aagcccaaag  2220
ccaaccagca aaagcaggac gacggccggg gtctggtgct tcctggctac aagtacctcg  2280
gacccttcaa cggactcgac aagggggagc ccgtcaacgc ggcggacgca gcggccctcg  2340
agcacgacaa ggcctacgac cagcagctgc aggcgggtga caatccgtac ctgcggtata  2400
accacgccga cgccgagttt caggagcgtc tgcaagaaga tacgtctttt gggggcaacc  2460
tcgggcgagc agtcttccag gccaagaagc gggttctcga acctctcggt ctggttgagg  2520
aaggcgctaa gacggctcct ggaaagaaga gaccggtaga gccatcaccc cagcgttctc  2580
cagactcctc tacgggcatc ggcaagaaag gccaacagcc cgccagaaaa agactcaatt  2640
ttggtcagac tggcgactca gagtcagttc cagaccctca acctctcgga gaacctccag  2700
cagcgccctc tggtgtggga cctaatacaa tggctgcagg cggtggcgca ccaatggcag  2760
acaataacga aggcgccgac ggagtgggta gttcctcggg aaattggcat tgcgattcca  2820
catggctggg cgacagagtc atcaccacca gcacccgaac ctgggccctg cccacctaca  2880
acaaccacct ctacaagcaa atctccaacg ggacatcggg aggagccacc aacgacaaca  2940
cctacttcgg ctacagcacc ccctgggggt attttgactt taacagattc cactgccact  3000
tttcaccacg tgactggcag cgactcatca acaacaactg ggattccggg cccaagagac  3060
tcagcttcaa gctcttcaac atccaggtca aggaggtcac gcagaatgaa ggcaccaaga  3120
ccatcgccaa taacctcacc agcaccatcc aggtgtttac ggactcggag taccagctgc  3180
cgtacgttct cggctctgcc caccagggct gcctgcctcc gttcccggcg gacgtgttca  3240
tgattcccca gtacggctac ctaacactca acaacggtag tcaggccgtg ggacgctcct  3300
ccttctactg cctggaatac tttccttcgc agatgctgag aaccggcaac aacttccagt  3360
ttacttacac cttcgaggac gtgcctttcc acagcagcta cgcccacagc cagagcttgg  3420
accggctgat gaatcctctg attgaccagt acctgtacta cttgtctcgg actcaaacaa  3480
```

-continued

```
caggaggcac ggcaaatacg cagactctgg gcttcagcca aggtgggcct aatacaatgg  3540
ccaatcaggc aaagaactgg ctgccaggac cctgttaccg ccaacaacgc gtctcaacga  3600
caaccgggca aaacaacaat agcaactttg cctggactgc tgggaccaaa taccatctga  3660
atggaagaaa ttcattggct aatcctggca tcgctatggc aacacacaaa gacgacgagg  3720
agcgtttttt tcccagtaac gggatcctga tttttggcaa acaaaatgct gccagagaca  3780
atgcggatta cagcgatgtc atgctcacca gcgaggaaga aatcaaaacc actaaccctg  3840
tggctacaga ggaatacggt atcgtggcag ataacttgca gcagcaaaac acggctcctc  3900
aaattggaac tgtcaacagc caggggggcct tacccggtat ggtctggcag aaccgggacg  3960
tgtacctgca gggtcccatc tgggccaaga ttcctcacac ggacggcaac ttccacccgt  4020
ctccgctgat gggcggcttt ggcctgaaac atcctccgcc tcagatcctg atcaagaaca  4080
cgcctgtacc tgcggatcct ccgaccacct tcaaccagtc aaagctgaac tctttcatca  4140
cgcaatacag caccggacag gtcagcgtgg aaattgaatg ggagctgcag aaggaaaaca  4200
gcaagcgctg gaaccccgag atccagtaca cctccaacta ctacaaatct acaagtgtgg  4260
actttgctgt taatacagaa ggcgtgtact ctgaaccccg ccccattggc acccgttacc  4320
tcacccgtaa tctgtaattg cctgttaatc aataaaccgg ttgattcgtt tcagttgaac  4380
tttggtctct gcg                                                  4393

SEQ ID NO: 10          moltype = DNA  length = 4385
FEATURE                Location/Qualifiers
source                 1..4385
                       mol_type = genomic DNA
                       organism = Adeno-associated virus 9
SEQUENCE: 10
cagagaggga gtggccaact ccatcactag gggtaatcgc gaagcgcctc ccacgctgcc  60
gcgtcagcgc tgacgtagat tacgtcatag gggagtggtc ctgtattagc tgtcacgtga  120
gtgcttttgc gacattttgc gacaccacat ggccatttga ggtatatatg gccgagtgag  180
cgagcaggat ctccattttg accgcgaaat ttgaacgagc agcagccatg ccgggcttct  240
acgagattgt gatcaaggtg ccgagcgacc tggacgagca cctgccgggc atttctgact  300
cttttgtgaa ctgggtggcc gagaaggaat gggagctgcc cccggattct gacatggatc  360
ggaatctgat cgagcaggca cccctgaccg tggccgagaa gctgcagcgc gacttcctgg  420
tccaatggcg ccgcgtgagt aaggccccgg aggccctctt ctttgttcag ttcgagaagg  480
gcgagagcta ctttcacctg cacgttctgg tcgagaccac gggggtcaag tccatggtgc  540
taggccgctt cctgagtcag attcgggaga agctggtcca gaccatctac cgcgggatcg  600
agccgaccct gcccaactgg ttcgcggtga ccaagacgcg taatggcgcc ggcgggggga  660
acaaggtggt ggacgagtgc tacatcccca actacctcct gcccaagact cagcccgagc  720
tgcagtgggc gtggactaac atggaggagt atataagcgc gtgcttgaac ctggccgagc  780
gcaaacggct cgtggcgcag cacctgaccc acgtcagcca gacgcaggag cagaacaagg  840
agaatctgaa ccccaattct gacgcgcccg tgatcaggtc aaaaacctcc gcgcgctaca  900
tggagctggt cgggtggctg gtggaccggg gcatcacctc cgagaagcag tggatccagg  960
aggaccaggc ctcgtacatc tccttcaacg ccgcctccaa ctcgcggtcc cagatcaagg  1020
ccgcgctgga caatgccggc aagatcatgg cgctgaccaa atccgcgccc gactacctgg  1080
taggcccttc acttccggtg gacattacgc agaaccgcat ctaccgcatc ctgcagctca  1140
acggctacga ccctgcctac gccggctccg tctttctcgg ctgggcacaa aagaagttcg  1200
ggaaacgcaa caccatctgg ctgtttgggc cggccaccac gggaaagacc aacatcgcag  1260
aagccattgc ccacgccgtg cccttctacg gctgcgtcaa ctggaccaat gagaactttc  1320
ccttcaacga ttgcgtcgac aagatggtga tctggtggga ggagggcaag atgacggcca  1380
aggtcgtgga gtccgccaag gccattctcg gcggcagcaa ggtgcgcgtg gaccaaaagt  1440
gcaagtcgtc cgcccagatc gaccccactc ccgtgatcgt cacctccaac accaacatgt  1500
gcgccgtgat tgacgggaac agcaccacct tcgagcacca gcagcctctc caggaccgga  1560
tgtttaagtt cgaactcacc cgccgtctgg agcacgactt tggcaaggtg acaaagcagg  1620
aagtcaaaga gttcttccgc tgggccagtg atcacgtgac cgaggtggcg catgagtttt  1680
acgtcagaaa gggcggagcc agcaaaagac ccgcccccga tgacgcggat aaaagcgagc  1740
ccaagcgggc ctgcccctca gtcgcggatc catcgacgtc agacgcggaa ggagctccgg  1800
tggactttgc cgacaggtac caaaacaaat gttctcgtca cgcgggcatg cttcagatgc  1860
tgcttccctg caaaacgtgc gagagaatga atcagaattt caacatttgc ttcacacacg  1920
gggtcagaga ctgctcagag tgtttccccg gcgtgtcaga atctcaaccg gtcgtcagaa  1980
agaggacgta tcggaaactc tgtgcgattc atcatctgct ggggcgggct cccgagattg  2040
cttgctcggc ctgcgatctg gtcaacgtgg acctggatga ctgtgtttct gagcaataaa  2100
tgacttaaac caggtatggc tgccgatggt tatcttccag attggctcga ggacaacctc  2160
tctgagggca ttcgcgagtg gtgggcgctg aaacctggag ccccgaagcc caaagccaac  2220
cagcaaaagc aggacgacgg ccggggtctg gtgcttcctg gctacaagta cctcggaccc  2280
ttcaacggac tcgacaaggg ggagcccgtc aacgcggcgg acgcagcggc cctcgagcac  2340
ggcaaggcct acgaccagca gctgcaggcg ggtgacaatc cgtacctgcg gtataaccac  2400
gccgacgccg agtttcagga gcgtctgcaa gaagatacgt cttttggggg caacctcggg  2460
cgagcagtct tccaggccaa gaagcgggtt ctcgaacctc tcggtctggt tgaggaaggc  2520
gctaagacgg ctcctggaaa gaagagaccg gtagagccat caccccagcg ttctccagac  2580
tcctctacgg gcatcggcaa gaaaggccaa cagcccgcca gaaaaagact caattttggt  2640
cagactggcg actcagagtc agttccagac cctcaacctc tcggagaacc tccagcagcg  2700
ccctctggtg tgggacctaa tacaatggct gcaggcggtg gcgcaccaat ggcagacaat  2760
aacgaaggcg ccgacggagt gggtaattcc tcgggaaatt ggcattgcga ttccacatgg  2820
ctgggggaca gagtcatcac caccagcacc cgaacctggg cattgcccac ctacaacaac  2880
cacctctaca agcaaatctc caatggaaca tcgggaggaa gcaccaacga caacacctac  2940
tttggctaca gcaccccctg gggtatttt gacttcaaca gattccactg ccacttctca  3000
ccacgtgact ggcagcgact catcaacaac aactggggat tccggccaaa gagactcaac  3060
ttcaagctgt tcaacatcca ggtcaaggag gttacgacga acgaaggcac caagaccatc  3120
gccaataacc ttaccagcac cgtccaggtc tttacggact cggagtacca gctaccgtac  3180
gtcctaggct ctgcccacca aggatgcctg ccaccgtttc ctgcagacgt cttcatggtt  3240
cctcagtacg gctacctgac gctcaacaat ggaagtcaag cgttaggacg ttcttctttc  3300
tactgtctgg aatacttccc ttctcagatg ctgagaaccg gcaacaactt tcagttcagc  3360
```

```
tacactttcg aggacgtgcc tttccacagc agctacgcac acagccagag tctagatcga  3420
ctgatgaacc ccctcatcga ccagtaccta tactacctgg tcagaacaca gacaactgga  3480
actgggggaa ctcaaacttt ggcattcagc caagcaggcc ctagctcaat ggccaatcag  3540
gctagaaact gggtacccgg gccttgctac cgtcagcagc gcgtctccac aaccaccaac  3600
caaaataaca acagcaactt tgcgtggacg ggagctgcta aattcaagct gaacgggaga  3660
gactcgctaa tgaatcctgg cgtggctatg gcatcgcaca aagacgacga ggaccgcttc  3720
tttccatcaa gtggcgttct catatttggc aagcaaggag ccgggaacga tggagtcgac  3780
tacagccagg tgctgattac agatgaggaa gaaattaaag ccaccaaccc tgtagccaca  3840
gaggaatacg gagcagtggc catcaacaac caggccgcta acacgcaggc gcaaactgga  3900
cttgtgcata accagggagt tattcctggt atggtctggc agaaccggga cgtgtacctg  3960
cagggcccta tttgggctaa aatacctcac acagatggca actttcaccc gtctcctctg  4020
atgggtggat ttggactgaa acacccacct ccacagattc taattaaaaa tacaccagtg  4080
ccggcagatc ctcctcttac cttcaatcaa gccaagctga actctttcat cacgcagtac  4140
agcacgggac aagtcagcgt ggaaatcgag tgggagctgc agaaagaaaa cagcaagcgc  4200
tggaatccag agatccagta tacttcaaac tactacaaat ctacaaatgt ggactttgct  4260
gtcaatacca aaggtgttta ctctgagcct cgccccattg gtactcgtta cctcacccgt  4320
aatttgtaat tgcctgttaa tcaataaacc ggttaattcg tttcagttga actttggtct  4380
ctgcg                                                              4385

SEQ ID NO: 11          moltype = DNA  length = 4087
FEATURE                Location/Qualifiers
source                 1..4087
                       mol_type = genomic DNA
                       organism = Adeno-associated virus 11
SEQUENCE: 11
atgccgggct tctacgagat cgtgatcaag gtgccgagcg acctggacga gcacctgccg  60
ggcatttctg actcgtttgt gaactgggtg gccgagaagg aatgggagct gcccccggat  120
tctgacatgg atcggaatct gatcgagcag gcacccctga ccgtggccga gaagctgcag  180
cgcgacttcc tggtccactg gcgccgcgtg agtaaggccc cggaggccct cttctttgtt  240
cagttcgaga agggcgagtc ctacttccac ctccacgttc tcgtcgagac cacgggggtc  300
aagtccatgg tcctgggccg cttcctgagt cagatcagag acaggctggt gcagaccatc  360
taccgcgggg tcgagcccac gctgcccaac tggttcgcgg tgaccaagac gcgaaatggc  420
gccggcgggg ggaacaaggt ggtggacgag tgctacatcc ccaactacct cctgcccaag  480
acccagcccg agctgcagtg ggcgtggact aacatggagg agtatataag cgcgtgtcta  540
aacctcgcgg agcgtaaacg gctcgtggcg cagcacctga cccacgtcag ccagacgcag  600
gagcagaaca aggagaatct gaacccgaat tctgacgcgc ccgtgatcag gtcaaaaacc  660
tccgcgcgct acatggagct ggtcgggtgg ctggtggacc ggggcatcac ctccgagaag  720
cagtggatcc aggaggacca ggcctcgtac atctccttca acgccgcctc caactcgcgg  780
tcccagatca aggccgcgct ggacaatgcc ggaaagatca tggcgctgac caaatccgcg  840
cccgactacc tggtaggccc gtccttaccc gcggacatta aggccaaccg catctaccgc  900
atcctggagc tcaacggcta cgacccccgcc tacgccggct ccgtcttcct gggctgggcg  960
cagaaaaagt tcggtaaacg caacaccatc tggctgtttg ggcccgccac caccggcaag  1020
accaacatcg cggaagccat agcccacgcc gtgcccttct acggctgcgt gaactggacc  1080
aatgagaact ttcccttcaa cgattgcgtc gacaagatgg tgatctggtg ggaggagggc  1140
aagatgaccg ccaaggtcgt ggagtccgcc aaggccattc tgggcggaag caaggtgcgc  1200
gtggaccaaa agtgcaagtc ctcggcccag atcgacccca cgcccgtgat cgtcacctcc  1260
aacaccaaca tgtgcgccgt gatcgacggg aacagcacca ccttcgagca ccagcagccg  1320
ctgcaggacc gcatgttcaa gttcgagctc acccgccgtc tggagcacga ctttggcaag  1380
gtgaccaagc aggaagtcaa agagttcttc cgctgggctc aggatcacgt gactgaggtg  1440
gcgcatgagt tctacgtcag aaagggcgga gccaccaaaa gacccgcccc cagtgacgcg  1500
gatataagcg agcccaagcg ggcctgcccc tcagttccgg agccatcgac gtcagacgcg  1560
gaagcaccgg tggactttgc ggacaggtac caaaacaaat gttctcgtca cgcgggcatg  1620
cttcagatgc tgtttccctg caagacatgc gagagaatga atcagaattt caacgtctgc  1680
ttcacgcacg gggtcagaga ctgctcagag tgcttccccg gcgcgtcaga atctcaaccc  1740
gtcgtcagaa aaaagacgta tcagaaactg tgcgcgattc atcatctgct ggggcgggca  1800
cccgagattg cgtgttcggc ctgcgatctc gtcaacgtgg acttggatga ctgtgtttct  1860
gagcaataaa tgacttaaac caggtatggc tgctgacggt tatcttccag attggctcga  1920
ggacaacctc tctgagggca ttcgcgagtg gtgggacctg aaacctggag ccccgaagcc  1980
caaggccaac cagcagaagc aggacgacgg ccggggtctg gtgcttcctg gctacaagta  2040
cctcggaccc ttcaacggac tcgacaaggg ggagcccgtc aacgcggcgg acgcagcggc  2100
cctcgagcac gacaaggcct acgaccagca gctcaaagcg ggtgacaatc cgtacctgcg  2160
gtataaccac gccgacgccg agtttcagga gcgtctgcaa gaagatacgt cttttggggg  2220
caacctcggg cgagcagtct tccaggccaa gaagagggta ctcgaacctc tgggcctggt  2280
tgaagaaggt gctaaaacgg ctcctggaaa gaagagaccg ttagagtcac cacaagagcc  2340
cgactcctcc tcgggcatcg gcaaaaaagg caaacaacca gccagaaaga ggctcaactt  2400
tgaagaggac actggagccg gagacggacc ccctgaagga tcagatacca gcgccatgtc  2460
ttcagacatt gaaatgcgtg cagcaccggg cggaaatgct gtcgatgcgg gacaaggttc  2520
cgatggagtg ggtaatgcct cgggtgattg gcattgcgat tccacctggt ctgagggcaa  2580
ggtcacaaca acctcgacca gaacctgggt cttgcccacc tacaacaacc acttgtacct  2640
gcgtctcgga acaacatcaa gcagcaacac ctacaacgga ttctccaccc cctggggata  2700
ttttgacttc aacagattcc actgtcactt ctcaccacgt gactggcaaa gactcatcaa  2760
caacaactgg ggactacgac caaaagccat gcgcgttaaa atcttcaata tccaagttaa  2820
ggaggtcaca acgtcgaacg gcgagactac ggtcgctaat aaccttacca gcacggttca  2880
gatatttgcg gactcgtcgt atgagctccc gtacgtgatg gacgctggac aagaggggag  2940
cctgcctcct ttccccaatg acgtgttcat ggtgcctcaa tatggctact gtggcatcgt  3000
gactggcgag aatcagaacc aaacggacag aaacgctttc tactgcctgg agtattttcc  3060
ttcgcaaatg ttgagaactg gcaacaactt tgaaatggct tacaactttg agaaggtgcc  3120
gttccactca atgtatgctc acagccagag cctggacaga ctgatgaatc ccctcctgga  3180
ccagtacctg tggcacttac agtcgactac ctctggagag actctgaatc aaggcaatgc  3240
```

-continued

```
agcaaccaca tttggaaaaa tcaggagtgg agactttgcc ttttacagaa agaactggct  3300
gcctgggcct tgtgttaaac agcagagatt ctcaaaaact gccagtcaaa attacaagat  3360
tcctgccagc gggggcaacg ctctgttaaa gtatgacacc cactatacct taaacaaccg  3420
ctggagcaac atcgcgcccg gacctccaat ggccacagcc ggaccttcgg atggggactt  3480
cagtaacgcc cagcttatat tccctggacc atctgttacc ggaaatacaa caacttcagc  3540
caacaatctg ttgtttacat cagaagaaga aattgctgcc accaacccaa gagacacgga  3600
catgtttggc cagattgctg acaataatca gaatgctaca actgctccca taaccggcaa  3660
cgtgactgct atgggagtgc tgcctggcat ggtgtggcaa aacagagaca tttactacca  3720
agggccaatt tgggccaaga tcccacacgc ggacggacat tttcatcctt caccgctgat  3780
tggtgggttt ggactgaaac acccgcctcc ccagatattc atcaagaaca ctcccgtacc  3840
tgccaatcct gcgacaacct tcactgcagc cagagtggac tctttcatca cacaatacag  3900
caccggccag gtcgctgttc agattgaatg ggaaattgaa aaggaacgct ccaaacgctg  3960
gaatcctgaa gtgcagttta cttcaaacta tgggaaccag tcttctatgt tgtgggctcc  4020
tgatacaact gggaagtata cagagccgcg ggttattggc tctcgttatt tgactaatca  4080
tttgtaa                                                            4087

SEQ ID NO: 12           moltype = DNA  length = 4180
FEATURE                 Location/Qualifiers
source                  1..4180
                        mol_type = genomic DNA
                        organism = Adeno-associated virus 13
SEQUENCE: 12
ccgcgagtga gcgaaccagg agctccattt tgcccgcgaa ttttgaacga gcagcagcca  60
tgccgggatt ctacgagatt gtcctgaagg tgcccagcga cctggacgag cacctgcctg  120
gcatttctga ctcttttgta aactgggtgg cggagaagga atgggagctg ccgccggatt  180
ctgacatgga tctgaatctg attgagcagg caccccctaac cgtggccgaa aagctgcaac  240
gcgaattcct ggtcgagtgg cgccgcgtga gtaaggcccc ggaggccctc ttctttgttc  300
agttcgagaa gggggacagc tacttccacc tacacattct ggtggagacc gtgggcgtga  360
aatccatggt ggtgggccgc tacgtgagcc agattaaaga gaagctggtg acccgcatct  420
accgcggggt cgagccgcag cttccgaact ggttcgcggt gaccaagacg cgtaatggcg  480
ccggaggcgg gaacaaggtg gtggacgact gctacatccc caactacctg ctccccaaga  540
cccagcccga gctccagtgg gcgtggacta atatggacca gtatttaagc gcctgtttga  600
atctcgcgga gcgtaaacgg ctggtggcgc agcatctgac gcacgtgtcg cagacgcagg  660
agcagaacaa agagaaccag aatcccaatt ctgacgcgcc ggtgatcaga tcaaaaacct  720
ccgcgaggta catggagctg gtcgggtggc tggtggaccg cgggatcacg tcagaaaagc  780
aatggatcca ggaggaccag gcctcttaca tctccttcaa cgccgcctcc aactcgcggt  840
cacaaatcaa ggccgcactg gacaatgcct ccaaatttat gagcctgaca aaaacggctc  900
cggactacct ggtgggaaac aacccgccgg aggacattac cagcaaccgg atctacaaaa  960
tcctcgagat gaacgggtac gatccgcagt acgcggcctc cgtcttcctg ggctgggcgc  1020
aaaagaagtt cgggaagagg aacaccatct ggctctttgg gccggccacg acgggtaaaa  1080
ccaacatcgc tgaagctatc gcccacgccg tgccctttta cggctgcgtg aactggacca  1140
atgagaactt tccgttcaac gattgcgtcg acaagatggt gatctggtgg gaggagggca  1200
agatgacggc caaggtcgtg gagtccgcca aggccattct gggcggaagc aaggtgcgcg  1260
tggaccaaaa gtgcaagtca tcggcccaga tcgacccaac tcccgtcatc gtcacctcca  1320
acaccaacat gtgcgcggtc atcgacggaa attccaccac cttcgagcac caacaaccac  1380
tccaagaccg gatgttcaag ttcgagctca ccaagcgcct ggagcacgac tttggcaagg  1440
tcaccaagca ggaagtcaag gactttttcc ggtgggcgtc agatcacgtg actgaggtgt  1500
ctcacgagtt ttacgtcaga aagggtggag ctagaaagag gcccgccccc aatgacgcag  1560
atataagtga gcccaagcgg gcctgtccgt cagttgcgca gccatcgacg tcagacgcgg  1620
aagctccggt ggactacgcg gacaggtacc aaaacaaatg ttctcgtcac gtgggcatga  1680
atctgatgct tttccctgc cggcaatgcg agagaatgaa tcagaatgtg gacatttgct  1740
tcacgcacgg ggtcatggac tgtgccgagt gcttccccgt gtcagaatct caacccgtgt  1800
ctgtcgtcag aaagcggaca tatcagaaac tgtgtccgat tcatcacatc atggggaggg  1860
cgcccgaggt ggcttgttcg gcctgcgatc tggccaatgt ggacttggat gactgtgaca  1920
tggagcaata aatgactcaa accagatatg actgacggtt accttccaga ttggctagag  1980
gacaacctct ctgaaggcgt tcgagagtgg tgggcgctgc aacctggagc ccctaaaccc  2040
aaggcaaatc aacaacatca ggacaacgct cggggtcttg tgcttccggg ttacaaatac  2100
ctcggacccg gcaacggact tgacaagggg gaacccgtca acgcagcgga cgcggcagcc  2160
ctcgaacacg acaaggccta cgaccagcag ctcaaggccg gtgacaaccc ctacctcaag  2220
tacaaccacg ccgacgccga gtttcaggag cgtcttcaag aagatacgtc ttttgggggc  2280
aacctcggac gagcagtctt ccaggccaaa aagaggatcc ttgagcctct gggtctggtt  2340
gaggaagcgg ctaagacggc tcctggaaaa aagagacctg tagagcaatc tccagcagaa  2400
ccggactcct cttcgggcat cggcaaatca ggccagcagc ccgctagaaa aagactgaat  2460
tttggtcaga ctggcgacac agagtcagtc ccagaccctc aaccactcgg acaacctccc  2520
gcagcccccct ctggtgtggg atctactaca atggcttcag gcggtggcgc accaatggca  2580
gacaataacg agggtgccga tggagtgggt aattcctcag gaaattggca ttgcgattcc  2640
caatggctgg gcgacagagt catcaccacc agcacccgca cctgggccct gcccacctac  2700
aacaatcacc tctacaagca aatctccagc caatcaggag ccaccaacga caaccactac  2760
tttggctaca gcacccccctg ggggtatttt gacttcaaca gattccactg ccacttttca  2820
ccacgtgact ggcaaagact catcaacaac aactggggat tccgacccaa gagactcaac  2880
ttcaagctct ttaacattca agtcaaagag gtcacgcaga atgacggtac gacgacgatt  2940
gccaataacc ttaccagcac ggttcaggtg tttactgact ccgagtacca gctcccgtac  3000
gtcctcggct cggcgcatca gggatgcctc ccgccgttcc cagcagacgt cttcatggtc  3060
ccacagtatg gatacctcac cctgaacaac gggagtcagg cggtaggacg ctcttccttt  3120
tactgcctgg agtactttcc ttctcagatg ctgcgtactg gaaacaactt tcagtttagc  3180
tacacttttg aagacgtgcc tttccacagc agctacgctc acagccaaag tctggaccgt  3240
ctcatgaatc ctctgatcga ccagtacctg tactatctga acaggacaca aacagccagt  3300
ggaactcagc agtctcggct actgtttagc caagctggac ccaccagtat gtctcttcaa  3360
gctaaaaact ggctgcctgg accttgctac agacagcagc gtctgtcaaa gcaggcaaac  3420
```

-continued

```
gacaacaaca acagcaactt tccctggact ggtgccacca aatatcatct gaatggccgg  3480
gactcattgg tgaacccggg ccctgctatg gccagtcaca aggatgacaa agaaaagttt  3540
ttccccatgc atggaaccct gatatttggt aaagaaggaa caaatgccaa caacgcggat  3600
ttggaaaatg tcatgattac agatgaagaa gaaatccgca ccaccaatcc cgtggctacg  3660
gagcagtacg ggactgtgtc aaataatttg caaaactcaa acgctggtcc aactactgga  3720
actgtcaatc accaaggagc gttacctggt atggtgtggc aggatcgaga cgtgtacctg  3780
cagggaccca tttgggccaa gattcctcac accgatggac actttcatcc ttctccactg  3840
atgggaggtt ttgggctcaa acacccgcct cctcagatca tgatcaaaaa cactcccgtt  3900
ccagccaatc ctcccacaaa ctttagtgcg gcaaagtttg cttccttcat cacacagtac  3960
tccacggggc aggtcagcgt ggagatcgag tgggagctgc agaaggagaa cagcaaacgc  4020
tggaatcccg aaattcagta cacttccaac tacaacaaat ctgttaatgt ggactttact  4080
gtggacacta atggtgtgta ttcagagcct cgccccattg gcaccagata cctgactcgt  4140
aatctgtaat tgcttgttaa tcaataaacc ggttaattcg                        4180

SEQ ID NO: 13          moltype = DNA  length = 5594
FEATURE                Location/Qualifiers
source                 1..5594
                       mol_type = genomic DNA
                       organism = Human parvovirus B19
SEQUENCE: 13
ccaaatcaga tgccgccggt cgccgccggt aggcgggact tccggtacaa gatggcggac  60
aattacgtca tttcctgtga cgtcatttcc tgtgacgtca cttccggtgg gcgggacttc  120
cggaattagg gttggctctg ggccagcttg cttggggttg ccttgacact aagacaagcg  180
gcgcgccgct tgtcttagtg gcacgtcaac cccaagcgct ggcccagagc caaccctaat  240
tccggaagtc ccgcccaccg gaagtgacgt cacaggaaat gacgtcacag gaaatgacgt  300
aattgtccgc catcttgtac cggaagtccc gcctaccggc ggcgaccggc ggcatctgat  360
ttggtgtctt cttttaaatt ttagcgggct tttttcccgc cttatgcaaa tgggcagcca  420
ttttaagtgt ttcactataa ttttattggt cagttttgta acggttaaaa tgggcggagc  480
gtaggcgggg actacagtat atatagcacg gcactgccgc agctctttct ttctgggctg  540
ctttttcctg gactttcttg ctgttttttg tgagctaact aacaggtatt tatactactt  600
gttaacatac taacatggag ctatttagag gggtgcttca agtttcttct aatgttctgg  660
actgtgctaa cgataactgg tggtgctctt tactggattt agacacttct gactgggaac  720
cactaactca tactaacaga ctaatggcaa tatacttaag cagtgtggct tctaagcttg  780
actttaccgg ggggccacta gcggggtgct tgtacttttt tcaagtagaa tgtaacaaat  840
ttgaagaagg ctatcatatt catgtggtta ttggggggcc agggttaaac cccagaaacc  900
tcacagtgtg tgtagagggg ttatttaata atgtacttta tcaccttgta actgaaaatg  960
taaagctaaa atttttgcca ggaatgacta caaaaggcaa atactttaga gatggagagc  1020
agtttataga aaactattta atgaaaaaaa tacctttaaa tgttgtatgg tgtgttacta  1080
atattgatgg atatatagat acctgtattt ctgctacttt tagaagggga gcttgccatg  1140
ccaagaaacc ccgcattacc acagccataa atgacactag tagtgatgct ggggagtcta  1200
gcggcacagg ggcagaggtt gtgccaatta atgggaaggg aactaaggct agcataaagt  1260
ttcaaactat ggtaaactgg ttgtgtgaaa acagagtgtt tacagaggat aagtggaaac  1320
tagttgactt taaccagtac actttactaa gcagtagtca cagtggaagt tttcaaattc  1380
aaagtgcact aaaactagca atttataaag caactaattt agtgcctaca agcacatttc  1440
tattgcatac agactttgag caggttatgt gtattaaaga caataaaatt gttaaattgt  1500
tactttgtca aaactatgac cccctattag tggggcagca tgtgttaaag tggattgata  1560
aaaaatgtgg caagaaaaat acactgtggt tttatgggcc gccaagtaca ggaaaaacaa  1620
acttggcaat ggccattgct aaaagtgttc cagtatatgg catggttaac tggaataatg  1680
aaaactttcc atttaatgat gtagcaggga aaagcttggt ggtctgggat gaaggtatta  1740
ttaagtctac aattgtagaa gctgcaaaag ccattttagg cgggcaaccc accagggtag  1800
atcaaaaaat gcgtggaagt gtagctgtgc ctggagtacc tgtggttata accagcaatg  1860
gtgacattac ttttgttgta agcgggaaca ctacaacaac tgtacatgct aaagccttaa  1920
aagagcgaat ggtaaagtta aactttactg taagatgcag ccctgacatg gggttactaa  1980
cagaggctga tgtacaacag tggcttacat ggtgtaatgc acaaagctgg gaccactatg  2040
aaaactgggc aataaactac acttttgatt tccctggaat taatgcagat gccctccacc  2100
cagacctcca aaccaccccca attgtcacag acaccagtat cagcagcagt ggtggtgaaa  2160
gctctgaaga actcagtgaa agcagctttt ttaacctcat caccccaggc gcctggaaca  2220
ctgaaacccc gcgctctagt acgcccatcc ccgggaccag ttcaggagaa tcatttgtcg  2280
gaagctcagt ttcctccgaa gttgtagctg catcgtggga agaagccttc tacacacctt  2340
tggcagacca gtttcgtgaa ctgttagttg gggttgatta tgtgtgggac ggtgtaaggg  2400
gtttacctgt gtgttgtgtg caacatatta acaatagtgg gggaggcttg ggactttgtc  2460
cccattgcat taatgtaggg gcttggtata atggatggaa atttcgagaa tttaccccag  2520
atttggtgcg gtgtagctgc catgtgggag cttctaatcc cttttctgtg ctaacctgca  2580
aaaaatgtgc ttacctgtct ggattgcaaa gctttgtaga ttatgagtaa agaaagtggc  2640
aaatggtggg aaagtgatga taaatttgct aaagctgtgt atcagcaatt tgtggaattt  2700
tatgaaaagg ttactggaac agacttagag cttattcaaa tattaaaaga tcactataat  2760
atttctttag ataatcccct agaaaaccca tcctctctgt ttgacttagt tgctcgtatt  2820
aaaaataacc ttaaaaactc tccagactta tatagtcatc attttcaaag tcatggacag  2880
ttatctgacc acccccatgc cttatcatcc agtagcagtc atgcagaacc tagaggagaa  2940
aatgcagtat tatctagtga agacttacac aagcctgggc aagttagcgt acaactaccc  3000
ggtactaact atgttgggcc tggcaatgag ctacaagctg ggcccccgca aagtgctgtt  3060
gacagtgctg caaggattca tgactttagg tatagccaac tggctaagtt gggaataaat  3120
ccatatactc attggactgt agcagatgaa gagcttttaa aaaatataaa aaatgaaact  3180
gggtttcaag cacaagtagt aaaagactac tttactttaa aaggtgcagc tgcccctgtg  3240
gcccattttc aaggaagttt gccggaagtt cccgcttaca acgcctcaga aaaataccca  3300
agcatgactt cagttaattc tgcagaagcc agcactggtg caggaggggg tggcagtaat  3360
cctgtcaaaa gcatgtggag tgaggggggcc acttttagtg ccaactctgt aacttgtaca  3420
ttttccagac agtttttaat tccttatgac ccagagcacc attataaggt gttttctccc  3480
gcagcaagca gctgccacaa tgccagtgga aaggaggcaa aggtttgcac aattagtccc  3540
```

-continued

```
ataatgggat actcaacccc atggagatat ttagatttta atgctttaaa tttatttttt  3600
tcacctttag agtttcagca cttaattgaa aattatggaa gtatagctcc tgatgcttta  3660
actgtaacca tatcagaaat tgctgttaag gatgttacag acaaaactgg aggggggggta  3720
caggttactg acagcactac agggcgccta tccatgttag tagaccatga atacaagtac  3780
ccatatgtgt taggacaagg tcaggatact ttagccccag aacttcctat ttgggtatac  3840
tttcccccctc aatatgctta cttaacagta ggagatgtta acacacaagg aatctctgga  3900
gacagcaaaa aattagcaag tgaagaatca gcattttatg ttttggaaca cagttctttt  3960
cagcttttag gtacaggagg tacagcaact atgtcttata agtttcctcc agtgccccca  4020
gaaaatttag agggctgcag tcaacacttt tatgaaatgt acaatccctt atacggatcc  4080
cgcttagggg ttcctgacac attaggaggt gacccaaaat ttagatcttt aacacatgaa  4140
gaccatgcaa ttcagcccca aaacttcatg ccagggccac tagtaaactc agtgtctaca  4200
aaggagggag acagctctaa tactggagct ggaaaagcct taacaggcct tagcacaggc  4260
acctctcaaa acactagaat atccttacgc cctgggccag tgtcacagcc ataccaccac  4320
tgggacacag ataaatatgt tccaggaata aatgccattt ctcatggtca gaccacttat  4380
ggtaacgctg aagacaaaga gtatcagcaa ggagtgggta gatttccaaa tgaaaaagaa  4440
cagctaaaac agttacaggg tttaaacatg cacacctatt tccccaataa aggaacccag  4500
caatatacag atcaaattga gcgcccccta atggtgggtt ctgtatggaa cagaagagcc  4560
cttcactatg aaagccagct gtggagtaaa attccaaatt tagatgacag ttttaaaact  4620
cagtttgcag ccttaggagg atggggtttg catcagccac ctcctcaaat atttttaaaa  4680
atattaccac aaagtgggcc aattggaggt attaaatcaa tgggaattac taccttagtt  4740
cagtatgccg tgggaattat gacagtaact atgacattta aattggggcc ccgtaaagct  4800
acgggacggt ggaatcctca acctggagta tatcccccgc acgcagcagg tcatttacca  4860
tatgtactat atgaccccac agctacagat gcaaaacaac accacaggca tggatacgaa  4920
aagcctgaag aattgtggac agccaaaagc cgtgtgcacc cattgtaaac actccccacc  4980
gtgccctcag ccaggatgcg taactaaacg cccaccagta ccacccagac tgtacctgcc  5040
ccctcctgta cctataagac agcctaacac aaaagatata gacaatgtag aatttaagta  5100
cttaaccaga tatgaacaac atgttattag aatgttaaga ttgtgtaata tgtatcaaaa  5160
tttagaaaaa taaacatttg ttgtggttaa aaaattatgt tgttgcgctt taaaaattta  5220
aaagaagaca ccaaatcaga tgccgccggt cgccgccggt aggcgggact tccggtacaa  5280
gatggcggac aattacgtca tttcctgtga cgtcatttcc tgtgacgtca cttccggtgg  5340
gcgggacttc cggaattagg gttggctctg ggccagcgct tggggttgac gtgccactaa  5400
gacaagcggc gcgccgcttg tcttagtgtc aaggcaaccc caagcaagct ggcccagagc  5460
caaccctaat tccggaagtc ccgcccaccg gaagtgacgt cacaggaaat gacgtcacag  5520
gaaatgacgt aattgtccgc catcttgtac cggaagtccc gcctaccggc ggcgaccggc  5580
ggcatctgat ttgg                                                    5594

SEQ ID NO: 14          moltype = DNA  length = 5149
FEATURE                Location/Qualifiers
source                 1..5149
                       mol_type = genomic DNA
                       organism = Minute virus of mice
SEQUENCE: 14
atttttagaa ctgaccaacc atgttcacgt aagtgacgtg atgacgcgcg ctgcgcgcgc  60
gccttcggac gtcacacgtc acttacgttt cacatggttg gtcagttcta aaaatgataa  120
gcggttcagg gagtttaaac caaggcgcga aaaggaagtg ggcgtggttt aaagtatata  180
agcaactact gaagtcagtt acttatcttt tctttcattc tgtgagtcga gacgcacaga  240
aagagagtaa ccaactaacc atggctggaa atgcttactc tgatgaagtt ttgggagcaa  300
ccaactggtt aaaggaaaaa agtaaccagg aagtgttctc atttgttttt aaaaatgaaa  360
atgttcaact gaatggaaaa gatatcggat ggaatagtta caaaaaagag ctgcaggagg  420
acgagctgaa atctttacaa cgaggagcgg aaactacttg ggaccaaagc gaggacatgg  480
aatgggaaac cacagtggat gaaatgacca aaaagcaagt attcattttt gattctttgg  540
ttaaaaaatg tttatttgaa gtgcttaaca caaagaatat atttcctggt gatgttaatt  600
ggtttgtgca acatgaatgg ggaaaagacc aaggctggca ctgccatgta ctaattggag  660
gaaaggactt tagtcaagct caagggaaat ggtggagaag gcaactaaat gtttactgga  720
gcagatggtt ggtaacagcc tgtaatgtgc aactaacacc agctgaaaga attaaactaa  780
gagaaatagc agaagacaat gagtgggtta ctctacttac ttataagcat aagcaaacca  840
aaaaagacta taccaagtgt gttctttttg gaaacatgat tgcttactat tttttaacta  900
aaaagaaaat aagcactagt ccaccaagag acggaggcta ttttcttagc agtgactctg  960
gctggaaaac taacttttta aaagaaggcg agcgccatct agtgagcaaa ctatacactg  1020
atgacatgcg gccagaaacg gttgaaacca cagtaaccac tgcgcaggaa actaagcgcg  1080
gcagaattca aactaaaaaa gaagtttcta ttaaaactac acttaaagag ctggtgcata  1140
aaagagtaac ctcaccagag gactggatga tgatgcagcc agacagttac attgaaatga  1200
tggctcaacc aggtggagaa aacctgctga aaaatacgct agagatttgt acactaactc  1260
tagccagaac caaaacagca tttgacttaa ttttagaaaa agctgaaacc agcaaactaa  1320
ccaacttttc actgcctgac acaagaacct gcagaatttt tgcttttcat ggctggaact  1380
atgttaaagt ttgccatgct atttgctgtg ttttaaacag acaaggaggc aaaagaaata  1440
ctgtttttatt tcatggacca gccagcacag gcaaatctat tattgcacaa gccatagcac  1500
aagcagttgg caatgttggt tgctataatg cagccaatgt aaactttcca tttaatgact  1560
gtaccaacaa gaacttgatt tgggtagaag aagctggtaa ctttggacag caagtaaacc  1620
agtttaaagc catttgctct ggtcaaacta ttcgcattga tcaaaaagga aaaggcagca  1680
aacagattga accaacacca gtcatcatga ccacaaatga gaacattaca gtggtcagaa  1740
taggctgcga agaaagacca gaacacactc aaccaatcag agacagaatg cttaacattc  1800
atctaacaca taccttgcct ggtgactttg gtttggttga caaaaatgaa tggcccatga  1860
tttgtgcttg gttggtaaag aatggttacc aatctaccat ggcaagctac tgtgctaaat  1920
ggggcaaagt tcctgattgg tcagaaaact gggcggagcc aaaggtgcca actcctataa  1980
atttactagg ttcggcacgc tcaccattca cgacaccgaa aagtacgcct ctcagccaga  2040
actatgcact aactccactt gcatcggatc tcgaggacct ggctttagag ccttggagca  2100
caccaaatac tcctgttgcg ggcactgcag aaacccagaa cactggggaa gctggttcca  2160
aagcctgcca agatggtcaa ctgagcccaa cttggtcaga gatcgaggag gatttgagag  2220
```

-continued

```
cgtgcttcgg tgcggaaccg ttgaagaaag acttcagcga gccgctgaac ttggactaag  2280
gtacgatggc gcctccagct aaaagagcta aaagaggtaa gggtttaagg gatggttggt  2340
tggtggggta ttaatgttta attacctgtt ttacaggcct gaaatcactt ggttttaggt  2400
tgggtgcctc ctggctacaa gtacctggga ccagggaaca gccttgacca aggagaacca  2460
accaatccat ctgacgccgc tgccaaagag cacgacgagg cctatgatca atacatcaaa  2520
tctggaaaaa atccttacct gtacttctct gctgctgatc aacgctttat tgaccaaacc  2580
aaggacgcca aagactgggg aggcaaggtt ggtcactact tttttagaac caagcgcgct  2640
tttgcaccta agcttgctac tgactctgaa cctggaactt ctggtgtaag cagagctggt  2700
aaacgcacta gaccacctgc ttacattttt attaaccaag ccagagctaa aaaaaaactt  2760
acttcttctg ctgcacagca aagcagtcaa accatgagtg atggcaccag ccaacctgac  2820
agcggaaacg ctgtccactc agctgcaaga gttgaacgag cagctgacgg ccctggaggc  2880
tctgggggtg ggggctctgg cgggggtggg gttggtgttt ctactgggtc ttatgataat  2940
caaacgcatt atagattctt gggtgacggc tgggtagaaa ttactgcact agcaactaga  3000
ctagtacatt taaacatgcc taaatcagaa aactattgca gaatcagagt tcacaataca  3060
acagacacat cagtcaaagg caacatggca aaagatgatg ctcatgagca aatttggaca  3120
ccatggagct tggtggatgc taatgcttgg ggagtttggc tccagccaag tgactggcaa  3180
tacatttgca acaccatgag ccagcttaac ttggtatcac ttgatcaaga aatattcaat  3240
gtagtgctga aaactgttac agagcaagac ttaggaggtc aagctataaa aatatacaac  3300
aatgacctta cagcttgcat gatggttgca gtagactcaa acaacatttt gccatacaca  3360
cctgcagcaa actcaatgga aacacttggt ttctacccct ggaaaccaac catagcatca  3420
ccatacaggt actattttg cgttgacaga gatctttcag tgacctacga aaatcaagaa  3480
ggcacagttg aacataatgt gatgggaaca ccaaaaggaa tgaattctca attttttacc  3540
attgagaaca cacaacaaat cacattgctc agaacagggg acgaatttgc cacaggtact  3600
tactactttg acacaaattc agttaaactc acacacacgt ggcaaaccaa ccgtcaactt  3660
ggacagcctc cactgctgtc aacctttcct gaagctgaca ctgatgcagg tacacttact  3720
gctcaaggga gcagacatgg aacaacacaa atgggggtta actgggtgag tgaagcaatc  3780
agaaccagac ctgctcaagt aggattttgt caaccacaca atgactttga agccagcaga  3840
gctggaccat ttgctgcccc aaaagttcca gcagatatta ctcaaggagt agacaaagaa  3900
gccaatggca gtgttagata cagttatggc aaacagcatg gtgaaaattg ggcttcacat  3960
ggaccagcac cagagcgcta cacatgggat gaaacaagct ttggttcagg tagagacacc  4020
aaagatggtt ttattcaatc agcaccacta gttgttccac caccactaaa tggcattctt  4080
acaaatgcaa accctattgg gactaaaaat gacattcatt tttcaaatgt ttttaacagc  4140
tatggtccac taactgcatt ttcacaccca agtcctgtat accctcaagg acaaatatgg  4200
gacaaagaac tagatcttga acacaaacct agacttcaca taactgctcc atttgtttgt  4260
aaaaacaatg cacctggaca aatgttggtt agattaggac caaacctaac tgaccaatat  4320
gatccaaacg gagccacact ttctagaatt gttacatacg gtacattttt ctggaaagga  4380
aaactaacca tgagagcaaa acttagagct aacaccactt ggaacccagt gtaccaagta  4440
agtgctgaag acaatggcaa ctcatacatg agtgtaacta aatggttacc aactgctact  4500
ggaaacatgc agtctgtgcc gcttataaca agacctgttg ctagaaatac ttactaacta  4560
accatgcttt ttctttctgt acttcatata ttattaagac taataaagat acaacataga  4620
aatataatat tacgtataga tttaagaaat agaataatat ggtacttagt aactgttaaa  4680
aataatagaa cctttggaat aacaagatag ttagttggtt aatgttagat agaataagaa  4740
gatcatgtat aatgaataaa agggtggaag ggtggttggt aggttaatgt tagatagaat  4800
aagaagatca tgtataatga ataaaagggt ggaagggtgg ttggtaggta ttcccttaga  4860
cttgatgtta aggaccaaaa aaataataaa acttttttaa aactcaacca agactactgt  4920
ctattcagtg aaccaactga accattagta ttactatgtt tttagggtgg gagggtggga  4980
gatacatgtg ttcgctatga gcgaactggt actggttggt tgctctgctc aaccaaccag  5040
accggcaaag ccggtctggt tggttgagcg caaccaacca gtaccagttc gctcatagcg  5100
aacacatgta tctcccaccc tcccacccta aaaacatagt aatactaat             5149

SEQ ID NO: 15           moltype = DNA  length = 5106
FEATURE                 Location/Qualifiers
source                  1..5106
                        mol_type = genomic DNA
                        organism = Goose parvovirus
SEQUENCE: 15
ctcattggag ggttcgttcg ttcgaaccag ccaatcaggg gagggggaag tgacgcaagt  60
tccggtcaca tgcttccggt gacgcacatc cggtgacgta gttccggtca cgtgcttcct  120
gtcacgtgtt tccggtcacg tgacttccgg tcatgtgact tccggtgacg tgtttccggc  180
tgttaggttg accacgcgca tgccgcgcgg tcagcccaat agttaagccg gaaacacgtc  240
accggaagtc acatgaccgg aagtcacgtg accggaaaca cgtgacagga agcacgtgac  300
cggaactacg tcaccggatg tgcgtcaccg gaagcatgtg accggaactt gcgtcacttc  360
cccctcccct gattggctgg ttcgaacgaa cgaaccctcc aatgagactc aaggacaaga  420
ggatattttg cgcgccagga agtgacgtgc aatgccaccc tatataagcc aggaaacttc  480
cggtttagtt cattcgttac tctgctctca gagagaacgg acctcaggtc ggagagatgg  540
cactttctag gcctcttcag atttcttctg ataaattcta tgaagttatt attagattat  600
catcggatat tgatcaagat gtccccggtc tgtctcttaa ctttgtagaa tggctttcta  660
ccggagtttg ggagcccacg ggcatctgga acatggagca tgtgaatcta ccgatggtga  720
ccttggcaga gaagatcaag aacattttca tacaaagatg gaatcagttc aaccaggacg  780
aaacggactt cttctttcaa ctggaagaag gcagtgagta cattcatctt cattgctgta  840
ttgcccaggg caatgtacgg tcttttgttc tcgggagata tatgtctcag ataaaagact  900
ctatcataag agatgtatat gaagggaaac aaatcaagat ccccgattgg tttgctatta  960
ctaaaaccaa gaggggagga cagaataaga ccgtgactgc agcatacata ctgcattacc  1020
ttattcctaa aaagcaacct gaactgcaat gggcctttac caatatgcct ttattcactg  1080
ctgctgctct ttgtctgcaa aagcggcaag aattgctgga tgcatttcaa gaaagtgatt  1140
tggctgcccc tttacctgat cctcaagcat caactgtggc accgcttatt tccaacagag  1200
cggcaaagaa ctatagcaac cttgttgatt ggctcattga aatggggata acatctgaga  1260
agcaatggct cactgagaac cgagagagct acagaagctt tcaagcaact tcttcaaata  1320
atagacaagt gaaagctgca ctggaaaatg cccgtgctga aatgttattg acaaagactg  1380
```

```
caactgatta cctgatagga aaagaccctg tcctggatat aactaagaat agggtctatc  1440
aaattctgaa aatgaataac tacaaccctc aatacatagg aagtatcctg tgcggctggg  1500
tgaagagaga gttcaacaaa agaaacgcca tatggctcta cggacctgcc accaccggga  1560
agaccaacat tgcagaagct attgcccatg ctgtaccctt ctatggctgt gttaactgga  1620
ctaatgagaa ctttcctttt aatgattgtg ttgataaaat gctgatttgg tgggaggagg  1680
gaaaaatgac taataaggtt gttgaatctg caaaagcaat tttgggaggg tctgctgtcc  1740
gggtagacca gaaatgtaaa ggatctgttt gtattgaacc tactcctgta attattacta  1800
gtaatactga tatgtgtatg attgttgatg gcaactctac tacaatggaa catagaatac  1860
cattagagga gcgtatgttt caaattgtcc tatcacataa attggagcct tcttttggaa  1920
aaatttctaa aaaagaagtc agagaatttt tcaaatgggc caatgacaat ctagttcctg  1980
ttgtgtctga gttcaaagtc cgaactaatg aacaaaccaa cttgccagag cccgttcctg  2040
aacgagcgaa cgagccggag gagcctccta agatctgggc tcctcctact agggaggagt  2100
tagaagagct tttaagagcc agcccagaat tgttctcatc agtcgctcca attcctgtga  2160
ctcctcagaa ctcccctgag cctaagagaa gcaggaacaa ttaccaggta cgctgcgctt  2220
tgcatactta tgacaattct atggatgtat ttgaatgtat ggaatgtgag aaagcaaact  2280
ttcctgaatt tcaacctctg ggagaaaatt attgtgatga acatgggtgg tatgattgtg  2340
ctatatgtaa agagttgaaa aatgaacttg cagaaattga gcatgtgttt gagcttgatg  2400
atgctgaaaa tgaacaataa agatgactca aagcagatat gtctactttt ttagattctt  2460
ttgaagagtg gtatgagact gcagccgcct cgtggcggaa tctgaaagct ggagcccctc  2520
agccaaaacc aaaccagcag tctcagtctg tgtctccaga cagagaaccc gaacgaaaag  2580
ataataatcg gggctttgta cttcctggct ataagtatct tgggcctggt aacggcctgg  2640
ataaaggccc acctgtcaat aaggcggaca gcgtcgcgct tgaacacgac aaggcctatg  2700
accagcagct taaagcggga gacaacccat atataaaatt caatcacgct gaccaggact  2760
ttatagatag cctccaagac gaccagtcat tcggaggtaa tcttggaaag gctgtatttc  2820
aggccaaaaa acgtatctta gagccatttg gcctagtaga agatcctgtc aacacggcac  2880
ctgcaaaaaa aaatacaggg aagcttactg accattaccc ggtagttaag aagcctaaac  2940
ttaccgagga agtcagtgcg ggaggtggta gcagtgccgt acaagacgga ggagccaccg  3000
cggagggcac cgaacctgtg gcagcatctg aaatggcaga gggaggaggc ggagctatgg  3060
gcgactcttc aggggggtgcc gatggagtgg gtaatgcctc gggaaattgg cattgcgatt  3120
cccaatggat gggaaacaca gtcatcacaa agaccaccag aacctgggtc ctgccaagct  3180
acaacaacca catctacaaa gcaattacca gcggaacctc tcaagatgca aatgtccagt  3240
atgcaggata cagtaccccc tgggggtact ttgatttcaa ccgcttccac tgccacttct  3300
cccctagaga ctggcagaga cttatcaaca accattgggg aatcagaccc aagtctctta  3360
aattcaagat cttcaatgtc caagtcaaag aagtcacaac gcaggatcag acaaagacca  3420
ttgcaaacaa tctcacctca acaattcaag tctttacgga tgatgagcat caactcccgt  3480
atgtcctggg ctcggctacg gaaggcacca tgccgccgtt cccgtcggat gtctatgccc  3540
tgccgcagta cgggtactgc acaatgcaca ccaaccagaa tggagcacgg ttcaatgacc  3600
gtagtgcatt ctactgctta gagtacttcc ctagtcagat gctaagaaca ggcaacaact  3660
ttgagttcac atttgacttt gaagaagttc ctttccatag catgttcgct cattcacagg  3720
acttagacag gctgatgaac cccctagtgg atcaatacct ctggaatttc aatgaggtag  3780
acagcagcag aaatgctcaa tttaaaaagg ctgtgaaagg ggcttatggc accatgggcc  3840
gcaattggct gccaggacct aaattcctgg atcaaagagt tagggcctac acaggaggaa  3900
cagacaacta tgcaaactgg aacatctgga gtaatgggaa caaggtgaat ttgaaagaca  3960
gacagtatct cctacaaccc ggacctgtgt cagctactta cacagaaggg gaggcttcca  4020
gccttccagc tcaaaatatt ttagggatag ctaaagatcc atacagatca ggcagcacta  4080
cagcaggaat aagtgacatt atggtcacgg aagaacaaga agtagcacct acaaatggag  4140
tagggtggaa accatatggt aggactgtaa cgaatgaaca aaacactact acagctccta  4200
caagttcaga tctggatgtt cttggagctt taccaggaat ggtttggcag aacagggata  4260
tatatctgca gggacctatt ggggcaaaaa taccgaagac tgatggtaaa ttccatcctt  4320
ctccgaatct cggaggattt ggcctgcaca atccaccacc gcaggtgttc atcaagaata  4380
caccagtgcc tgcagaccct ccagtagaat acgtgcacca gaagtggaat tcctacataa  4440
cccagtactc tacgggccag tgtacagtag agatggtgtg ggagctgaga aaagagaatt  4500
caaagagatg gaacccagaa atccagttca ccagtaattt cagtaacaga acaagcataa  4560
tgtttgcacc taatgaaact ggtggatatg tagaagatag attgattgga accagatatc  4620
taactcaaaa tctgtaaatt ctgtgtaaaa attcaaataa agcacttcct ggcgcgcaaa  4680
atatcctctt gtccttgagt ctcattggag ggttcgttcg ttcgaaccag ccaatcaggg  4740
gagggggaag tgacgcaagt tccggtcaca tgcttccggt gacgcacatc cggtgacgta  4800
gttccggtca cgtgcttcct gtcacgtgtt tccggtcacg tgacttccgg tcatgtgact  4860
tccggtgacg tgtttccggc ttaactattg ggctgaccgc gcgcatgcgc gtggtcaacc  4920
taacagccgg aaacacgtca ccggaagtca catgaccgga agtcacgtga ccggaaacac  4980
gtgacaggaa gcacgtgacc ggaactacgt caccggatgt gcgtcaccgg aagcatgtga  5040
ccggaacttg cgtcacttcc ccctccccctg attggctggt tcgaacgaac gaaccctcca  5100
atgaga                                                              5106
```

```
SEQ ID NO: 16          moltype = DNA  length = 4432
FEATURE                Location/Qualifiers
source                 1..4432
                       mol_type = genomic DNA
                       organism = Snake parvovirus 1
SEQUENCE: 16
cgccccaccc ctagtgatcg cgcgcgctct ctcttggggc ctgacggccg aaggccgtca  60
gctgccgagc ttcgctcggc aggccccaag agagagcgcg cgcgatcact aggggtgggg  120
cgagtgccct gctcaacggg tttttggtg ggcggagcaa tgacgtcagc ggacatgtct  180
ggacatgtct ttgagcaagt ccatataagg agttccgccg gatatgcaaa tgagcaatcg  240
cgcaaagcat tttgggtagt caccatgaat aaaaaggaca gcaagaaaga tgacgcccca  300
taattttaat aggaatttta accatggcgt tttacgaggt tgtgtttcgt ttgccaagag  360
acaataacaa cttgttggat gaagatagat atcagccaga gttgaaagaa gaagatgact  420
ggcctgagga atatttaacc agtgaagatg ccagctttat cggactagcg tatgctgtgc  480
taagtgaaat tcggagattc tttggaaagg aactacaatg gtttgcccag gttgaatggt  540
```

-continued

```
gtcctactgc tggttaccac atgcatgttt tgttgaacca tcctaagctg agtaaccaga  600
cttatggaag aaaggtcaat gaactggctt gccgtatagt cgataccttt ggcctaatta  660
atccagaaga agtcatcagt acccattatg ttaaaagcaa ctatggacat aaaaaggtga  720
gagtcattca cctagagtct tatttgaaga actacttttt cagaaagact ttagctcctc  780
ccaattatac cgaggaagga gactataaaa gagaggaaga agtcgtgctg tgggcattta  840
cgaatatcgt cgcttggaag ccattcgtgc ggaatctcat caagagatcg gagctagcga  900
ctgttcctaa gcaaccagag aatccggcgg gagacggacc ggcacctcga gtgactgcag  960
gaacccgcca ttttatggaa accatcgact ggttggtgaa acatggaatt actacagaac  1020
gagaattctg ccacgccaac cgccctttgt acctgtctat gctggcttct acttcgggtg  1080
ctgggcagat taaaagagcg ctggaccagg cgaaacacat gatgaccagc accatgtcag  1140
cagaggatta cctgacaaca gaagaggatg tgatcgaacc acctactgaa aatagaatct  1200
acaagattat gaaactgaat cgctatgatc cagaactagc agctgctctc ttctacggct  1260
ggacctgcaa gaactttggc aagagaaaca ccatctggct gtatggtcca gctactaccg  1320
gcaaaaccat catcgctcaa gctattgcac atgctgttaa actgtttgct ggtgttaatt  1380
ggactaatga aaactttccc ttctgtaact gtccagggaa actgcttatc tggtgggagg  1440
agggcaagat gacaaacaaa atggtggaga cggctaaatg tatactgggg ggatctgctg  1500
tacctgtaga catcaaaggc aaacccgctg aaatgtgtcc tcaaacaccc tgtattatta  1560
ctagcaatac taacatgtgt caagtatatg atggtaatag ttctagcttt gagcaccaag  1620
aacccctaga ggaacgcatg tttatgttca gacttaatac taaactgcca tcgacctttg  1680
gcaagatcac agaagaggaa gtcaaacagt ttattacctg gggaggagc ttaaaggttc  1740
aagttccaca tcagttcaga gtgcctacca caggagagta taaaaggcca gcccccgagg  1800
cgaaagctca ttcttcggat gagccgccaa aagagaaggt cgcgcgtatt gatgactctc  1860
taaccaggta tgttaacaat attgatgagt cagctaccag tagagaaatg tttctagaga  1920
ttgctaatac taatcaatgt atgttgcatc attgcttttc ttgtaccgaa tgttatcctg  1980
aattgcttga tgacatggac aaggaacaat aaacttactg ataacagata tggatttttct  2040
cgatgatttc tttgcagata aatataaaga gactgttaac gaactcggta aaccggtcaa  2100
tcctaaacct gtaaaacaca ttagcgaagc tcactcgcaa cctggcagca ggaggggctt  2160
tgtggtgcct gggtatcggt atcttgggcc tggtaatagc ttggaccgtg gaaagcccgt  2220
taacaaagca gacgaggctg ctaaaaagca cgatcaagaa tacgatcaac agcttaaagc  2280
gggagacaat ccctacataa aatataatca cgcggacgaa cagttccaga aagacctaca  2340
aggtgatacc agtctagccg gcaacgcggc taacgctcta tttcaaggca aaaagactct  2400
actagcgccc cttggcctag tagagacccc tgtcggcaaa acgtctgaaa agcacaaatt  2460
agacgaatac tatcctaaag ctaaaaaggc caaacaaggc ttgcagatac cagctccacc  2520
taaaggcgga gaagaagaag ctacatcgtc acaatctgga gggagcccag caggttccga  2580
tactagcggc acatctgtca tggctacagg aggaggcggt ccgatggcag acgataacca  2640
gggcgccgag ggagtgggta attcctcagg tgattggcat tgcgatacca agtggatggg  2700
agaccacgtc attacaaagt caaccagaac ttgggtgctc cccacttacg ggaatcatct  2760
ctacgggcct atcaactttg acggcaccac aggttcgggt gctaatgcag cctatgcagg  2820
atacaagact ccctgggggt actttgactt caatcgattc cattgccact tctccccccg  2880
agactggcaa agactcatca acaaccacac aggcatcagg ccgaaaggac tcaaaatcaa  2940
agtctttaac gtccaagtca aagaagttac aacacaagat tcaacgaaaa caattgccaa  3000
caatctcacc agcaccgtac agatctttgc ggacgagaac tacgacttac catatgtatt  3060
aggcagtgct acacaaggca catttcctcc atttcccaat gatgtattta tgttaccaca  3120
atatgcttat tgtacacttc aaggaaattc ggggaaattt gtagatagaa gtgcctttta  3180
ttgtttagaa tattttcctt cacaaatgct gagaacagga aacaattttg agttccagtt  3240
taaatttgaa gaagttccct ttcattctgg atgggcacag agtcaaagcc tagacagatt  3300
gatgaatccg ttgcttgatc aatatctgat aggagactat ggaacagatg catcaggaaa  3360
ccttatttat cacagagctg gtccaaatga tttgaatgaa ttctacaaga attgggcacc  3420
tgcaccctat gaatgtatcc agaatattaa cagcagtgat aataccaaga atgctaattc  3480
tataaatggt tcaaattcta ccaacaaatg gggactacaa ggaagacaag catgggatgc  3540
tccaggattt gttcaagcta gtacctatga aggtgcagca gcaggacaat ctcttcttaa  3600
tggcgtactt actttcgata aaagttcagc tactacttca tctccagctg ctactgcagt  3660
aaacagaaca attgaagacg aaatacaggg taccaataat tttggtaatg ctagaaataa  3720
cattgttgct atcaatcaac aaacgaaagg aacaaatcca acaacaggta gtacatctca  3780
atttgagaca atgccaggta tggtgtggtc taatagagac atttacttac aggggcctat  3840
ttgggctaaa attccaaata cagatggaca ttttcatcct tctcccagaa tgggtggttt  3900
tggattaaaa catcctccgc ctatgattct gatcaaaaat acaccagttc ctgctgatcc  3960
tccaactacc ttcaatccaa tgccacagac tagtttcatt actgaataca gtacaggaca  4020
agtaactgtt gaaatgttgt gggaggtaca gaaagaatcc tccaaaagat ggaatccaga  4080
agtacagttt acttccaatt ttggaacttc agatccagct gttgatggaa taccgtttgg  4140
aattaataat ttgggtactt atgttgaatc tagacctatt ggaactcgtt atatttctaa  4200
acacttgtaa ataataaaaa ttgtcaaatt tgcactaaga attgttgtca cgtggttgtt  4260
tacatgcttg ctaaaacacg cccaccaaaa aacccgttga gcagggcact cgccccaccc  4320
ctagtgatcg cgcgcgctct ctcttggggc ctgccgagcg aagctcggca gctgacggcc  4380
ttcggccgtc aggccccaag agagagcgcg cgcgatcact aggggtgggg cg          4432
```

```
SEQ ID NO: 17          moltype = DNA  length = 165
FEATURE                Location/Qualifiers
misc_feature           1..165
                       note = Chimeric ITR sequence
source                 1..165
                       mol_type = other DNA
                       organism = synthetic construct
SEQUENCE: 17
aggaacccct agtgatggag ttggccactc cctctctgcg cgctcgctcg ctcactgagg  60
gcgggcgacc aaaggtcgcc cgagcccggc cctttgggcc gggcccctca gtgagcgagc  120
gagcgcgcag agagggagtg gccaactcca tcactagggg ttcct                  165

SEQ ID NO: 18          moltype = DNA  length = 198
```

-continued

```
FEATURE                 Location/Qualifiers
misc_feature            1..198
                        note = Chimeric ITR sequence
source                  1..198
                        mol_type = other DNA
                        organism = synthetic construct
SEQUENCE: 18
tacaaaacct ccttgcttga gagtgtggca ctctcccccc tgtcgcgttc gctcgctcgc  60
tggctcgttt ggggggcga cggcccaaag ggccgtcgtc tggcagctct ttgagctgcc  120
acccccccaa acgagccagc gagcgagcga acgcgacagg ggggagagtg ccacactctc  180
aagcaaggag gttttgta                                                198

SEQ ID NO: 19           moltype = DNA  length = 189
FEATURE                 Location/Qualifiers
misc_feature            1..189
                        note = Chimeric ITR sequence
source                  1..189
                        mol_type = other DNA
                        organism = synthetic construct
SEQUENCE: 19
aggaacccct agtgatggag ttggccactc cctcccccct gtcgcgttcg cgcgctcgct  60
cgctcactga gggcgggcga ccaaaggtcg cccgagcccg gccctttggg ccgggcccct  120
cagtgagcga gcgagcgcgc gaacgcgaca ggggggaggg agtggccaac tccatcacta  180
ggggttcct                                                          189

SEQ ID NO: 20           moltype = DNA  length = 190
FEATURE                 Location/Qualifiers
misc_feature            1..190
                        note = Chimeric ITR sequence
source                  1..190
                        mol_type = other DNA
                        organism = synthetic construct
SEQUENCE: 20
tacaaaacct ccttgcttga gagtgtggca ctctcccccc tgtcgcgttc gcgcgctcgc  60
tcgctcactg agggcgggcg accaaaggtc gcccgagccc ggccctttgg gccgggcccc  120
tcagtgagcg agcgagcgcg cgaacgcgac aggggggaga gtgccacact ctcaagcaag  180
gaggttttgt                                                         190

SEQ ID NO: 21           moltype = DNA  length = 196
FEATURE                 Location/Qualifiers
misc_feature            1..196
                        note = Chimeric ITR sequence
source                  1..196
                        mol_type = other DNA
                        organism = synthetic construct
SEQUENCE: 21
aggaacccct agtgatggag ttggccactc cctcccccct gtcgcgttcg ctcgctcgct  60
ggctcgtttg ggggggcgac ggcccaaagg gccgtcgtct ggcagctctt tgagctgcca  120
cccccccaaa cgagccagcg agcgagcgaa cgcgacaggg gggagggagt ggccaactcc  180
atcactaggg gttcct                                                  196

SEQ ID NO: 22           moltype = DNA  length = 170
FEATURE                 Location/Qualifiers
misc_feature            1..170
                        note = Chimeric ITR sequence
source                  1..170
                        mol_type = other DNA
                        organism = synthetic construct
SEQUENCE: 22
tacaaaacct ccttgcttga gagtgtggca ctctctctgc gcgctcgctc gctcactgag  60
ggcgggcgac caaaggtcgc ccgacgcccg gccctttggg ccgggcggcc ctcagtgagc  120
gagcgagcgc gcagagagag tgccacactc tcaagcaagg aggttttgta             170

SEQ ID NO: 23           moltype = DNA  length = 164
FEATURE                 Location/Qualifiers
misc_feature            1..164
                        note = Chimeric ITR sequence
source                  1..164
                        mol_type = other DNA
                        organism = synthetic construct
SEQUENCE: 23
aggaacccct agtgatggag tggccctccc tctctgcgcg ctcgctcgct cactgagggc  60
gggcgaccaa aggtcgcccg acgcccggcc ctttgggccg ggcggccctc agtgagcgag  120
cgagcgcgca gagagggagg gccactccat cactaggggt tcct                   164

SEQ ID NO: 24           moltype = DNA  length = 202
FEATURE                 Location/Qualifiers
misc_feature            1..202
                        note = Chimeric ITR sequence
```

```
source                  1..202
                        mol_type = other DNA
                        organism = synthetic construct
SEQUENCE: 24
tacaaaacct ccttgcttga gagtgttgga cactctcccc cctgtcgcgt tcgctcgctc  60
gctggctcgt ttgggggggc gacggcccaa agggccgtcg tctggcagct ctttgagctg  120
ccaccccccc aaacgagcca gcgagcgagc gaacgcgaca ggggggagag tgtccaacac  180
tctcaagcaa ggaggttttg ta                                           202

SEQ ID NO: 25           moltype = DNA  length = 161
FEATURE                 Location/Qualifiers
misc_feature            1..161
                        note = Chimeric ITR sequence
source                  1..161
                        mol_type = other DNA
                        organism = synthetic construct
SEQUENCE: 25
aggaacccct agtatggagt tggccactcc attctgcgcg ctcgctcgct cactgagggc  60
gggcgaccaa aggtcgcccg agcccggccc tttgggccgg gcccctcagt gagcgagcga  120
gcgcgcagaa tggagtggcc aactccatac taggggttcc t                      161

SEQ ID NO: 26           moltype = DNA  length = 202
FEATURE                 Location/Qualifiers
misc_feature            1..202
                        note = Chimeric ITR sequence
source                  1..202
                        mol_type = other DNA
                        organism = synthetic construct
SEQUENCE: 26
tacaaaacct ccttgcttgg agagtgtggc actctccccc cctgtcgcgt tcgctcgctc  60
gctggctcgt ttgggggggc gacggcccaa agggccgtcg tctggcagct ctttgagctg  120
ccaccccccc aaacgagcca gcgagcgagc gaacgcgaca ggggggggaga gtgccacact  180
ctccaagcaa ggaggttttg ta                                           202

SEQ ID NO: 27           moltype = DNA  length = 155
FEATURE                 Location/Qualifiers
misc_feature            1..155
                        note = Chimeric ITR sequence
source                  1..155
                        mol_type = other DNA
                        organism = synthetic construct
SEQUENCE: 27
aggaacccct agtgctggag ttggccactc ccgcgcgctc gctcgctcac tgagggcggg  60
cgaccaaagg tcgcccgagc ccggcccttt gggccgggcc cctcagtgag cgagcgagcg  120
cgcgggagtg gccaactcca gcactagggg ttcct                             155

SEQ ID NO: 28           moltype = DNA  length = 153
FEATURE                 Location/Qualifiers
misc_feature            1..153
                        note = Chimeric ITR sequence
source                  1..153
                        mol_type = other DNA
                        organism = synthetic construct
SEQUENCE: 28
aggaacccct agtggagttg gccactcctc tgcgcgctcg ctcgctcact gagggcgggc  60
gaccaaaggt cgcccgagcc cggccctttg ggccgggccc ctcagtgagc gagcgagcgc  120
gcagaggagt ggccaactcc actaggggtt cct                               153

SEQ ID NO: 29           moltype = DNA  length = 182
FEATURE                 Location/Qualifiers
misc_feature            1..182
                        note = Chimeric ITR sequence
source                  1..182
                        mol_type = other DNA
                        organism = synthetic construct
SEQUENCE: 29
aggaacccct agtgatggag ttggccactc cctccacgcg ttctgcgcgc tcgctcgctc  60
actgagggcg ggcgaccaaa ggtcgcccga cgcccggccc tttgggccgg gcggccctca  120
gtgagcgagc gagcgcgcag aacgcgtgga gggagtggcc aactccatca ctaggggttc  180
ct                                                                 182

SEQ ID NO: 30           moltype = DNA  length = 161
FEATURE                 Location/Qualifiers
misc_feature            1..161
                        note = Chimeric ITR sequence
source                  1..161
                        mol_type = other DNA
                        organism = synthetic construct
SEQUENCE: 30
```

```
aggaacccct agtggatgga gttggccact ccctcctctg cgcgctcgct cgctcactga  60
gggcgggcga ccaaaggtcg cccgagcccg gccctttggg ccgggcccct cagtgagcga  120
gcgagcgcgc agaggagtgg ccaactccac taggggttcc t                      161

SEQ ID NO: 31          moltype = DNA  length = 182
FEATURE                Location/Qualifiers
misc_feature           1..182
                       note = Chimeric ITR sequence
source                 1..182
                       mol_type = other DNA
                       organism = synthetic construct
SEQUENCE: 31
aggaacccct agtgatggag ttggccactc cctccacgcg ttctgcgcgc tcgctcgctc  60
actgagggcg ggcgaccaaa ggtcgcccga cgcccggccc tttgggccgg gcggccctca  120
gtgagcgagc gagcgcgcag aacgcgtgga gggagtggcc aactccatca ctaggggttc  180
ct                                                                 182

SEQ ID NO: 32          moltype = DNA  length = 177
FEATURE                Location/Qualifiers
misc_feature           1..177
                       note = Chimeric ITR sequence
source                 1..177
                       mol_type = other DNA
                       organism = synthetic construct
SEQUENCE: 32
aggaacccct agtcgtgatg gagttggcca ctccctcacg tctgcgcgct cgctcgctca  60
ctgagggcgg gcgaccaaag gtcgcccgag cccggccctt tgggccgggc ccctcagtga  120
gcgagcgagc gcgcagacgt gagggagtgg ccaactccat cacgactagg ggttcct     177

SEQ ID NO: 33          moltype = DNA  length = 177
FEATURE                Location/Qualifiers
misc_feature           1..177
                       note = Chimeric ITR sequence
source                 1..177
                       mol_type = other DNA
                       organism = synthetic construct
SEQUENCE: 33
aggaacccct agtgatggag ttggccactc cctccccccct gtcgcgttcg cgcgctcgct  60
cgctcactga gggcgggcga ccaaaggtcg cccgagcccg gccctttggg ccgggcccct  120
cagtgagcga gcgagcgcgc agagagggag tggccaactc catcactagg ggttcct     177

SEQ ID NO: 34          moltype = DNA  length = 173
FEATURE                Location/Qualifiers
misc_feature           1..173
                       note = Chimeric ITR sequence
source                 1..173
                       mol_type = other DNA
                       organism = synthetic construct
SEQUENCE: 34
tacaaaacct ccttgcttga gagtgtggca ctcttctgct cgctcgctgg ctcgtttggg  60
ggggcgacgg cccaaagggc cgtcgtctgg cagctctttg agctgccacc cccccaaacg  120
agccagcgag cgagcagaga gagtgccaca ctctcaagca aggaggtttt gta         173

SEQ ID NO: 35          moltype = DNA  length = 194
FEATURE                Location/Qualifiers
misc_feature           1..194
                       note = Chimeric ITR sequence
source                 1..194
                       mol_type = other DNA
                       organism = synthetic construct
SEQUENCE: 35
tacaaaacct ccttgcttag agtgtggcac tctccccctg tcgcgttcgc tcgctcgctg  60
gctcgtttgg gggggcgacg gcccaaaggg ccgtcgtctg gcagctcttt gagctgccac  120
ccccccaaac gagccagcga gcgagcgaac gcgacagggg gagagtgcca cactctaagc  180
aaggaggttt tgta                                                    194

SEQ ID NO: 36          moltype = DNA  length = 206
FEATURE                Location/Qualifiers
misc_feature           1..206
                       note = Chimeric ITR sequence
source                 1..206
                       mol_type = other DNA
                       organism = synthetic construct
SEQUENCE: 36
tacaaaacct ccttgcttga gagagtgtgg cactctctcc cccctgtcgc gttcgctcgc  60
tcgctggctc gtttgggggg gcgacggccc aaagggccgt cgtctggcag ctctttgagc  120
tgccaccccc ccaaacgagc cagcgagcga gcgaacgcga cagggggggag agagtgccac  180
actctctcaa gcaaggaggt tttgta                                      206
```

-continued

```
SEQ ID NO: 37          moltype = DNA  length = 210
FEATURE                Location/Qualifiers
misc_feature           1..210
                       note = Chimeric ITR sequence
source                 1..210
                       mol_type = other DNA
                       organism = synthetic construct
SEQUENCE: 37
tacaaaacct ccttgcttga gagtgtggca ctctacgcgt ccccccctgtc gcgttcgctc  60
gctcgctggc tcgtttgggg gggcgacggc ccaaagggcc gtcgtctggc agctctttga  120
gctgccaccc ccccaaacga gccagcgagc gagcgaacgc gacagggggc gcgtggagag  180
tgccacactc tcaagcaagg aggttttgta                                    210

SEQ ID NO: 38          moltype = DNA  length = 227
FEATURE                Location/Qualifiers
misc_feature           1..227
                       note = Chimeric ITR sequence
source                 1..227
                       mol_type = other DNA
                       organism = synthetic construct
SEQUENCE: 38
tacaaaacct ccttgcttga gagtgtggca ctctcacgcg tagatctaga cccccctgtcg  60
cgttcgctcg ctcgctggct cgtttggggg ggcgacggcc caaagggccg tcgtctggca  120
gctctttgag ctgccacccc cccaaacgag ccagcgagcg agcgaacgcg acagggggtc  180
tagatctacg gtgagagtgc cacactctca agcaaggagg ttttgta                 227

SEQ ID NO: 39          moltype = DNA  length = 198
FEATURE                Location/Qualifiers
misc_feature           1..198
                       note = Chimeric ITR sequence
source                 1..198
                       mol_type = other DNA
                       organism = synthetic construct
SEQUENCE: 39
tacaaaacct ccttgcttga gagtgtggca ctctccccgc tcgctcgctc gctcgctcgc  60
tggctcgttt gggggggcga cggcccaaag ggccgtcgtc tggcagctct ttgagctgcc  120
acccccccaa acgagccagc gagcgagcga gcgagcgagc ggggagagtg ccacactctc  180
aagcaaggag gttttgta                                                 198

SEQ ID NO: 40          moltype = DNA  length = 198
FEATURE                Location/Qualifiers
misc_feature           1..198
                       note = Chimeric ITR sequence
source                 1..198
                       mol_type = other DNA
                       organism = synthetic construct
SEQUENCE: 40
tacaaaacct ccttgcttga gagtgtggca ctctccccag ctaagatgca gctcgctcgc  60
tggctcgttt gggggggcga cggcccaaag ggccgtcgtc tggcagctct ttgagctgcc  120
acccccccaa acgagccagc gagcgagctg catcttagct ggggagagtg ccacactctc  180
aagcaaggag gttttgta                                                 198

SEQ ID NO: 41          moltype = DNA  length = 181
FEATURE                Location/Qualifiers
misc_feature           1..181
                       note = Chimeric ITR sequence
source                 1..181
                       mol_type = other DNA
                       organism = synthetic construct
SEQUENCE: 41
aggaacccct agtgatggag ttggccactc cctctctgct cgctcgcgcg ctcgctcgct  60
cactgagggc gggcgaccaa aggtcgcccg agcccggccc tttgggccgg gcccctcagt  120
gagcgagcga gcgcgcgagc gagcagagag ggagtggcca actccatcac taggggttcc  180
t                                                                   181

SEQ ID NO: 42          moltype = DNA  length = 198
FEATURE                Location/Qualifiers
misc_feature           1..198
                       note = Chimeric ITR sequence
source                 1..198
                       mol_type = other DNA
                       organism = synthetic construct
SEQUENCE: 42
tacaaaacct ccttgcttga gagtgtggca ctctcccccc tgtcgcgttc gctcagctaa  60
gatgcagttt gggggggcga cggcccaaag ggccgtcgtc tggcagctct ttgagctgcc  120
acccccccaa actgcatctt agctgagcga acgcgacagg ggggagagtg ccacactctc  180
aagcaaggag gttttgta                                                 198

SEQ ID NO: 43          moltype = DNA  length = 180
```

```
FEATURE                 Location/Qualifiers
misc_feature            1..180
                        note = Chimeric ITR sequence
source                  1..180
                        mol_type = other DNA
                        organism = synthetic construct
SEQUENCE: 43
aggaacccct agtgatggag ttggccactc cctctctgct cgctcgcgcg ctcaagatgc  60
actgagggcg ggcgaccaaa ggtcgcccga gcccggccct ttgggccggg cccctcagtt  120
gcatcttgag cgcgcgagcg agcagagagg gagtggccaa ctccatcact aggggttcct  180

SEQ ID NO: 44           moltype = DNA  length = 197
FEATURE                 Location/Qualifiers
misc_feature            1..197
                        note = Chimeric ITR sequence
source                  1..197
                        mol_type = other DNA
                        organism = synthetic construct
SEQUENCE: 44
tacaaaacct ccttgcttga gagtgtggca ctctcccccc tgtcgcgttc gctcgctcgc  60
tggctcgttt ggggggggcgg gcgaccaaag gtcgcccgag cccggccctt tgggccgggc  120
cccccccaaa cgagccagcg agcgagcgaa cgcgacaggg gggagagtgc cacactctca  180
agcaaggagg ttttgta                                                 197

SEQ ID NO: 45           moltype = DNA  length = 135
FEATURE                 Location/Qualifiers
misc_feature            1..135
                        note = Chimeric ITR sequence
source                  1..135
                        mol_type = other DNA
                        organism = synthetic construct
SEQUENCE: 45
aggaacccct agtgatggag ttggccactc cctctctgcg cgctcgctcg ctcactgagg  60
cggccctttg ggccgcctca gtgagcgagc gagcgcgcag agagggagtg gccaactcca  120
tcactagggg ttcct                                                   135

SEQ ID NO: 46           moltype = DNA  length = 153
FEATURE                 Location/Qualifiers
misc_feature            1..153
                        note = Chimeric ITR sequence
source                  1..153
                        mol_type = other DNA
                        organism = synthetic construct
SEQUENCE: 46
aggaacccct agtgatggag ttggggtctg cgcgcgctcg ctcgctcact gagggcgggc  60
gaccaaaggt cgcccgagcc cggccctttg ggccgggccc ctcagtgagc gagcgagcgc  120
gcgcagaccc caactccatc actaggggtt cct                               153

SEQ ID NO: 47           moltype = DNA  length = 164
FEATURE                 Location/Qualifiers
misc_feature            1..164
                        note = Chimeric ITR sequence
source                  1..164
                        mol_type = other DNA
                        organism = synthetic construct
SEQUENCE: 47
aggaacccct agtgatggag ttgggactcc ctctctgcgc gctcgctcgc tcactgaggg  60
cgggcgacca aaggtcgccc gagcccggcc ctttgggccg ggcccctcag tgagcgagcg  120
agcgcgcaga gagggagtcc ccaactccat cactaggggt tcct                   164

SEQ ID NO: 48           moltype = DNA  length = 159
FEATURE                 Location/Qualifiers
misc_feature            1..159
                        note = Chimeric ITR sequence
source                  1..159
                        mol_type = other DNA
                        organism = synthetic construct
SEQUENCE: 48
aggaacccct agtgatggag ttggggttaa ctctgcgcgc tcgctcgctc actgagggcg  60
ggcgaccaaa ggtcgcccga gcccggccct ttgggccggg cccctcagtg agcgagcgag  120
cgcgcagagt taaccccaac tccatcacta ggggttcct                         159

SEQ ID NO: 49           moltype = DNA  length = 157
FEATURE                 Location/Qualifiers
misc_feature            1..157
                        note = Chimeric ITR sequence
source                  1..157
                        mol_type = other DNA
                        organism = synthetic construct
```

```
SEQUENCE: 49
aggaacccct agtgatggag ttggtccctc tctgcgcgct cgctcgctca ctgagggcgg  60
gcgaccaaag gtcgcccgag cccggccctt tgggccgggc ccctcagtga gcgagcgagc  120
gcgcagagag ggaccaactc catcactagg ggttcct                           157

SEQ ID NO: 50          moltype = DNA  length = 165
FEATURE                Location/Qualifiers
misc_feature           1..165
                       note = Chimeric ITR sequence
source                 1..165
                       mol_type = other DNA
                       organism = synthetic construct
SEQUENCE: 50
aggaacccct agtgatggag ttggggttaa cccctctgcg cgctcgctcg ctcactgagg  60
gcgggcgacc aaaggtcgcc cgagcccggc cctttgggcc gggcccctca gtgagcgagc  120
gagcgcgcag aggggttaac cccaactcca tcactagggg ttcct                  165

SEQ ID NO: 51          moltype = DNA  length = 172
FEATURE                Location/Qualifiers
misc_feature           1..172
                       note = Chimeric ITR sequence
source                 1..172
                       mol_type = other DNA
                       organism = synthetic construct
SEQUENCE: 51
aggaacccct agtgatggag ttggccactc cctcttcgct cgctcgctgg ctcgtttggg  60
ggggcgacgg cccaaagggc cgtcgtctgg cagctctttg agctgccacc cccccaaacg  120
agccagcgag cgagcgaaga gggagtggcc aactccatca ctaggggttc ct          172

SEQ ID NO: 52          moltype = DNA  length = 181
FEATURE                Location/Qualifiers
misc_feature           1..181
                       note = Chimeric ITR sequence
source                 1..181
                       mol_type = other DNA
                       organism = synthetic construct
SEQUENCE: 52
aggaacccct agtgatggag ttggggttaa ccccactccc tctctgcgcg ctcgctcgct  60
cactgagggc gggcgaccaa aggtcgcccg agcccggccc tttgggccgg gcccctcagt  120
gagcgagcga gcgcgcagag agggagtggg gttaacccca actccatcac taggggttcc  180
t                                                                  181

SEQ ID NO: 53          moltype = AA  length = 621
FEATURE                Location/Qualifiers
REGION                 1..621
                       note = Chimeric Rep protein sequence
source                 1..621
                       mol_type = protein
                       organism = synthetic construct
SEQUENCE: 53
MATFYEVIVR VPFDVEEHLP GISDSFVDWV TGQIWELPPE SDLNLTLVEQ PQLTVADRIR  60
RVFLYEWNKF SKAPEALFFV QFEKGESYFH MHVLVETTGV KSMVLGRFLS QIREKLIQRI  120
YRGIEPTLPN WFAVTKTRNG AGGGNKVVDE CYIPNYLLPK TQPELQWAWT NMEQYLSACL  180
NLTERKRLVA QHLTHVSQTQ EQNKENQNPN SDAPVIRSKT SARYMELVGW LVDKGITSEK  240
QWIQEDQASY ISFNAASNSR SQIKAALDNA GKIMSLTKTA PDYLVGQQPV EDISSNRIYK  300
ILELNGYDPQ YAASVFLGWA TKKFGKRNTI WLFGPATTGK TNIAEAIAHT VPFYGCVNWT  360
NENFPFNDCV DKMVIWWEEG KMTAKVVESA KAILGGSKVR VDQKCKSSAQ IDPTPVIVTS  420
NTNMCAVIDG NSTTFEHQQP LQDRMFKFEL TRRLDHDFGK VTKQEVKDFF RWAKDHVVEV  480
EHEFYVKKGG AKKRPAPSDA DISEPKRVRE SVAQPSTSDA EASINYADRY QNKCSRHVGM  540
NLMLFPCRQC ERMNQNSNIC FTHGQKDCLE CFPVSESQPV SVVKKAYQKL CYIHHIMGKV  600
PDACTACDLV NVDLDDCIFE Q                                            621

SEQ ID NO: 54          moltype = AA  length = 620
FEATURE                Location/Qualifiers
REGION                 1..620
                       note = Chimeric Rep protein sequence
source                 1..620
                       mol_type = protein
                       organism = synthetic construct
SEQUENCE: 54
MATFYEVIVR VPFDVEEHLP GISDSFVDWV TGQIWELPPE SDLNLTLVEQ PQLTVADRIR  60
RVFLYEWNKF SKQESKFFVQ FEKGESYFHM HVLVETTGVK SMVLGRFLSQ IREKLIQRIY  120
RGIEPTLPNW FAVTKTRNGA GGGNKVVDEC YIPNYLLPKT QPELQWAWTN MEQYLSACLN  180
LTERKRLVAQ HLTHVSQTQE QNKENQNPNS DAPVIRSKTS ARYMELVGWL VDKGITSEKQ  240
WIQEDQASYI SFNAASNSRS QIKAALDNAG KIMSLTKTAP DYLVGQQPVE DISSNRIYKI  300
LELNGYDPQY AASVFLGWAT KKFGKRNTIW LFGPATTGKT NIAEAIAHTV PFYGCVNWTN  360
ENFPFNDCVD KMVIWWEEGK MTAKVVESAK AILGGSKVRV DQKCKSSAQI DPTPVIVTSN  420
TNMCAVIDGN STTFEHQQPL QDRMFKFELT RRLDHDFGKV TKQEVKDFFR WAKDHVVEVE  480
HEFYVKKGGA KKRPAPSDAD ISEPKRVRES VAQPSTSDAE ASINYADRYQ NKCSRHVGMN  540
```

-continued

```
LMLFPCRQCE RMNQNSNICF THGQKDCLEC FPVSESQPVS VVKKAYQKLC YIHHIMGKVP  600
DACTACDLVN VDLDDCIFEQ                                              620

SEQ ID NO: 55          moltype = AA  length = 620
FEATURE                Location/Qualifiers
REGION                 1..620
                       note = Chimeric Rep protein sequence
source                 1..620
                       mol_type = protein
                       organism = synthetic construct
SEQUENCE: 55
MATFYEVIVR VPFDVEEHLP GISDSFVDWV TGQIWELPPE SDLNLTLVEQ PQLTVADRIR  60
RVFLYEWNKF SKQESKFFVQ FEKGSEYFHL HTLVETSGIS SMVLGRYVSQ IREKLIQRIY  120
RGIEPTLPNW FAVTKTRNGA GGGNKVVDEC YIPNYLLPKT QPELQWAWTN MEQYLSACLN  180
LTERKRLVAQ HLTHVSQTQE QNKENQNPNS DAPVIRSKTS ARYMELVGWL VDKGITSEKQ  240
WIQEDQASYI SFNAASNSRS QIKAALDNAG KIMSLTKTAP DYLVGQQPVE DISSNRIYKI  300
LELNGYDPQY AASVFLGWAT KKFGKRNTIW LFGPATTGKT NIAEAIAHTV PFYGCVNWTN  360
ENFPFNDCVD KMVIWWEEGK MTAKVVESAK AILGGSKVRV DQKCKSSAQI DPTPVIVTSN  420
TNMCAVIDGN STTFEHQQPL QDRMFKFELT RRLDHDFGKV TKQEVKDFFR WAKDHVVEVE  480
HEFYVKKGGA KKRPAPSDAD ISEPKRVRES VAQPSTSDAE ASINYADRYQ NKCSRHVGMN  540
LMLFPCRQCE RMNQNSNICF THGQKDCLEC FPVSESQPVS VVKKAYQKLC YIHHIMGKVP  600
DACTACDLVN VDLDDCIFEQ                                              620

SEQ ID NO: 56          moltype = AA  length = 620
FEATURE                Location/Qualifiers
REGION                 1..620
                       note = Chimeric Rep protein sequence
source                 1..620
                       mol_type = protein
                       organism = synthetic construct
SEQUENCE: 56
MATFYEVIVR VPFDVEEHLP GISDSFVDWV TGQIWELPPE SDLNLTLVEQ PQLTVADRIR  60
RVFLYEWNKF SKQESKFFVQ FEKGSEYFHL HTLVETSGIS SMVLGRYVSQ IRAQLVKVVF  120
QGIEPTLPNW FAVTKTRNGA GGGNKVVDEC YIPNYLLPKT QPELQWAWTN MEQYLSACLN  180
LTERKRLVAQ HLTHVSQTQE QNKENQNPNS DAPVIRSKTS ARYMELVGWL VDKGITSEKQ  240
WIQEDQASYI SFNAASNSRS QIKAALDNAG KIMSLTKTAP DYLVGQQPVE DISSNRIYKI  300
LELNGYDPQY AASVFLGWAT KKFGKRNTIW LFGPATTGKT NIAEAIAHTV PFYGCVNWTN  360
ENFPFNDCVD KMVIWWEEGK MTAKVVESAK AILGGSKVRV DQKCKSSAQI DPTPVIVTSN  420
TNMCAVIDGN STTFEHQQPL QDRMFKFELT RRLDHDFGKV TKQEVKDFFR WAKDHVVEVE  480
HEFYVKKGGA KKRPAPSDAD ISEPKRVRES VAQPSTSDAE ASINYADRYQ NKCSRHVGMN  540
LMLFPCRQCE RMNQNSNICF THGQKDCLEC FPVSESQPVS VVKKAYQKLC YIHHIMGKVP  600
DACTACDLVN VDLDDCIFEQ                                              620

SEQ ID NO: 57          moltype = AA  length = 618
FEATURE                Location/Qualifiers
REGION                 1..618
                       note = Chimeric Rep protein sequence
source                 1..618
                       mol_type = protein
                       organism = synthetic construct
SEQUENCE: 57
MATFYEVIVR VPFDVEEHLP GISDSFVDWV TGQIWELPPE SDLNLTLVEQ PQLTVADRIR  60
RVFLYEWNKF SKQESKFFVQ FEKGSEYFHL HTLVETSGIS SMVLGRYVSQ IRAQLVKVVF  120
QGIEPQINDW VAITKVKKGG GNKVVDECYI PNYLLPKTQP ELQWAWTNME QYLSACLNLT  180
ERKRLVAQHL THVSQTQEQN KENQNPNSDA PVIRSKTSAR YMELVGWLVD KGITSEKQWI  240
QEDQASYISF NAASNSRSQI KAALDNAGKI MSLTKTAPDY LVGQQPVEDI SSNRIYKILE  300
LNGYDPQYAA SVFLGWATKK FGKRNTIWLF GPATTGKTNI AEAIAHTVPF YGCVNWTNEN  360
FPFNDCVDKM VIWWEEGKMT AKVVESAKAI LGGSKVRVDQ KCKSSAQIDP TPVIVTSNTN  420
MCAVIDGNST TFEHQQPLQD RMFKFELTRR LDHDFGKVTK QEVKDFFRWA KDHVVEVEHE  480
FYVKKGGAKK RPAPSDADIS EPKRVRESVA QPSTSDAEAS INYADRYQNK CSRHVGMNLM  540
LFPCRQCERM NQNSNICFTH GQKDCLECFP VSESQPVSVV KKAYQKLCYI HHIMGKVPDA  600
CTACDLVNVD LDDCIFEQ                                                618

SEQ ID NO: 58          moltype = AA  length = 617
FEATURE                Location/Qualifiers
REGION                 1..617
                       note = Chimeric Rep protein sequence
source                 1..617
                       mol_type = protein
                       organism = synthetic construct
SEQUENCE: 58
MATFYEVIVR VPFDVEEHLP GISDSFVDWV TGQIWELPPE SDLNLTLVEQ PQLTVADRIR  60
RVFLYEWNKF SKQESKFFVQ FEKGSEYFHL HTLVETSGIS SMVLGRYVSQ IRAQLVKVVF  120
QGIEPQINDW VAITKVKKGG ANKVVDSGYI PAYLLPKVQP ELQWAWTNME QYLSACLNLT  180
ERKRLVAQHL THVSQTQEQN KENQNPNSDA PVIRSKTARY MELVGWLVDK GITSEKQWIQ  240
EDQASYISFN AASNSRSQIK AALDNAGKIM SLTKTAPDYL VGQQPVEDIS SNRIYKILEL  300
NGYDPQYAAS VFLGWATKKF GKRNTIWLFG PATTGKTNIA EAIAHTVPFY GCVNWTNENF  360
PFNDCVDKMV IWWEEGKMTA KVVESAKAIL GGSKVRVDQK CKSSAQIDPT PVIVTSNTNM  420
CAVIDGNSTT FEHQQPLQDR MFKFELTRRL DHDFGKVTKQ EVKDFFRWAK DHVVEVEHEF  480
```

```
YVKKGGAKKR PAPSDADISE PKRVRESVAQ PSTSDAEASI NYADRYQNKC SRHVGMNLML  540
FPCRQCERMN QNSNICFTHG QKDCLECFPV SESQPVSVVK KAYQKLCYIH HIMGKVPDAC  600
TACDLVNVDL DDCIFEQ                                                617

SEQ ID NO: 59          moltype = AA  length = 616
FEATURE                Location/Qualifiers
REGION                 1..616
                       note = Chimeric Rep protein sequence
source                 1..616
                       mol_type = protein
                       organism = synthetic construct
SEQUENCE: 59
MATFYEVIVR VPFDVEEHLP GISDSFVDWV TGQIWELPPE SDLNLTLVEQ PQLTVADRIR  60
RVFLYEWNKF SKQESKFFVQ FEKGSEYFHL HTLVETSGIS SMVLGRYVSQ IRAQLVKVVF  120
QGIEPQINDW VAITKVKKGG ANKVVDSGYI PAYLLPKVQP ELQWAWTNLD EYKLACLNLT  180
ERKRLVAQHL THVSQTQEQN KENQNPNDAP VIRSKTARYM ELVGWLVDKG ITSEKQWIQE  240
DQASYISFNA ASNSRSQIKA ALDNAGKIMS LTKTAPDYLV GQQPVEDISS NRIYKILELN  300
GYDPQYAASV FLGWATKKFG KRNTIWLFGP ATTGKTNIAE AIAHTVPFYG CVNWTNENFP  360
FNDCVDKMVI WWEEGKMTAK VVESAKAILG GSKVRVDQKC KSSAQIDPTP VIVTSNTNMC  420
AVIDGNSTTF EHQQPLQDRM FKFELTRRLD HDFGKVTKQE VKDFFRWAKD HVVEVEHEFY  480
VKKGGAKKRP APSDADISEP KRVRESVAQP STSDAEASIN YADRYQNKCS RHVGMNLMLF  540
PCRQCERMNQ NSNICFTHGQ KDCLECFPVS ESQPVSVVKK AYQKLCYIHH IMGKVPDACT  600
ACDLVNVDLD DCIFEQ                                                 616

SEQ ID NO: 60          moltype = AA  length = 621
FEATURE                Location/Qualifiers
REGION                 1..621
                       note = Chimeric Rep protein sequence
source                 1..621
                       mol_type = protein
                       organism = synthetic construct
SEQUENCE: 60
MATFYEVIVR VPFDVEEHLP GISDSFVDWV TGQIWELPPE SDLNLTLVEQ PQLTVADRIR  60
RVFLYEWNKF SKQESKFFVQ FEKGSEYFHL HTLVETSGIS SMVLGRYVSQ IRAQLVKVVF  120
QGIEPQINDW VAITKVKKGG ANKVVDSGYI PAYLLPKVQP ELQWAWTNLD EYKLAALNLE  180
ERKRRKRLVA QHLTHVSQTQ EQNKENQNPN SDAPVIRSKT SARYMELVGW LVDKGITSEK  240
QWIQEDQASY ISFNAASNSR SQIKAALDNA GKIMSLTKTA PDYLVGQQPV EDISSNRIYK  300
ILELNGYDPQ YAASVFLGWA TKKFGKRNTI WLFGPATTGK TNIAEAIAHT VPFYGCVNWT  360
NENFPFNDCV DKMVIWWEEG KMTAKVVESA KAILGGSKVR VDQKCKSSAQ IDPTPVIVTS  420
NTNMCAVIDG NSTTFEHQQP LQDRMFKFEL TRRLDHDFGK VTKQEVKDFF RWAKDHVVEV  480
EHEFYVKKGG AKKRPAPSDA DISEPKRVRE SVAQPSTSDA EASINYADRY QNKCSRHVGM  540
NLMLFPCRQC ERMNQNSNIC FTHGQKDCLE CFPVSESQPV SVVKKAYQKL CYIHHIMGKV  600
PDACTACDLV NVDLDDCIFE Q                                           621

SEQ ID NO: 61          moltype = AA  length = 617
FEATURE                Location/Qualifiers
REGION                 1..617
                       note = Chimeric Rep protein sequence
source                 1..617
                       mol_type = protein
                       organism = synthetic construct
SEQUENCE: 61
MATFYEVIVR VPFDVEEHLP GISDSFVDWV TGQIWELPPE SDLNLTLVEQ PQLTVADRIR  60
RVFLYEWNKF SKQESKFFVQ FEKGSEYFHL HTLVETSGIS SMVLGRYVSQ IRAQLVKVVF  120
QGIEPQINDW VAITKVKKGG ANKVVDSGYI PAYLLPKVQP ELQWAWTNLD EYKLAALNLE  180
ERKRLVAQFL AESSQRSEQN KENQNPNSDA PVIRSKSARY MELVGWLVDK GITSEKQWIQ  240
EDQASYISFN AASNSRSQIK AALDNAGKIM SLTKTAPDYL VGQQPVEDIS SNRIYKILEL  300
NGYDPQYAAS VFLGWATKKF GKRNTIWLFG PATTGKTNIA EAIAHTVPFY GCVNWTNENF  360
PFNDCVDKMV IWWEEGKMTA KVVESAKAIL GGSKVRVDQK CKSSAQIDPT PVIVTSNTNM  420
CAVIDGNSTT FEHQQPLQDR MFKFELTRRL DHDFGKVTKQ EVKDFFRWAK DHVVEVEHEF  480
YVKKGGAKKR PAPSDADISE PKRVRESVAQ PSTSDAEASI NYADRYQNKC SRHVGMNLML  540
FPCRQCERMN QNSNICFTHG QKDCLECFPV SESQPVSVVK KAYQKLCYIH HIMGKVPDAC  600
TACDLVNVDL DDCIFEQ                                                617

SEQ ID NO: 62          moltype = AA  length = 610
FEATURE                Location/Qualifiers
REGION                 1..610
                       note = Chimeric Rep protein sequence
source                 1..610
                       mol_type = protein
                       organism = synthetic construct
SEQUENCE: 62
MPGFYEIVIK VPSDLDGHLP GISDSFVNWV AEKEWELPPD SDMDLNLIEQ APLTVAEKLQ  60
RDFLTEWRRV SKQESKFFVQ FEKGSEYFHL HTLVETSGIS SMVLGRYVSQ IRAQLVKVVF  120
QGIEPQINDW VAITKVKKGG ANKVVDSGYI PAYLLPKVQP ELQWAWTNLD EYKLAALNLE  180
ERKRLVAQFL AESSQRSQEA ASQREFSADP VIKSKTSQKY MALVNWLVEH GITSEKQWIQ  240
ENQESYLSFN STGNSRSQIK AALDNATKIM SLTKSAVDYL VGSSVPEDIS KNRIWQIFEM  300
NGYDPAYAGS ILYGWCQRSF NKRNTVWLYG PATTGKTNIA EAIAHTVPFY GCVNWTNENF  360
PFNDCVDKML IWWEEGKMTN KVVESAKAIL GGSKVRVDQK CKSSVQIDST PVIVTSNTNM  420
```

```
CVVVDGNSTT FEHQQPLEDR MFKFELTKRL PPDFGKITKQ EVKDFFAWAK VNQVPVTHEF  480
KVPRELAGTK GAEKSLKRPL GDVTNTSYKS LEKRARLSFV PETPRSSDVT VDPAPLRPLN  540
WNSRYDCKCD YHAQFDNISN KCDECEYLNR GKNGCICHNV THCQICHGIP PWEKENLSDF  600
GDFDDANKEQ                                                         610

SEQ ID NO: 63          moltype = AA  length = 611
FEATURE                Location/Qualifiers
REGION                 1..611
                       note = Chimeric Rep protein sequence
source                 1..611
                       mol_type = protein
                       organism = synthetic construct
SEQUENCE: 63
MPGFYEIVIK VPSDLDGHLP GISDSFVNWV AEKEWELPPD SDMDLNLIEQ APLTVAEKLQ  60
RDFLTEWRRV SKAPEALFFV QFEKGSEYFH LHTLVETSGI SSMVLGRYVS QIRAQLVKVV  120
FQGIEPQIND WVAITKVKKG GANKVVDSGY IPAYLLPKVQ PELQWAWTNL DEYKLAALNL  180
EERKRLVAQF LAESSQRSQE AASQREFSAD PVIKSKTSQK YMALVNWLVE HGITSEKQWI  240
QENQESYLSF NSTGNSRSQI KAALDNATKI MSLTKSAVDY LVGSSVPEDI SKNRIWQIFE  300
MNGYDPAYAG SILYGWCQRS FNKRNTVWLY GPATTGKTNI AEAIAHTVPF YGCVNWTNEN  360
FPFNDCVDKM LIWWEEGKMT NKVVESAKAI LGGSKVRVDQ KCKSSVQIDS TPVIVTSNTN  420
MCVVVDGNST TFEHQQPLED RMFKFELTKR LPPDFGKITK QEVKDFFAWA KVNQVPVTHE  480
FKVPRELAGT KGAEKSLKRP LGDVTNTSYK SLEKRARLSF VPETPRSSDV TVDPAPLRPL  540
NWNSRYDCKC DYHAQFDNIS NKCDECEYLN RGKNGCICHN VTHCQICHGI PPWEKENLSD  600
FGDFDDANKE Q                                                       611

SEQ ID NO: 64          moltype = AA  length = 611
FEATURE                Location/Qualifiers
REGION                 1..611
                       note = Chimeric Rep protein sequence
source                 1..611
                       mol_type = protein
                       organism = synthetic construct
SEQUENCE: 64
MPGFYEIVIK VPSDLDGHLP GISDSFVNWV AEKEWELPPD SDMDLNLIEQ APLTVAEKLQ  60
RDFLTEWRRV SKAPEALFFV QFEKGESYFH MHVLVETSGI SSMVLGRYVS QIRAQLVKVV  120
FQGIEPQIND WVAITKVKKG GANKVVDSGY IPAYLLPKVQ PELQWAWTNL DEYKLAALNL  180
EERKRLVAQF LAESSQRSQE AASQREFSAD PVIKSKTSQK YMALVNWLVE HGITSEKQWI  240
QENQESYLSF NSTGNSRSQI KAALDNATKI MSLTKSAVDY LVGSSVPEDI SKNRIWQIFE  300
MNGYDPAYAG SILYGWCQRS FNKRNTVWLY GPATTGKTNI AEAIAHTVPF YGCVNWTNEN  360
FPFNDCVDKM LIWWEEGKMT NKVVESAKAI LGGSKVRVDQ KCKSSVQIDS TPVIVTSNTN  420
MCVVVDGNST TFEHQQPLED RMFKFELTKR LPPDFGKITK QEVKDFFAWA KVNQVPVTHE  480
FKVPRELAGT KGAEKSLKRP LGDVTNTSYK SLEKRARLSF VPETPRSSDV TVDPAPLRPL  540
NWNSRYDCKC DYHAQFDNIS NKCDECEYLN RGKNGCICHN VTHCQICHGI PPWEKENLSD  600
FGDFDDANKE Q                                                       611

SEQ ID NO: 65          moltype = AA  length = 611
FEATURE                Location/Qualifiers
REGION                 1..611
                       note = Chimeric Rep protein sequence
source                 1..611
                       mol_type = protein
                       organism = synthetic construct
SEQUENCE: 65
MPGFYEIVIK VPSDLDGHLP GISDSFVNWV AEKEWELPPD SDMDLNLIEQ APLTVAEKLQ  60
RDFLTEWRRV SKAPEALFFV QFEKGESYFH MHVLVETTGV KSMVLGRFLS QIREKLVKVV  120
FQGIEPQIND WVAITKVKKG GANKVVDSGY IPAYLLPKVQ PELQWAWTNL DEYKLAALNL  180
EERKRLVAQF LAESSQRSQE AASQREFSAD PVIKSKTSQK YMALVNWLVE HGITSEKQWI  240
QENQESYLSF NSTGNSRSQI KAALDNATKI MSLTKSAVDY LVGSSVPEDI SKNRIWQIFE  300
MNGYDPAYAG SILYGWCQRS FNKRNTVWLY GPATTGKTNI AEAIAHTVPF YGCVNWTNEN  360
FPFNDCVDKM LIWWEEGKMT NKVVESAKAI LGGSKVRVDQ KCKSSVQIDS TPVIVTSNTN  420
MCVVVDGNST TFEHQQPLED RMFKFELTKR LPPDFGKITK QEVKDFFAWA KVNQVPVTHE  480
FKVPRELAGT KGAEKSLKRP LGDVTNTSYK SLEKRARLSF VPETPRSSDV TVDPAPLRPL  540
NWNSRYDCKC DYHAQFDNIS NKCDECEYLN RGKNGCICHN VTHCQICHGI PPWEKENLSD  600
FGDFDDANKE Q                                                       611

SEQ ID NO: 66          moltype = AA  length = 611
FEATURE                Location/Qualifiers
REGION                 1..611
                       note = Chimeric Rep protein sequence
source                 1..611
                       mol_type = protein
                       organism = synthetic construct
SEQUENCE: 66
MPGFYEIVIK VPSDLDGHLP GISDSFVNWV AEKEWELPPD SDMDLNLIEQ APLTVAEKLQ  60
RDFLTEWRRV SKAPEALFFV QFEKGESYFH MHVLVETTGV KSMVLGRFLS QIREKLIQRI  120
YRGIEPQIND WVAITKVKKG GANKVVDSGY IPAYLLPKVQ PELQWAWTNL DEYKLAALNL  180
EERKRLVAQF LAESSQRSQE AASQREFSAD PVIKSKTSQK YMALVNWLVE HGITSEKQWI  240
QENQESYLSF NSTGNSRSQI KAALDNATKI MSLTKSAVDY LVGSSVPEDI SKNRIWQIFE  300
MNGYDPAYAG SILYGWCQRS FNKRNTVWLY GPATTGKTNI AEAIAHTVPF YGCVNWTNEN  360
```

-continued

```
FPFNDCVDKM LIWWEEGKMT NKVVESAKAI LGGSKVRVDQ KCKSSVQIDS TPVIVTSNTN  420
MCVVVDGNST TFEHQQPLED RMFKFELTKR LPPDFGKITK QEVKDFFAWA KVNQVPVTHE  480
FKVPRELAGT KGAEKSLKRP LGDVTNTSYK SLEKRARLSF VPETPRSSDV TVDPAPLRPL  540
NWNSRYDCKC DYHAQFDNIS NKCDECEYLN RGKNGCICHN VTHCQICHGI PPWEKENLSD  600
FGDFDDANKE Q                                                      611

SEQ ID NO: 67          moltype = AA  length = 613
FEATURE                Location/Qualifiers
REGION                 1..613
                       note = Chimeric Rep protein sequence
source                 1..613
                       mol_type = protein
                       organism = synthetic construct
SEQUENCE: 67
MPGFYEIVIK VPSDLDGHLP GISDSFVNWV AEKEWELPPD SDMDLNLIEQ APLTVAEKLQ  60
RDFLTEWRRV SKAPEALFFV QFEKGESYFH MHVLVETTGV KSMVLGRFLS QIREKLIQRI  120
YRGIEPTLPN WFAVTKTRNG AGGANKVVDS GYIPAYLLPK VQPELQWAWT NLDEYKLAAL  180
NLEERKRLVA QFLAESSQRS QEAASQREFS ADPVIKSKTS QKYMALVNWL VEHGITSEKQ  240
WIQENQESYL SFNSTGNSRS QIKAALDNAT KIMSLTKSAV DYLVGSSVPE DISKNRIWQI  300
FEMNGYDPAY AGSILYGWCQ RSFNKRNTVW LYGPATTGKT NIAEAIAHTV PFYGCVNWTN  360
ENFPFNDCVD KMLIWWEEGK MTNKVVESAK AILGGSKVRV DQKCKSSVQI DSTPVIVTSN  420
TNMCVVVDGN STTFEHQQPL EDRMFKFELT KRLPPDFGKI TKQEVKDFFA WAKVNQVPVT  480
HEFKVPRELA GTKGAEKSLK RPLGDVTNTS YKSLEKRARL SFVPETPRSS DVTVDPAPLR  540
PLNWNSRYDC KCDYHAQFDN ISNKCDECEY LNRGKNGCIC HNVTHCQICH GIPPWEKENL  600
SDFGDFDDAN KEQ                                                    613

SEQ ID NO: 68          moltype = AA  length = 613
FEATURE                Location/Qualifiers
REGION                 1..613
                       note = Chimeric Rep protein sequence
source                 1..613
                       mol_type = protein
                       organism = synthetic construct
SEQUENCE: 68
MPGFYEIVIK VPSDLDGHLP GISDSFVNWV AEKEWELPPD SDMDLNLIEQ APLTVAEKLQ  60
RDFLTEWRRV SKAPEALFFV QFEKGESYFH MHVLVETTGV KSMVLGRFLS QIREKLIQRI  120
YRGIEPTLPN WFAVTKTRNG AGGGNKVVDS GYIPAYLLPK VQPELQWAWT NLDEYKLAAL  180
NLEERKRLVA QFLAESSQRS QEAASQREFS ADPVIKSKTS QKYMALVNWL VEHGITSEKQ  240
WIQENQESYL SFNSTGNSRS QIKAALDNAT KIMSLTKSAV DYLVGSSVPE DISKNRIWQI  300
FEMNGYDPAY AGSILYGWCQ RSFNKRNTVW LYGPATTGKT NIAEAIAHTV PFYGCVNWTN  360
ENFPFNDCVD KMLIWWEEGK MTNKVVESAK AILGGSKVRV DQKCKSSVQI DSTPVIVTSN  420
TNMCVVVDGN STTFEHQQPL EDRMFKFELT KRLPPDFGKI TKQEVKDFFA WAKVNQVPVT  480
HEFKVPRELA GTKGAEKSLK RPLGDVTNTS YKSLEKRARL SFVPETPRSS DVTVDPAPLR  540
PLNWNSRYDC KCDYHAQFDN ISNKCDECEY LNRGKNGCIC HNVTHCQICH GIPPWEKENL  600
SDFGDFDDAN KEQ                                                    613

SEQ ID NO: 69          moltype = AA  length = 613
FEATURE                Location/Qualifiers
REGION                 1..613
                       note = Chimeric Rep protein sequence
source                 1..613
                       mol_type = protein
                       organism = synthetic construct
SEQUENCE: 69
MPGFYEIVIK VPSDLDGHLP GISDSFVNWV AEKEWELPPD SDMDLNLIEQ APLTVAEKLQ  60
RDFLTEWRRV SKAPEALFFV QFEKGESYFH MHVLVETTGV KSMVLGRFLS QIREKLIQRI  120
YRGIEPTLPN WFAVTKTRNG AGGGNKVVDE CYIPNYLLPK TQPELQWAWT NLDEYKLAAL  180
NLEERKRLVA QFLAESSQRS QEAASQREFS ADPVIKSKTS QKYMALVNWL VEHGITSEKQ  240
WIQENQESYL SFNSTGNSRS QIKAALDNAT KIMSLTKSAV DYLVGSSVPE DISKNRIWQI  300
FEMNGYDPAY AGSILYGWCQ RSFNKRNTVW LYGPATTGKT NIAEAIAHTV PFYGCVNWTN  360
ENFPFNDCVD KMLIWWEEGK MTNKVVESAK AILGGSKVRV DQKCKSSVQI DSTPVIVTSN  420
TNMCVVVDGN STTFEHQQPL EDRMFKFELT KRLPPDFGKI TKQEVKDFFA WAKVNQVPVT  480
HEFKVPRELA GTKGAEKSLK RPLGDVTNTS YKSLEKRARL SFVPETPRSS DVTVDPAPLR  540
PLNWNSRYDC KCDYHAQFDN ISNKCDECEY LNRGKNGCIC HNVTHCQICH GIPPWEKENL  600
SDFGDFDDAN KEQ                                                    613

SEQ ID NO: 70          moltype = AA  length = 613
FEATURE                Location/Qualifiers
REGION                 1..613
                       note = Chimeric Rep protein sequence
source                 1..613
                       mol_type = protein
                       organism = synthetic construct
SEQUENCE: 70
MPGFYEIVIK VPSDLDGHLP GISDSFVNWV AEKEWELPPD SDMDLNLIEQ APLTVAEKLQ  60
RDFLTEWRRV SKAPEALFFV QFEKGESYFH MHVLVETTGV KSMVLGRFLS QIREKLIQRI  120
YRGIEPTLPN WFAVTKTRNG AGGGNKVVDE CYIPNYLLPK TQPELQWAWT NMEQYLSACL  180
NLTERKRLVA QFLAESSQRS QEAASQREFS ADPVIKSKTS QKYMALVNWL VEHGITSEKQ  240
WIQENQESYL SFNSTGNSRS QIKAALDNAT KIMSLTKSAV DYLVGSSVPE DISKNRIWQI  300
```

```
FEMNGYDPAY AGSILYGWCQ RSFNKRNTVW LYGPATTGKT NIAEAIAHTV PFYGCVNWTN  360
ENFPFNDCVD KMLIWWEEGK MTNKVVESAK AILGGSKVRV DQKCKSSVQI DSTPVIVTSN  420
TNMCVVVDGN STTFEHQQPL EDRMFKFELT KRLPPDFGKI TKQEVKDFFA WAKVNQVPVT  480
HEFKVPRELA GTKGAEKSLK RPLGDVTNTS YKSLEKRARL SFVPETPRSS DVTVDPAPLR  540
PLNWNSRYDC KCDYHAQFDN ISNKCDECEY LNRGKNGCIC HNVTHCQICH GIPPWEKENL  600
SDFGDFDDAN KEQ                                                     613

SEQ ID NO: 71          moltype = AA  length = 614
FEATURE                Location/Qualifiers
REGION                 1..614
                       note = Chimeric Rep protein sequence
source                 1..614
                       mol_type = protein
                       organism = synthetic construct
SEQUENCE: 71
MPGFYEIVIK VPSDLDGHLP GISDSFVNWV AEKEWELPPD SDMDLNLIEQ APLTVAEKLQ  60
RDFLTEWRRV SKAPEALFFV QFEKGESYFH MHVLVETTGV KSMVLGRFLS QIREKLIQRI  120
YRGIEPTLPN WFAVTKTRNG AGGGNKVVDE CYIPNYLLPK TQPELQWAWT NMEQYLSACL  180
NLTERKRLVA QHLTHVSQTQ EQNKENQPN SDAPVIKSKT SQKYMALVNW LVEHGITSEK  240
QWIQENQESY LSFNSTGNSR SQIKAALDNA TKIMSLTKSA VDYLVGSSVP EDISKNRIWQ  300
IFEMNGYDPA YAGSILYGWC QRSFNKRNTV WLYGPATTGK TNIAEAIAHT VPFYGCVNWT  360
NENFPFNDCV DKMLIWWEEG KMTNKVVESA KAILGGSKVR VDQKCKSSVQ IDSTPVIVTS  420
NTNMCVVVDG NSTTFEHQQP LEDRMFKFEL TKRLPPDFGK ITKQEVKDFF AWAKVNQVPV  480
THEFKVPREL AGTKGAEKSL KRPLGDVTNT SYKSLEKRAR LSFVPETPRS SDVTVDPAPL  540
RPLNWNSRYD CKCDYHAQFD NISNKCDECE YLNRGKNGCI CHNVTHCQIC HGIPPWEKEN  600
LSDFGDFDDA NKEQ                                                    614

SEQ ID NO: 72          moltype = AA  length = 612
FEATURE                Location/Qualifiers
REGION                 1..612
                       note = Chimeric Rep protein sequence
source                 1..612
                       mol_type = protein
                       organism = synthetic construct
SEQUENCE: 72
MATFYEVIVR VPFDVEEHLP GISDSFVDWV TGQIWELPPE SDLNLTLVEQ PQLTVADRIR  60
RVFLYEWNKF SKQESKFFVQ FEKGSEYFHL HTLVETSGIS SMVLGRYVSQ IREKLIQRIY  120
RGIEPTLPNW FAVTKTRNGA GGGNKVVDSG YIPAYLLPKV QPELQWAWTN LDEYKLAALN  180
LEERKRLVAQ FLAESSQRSQ EAASQREFSA DPVIKSKTSQ KYMALVNWLV EHGITSEKQW  240
IQENQESYLS FNSTGNSRSQ IKAALDNATK IMSLTKSAVD YLVGSSVPED ISKNRIWQIF  300
EMNGYDPAYA GSILYGWCQR SFNKRNTVWL YGPATTGKTN IAEAIAHTVP FYGCVNWTNE  360
NFPFNDCVDK MLIWWEEGKM TNKVVESAKA ILGGSKVRVD QKCKSSVQID STPVIVTSNT  420
NMCVVVDGNS TTFEHQQPLE DRMFKFELTK RLPPDFGKIT KQEVKDFFAW AKVNQVPVTH  480
EFKVPRELAG TKGAEKSLKR PLGDVTNTSY KSLEKRARLS FVPETPRSSD VTVDPAPLRP  540
LNWNSRYDCK CDYHAQFDNI SNKCDECEYL NRGKNGCICH NVTHCQICHG IPPWEKENLS  600
DFGDFDDANK EQ                                                      612

SEQ ID NO: 73          moltype = AA  length = 610
FEATURE                Location/Qualifiers
REGION                 1..610
                       note = Chimeric Rep protein sequence
source                 1..610
                       mol_type = protein
                       organism = synthetic construct
SEQUENCE: 73
MATFYEVIVR VPFDVEEHLP GISDSFVDWV TGQIWELPPE SDLNLTLVEQ PQLTVADRIR  60
RVFLYEWNKF SKQESKFFVQ FEKGSEYFHL HTLVETSGIS SMVLGRYVSQ IRAQLVKVVF  120
QGIEPQINDW VAITKVKKGG ANKVVDECYI PNYLLPKTQP ELQWAWTNME QYLSACLNLT  180
ERKRLVAQFL AESSQRSQEA ASQREFSADP VIKSKTSQKY MALVNWLVEH GITSEKQWIQ  240
ENQESYLSFN STGNSRSQIK AALDNATKIM SLTKSAVDYL VGSSVPEDIS KNRIWQIFEM  300
NGYDPAYAGS ILYGWCQRSF NKRNTVWLYG PATTGKTNIA EAIAHTVPFY GCVNWTNENF  360
PFNDCVDKML IWWEEGKMTN KVVESAKAIL GGSKVRVDQK CKSSVQIDST PVIVTSNTNM  420
CVVVDGNSTT FEHQQPLEDR MFKFELTKRL PPDFGKITKQ EVKDFFAWAK VNQVPVTHEF  480
KVPRELAGTK GAEKSLKRPL GDVTNTSYKS LEKRARLSFV PETPRSSDVT VDPAPLRPLN  540
WNSRYDCKCD YHAQFDNISN KCDECEYLNR GKNGCICHNV THCQICHGIP PWEKENLSDF  600
GDFDDANKEQ                                                         610

SEQ ID NO: 74          moltype = AA  length = 612
FEATURE                Location/Qualifiers
REGION                 1..612
                       note = Chimeric Rep protein sequence
source                 1..612
                       mol_type = protein
                       organism = synthetic construct
SEQUENCE: 74
MATFYEVIVR VPFDVEEHLP GISDSFVDWV TGQIWELPPE SDLNLTLVEQ PQLTVADRIR  60
RVFLYEWNKF SKQESKFFVQ FEKGSEYFHL HTLVETSGIS SMVLGRYVSQ IREKLIQRIY  120
RGIEPTLPNW FAVTKTRNGA GGGNKVVDEC YIPNYLLPKT QPELQWAWTN MEQYLSACLN  180
LTERKRLVAQ FLAESSQRSQ EAASQREFSA DPVIKSKTSQ KYMALVNWLV EHGITSEKQW  240
```

```
IQENQESYLS FNSTGNSRSQ IKAALDNATK IMSLTKSAVD YLVGSSVPED ISKNRIWQIF  300
EMNGYDPAYA GSILYGWCQR SFNKRNTVWL YGPATTGKTN IAEAIAHTVP FYGCVNWTNE  360
NFPFNDCVDK MLIWWEEGKM TNKVVESAKA ILGGSKVRVD QKCKSSVQID STPVIVTSNT  420
NMCVVVDGNS TTFEHQQPLE DRMFKFELTK RLPPDFGKIT KQEVKDFFAW AKVNQVPVTH  480
EFKVPRELAG TKGAEKSLKR PLGDVTNTSY KSLEKRARLS FVPETPRSSD VTVDPAPLRP  540
LNWNSRYDCK CDYHAQFDNI SNKCDECEYL NRGKNGCICH NVTHCQICHG IPPWEKENLS  600
DFGDFDDANK EQ                                                      612

SEQ ID NO: 75          moltype = AA  length = 619
FEATURE                Location/Qualifiers
REGION                 1..619
                       note = Chimeric Rep protein sequence
source                 1..619
                       mol_type = protein
                       organism = synthetic construct
SEQUENCE: 75
MPGFYEIVIK VPSDLDGHLP GISDSFVNWV AEKEWELPPD SDMDLNLIEQ APLTVAEKLQ  60
RDFLTEWRRV SKAPEALFFV QFEKGESYFH MHVLVETSGI SSMVLGRYVS QIRAQLVKVV  120
FQGIEPQIND WVAITKVKKG GANKVVDECY IPNYLLPKTQ PELQWAWTNM EQYLSACLNL  180
TERKRLVAQH LTHVSQTQEQ NKENQNPNSD APVIRSKTSA RYMELVGWLV DKGITSEKQW  240
IQEDQASYIS FNAASNSRSQ IKAALDNAGK IMSLTKTAPD YLVGQQPVED ISSNRIYKIL  300
ELNGYDPQYA ASVFLGWATK KFGKRNTIWL FGPATTGKTN IAEAIAHTVP FYGCVNWTNE  360
NFPFNDCVDK MVIWWEEGKM TAKVVESAKA ILGGSKVRVD QKCKSSAQID PTPVIVTSNT  420
NMCAVIDGNS TTFEHQQPLQ DRMFKFELTR RLDHDFGKVT KQEVKDFFRW AKDHVVEVEH  480
EFYVKKGGAK KRPAPSDADI SEPKRVRESV AQPSTSDAEA SINYADRYQN KCSRHVGMNL  540
MLFPCRQCER MNQNSNICFT HGQKDCLECF PVSESQPVSV VKKAYQKLCY IHHIMGKVPD  600
ACTACDLVNV DLDDCIFEQ                                               619

SEQ ID NO: 76          moltype = AA  length = 624
FEATURE                Location/Qualifiers
REGION                 1..624
                       note = Chimeric Rep protein sequence
source                 1..624
                       mol_type = protein
                       organism = synthetic construct
SEQUENCE: 76
MPGFYEIVIK VPSDLDGHLP GISDSFVNWV AEKEWELPPD SDMDLNLIEQ APLTVAEKLQ  60
RDFLTEWRRV SKAPEALFFV QFEKGESYFH MHVLVETTGV KSMVLGRFLS QIREKLIQRI  120
YRGIEPTLPN WFAVTKTRNG AGGGNKVVDS GYIPAYLLPK VQPELQWAWT NLDEYKLAAL  180
NLEERKRRKR LVAQHLTHVS QTQEQNKENQ NPNSDAPVIR SKTSARYMEL VGWLVDKGIT  240
SEKQWIQEDQ ASYISFNAAS NSRSQIKAAL DNAGKIMSLT KTAPDYLVGQ QPVEDISSNR  300
IYKILELNGY DPQYAASVFL GWATKKFGKR NTIWLFGPAT TGKTNIAEAI AHTVPFYGCV  360
NWTNENFPFN DCVDKMVIWW EEGKMTAKVV ESAKAILGGS KVRVDQKCKS SAQIDPTPVI  420
VTSNTNMCAV IDGNSTTFEH QQPLQDRMFK FELTRRLDHD FGKVTKQEVK DFFRWAKDHV  480
VEVEHEFYVK KGGAKKRPAP SDADISEPKR VRESVAQPST SDAEASINYA DRYQNKCSRH  540
VGMNLMLFPC RQCERMNQNS NICFTHGQKD CLECFPVSES QPVSVVKKAY QKLCYIHHIM  600
GKVPDACTAC DLVNVDLDDC IFEQ                                         624

SEQ ID NO: 77          moltype = AA  length = 622
FEATURE                Location/Qualifiers
REGION                 1..622
                       note = Chimeric Rep protein sequence
source                 1..622
                       mol_type = protein
                       organism = synthetic construct
SEQUENCE: 77
MPGFYEIVIK VPSDLDGHLP GISDSFVNWV AEKEWELPPD SDMDLNLIEQ APLTVAEKLQ  60
RDFLTEWRRV SKAPEALFFV QFEKGESYFH MHVLVETSGI SSMVLGRYVS QIRAQLVKVV  120
FQGIEPQIND WVAITKVKKG GANKVVDSGY IPAYLLPKVQ PELQWAWTNL DEYKLAALNL  180
EERKRRKRLV AQHLTHVSQT QEQNKENQNP NSDAPVIRSK TSARYMELVG WLVDKGITSE  240
KQWIQEDQAS YISFNAASNS RSQIKAALDN AGKIMSLTKT APDYLVGQQP VEDISSNRIY  300
KILELNGYDP QYAASVFLGW ATKKFGKRNT IWLFGPATTG KTNIAEAIAH TVPFYGCVNW  360
TNENFPFNDC VDKMVIWWEE GKMTAKVVES AKAILGGSKV RVDQKCKSSA QIDPTPVIVT  420
SNTNMCAVID GNSTTFEHQQ PLQDRMFKFE LTRRLDHDFG KVTKQEVKDF FRWAKDHVVE  480
VEHEFYVKKG GAKKRPAPSD ADISEPKRVR ESVAQPSTSD AEASINYADR YQNKCSRHVG  540
MNLMLFPCRQ CERMNQNSNI CFTHGQKDCL ECFPVSESQP VSVVKKAYQK LCYIHHIMGK  600
VPDACTACDL VNVDLDDCIF EQ                                           622

SEQ ID NO: 78          moltype = DNA  length = 1857
FEATURE                Location/Qualifiers
misc_feature           1..1857
                       note = Chimeric Rep protein coding sequence
source                 1..1857
                       mol_type = other DNA
                       organism = synthetic construct
SEQUENCE: 78
atggctacct tctatgaagt cattgttcgc gtcccatttg acgtggagga acatctgcct  60
ggaatttctg acagctttgt ggactgggta actggtcaaa tttgggagct gcctccagag  120
tcagatttaa atttgactct ggttgaacag cctcagttga cggtggctga tagaattcgc  180
```

```
cgcgtgttcc tgtacgagtg gaacaaattt tccaagcagg agtccaaatt ctttgtgcag  240
tttgaaaagg gatctgaata ttttcatctg cacacgcttg tggagacctc cggcatctct  300
tccatggtcc tcggccgcta cgtgagtcag attcgcgccc agctggtgaa agtggtcttc  360
cagggaattg aaccccagat caacgactgg gtcgccatca ccaaggtaaa gaagggcgga  420
gccaataagg tggtggatga gtgctacatc cccaattact tgctccccaa aacccagcct  480
gagctccagt gggcgtggac taatatggaa cagtatttaa gcgcctgttt gaatctcacg  540
gagcgtaaac ggttggtggc gcagcatctg acgcacgtgt cgcagacgca ggagcagaac  600
aaagagaatc agaatcccaa ttctgatgcg ccggtgatca gatcaaaaac ttcagccagg  660
tacatggagc tggtcgggtg gctcgtggac aaggggatta cctcggagaa gcagtggatc  720
caggaggacc aggcctcata catctccttc aatgcggcct ccaactcgcg gtcccaaatc  780
aaggctgcct tggacaatgc gggaaagatt atgagcctga ctaaaaccgc ccccgactac  840
ctggtgggcc agcagcccgt ggaggacatt tccagcaatc ggatttataa aattttggaa  900
ctaaacgggt acgatcccca atatgcggct tccgtctttc tgggatgggc cacgaaaaag  960
ttcggcaaga ggaacaccat ctggctgttt gggcctgcaa ctaccgggaa gaccaacatc  1020
gcggaggcca tagcccacac tgtgcccttc tacgggtgcg taaactggac caatgagaac  1080
tttcccttca acgactgtgt cgacaagatg gtgatctggt gggaggaggg gaagatgacc  1140
gccaaggtcg tggagtcggc caaagccatt ctcggaggaa gcaaggtgcg cgtggaccag  1200
aaatgcaagt cctcggccca gatagacccg actcccgtga tcgtcacctc caacaccaac  1260
atgtgcgccg tgattgacgg gaactcaacg accttcgaac accagcagcc gttgcaagac  1320
cggatgttca aatttgaact cacccgccgt ctggatcatg actttgggaa ggtcaccaag  1380
caggaagtca aagacttttt ccggtgggca aaggatcacg tggttgaggt ggagcatgaa  1440
ttctacgtca aaaagggtgg agccaagaaa agacccgccc ccagtgacgc agatataagt  1500
gagcccaaac gggtgcgcga gtcagttgcg cagccatcga cgtcagacgc ggaagcttcg  1560
atcaactacg cagacaggta ccaaaacaaa tgttctcgtc acgtgggcat gaatctgatg  1620
ctgtttccct gcagacaatg cgagagaatg aatcagaatt caaatatctg cttcactcac  1680
ggacagaaag actgtttaga gtgctttccc gtgtcagaat ctcaacccgt ttctgtcgtc  1740
aaaaaggcgt atcagaaact gtgctacatt catcatatca tgggaaaggt gccagacgct  1800
tgcactgcct gcgatctggt caatgtggat ttggatgact gcatctttga acaataa     1857
```

```
SEQ ID NO: 79          moltype = AA  length = 618
FEATURE                Location/Qualifiers
REGION                 1..618
                       note = Chimeric Rep protein sequence
source                 1..618
                       mol_type = protein
                       organism = synthetic construct
SEQUENCE: 79
MATFYEVIVR VPFDVEEHLP GISDSFVDWV TGQIWELPPE SDLNLTLVEQ PQLTVADRIR  60
RVFLYEWNKF SKQESKFFVQ FEKGSEYFHL HTLVETSGIS SMVLGRYVSQ IRAQLVKVVF  120
QGIEPQINDW VAITKVKKGG ANKVVDECYI PNYLLPKTQP ELQWAWTNME QYLSACLNLT  180
ERKRLVAQHL THVSQTQEQN KENQNPNSDA PVIRSKTSAR YMELVGWLVD KGITSEKQWI  240
QEDQASYISF NAASNSRSQI KAALDNAGKI MSLTKTAPDY LVGQQPVEDI SSNRIYKILE  300
LNGYDPQYAA SVFLGWATKK FGKRNTIWLF GPATTGKTNI AEAIAHTVPF YGCVNWTNEN  360
FPFNDCVDKM VIWWEEGKMT AKVVESAKAI LGGSKVRVDQ KCKSSAQIDP TPVIVTSNTN  420
MCAVIDGNST TFEHQQPLQD RMFKFELTRR LDHDFGKVTK QEVKDFFRWA KDHVVEVEHE  480
FYVKKGGAKK RPAPSDADIS EPKRVRESVA QPSTSDAEAS INYADRYQNK CSRHVGMNLM  540
LFPCRQCERM NQNSNICFTH GQKDCLECFP VSESQPVSVV KKAYQKLCYI HHIMGKVPDA  600
CTACDLVNVD LDDCIFEQ                                                618
```

```
SEQ ID NO: 80          moltype = DNA  length = 1857
FEATURE                Location/Qualifiers
misc_feature           1..1857
                       note = Chimeric Rep protein coding sequence
source                 1..1857
                       mol_type = other DNA
                       organism = synthetic construct
SEQUENCE: 80
atggctacct tctatgaagt cattgttcgc gtcccatttg acgtggagga acatctgcct  60
ggaatttctg acagctttgt ggactgggta actggtcaaa tttgggagct gcctccagag  120
tcagatttaa atttgactct ggttgaacag cctcagttga cggtggctga tagaattcgc  180
cgcgtgttcc tgtacgagtg gaacaaattt tccaagcagg agtccaaatt ctttgtgcag  240
tttgaaaagg gatctgaata ttttcatctg cacacgcttg tggagacctc cggcatctct  300
tccatggtcc tcggccgcta cgtgagtcag attcgcgccc agctggtgaa agtggtcttc  360
cagggaattg aaccccagat caacgactgg gtcgccatca ccaaggtaaa gaagggcgga  420
gccaataagg tggtggattc ttgctacatc cccaattact tgctccccaa aacccagcct  480
gagctccagt gggcgtggac taatatggaa cagtatttaa gcgcctgttt gaatctcacg  540
gagcgtaaac ggttggtggc gcagcatctg acgcacgtgt cgcagacgca ggagcagaac  600
aaagagaatc agaatcccaa ttctgatgcg ccggtgatca gatcaaaaac ttcagccagg  660
tacatggagc tggtcgggtg gctcgtggac aaggggatta cctcggagaa gcagtggatc  720
caggaggacc aggcctcata catctccttc aatgcggcct ccaactcgcg gtcccaaatc  780
aaggctgcct tggacaatgc gggaaagatt atgagcctga ctaaaaccgc ccccgactac  840
ctggtgggcc agcagcccgt ggaggacatt tccagcaatc ggatttataa aattttggaa  900
ctaaacgggt acgatcccca atatgcggct tccgtctttc tgggatgggc cacgaaaaag  960
ttcggcaaga ggaacaccat ctggctgttt gggcctgcaa ctaccgggaa gaccaacatc  1020
gcggaggcca tagcccacac tgtgcccttc tacgggtgcg taaactggac caatgagaac  1080
tttcccttca acgactgtgt cgacaagatg gtgatctggt gggaggaggg gaagatgacc  1140
gccaaggtcg tggagtcggc caaagccatt ctcggaggaa gcaaggtgcg cgtggaccag  1200
aaatgcaagt cctcggccca gatagacccg actcccgtga tcgtcacctc caacaccaac  1260
atgtgcgccg tgattgacgg gaactcaacg accttcgaac accagcagcc gttgcaagac  1320
```

```
cggatgttca aatttgaact cacccgccgt ctggatcatg actttgggaa ggtcaccaag  1380
caggaagtca aagacttttt ccggtgggca aaggatcacg tggttgaggt ggagcatgaa  1440
ttctacgtca aaaagggtgg agccaagaaa agacccgccc ccagtgacgc agatataagt  1500
gagcccaaac gggtgcgcga gtcagttgcg cagccatcga cgtcagacgc ggaagcttcg  1560
atcaactacg cagacaggta ccaaaacaaa tgttctcgtc acgtgggcat gaatctgatg  1620
ctgtttccct gcagacaatg cgagagaatg aatcagaatt caaatatctg cttcactcac  1680
ggacagaaag actgtttaga gtgctttccc gtgtcagaat ctcaacccgt ttctgtcgtc  1740
aaaaaggcgt atcagaaact gtgctacatt catcatatca tgggaaaggt gccagacgct  1800
tgcactgcct gcgatctggt caatgtggat ttggatgact gcatctttga acaataa     1857

SEQ ID NO: 81          moltype = AA  length = 618
FEATURE                Location/Qualifiers
REGION                 1..618
                       note = Chimeric Rep protein sequence
source                 1..618
                       mol_type = protein
                       organism = synthetic construct
SEQUENCE: 81
MATFYEVIVR VPFDVEEHLP GISDSFVDWV TGQIWELPPE SDLNLTLVEQ PQLTVADRIR  60
RVFLYEWNKF SKQESKFFVQ FEKGSEYFHL HTLVETSGIS SMVLGRYVSQ IRAQLVKVVF  120
QGIEPQINDW VAITKVKKGG ANKVVDSCYI PNYLLPKTQP ELQWAWTNME QYLSACLNLT  180
ERKRLVAQHL THVSQTQEQN KENQNPNSDA PVIRSKTSAR YMELVGWLVD KGITSEKQWI  240
QEDQASYISF NAASNSRSQI KAALDNAGKI MSLTKTAPDY LVGQQPVEDI SSNRIYKILE  300
LNGYDPQYAA SVFLGWATKK FGKRNTIWLF GPATTGKTNI AEAIAHTVPF YGCVNWTNEN  360
FPFNDCVDKM VIWWEEGKMT AKVVESAKAI LGGSKVRVDQ KCKSSAQIDP TPVIVTSNTN  420
MCAVIDGNST TFEHQQPLQD RMFKFELTRR LDHDFGKVTK QEVKDFFRWA KDHVVEVEHE  480
FYVKKGGAKK RPAPSDADIS EPKRVRESVA QPSTSDAEAS INYADRYQNK CSRHVGMNLM  540
LFPCRQCERM NQNSNICFTH GQKDCLECFP VSESQPVSVV KKAYQKLCYI HHIMGKVPDA  600
CTACDLVNVD LDDCIFEQ                                                618

SEQ ID NO: 82          moltype = DNA  length = 1857
FEATURE                Location/Qualifiers
misc_feature           1..1857
                       note = Chimeric Rep protein coding sequence
source                 1..1857
                       mol_type = other DNA
                       organism = synthetic construct
SEQUENCE: 82
atggctacct tctatgaagt cattgttcgc gtcccatttg acgtggagga acatctgcct  60
ggaatttctg acagctttgt ggactgggta actggtcaaa tttgggagct gcctccagag  120
tcagatttaa atttgactct ggttgaacag cctcagttga cggtggctga tagaattcgc  180
cgcgtgttcc tgtacgagtg gaacaaattt tccaagcagg agtccaaatt ctttgtgcag  240
tttgaaaagg gatctgaata ttttcatctg cacacgcttg tggagacctc cggcatctct  300
tccatggtcc tcggccgcta cgtgagtcag attcgcgccc agctggtgaa agtggtcttc  360
cagggaattg aaccccagat caacgactgg gtcgccatca ccaaggtaaa gaagggcgga  420
gccaataagg tggtggattc tgggtatatt cccaattact tgctccccaa aacccagcct  480
gagctccagt gggcgtggac taatatggaa cagtatttaa gcgcctgttt gaatctcacg  540
gagcgtaaac ggttggtggc gcagcatctg acgcacgtgt cgcagacgca ggagcagaac  600
aaagagaatc agaatcccaa ttctgatgcg ccggtgatca gatcaaaaac ttcagccagg  660
tacatggagc tggtcgggtg gctcgtggac aaggggatta cctcggagaa gcagtggatc  720
caggaggacc aggcctcata catctccttc aatgcggcct ccaactcgcg gtcccaaatc  780
aaggctgcct tggacaatgc gggaaagatt atgagcctga ctaaaaccgc ccccgactac  840
ctggtgggcc agcagcccgt ggaggacatt tccagcaatc ggatttataa aattttggaa  900
ctaaacgggt acgatcccca atatgcggct tccgtctttc tgggatgggc cacgaaaaag  960
ttcggcaaga ggaacaccat ctggctgttt gggcctgcaa ctaccgggaa gaccaacatc  1020
gcggaggcca tagcccacac tgtgcccttc tacgggtgcg taaactggac caatgagaac  1080
tttcccttca acgactgtgt cgacaagatg gtgatctggt gggaggaggg gaagatgacc  1140
gccaaggtcg tggagtcggc caaagccatt ctcggaggaa gcaaggtgcg cgtggaccag  1200
aaatgcaagt cctcggccca gatagacccg actcccgtga tcgtcacctc caacaccaac  1260
atgtgcgccg tgattgacgg gaactcaacg accttcgaac accagcagcc gttgcaagac  1320
cggatgttca aatttgaact cacccgccgt ctggatcatg actttgggaa ggtcaccaag  1380
caggaagtca aagacttttt ccggtgggca aaggatcacg tggttgaggt ggagcatgaa  1440
ttctacgtca aaaagggtgg agccaagaaa agacccgccc ccagtgacgc agatataagt  1500
gagcccaaac gggtgcgcga gtcagttgcg cagccatcga cgtcagacgc ggaagcttcg  1560
atcaactacg cagacaggta ccaaaacaaa tgttctcgtc acgtgggcat gaatctgatg  1620
ctgtttccct gcagacaatg cgagagaatg aatcagaatt caaatatctg cttcactcac  1680
ggacagaaag actgtttaga gtgctttccc gtgtcagaat ctcaacccgt ttctgtcgtc  1740
aaaaaggcgt atcagaaact gtgctacatt catcatatca tgggaaaggt gccagacgct  1800
tgcactgcct gcgatctggt caatgtggat ttggatgact gcatctttga acaataa     1857

SEQ ID NO: 83          moltype = AA  length = 618
FEATURE                Location/Qualifiers
REGION                 1..618
                       note = Chimeric Rep protein sequence
source                 1..618
                       mol_type = protein
                       organism = synthetic construct
```

```
SEQUENCE: 83
MATFYEVIVR VPFDVEEHLP GISDSFVDWV TGQIWELPPE SDLNLTLVEQ PQLTVADRIR  60
RVFLYEWNKF SKQESKFFVQ FEKGSEYFHL HTLVETSGIS SMVLGRYVSQ IRAQLVKVVF  120
QGIEPQINDW VAITKVKKGG ANKVVDSGYI PNYLLPKTQP ELQWAWTNME QYLSACLNLT  180
ERKRLVAQHL THVSQTQEQN KENQNPNSDA PVIRSKTSAR YMELVGWLVD KGITSEKQWI  240
QEDQASYISF NAASNSRSQI KAALDNAGKI MSLTKTAPDY LVGQQPVEDI SSNRIYKILE  300
LNGYDPQYAA SVFLGWATKK FGKRNTIWLF GPATTGKTNI AEAIAHTVPF YGCVNWTNEN  360
FPFNDCVDKM VIWWEEGKMT AKVVESAKAI LGGSKVRVDQ KCKSSAQIDP TPVIVTSNTN  420
MCAVIDGNST TFEHQQPLQD RMFKFELTRR LDHDFGKVTK QEVKDFFRWA KDHVVEVEHE  480
FYVKKGGAKK RPAPSDADIS EPKRVRESVA QPSTSDAEAS INYADRYQNK CSRHVGMNLM  540
LFPCRQCERM NQNSNICFTH GQKDCLECFP VSESQPVSVV KKAYQKLCYI HHIMGKVPDA  600
CTACDLVNVD LDDCIFEQ                                                618

SEQ ID NO: 84          moltype = AA  length = 312
FEATURE                Location/Qualifiers
source                 1..312
                       mol_type = protein
                       organism = Adeno-associated virus 1
SEQUENCE: 84
MELVGWLVDR GITSEKQWIQ EDQASYISFN AASNSRSQIK AALDNAGKIM ALTKSAPDYL  60
VGPAPPADIK TNRIYRILEL NGYEPAYAGS VFLGWAQKRF GKRNTIWLFG PATTGKTNIA  120
EAIAHAVPFY GCVNWTNENF PFNDCVDKMV IWWEEGKMTA KVVESAKAIL GGSKVRVDQK  180
CKSSAQIDPT PVIVTSNTNM CAVIDGNSTT FEHQQPLQDR MFKFELTRRL EHDFGKVTKQ  240
EVKEFFRWAQ DHVTEVAHEF YVRKGGANKR PAPDDADKSE PKRACPSVAD PSTSDAEGAP  300
VDFADLARGQ PL                                                      312

SEQ ID NO: 85          moltype = AA  length = 312
FEATURE                Location/Qualifiers
source                 1..312
                       mol_type = protein
                       organism = Adeno-associated virus 2
SEQUENCE: 85
MELVGWLVDK GITSEKQWIQ EDQASYISFN AASNSRSQIK AALDNAGKIM SLTKTAPDYL  60
VGQQPVEDIS SNRIYKILEL NGYDPQYAAS VFLGWATKKF GKRNTIWLFG PATTGKTNIA  120
EAIAHTVPFY GCVNWTNENF PFNDCVDKMV IWWEEGKMTA KVVESAKAIL GGSKVRVDQK  180
CKSSAQIDPT PVIVTSNTNM CAVIDGNSTT FEHQQPLQDR MFKFELTRRL DHDFGKVTKQ  240
EVKDFFRWAK DHVVEVEHEF YVKKGGAKKR PAPSDADISE PKRVRESVAQ PSTSDAEASI  300
NYADRLARGH SL                                                      312

SEQ ID NO: 86          moltype = AA  length = 311
FEATURE                Location/Qualifiers
source                 1..311
                       mol_type = protein
                       organism = Adeno-associated virus 3A
SEQUENCE: 86
MELVGWLVDR GITSEKQWIQ EDQASYISFN AASNSRSQIK AALDNASKIM SLTKTAPDYL  60
VGSNPPEDIT KNRIYQILEL NGYDPQYAAS VFLGWAQKKF GKRNTIWLFG PATTGKTNIA  120
EAIAHAVPFY GCVNWTNENF PFNDCVDKMV IWWEEGKMTA KVVESAKAIL GGSKVRVDQK  180
CKSSAQIEPT PVIVTSNTNM CAVIDGNSTT FEHQQPLQDR MFEFELTRRL DHDFGKVTKQ  240
EVKDFFRWAS DHVTDVAHEF YVRKGGAKKR PASNDADVSE PKRECTSLAQ PTTSDAEAPA  300
DYADLARGQP F                                                       311

SEQ ID NO: 87          moltype = AA  length = 311
FEATURE                Location/Qualifiers
source                 1..311
                       mol_type = protein
                       organism = Adeno-associated virus 3B
SEQUENCE: 87
MELVGWLVDR GITSEKQWIQ EDQASYISFN AASNSRSQIK AALDNASKIM SLTKTAPDYL  60
VGSNPPEDIT KNRIYQILEL NGYDPQYAAS VFLGWAQKKF GKRNTIWLFG PATTGKTNIA  120
EAIAHAVPFY GCVNWTNENF PFNDCVDKMV IWWEEGKMTA KVVESAKAIL GGSKVRVDQK  180
CKSSAQIEPT PVIVTSNTNM CAVIDGNSTT FEHQQPLQDR MFKFELTRRL DHDFGKVTKQ  240
EVKDFFRWAS DHVTDVAHEF YVRKGGAKKR PASNDADVSE PKRQCTSLAQ PTTSDAEAPA  300
DYADLARGQP F                                                       311

SEQ ID NO: 88          moltype = AA  length = 311
FEATURE                Location/Qualifiers
source                 1..311
                       mol_type = protein
                       organism = Adeno-associated virus 4
SEQUENCE: 88
MELVGWLVDR GITSEKQWIQ EDQASYISFN AASNSRSQIK AALDNASKIM SLTKTAPDYL  60
VGQNPPEDIS SNRIYRILEM NGYDPQYAAS VFLGWAQKKF GKRNTIWLFG PATTGKTNIA  120
EAIAHAVPFY GCVNWTNENF PFNDCVDKMV IWWEEGKMTA KVVESAKAIL GGSKVRVDQK  180
CKSSAQIDPT PVIVTSNTNM CAVIDGNSTT FEHQQPLQDR MFKFELTKRL EHDFGKVTKQ  240
EVKDFFRWAS DHVTEVTHEF YVRKGGARKR PAPNDADISE PKRACPSVAQ PSTSDAEAPV  300
DYADLARGQP L                                                       311
```

```
SEQ ID NO: 89          moltype = AA  length = 329
FEATURE                Location/Qualifiers
source                 1..329
                       mol_type = protein
                       organism = Adeno-associated virus 5
SEQUENCE: 89
MALVNWLVEH GITSEKQWIQ ENQESYLSFN STGNSRSQIK AALDNATKIM SLTKSAVDYL  60
VGSSVPEDIS KNRIWQIFEM NGYDPAYAGS ILYGWCQRSF NKRNTVWLYG PATTGKTNIA  120
EAIAHTVPFY GCVNWTNENF PFNDCVDKML IWWEEGKMTN KVVESAKAIL GGSKVRVDQK  180
CKSSVQIDST PVIVTSNTNM CVVVDGNSTT FEHQQPLEDR MFKFELTKRL PPDFGKITKQ  240
EVKDFFAWAK VNQVPVTHEF KVPRELAGTK GAEKSLKRPL GDVTNTSYKS LEKRARLSFV  300
PETPRSSDVT VDPAPLRPLN WNSLVGPSW                                   329

SEQ ID NO: 90          moltype = AA  length = 312
FEATURE                Location/Qualifiers
source                 1..312
                       mol_type = protein
                       organism = Adeno-associated virus 6
SEQUENCE: 90
MELVGWLVDR GITSEKQWIQ EDQASYISFN AASNSRSQIK AALDNAGKIM ALTKSAPDYL  60
VGPAPPADIK TNRIYRILEL NGYDPAYAGS VFLGWAQKRF GKRNTIWLFG PATTGKTNIA  120
EAIAHAVPFY GCVNWTNENF PFNDCVDKMV IWWEEGKMTA KVVESAKAIL GGSKVRVDQK  180
CKSSAQIDPT PVIVTSNTNM CAVIDGNSTT FEHQQPLQDR MFKFELTRRL EHDFGKVTKQ  240
EVKEFFRWAQ DHVTEVAHEF YVRKGGANKR PAPDDADKSE PKRACPSVAD PSTSDAEGAP  300
VDFADLARGQ PL                                                     312

SEQ ID NO: 91          moltype = AA  length = 312
FEATURE                Location/Qualifiers
source                 1..312
                       mol_type = protein
                       organism = Adeno-associated virus 7
SEQUENCE: 91
MELVGWLVDR GITSEKQWIQ EDQASYISFN AASNSRSQIK AALDNAGKIM ALTKSAPDYL  60
VGPSLPADIK TNRIYRILEL NGYDPAYAGS VFLGWAQKKF GKRNTIWLFG PATTGKTNIA  120
EAIAHAVPFY GCVNWTNENF PFNDCVDKMV IWWEEGKMTA KVVESAKAIL GGSKVRVDQK  180
CKSSAQIDPT PVIVTSNTNM CAVIDGNSTT FEHQQPLQDR MFKFELTRRL EHDFGKVTKQ  240
EVKEFFRWAS DHVTEVAHEF YVRKGGASKR PAPDDADISE PKRACPSVAD PSTSDAEGAP  300
VDFADLARGQ PL                                                     312

SEQ ID NO: 92          moltype = AA  length = 312
FEATURE                Location/Qualifiers
source                 1..312
                       mol_type = protein
                       organism = Adeno-associated virus 8
SEQUENCE: 92
MELVGWLVDR GITSEKQWIQ EDQASYISFN AASNSRSQIK AALDNAGKIM ALTKSAPDYL  60
VGPSLPADIT QNRIYRILAL NGYDPAYAGS VFLGWAQKKF GKRNTIWLFG PATTGKTNIA  120
EAIAHAVPFY GCVNWTNENF PFNDCVDKMV IWWEEGKMTA KVVESAKAIL GGSKVRVDQK  180
CKSSAQIDPT PVIVTSNTNM CAVIDGNSTT FEHQQPLQDR MFKFELTRRL EHDFGKVTKQ  240
EVKEFFRWAS DHVTEVAHEF YVRKGGASKR PAPDDADKSE PKRACPSVAD PSTSDAEGAP  300
VDFADLARGQ PL                                                     312

SEQ ID NO: 93          moltype = AA  length = 311
FEATURE                Location/Qualifiers
REGION                 1..311
                       note = AAV Rep40 consensus sequence
SITE                   63
                       note = MISC_FEATURE - Xaa can be Gln, Pro or Ser
SITE                   290
                       note = MISC_FEATURE - Xaa can be Asp, Gln or Thr
source                 1..311
                       mol_type = protein
                       organism = synthetic construct
SEQUENCE: 93
MELVGWLVDR GITSEKQWIQ EDQASYISFN AASNSRSQIK AALDNAGKIM ALTKSAPDYL  60
VGXSPPEDIS TNRIYRILAL NGYDPAYAGS VFLGWAQKKF GKRNTIWLFG PATTGKTNIA  120
EAIAHAVPFY GCVNWTNENF PFNDCVDKMV IWWEEGKMTA KVVESAKAIL GGSKVRVDQK  180
CKSSAQIDPT PVIVTSNTNM CAVIDGNSTT FEHQQPLQDR MFKFELTRRL EHDFGKVTKQ  240
EVKEFFRWAS DHVTEVAHEF YVRKGGAKKR PAPDDADKSE PKRACPSVAX PSTSDAEAPV  300
DFADLARGQP L                                                      311

SEQ ID NO: 94          moltype = AA  length = 399
FEATURE                Location/Qualifiers
source                 1..399
                       mol_type = protein
                       organism = Adeno-associated virus 1
```

```
SEQUENCE: 94
MELVGWLVDR GITSEKQWIQ EDQASYISFN AASNSRSQIK AALDNAGKIM ALTKSAPDYL  60
VGPAPPADIK TNRIYRILEL NGYEPAYAGS VFLGWAQKRF GKRNTIWLFG PATTGKTNIA  120
EAIAHAVPFY GCVNWTNENF PFNDCVDKMV IWWEEGKMTA KVVESAKAIL GGSKVRVDQK  180
CKSSAQIDPT PVIVTSNTNM CAVIDGNSTT FEHQQPLQDR MFKFELTRRL EHDFGKVTKQ  240
EVKEFFRWAQ DHVTEVAHEF YVRKGGANKR PAPDDADKSE PKRACPSVAD PSTSDAEGAP  300
VDFADRYQNK CSRHAGMLQM LFPCKTCERM NQNFNICFTH GTRDCSECFP GVSESQPVVR  360
KRTYRKLCAI HHLLGRAPEI ACSACDLVNV DLDDCVSEQ                        399

SEQ ID NO: 95          moltype = AA  length = 397
FEATURE                Location/Qualifiers
source                 1..397
                       mol_type = protein
                       organism = Adeno-associated virus 2
SEQUENCE: 95
MELVGWLVDK GITSEKQWIQ EDQASYISFN AASNSRSQIK AALDNAGKIM SLTKTAPDYL  60
VGQQPVEDIS SNRIYKILEL NGYDPQYAAS VFLGWATKKF GKRNTIWLFG PATTGKTNIA  120
EAIAHTVPFY GCVNWTNENF PFNDCVDKMV IWWEEGKMTA KVVESAKAIL GGSKVRVDQK  180
CKSSAQIDPT PVIVTSNTNM CAVIDGNSTT FEHQQPLQDR MFKFELTRRL DHDFGKVTKQ  240
EVKDFFRWAK DHVVEVEHEF YVKKGGAKKR PAPSDADISE PKRVRESVAQ PSTSDAEASI  300
NYADRYQNKC SRHVGMNLML FPCRQCERMN QNSNICFTHG QKDCLECFPV SESQPVSVVK  360
KAYQKLCYIH HIMGKVPDAC TACDLVNVDL DDCIFEQ                          397

SEQ ID NO: 96          moltype = AA  length = 400
FEATURE                Location/Qualifiers
source                 1..400
                       mol_type = protein
                       organism = Adeno-associated virus 3A
SEQUENCE: 96
MELVGWLVDR GITSEKQWIQ EDQASYISFN AASNSRSQIK AALDNASKIM SLTKTAPDYL  60
VGSNPPEDIT KNRIYQILEL NGYDPQYAAS VFLGWAQKKF GKRNTIWLFG PATTGKTNIA  120
EAIAHAVPFY GCVNWTNENF PFNDCVDKMV IWWEEGKMTA KVVESAKAIL GGSKVRVDQK  180
CKSSAQIEPT PVIVTSNTNM CAVIDGNSTT FEHQQPLQDR MFEFELTRRL DHDFGKVTKQ  240
EVKDFFRWAS DHVTDVAHEF YVRKGGAKKR PASNDADVSE PKRECTSLAQ PTTSDAEAPA  300
DYADRYQNKC SRHVGMNLML FPCKTCERMN QISNVCFTHG QRDCGECFPG MSESQPVSVV  360
KKKTYQKLCP IHHILGRAPE IACSACDLAN VDLDDCVSEQ                       400

SEQ ID NO: 97          moltype = AA  length = 400
FEATURE                Location/Qualifiers
source                 1..400
                       mol_type = protein
                       organism = Adeno-associated virus 3B
SEQUENCE: 97
MELVGWLVDR GITSEKQWIQ EDQASYISFN AASNSRSQIK AALDNASKIM SLTKTAPDYL  60
VGSNPPEDIT KNRIYQILEL NGYDPQYAAS VFLGWAQKKF GKRNTIWLFG PATTGKTNIA  120
EAIAHAVPFY GCVNWTNENF PFNDCVDKMV IWWEEGKMTA KVVESAKAIL GGSKVRVDQK  180
CKSSAQIEPT PVIVTSNTNM CAVIDGNSTT FEHQQPLQDR MFKFELTRRL DHDFGKVTKQ  240
EVKDFFRWAS DHVTDVAHEF YVRKGGAKKR PASNDADVSE PKRQCTSLAQ PTTSDAEAPA  300
DYADRYQNKC SRHVGMNLML FPCKTCERMN QISNVCFTHG QRDCGECFPG MSESQPVSVV  360
KKKTYQKLCP IHHILGRAPE IACSACDLAN VDLDDCVSEQ                       400

SEQ ID NO: 98          moltype = AA  length = 399
FEATURE                Location/Qualifiers
source                 1..399
                       mol_type = protein
                       organism = Adeno-associated virus 4
SEQUENCE: 98
MELVGWLVDR GITSEKQWIQ EDQASYISFN AASNSRSQIK AALDNASKIM SLTKTAPDYL  60
VGQNPPEDIS SNRIYRILEM NGYDPQYAAS VFLGWAQKKF GKRNTIWLFG PATTGKTNIA  120
EAIAHAVPFY GCVNWTNENF PFNDCVDKMV IWWEEGKMTA KVVESAKAIL GGSKVRVDQK  180
CKSSAQIDPT PVIVTSNTNM CAVIDGNSTT FEHQQPLQDR MFKFELTKRL EHDFGKVTKQ  240
EVKDFFRWAS DHVTEVTHEF YVRKGGARKR PAPNDADISE PKRACPSVAQ PSTSDAEAPV  300
DYADRYQNKC SRHVGMNLML FPCRQCERMN QNVDICFTHG VMDCAECFPV SESQPVSVVR  360
KRTYQKLCPI HHIMGRAPEV ACSACELANV DLDDCDMEQ                        399

SEQ ID NO: 99          moltype = AA  length = 390
FEATURE                Location/Qualifiers
source                 1..390
                       mol_type = protein
                       organism = Adeno-associated virus 5
SEQUENCE: 99
MALVNWLVEH GITSEKQWIQ ENQESYLSFN STGNSRSQIK AALDNATKIM SLTKSAVDYL  60
VGSSVPEDIS KNRIWQIFEM NGYDPAYAGS ILYGWCQRSF NKRNTVWLYG PATTGKTNIA  120
EAIAHTVPFY GCVNWTNENF PFNDCVDKML IWWEEGKMTN KVVESAKAIL GGSKVRVDQK  180
CKSSVQIDST PVIVTSNTNM CVVVDGNSTT FEHQQPLEDR MFKFELTKRL PPDFGKITKQ  240
EVKDFFAWAK VNQVPVTHEF KVPRELAGTK GAEKSLKRPL GDVTNTSYKS LEKRARLSFV  300
PETPRSSDVT VDPAPLRPLN WNSRYDCKCD YHAQFDNISN KCDECEYLNR GKNGCICHNV  360
THCQICHGIP PWEKENLSDF GDFDDANKEQ                                  390
```

```
SEQ ID NO: 100         moltype = AA  length = 399
FEATURE                Location/Qualifiers
source                 1..399
                       mol_type = protein
                       organism = Adeno-associated virus 6
SEQUENCE: 100
MELVGWLVDR GITSEKQWIQ EDQASYISFN AASNSRSQIK AALDNAGKIM ALTKSAPDYL  60
VGPAPPADIK TNRIYRILEL NGYDPAYAGS VFLGWAQKRF GKRNTIWLFG PATTGKTNIA  120
EAIAHAVPFY GCVNWTNENF PFNDCVDKMV IWWEEGKMTA KVVESAKAIL GGSKVRVDQK  180
CKSSAQIDPT PVIVTSNTNM CAVIDGNSTT FEHQQPLQDR MFKFELTRRL EHDFGKVTKQ  240
EVKEFFRWAQ DHVTEVAHEF YVRKGGANKR PAPDDADKSE PKRACPSVAD PSTSDAEGAP  300
VDFADRYQNK CSRHAGMLQM LFPCKTCERM NQNFNICFTH GTRDCSECFP GVSESQPVVR  360
KRTYRKLCAI HHLLGRAPEI ACSACDLVNV DLDDCVSEQ                        399

SEQ ID NO: 101         moltype = AA  length = 399
FEATURE                Location/Qualifiers
source                 1..399
                       mol_type = protein
                       organism = Adeno-associated virus 7
SEQUENCE: 101
MELVGWLVDR GITSEKQWIQ EDQASYISFN AASNSRSQIK AALDNAGKIM ALTKSAPDYL  60
VGPSLPADIK TNRIYRILEL NGYDPAYAGS VFLGWAQKKF GKRNTIWLFG PATTGKTNIA  120
EAIAHAVPFY GCVNWTNENF PFNDCVDKMV IWWEEGKMTA KVVESAKAIL GGSKVRVDQK  180
CKSSAQIDPT PVIVTSNTNM CAVIDGNSTT FEHQQPLQDR MFKFELTRRL EHDFGKVTKQ  240
EVKEFFRWAS DHVTEVAHEF YVRKGGASKR PAPDDADISE PKRACPSVAD PSTSDAEGAP  300
VDFADRYQNK CSRHAGMIQM LFPCKTCERM NQNFNICFTH GVRDCLECFP GVSESQPVVR  360
KKTYRKLCAI HHLLGRAPEI ACSACDLVNV DLDDCVSEQ                        399

SEQ ID NO: 102         moltype = AA  length = 399
FEATURE                Location/Qualifiers
source                 1..399
                       mol_type = protein
                       organism = Adeno-associated virus 8
SEQUENCE: 102
MELVGWLVDR GITSEKQWIQ EDQASYISFN AASNSRSQIK AALDNAGKIM ALTKSAPDYL  60
VGPSLPADIT QNRIYRILAL NGYDPAYAGS VFLGWAQKKF GKRNTIWLFG PATTGKTNIA  120
EAIAHAVPFY GCVNWTNENF PFNDCVDKMV IWWEEGKMTA KVVESAKAIL GGSKVRVDQK  180
CKSSAQIDPT PVIVTSNTNM CAVIDGNSTT FEHQQPLQDR MFKFELTRRL EHDFGKVTKQ  240
EVKEFFRWAS DHVTEVAHEF YVRKGGASKR PAPDDADKSE PKRACPSVAD PSTSDAEGAP  300
VDFADRYQNK CSRHAGMLQM LFPCKTCERM NQNFNICFTH GVRDCSECFP GVSESQPVVR  360
KRTYRKLCAI HHLLGRAPEI ACSACDLVNV DLDDCVSEQ                        399

SEQ ID NO: 103         moltype = AA  length = 398
FEATURE                Location/Qualifiers
REGION                 1..398
                       note = AAV Rep52 consensus sequence
SITE                   63
                       note = MISC_FEATURE - Xaa can be Gln, Pro or Ser
SITE                   317
                       note = MISC_FEATURE - Xaa can be Asn, Asp, Ile or Leu
SITE                   333
                       note = MISC_FEATURE - Xaa can be Lys, Phe, Ser or Val
SITE                   341
                       note = MISC_FEATURE - Xaa can be Gln, Thr or Val
SITE                   345
                       note = MISC_FEATURE - Xaa can be Ala, Gln, Gly, Leu or Ser
SITE                   356
                       note = MISC_FEATURE - Xaa can be Pro or Ser
SITE                   364
                       note = MISC_FEATURE - Xaa can be Gln or Arg
SITE                   368
                       note = MISC_FEATURE - Xaa can be Ala, Pro or Tyr
source                 1..398
                       mol_type = protein
                       organism = synthetic construct
SEQUENCE: 103
MELVGWLVDR GITSEKQWIQ EDQASYISFN AASNSRSQIK AALDNAGKIM ALTKSAPDYL  60
VGXSPPEDIS TNRIYRILAL NGYDPAYAGS VFLGWAQKKF GKRNTIWLFG PATTGKTNIA  120
EAIAHAVPFY GCVNWTNENF PFNDCVDKMV IWWEEGKMTA KVVESAKAIL GGSKVRVDQK  180
CKSSAQIDPT PVIVTSNTNM CAVIDGNSTT FEHQQPLQDR MFKFELTRRL EHDFGKVTKQ  240
EVKEFFRWAS DHVTEVAHEF YVRKGGAKKR PAPDDADKSE PKRACPSVAD PSTSDAEAPV  300
DFADRYQNKC SRHAGMXQML FPCKTCERMN QNXNICFTHG XRDCXECFPG VSESQXVVRK  360
RTYXKLCXIH HLLGRAPEIA CSACDLVNVD LDDCVSEQ                         398

SEQ ID NO: 104         moltype = AA  length = 536
FEATURE                Location/Qualifiers
source                 1..536
                       mol_type = protein
                       organism = Adeno-associated virus 1
```

```
SEQUENCE: 104
MPGFYEIVIK VPSDLDEHLP GISDSFVSWV AEKEWELPPD SDMDLNLIEQ APLTVAEKLQ  60
RDFLVQWRRV SKAPEALFFV QFEKGESYFH LHILVETTGV KSMVLGRFLS QIRDKLVQTI  120
YRGIEPTLPN WFAVTKTRNG AGGGNKVVDE CYIPNYLLPK TQPELQWAWT NMEEYISACL  180
NLAERKRLVA QHLTHVSQTQ EQNKENLNPN SDAPVIRSKT SARYMELVGW LVDRGITSEK  240
QWIQEDQASY ISFNAASNSR SQIKAALDNA GKIMALTKSA PDYLVGPAPP ADIKTNRIYR  300
ILELNGYEPA YAGSVFLGWA QKRFGKRNTI WLFGPATTGK TNIAEAIAHA VPFYGCVNWT  360
NENFPFNDCV DKMVIWWEEG KMTAKVVESA KAILGGSKVR VDQKCKSSAQ IDPTPVIVTS  420
NTNMCAVIDG NSTTFEHQQP LQDRMFKFEL TRRLEHDFGK VTKQEVKEFF RWAQDHVTEV  480
AHEFYVRKGG ANKRPAPDDA DKSEPKRACP SVADPSTSDA EGAPVDFADL ARGQPL      536

SEQ ID NO: 105          moltype = AA  length = 536
FEATURE                 Location/Qualifiers
source                  1..536
                        mol_type = protein
                        organism = Adeno-associated virus 2
SEQUENCE: 105
MPGFYEIVIK VPSDLDEHLP GISDSFVNWV AEKEWELPPD SDMDLNLIEQ APLTVAEKLQ  60
RDFLTEWRRV SKAPEALFFV QFEKGESYFH MHVLVETTGV KSMVLGRFLS QIREKLIQRI  120
YRGIEPTLPN WFAVTKTRNG AGGGNKVVDE CYIPNYLLPK TQPELQWAWT NMEQYLSACL  180
NLTERKRLVA QHLTHVSQTQ EQNKENQNPN SDAPVIRSKT SARYMELVGW LVDKGITSEK  240
QWIQEDQASY ISFNAASNSR SQIKAALDNA GKIMSLTKTA PDYLVGQQPV EDISSNRIYK  300
ILELNGYDPQ YAASVFLGWA TKKFGKRNTI WLFGPATTGK TNIAEAIAHT VPFYGCVNWT  360
NENFPFNDCV DKMVIWWEEG KMTAKVVESA KAILGGSKVR VDQKCKSSAQ IDPTPVIVTS  420
NTNMCAVIDG NSTTFEHQQP LQDRMFKFEL TRRLDHDFGK VTKQEVKDFF RWAKDHVVEV  480
EHEFYVKKGG AKKRPAPSDA DISEPKRVRE SVAQPSTSDA EASINYADRL ARGHSL      536

SEQ ID NO: 106          moltype = AA  length = 535
FEATURE                 Location/Qualifiers
source                  1..535
                        mol_type = protein
                        organism = Adeno-associated virus 3A
SEQUENCE: 106
MPGFYEIVLK VPSDLDERLP GISNSFVNWV AEKEWDVPPD SDMDPNLIEQ APLTVAEKLQ  60
REFLVEWRRV SKAPEALFFV QFEKGETYFH LHVLIETIGV KSMVVGRYVS QIKEKLVTRI  120
YRGVEPQLPN WFAVTKTRNG AGGGNKVVDD CYIPNYLLPK TQPELQWAWT NMDQYLSACL  180
NLAERKRLVA QHLTHVSQTQ EQNKENQNPN SDAPVIRSKT SARYMELVGW LVDRGITSEK  240
QWIQEDQASY ISFNAASNSR SQIKAALDNA SKIMSLTKTA PDYLVGSNPP EDITKNRIYQ  300
ILELNGYDPQ YAASVFLGWA QKKFGKRNTI WLFGPATTGK TNIAEAIAHA VPFYGCVNWT  360
NENFPFNDCV DKMVIWWEEG KMTAKVVESA KAILGGSKVR VDQKCKSSAQ IEPTPVIVTS  420
NTNMCAVIDG NSTTFEHQQP LQDRMFEFEL TRRLDHDFGK VTKQEVKDFF RWASDHVTDV  480
AHEFYVRKGG AKKRPASNDA DVSEPKRECT SLAQPTTSDA EAPADYADLA RGQPF       535

SEQ ID NO: 107          moltype = AA  length = 535
FEATURE                 Location/Qualifiers
source                  1..535
                        mol_type = protein
                        organism = Adeno-associated virus 3B
SEQUENCE: 107
MPGFYEIVLK VPSDLDEHLP GISNSFVNWV AEKEWELPPD SDMDPNLIEQ APLTVAEKLQ  60
REFLVEWRRV SKAPEALFFV QFEKGETYFH LHVLIETIGV KSMVVGRYVS QIKEKLVTRI  120
YRGVEPQLPN WFAVTKTRNG AGGGNKVVDD CYIPNYLLPK TQPELQWAWT NMDQYLSACL  180
NLAERKRLVA QHLTHVSQTQ EQNKENQNPN SDAPVIRSKT SARYMELVGW LVDRGITSEK  240
QWIQEDQASY ISFNAASNSR SQIKAALDNA SKIMSLTKTA PDYLVGSNPP EDITKNRIYQ  300
ILELNGYDPQ YAASVFLGWA QKKFGKRNTI WLFGPATTGK TNIAEAIAHA VPFYGCVNWT  360
NENFPFNDCV DKMVIWWEEG KMTAKVVESA KAILGGSKVR VDQKCKSSAQ IEPTPVIVTS  420
NTNMCAVIDG NSTTFEHQQP LQDRMFKFEL TRRLDHDFGK VTKQEVKDFF RWASDHVTDV  480
AHEFYVRKGG AKKRPASNDA DVSEPKRQCT SLAQPTTSDA EAPADYADLA RGQPF       535

SEQ ID NO: 108          moltype = AA  length = 535
FEATURE                 Location/Qualifiers
source                  1..535
                        mol_type = protein
                        organism = Adeno-associated virus 4
SEQUENCE: 108
MPGFYEIVLK VPSDLDEHLP GISDSFVSWV AEKEWELPPD SDMDLNLIEQ APLTVAEKLQ  60
REFLVEWRRV SKAPEALFFV QFEKGDSYFH LHILVETVGV KSMVVGRYVS QIKEKLVTRI  120
YRGVEPQLPN WFAVTKTRNG AGGGNKVVDD CYIPNYLLPK TQPELQWAWT NMDQYISACL  180
NLAERKRLVA QHLTHVSQTQ EQNKENQNPN SDAPVIRSKT SARYMELVGW LVDRGITSEK  240
QWIQEDQASY ISFNAASNSR SQIKAALDNA SKIMSLTKTA PDYLVGQNPP EDISSNRIYR  300
ILEMNGYDPQ YAASVFLGWA QKKFGKRNTI WLFGPATTGK TNIAEAIAHA VPFYGCVNWT  360
NENFPFNDCV DKMVIWWEEG KMTAKVVESA KAILGGSKVR VDQKCKSSAQ IDPTPVIVTS  420
NTNMCAVIDG NSTTFEHQQP LQDRMFKFEL TKRLEHDFGK VTKQEVKDFF RWASDHVTEV  480
THEFYVRKGG ARKRPAPNDA DISEPKRACP SVAQPSTSDA EAPVDYADLA RGQPL       535

SEQ ID NO: 109          moltype = AA  length = 549
FEATURE                 Location/Qualifiers
source                  1..549
                        mol_type = protein
```

-continued

```
                         organism = Adeno-associated virus 5
SEQUENCE: 109
MATFYEVIVR VPFDVEEHLP GISDSFVDWV TGQIWELPPE SDLNLTLVEQ PQLTVADRIR  60
RVFLYEWNKF SKQESKFFVQ FEKGSEYFHL HTLVETSGIS SMVLGRYVSQ IRAQLVKVVF  120
QGIEPQINDW VAITKVKKGG ANKVVDSGYI PAYLLPKVQP ELQWAWTNLD EYKLAALNLE  180
ERKRLVAQFL AESSQRSQEA ASQREFSADP VIKSKTSQKY MALVNWLVEH GITSEKQWIQ  240
ENQESYLSFN STGNSRSQIK AALDNATKIM SLTKSAVDYL VGSSVPEDIS KNRIWQIFEM  300
NGYDPAYAGS ILYGWCQRSF NKRNTVWLYG PATTGKTNIA EAIAHTVPFY GCVNWTNENF  360
PFNDCVDKML IWWEEGKMTN KVVESAKAIL GGSKVRVDQK CKSSVQIDST PVIVTSNTNM  420
CVVVDGNSTT FEHQQPLEDR MFKFELTKRL PPDFGKITKQ EVKDFFAWAK VNQVPVTHEF  480
KVPRELAGTK GAEKSLKRPL GDVTNTSYKS LEKRARLSFV PETPRSSDVT VDPAPLRPLN  540
WNSLVGPSW                                                          549

SEQ ID NO: 110           moltype = AA  length = 536
FEATURE                  Location/Qualifiers
source                   1..536
                         mol_type = protein
                         organism = Adeno-associated virus 6
SEQUENCE: 110
MPGFYEIVIK VPSDLDEHLP GISDSFVNWV AEKEWELPPD SDMDLNLIEQ APLTVAEKLQ  60
RDFLVQWRRV SKAPEALFFV QFEKGESYFH LHILVETTGV KSMVLGRFLS QIRDKLVQTI  120
YRGIEPTLPN WFAVTKTRNG AGGGNKVVDE CYIPNYLLPK TQPELQWAWT NMEEYISACL  180
NLAERKRLVA HDLTHVSQTQ EQNKENLNPN SDAPVIRSKT SARYMELVGW LVDRGITSEK  240
QWIQEDQASY ISFNAASNSR SQIKAALDNA GKIMALTKSA PDYLVGPAPP ADIKTNRIYR  300
ILELNGYDPA YAGSVFLGWA QKRFGKRNTI WLFGPATTGK TNIAEAIAHA VPFYGCVNWT  360
NENFPFNDCV DKMVIWWEEG KMTAKVVESA KAILGGSKVR VDQKCKSSAQ IDPTPVIVTS  420
NTNMCAVIDG NSTTFEHQQP LQDRMFKFEL TRRLEHDFGK VTKQEVKEFF RWAQDHVTEV  480
AHEFYVRKGG ANKRPAPDDA DKSEPKRACP SVADPSTSDA EGAPVDFADL ARGQPL      536

SEQ ID NO: 111           moltype = AA  length = 536
FEATURE                  Location/Qualifiers
source                   1..536
                         mol_type = protein
                         organism = Adeno-associated virus 7
SEQUENCE: 111
MPGFYEIVIK VPSDLDEHLP GISDSFVNWV AEKEWELPPD SDMDLNLIEQ APLTVAEKLQ  60
RDFLVQWRRV SKAPEALFFV QFEKGESYFH LHVLVETTGV KSMVLGRFLS QIREKLVQTI  120
YRGVEPTLPN WFAVTKTRNG AGGGNKVVDE CYIPNYLLPK TQPELQWAWT NMEEYISACL  180
NLAERKRLVA QHLTHVSQTQ EQNKENLNPN SDAPVIRSKT SARYMELVGW LVDRGITSEK  240
QWIQEDQASY ISFNAASNSR SQIKAALDNA GKIMALTKSA PDYLVGPSLP ADIKTNRIYR  300
ILELNGYDPA YAGSVFLGWA QKKFGKRNTI WLFGPATTGK TNIAEAIAHA VPFYGCVNWT  360
NENFPFNDCV DKMVIWWEEG KMTAKVVESA KAILGGSKVR VDQKCKSSAQ IDPTPVIVTS  420
NTNMCAVIDG NSTTFEHQQP LQDRMFKFEL TRRLEHDFGK VTKQEVKEFF RWASDHVTEV  480
AHEFYVRKGG ASKRPAPDDA DISEPKRACP SVADPSTSDA EGAPVDFADL ARGQPL      536

SEQ ID NO: 112           moltype = AA  length = 538
FEATURE                  Location/Qualifiers
source                   1..538
                         mol_type = protein
                         organism = Adeno-associated virus 8
SEQUENCE: 112
MPGFYEIVIK VPSDLDEHLP GISDSFVNWV AEKEWELPPD SDMDRNLIEQ APLTVAEKLQ  60
RDFLVQWRRV SKAPEALFFV QFEKGESYFH LHVLVETTGV KSMVLGRFLS QIREKLGPDH  120
LPAGSSPTLP NWFAVTKDAV MAPAGGNKVV DECYIPNYLL PKTQPELQWA WTNMEEYISA  180
CLNLAERKRL VAQHLTHVSQ TQEQNKENLN PNSDAPVIRS KTSARYMELV GWLVDRGITS  240
EKQWIQEDQA SYISFNAASN SRSQIKAALD NAGKIMALTK SAPDYLVGPS LPADITQNRI  300
YRILALNGYD PAYAGSVFLG WAQKKFGKRN TIWLFGPATT GKTNIAEAIA HAVPFYGCVN  360
WTNENFPFND CVDKMVIWWE EGKMTAKVVE SAKAILGGSK VRVDQKCKSS AQIDPTPVIV  420
TSNTNMCAVI DGNSTTFEHQ QPLQDRMFKF ELTRRLEHDF GKVTKQEVKE FFRWASDHVT  480
EVAHEFYVRK GGASKRPAPD DADKSEPKRA CPSVADPSTS DAEGAPVDFA DLARGQPL    538

SEQ ID NO: 113           moltype = AA  length = 623
FEATURE                  Location/Qualifiers
source                   1..623
                         mol_type = protein
                         organism = Adeno-associated virus 1
SEQUENCE: 113
MPGFYEIVIK VPSDLDEHLP GISDSFVSWV AEKEWELPPD SDMDLNLIEQ APLTVAEKLQ  60
RDFLVQWRRV SKAPEALFFV QFEKGESYFH LHILVETTGV KSMVLGRFLS QIRDKLVQTI  120
YRGIEPTLPN WFAVTKTRNG AGGGNKVVDE CYIPNYLLPK TQPELQWAWT NMEEYISACL  180
NLAERKRLVA QHLTHVSQTQ EQNKENLNPN SDAPVIRSKT SARYMELVGW LVDRGITSEK  240
QWIQEDQASY ISFNAASNSR SQIKAALDNA GKIMALTKSA PDYLVGPAPP ADIKTNRIYR  300
ILELNGYEPA YAGSVFLGWA QKRFGKRNTI WLFGPATTGK TNIAEAIAHA VPFYGCVNWT  360
NENFPFNDCV DKMVIWWEEG KMTAKVVESA KAILGGSKVR VDQKCKSSAQ IDPTPVIVTS  420
NTNMCAVIDG NSTTFEHQQP LQDRMFKFEL TRRLEHDFGK VTKQEVKEFF RWAQDHVTEV  480
AHEFYVRKGG ANKRPAPDDA DKSEPKRACP SVADPSTSDA EGAPVDFADR YQNKCSRHAG  540
MLQMLFPCKT CERMNQNFNI CFTHGTRDCS ECFPGVSESQ PVVRKRTYRK LCAIHHLLGR  600
APEIACSACD LVNVDLDDCV SEQ                                          623
```

-continued

```
SEQ ID NO: 114         moltype = AA  length = 621
FEATURE                Location/Qualifiers
source                 1..621
                       mol_type = protein
                       organism = Adeno-associated virus 2
SEQUENCE: 114
MPGFYEIVIK VPSDLDEHLP GISDSFVNWV AEKEWELPPD SDMDLNLIEQ APLTVAEKLQ  60
RDFLTEWRRV SKAPEALFFV QFEKGESYFH MHVLVETTGV KSMVLGRFLS QIREKLIQRI  120
YRGIEPTLPN WFAVTKTRNG AGGGNKVVDE CYIPNYLLPK TQPELQWAWT NMEQYLSACL  180
NLTERKRLVA QHLTHVSQTQ EQNKENQNPN SDAPVIRSKT SARYMELVGW LVDKGITSEK  240
QWIQEDQASY ISFNAASNSR SQIKAALDNA GKIMSLTKTA PDYLVGQQPV EDISSNRIYK  300
ILELNGYDPQ YAASVFLGWA TKKFGKRNTI WLFGPATTGK TNIAEAIAHT VPFYGCVNWT  360
NENFPFNDCV DKMVIWWEEG KMTAKVVESA KAILGGSKVR VDQKCKSSAQ IDPTPVIVTS  420
NTNMCAVIDG NSTTFEHQQP LQDRMFKFEL TRRLDHDFGK VTKQEVKDFF RWAKDHVVEV  480
EHEFYVKKGG AKKRPAPSDA DISEPKRVRE SVAQPSTSDA EASINYADRY QNKCSRHVGM  540
NLMLFPCRQC ERMNQNSNIC FTHGQKDCLE CFPVSESQPV SVVKKAYQKL CYIHHIMGKV  600
PDACTACDLV NVDLDDCIFE Q                                           621

SEQ ID NO: 115         moltype = AA  length = 624
FEATURE                Location/Qualifiers
source                 1..624
                       mol_type = protein
                       organism = Adeno-associated virus 3A
SEQUENCE: 115
MPGFYEIVLK VPSDLDERLP GISNSFVNWV AEKEWDVPPD SDMDPNLIEQ APLTVAEKLQ  60
REFLVEWRRV SKAPEALFFV QFEKGETYFH LHVLIETIGV KSMVVGRYVS QIKEKLVTRI  120
YRGVEPQLPN WFAVTKTRNG AGGGNKVVDD CYIPNYLLPK TQPELQWAWT NMDQYLSACL  180
NLAERKRLVA QHLTHVSQTQ EQNKENQNPN SDAPVIRSKT SARYMELVGW LVDRGITSEK  240
QWIQEDQASY ISFNAASNSR SQIKAALDNA SKIMSLTKTA PDYLVGSNPP EDITKNRIYQ  300
ILELNGYDPQ YAASVFLGWA QKKFGKRNTI WLFGPATTGK TNIAEAIAHA VPFYGCVNWT  360
NENFPFNDCV DKMVIWWEEG KMTAKVVESA KAILGGSKVR VDQKCKSSAQ IEPTPVIVTS  420
NTNMCAVIDG NSTTFEHQQP LQDRMFEFEL TRRLDHDFGK VTKQEVKDFF RWASDHVTDV  480
AHEFYVRKGG AKKRPASNDA DVSEPKRECT SLAQPTTSDA EAPADYADRY QNKCSRHVGM  540
NLMLFPCKTC ERMNQISNVC FTHGQRDCGE CFPGMSESQP VSVVKKKTYQ KLCPIHHILG  600
RAPEIACSAC DLANVDLDDC VSEQ                                        624

SEQ ID NO: 116         moltype = AA  length = 624
FEATURE                Location/Qualifiers
source                 1..624
                       mol_type = protein
                       organism = Adeno-associated virus 3B
SEQUENCE: 116
MPGFYEIVLK VPSDLDEHLP GISNSFVNWV AEKEWELPPD SDMDPNLIEQ APLTVAEKLQ  60
REFLVEWRRV SKAPEALFFV QFEKGETYFH LHVLIETIGV KSMVVGRYVS QIKEKLVTRI  120
YRGVEPQLPN WFAVTKTRNG AGGGNKVVDD CYIPNYLLPK TQPELQWAWT NMDQYLSACL  180
NLAERKRLVA QHLTHVSQTQ EQNKENQNPN SDAPVIRSKT SARYMELVGW LVDRGITSEK  240
QWIQEDQASY ISFNAASNSR SQIKAALDNA SKIMSLTKTA PDYLVGSNPP EDITKNRIYQ  300
ILELNGYDPQ YAASVFLGWA QKKFGKRNTI WLFGPATTGK TNIAEAIAHA VPFYGCVNWT  360
NENFPFNDCV DKMVIWWEEG KMTAKVVESA KAILGGSKVR VDQKCKSSAQ IEPTPVIVTS  420
NTNMCAVIDG NSTTFEHQQP LQDRMFKFEL TRRLDHDFGK VTKQEVKDFF RWASDHVTDV  480
AHEFYVRKGG AKKRPASNDA DVSEPKRQCT SLAQPTTSDA EAPADYADRY QNKCSRHVGM  540
NLMLFPCKTC ERMNQISNVC FTHGQRDCGE CFPGMSESQP VSVVKKKTYQ KLCPIHHILG  600
RAPEIACSAC DLANVDLDDC VSEQ                                        624

SEQ ID NO: 117         moltype = AA  length = 623
FEATURE                Location/Qualifiers
source                 1..623
                       mol_type = protein
                       organism = Adeno-associated virus 4
SEQUENCE: 117
MPGFYEIVLK VPSDLDEHLP GISDSFVSWV AEKEWELPPD SDMDLNLIEQ APLTVAEKLQ  60
REFLVEWRRV SKAPEALFFV QFEKGDSYFH LHILVETVGV KSMVVGRYVS QIKEKLVTRI  120
YRGVEPQLPN WFAVTKTRNG AGGGNKVVDD CYIPNYLLPK TQPELQWAWT NMDQYISACL  180
NLAERKRLVA QHLTHVSQTQ EQNKENQNPN SDAPVIRSKT SARYMELVGW LVDRGITSEK  240
QWIQEDQASY ISFNAASNSR SQIKAALDNA SKIMSLTKTA PDYLVGQNPP EDISSNRIYR  300
ILEMNGYDPQ YAASVFLGWA QKKFGKRNTI WLFGPATTGK TNIAEAIAHA VPFYGCVNWT  360
NENFPFNDCV DKMVIWWEEG KMTAKVVESA KAILGGSKVR VDQKCKSSAQ IDPTPVIVTS  420
NTNMCAVIDG NSTTFEHQQP LQDRMFKFEL TKRLEHDFGK VTKQEVKDFF RWASDHVTEV  480
THEFYVRKGG ARKRPAPNDA DISEPKRACP SVAQPSTSDA EAPVDYADRY QNKCSRHVGM  540
NLMLFPCRQC ERMNQNVDIC FTHGVMDCAE CFPVSESQPV SVVRKRTYQK LCPIHHIMGR  600
APEVACSACE LANVDLDDCD MEQ                                         623

SEQ ID NO: 118         moltype = AA  length = 610
FEATURE                Location/Qualifiers
source                 1..610
                       mol_type = protein
                       organism = Adeno-associated virus 5
SEQUENCE: 118
MATFYEVIVR VPFDVEEHLP GISDSFVDWV TGQIWELPPE SDLNLTLVEQ PQLTVADRIR  60
```

-continued

```
RVFLYEWNKF SKQESKFFVQ FEKGSEYFHL HTLVETSGIS SMVLGRYVSQ IRAQLVKVVF  120
QGIEPQINDW VAITKVKKGG ANKVVDSGYI PAYLLPKVQP ELQWAWTNLD EYKLAALNLE  180
ERKRLVAQFL AESSQRSQEA ASQREFSADP VIKSKTSQKY MALVNWLVEH GITSEKQWIQ  240
ENQESYLSFN STGNSRSQIK AALDNATKIM SLTKSAVDYL VGSSVPEDIS KNRIWQIFEM  300
NGYDPAYAGS ILYGWCQRSF NKRNTVWLYG PATTGKTNIA EAIAHTVPFY GCVNWTNENF  360
PFNDCVDKML IWWEEGKMTN KVVESAKAIL GGSKVRVDQK CKSSVQIDST PVIVTSNTNM  420
CVVVDGNSTT FEHQQPLEDR MFKFELTKRL PPDFGKITKQ EVKDFFAWAK VNQVPVTHEF  480
KVPRELAGTK GAEKSLKRPL GDVTNTSYKS LEKRARLSFV PETPRSSDVT VDPAPLRPLN  540
WNSRYDCKCD YHAQFDNISN KCDECEYLNR GKNGCICHNV THCQICHGIP PWEKENLSDF  600
GDFDDANKEQ                                                        610

SEQ ID NO: 119          moltype = AA  length = 623
FEATURE                 Location/Qualifiers
source                  1..623
                        mol_type = protein
                        organism = Adeno-associated virus 6
SEQUENCE: 119
MPGFYEIVIK VPSDLDEHLP GISDSFVNWV AEKEWELPPD SDMDLNLIEQ APLTVAEKLQ  60
RDFLVQWRRV SKAPEALFFV QFEKGESYFH LHILVETTGV KSMVLGRFLS QIRDKLVQTI  120
YRGIEPTLPN WFAVTKTRNG AGGGNKVVDE CYIPNYLLPK TQPELQWAWT NMEEYISACL  180
NLAERKRLVA HDLTHVSQTQ EQNKENLNPN SDAPVIRSKT SARYMELVGW LVDRGITSEK  240
QWIQEDQASY ISFNAASNSR SQIKAALDNA GKIMALTKSA PDYLVGPAPP ADIKTNRIYR  300
ILELNGYDPA YAGSVFLGWA QKRFGKRNTI WLFGPATTGK TNIAEAIAHA VPFYGCVNWT  360
NENFPFNDCV DKMVIWWEEG KMTAKVVESA KAILGGSKVR VDQKCKSSAQ IDPTPVIVTS  420
NTNMCAVIDG NSTTFEHQQP LQDRMFKFEL TRRLEHDFGK VTKQEVKEFF RWAQDHVTEV  480
AHEFYVRKGG ANKRPAPDDA DKSEPKRACP SVADPSTSDA EGAPVDFADR YQNKCSRHAG  540
MLQMLFPCKT CERMNQNFNI CFTHGTRDCS ECFPGVSESQ PVVRKRTYRK LCAIHHLLGR  600
APEIACSACD LVNVDLDDCV SEQ                                         623

SEQ ID NO: 120          moltype = AA  length = 623
FEATURE                 Location/Qualifiers
source                  1..623
                        mol_type = protein
                        organism = Adeno-associated virus 7
SEQUENCE: 120
MPGFYEIVIK VPSDLDEHLP GISDSFVNWV AEKEWELPPD SDMDLNLIEQ APLTVAEKLQ  60
RDFLVQWRRV SKAPEALFFV QFEKGESYFH LHVLVETTGV KSMVLGRFLS QIREKLVQTI  120
YRGVEPTLPN WFAVTKTRNG AGGGNKVVDE CYIPNYLLPK TQPELQWAWT NMEEYISACL  180
NLAERKRLVA QHLTHVSQTQ EQNKENLNPN SDAPVIRSKT SARYMELVGW LVDRGITSEK  240
QWIQEDQASY ISFNAASNSR SQIKAALDNA GKIMALTKSA PDYLVGPSLP ADIKTNRIYR  300
ILELNGYDPA YAGSVFLGWA QKKFGKRNTI WLFGPATTGK TNIAEAIAHA VPFYGCVNWT  360
NENFPFNDCV DKMVIWWEEG KMTAKVVESA KAILGGSKVR VDQKCKSSAQ IDPTPVIVTS  420
NTNMCAVIDG NSTTFEHQQP LQDRMFKFEL TRRLEHDFGK VTKQEVKEFF RWASDHVTEV  480
AHEFYVRKGG ASKRPAPDDA DISEPKRACP SVADPSTSDA EGAPVDFADR YQNKCSRHAG  540
MIQMLFPCKT CERMNQNFNI CFTHGVRDCL ECFPGVSESQ PVVRKKTYRK LCAIHHLLGR  600
APEIACSACD LVNVDLDDCV SEQ                                         623

SEQ ID NO: 121          moltype = AA  length = 625
FEATURE                 Location/Qualifiers
source                  1..625
                        mol_type = protein
                        organism = Adeno-associated virus 8
SEQUENCE: 121
MPGFYEIVIK VPSDLDEHLP GISDSFVNWV AEKEWELPPD SDMDRNLIEQ APLTVAEKLQ  60
RDFLVQWRRV SKAPEALFFV QFEKGESYFH LHVLVETTGV KSMVLGRFLS QIREKLGPDH  120
LPAGSSPTLP NWFAVTKDAV MAPAGGNKVV DECYIPNYLL PKTQPELQWA WTNMEEYISA  180
CLNLAERKRL VAQHLTHVSQ TQEQNKENLN PNSDAPVIRS KTSARYMELV GWLVDRGITS  240
EKQWIQEDQA SYISFNAASN SRSQIKAALD NAGKIMALTK SAPDYLVGPS LPADITQNRI  300
YRILALNGYD PAYAGSVFLG WAQKKFGKRN TIWLFGPATT GKTNIAEAIA HAVPFYGCVN  360
WTNENFPFND CVDKMVIWWE EGKMTAKVVE SAKAILGGSK VRVDQKCKSS AQIDPTPVIV  420
TSNTNMCAVI DGNSTTFEHQ QPLQDRMFKF ELTRRLEHDF GKVTKQEVKE FFRWASDHVT  480
EVAHEFYVRK GGASKRPAPD DADKSEPKRA CPSVADPSTS DAEGAPVDFA DRYQNKCSRH  540
AGMLQMLFPC KTCERMNQNF NICFTHGVRD CSECFPGVSE SQPVVRKRTY RKLCAIHHLL  600
GRAPEIACSA CDLVNVDLDD CVSEQ                                       625

SEQ ID NO: 122          moltype = AA  length = 622
FEATURE                 Location/Qualifiers
REGION                  1..622
                        note = AAV Rep78 consensus sequence
SITE                    118
                        note = MISC_FEATURE - Xaa can be Gln, Lys, Pro or Thr
SITE                    119
                        note = MISC_FEATURE - Xaa can be Arg, Asp, Thr or Val
SITE                    287
                        note = MISC_FEATURE - Xaa can be Gln, Pro or Ser
SITE                    541
                        note = MISC_FEATURE - Xaa can be Asn, Asp, Ile and Leu
SITE                    557
                        note = MISC_FEATURE - Xaa can be Lys, Phe, Ser or Val
```

```
SITE                    565
                        note = MISC_FEATURE - Xaa can be Gln, Thr or Val
SITE                    569
                        note = MISC_FEATURE - Xaa can be Ala, Gln, Gly, Leu or Ser
SITE                    580
                        note = MISC_FEATURE - Xaa can be Pro or Ser
SITE                    588
                        note = MISC_FEATURE - Xaa can be Arg or Gln
SITE                    592
                        note = MISC_FEATURE - Xaa can be Ala, Pro or Tyr
source                  1..622
                        mol_type = protein
                        organism = synthetic construct
SEQUENCE: 122
MPGFYEIVIK VPSDLDEHLP GISDSFVNWV AEKEWELPPD SDMDRNLIEQ APLTVAEKLQ  60
RDFLVQWRRV SKAPEALFFV QFEKGESYFH LHVLVETTGV KSMVLGRFLS QIREKLVXXI  120
YRGIEPTLPN WFAVTKTRNG AGGGNKVVDE CYIPNYLLPK TQPELQWAWT NMEEYISACL  180
NLAERKRLVA QHLTHVSQTQ EQNKENLNPN SDAPVIRSKT SARYMELVGW LVDRGITSEK  240
QWIQEDQASY ISFNAASNSR SQIKAALDNA GKIMALTKSA PDYLVGXSPP EDISTNRIYR  300
ILALNGYDPA YAGSVFLGWA QKKFGKRNTI WLFGPATTGK TNIAEAIAHA VPFYGCVNWT  360
NENFPFNDCV DKMVIWWEEG KMTAKVVESA KAILGGSKVR VDQKCKSSAQ IDPTPVIVTS  420
NTNMCAVIDG NSTTFEHQQP LQDRMFKFEL TRRLEHDFGK VTKQEVKEFF RWASDHVTEV  480
AHEFYVRKGG AKKRPAPDDA DKSEPKRACP SVADPSTSDA EAPVDFADRY QNKCSRHAGM  540
XQMLFPCKTC ERMNQNXNIC FTHGXRDCXE CFPGVSESQX VVRKRTYXKL CXIHHLLGRA  600
PEIACSACDL VNVDLDDCVS EQ                                          622

SEQ ID NO: 123          moltype = DNA  length = 122
FEATURE                 Location/Qualifiers
source                  1..122
                        mol_type = other DNA
                        organism = Snake parvovirus
SEQUENCE: 123
cgccccaccc ctagtgatcg cgcgcgctct ctcttggggc ctgacggccg aaggccgtca  60
gctgccgagc ttcgctcggc aggccccaag agagagcgcg cgcgatcact aggggtgggg  120
cg                                                                122

SEQ ID NO: 124          moltype = DNA  length = 6107
FEATURE                 Location/Qualifiers
misc_feature            1..6107
                        note = Snake ITR eGFP vector sequence
source                  1..6107
                        mol_type = other DNA
                        organism = synthetic construct
SEQUENCE: 124
gtggcacttt tcggggaaat gtgcgcggaa cccctatttg tttatttttc taaatacatt  60
caaatatgta tccgctcatg agacaataac cctgataaat gcttcaataa tattgaaaaa  120
ggaagagtat gagtattcaa catttccgtg tcgcccttat tccctttttt gcggcatttt  180
gccttcctgt ttttgctcac ccagaaacgc tggtgaaagt aaaagatgct gaagatcagt  240
tgggtgcacg agtgggttac atcgaactgg atctcaacag cggtaagatc cttgagagtt  300
ttcgccccga agaacgtttt ccaatgatga gcacttttaa agttctgcta tgtggcgcgg  360
tattatcccg tattgacgcc gggcaagagc aactcggtcg ccgcatacac tattctcaga  420
atgacttggt tgagtactca ccagtcacag aaaagcatct tacggatggc atgacagtaa  480
gagaattatg cagtgctgcc ataaccatga gtgataacac tgcggccaac ttacttctga  540
caacgatcgg aggaccgaag gagctaaccg cttttttgca caacatgggg gatcatgtaa  600
ctcgccttga tcgttgggaa ccggagctga atgaagccat accaaacgac gagcgtgaca  660
ccacgatgcc tgtagcaatg gcaacaacgt tgcgcaaact attaactggc gaactactta  720
ctctagcttc ccggcaacaa ttaatagact ggatggaggc ggataaagtt gcaggaccac  780
ttctgcgctc ggcccttccg gctggctggt ttattgctga taaatctgga gccggtgagc  840
gtgggtctcg cggtatcatt gcagcactgg ggccagatgg taagccctcc cgtatcgtag  900
ttatctacac gacggggagt caggcaacta tggatgaacg aaatagacag atcgctgaga  960
taggtgcctc actgattaag cattggtaac tgtcagacca agtttactca tatatacttt  1020
agattgattt aaaacttcat ttttaattta aaaggatcta ggtgaagatc ctttttgata  1080
atctcatgac caaaatccct taacgtgagt tttcgttcca ctgagcgtca gaccccgtag  1140
aaaagatcaa aggatcttct tgagatcctt tttttctgcg cgtaatctgc tgcttgcaaa  1200
caaaaaaacc accgctacca gcggtggttt gtttgccgga tcaagagcta ccaactcttt  1260
ttccgaaggt aactggcttc agcagagcgc agataccaaa tactgtcctt ctagtgtagc  1320
cgtagttagg ccaccacttc aagaactctg tagcaccgcc tacatacctc gctctgctaa  1380
tcctgttacc agtggctgct gccagtggcg ataagtcgtg tcttaccggg ttggactcaa  1440
gacgatagtt accggataag gcgcagcggt cgggctgaac ggggggttcg tgcacacagc  1500
ccagcttgga gcgaacgacc tacaccgaac tgagatacct acagcgtgag ctatgagaaa  1560
gcgccacgct tcccgaaggg agaaaggcgg acaggtatcc ggtaagcggc agggtcggaa  1620
caggagagcg cacgagggag cttccagggg gaaacgcctg gtatctttat agtcctgtcg  1680
ggtttcgcca cctctgactt gagcgtcgat ttttgtgatg ctcgtcaggg gggcggagcc  1740
tatggaaaaa cgccagcaac gcggcctttt tacggttcct ggccttttgc tggccttttg  1800
ctcacatgtt ctttcctgcg ttatcccctg attctgtgga taaccgtatt accgcctttg  1860
agtgagctga taccgctcgc cgcagccgaa cgaccgagcg cagcgagtca gtgagcgagg  1920
aagcggaaga gcgcccaata cgcaaaccgc ctctccccgc gcgttggccg attcattaat  1980
gcagctggca cgacaggttt cccgactgga aagcgggcag tgagcgcaac gcaattaatg  2040
tgagttagct cactcattag gcaccccagg ctttacactt tatgcttccg gctcgtatgt  2100
```

```
tgtgtggaat tgtgagcgga taacaatttc acacaggaaa cagctatgac catgattacg  2160
ccaagcgcgc aattaaccct cactaaaggg aacaaaagct gggtaccggg ccccccctcg  2220
aggtcgacgg tatcgataag cttgatcgcc ccacccctag tgatcgcgcg cgctctctct  2280
tggggcctga cggccgaagg ccgtcagctg ccgagcttcg ctcggcaggc cccaagagag  2340
agcgcgcgcg atcactaggg gtggggcgag tgccctgctc aacgggtttt ttggtgggcg  2400
gagcaatgac gtcagcggac atgtctggac atgtctttga gcaagtccat ataaggagtt  2460
ccgccggata tgcaaatgag caatcgcgca aagcattttg ggtagtcacc atgaataaaa  2520
aggacagcaa gaaagatgac gccccataat tttaatagga attttaacca tgttctttcc  2580
tgcgttatcc cctgattctg tggataaccg tattaccgcc tttgagtgag ctgataccgc  2640
tcgccgcagc cgaacgaccg agcgcagcga gtcagtgagc gaggaagcgg aagagcgccc  2700
aatacgcaaa ccgcctctcc ccgcgcgttg gccgattcat taatgcagct ggcacgacag  2760
gtttcccgac tggaaagcgg gcagtgagcg caacgcaatt aatgtgagtt agctcactca  2820
ttaggcaccc caggctttac actttatgct tccggctcgt atgttgtgtg gaattgtgag  2880
cggataacaa tttcacacag gaaacagcta tgaccatgat tacgaattgt tgttgttaac  2940
ttgtttattg cagcttataa tggttacaaa taaagcaata gcatcacaaa tttcacaaat  3000
aaagcatttt tttcactgca ttctagttgt ggtttgtcca aactcatcaa tgtatcttat  3060
catgtctgga tccccgcggc cgctttactt gtacagctcg tccatgccga gagtgatccc  3120
ggcggcggtc acgaactcca gcaggaccat gtgatcgcgc ttctcgttgg ggtctttgct  3180
cagggcggac tgggtgctca ggtagtggtt gtcgggcagc agcacggggc cgtcgccgat  3240
gggggtgttc tgctggtagt ggtcggcgag ctgcacgctg ccgtcctcga tgttgtggcg  3300
gatcttgaag ttcaccttga tgccgttctt ctgcttgtcg gccatgatat agacgttgtg  3360
gctgttgtag ttgtactcca gcttgtgccc caggatgttg ccgtcctcct tgaagtcgat  3420
gcccttcagc tcgatgcggt tcaccagggt gtcgccctcg aacttcacct cggcgcgggt  3480
cttgtagttg ccgtcgtcct tgaagaagat ggtgcgctcc tggacgtagc cttcgggcat  3540
ggcggacttg aagaagtcgt gctgcttcat gtggtcgggg tagcggctga agcactgcac  3600
gccgtaggtc agggtggtca cgagggtggg ccagggcacg ggcagcttgc cggtggtgca  3660
gatgaacttc agggtcagct tgccgtaggt ggcatcgccc tcgccctcgc cggacacgct  3720
gaacttgtgg ccgtttacgt cgccgtccag ctcgaccagg atgggcacca ccccggtgaa  3780
cagctcctcg cccttgctca ccatggtggc gaccggtgga tcccgggccg cgggtacaat  3840
tccgcagctt ttagagcaga agtaacactt ccgtacaggc ctagaagtaa aggcaacatc  3900
cactgaggag cagttctttg atttgcacca ccaccggatc cgggacctga aataaaagac  3960
aaaaagacta aacttaccag ttaactttct ggtttttcag ttcctcgagt accggatcct  4020
ctagagtccg gaggctggat cggtcccggt gtcttctatg gaggtcaaaa cagcgtggat  4080
ggcgtctcca ggcgatctga cggttcacta aacgagctct gcttatatag acctcccacc  4140
gtacacgcct accgcccatt tgcgtcaatg gggcggagtt gttacgacat tttggaaagt  4200
cccgttgatt ttggtgccaa aacaaactcc cattgacgtc aatggggtgg agacttggaa  4260
atccccgtga gtcaaaccgc tatccacgcc cattgatgta ctgccaaaac cgcatcacca  4320
tggtaatagc gatgactaat acgtagatgt actgccaagt aggaaagtcc cataaggtca  4380
tgtactgggc ataatgccag gcgggccatt taccgtcatt gacgtcaata gggggcgtac  4440
ttggcatatg atacacttga tgtactgcca agtgggcagt ttaccgtaaa tactccaccc  4500
attgacgtca atggaaagtc cctattggcg ttactattga cgtcaatggg cgggggtcgt  4560
tgggcggtca gccaggcggg ccatttaccg taagttatgt aacgggtacc cggggatcct  4620
ctagagtcga cctgcagtaa acagaacaat tgaagacgaa atacagggta ccaataattt  4680
tggtaatgct agaaataaca ttgttgctat caatcaacaa acgaaaggaa caaatccaac  4740
aacaggtagt acatctcaat ttgagacaat gccaggtatg gtgtggtcta atagagacat  4800
ttacttacag ggccctattt gggctaaaat tccaaataca gatggacatt ttcatccttc  4860
tcccagaatg ggtggttttg gattaaaaca tcctccgcct atgattctga tcaaaaatac  4920
accagttcct gctgatcctc caactacctt caatccaatg ccacagacta gtttcattac  4980
tgaatacagt acaggacaag taactgttga aatgttgtgg gaggtacaga aagaatcctc  5040
caaaagatgg aatccagaag tacagtttac ttccaatttt ggaacttcag atccagctgt  5100
tgatggaata ccgtttggaa ttaataattt gggtacttat gttgaatcta gacctattgg  5160
aactcgttat atttctaaac acttgtaaat aataaaaatt gtcaaatttg cactaagaat  5220
tgttgtcacg tggttgttta catgcttgct aaaacacgcc caccaaaaaa cccgttgagc  5280
agggcactcg ccccacccct agtgatcgcg cgcgctctct cttggggcct gccgagcgaa  5340
gctcggcagc tgacggcctt cggccgtcag gccccaagag agagcgcgcg cgatcactag  5400
gggtggggcg gggggatcca ctagttctag agcggccgcc accgcggtgg agctccaatt  5460
cgccctatag tgagtcgtat tacgcgcgct cactggccgt cgttttacaa cgtcgtgact  5520
gggaaaaccc tggcgttacc caacttaatc gccttgcagc acatccccct ttcgccagct  5580
ggcgtaatag cgaagaggcc cgcaccgatc gcccttccca acagttgcgc agcctgaatg  5640
gcgaatggga cgcgccctgt agcggcgcat taagcgcggc gggtgtggtg gttacgcgca  5700
gcgtgaccgc tacacttgcc agcgccctag cgcccgctcc tttcgctttc ttcccttcct  5760
ttctcgccac gttcgccggc tttccccgtc aagctctaaa tcgggggctc cctttagggt  5820
tccgatttag tgctttacgg cacctcgacc ccaaaaaact tgattagggt gatggttcac  5880
gtagtgggcc atcgccctga tagacggttt ttcgcccttt gacgttggag tccacgttct  5940
ttaatagtgg actcttgttc caaactggaa caacactcaa ccctatctcg gtctattctt  6000
ttgatttata agggattttg ccgatttcgg cctattggtt aaaaaatgag ctgatttaac  6060
aaaaatttaa cgcgaatttt aacaaaatat taacgcttac aatttag                6107

SEQ ID NO: 125          moltype = DNA  length = 7302
FEATURE                 Location/Qualifiers
misc_feature            1..7302
                        note = pSnRepCap2 plasmid sequence
source                  1..7302
                        mol_type = other DNA
                        organism = synthetic construct
SEQUENCE: 125
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
```

-continued

```
accatatgcg gtgtgaaata ccgcacagat gcgtaaggag aaaataccgc atcaggaaat  240
tgtaaacgtt aatattttgt taaaattcgc gttaaatttt tgttaaatca gctcattttt  300
taaccaatag gccgaaatcg gcaaaatccc ttataaatca aaagaataga ccgagatagg  360
gttgagtgtt gttccagttt ggaacaagag tccactatta aagaacgtgg actccaacgt  420
caaagggcga aaaaccgtct atcagggcga tggcccacta cgtgaaccat caccctaatc  480
aagttttttg gggtcgaggt gccgtaaagc actaaatcgg aaccctaaag ggagcccccg  540
atttagagct tgacggggaa agccggcgaa cgtggcgagg aaggaaggga agaaagcgaa  600
aggagcgggc gctagggcgc tggcaagtgt agcggtcacg ctgcgcgtaa ccaccacacc  660
cgccgcgctt aatgcgccgc tacagggcgc gtcgcgccat tcgccattca ggctgcgcaa  720
ctgttgggaa gggcgatcgg tgcgggcctc ttcgctatta cgccagctgg cgaaaggggg  780
atgtgctgca aggcgattaa gttgggtaac gccagggttt tcccagtcac gacgttgtaa  840
aacgacggcc agtgaattgt aatacgactc actatagggc gaattcgagc tcgcagcgga  900
catgtctgga catgtctttg agcaagtcca tataaggagt tccgccggat atgcaaatga  960
gcaatcgcgc aaagcatttt gggtagtcac catgaataaa aaggacagca agaaagatga  1020
cgccccataa ttttaatagg aattttaacc atggcgtttt acgaggttgt gtttcgtttg  1080
ccaagagaca ataacaactt gttggatgaa gatagatatc agccagagtt gaaagaagaa  1140
gatgactggc ctgaggaata tttaaccagt gaagatgcca gctttatcgg actagcgtat  1200
gctgtgctaa gtgaaattcg gagattcttt ggaaaggaac tacaatggtt tgcccaggtt  1260
gaatggtgtc ctactgctgg ttaccacatg catgttttgt tgaaccatcc taagctgagt  1320
aaccagactt atggaagaaa ggtcaatgaa ctggcttgcc gtatagtcga tacctttggc  1380
ctaattaatc cagaagaagt catcagtacc cattatgtta aaagcaacta tggacataaa  1440
aaggtgagag tcattcacct agagtcttat ttgaagaact actttttcag aaagacttta  1500
gctcctccca attataccga ggaaggagac tataaaagag aggaagaagt cgtgctgtgg  1560
gcatttacga atatcgtcgc ttggaagcca ttcgtgcgga atctcatcaa gagatcggag  1620
ctagcgactg ttcctaagca accagagaat ccggcgggag acggaccggc acctcgagtg  1680
actgcaggaa cccgccattt tatggaaacc atcgactggt tggtgaaaca tggaattact  1740
acagaacgag aattctgcca cgccaaccgc cctttgtacc tgtctatgct ggcttctact  1800
tcgggtgctg ggcagattaa aagagcgctg gaccaggcga aacacatgat gaccagcacc  1860
atgtcagcag aggattacct gacaacagaa gaggatgtga tcgaaccacc tactgaaaat  1920
agaatctaca agattatgaa actgaatcgc tatgatccag aactagcagc tgctctcttc  1980
tacggctgga cctgcaagaa ctttggcaag agaaacacca tctggctgta tggtccagct  2040
actaccggca aaaccatcat cgctcaagct attgcacatg ctgttaaact gtttgctggt  2100
gttaattgga ctaatgaaaa ctttcccttc tgtaactgtc cagggaaact gcttatctgg  2160
tgggaggagg gcaagatgac aaacaaaatg gtggagacgg ctaaatgtat actgggggga  2220
tctgctgtac ctgtagacat caaaggcaaa cccgctgaaa tgtgtcctca aacaccctgt  2280
attattacta gcaatactaa catgtgtcaa gtatatgatg gtaatagttc tagctttgag  2340
caccaagaac ccctagagga acgcatgttt atgttcagac ttaatactaa actgccatcg  2400
acctttggca agatcacaga agaggaagtc aaacagttta ttacctgggg gaggagctta  2460
aaggttcaag ttccacatca gttcagagtg cctaccacag gagagtataa aaggccagcc  2520
cccgaggcga aagctcattc ttcggatgag ccgccaaaag agaaggtcgc gcgtattgat  2580
gactctctaa ccaggtatgt taacaatatt gatgagtcag ctaccagtag agaaatgttt  2640
ctagagattg ctaatactaa tcaatgtatg ttgcatcatt gcttttcttg taccgaatgt  2700
tatcctgaat tgcttgatga catggacaag gaacaataaa cttactgata acagatatgg  2760
ctgccgatgg ttatcttcca gattggctcg aggacactct ctctgaagga ataagacagt  2820
ggtggaagct caaacctggc ccaccaccac caaagcccgc agagcggcat aaggacgaca  2880
gcaggggtct tgtgcttcct gggtacaagt acctcggacc cttcaacgga ctcgacaagg  2940
gagagccggt caacgaggca gacgccgcgg ccctcgagca cgacaaagcc tacgaccggc  3000
agctcgacag cggagacaac ccgtacctca agtacaacca cgccgacgcg gagtttcagg  3060
agcgccttaa agaagatacg tcttttgggg gcaacctcgg acgagcagtc ttccaggcga  3120
aaaagagggt tcttgaacct ctgggcctgg ttgaggaacc tgttaagacg gctccgggaa  3180
aaaagaggcc ggtagagcac tctcctgtgg agccagactc ctcctcggga accggaaagg  3240
cgggccagca gcctgcaaga aaaagattga attttggtca gactggagac gcagactcag  3300
tacctgaccc ccagcctctc ggacagccac cagcagcccc ctctggtctg ggaactaata  3360
cgatggctac aggcagtggc gcaccaatgg cagacaataa cgagggcgcc gacggagtgg  3420
gtaattcctc gggaaattgg cattgcgatt ccacatggat gggcgacaga gtcatcacca  3480
ccagcacccg aacctgggcc ctgcccacct acaacaacca cctctacaaa caaatttcca  3540
gccaatcagg agcctcgaac gacaatcact actttggcta cagcacccct tgggggtatt  3600
ttgacttcaa cagattccac tgccactttt caccacgtga ctggcaaaga ctcatcaaca  3660
acaactgggg attccgaccc aagagactca acttcaagct ctttaacatt caagtcaaag  3720
aggtcacgca gaatgacggt acgacgacga ttgccaataa ccttaccagc acggttcagg  3780
tgtttactga ctcggagtac cagctcccgt acgtcctcgg ctcggcgcat caaggatgcc  3840
tcccgccgtt cccagcagac gtcttcatgg tgccacagta tggatacctc accctgaaca  3900
acgggagtca ggcagtagga cgctcttcat tttactgcct ggagtacttt ccttctcaga  3960
tgctgcgtac cggaaacaac tttaccttca gctacacttt tgaggacgtt cctttccaca  4020
gcagctacgc tcacagccag agtctggacc gtctcatgaa tcctctcatc gaccagtacc  4080
tgtattactt gagcagaaca aacactccaa gtggaaccac cacgcagtca aggcttcagt  4140
tttctcaggc cggagcgagt gacattcggg accagtctag gaactggctt cctggaccct  4200
gttaccgcca gcagcgagta tcaaagacat ctgcggataa caacaacagt gaatactcgt  4260
ggactggagc taccaagtac cacctcaatg gcagagactc tctggtgaat ccgggcccgg  4320
ccatggcaag ccacaaggac gatgaagaaa agtttttttcc tcagagcggg gttctcatct  4380
ttgggaagca aggctcagag aaaacaaatg tggacattga aaaggtcatg attacagacg  4440
aagaggaaat caggacaacc aatcccgtgg ctacggagca gtatggttct gtatctacca  4500
acctccagag aggcaacaga caagcagcta ccgcagatgt caacacacaa ggcgttcttc  4560
caggcatggt ctggcaggac agagatgtgt accttcaggg gcccatctgg gcaaagattc  4620
cacacacgga cggacatttt cacccctctc ccctcatggg tggattcgga cttaaacacc  4680
ctcctccaca gattctcatc aagaacaccc cggtacctgc gaatccttcg accaccttca  4740
gtgcggcaaa gtttgcttcc ttcatcacac agtactccac gggacaggtc agcgtggaga  4800
tcgagtggga gctgcagaag gaaaacagca aacgctggaa tcccgaaatt cagtacactt  4860
ccaactacaa caagtctgtt aatgtggact ttactgtgga cactaatggc gtgtattcag  4920
```

-continued

```
agcctcgccc cattggcacc agatacctga ctcgtaatct gtaattgctt gttaatcaat  4980
aaaccgttta attcgtttca gttgaacttt ggtgtcgcgg ccgctcgata agcttttgtt  5040
ccctttagtg agggttaatt ccgagcttgg cgtaatcatg gtcatagctg tttcctgtgt  5100
gaaattgtta tccgctcaca attccacaca acatacgagc cggaagcata aagtgtaaag  5160
cctggggtgc ctaatgagtg agctaactca cattaattgc gttgcgctca ctgcccgctt  5220
tccagtcggg aaacctgtcg tgccagctgc attaatgaat cggccaacgc gcggggagag  5280
gcggtttgcg tattgggcgc tcttccgctt cctcgctcac tgactcgctg cgctcggtcg  5340
ttcggctgcg gcgagcggta tcagctcact caaaggcggt aatacggtta tccacagaat  5400
caggggataa cgcaggaaag aacatgtgag caaaaggcca gcaaaaggcc aggaaccgta  5460
aaaaggccgc gttgctggcg tttttccata ggctccgccc ccctgacgag catcacaaaa  5520
atcgacgctc aagtcagagg tggcgaaacc cgacaggact ataaagatac caggcgtttc  5580
cccctggaag ctccctcgtg cgctctcctg ttccgaccct gccgcttacc ggatacctgt  5640
ccgcctttct cccttcggga agcgtggcgc tttctcatag ctcacgctgt aggtatctca  5700
gttcggtgta ggtcgttcgc tccaagctgg gctgtgtgca cgaacccccc gttcagcccg  5760
accgctgcgc cttatccggt aactatcgtc ttgagtccaa cccggtaaga cacgacttat  5820
cgccactggc agcagccact ggtaacagga ttagcagagc gaggtatgta ggcggtgcta  5880
cagagttctt gaagtggtgg cctaactacg gctacactag aaggacagta tttggtatct  5940
gcgctctgct gaagccagtt accttcggaa aaagagttgg tagctcttga tccggcaaac  6000
aaaccaccgc tggtagcggt ggtttttttg tttgcaagca gcagattacg cgcagaaaaa  6060
aaggatctca agaagatcct ttgatctttt ctacggggtc tgacgctcag tggaacgaaa  6120
actcacgtta agggattttg gtcatgagat tatcaaaaag gatcttcacc tagatccttt  6180
taaattaaaa atgaagtttt aaatcaatct aaagtatata tgagtaaact tggtctgaca  6240
gttaccaatg cttaatcagt gaggcaccta tctcagcgat ctgtctattt cgttcatcca  6300
tagttgcctg actccccgtc gtgtagataa ctacgatacg ggagggctta ccatctggcc  6360
ccagtgctgc aatgataccg cgagacccac gctcaccggc tccagattta tcagcaataa  6420
accagccagc cggaagggcc gagcgcagaa gtggtcctgc aactttatcc gcctccatcc  6480
agtctattaa ttgttgccgg gaagctagag taagtagttc gccagttaat agtttgcgca  6540
acgttgttgc cattgctaca ggcatcgtgg tgtcacgctc gtcgtttggt atggcttcat  6600
tcagctccgg ttcccaacga tcaaggcgag ttacatgatc ccccatgttg tgcaaaaaag  6660
cggttagctc cttcggtcct ccgatcgttg tcagaagtaa gttggccgca gtgttatcac  6720
tcatggttat ggcagcactg cataattctc ttactgtcat gccatccgta agatgctttt  6780
ctgtgactgg tgagtactca accaagtcat tctgagaata gtgtatgcgg cgaccgagtt  6840
gctcttgccc ggcgtcaata cgggataata ccgcgccaca tagcagaact ttaaaagtgc  6900
tcatcattgg aaaacgttct tcggggcgaa aactctcaag gatcttaccg ctgttgagat  6960
ccagttcgat gtaacccact cgtgcaccca actgatcttc agcatctttt actttcacca  7020
gcgtttctgg gtgagcaaaa acaggaaggc aaaatgccgc aaaaaaggga ataagggcga  7080
cacggaaatg ttgaatactc atactcttcc tttttcaata ttattgaagc atttatcagg  7140
gttattgtct catgagcgga tacatatttg aatgtattta gaaaaataaa caaatagggg  7200
ttccgcgcac atttccccga aaagtgccac ctgacgtcta agaaaccatt attatcatga  7260
cattaaccta taaaaatagg cgtatcacga ggccctttcg tc                    7302

SEQ ID NO: 126         moltype = DNA  length = 30
FEATURE                Location/Qualifiers
misc_feature           1..30
                       note = PCR primer
source                 1..30
                       mol_type = other DNA
                       organism = synthetic construct
SEQUENCE: 126
cgaaaagtgc cacctgacgt ctaagaaacc                                   30

SEQ ID NO: 127         moltype = DNA  length = 35
FEATURE                Location/Qualifiers
misc_feature           1..35
                       note = PCR primer
source                 1..35
                       mol_type = other DNA
                       organism = synthetic construct
SEQUENCE: 127
tcgaattcga cggccagtga attgtaatac gactc                             35

SEQ ID NO: 128         moltype = DNA  length = 37
FEATURE                Location/Qualifiers
misc_feature           1..37
                       note = PCR primer
source                 1..37
                       mol_type = other DNA
                       organism = synthetic construct
SEQUENCE: 128
ccatgattac gccaagctcg gaattaaccg catgcga                           37

SEQ ID NO: 129         moltype = DNA  length = 23
FEATURE                Location/Qualifiers
misc_feature           1..23
                       note = PCR primer
source                 1..23
                       mol_type = other DNA
                       organism = synthetic construct
SEQUENCE: 129
```

```
ccatggccgg gcccggattc acc                                          23

SEQ ID NO: 130         moltype = DNA  length = 69
FEATURE                Location/Qualifiers
misc_feature           1..69
                       note = PCR primer
source                 1..69
                       mol_type = other DNA
                       organism = synthetic construct
SEQUENCE: 130
ttcaccccgg tggtttccac gagcacgtgc atgtggaagt agctctctcc cttttcaaac  60
tgcacaaag                                                          69

SEQ ID NO: 131         moltype = DNA  length = 45
FEATURE                Location/Qualifiers
misc_feature           1..45
                       note = PCR primer
source                 1..45
                       mol_type = other DNA
                       organism = synthetic construct
SEQUENCE: 131
cctcggccgc tacgtgagtc agattcgcga aaaactgatt cagag                  45

SEQ ID NO: 132         moltype = DNA  length = 48
FEATURE                Location/Qualifiers
misc_feature           1..48
                       note = PCR primer
source                 1..48
                       mol_type = other DNA
                       organism = synthetic construct
SEQUENCE: 132
gtggtcttcc agggaattga acccactttg ccaaactggt tcgcggtc               48

SEQ ID NO: 133         moltype = DNA  length = 55
FEATURE                Location/Qualifiers
misc_feature           1..55
                       note = PCR primer
source                 1..55
                       mol_type = other DNA
                       organism = synthetic construct
SEQUENCE: 133
ctgggtcgcc atcaccaagg taaagaaggg aggcgggaac aaggtggtgg atgag       55

SEQ ID NO: 134         moltype = DNA  length = 50
FEATURE                Location/Qualifiers
misc_feature           1..50
                       note = PCR primer
source                 1..50
                       mol_type = other DNA
                       organism = synthetic construct
SEQUENCE: 134
gcggagccaa taaggtggtg gatgagtgct acatccccaa ttacttgctc             50

SEQ ID NO: 135         moltype = DNA  length = 35
FEATURE                Location/Qualifiers
misc_feature           1..35
                       note = PCR primer
source                 1..35
                       mol_type = other DNA
                       organism = synthetic construct
SEQUENCE: 135
actggagctc aggttggacc ttcggcagca ggtag                             35

SEQ ID NO: 136         moltype = DNA  length = 57
FEATURE                Location/Qualifiers
misc_feature           1..57
                       note = PCR primer
source                 1..57
                       mol_type = other DNA
                       organism = synthetic construct
SEQUENCE: 136
cgtggacaaa cctggacgag tataaattgg cctgtttgaa tctcacggag cgtaaac     57

SEQ ID NO: 137         moltype = DNA  length = 48
FEATURE                Location/Qualifiers
misc_feature           1..48
                       note = PCR primer
source                 1..48
                       mol_type = other DNA
```

```
                        organism = synthetic construct
SEQUENCE: 137
ctgaatctgg aggagcgcaa acggttggtg gcgcagcatc tgacgcac               48

SEQ ID NO: 138          moltype = DNA  length = 36
FEATURE                 Location/Qualifiers
misc_feature            1..36
                        note = PCR primer
source                  1..36
                        mol_type = other DNA
                        organism = synthetic construct
SEQUENCE: 138
gatcaccggc gcatccgaga actcacgctg cgaagc                            36

SEQ ID NO: 139          moltype = DNA  length = 47
FEATURE                 Location/Qualifiers
misc_feature            1..47
                        note = PCR primer
source                  1..47
                        mol_type = other DNA
                        organism = synthetic construct
SEQUENCE: 139
taaggccccg gaggcccttt tctttgtgca gtttgaaaag ggatctg                47

SEQ ID NO: 140          moltype = DNA  length = 50
FEATURE                 Location/Qualifiers
misc_feature            1..50
                        note = PCR primer
source                  1..50
                        mol_type = other DNA
                        organism = synthetic construct
SEQUENCE: 140
ccacatgcac gtgctcgtgg aaacctccgg catctcttcc atggtcctcg             50

SEQ ID NO: 141          moltype = DNA  length = 38
FEATURE                 Location/Qualifiers
misc_feature            1..38
                        note = PCR primer
source                  1..38
                        mol_type = other DNA
                        organism = synthetic construct
SEQUENCE: 141
tcagattcgc gaaaaactgg tgaaagtggt cttccagg                          38

SEQ ID NO: 142          moltype = DNA  length = 47
FEATURE                 Location/Qualifiers
misc_feature            1..47
                        note = PCR primer
source                  1..47
                        mol_type = other DNA
                        organism = synthetic construct
SEQUENCE: 142
gaatttaccg cgggatcgag ccgcagatca acgactgggt cgccatc                47

SEQ ID NO: 143          moltype = DNA  length = 54
FEATURE                 Location/Qualifiers
misc_feature            1..54
                        note = PCR primer
source                  1..54
                        mol_type = other DNA
                        organism = synthetic construct
SEQUENCE: 143
ggtcacaaag accagaaatg gcgccggcgg agccaataag gtggtggatt ctgg        54

SEQ ID NO: 144          moltype = DNA  length = 48
FEATURE                 Location/Qualifiers
misc_feature            1..48
                        note = PCR primer
source                  1..48
                        mol_type = other DNA
                        organism = synthetic construct
SEQUENCE: 144
gaggcgggaa caaggtggtg gattctgggt atattcccgc ctacctgc               48

SEQ ID NO: 145          moltype = DNA  length = 34
FEATURE                 Location/Qualifiers
misc_feature            1..34
                        note = PCR primer
source                  1..34
```

```
                        mol_type = other DNA
                        organism = synthetic construct
SEQUENCE: 145
ccagcctgag ctccagtggg cgtggacaaa cctg                              34

SEQ ID NO: 146          moltype = DNA  length = 48
FEATURE                 Location/Qualifiers
misc_feature            1..48
                        note = PCR primer
source                  1..48
                        mol_type = other DNA
                        organism = synthetic construct
SEQUENCE: 146
gtttgaatct cacggagcgt aaacggctcg tcgcgcagtt tctggcag               48

SEQ ID NO: 147          moltype = DNA  length = 42
FEATURE                 Location/Qualifiers
misc_feature            1..42
                        note = PCR primer
source                  1..42
                        mol_type = other DNA
                        organism = synthetic construct
SEQUENCE: 147
atgcgccggt gatcaaaagc aagacttccc agaaatacat gg                     42

SEQ ID NO: 148          moltype = DNA  length = 29
FEATURE                 Location/Qualifiers
misc_feature            1..29
                        note = PCR primer
source                  1..29
                        mol_type = other DNA
                        organism = synthetic construct
SEQUENCE: 148
attataggta ccaggaaccc ctagtgatg                                    29

SEQ ID NO: 149          moltype = DNA  length = 22
FEATURE                 Location/Qualifiers
misc_feature            1..22
                        note = PCR primer
source                  1..22
                        mol_type = other DNA
                        organism = synthetic construct
SEQUENCE: 149
taatagggcc caaagggccg gg                                           22

SEQ ID NO: 150          moltype = DNA  length = 22
FEATURE                 Location/Qualifiers
misc_feature            1..22
                        note = PCR primer
source                  1..22
                        mol_type = other DNA
                        organism = synthetic construct
SEQUENCE: 150
ttaataggcc ctttgggccg gg                                           22

SEQ ID NO: 151          moltype = DNA  length = 32
FEATURE                 Location/Qualifiers
misc_feature            1..32
                        note = PCR primer
source                  1..32
                        mol_type = other DNA
                        organism = synthetic construct
SEQUENCE: 151
tataataagc ttaggaaccc ctagtgatgg ag                                32

SEQ ID NO: 152          moltype = DNA  length = 33
FEATURE                 Location/Qualifiers
misc_feature            1..33
                        note = PCR primer
source                  1..33
                        mol_type = other DNA
                        organism = synthetic construct
SEQUENCE: 152
attataggta cctacaaaac ctccttgctt gag                               33

SEQ ID NO: 153          moltype = DNA  length = 24
FEATURE                 Location/Qualifiers
misc_feature            1..24
                        note = PCR primer
```

-continued

```
source                  1..24
                        mol_type = other DNA
                        organism = synthetic construct
SEQUENCE: 153
ttaataggcc ctttgggccg tcgc                                         24

SEQ ID NO: 154          moltype = DNA  length = 25
FEATURE                 Location/Qualifiers
misc_feature            1..25
                        note = PCR primer
source                  1..25
                        mol_type = other DNA
                        organism = synthetic construct
SEQUENCE: 154
ttaataggcc caaagggccg tcgtc                                        25

SEQ ID NO: 155          moltype = DNA  length = 35
FEATURE                 Location/Qualifiers
misc_feature            1..35
                        note = PCR primer
source                  1..35
                        mol_type = other DNA
                        organism = synthetic construct
SEQUENCE: 155
tataataagc tttacaaaac ctccttgctt gagag                             35
```

RESTRICTIVE INVERTED TERMINAL REPEATS FOR VIRAL VECTORS

RELATED APPLICATIONS

This application is a divisional of and claims priority to U.S. patent application Ser. No. 16/953,109, filed Nov. 19, 2020, now allowed, which is a divisional of and claims priority to U.S. patent application Ser. No. 16/271,163, filed Feb. 8, 2019, now U.S. Pat. No. 10,858,632, which is a divisional of and claims priority to U.S. patent application Ser. No. 14/922,935, filed Oct. 26, 2015, now U.S. Pat. No. 10,233,428, which is a divisional application of and claims priority to U.S. patent application Ser. No. 13/521,448, filed Jul. 11, 2012, now U.S. Pat. No. 9,169,494, which claims priority to and is a 35 U.S.C. § 371 national phase application of PCT Application PCT/US2011/020939, filed Jan. 12, 2011 which claims the benefit of U.S. Provisional Application No. 61/294,181, filed Jan. 12, 2010. The entire content of each of these applications is incorporated herein by reference.

STATEMENT OF FEDERAL SUPPORT

This invention was made with government support under GM059299, HL066973, HL051818, AI072176, AI007419 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-547TSDV4_ST26.txt, 319,087 bytes in size, generated on Nov. 30, 2022, and filed electronically, is provided in lieu of a paper copy. This Sequence Listing is hereby incorporated by reference into the specification for its disclosures.

FIELD OF THE INVENTION

This invention relates to modified parvovirus inverted terminal repeats (ITRs) that do not functionally interact with wild-type large Rep proteins, synthetic Rep proteins that functionally interact with the modified ITRs, and methods of using the same for delivery of nucleic acids to a cell or a subject. The modifications provide a novel Rep-ITR interaction that may limit vector mobilization, increasing the safety of viral vectors.

BACKGROUND OF THE INVENTION

The adeno-associated viruses (AAV) are members of the family Parvoviridae and the genera Dependoviruses. Serotypes 1 through 4 were originally identified as contaminates of adenovirus preparations (Carter and Laughlin (1984) in, The Parvoviruses p. 67-152 New York, N.Y.) whereas type 5 was isolated from a patient wart that was HPV positive. To date, twelve molecular clones have been generated representing the serotypes of human/primate AAV (Bantel-Schaal et al. (1999) *J. Virol.* 73: 939; Chiorini at al. (1997) *J. Virol.* 71:6823; Chiorini et al. (1999) *J. Virol.* 73:1309; Gao et al. (2002) *Proc. Nat. Acad. Sci. USA* 99:11854; Mori et al. (2004) *Virol.* 330:375; Muramatsu et al. (1996) *Virol.* 221:208; Ruffing et al. (1994) *J. Gen. Virol.* 75:3385; Rutledge et al. (1998) *J. Virol.* 72:309; Schmidt et al. (2008) *J. Virol.* 82:8911; Srivastava et al. (1983) *J. Virol.* 45:555; Xiao et al.

(1999) *J. Virol.* 73:3994). These clones have provided valuable reagents for studying the molecular biology of serotype specific infection. Transduction of these viruses naturally results in latent infections, with completion of the life cycle generally requiring helper functions not associated with AAV viral gene products. As a result, all of these serotypes are classified as non-pathogenic and are believed to share a safety profile similar to the more extensively studied AAV type 2 (Carter and Laughlin (1984) in, The Parvoviruses p. 67-152 New York, N.Y.).

General understanding of the mechanisms required for function at origins of replication has grown immensely since the first prokaryotic origins were characterized. While the DNA-protein interactions necessary for replication in prokaryotes, lower eukaryotes, and bacteriophages are generally well understood, mechanisms employed in the majority of higher eukaryotes and vertebrate viruses, such as AAV, are still being determined. The inverted terminal repeats (ITRs) of AAV and other Parvoviruses act as the origin of replication. These elements flank the short, single stranded genome and typically possess a T-shaped secondary structure. The replication strategies of the genus Dependovirus, including those of AAV, have been well characterized. The viral non-structural or Replication proteins (Rep) are the only factors required to interact with the ITR in order to catalyze replication (Im and Muzyczka (1990) *Cell* 61:447). The majority of AAV serotypes possess highly conserved origins of replication with interchangeable DNA-protein interactions. However, the Rep proteins of several serotypes interact exclusively with their cognate ITR. Discovering the mechanisms which drive Rep-ITR specificity promises to advance our understanding of DNA-protein interactions at viral origins of replication. These findings also promise to shed light on how eukaryotic and prokaryotic proteins achieve selectivity to DNA substrates.

The AAV rep gene encodes four multifunctional proteins (Hermonat et al. (1984) *J. Virol.* 51:329; Tratschin et al. (1984) *J. Virol.* 51:611; Mendelson et al. (1986) *J. Virol.* 60:823; Trempe et al. (1987) *Virol.* 161:18) that are expressed from two promoters at map units 5 (p5) and 19 (p19). The larger Rep proteins transcribed from the p5 promoter (Rep78 and Rep68), are essentially identical except for unique carboxy termini generated from unspliced (Rep78) and spliced (Rep68) transcripts, respectively (Srivastava et al, (1983) *J. Virol.* 45:555). The two smaller Rep proteins, Rep52 and Rep40, are transcribed from the p19 promoter and represent amino terminal truncations of Rep78 and Rep68, respectively.

Several biochemical activities of Rep78 and Rep68 have been characterized as involved in AAV replication. These include specific binding to the AAV ITR (Ashktorab et al. (1989) *J. Virol.* 63:3034; Im et al. (1989) *J. Virol.* 63:3095; Snyder et al. (1993) *J. Virol.* 67:6096) and site-specific endonuclease cleavage at the terminal resolution site (trs) (Im et al. (1990) *J. Virol.* 63:447; Im et al. (1992) *J. Virol.* 66:1119; Snyder et al., (1990) *Cell* 60:105; Snyder et al. (1990) *J. Virol.* 64:6204). Rep78/68 also possess ATP dependent DNA-DNA helicase (Im et al., (1990) *J. Virol.* 63:447; Im et al. (1992) *J. Virol.* 66:1119) and DNA-RNA helicase as well as ATPase activities (Wonderling et al. (1995) *J. Virol.* 69:3542). In addition to these activities involved in replication, Rep78/68 also regulate transcription from the viral promoters (Beaton et al. (1989) *J. Virol.* 63:4450; Labow et al. (1986) *J. Virol.* 60:251; Tratschin et al. (1986) *Mol. Cell. Biol.* 6:2884; Kyostio et al. (1994) *J. Virol.* 68:2947; Pereira et al. (1997) *J. Virol.* 71:1079), and have been shown to mediate viral targeted integration (Xiao, W., (1996), "Characterization of cis and trans elements essential for the targeted integration of recombinant adeno-associated virus plasmid vectors", Ph.D. Dissertation, University of North Carolina-Chapel Hill; Balague et al. (1997) *J. Virol.* 71:3299; LaMartina et al. (1998) *J. Virol.* 72:7653; Pieroni et al. (1998) *Virol.* 249:249).

Like Rep proteins, the AAV ITRs are involved in nearly every aspect of the viral life-cycle. The secondary structure of the ITR is necessary to prime synthesis of the second strand to allow transcription of the viral genes (Hauswirth and Berns (1977) *J. Virol.* 78:488). The full length Rep proteins contain a unique N-terminal DNA binding region which specifically recognizes the ITR at the 16 nt Rep-binding element (RBE) and at the tip of one of the hairpin stems known as the RBE' (FIG. 1A) (Ryan et al. (1996) *J. Virol.* 70:1542; Brister and Muzyczka (2000) *J. Virol.* 74:7762). Rep molecules multimerize on the ITR allowing the C-terminus of Rep, acting as an ATP-dependent SF3 helicase, to unwind the ITR and form a putative internal hairpin (Im and Muzyczka (1990) *Cell* 61:447; Hermonat and Batchu (1997) *FEBS Lett.* 20:180). This hairpin, (here, termed 'nicking stem') contains the terminal resolution site (trs) where Rep nicks the ITR in a site-specific manner (Brister and Muzyczka (1999) *J. Virol.* 73:9325). This DNA cleavage is important for replication of the closed ITR and to initiate subsequent rounds of genomic replication. Replicated genomes can undergo replication again or be encapsidated in the presence of the smaller Rep proteins (King et al. (2001) *EMBO J.* 20:3282).

The ITR sequences of twelve human/primate AAV serotypes have been published. These sequences typically display 80% or greater nucleotide conservation and segregate into two groups (Hewitt et al. (2009) *J. Virol.* 83:3919). The AAV2 Rep proteins (Rep2) are able to function on the ITR of every known AAV serotype except those of AAV5 (ITR5; Hewitt et al. (2009) *J. Virol.* 83:3919; Grimm et al. (2006) *J. Virol.* 80:426). Consistently, the AAV5 Rep proteins (Rep5) are unable to catalyze replication of the ITR of AAV2 (ITR2). Replicative specificity between these serotypes does not exist at the level of binding, as Rep2 and Rep5 can bind interchangeably to ITR2 or ITR5 (Chiorini et al. (1999) *J. Virol.* 73:4293). Instead, specificity is created by the inability of Rep to cleave the ITR of the opposite serotype. This occurs despite high conservation between the ITR2 and ITR5 sequence, secondary structure, and location of elements required for Rep interaction (RBE, RBE', trs, nicking stem).

All current AAV vectors in clinical trials utilize ITR2s. However, using ITR2s for therapeutic purposes creates a safety risk due to the ubiquity of AAV2 in the human population as well as other AAVs whose Rep proteins can replicate ITR2s. In this manner, rAAV vectors have the potential to be "mobilized" out of the target tissue into different tissues of the body or into other individuals in the population (Hewitt et al. (2009) *J. Virol.* 83:3919).

The present invention provides a solution to vector mobilization through the creation of a novel Rep-ITR interaction. A vector utilizing this novel interaction cannot be mobilized by one or more of the wild-type AAV serotypes which infect humans, nor the non-human serotypes which can potentially infect human hosts.

SUMMARY OF THE INVENTION

The present invention relates to the discovery of unique mechanisms at the DNA and protein level to achieve Rep-ITR specificity and utilizes these factors to create novel AAV origins of replication. Thus, one aspect of the invention relates to a polynucleotide comprising at least one parvovirus inverted terminal repeat (ITR), wherein said ITR comprises: (a) a first structural element that functionally interacts with a large Rep protein from a first AAV but does not functionally interact with a large Rep protein from a second AAV; and (b) a second structural element that that functionally interacts with the large Rep protein from the second AAV but does not functionally interact with the large Rep protein from the first AAV; wherein the ITR functionally interacts with a synthetic AAV large Rep protein. The invention further relates to a viral vector and a recombinant parvovirus particle comprising the polynucleotide of the invention. Further provided are pharmaceutical formulations comprising a virus particle of the invention in a pharmaceutically acceptable carrier.

Another aspect of the invention relates to a synthetic large Rep protein comprising a first portion that functionally interacts with a first structural element of a parvovirus ITR and a second portion that functionally interacts with a second structural element of a parvovirus ITR, wherein said first structural element functionally interacts with a large Rep protein from a first AAV and said second structural element functionally interacts with a large Rep protein from a second AAV that is different from the first AAV. The invention further relates to polynucleotides encoding the synthetic large Rep protein and vectors and cells comprising the polynucleotide.

An additional aspect of the invention relates to a method of producing a recombinant parvovirus particle, comprising providing to a cell permissive for parvovirus replication: (a) a recombinant parvovirus template comprising (i) a heterologous nucleotide sequence, and (ii) the parvovirus terminal repeat sequence of the invention; (b) a polynucleotide encoding a Rep protein of the invention; under conditions sufficient for the replication and packaging of the recombinant parvovirus template; whereby recombinant parvovirus particles comprising the parvovirus capsid encoded by the cap coding sequences and packaging the recombinant parvovirus template are produced in the cell.

A further aspect of the invention relates to a method of delivering a nucleic acid to a cell, comprising introducing into a cell the recombinant parvovirus particle of the invention.

Another aspect of the invention relates to a method of administering a nucleic acid to a mammalian subject comprising administering to the mammalian subject a cell that has been contacted with the recombinant parvovirus particle of the invention under conditions sufficient for the parvovirus particle vector genome to enter the cell.

A further aspect of the invention relates to a method of administering a nucleic acid to a mammalian subject comprising administering to the mammalian subject the recombinant parvovirus particle of the invention.

An additional aspect of the invention relates to a parvovirus template comprising (i) a heterologous nucleotide sequence, and (ii) at least one snake AAV ITR sequence and a parvovirus particle comprising the parvovirus template.

A further aspect of the invention relates to a method of producing a parvovirus particle, comprising providing to a cell permissive for parvovirus replication: (a) a recombinant parvovirus template comprising (i) a heterologous nucleotide sequence, and (ii) at least one snake AAV ITR sequence; (b) a polynucleotide encoding snake AAV Rep protein and mammalian AAV Cap protein; (c) a polynucleotide encoding mammalian Rep52 and/or Rep40 proteins; under conditions sufficient for the replication and packaging of the recombinant parvovirus template; whereby recombinant parvovirus particles comprising a parvovirus capsid encoded by the cap coding sequences and packaging the recombinant parvovirus template are produced in the cell.

Another aspect of the invention relates to use of the recombinant parvovirus particle of the invention for delivering a nucleic acid to a cell.

An additional aspect of the invention relates to use of a cell that has been contacted with the recombinant parvovirus particle of the invention for delivering a nucleic acid to a mammalian subject.

A further aspect of the invention relates to use of the recombinant parvovirus particle of the invention for delivering a nucleic acid to a mammalian subject.

Another aspect of the invention relates to use of the recombinant parvovirus particle of the invention for the manufacture of a medicament for delivering a nucleic acid to a cell.

An additional aspect of the invention relates to use of a cell that has been contacted with the recombinant parvovirus particle of the invention for the manufacture of a medicament for delivering a nucleic acid to a mammalian subject.

A further aspect of the invention relates to use of the recombinant parvovirus particle of the invention for the manufacture of a medicament for delivering a nucleic acid to a mammalian subject.

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

These and other aspects of the invention are set forth in more detail in the description of the invention below.

BRIEF DESCRIPTION OF THE DRAWINGS

(FIG. 1A) Sequence and structure of ITR2 (SEQ ID NO:17) (black) and ITR5 (SEQ ID NO:18) (italic) shown with incorporation of SfiI sites for cloning (bold). Length in nt of ITR elements indicated above brackets. RBE is boxed. RBE' is indicated by a hatched circle. Nicking stem is extruded with arrow indicating the nicking site and hatched box indicating the trs. The four initial chimeric ITRs generated (SEQ ID NOS:19-22) are shown (right). (FIG. 1B) Replication assay and quantitation of chimeric Reps. Replication products from the indicated ITR and either Rep2 or Rep5 were analyzed by Southern blot. Monomeric (m) and dimeric (d) replicating species are indicated. The level of replication of each sample was measured by densitometric analysis and compared to wt replication.

(FIG. 2A) Sequence of nicking stem in an otherwise ITR2 context (SEQ ID NOS: 17, 18, 23, 25, 30, 32, 28). Arrow indicates trs site. Brackets indicate height of putative stems in nt from the base of the stem to the putative nicking site. Predicted AG values for the hairpins are below. Southern blot analysis of the ITRs replicated by Rep2 or Rep5 are shown below. (FIG. 2B) Quantitation of the Southern blots relative to wt replication from FIG. 2A. (FIG. 2C) Same as FIG. 2A, except nicking stems indicated were used in an ITR5 context (SEQ ID NOS:17, 18, 24, 26, 35). (FIG. 2D) Quantitation of the Southern blots relative to wt replication from FIG. 2C.

(FIG. 3A) ITR2 mutants were synthesized with the indicated spacing between the RBE and nicking stem (SEQ ID NOS:17, 31, 33). (FIG. 3B) Southern blot analysis of the ITRs depicted in FIG. 3A replicated by either Rep2 or Rep5 (Left). Quantitation of Southern blots relative to wt replication (Right). (FIG. 3C) ITR5 mutants synthesized as in FIG. 3A (SEQ ID NOS:34, 18, 37, 38). (FIG. 3D) Southern blot analysis and quantitation of FIG. 3C.

(FIG. 4A) ITR5 mutants were synthesized with the indicated RBE and spacer sequence (SEQ ID NOS:18, 40, 39, 42). Brackets indicate individual tetranucleotide repeats bound by Rep monomers. Both strands of the wt ITR5 sequence are shown to illustrate conservation with the GAGY motif (indicated by *). Only one strand shown on others. (FIG. 4B) Southern blot analysis of the ITRs depicted in FIG. 4A replicated by either Rep2 or Rep5 (Left). Quantitation of Southern blots relative to wt replication (Right). (FIG. 4C) ITR2 mutants were generated with the RBE and spacer sequences indicated (SEQ ID NOS:17, 29, 41, 43). (FIG. 4D) Southern blot analysis and quantitation for FIG. 4C.

FIGS. 5A-5E show the cloning and characterization of chimeric Reps. (FIG. 5A) An alignment of the N-termini of Rep2 (SEQ ID NO:114) and Rep5 (SEQ ID NO:118). (*) represents conserved amino acids. (:) and (.) indicate conservative substitutions. (^) indicates residues implicated in RBE binding interactions. 0 indicates residues which participate in the endonucleolytic active site. (+) indicates residues implicated in RBE' binding. (FIG. 5B) Chimeric Reps created and their ability to replicate ITR2 or ITR5 flanked vectors. Numbers indicate the amino acid (aa) position of the switch from one Rep to the other. (+) indicates the presence of replication, (—) indicates the absence. (FIG. 5C) Western blot for expression of the chimeric Reps. (FIG. 5D) Southern blot demonstrating replication of an ITR2 or an ITR5 vector by the chimeric Reps. Note that the ITR5 vector is 500 bp larger than the ITR2 vector. (FIG. 5E) Level of replication of the chimeric Reps relative to wt Rep2 or Rep5.

(FIG. 6A) Chimeric Reps and their ability to replicate ITR2 or ITR5 flanked vectors. Numbers indicate the aa position of the switch from one Rep to the other. (+) indicates the presence of replication, (—) indicates the absence. Region 1 and 2 involved in Rep-ITR specificity are indicated. (FIG. 6B) Western blot for expression of chimeric Reps. (FIG. 6C) Southern blot demonstrating replication of an ITR2 or ITR5 vector by the chimeric Reps. Note that the ITR5 vector is 500 bp larger than the ITR2 vector. (FIG. 6D) Structural model illustrating the two Rep regions. The nucleophilic tyrosine is indicated. Black hatched circle indicates the predicted structural difference of region 1 in the major groove of the ITR. (FIG. 6E) Structural model as in FIG. 6D. The nucleophilic tyrosine is indicated. (FIG. 6F) Detailed structural view of region 1. The side-chains of non-conserved residues from Rep5 and Rep2 are shown. Three Rep5 residues implicated in RBE' binding are indicated. (FIG. 6G) Detailed structural view of region 2. Side chains of active site residues are shown in black. Side chains of non-conserved residues in this region are shown for Rep2 and Rep5. The nucleophilic tyrosine is indicated, as is the adjacent Rep2 Asn-155.

(FIG. 7A) Southern blot of Hirt DNA demonstrating replication of the indicated ITR vector by the indicated Rep. (FIG. 7B) Table indicating the presence (+) or absence (—) of replication of the gel from FIG. 7A. (FIG. 7C) Model of a novel AAV origin of replication. The chimeric ITR can be replicated only by a chimeric Rep protein. Rep5 sequence in region 1 is required for the extended RBE of ITR5. Rep2 sequence in region 2 is required to function on an ITR2 nicking stem.

FIG. 8 shows an illustrative genomic DNA sequence for AAV-1; GenBank Accession No. NC 002077; SEQ ID NO:1.

FIG. 9 shows an illustrative genomic DNA sequence for AAV-2; GenBank Accession No. NC 001401; SEQ ID NO:2.

FIG. 10 shows an illustrative genomic DNA sequence for AAV-3A; GenBank Accession No. NC 001729; SEQ ID NO:3.

FIG. 11 shows an illustrative genomic DNA sequence for AAV-3B; GenBank Accession No. NC 001863; SEQ ID NO:4.

FIG. 12 shows an illustrative genomic DNA sequence for AAV-4; GenBank Accession No. NC 001829; SEQ ID NO:5.

FIG. 13 shows an illustrative genomic DNA sequence for AAV-5; GenBank Accession No. NC 006152; SEQ ID NO:6.

FIG. 14 shows an illustrative genomic DNA sequence for AAV-6; GenBank Accession No. NC 001862; SEQ ID NO:7.

FIG. 15 shows an illustrative genomic DNA sequence for AAV-7; GenBank Accession No. AF513851; SEQ ID NO:8.

FIG. 16 shows an illustrative genomic DNA sequence for AAV-8; GenBank Accession No. AF513852; SEQ ID NO:9.

FIG. 17 shows an illustrative genomic DNA sequence for AAV-9; GenBank Accession No. AX753250; SEQ ID NO:10.

FIG. 18 shows an illustrative genomic DNA sequence for AAV-11; GenBank Accession No. AY631966; SEQ ID NO:11.

FIG. 19 shows an illustrative genomic DNA sequence for AAV-13; GenBank Accession No. EU285562; SEQ ID NO:12.

FIG. 20 shows an illustrative genomic DNA sequence for B19 parvovirus; GenBank Accession No. NC 000883; SEQ ID NO:13.

FIG. 21 shows an illustrative genomic DNA sequence for Minute Virus from Mouse (MVM); GenBank Accession No. NC 001510; SEQ ID NO:14.

FIG. 22 shows an illustrative genomic DNA sequence for goose parvovirus; GenBank Accession No. NC 001701; SEQ ID NO:15.

FIG. 23 shows an illustrative genomic DNA sequence for snake parvovirus 1; GenBank Accession No. NC 006148; SEQ ID NO:16.

FIG. 24 provides an exemplary listing of the chimeric ITRs that were synthesized as part of the Examples described below: ITR2 (SEQ ID NO:17), ITR5 (SEQ ID NO:18), ITR5+2SNS (SEQ ID NO:19), ITR2+5SNS (SEQ ID NO:20), ITR5+2NS (SEQ ID NO:21), ITR2+5NS (SEQ ID NO:22), ITR2-TA (SEQ ID NO:23), ITR5+TA (SEQ ID NO:24), ITR2-GC (SEQ ID NO:25), ITR5+GC (SEQ ID NO:26), ITR2-2 nt (SEQ ID NO:27), ITR2 5 nt (SEQ ID NO:28), ITR2+7 (SEQ ID NO:29), ITR2 9 nt (SEQ ID NO:30), ITR2 10 nt (SEQ ID NO:31), ITR2 11 nt (SEQ ID NO:32), ITR2 15 nt (SEQ ID NO:33), ITR5 3 nt (SEQ ID NO:34), ITR5 6 nt (SEQ ID NO:35), ITR5 9 bp NS (SEQ ID NO:36), ITR5 21 nt (SEQ ID NO:37), ITR5 30 nt (SEQ ID NO:38), ITR5 GAGY (SEQ ID NO:39), ITR5 no GAGY (SEQ ID NO:40), ITR2+8 nt GAGY (SEQ ID NO:41), ITR5 Spacer RBE (SEQ ID NO:42), ITR2+8-8 Spacer RBE (SEQ ID NO:43), ITR5 with ITR2 hairpins (SEQ ID NO:44), ITR2 no hairpins (SEQ ID NO:45), ITR2 T1 (SEQ ID NO:46), ITR2 T2 (SEQ ID NO:47), ITR2 T2 #2 (SEQ ID NO:48), ITR2 T3 (SEQ ID NO:49), ITR2 T4 (SEQ ID NO:50), ITR5+3 nt Spacer & ITR5 NS (SEQ ID NO:51), and ITR2 pHpa8 (SEQ ID NO:52).

FIG. 25 provides an exemplary listing of the chimeric Rep proteins that were synthesized as part of the Examples described below: Rep52aa73 (SEQ ID NO:53), Rep52aa84 (SEQ ID NO:54), Rep52aa110 (SEQ ID NO:55), Rep52aa126 (SEQ ID NO:56), Rep52aa138 (SEQ ID NO:57), Rep52aa160 (SEQ ID NO:58), Rep52aa175 (SEQ ID NO:59), Rep52aa187 (SEQ ID NO:60), Rep52aa207 (SEQ ID NO:61), Rep25aa73 (SEQ ID NO:62), Rep25aa77 (SEQ ID NO:63), Rep25aa97 (SEQ ID NO:64), Rep25aa116 (SEQ ID NO:65), Rep25aa125 (SEQ ID NO:66), Rep25aa141 (SEQ ID NO:67), Rep25aa149 (SEQ ID NO:68), Rep25aa166 (SEQ ID NO:69), Rep25aa187 (SEQ ID NO:70), Rep25aa216 (SEQ ID NO:71), Rep525aa110-148 (SEQ ID NO:72), Rep525aa146-187 (SEQ ID NO:73), Rep525aa110-187 (SEQ ID NO:74), Rep252aa97-146 (SEQ ID NO:75), Rep252aa149-187 (SEQ ID NO:76), and Rep252aa97-187 (SEQ ID NO:77).

FIG. 26 shows both the nucleotide and amino acid sequences of a chimeric Rep protein of the invention: Rep52aa146 (SEQ ID NO:78 and SEQ ID NO:79, respectively).

FIG. 27 shows both the nucleotide and amino acid sequences of a chimeric Rep protein of the invention: Rep52aa147 (SEQ ID NO:80 and SEQ ID NO:81, respectively).

FIG. 28 shows both the nucleotide and amino acid sequences of a chimeric Rep protein of the invention: Rep52aa151 (SEQ ID NO:82 and SEQ ID NO:83, respectively).

FIG. 29 shows an alignment of the amino acid sequences of exemplary Rep40 proteins from AAV1 (SEQ ID NO:84), AAV2 (SEQ ID NO:85), AAV3A (SEQ ID NO:86), AAV3B (SEQ ID NO:87), AAV4 (SEQ ID NO:88), AAV5 (SEQ ID NO:89), AAV6 (SEQ ID NO:90), AAV7 (SEQ ID NO:91) and AAV8 (SEQ ID NO:92), as well as a consensus sequence (SEQ ID NO:93). Dashes indicate gaps in the sequence and shading indicates positions of sequence homology.

FIG. 30 shows an alignment of the amino acid sequences of exemplary Rep52 proteins from AAV1 (SEQ ID NO:94), AAV2 (SEQ ID NO:95), AAV3A (SEQ ID NO:96), AAV3B (SEQ ID NO:97), AAV4 (SEQ ID NO:98), AAV5 (SEQ ID NO:99), AAV6 (SEQ ID NO:100), AAV7 (SEQ ID NO:101) and AAV8 (SEQ ID NO:102), as well as a consensus sequence (SEQ ID NO:103). Dashes indicate gaps in the sequence and shading indicates positions of sequence homology.

FIG. 31 shows an alignment of the amino acid sequences of exemplary Rep68 proteins from AAV1 (SEQ ID NO:104), AAV2 (SEQ ID NO:105), AAV3A (SEQ ID NO:106), AAV3B (SEQ ID NO:107), AAV4 (SEQ ID NO:108), AAV5

(SEQ ID NO:109), AAV6 (SEQ ID NO:110), AAV7 (SEQ ID NO:111) and AAV8 (SEQ ID NO:112). Dashes indicate gaps in the sequence and shading indicates positions of sequence homology.

FIG. 32 shows an alignment of the amino acid sequences of exemplary Rep78 proteins from AAV1 (SEQ ID NO:113), AAV2 (SEQ ID NO:114), AAV3A (SEQ ID NO:115), AAV3B (SEQ ID NO:116), AAV4 (SEQ ID NO:117), AAV5 (SEQ ID NO:118), AAV6 (SEQ ID NO:119), AAV7 (SEQ ID NO:120) and AAV8 (SEQ ID NO:121), as well as a consensus sequence (SEQ ID NO:122). Dashes indicate gaps in the sequence and shading indicates positions of sequence homology.

FIG. 33 shows the nucleotide sequence of the snake ITR utilized in Example 9 (SEQ ID NO:123).

FIG. 34 shows the nucleotide sequence of the snake ITR eGFP vector plasmid (SEQ ID NO:124) used to synthesize the snake vector described in Example 9.

FIG. 35 shows the nucleotide sequence of the pSnRep-Cap2 plasmid (SEQ ID NO:125) used to synthesize the snake vector described in Example 9.

Figure 36A:
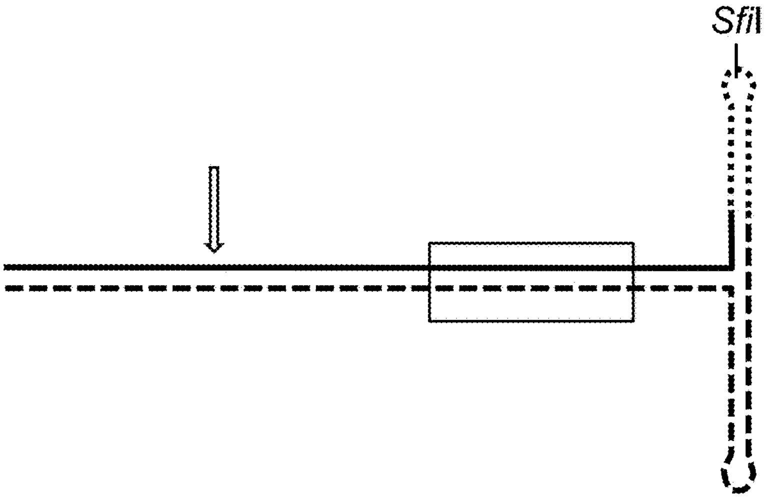
Figure 36B:
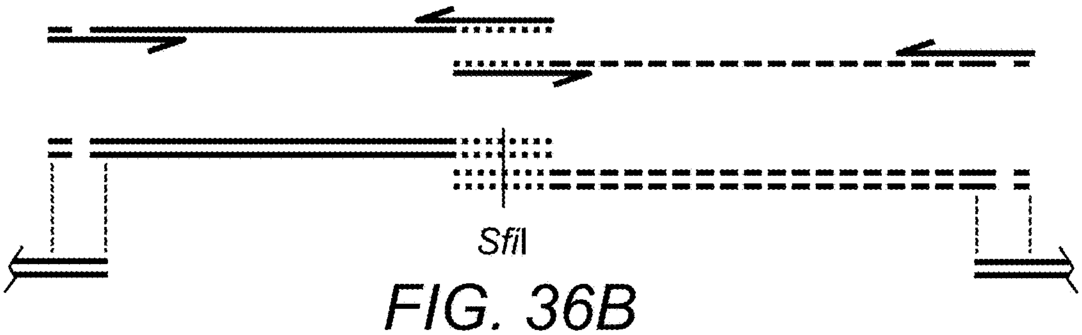
Figure 36C:
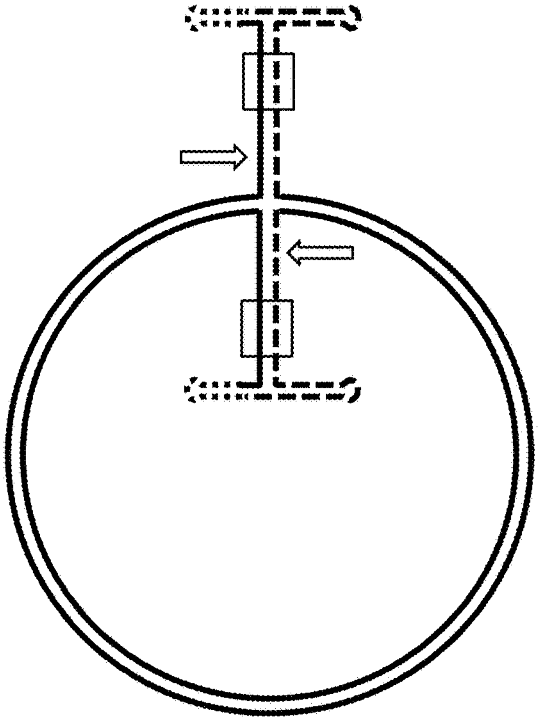

FIGS. 36A-36C shows a diagram of ITR synthesis. (FIG. 36A) The ITR was synthesized in two pieces (——— and – – –) overlapping across one hairpin stem holding the SfiI site (·········). (FIG. 36B) Each half was amplified via PCR prior to digestion and cloning. (FIG. 36C) Proper triple-ligation with pUC18-CMV GFP produced an ITR in DD format.

DETAILED DESCRIPTION OF THE INVENTION

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR § 1.822 and established usage. See, e.g., *PatentIn User Manual,* 99-102 (November 1990) (U.S. Patent and Trademark Office).

Except as otherwise indicated, standard methods known to those skilled in the art may be used for the construction of recombinant parvovirus and rAAV constructs, packaging vectors expressing the parvovirus Rep and/or Cap sequences, and transiently and stably transfected packaging cells. Such techniques are known to those skilled in the art. See, e.g., Sambrook et al. Molecular Cloning: A Laboratory Manual 2nd Ed. (Cold Spring Harbor, NY, 1989); Ausubel et al. Current Protocols in Molecular Biology (Green Publishing Associates, Inc. and John Wiley & Sons, Inc., New York).

Definitions

The following terms are used in the description herein and the appended claims:

The singular forms "a" and "an" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of 20%, 10%, 5%, 1%, 0.5%, or even 0.1% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" is to be interpreted as encompassing the recited materials or steps "and those that do not materially affect the basic and novel characteristic(s)" of the claimed invention (e.g., rAAV replication). See, *In re Herz,* 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "parvovirus" as used herein encompasses the family Parvoviridae, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus (See, e.g., FIGS. 20-23). Other autonomous parvoviruses are known to those skilled in the art. See, e.g., FIELDS et al. VIROLOGY, volume 2, chapter 69 (4th ed., Lippincott-Raven Publishers).

The genus Dependovirus contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIGS. 8-19; FIELDS et al. VIROLOGY, volume 2, chapter 69 (4th ed., Lippincott-Raven Publishers); and Table 1.

TABLE 1

| | GenBank Accession Number |
|---|---|
| Complete Genomes | |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |

TABLE 1-continued

| | GenBank Accession Number |
|---|---|
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |

TABLE 1-continued

| | GenBank Accession Number |
|---|---|
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu 14 (AAV9) | AY530579 |
| Hu31 | AY530596 |
| Hu32 | AY530597 |
| Clonal Isolate | |
| AAV5 | Y18065, AF085716 |
| AAV3 | NC_001729 |
| AAV3B | NC_001863 |
| AAV4 | NC_001829 |
| Rh34 | AY243001 |
| Rh33 | AY243002 |
| Rh32 | AY243003 |

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any other AAV now known or later discovered. See, e.g., FIELDS et al. VIROLOGY, volume 2, chapter 69 (4th ed., Lippincott-Raven Publishers). A number of relatively new AAV serotypes and clades have been identified (See, e.g., Gao et al. (2004) *J. Virol.* 78:6381; Moris et al. (2004) *Virol.* 33-:375; and Table 1).

The parvovirus particles and genomes of the present invention can be from, but are not limited to, AAV. The genomic sequences of various serotypes of AAV and the autonomous parvoviruses, as well as the sequences of the native ITRs, Rep proteins, and capsid subunits are known in the art. Such sequences may be found in the literature or in public databases such as GenBank. See, e.g., FIGS. 8-23; GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching parvovirus and AAV nucleic acid and amino acid sequences. See also, e.g., Bantel-Schaal et al. (1999) *J. Virol.* 73: 939; Chiorini et al. (1997) *J. Virol.* 71:6823; Chiorini et al. (1999) *J. Virol.* 73:1309; Gao et al. (2002) *Proc. Nat. Acad. Sci. USA* 99:11854; Moris et al. (2004) *Virol.* 33-:375-383; Mori et al. (2004) *Virol.* 330:375; Muramatsu et al. (1996) *Virol.* 221: 208; Ruffing et al. (1994) *J. Gen. Virol.* 75:3385; Rutledge et al. (1998) *J. Virol.* 72:309; Schmidt et al. (2008) *J. Virol.* 82:8911; Shade et al., (1986) *J. Virol.* 58:921; Srivastava et al. (1983) *J. Virol.* 45:555; Xiao et al. (1999) *J. Virol.* 73:3994; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, PA (incorporated herein it its entirety).

The term "tropism" as used herein refers to entry of the virus into the cell, optionally and preferably followed by expression (e.g., transcription and, optionally, translation) of sequences carried by the viral genome in the cell, e.g., for a recombinant virus, expression of the heterologous nucleotide sequences(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of AAV, gene expression from the viral genome may be from a stably integrated provirus, from a non-integrated episome, as well as any other form in which the virus may take within the cell.

As used herein, "transduction" or "infection" of a cell by a parvovirus or AAV means that the parvovirus/AAV enters the cell to establish an active (i.e., lytic) infection. As used herein, "transduction" of a cell by AAV means that the AAV enters the cell to establish a latent infection. See, e.g., FIELDS et al. VIROLOGY, volume 2, chapter 69 (3d ed., Lippincott-Raven Publishers).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), and can be either single or double stranded DNA sequences.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.,* 266:460 (1996); blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity with respect to the coding sequence of the polypeptides disclosed herein is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" polynucleotide (e.g., an "isolated DNA" or an "isolated RNA") means a polynucleotide separated or substantially free from at least some of the other components of the naturally occurring organism or virus, for example, the cell or viral structural components or other polypeptides or nucleic acids commonly found associated with the polynucleotide.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

A "therapeutic polypeptide" is a polypeptide that may alleviate or reduce symptoms that result from an absence or defect in a protein in a cell or subject. Alternatively, a "therapeutic polypeptide" is one that otherwise confers a benefit to a subject, e.g., anti-cancer effects or improvement in transplant survivability.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" or "purify" (or grammatical equivalents) a virus vector, it is meant that the virus vector is at least partially separated from at least some of the other components in the starting material.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous nucleotide sequence" and "heterologous nucleic acid" are used interchangeably herein and refer to a sequence that is not naturally occurring in the virus. Generally, the heterologous nucleic acid comprises an open reading frame that encodes a polypeptide or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of the invention.

A "rAAV vector genome" or "rAAV genome" is an AAV genome (i.e., vDNA) that comprises one or more heterologous nucleic acid sequences. rAAV vectors generally require only the 145 base ITR in cis to generate virus. All other viral sequences are dispensable and may be supplied in trans (Muzyczka (1992) *Curr. Topics Microbiol. Immunol.* 158: 97). Typically, the rAAV vector genome will only retain the one or more ITR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention the rAAV vector genome comprises at least one ITR sequence (e.g., AAV ITR sequence), optionally two ITRs (e.g., two AAV ITRs), which typically will be at the 5' and 3' ends of the vector genome and flank the heterologous nucleic acid, but need not be contiguous thereto. The ITRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The ITR can be an AAV ITR or a non-AAV ITR. For example, a non-AAV ITR sequence such as those of other parvoviruses (e.g., canine parvovirus, bovine parvovirus, mouse parvovirus, porcine parvovirus, human parvovirus B-19) or the SV40 hairpin that serves as the origin of SV40 replication can be used as an ITR, which can further be modified by truncation, substitution, deletion, insertion and/or addition. Further, the ITR can be partially or completely synthetic, such as the "double-D sequence" as described in U.S. Pat. No. 5,478,745 to Samulski et al. FIG. 24 provides examples of synthetic ITRs contemplated by the present invention.

Parvovirus genomes have palindromic sequences at both their 5' and 3' ends. The palindromic nature of the sequences leads to the formation of a hairpin structure that is stabilized by the formation of hydrogen bonds between the complementary base pairs. This hairpin structure is believed to adopt a "Y" or a "T" shape. See, e.g., FIELDS et al. VIROLOGY, volume 2, chapters 69 & 70 (4th ed., Lippincott-Raven Publishers).

An "AAV inverted terminal repeat" or "AAV ITR" may be from any AAV, including but not limited to serotypes 1, 2, 3a, 3b, 4, 5, 6, 7, 8, 9, 10, 11, or 13, snake AAV, avian AAV, bovine AAV, canine AAV, equine AAV, ovine AAV, goat AAV, shrimp AAV, or any other AAV now known or later discovered (see, e.g., Table 1). An AAV ITR need not have the native terminal repeat sequence (e.g., a native AAV ITR sequence may be altered by insertion, deletion, truncation and/or missense mutations), as long as the terminal repeat mediates the desired functions, e.g., replication, virus packaging, integration, and/or provirus rescue, and the like.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) *Mol. Therapy* 2:619.

Further, the viral capsid or genomic elements can contain other modifications, including insertions, deletions and/or substitutions.

As used herein, the term "amino acid" encompasses any naturally occurring amino acids, modified forms thereof, and synthetic amino acids.

Naturally occurring, levorotatory (L-) amino acids are shown in Table 2.

TABLE 2

| | Abbreviation | |
|---|---|---|
| Amino Acid Residue | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 3) or can be an amino acid that is modified by post-translation modification (e.g., acetylation, amidation, formylation, hydroxylation, methylation, phosphorylation or sulfatation).

TABLE 3

| Modified Amino Acid Residue<br>Amino Acid Residue Derivatives | Abbreviation |
|---|---|
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Or |
| 4-Chlorophenylalanine | Phe(4-Cl) |
| 2-Fluorophenylalanine | Phe(2-F) |
| 3 -Fluorophenylalanine | Phe(3-F) |
| 4-Fluorophenylalanine | Phe(4-F) |
| Phenylglycine | Phg |
| Beta-2-thienylalanine | Thi |

Further, the non-naturally occurring amino acid can be an "unnatural" amino acid as described by Wang et al. (2006) *Annu. Rev. Biophys. Biomol. Struct.* 35:225-49. These unnatural amino acids can advantageously be used to chemically link molecules of interest to the AAV capsid protein.

The term "template" or "substrate" is used herein to refer to a polynucleotide sequence that may be replicated to produce the parvovirus viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., Fields et al. Virology, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, for MVM, the NS-1 and NS-2 proteins (which are splice variants) may be expressed independently of one another. Likewise, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) *Human Gene Therapy* 13:1935).

As used herein, the term "synthetic large Rep protein" refers to a large Rep protein having an amino acid sequence that differs from a wild-type large Rep protein sequence. The sequence of the synthetic large Rep protein may differ from a wild-type sequence due to one or more deletions, additions, substitutions, or any combination thereof. The difference between the synthetic and wild-type sequences may be as little as a single amino acid change, e.g., a change in 1, 2, 3, 4, 5, 6, 7, 8, 9, 10, 15, 20, 25, 30, 35, 40, 45, 60, 60, 70, 80, 90, 100, 125, 150, 175, 200, 225, 250, 275, 300, 325, 350, 375, 400, 425, 450, 475, 500, 525, 550, 575, or 600 or more amino acids or any range therein. In certain embodiments, the synthetic large Rep protein is a chimeric Rep protein comprising portions of the wild-type sequence of two or more different large Rep proteins. In other embodiments, the synthetic large Rep protein is a chimeric Rep protein comprising portions of the wild-type sequence of two or more different large Rep proteins, one or more portions of which have been modified from the wild-type sequence.

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The capsid structure of autonomous parvoviruses and AAV are described in more detail in BERNARD N. FIELDS et al., VIROLOGY, volume 2, chapters 69 & 70 (4th ed., Lippincott-Raven Publishers).

As used herein, the term "structural element," when used with respect to a parvovirus ITR, refers to a portion of the ITR that, based on nucleotide sequence, secondary structure, or both, plays a role in the functional interaction of a large Rep protein with the ITR, e.g., a portion that, when removed from the ITR, prevents functional interaction with a large Rep protein. In some embodiments, the structural element physically interacts with the large Rep protein.

As used herein, the term "functionally interacts" refers to an interaction between an ITR and a large Rep protein (e.g., binding) that ultimately results in nicking of the ITR and replication of a polynucleotide in which the ITR is present.

As used herein, the term "nicking stem" refers to a hairpin loop structure present in a parvovirus ITR that is nicked by a large Rep protein during replication of a polynucleotide in which the ITR is present.

Figure 1A:
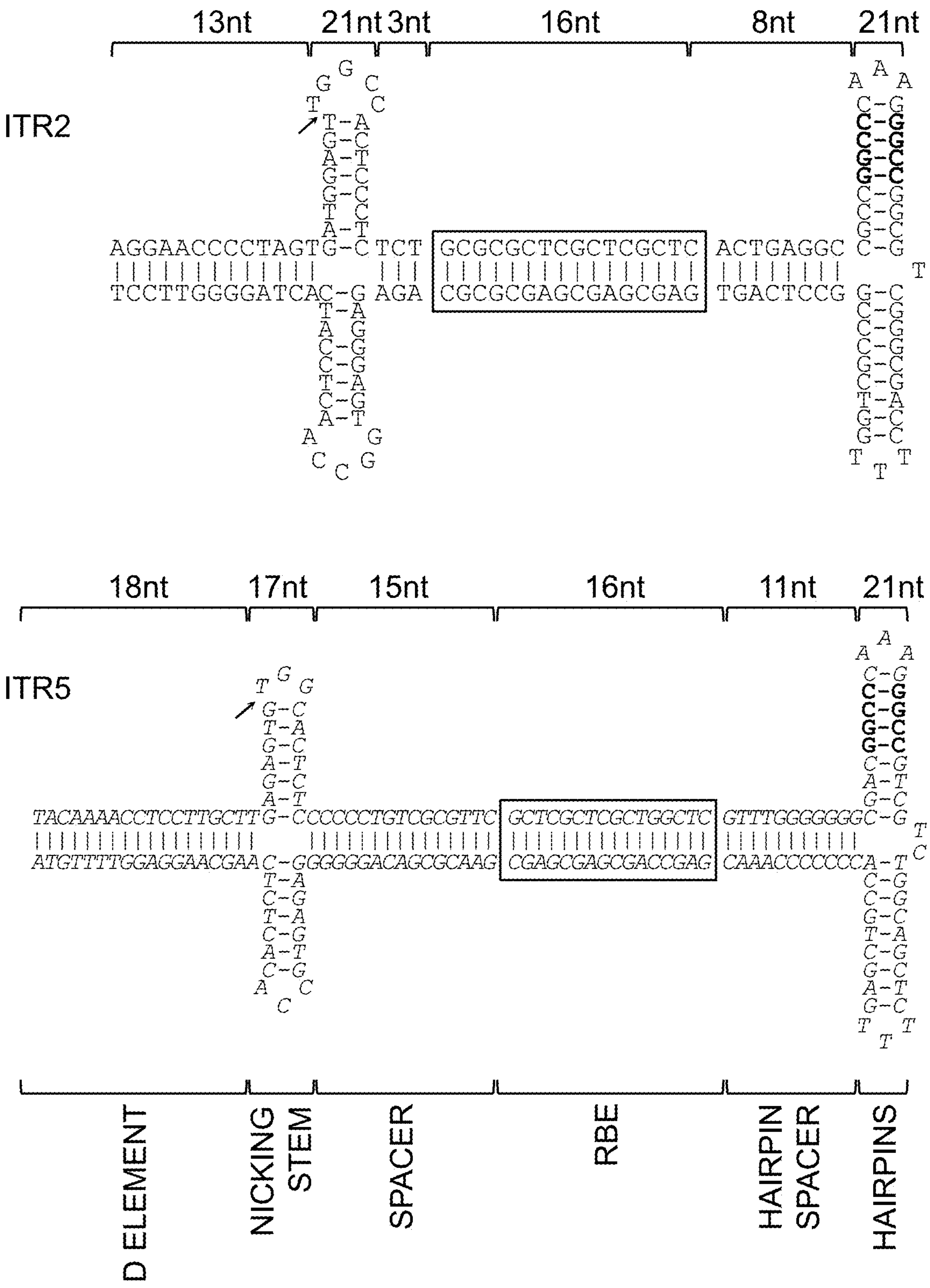
FIGS. 1A-1B show the cloning and characterization of chimeric ITRs.
Figure 1A:
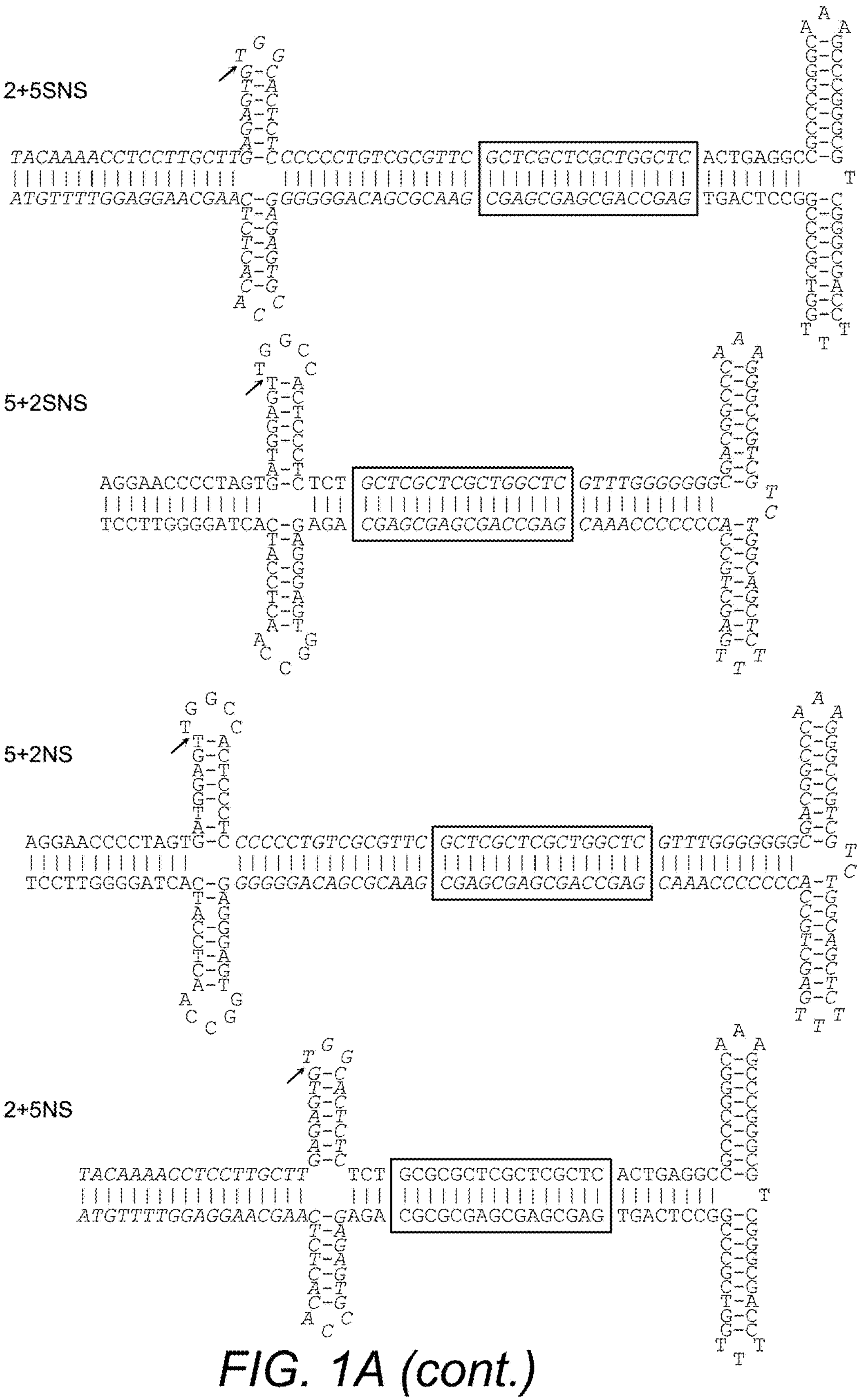

As used herein, the term "extended RBE" refers to the nucleotide sequence of a parvovirus ITR between the nicking stem and the RBE (the spacer sequence as shown in FIG. 1A) which, in certain parvoviruses (e.g., AAV5), functions as an extension of the RBE (i.e., is recognized and bound by a large Rep protein). The term "extended RBE" is only applicable to the spacer sequence when the sequence functions as an extension of the RBE.

Modified Parvovirus ITRs

The present invention provides modified parvovirus ITRs and synthetic Rep proteins that functionally interact with the modified ITRs. The modified ITRs are unique in that they do not functionally interact with wild-type Rep proteins and may reduce or avoid vector mobilization.

One aspect of the invention relates to a polynucleotide comprising at least one parvovirus ITR, wherein the ITR comprises: (a) a first structural element that functionally interacts with a large Rep protein from a AAV but does not functionally interact with a large Rep protein from a second AAV; and (b) a second structural element that functionally interacts with the large Rep protein from the second AAV but does not functionally interact with the large Rep protein from the first AAV; wherein the ITR functionally interacts with a synthetic AAV large Rep protein. In one embodiment, the ITR does not functionally interact with any wild-type large Rep protein, e.g., AAV2 Rep, AAV5 Rep, or any other known Rep protein. In particular embodiments, the synthetic large Rep protein comprises an amino acid sequence selected from the group consisting of SEQ ID NOS:79, 81, and 83 or an amino acid sequence having at least 80% identity to one of SEQ ID NOS: 79, 81, and 83, e.g., at least 85%, 90%, 95%, 96%, 97%, 98%, or 99% identity. In one embodiment, the ITR further comprises a third structural element that functionally interacts with a large Rep protein from an AAV that is the same as or different from the first and/or second AAV.

In one embodiment of the invention, the parvovirus ITR is from an autonomous parvovirus. In another embodiment, the parvovirus ITR is from an AAV, e.g., an AAV selected from the group consisting of AAV1, AAV2, AAV3, AAV4, AAV5, AAV6, AAV7, AAV8, AAV9, AAV10, AAV11, AAV12, and AAV13. In a further embodiment, the parvovirus ITR is from a non-human AAV such as snake AAV, avian AAV, bovine AAV, canine AAV, equine AAV, ovine AAV, goat AAV, or shrimp AAV.

The structural element of the ITR can be any structural element that is involved in the functional interaction of the ITR with a large Rep protein. In certain embodiments, the structural element provides selectivity to the interaction of an ITR with a large Rep protein, i.e., determines at least in part which Rep protein functionally interacts with the ITR. In other embodiments, the structural element physically interacts with a large Rep protein when the Rep protein is bound to the ITR. Each structural element can be, e.g., a secondary structure of the ITR, a nucleotide sequence of the ITR, a spacing between two or more elements, or a combination of any of the above. In one embodiment, the structural elements are selected from the group consisting of a nicking stem, a spacer, a RBE, an extended RBE, and any combination thereof. In a particular embodiment, the first structural element is a nicking stem. In another embodiment, the second structural element is a RBE. In a further embodiment, the second structural element is an extended RBE. In an additional embodiment, the second structural element is a spacer.

The ability of a structural element to functionally interact with a particular large Rep protein can be altered by modifying the structural element. For example, the nucleotide sequence of the structural element can be modified as compared to the wild-type sequence of the ITR. In one embodiment, the structural element (e.g., the nicking stem, spacer, RBE, and/or extended RBE) of an ITR can be removed and replaced with a wild-type structural element from a different parvovirus. For example, the replacement structure can be from AAV1, AAV2, AAV3, AAV4, AAV5, AAV6, AAV7, AAV8, AAV9, AAV10, AAV11, AAV12, AAV13, snake parvovirus (e.g., royal python parvovirus), bovine parvovirus, goat parvovirus, avian parvovirus, canine parvovirus, equine parvovirus, shrimp parvovirus, porcine parvovirus, or insect AAV. For example, the ITR can be an AAV2 ITR and the nicking stem or RBE can be replaced with a structural element from AAV5. In another example, the ITR can be an AAV5 ITR and the nicking stem, RBE, or extended RBE can be replaced with a structural element from AAV2. In one example, the ITR can be an AAV2 ITR with the nicking stem replaced with the AAV5 ITR nicking stem, e.g., the ITR of SEQ ID NO:22 or a modified sequence thereof. In another example, the AAV ITR can be an AAV5 ITR with the nicking stem replaced with the AAV2 ITR nicking stem, e.g., the ITR of SEQ ID NO:21 or a modified sequence thereof.

In one embodiment, the nucleotide sequence of the structural element can be modified (e.g., by modifying 1, 2, 3, 4, 5, 6, 7, 8, 9, 10, 11, 12, 13, 14, 15, 16, 17, 18, 19, or 20 or more nucleotides or any range therein) to produce a synthetic structural element. In certain embodiments, the specific ITRs exemplified herein (SEQ ID NOS:17-52) can be modified (e.g., by modifying 1, 2, 3, 4, 5, 6, 7, 8, 9, 10, 11, 12, 13, 14, 15, 16, 17, 18, 19, or 20 or more nucleotides or any range therein). In other embodiments, the ITR can have at least 80% identity with one of the ITRs of SEQ ID NOS:17-52, e.g., at least 85%, 90%, 95%, 96%, 97%, 98%, or 99% identity. In one embodiment, the structural element is a nicking stem and the modified sequence is a modified terminal resolution site (trs) sequence. For example, a nicking stem can be modified to comprise the ITR2 trs (GGT/TGG) or the ITR5 trs (AGTG/TGG). In another embodiment, the structural element is a RBE or an extended RBE and the sequence is a modified at the nucleotides responsible for binding specificity. For example, the sequence of a RBE or an extended RBE can be modified to make the sequence closer to or further from the consensus GAGY binding sites recognized by Rep. In one example, the spacer or extended RBE can be modified to comprise one or more exact GAGY repeats (e.g., the ITR of SEQ ID NO:39 or a modified sequence thereof), e.g., 1, 2, 3, or 4 or more exact GAGY repeats.

In a different embodiment, the structure of the structural element can be modified. For example, the structural element can be a nicking stem and the modification can be a change in the height of the stem and/or the number of nucleotides in the loop. For example, the height of the stem can be about 2, 3, 4, 5, 6, 7, 8, or 9 nucleotides or more or any range therein. In one embodiment, the nicking stem height can be about 5 nucleotides to about 9 nucleotides and functionally interacts with Rep2. In another embodiment, the nicking stem height can be about 7 nucleotides and functionally interacts with Rep5. In another example, the loop can have 3, 4, 5, 6, 7, 8, 9, or 10 nucleotides or more or any range therein. In another example, the structural element can be a RBE or an extended RBE and the number of GAGY binding sites or GAGY-related binding sites within the RBE or extended RBE can be increased or decreased. In one example, the RBE or extended RBE can comprise 1, 2, 3, 4, 5, or 6 or more GAGY binding sites or any range therein. Each GAGY binding site can independently be an exact GAGY sequence or a sequence similar to GAGY as long as the sequence is sufficient to bind a Rep protein.

In another embodiment, the spacing between two elements (such as the nicking stem and the RBE or the RBE and a hairpin) can be altered (e.g., increased or decreased) to alter functional interaction with a large Rep protein. For example, the spacing can be about 1, 2, 3, 4, 5, 6, 7, 8, 9, 10, 11, 12, 13, 14, 15, 16, 17, 18, 19, 20, or 21 nucleotides or more or any range therein. In one embodiment, the spacer between the nicking stem and the RBE is about 3 nucleotides in length and functionally interacts with Rep2. In another embodiment, the spacer between the nicking stem and the RBE is about 3 nucleotides (e.g., the ITR of SEQ ID NO:34 or a modified sequence thereof) to about 21 nucleotides in length (e.g., the ITR of SEQ ID NO:37 or a modified sequence thereof) and functionally interacts with Rep5. In one embodiment, the spacer is the 15 nucleotide spacer of the AAV5 ITR or a sequence having at least 80% identity thereto, e.g., at least 85%, 90%, 95%, 96%, 97%, 98%, or 99% identity.

In a representative embodiment, the polynucleotide comprises at least one parvovirus ITR, wherein said ITR comprises: (a) a first structural element that functionally interacts with a large Rep protein from one or more of AAV1, AAV2, AAV3, AAV4, AAV6, AAV7, AAV8, AAV9, AAV10, AAV11, AAV12, and AAV13 but does not functionally interact with a large Rep protein from AAV5; and (b) a second structural element that functionally interacts with the large Rep protein from AAV5 but does not functionally interact with the large Rep protein from one or more of AAV1, AAV2, AAV3, AAV4, AAV6, AAV7, AAV8, AAV9, AAV10, AAV11, AAV12, and AAV13; wherein the ITR functionally interacts with a synthetic AAV large Rep protein comprising an amino acid sequence selected from SEQ ID NOS: 79, 81, and 83.

In one aspect of the invention the polynucleotide comprising the modified ITR of the invention further comprises a second ITR which may be the same as or different from the first ITR. In one embodiment, the polynucleotide further comprises a heterologous nucleic acid, e.g., a sequence encoding a protein or a functional RNA. In some embodiments, the second ITR cannot be resolved by the Rep protein, i.e., resulting in a double stranded viral DNA.

The invention also provides a viral vector comprising the polynucleotide comprising the modified ITR of the invention. The viral vector can be a parvovirus vector, e.g., an AAV vector. The invention further provides a recombinant parvovirus particle (e.g., a recombinant AAV particle) comprising the modified ITR of the invention. Viral vectors and viral particles are discussed further below.

Synthetic Rep Proteins

One aspect of the invention relates to synthetic large Rep proteins that functionally interact with the modified ITRs of the invention. Thus, in one aspect, the invention relates to a synthetic large Rep protein comprising a first portion that functionally interacts with a first structural element of a parvovirus ITR and a second portion that functionally interacts with a second structural element of a parvovirus ITR, wherein said first structural element functionally interacts with a large Rep protein from a first AAV but does not functionally interact with a large Rep protein from a second AAV and said second structural element functionally interacts with a large Rep protein from a second AAV but does not functionally interact with a large Rep protein from the first AAV. In one embodiment, the protein comprises a third portion that functionally interacts with a third structural element that functionally interacts with a large Rep protein from an AAV that is the same as or different from the first and/or second AAV. In one embodiment, the first structural element is a nicking stem and the first portion of the synthetic large Rep protein functional interacts with the nicking stem. In another embodiment, the second structural element is a spacer, RBE, or extended RBE and the second portion of the synthetic large Rep protein functional interacts with the spacer, RBE, or extended RBE.

In one embodiment, one or more portions of the synthetic large Rep protein comprise a wild-type amino acid sequence from a parvovirus Rep protein. In another embodiment, one or more portions of the synthetic large Rep protein comprise an amino acid sequence that is modified as compared to the wild-type sequence of a parvovirus Rep protein. The modification can be an addition, deletion, substitution, or any combination thereof. The synthetic large Rep protein can comprise one or more modified amino acids, e.g., about 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 150, 175, 200, 225, 250, 275, 300, 325, 350, 375, 400, 425, 450, 475, 500, 525, 550, 575, or 600 or more amino acids or any range therein.

In one embodiment of the invention, the first and second portions (and/or the third portion) are directly linked to each other. In another embodiment, the portions are connected by a linker, e.g., 1, 2, 3, 4, 5, or 6 or more amino acids. The synthetic large Rep protein can comprise further portions (e.g., from Rep or another protein or synthetic sequences) that are not involved in the functional interaction with an ITR. Examples of other sequences can include, without limitation, localization signals, tags for improved isolation, etc.

In one embodiment, the first portion of the synthetic large Rep protein comprises, consists essentially of, or consists of an amino acid sequence from about residue 97 to about residues 146-151 of a wild-type AAV5 Rep sequence, e.g., SEQ ID NO:118. For example the first portion can comprise, consist essentially of, or consist of an amino acid sequence from about residue 1, 5, 10, 15, 20, 25, 30, 35, 40, 45, 50, 55, 60, 65, 70, 75, 80, 85, 90, or 95 to about residue 146, 147, 148, 149, 151, or 151 of a wild-type AAV5 Rep sequence or any range therein. In certain embodiments, the first portion comprises, consists essentially of, or consists of an amino acid sequence having at least 80% identity to a sequence from about residue 97 to about residues 146-151 of a wild-type AAV5 Rep sequence, e.g., at least 85%, 90%, 95%, 96%, 97%, 98%, or 99% identity.

In one embodiment, the second portion of the synthetic large Rep protein comprises, consists essentially of, or consists of an amino acid sequence from about residue 149 to about residue 187 of a wild-type AAV2 Rep sequence, e.g., SEQ ID NO:114. For example, the second portion can comprise, consist essentially of, or consist of an amino acid sequence from about residue 149 to about residue 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, or 620 of a wild-type AAV2 Rep sequence or any range therein. In certain embodiments, the second portion comprises, consists essentially of, or consists of an amino acid sequence having at least 80% identity to a sequence from about residue 149 to about residue 187 of a wild-type AAV5 Rep sequence, e.g., at least 85%, 90%, 95%, 96%, 97%, 98%, or 99% identity.

In a representative embodiment of the synthetic large Rep protein, the first portion comprises, consists essentially of, or consists of an amino acid sequence from about residue 97 to about residues 146-151 of a wild-type AAV5 Rep sequence and the second portion comprises, consists essentially of, or consists of an amino acid sequence from about residue 149 to about residue 187 of a wild-type AAV2 Rep sequence. In another representative embodiment, the first portion comprises, consists essentially of, or consists of an amino acid sequence from about residue 1 to about residues 146-151 of a wild-type AAV5 Rep sequence and the second portion comprises, consists essentially of, or consists of an amino acid sequence from about residue 149 to about residue 621 of a wild-type AAV2 Rep sequence. In certain embodiments, the synthetic large Rep protein comprises, consists essentially of, or consists of an amino acid sequence of SEQ ID NOS: 79, 81, and 83. In other embodiments, the synthetic large Rep protein comprises, consists essentially of, or consists of an amino acid sequence having at least 80% identity to an amino acid sequence of SEQ ID NOS: 79, 81, and 83, e.g., at least 85%, 90%, 95%, 96%, 97%, 98%, or 99% identity.

In certain embodiments, the portion of the synthetic large Rep protein from a wild-type AAV2 Rep sequence as described above can be replaced with the corresponding portion from another human AAV serotype Rep protein other than AAV5, e.g., AAV1, AAV3, AAV4, AAV6, AAV7, AAV8, AAV9, AAV10, AAV11, AAV12, or AAV13. The structural and functional similarity between the Rep proteins of AAV2 and other human serotypes (with the exception of AAV5) may allow substitution of Rep sequences between the serotypes (see FIGS. 31 and 32).

In certain embodiments, one or more of the portions the synthetic Rep proteins can be modified to differ from the wild-type sequence (e.g., by modifying 1, 2, 3, 4, 5, 6, 7, 8, 9, 10, 11, 12, 13, 14, 15, 16, 17, 18, 19, or 20 or more aa or any range therein). In other embodiments, the synthetic Rep proteins exemplified herein can be modified (e.g., by modifying 1, 2, 3, 4, 5, 6, 7, 8, 9, 10, 11, 12, 13, 14, 15, 16, 17, 18, 19, or 20 or more aa or any range therein). In some embodiments, the modified synthetic Rep proteins retain amino acid Y156 (numbering according to Rep2). In other embodiments, modified synthetic Rep proteins retain amino acids C151, N155, and/or T161 (numbering according to Rep2). In other embodiments, modified synthetic Rep proteins retain amino acids G148, A152, and/or V158 (numbering according to Rep5). These specific amino acids may be important for activity and/or specificity.

The invention also provides polynucleotides (optionally, isolated polynucleotides) encoding the synthetic Rep proteins of the invention. In some embodiments, the polynucleotides further encode one or more parvovirus Cap proteins. Further provided are vectors comprising the polynucleotides, and cells (in vivo or in culture) comprising the polynucleotides and/or vectors of the invention. Suitable vectors include, without limitation, viral vectors (e.g., adenovirus, AAV, herpesvirus, vaccinia, poxviruses, baculoviruses, Epstein-Barr virus, and the like), plasmids, phage, YACs, BACs, and the like. In some embodiments, the polynucleotide is stably integrated into the genome of a cell. Such polynucleotides, vectors and cells can be used, for example, as reagents (e.g., helper packaging constructs or packaging cells) for the production of virus vectors as described herein.

Snake AAV ITRs

One aspect of the invention relates to the discovery that a snake AAV ITR sequence can function as a part of a parvovirus vector yet is not recognized by the Rep proteins of mammalian (e.g., human or primate) parvoviruses. Vector mobilization may therefore be reduced or avoided. Thus, one aspect of the invention relates to a parvovirus template comprising (i) a heterologous nucleotide sequence, and (ii) at least one snake AAV ITR sequence. The snake AAV ITR sequence can be from a royal python AAV. In one embodiment, the snake AAV ITR sequence comprises the nucleotide sequence of SEQ ID NO:123. In a further embodiment, the snake AAV ITR sequence comprises the nucleotide sequence of SEQ ID NO:123 that has been modified (e.g., by modifying 1, 2, 3, 4, 5, 6, 7, 8, 9, 10, 11, 12, 13, 14, 15, 16, 17, 18, 19, or 20 or more nucleotides or any range therein). In other embodiments, the parvovirus template comprises at least a portion of a snake AAV ITR, e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, or 150 or more contiguous nucleotides of a snake AAV ITR or any range therein. In certain embodiments, the parvovirus template comprises two snake AAV ITR sequences.

The invention further relates to a parvovirus particle comprising the snake parvovirus template of the invention. In certain embodiments, the parvovirus particle comprises a mammalian capsid, e.g., a human or primate capsid.

In one aspect, the invention relates to the discovery of methods for producing parvovirus particles comprising a snake AAV ITR, including the requirement for a mammalian small Rep protein. Thus, one aspect of the invention relates to a method of producing a parvovirus particle, comprising providing to a cell (e.g., a mammalian cell such as a human or primate cell) permissive for parvovirus replication: (a) a recombinant parvovirus template comprising (i) a heterologous nucleotide sequence, and (ii) at least one snake AAV ITR sequence; (b) a polynucleotide encoding one or more snake AAV Rep proteins and mammalian AAV Cap protein(s); and (c) a polynucleotide encoding mammalian Rep52 and/or Rep40 proteins; under conditions sufficient for the replication and packaging of the recombinant parvovirus template; whereby recombinant parvovirus particles packaging the recombinant parvovirus template are produced in the cell. In one embodiment, the mammalian AAV Cap protein is a human or primate AAV Cap protein. In another embodiment, the mammalian AAV Rep 52 and/or Rep 40 proteins are human or primate Rep52 and/or Rep40 proteins (including modified forms thereof), e.g., from AAV2. In some embodiments, the polynucleotide encoding snake AAV Rep protein and mammalian AAV Cap protein also encodes the mammalian Rep52 and/or Rep40 proteins. In other embodiments, the polynucleotide encoding snake AAV Rep protein and mammalian AAV Cap protein is separate from the polynucleotide encoding the mammalian Rep52 and/or Rep40 proteins. In some embodiments, the polynucleotide encoding snake AAV Rep protein and mammalian AAV Cap protein is the plasmid pSnRepCap2 (SEQ ID NO:125).

In other embodiments, other non-human AAV ITR sequences not recognized by the Rep proteins of human or primate parvoviruses may be used. Examples include, without limitation, sequences from shrimp, insect, goat, bovine, equine, canine, and equine AAVs.

Methods of Producing Virus Vectors

The present invention further provides methods of producing virus vectors. In one particular embodiment, the present invention provides a method of producing a recombinant parvovirus particle, comprising providing to a cell permissive for parvovirus replication: (a) a recombinant parvovirus template comprising (i) a heterologous nucleotide sequence, and (ii) the modified parvovirus ITR of the invention; (b) a polynucleotide encoding a synthetic large Rep protein of the invention; under conditions sufficient for the replication and packaging of the recombinant parvovirus template; whereby recombinant parvovirus particles are produced in the cell. Conditions sufficient for the replication and packaging of the recombinant parvovirus template can be, e.g., the presence of AAV sequences sufficient for replication of the parvovirus template and encapsidation into parvovirus capsids (e.g., parvovirus rep sequences and parvovirus cap sequences) and helper sequences from adenovirus and/or herpesvirus. In particular embodiments, the parvovirus template comprises two parvovirus ITR sequences, which are located 5' and 3' to the heterologous nucleic acid sequence, although they need not be directly contiguous thereto.

In some embodiments, the recombinant parvovirus template comprises an ITR that is not resolved by Rep to make duplexed AAV vectors as described in international patent publication WO 01/92551

The parvovirus template and parvovirus rep and cap sequences are provided under conditions such that virus vector comprising the parvovirus template packaged within the parvovirus capsid is produced in the cell. The method can further comprise the step of collecting the virus vector from the cell. The virus vector can be collected from the medium and/or by lysing the cells.

The cell can be a cell that is permissive for parvovirus viral replication. Any suitable cell known in the art may be employed. In particular embodiments, the cell is a mammalian cell (e.g., a primate or human cell). As another option, the cell can be a trans-complementing packaging cell line that provide functions deleted from a replication-defective helper virus, e.g., 293 cells or other Ela trans-complementing cells.

The parvovirus replication and capsid sequences may be provided by any method known in the art. Current protocols typically express the parvovirus rep/cap genes on a single plasmid. The parvovirus replication and packaging sequences need not be provided together, although it may be convenient to do so. The parvovirus rep and/or cap sequences may be provided by any viral or non-viral vector. For example, the rep/cap sequences may be provided by a hybrid adenovirus or herpesvirus vector (e.g., inserted into the Ela or E3 regions of a deleted adenovirus vector). EBV vectors may also be employed to express the parvovirus cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) *Curr. Top. Microbiol. Immun.* 158:67).

As a further alternative, the rep/cap sequences may be stably incorporated into a cell.

Typically the parvovirus rep/cap sequences will not be flanked by the TRs, to prevent rescue and/or packaging of these sequences.

The parvovirus template can be provided to the cell using any method known in the art. For example, the template can be supplied by a non-viral (e.g., plasmid) or viral vector. In particular embodiments, the parvovirus template is supplied by a herpesvirus or adenovirus vector (e.g., inserted into the Ela or E3 regions of a deleted adenovirus). As another illustration, Palombo et al., (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the parvovirus template is provided by a replicating rAAV virus. In still other embodiments, an AAV provirus comprising the parvovirus template is stably integrated into the chromosome of the cell.

To enhance virus titers, helper virus functions (e.g., adenovirus or herpesvirus) that promote a productive parvovirus infection can be provided to the cell. Helper virus sequences necessary for parvovirus replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient parvovirus production as described by Ferrari et al., (1997) *Nature Med.* 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into parvovirus virions, e.g., are not flanked by TRs.

Those skilled in the art will appreciate that it may be advantageous to provide the parvovirus replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the parvovirus rep/cap genes.

In one particular embodiment, the parvovirus rep/cap sequences and the adenovirus helper sequences are supplied by a single adenovirus helper vector. This vector can further comprise the parvovirus template. The parvovirus rep/cap sequences and/or the parvovirus template can be inserted into a deleted region (e.g., the Ela or E3 regions) of the adenovirus.

In a further embodiment, the parvovirus rep/cap sequences and the adenovirus helper sequences are supplied by a single adenovirus helper vector. According to this embodiment, the parvovirus template can be provided as a plasmid template.

In another illustrative embodiment, the parvovirus rep/cap sequences and adenovirus helper sequences are provided by a single adenovirus helper vector, and the parvovirus template is integrated into the cell as a provirus. Alternatively, the parvovirus template is provided by an EBV vector that is maintained within the cell as an extrachromosomal element (e.g., as an EBV based nuclear episome).

In a further exemplary embodiment, the parvovirus rep/cap sequences and adenovirus helper sequences are provided by a single adenovirus helper. The parvovirus template can be provided as a separate replicating viral vector. For example, the parvovirus template can be provided by a parvovirus particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The parvovirus rep/cap sequences and, if present, the parvovirus template are embedded in the adenovirus backbone and are flanked by the 5' and 3' cis sequences, so that these sequences may be packaged into adenovirus capsids. As described above, the adenovirus helper sequences and the parvovirus rep/cap sequences are generally not flanked by TRs so that these sequences are not packaged into the parvovirus virions.

Zhang et al., ((2001) *Gene Ther.* 18:704-12) describe a chimeric helper comprising both adenovirus and the AAV rep and cap genes.

Herpesvirus may also be used as a helper virus in parvovirus packaging methods. Hybrid herpesviruses encoding the parvovirus Rep protein(s) may advantageously facilitate scalable parvovirus vector production schemes. A hybrid herpes simplex virus type I (HSV-1) vector expressing the AAV-2 rep and cap genes has been described (Conway et al., (1999) *Gene Ther.* 6:986 and WO 00/17377.

As a further alternative, the virus vectors of the invention can be produced in insect cells using baculovirus vectors to deliver the rep/cap genes and parvovirus template as described, for example, by Urabe et al., (2002) *Human Gene Ther.* 13:1935-43.

Parvovirus vector stocks free of contaminating helper virus may be obtained by any method known in the art. For example, parvovirus and helper virus may be readily differentiated based on size. Parvovirus may also be separated away from helper virus based on affinity for a heparin substrate (Zolotukhin et al. (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of parvovirus. Adenovirus mutants defective for late gene expression are known in the art (e.g., ts100K and ts149 adenovirus mutants).

Recombinant Virus Vectors

The virus vectors of the present invention are useful for the delivery of nucleic acids to cells in vitro, ex vivo, and in vivo. In particular, the virus vectors can be advantageously employed to deliver or transfer nucleic acids to animal, including mammalian, cells.

Any heterologous nucleic acid sequence(s) of interest may be delivered in the virus vectors of the present invention. Nucleic acids of interest include nucleic acids encoding polypeptides, including therapeutic (e.g., for medical or veterinary uses), immunogenic (e.g., for vaccines), or diagnostic polypeptides.

Therapeutic polypeptides include, but are not limited to, cystic fibrosis transmembrane regulator protein (CFTR), dystrophin (including mini- and micro-dystrophins (see, e.g., Vincent et al., (1993) *Nature Genetics* 5:130; U.S. Patent Publication No. 2003/017131; International publication WO/2008/088895, Wang et al., *Proc. Natl. Acad. Sci. USA* 97:13714-13719 (2000); and Gregorevic et al., *Mol. Ther.* 16:657-64 (2008)), myostatin propeptide, follistatin, activin type II soluble receptor, IGF-1, anti-inflammatory polypeptides such as the Ikappa B dominant mutant, sarcospan, utrophin (Tinsley et al., (1996) *Nature* 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, $\alpha_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor-α and -β, and the like), lysosomal acid α-glucosidase, α-galactosidase A, receptors (e.g., the tumor necrosis growth factor α soluble receptor), S100A1, parvalbumin, adenylyl cyclase type 6, a molecule that effects G-protein coupled receptor kinase type 2 knockdown such as a truncated constitutively active bARKct, anti-inflammatory factors such as IRAP, anti-myostatin proteins, aspartoacylase, and monoclonal antibodies (including single chain monoclonal antibodies; an exemplary Mab is the Herceptin® Mab). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. Parvovirus vectors can also be used to deliver monoclonal antibodies and antibody fragments, for example, an antibody or antibody fragment directed against myostatin (see, e.g., Fang et al., *Nature Biotechnol.* 23:584-590 (2005)).

Heterologous nucleic acid sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Alternatively, in particular embodiments of this invention, the heterologous nucleic acid may encode an antisense nucleic acid, a ribozyme (e.g., as described in U.S. Pat. No. 5,877,022), RNAs that effect spliceosome-mediated trans-splicing (see, Puttaraju et al., (1999) *Nature Biotech.* 17:246; U.S. Pat. Nos. 6,013,487; 6,083,702), interfering RNAs (RNAi) including siRNA, shRNA or miRNA that mediate gene silencing (see, Sharp et al., (2000) *Science* 287:2431), and other non-translated RNAs, such as "guide" RNAs (Gorman et al., (1998) *Proc. Nat. Acad. Sci. USA* 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al., *J. Gene Med.* 10:132-142 (2008) and Li et al., *Acta Pharmacol Sin.* 26:51-55 (2005)); phospholamban inhibitory or dominant-negative molecules such as phospholamban S16E (e.g., to treat cardiovascular disease, see, e.g., Hoshijima et al. *Nat. Med.* 8:864-871 (2002)), RNAi to adenosine kinase (e.g., for epilepsy), RNAi to a sarcoglycan [e.g., α, β, γ], RNAi against myostatin, myostatin propeptide, follistatin, or activin type II soluble receptor, RNAi against anti-inflammatory polypeptides such as the Ikappa B dominant mutant, and RNAi directed against pathogenic organisms and viruses (e.g., hepatitis B virus, human immunodeficiency virus, CMV, herpes simplex virus, human papilloma virus, etc.).

Alternatively, in particular embodiments of this invention, the heterologous nucleic acid may encode protein phosphatase inhibitor I (I-1), serca2a, zinc finger proteins that regulate the phospholamban gene, Barkct, β2-adrenergic receptor, β2-adrenergic receptor kinase (BARK), phosphoinositide-3 kinase (PI3 kinase), a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, enos, inos, or bone morphogenic proteins (including BNP 2, 7, etc., RANKL and/or VEGF).

The virus vector may also comprise a heterologous nucleic acid that shares homology with and recombines with a locus on a host chromosome. This approach can be utilized, for example, to correct a genetic defect in the host cell.

The present invention also provides virus vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccine vectors is known in the art (see, e.g., Miyamura et al., (1994) *Proc. Nat. Acad Sci USA* 91:8507; U.S. Pat. No. 5,916,563 to Young et al., U.S. Pat. No. 5,905,040 to Mazzara et al., U.S. Pat. Nos. 5,882,652, 5,863,541 to Samulski et al.). The antigen may be presented in the parvovirus capsid. Alternatively, the antigen may be expressed from a heterologous nucleic acid introduced into a recombinant vector genome. Any immunogen of interest as described herein and/or as is known in the art can be provided by the virus vector of the present invention.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia L1 or L8 gene products), a flavivirus immunogen (e.g., a yellow fever virus immunogen or a Japanese encephalitis virus immunogen), a Filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpes immunogen (e.g., CMV, EBV, HSV immunogens) a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell. Exemplary cancer and tumor cell antigens are described in S. A. Rosenberg (Immunity 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J. Exp. Med.,* 180:347; Kawakami et al., (1994) *Cancer Res.* 54:3124), MART-1, gp100 MAGE-1, MAGE-2, MAGE-3, CEA, TRP-1, TRP-2, P-15, tyrosinase (Brichard et al., (1993) *J. Exp. Med.* 178: 489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified (see, e.g., Rosenberg, (1996) *Ann. Rev. Med.* 47:481-91).

As a further alternative, the heterologous nucleic acid can encode any polypeptide that is desirably produced in a cell in vitro, ex vivo, or in vivo. For example, the virus vectors may be introduced into cultured cells and the expressed gene product isolated therefrom.

It will be understood by those skilled in the art that the heterologous nucleic acid(s) of interest can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present invention provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the present invention can be employed to deliver a heterologous nucleic acid encoding a polypeptide or functional RNA to treat and/or prevent any disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, follistatin, activin type II soluble receptor, anti-inflammatory polypeptides such as the Ikappa B dominant mutant, sarcospan, utrophin, mini-utrophin, RNAi against splice junctions in the dystrophin gene to induce exon skipping [see, e.g., WO/2003/095647], antisense against U7 snRNAs to induce exon skipping [see, e.g., WO/2006/021724], and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic defects, congenital emphysema (al-antitrypsin), Lesch-Nyhan Syndrome (hypoxanthine guanine phosphoribosyl transferase), Niemann-Pick disease (sphingomyelinase), Tays Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1), serca2a, zinc finger proteins that regulate the phospholamban gene, Barkct, β2-adrenergic receptor, β2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as TRAP and TNFα soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

Gene transfer has substantial potential use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors according to the present invention permit the treatment and/or prevention of genetic diseases.

The virus vectors according to the present invention may also be employed to provide a functional RNA to a cell in vitro or in vivo. Expression of the functional RNA in the cell, for example, can diminish expression of a particular target protein by the cell. Accordingly, functional RNA can be administered to decrease expression of a particular protein in a subject in need thereof. Functional RNA can also be administered to cells in vitro to regulate gene expression and/or cell physiology, e.g., to optimize cell or tissue culture systems or in screening methods.

Virus vectors according to the instant invention find use in diagnostic and screening methods, whereby a nucleic acid of interest is transiently or stably expressed in a cell culture system, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the virus vectors of the present invention may be used to produce an immune response in a subject. According to this embodiment, a virus vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the virus vector may be administered to a cell ex vivo and the altered cell is administered to the subject. The virus vector comprising the heterologous nucleic acid is introduced into the cell, and the cell is administered to the subject, where the heterologous nucleic acid encoding the immunogen can be expressed and induce an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to an immunogen by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In particular embodiments, the virus vector or cell comprising the heterologous nucleic acid can be administered in an immunogenically effective amount, as described below.

The virus vectors of the present invention can also be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vivo or by using ex vivo methods, as described herein. Alternatively, the cancer antigen can be expressed as part of the virus capsid or be otherwise associated with the virus capsid as described above.

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the invention provides a method of treating and/or preventing tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In particular embodiments, cells may be removed from a subject with cancer and contacted with a virus vector according to the instant invention. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector.

Cytokines may be administered by any method known in the art. Exogenous cytokines may be administered to the subject, or alternatively, a nucleic acid encoding a cytokine may be delivered to the subject using a suitable vector, and the cytokine produced in vivo.

Subjects, Pharmaceutical Formulations, and Modes of Administration

Virus vectors and capsids according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles and adults.

In particular embodiments, the present invention provides a pharmaceutical composition comprising a virus vector and/or capsid of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, more preferably at least about $10^5$ infectious units are introduced to the cell.

The cell(s) into which the virus vector is introduced can be of any type, including but not limited to neural cells (including cells of the peripheral and central nervous systems, in particular, brain cells such as neurons and oligodendrocytes), lung cells, cells of the eye (including retinal cells, retinal pigment epithelium, and corneal cells), blood vessel cells (e.g., endothelial cells, intimal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, kidney cells, myocardial cells, bone cells (e.g., bone marrow stem cells), hematopoietic stem cells, spleen cells, keratinocytes, fibroblasts, endothelial cells, prostate cells, germ cells, and the like. In representative embodiments, the cell can be any progenitor cell. As a further possibility, the cell can be a stem cell (e.g., neural stem cell, liver stem cell). As still a further alternative, the cell can be a cancer or tumor cell. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo gene delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the virus vector to subjects. Administration of the virus vectors and/or capsids according to the present invention to a human subject or an animal in need thereof can be by any means known in the art. Optionally, the virus vector and/or capsid is delivered in a treatment effective or prevention effective dose in a pharmaceutically acceptable carrier.

The virus vectors and/or capsids of the invention can further be administered to elicit an immunogenic response (e.g., as a vaccine). Typically, immunogenic compositions of the present invention comprise an immunogenically effective amount of virus vector and/or capsid in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^{13}$, $10^{14}$, $10^{15}$ transducing units, optionally about $10^8$-$10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, intraendothelial, in utero (or in ovo), parenteral (e.g., intravenous, subcutaneous, intradermal, intracranial, intramuscular [including administration to skeletal, diaphragm and/or cardiac muscle], intrapleural, intracerebral, and intraarticular), topical (e.g., to both skin and mucosal surfaces, including airway surfaces, and transdermal administration), intralymphatic, and the like, as well as direct tissue or organ injection (e.g., to liver, eye, skeletal muscle, cardiac muscle, diaphragm muscle or brain).

Administration can be to any site in a subject, including, without limitation, a site selected from the group consisting of the brain, a skeletal muscle, a smooth muscle, the heart, the diaphragm, the airway epithelium, the liver, the kidney, the spleen, the pancreas, the skin, and the eye.

Administration can also be to a tumor (e.g., in or near a tumor or a lymph node). The most suitable route in any given case will depend on the nature and severity of the condition being treated and/or prevented and on the nature of the particular vector that is being used.

Administration to skeletal muscle according to the present invention includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis brevis, abductor pollicis longus, adductor brevis, adductor hallucis, adductor longus, adductor magnus, adductor pollicis, anconeus, anterior scalene, articularis genus, biceps brachii, biceps femoris, brachialis, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis brevis, extensor carpi radialis longus, extensor carpi ulnaris, extensor digiti minimi, extensor digitorum, extensor digitorum brevis, extensor digitorum longus, extensor hallucis brevis, extensor hallucis longus, extensor indicis, extensor pollicis brevis, extensor pollicis longus, flexor carpi radialis, flexor carpi ulnaris, flexor digiti minimi brevis (in the hand), flexor digiti minimi brevis (in the foot), flexor digitorum brevis, flexor digitorum longus, flexor digitorum profundus, flexor digitorum superficialis, flexor hallucis brevis, flexor hallucis longus, flexor pollicis brevis, flexor pollicis longus, frontalis, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris brevis, palmaris longus, pectineus, pectoralis major, pectoralis minor, peroneus brevis, peroneus longus, peroneus tertius, piriformis, plantar interossei, plantaris, platysma, popliteus, posterior scalene, pronator quadratus, pronator teres, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus intermedius, vastus lateralis, vastus medialis, zygomaticus major, and zygomaticus minor, and any other suitable skeletal muscle as known in the art.

The virus vector can be delivered to skeletal muscle by intravenous administration, intra-arterial administration, intraperitoneal administration, limb perfusion, (optionally, isolated limb perfusion of a leg and/or arm; see, e.g. Arruda et al., (2005) *Blood* 105: 3458-3464), and/or direct intramuscular injection. In particular embodiments, the virus vector and/or capsid is administered to a limb (arm and/or leg) of a subject (e.g., a subject with muscular dystrophy such as DMD) by limb perfusion, optionally isolated limb perfusion (e.g., by intravenous or intra-articular administration. In embodiments of the invention, the virus vectors and/or capsids of the invention can advantageously be administered without employing "hydrodynamic" techniques. Tissue delivery (e.g., to muscle) of prior art vectors is often enhanced by hydrodynamic techniques (e.g., intravenous/intravenous administration in a large volume), which increase pressure in the vasculature and facilitate the ability of the vector to cross the endothelial cell barrier. In particular embodiments, the viral vectors and/or capsids of the invention can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome.

Administration to cardiac muscle includes administration to the left atrium, right atrium, left ventricle, right ventricle and/or septum. The virus vector and/or capsid can be delivered to cardiac muscle by intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Administration to smooth muscle can be by any suitable method including intravenous administration, intra-arterial administration, and/or intra-peritoneal administration. In one embodiment, administration can be to endothelial cells present in, near, and/or on smooth muscle.

Delivery to a target tissue can also be achieved by delivering a depot comprising the virus vector and/or capsid. In representative embodiments, a depot comprising the virus vector and/or capsid is implanted into skeletal, smooth, cardiac and/or diaphragm muscle tissue or the tissue can be contacted with a film or other matrix comprising the virus vector and/or capsid. Such implantable matrices or substrates are described in U.S. Pat. No. 7,201,898.

In particular embodiments, a virus vector according to the present invention is administered to skeletal muscle, diaphragm muscle and/or cardiac muscle (e.g., to treat and/or prevent muscular dystrophy or heart disease [for example, PAD or congestive heart failure]).

In representative embodiments, the invention is used to treat and/or prevent disorders of skeletal, cardiac and/or diaphragm muscle.

In a representative embodiment, the invention provides a method of treating and/or preventing muscular dystrophy in a subject in need thereof, the method comprising: administering a treatment or prevention effective amount of a virus vector of the invention to a mammalian subject, wherein the virus vector comprises a heterologous nucleic acid encoding dystrophin, a mini-dystrophin, a micro-dystrophin, myostatin propeptide, follistatin, activin type II soluble receptor, IGF-1, anti-inflammatory polypeptides such as the Ikappa B dominant mutant, sarcospan, utrophin, a micro-dystrophin, laminin-α2, α-sarcoglycan, β-sarcoglycan, γ-sarcoglycan, δ-sarcoglycan, IGF-1, an antibody or antibody fragment against myostatin or myostatin propeptide, and/or RNAi against myostatin. In particular embodiments, the virus vector can be administered to skeletal, diaphragm and/or cardiac muscle as described elsewhere herein.

Alternatively, the invention can be practiced to deliver a nucleic acid to skeletal, cardiac or diaphragm muscle, which is used as a platform for production of a polypeptide (e.g., an enzyme) or functional RNA (e.g., RNAi, microRNA, antisense RNA) that normally circulates in the blood or for systemic delivery to other tissues to treat and/or prevent a disorder (e.g., a metabolic disorder, such as diabetes (e.g., insulin), hemophilia (e.g., Factor IX or Factor VIII), a mucopolysaccharide disorder (e.g., Sly syndrome, Hurler Syndrome, Scheie Syndrome, Hurler-Scheie Syndrome, Hunter's Syndrome, Sanfilippo Syndrome A, B, C, D, Morquio Syndrome, Maroteaux-Lamy Syndrome, etc.) or a lysosomal storage disorder (such as Gaucher's disease [glucocerebrosidase], Pompe disease [lysosomal acid α-glucosidase] or Fabry disease [α-galactosidase A]) or a glycogen storage disorder (such as Pompe disease [lysosomal acid α glucosidase]). Other suitable proteins for treating and/or preventing metabolic disorders are described above. The use of muscle as a platform to express a nucleic acid of interest is described in U.S. Patent Publication No. 2002/0192189.

Thus, as one aspect, the invention further encompasses a method of treating and/or preventing a metabolic disorder in a subject in need thereof, the method comprising: administering a treatment or prevention effective amount of a virus vector of the invention to a subject (e.g., to skeletal muscle of a subject), wherein the virus vector comprises a heterologous nucleic acid encoding a polypeptide, wherein the metabolic disorder is a result of a deficiency and/or defect in the polypeptide. Illustrative metabolic disorders and heterologous nucleic acids encoding polypeptides are described herein. Optionally, the polypeptide is secreted (e.g., a polypeptide that is a secreted polypeptide in its native state or that has been engineered to be secreted, for example, by operable association with a secretory signal sequence as is known in the art). Without being limited by any particular theory of the invention, according to this embodiment, administration to the skeletal muscle can result in secretion of the polypeptide into the systemic circulation and delivery to target tissue(s). Methods of delivering virus vectors to skeletal muscle are described in more detail herein.

The invention can also be practiced to produce antisense RNA, RNAi or other functional RNA (e.g., a ribozyme) for systemic delivery.

The invention also provides a method of treating and/or preventing congenital heart failure or PAD in a subject in need thereof, the method comprising administering a treatment or prevention effective amount of a virus vector of the invention to a mammalian subject, wherein the virus vector comprises a heterologous nucleic acid encoding, for example, a sarcoplasmic endoreticulum $Ca^{2+}$-ATPase (SERCA2a), an angiogenic factor, phosphatase inhibitor I (I-1), RNAi against phospholamban; a phospholamban inhibitory or dominant-negative molecule such as phospholamban S16E, a zinc finger protein that regulates the phospholamban gene, β2-adrenergic receptor, β2-adrenergic receptor kinase (BARK), PI3 kinase, calsarcan, a β-adrenergic receptor kinase inhibitor (βARKct), inhibitor 1 of protein phosphatase 1, S100A1, parvalbumin, adenylyl cyclase type 6, a molecule that effects G-protein coupled receptor kinase type 2 knockdown such as a truncated constitutively active bARKct, Pim-1, PGC-1α, SOD-1, SOD-2, EC-SOD, kallikrein, HIF, thymosin-β4, mir-1, mir-133, mir-206 and/or mir-208.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local rather than systemic manner, for example, in a depot or sustained-release formulation. Further, the virus vector and/or virus capsid can be delivered adhered to a surgically implantable matrix (e.g., as described in U.S. Patent Publication No. 2004-0013645).

The virus vectors disclosed herein can be administered to the lungs of a subject by any suitable means, optionally by administering an aerosol suspension of respirable particles comprised of the virus vectors and/or virus capsids, which the subject inhales. The respirable particles can be liquid or solid. Aerosols of liquid particles comprising the virus vectors and/or virus capsids may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors and/or capsids may likewise be produced with any solid particulate medicament aerosol generator, by techniques known in the pharmaceutical art.

The virus vectors can be administered to tissues of the CNS (e.g., brain, eye) and may advantageously result in broader distribution of the virus vector or capsid than would be observed in the absence of the present invention.

In particular embodiments, the delivery vectors of the invention may be administered to treat diseases of the CNS, including genetic disorders, neurodegenerative disorders, psychiatric disorders and tumors. Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present invention can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector of the invention.

Retinitis pigmentosa, by comparison, is characterized by retinal degeneration. In representative embodiments, retinitis pigmentosa can be treated by intraocular (e.g., vitreal administration) of a delivery vector encoding one or more neurotrophic factors.

Age-related macular degeneration involves both angiogenesis and retinal degeneration. This disorder can be treated by administering the inventive delivery vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other embodiments, the present invention may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, the invention can also be used to treat epilepsy, which is marked by multiple seizures over time.

In one representative embodiment, somatostatin (or an active fragment thereof) is administered to the brain using a delivery vector of the invention to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins as are known in the art.

In particular embodiments, the vector can comprise a secretory signal as described in U.S. Pat. No. 7,071,172.

In representative embodiments of the invention, the virus vector and/or virus capsid is administered to the CNS (e.g., to the brain or to the eye). The virus vector and/or capsid may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes. cortex, basal ganglia, hippocampus and portaamygdala), limbic system, neocortex, corpus striatum, cerebrum, and inferior colliculus. The virus vector and/or capsid may also be administered to different regions of the eye such as the retina, cornea and/or optic nerve.

The virus vector and/or capsid may be delivered into the cerebrospinal fluid (e.g., by lumbar puncture) for more disperse administration of the delivery vector. The virus vector and/or capsid may further be administered intravascularly to the CNS in situations in which the blood-brain barrier has been perturbed (e.g., brain tumor or cerebral infarct).

The virus vector and/or capsid can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intra-ocular (e.g., intra-vitreous, sub-retinal, anterior chamber) and peri-ocular (e.g., sub-Tenon's region) delivery as well as intramuscular delivery with retrograde delivery to motor neurons.

In particular embodiments, the virus vector and/or capsid is administered in a liquid formulation by direct injection (e.g., stereotactic injection) to the desired region or compartment in the CNS. In other embodiments, the virus vector and/or capsid may be provided by topical application to the desired region or by intra-nasal administration of an aerosol formulation. Administration to the eye, may be by topical application of liquid droplets. As a further alternative, the virus vector and/or capsid may be administered as a solid, slow-release formulation (see, e.g., U.S. Pat. No. 7,201,898).

In yet additional embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

Having described the present invention, the same will be explained in greater detail in the following examples, which are included herein for illustration purposes only, and which are not intended to be limiting to the invention.

Example 1

Materials and Methods

Rep Cloning—pXR2 (Rep2Cap2) and pRep5Cap2 AAV helper plasmids served as templates for Rep cloning. The primer sequences used are indicated in Table 4. Two cloning strategies were used. Existing restriction sites were incorporated into primers for PCR (PCR-RD in Table 4) utilizing either pXR out fw or pXR out rev primers. PfuTurbo DNA Polymerase (Stratagene, La Jolla, CA) was used at the manufacturer's recommendations for all PCR reactions. PCR-RD products were digested with the enzymes indicated in Table 4 (NEB, Ipswich, MA) prior to ligation with T4

DNA Ligase (Invitrogen, Carlsbad, CA) according to the manufacturer's instructions. Alternately, an overlap-extension mediated PCR (OE-PCR) approach was used to produce Rep chimeras (Higuchi et al. (1988) *Nucleic Acids Res.* 16:7351). The Rep2 and Rep5 junction was incorporated into forward and reverse primers which were used in separate PCR reactions with the pXR out fw and rev primers (Table 4, only fw oligos indicated, rev oligos complimentary to fw). These overlapping PCR products were combined into a single PCR reaction and cycled as follows: 1 cycle at 94° C. for 30 seconds, 18 cycles of 30 seconds at 94° C., 30 seconds at 65° C., and 4 minutes at 72° C., 1 cycle of 10 minutes at 72° C. 1 μl of this reaction was used as template for a nested PCR with the pXR in fw and rev primers. Chimeras with the N-terminus of Rep2 and C-terminus of Rep5 were cloned into the Rep25aa166 construct between the PpuMI and MfeI sites. Chimeras with the N-terminus of Rep5 and C-terminus of Rep2 were cloned into the 52aa160 construct between the PpuMI and BstBI sites. All constructs were verified by DNA sequencing at the UNC-CH Genome Analysis Facility.

TABLE 4

| Clone/ Primer | Cloning Method | Orien- tation | Sequence | SEQ ID NO |
|---|---|---|---|---|
| pXR out fw | | Forward | 5' CGAAAAGTGCCACCTGACGTCTAAGAAACC | 126 |
| pXR in fw | | Forward | 5' TCGAATTCGACGGCCAGTGAATTGTAATACGACTC | 127 |
| pXR out rev | | Reverse | 5' CCATGATTACGCCAAGCTCGGAATTAACCGCATGC GA | 128 |
| pXR in rev | | Reverse | 5' CCATGGCCGGGCCCGGATTCACC | 129 |
| Rep52aa84 | PCR-RD AleI | Reverse | 5' TTCACCCCGGTGGTTTCCACGAGCACGTGCATGTG GAAGTAGCTCTCTCCCTTTTCAAACTGCACAAAG | 130 |
| Rep52aa110 | PCR-RD EagI | Forward | 5' CCTCGGCCGCTACGTGAGTCAGATTCGCGAAAAAC TGATTCAGAG | 131 |
| Rep52aa126 | OE PCR | Forward | 5' GTGGTCTTCCAGGGAATTGAACCCACTTTGCCAAA CTGGTTCGCGGTC | 132 |
| Rep52aa138 | OE PCR | Forward | 5' CTGGGTCGCCATCACCAAGGTAAAGAAGGGAGGCG GGAACAAGGTGGTGGATGAG | 133 |
| Rep52aa146 | OE PCR | Forward | 5' GCGGAGCCAATAAGGTGGTGGATGAGTGCTACATC CCCAATTACTTGCTC | 134 |
| Rep52aa160 | PCR-RD Bpu10I | Reverse | 5' ACTGGAGCTCAGGTTGGACCTTCGGCAGCAGGTAG | 135 |
| Rep52aa175 | OE PCR | Forward | 5' CGTGGACAAACCTGGACGAGTATAAATTGGCCTGT TTGAATCTCACGGAGCGTAAAC | 136 |
| Rep52aa187 | OE PCR | Forward | 5' CTGAATCTGGAGGAGCGCAAACGGTTGGTGGCGCA GCATCTGACGCAC | 137 |
| Rep52aa207 | PCR-RD SgrAI | Reverse | 5' GATCACCGGCGCATCCGAGAACTCACGCTGCGAAG C | 138 |
| Rep25aa77 | OE PCR | Forward | 5' TAAGGCCCCGGAGGCCCTTTTCTTTGTGCAGTTTG AAAAGGGATCTG | 139 |
| Rep25aa97 | OE PCR | Forward | 5' CCACATGCACGTGCTCGTGGAAACCTCCGGCATCT CTTCCATGGTCCTCG | 140 |
| Rep25aa116 | PCR-RD NruI | Forward | 5' TCAGATTCGCGAAAAACTGGTGAAAGTGGTCTTCC AGG | 141 |
| Rep25aa125 | OE PCR | Forward | 5' GAATTTACCGCGGGATCGAGCCGCAGATCAACGAC TGGGTCGCCATC | 142 |
| Rep25aa141 | OE PCR | Forward | 5' GGTCACAAAGACCAGAAATGGCGCCGGCGGAGCCA ATAAGGTGGTGGATTCTGG | 143 |
| Rep25aa149 | OE PCR | Forward | 5' GAGGCGGGAACAAGGTGGTGGATTCTGGGTATATT CCCGCCTACCTGC | 144 |
| Rep25aa166 | PCR-RD Bpu10I | Forward | 5' CCAGCCTGAGCTCCAGTGGGCGTGGACAAACCTG | 145 |
| Rep25aa187 | OE PCR | Forward | 5' GTTTGAATCTCACGGAGCGTAAACGGCTCGTCGCG CAGTTTCTGGCAG | 146 |
| Rep25aa216 | PCR-RD SgrAI | Forward | 5' ATGCGCCGGTGATCAAAAGCAAGACTTCCCAGAAA TACATGG | 147 |

TABLE 4-continued

| Clone/ Primer | Cloning Method | Orien- tation | Sequence | SEQ ID NO |
|---|---|---|---|---|
| ITR2 Half1 Kpn | | Forward | 5' ATTATAGGTACCAGGAACCCCTAGTGATG | 148 |
| ITR2 Half1 Sfi | | Reverse | 5' TAATAGGGCCCAAAGGGCCGGG | 149 |
| ITR2 Half2 Sfi | | Forward | 5' TTAATAGGCCCTTTGGGCCGGG | 150 |
| ITR2 Half2 Hind | | Reverse | 5' TATAATAAGCTTAGGAACCCCTAGTGATGGAG | 151 |
| ITR5 Half1 Kpn | | Forward | 5' ATTATAGGTACCTACAAAACCTCCTTGCTTGAG | 152 |
| ITR5 Half1 Sfi | | Reverse | 5' TTAATAGGCCCTTTGGGCCGTCGC | 153 |
| ITR5 Half2 Sfi | | Forward | 5' TTAATAGGCCCAAAGGGCCGTCGTC | 154 |
| ITR5 Half2 Hind | | Reverse | 5' TATAATAAGCTTTACAAAACCTCCTTGCTTGAGAG | 155 |

ITR Cloning—ITRs were cloned into a pUC-18 plasmid with a GFP cassette (CMV promoter, SV40 polyA) cloned between the KpnI and EcoRI restriction sites. The ITRs were synthesized in two halves as 4 nmol Ultramer DNA oligos (Integrated DNA Technologies, Coralville, IA). SfiI restriction sites were incorporated into one hairpin arm the ITR for cloning (FIG. 1A). Due to inconsistencies of the reported sequence at the tip of the ITR5 hairpins between Chiorini et al. (1999), the published GenBank sequence (accession number NC_006152), and restriction mapping, an ITR2 hairpin was utilized for the ITR5 construct (FIG. 1A). 200 pg of each oligo was amplified in a PCR reaction using the ITR primers listed in Table 4. 2.5 U of PfuTurbo DNA Polymerase (Stratagene, La Jolla, CA) was used to amplify each half of the ITR as follows: 1 cycle at 94° C. for 4 minutes, 35 cycles of 45 seconds at 94° C., 30 seconds at 50° C., and 30 seconds at 72° C., 1 cycle of 10 minutes at 72° C. PCR reactions were purified and subject to digestion by KpnI and SfiI or HindIII and SfiI (NEB, Ipswich, MA). A triple ligation with the pUC-18 GFP plasmid and each half of the ITR was performed with T4 DNA Ligase (Invitrogen, Carlsbad, CA) for 1.5 hours at room temperature. All constructs were verified by DNA sequencing at the UNC-CH Genome Analysis Facility after linearization of the plasmid and ablation of the ITR secondary structure by SfiI digestion.

Western Blot Analysis—Samples for Western blot analysis were harvested 48-72 hours after transfection of Ad-helper plasmid and the appropriate AAV helper construct. Cells were washed and resuspended in 100 μl PBS prior to addition of 100 μl 2× Laemmli Sample Buffer (100 mM Tris pH 6.8, 4% SDS, 200 mM DTT, 20% glycerol, 0.1% Bromophenol Blue). Samples were briefly sonicated and boiled for 10 minutes. Samples were run on NUPAGE 4-12% Bis-Tris gels (Invitrogen, Carlsbad, CA) at 160 volts for 90 minutes. Protein was transferred to a Nitrocellulose membrane (Invitrogen, Carlsbad, CA) via a wet transfer for 60 minutes at 30 volts. Gels were blocked overnight in 10% nonfat dry milk in 1×PBS/Tween (0.05%). Detection of both Rep2 and Rep5 proteins (all four sizes) was achieved with a monoclonal Anti-Adeno-Associated Virus Rep Protein antibody (clone 259.5, American Research Products, Belmont, MA) at a 1:20 dilution in PBS/Tween for 60 minutes at room temperature. After washing, a secondary HRP anti-mouse antibody was added at a 1:5,000 dilution in PBS/Tween for one hour at room temperature. After washing, SuperSignal West Femto Maximum Sensitivity Substrate (Pierce, Rockford, IL) was added and blots were exposed to X-ray film.

Cell Culture and rAAV Production—HEK 293 cells were obtained from ATCC and cultured in Dulbecco Modified Eagle Medium (DMEM) supplemented with 10% Fetal Bovine Serum (Sigma, St. Louis, MO) and 100 units/ml penicillin and 100 μg/ml streptomycin and grown at 37° C. with 5% $CO_2$ saturation. Transfections were performed in six-well cell culture plates. 0.75 μg each of Ad-helper plasmid, AAV helper plasmid (either Rep2Cap2, Rep5Cap2, or the Rep mutant described), and the GFP plasmid containing the ITR (mutant or wt ITR as specified in text) were triple-transfected with polyethyleneimine (PEI) (25,000 linear molecular weight) as described (Xiao et al. (1998) *J. Virol.* 72:2224). Cells were harvested 48-72 hours post-transfection.

Hirt DNA Purification and Southern Blot Analysis—Hirt DNA purification was performed as described (Hirt (1967) *J. Mol. Biol.* 26:365). Cells were harvested 48-72 hours post-transfection, washed in PBS, and resuspended in 370 μl Hirt Solution (0.01M Tris-HCl pH 7.5 and 0.1M EDTA) prior to addition of 25 μl 10% SDS and 165 μl 5 M NaCl. Samples were incubated at 4° C. overnight prior to centrifugation. DNA was purified by phenol chloroform extraction and precipitated by an equal volume of isopropanol prior to resuspension in 50 μl sterile $ddH_2O$. 5 ul of each sample was digested with 4 U DpnI (NEB, Ipswich, MA) 2-4 hours at 37° C. prior to gel electrophoresis and Southern blot analysis to remove non-replicated transfected plasmid (Chomczynski (1992) *Anal. Biochem.* 201:134). The nylon membrane (Hybond-XL; GE Healthcare Life Sciences, Piscataway, NJ) was hybridized to a probe corresponding to the GFP open reading frame labeled with the Random Primed DNA Labeling Kit (Roche, Indianapolis, IN) and d-CTP $P^{32}$. Blots were visualized after exposure to a phosphorimager screen (GE Healthcare Life Sciences, Piscataway, NJ).

Densitometry—Densitometry was performed using the public domain NIH Image program (developed at the U.S. National Institutes of Health available on the Internet at the NIH website). Densitometry analysis of a DpnI resistant band on the agarose gel prior to transfer was used as a loading control to normalize values obtained from the Southern blot. The lowest value (absence of any vector replication) was subtracted from all values to account for background. In order to gauge relative replication efficiency, values for ITR2 vectors were divided by the value obtained from the Rep2-ITR2 control. ITR5 vectors were compared to the Rep5-ITR5 control. All values were obtained in triplicate (n=3). Error bars represent standard error (standard deviation divided by the root of 3). All samples were compared to controls on the same blot.

Molecular Modeling—Molecular models were generated using Swiss-Model (available at the expasy.org website). The published crystal structure of the N-terminus of Rep5 complexed with the RBE (PDB accession #1rz9) was used as a template for all models. Visualization of protein structure rendering of images were performed with PyMOL (available at pymol.org). DNA folding was performed using the DNA mfold server (available at mfold.bioinfo.rpi.edu).

Example 2

Construction and Characterization of Chimeric ITRs

Previously, AAV replicative specificity was postulated to be driven by the trs sequence (Chiorini et al. (1999) *J. Virol.* 73:4293; Chiorini et al. (1999) *J. Virol.* 73:1309). Rep2 can nick the ITR2 trs (AGT/TGG) and the AAVS1 trs of human chromosome 19 (GGT/TGG) (Wu et al. (2001) *Arch. Biochem. Biophys.* 389:271). Rep5 nicks only the ITR5 trs (AGTG/TGG). However, alignment of the ITR2 and ITR5 sequences revealed several significant sequence and structural differences outside the trs sequence (FIG. 1A). The spacing between the putative RBE and the nicking stem was significantly different; three nucleotides (nt) for ITR2 and 15 nt for ITR5. Additionally, while the trs sequence is not tightly conserved between ITR2 and ITR5, neither is the height or overall length of the putative nicking stem.

A novel method was used to generate mutant ITRs in order to determine which portions of the ITR were responsible for replicative specificity. Previous studies have investigated Rep-ITR interactions in vitro largely due to the difficulty of synthesizing full length ITRs for in vivo assays. PCR through the secondary structure of the ITR is inefficient and sequencing through these elements typically requires radiolabeled chain-terminator sequencing (Young et al. (2000) *J. Virol.* 74:3953). The AAV ITRs are highly recombinogenic and are frequently mutated even in a plasmid context (Samulski et al. (1983) *Cell* 33:135).

In order to address these concerns, the ITRs were synthesized and amplified in halves (FIGS. 36A-36C). To assemble the halves, a SfiI site was included in one of the hairpin arms of the ITR. SfiI allowed the conservation of the RBE' sequence (Brister and Muzyczka (2000) *J. Virol.* 74:7762). Cloning the ITR in a double D element (DD) format required only one ITR per plasmid for replication (Xiao et al. (1997) *J. Virol.* 71:941). The three core Rep functions necessary for AAV replication (Rep binding, helicase, and nicking) were analyzed by the presence or absence of intracellular replication of the plasmid. This assay provided the ability to quantitate Rep-ITR function in a physiological setting, removing the concern that highly purified Rep protein might take on aberrant function in vitro. This system also avoided concerns that previous in vitro assays used only a fragment of the ITR or that oligos used to recapitulate the ITR might not fold correctly.

An alignment of ITR2 (SEQ ID NO:17) and ITR5 (SEQ ID NO:18) (FIG. 1A) revealed several divergent elements which might confer Rep specificity. The spacer and nicking stem elements appeared to be the most likely candidates for unique interactions with their cognate Rep protein. This hypothesis was supported by low homology of these elements between AAV2 and AAV5.

Figure 1B:
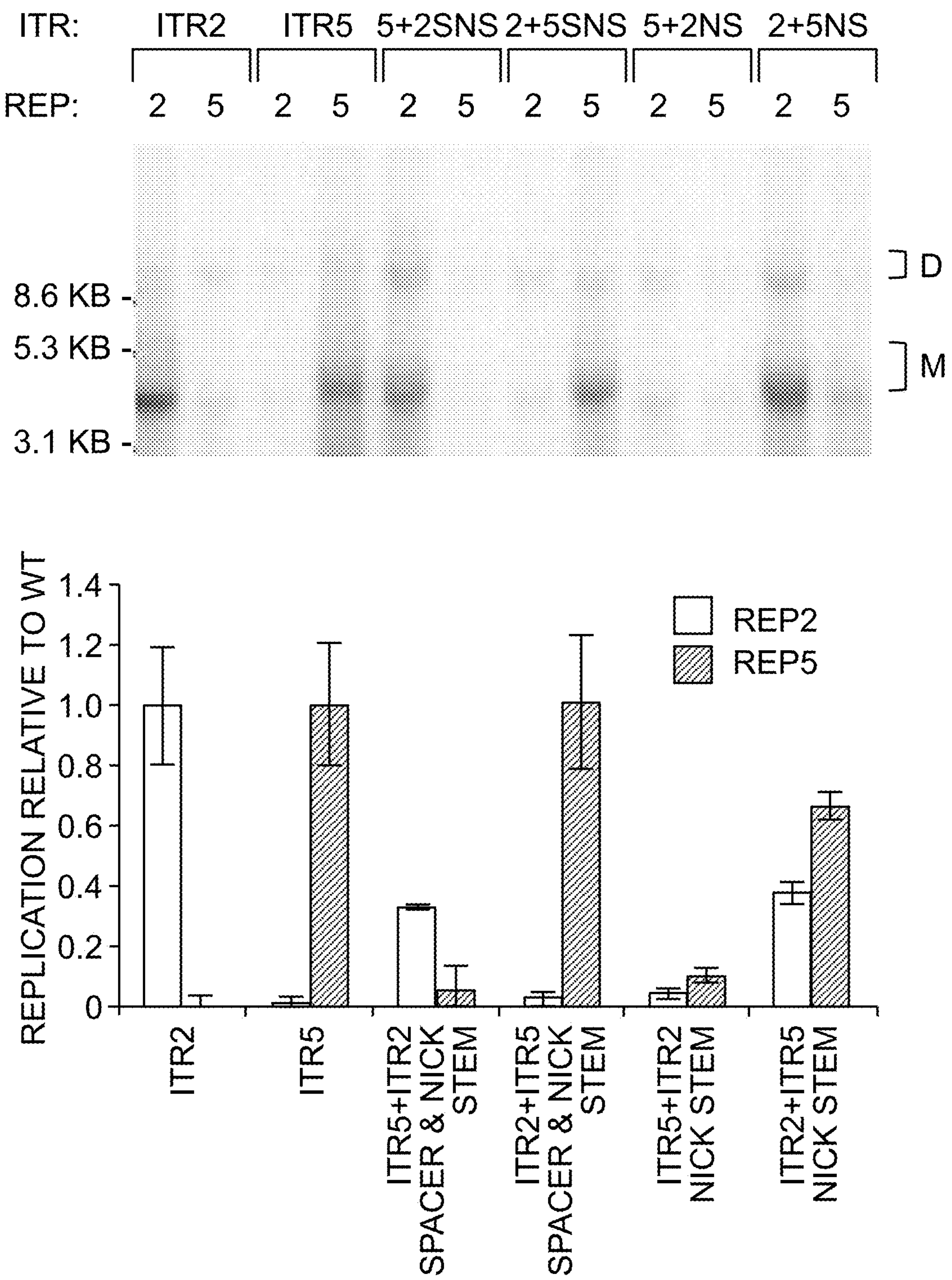

Wt ITRs containing the SfiI site functioned as expected with Rep2 specific to ITR2 and Rep5 specific to ITR5 (FIG. 1B). Rep2-ITR2 replicated approximately 2-fold better than Rep5-ITR5, potentially due to the lower folding energy of ITR5 resulting in reduced plasmid stability prior to replication. Due to this minor difference in replicative fidelity, all ITRs replicated with Rep2 were normalized to Rep2-ITR2, while ITRs replicated with Rep5 were normalized to Rep5-ITR5 (FIG. 1B).

In order to confirm that the RBE and hairpin arms played no role in Rep specificity, we generated a chimeric ITR with ITR5 binding elements and an ITR2 spacer and nicking stem (ITR5+2SNS, SEQ ID NO:19). Only Rep2 replicated this ITR, confirming the determinants of replicative specificity lie in the spacer/nicking stem elements (FIG. 1B). While ITR5+2SNS replication was not as efficient as ITR2-Rep2, it was replicated at ITR5-Rep5 levels. Conversely, Rep5 specifically replicated an ITR comprised of ITR2 hairpins and hairpin spacer and the ITR5 spacer and nicking stem (ITR2+5SNS, SEQ ID NO:20, FIG. 1B). Rep5 replicated this ITR at wt levels. These data demonstrated that Rep-ITR specificity lies outside of the ITR binding regions.

Next, chimeric ITRs were created to explore whether the nicking stem or the spacing between the RBE and nicking stem harbored unique interactions with the Rep protein. An ITR with the ITR5 binding elements and spacer and the ITR2 nicking stem could not be replicated by either Rep2 or Rep5 (ITR5+2NS, SEQ ID NO:21, FIG. 1B). The corresponding chimeric ITR (ITR2 binding elements and spacer with an ITR5 nicking stem) was replicated by both Rep2 and Rep5 (ITR2+5NS, SEQ ID NO:22, FIG. 1B). This disparity suggested that the spacer and nicking stem play different roles in Rep-ITR specificity between AAV2 and AAV5.

Example 3

The Nicking Stem is Important for ITR5 Specificity

Figure 2A:
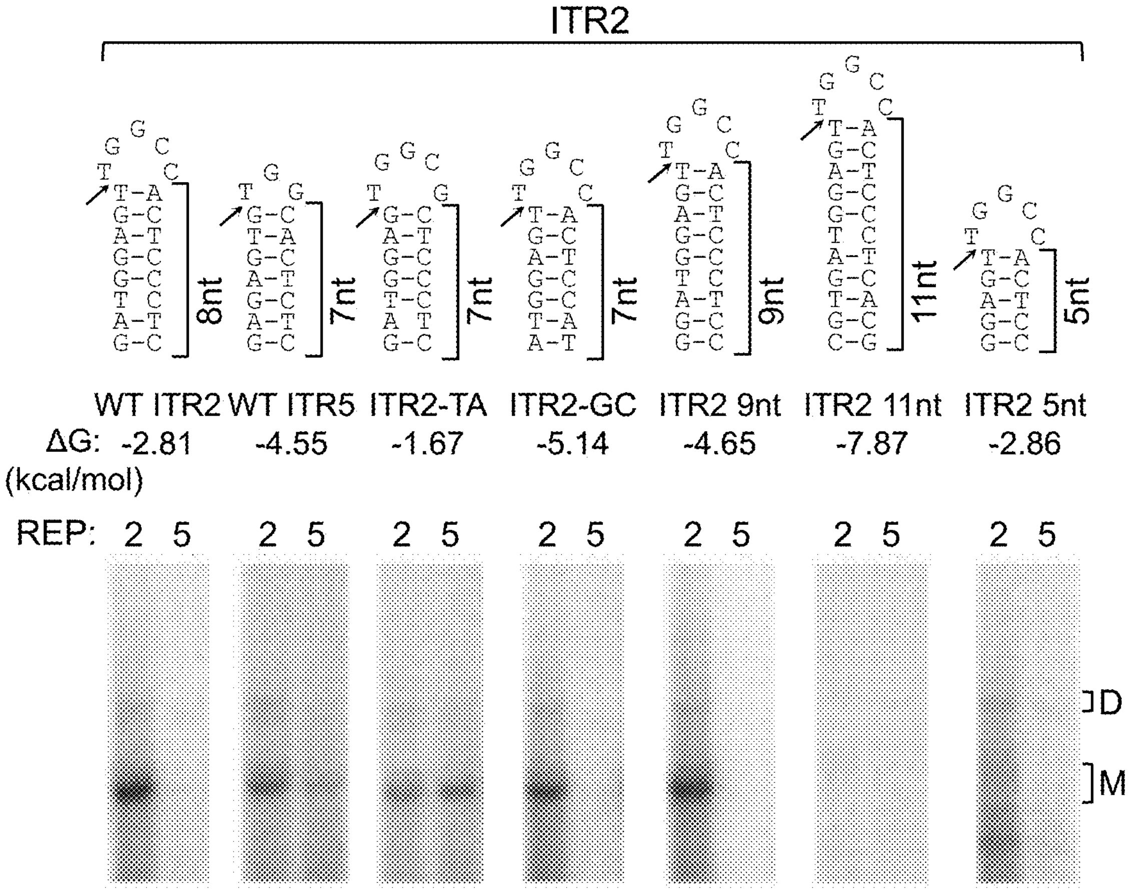
FIGS. 2A-2D show the relation of nicking stem height and sequence to Rep-ITR specificity.

ITR2+5NS (SEQ ID NO:22) established that Rep2 is capable of nicking an ITR with an ITR5 nicking stem and that Rep-ITR specificity is not driven exclusively by the trs sequence (FIG. 1B). In order to determine the flexibility of Rep2 toward mutant nicking stems, ITR2s containing altered forms of the hairpin were generated (FIG. 2A). Rep2 is able to replicate an ITR with an ITR5 nicking stem even though the ITR5 nicking stem contains a different trs sequence, is one bp shorter, and has two fewer unpaired nucleotides at its tip (FIG. 2A). The substitution of the ITR5 nicking stem into ITR2 also allowed replication by Rep5.

To determine which element of the ITR2 nicking stem prevented Rep5 activity, specific portions of the ITR2 stem were altered. First, one bp at the top of the putative ITR2 nicking stem was removed to lower the height to that of ITR5 (ITR2-TA, SEQ ID NO:23). Removing the T-A bp also resulted in a trs resembling ITR5, nicking between G/T opposed to T/T. Rep2 continued to function on this ITR as did Rep5, demonstrating that Rep5 can tolerate five unpaired nucleotides at the tip of the stem as long as the stem height and nt sequence are correct. A similar deletion from the base of the ITR2 nicking stem reduced the height to that of ITR5 while retaining the ITR2 nicking site (ITR2-GC, SEQ ID NO:25). Rep2 continued to function efficiently on this ITR while Rep5 activity was ablated. This data suggested that the inability of Rep5 to function on ITR2 is primarily the sequence of the trs, specifically the requirement for a nick to be generated between G/T.

To determine the extent of Rep2 flexibility for different nicking stems, three additional ITR2 mutants were created. Extending the nicking stem by one bp at the base had no effect on replication by Rep2 (ITR2 9 nt, SEQ ID NO:30). However, a three bp extension was sufficient to ablate Rep2 function on the ITR (ITR2 11 nt, SEQ ID NO:32). Surprisingly, Rep2 was able to tolerate a three bp deletion from the base of the stem, underlining the flexibility of Rep2 with respect to nicking stem substrates (ITR2 5 nt, SEQ ID NO:28).

Figure 2B:
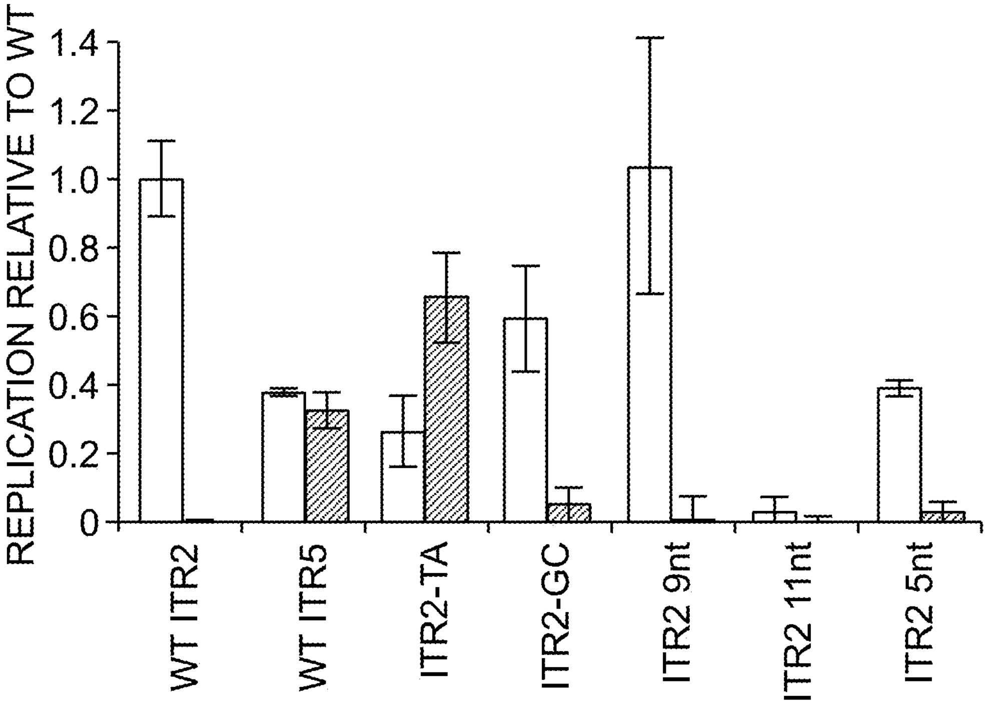
Figure 2C:
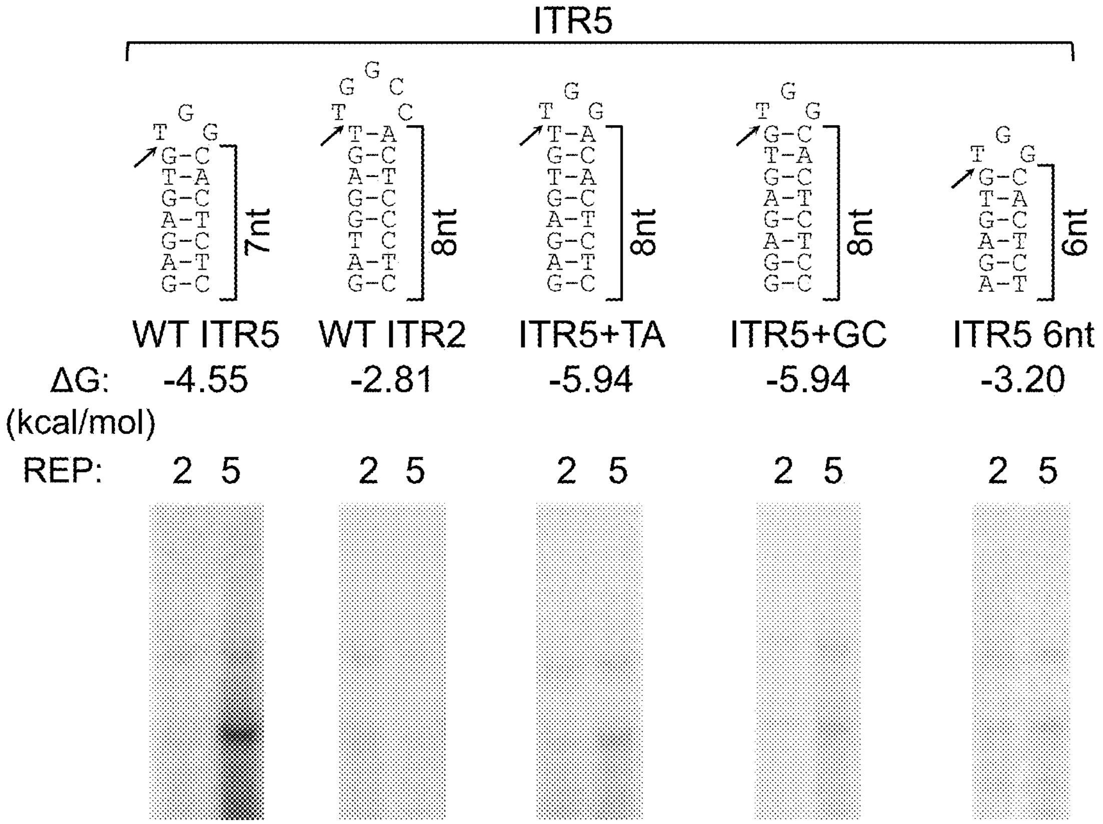
Figure 2D:
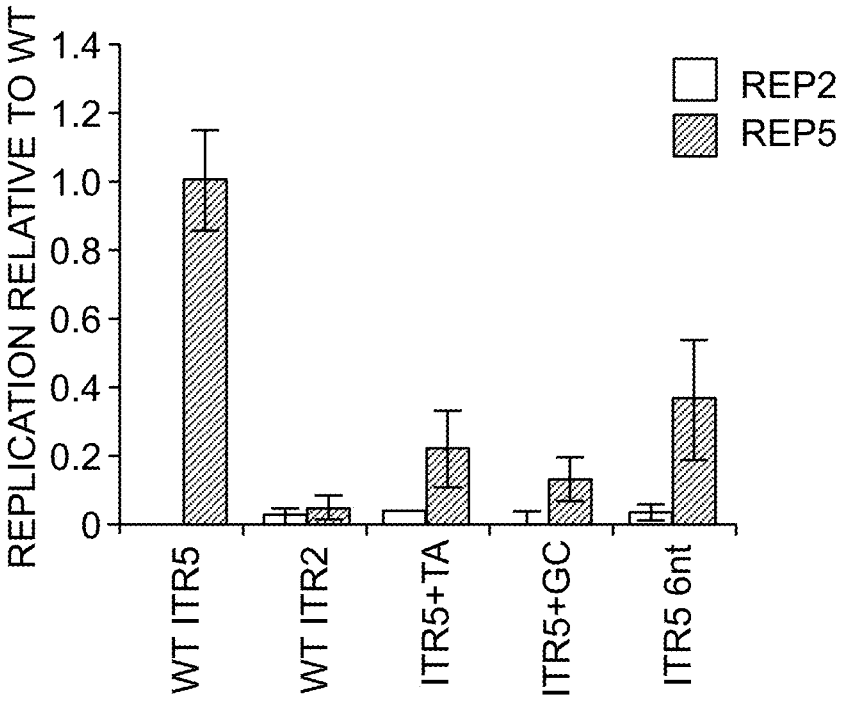

In order to explore the level of flexibility Rep5 possessed toward non-wt nicking stems, a panel of mutant ITR5s harboring altered nicking stems were created (FIG. 2C). Curiously, Rep2 replicated none of these ITRs, suggesting an element outside the ITR5 nicking stem is responsible for preventing Rep2 function. As in FIG. 1B, replacement of the ITR5 nicking stem with that of ITR2 resulted in the ablation of replication by Rep5, attributable to the incompatible trs sequence. The addition of one bp at the top of the ITR5 nicking stem severely decreased the ability of Rep5 to replicate the ITR (ITR5+TA, SEQ ID NO:24, FIG. 2D). This insertion disrupted the ITR5 trs sequence and increased the size of the stem one bp. However, the low level of replication by Rep5 on ITR5+TA suggests that the entire trs site of ITR2 is necessary to confer Rep2 specificity, not just the presence of a T/T nick site.

The addition of one bp to the base of the ITR5 nicking stem, preserving the ITR5 trs at the tip, nearly eliminated replication by Rep5 (ITR5+GC, SEQ ID NO:26). Likewise, the removal of one bp from the base of the ITR5 nicking stem strongly decreased replication by Rep5 (ITR5 6 nt, SEQ ID NO:35, FIG. 2D). This data suggests that Rep5 is sensitive both to the height of the nicking stem as well as to the sequence of the trs. Thus, Rep5 is unable to replicate ITR2 because the ITR2 nicking stem is one bp too tall and has an incompatible trs sequence.

Example 4

Spacer Length is Important for ITR2, not ITR5

While Rep2 can replicate a vector with an ITR5 nicking stem, it can not replicate wt ITR5 (FIG. 1B). The only difference between ITR5+2SNS (which Rep2 can replicate) and ITR5+2NS (which Rep2 cannot replicate) is the ITR5 spacer (FIG. 1B). The wt Rep2 spacer is three nt long while the wt Rep5 spacer is 15 nt long. Thus, we hypothesized that Rep2 may be sensitive to spacer length.

Figure 3A:
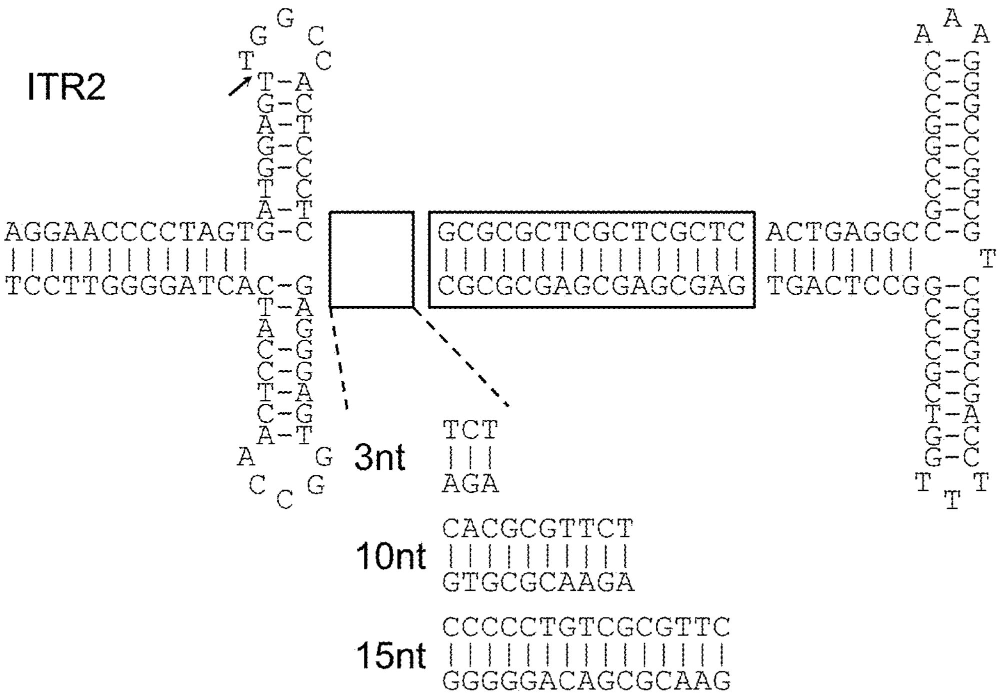
FIGS. 3A-3D show the effect of RBE-nicking stem spacing on Rep-ITR specificity.
Figure 3B:
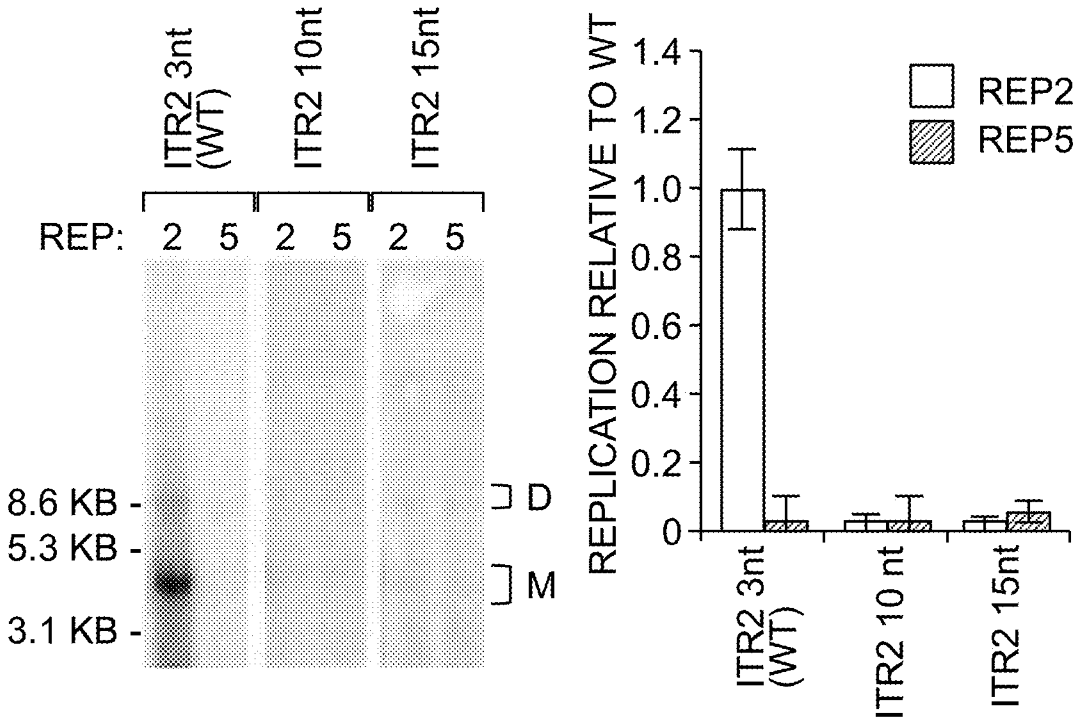
Figure 3C:
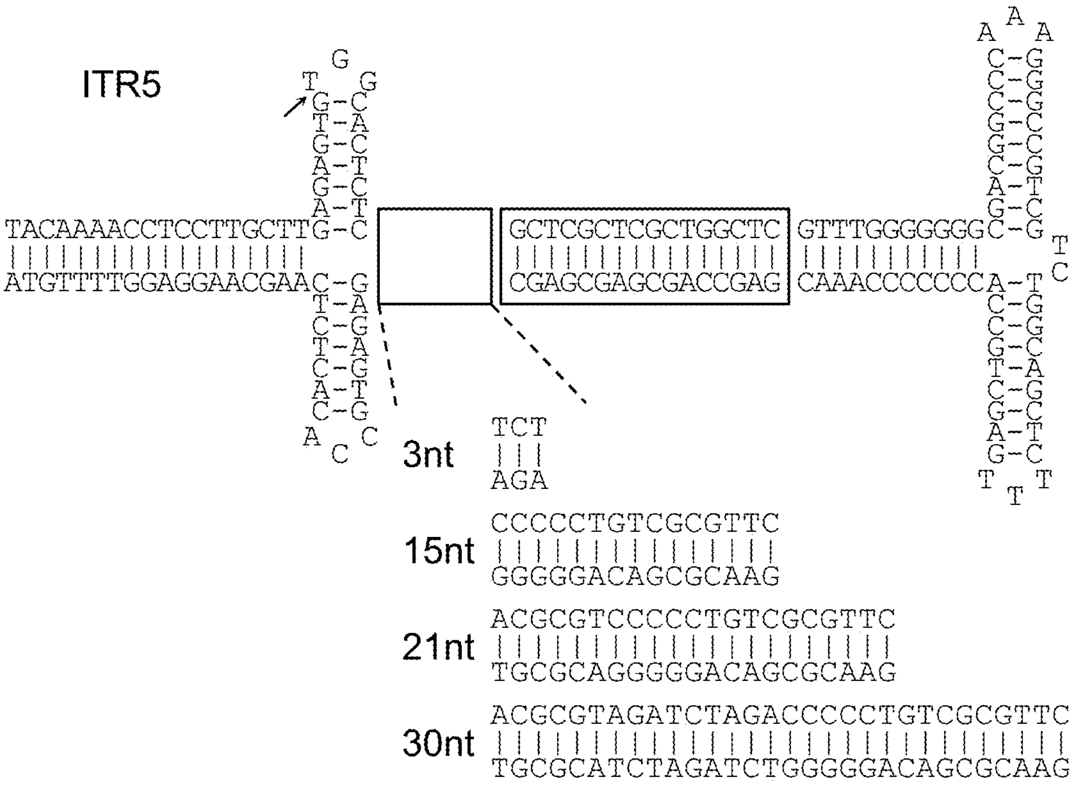

To explore the effect of spacer length on ITR2 and ITR5, a series of mutant ITR2s and ITR5s with differing spacer lengths were generated (FIGS. 3A and 3C). An insertion extending the ITR2 spacer to 10 nt ablated replication by Rep2 (ITR2 10 nt, SEQ ID NO:31, FIG. 3B). Similarly, substitution of the ITR2 spacer with the 15 nt spacer of ITR5 also ablated replication by Rep2 (ITR2 15 nt, SEQ ID NO:33, FIG. 3B). Rep5 was unable to replicate any of these vectors due to the presence of the ITR2 stem loop.

Figure 3D:
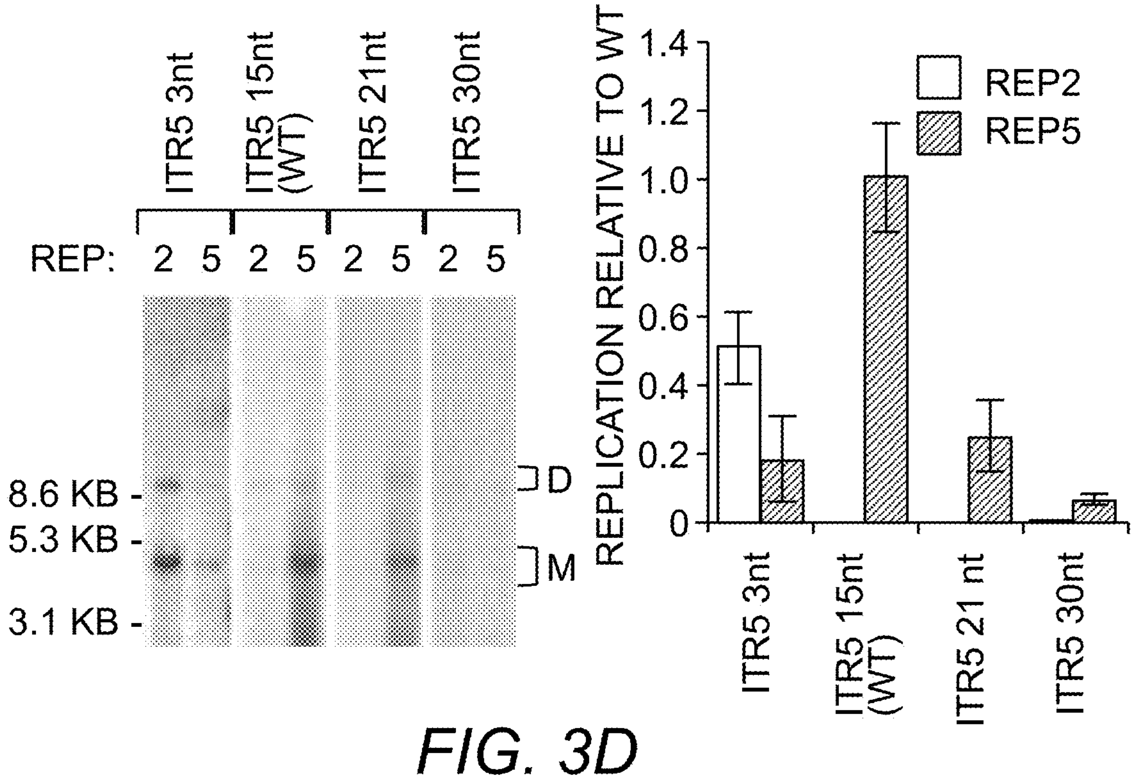

Rep5 displayed greater flexibility toward spacer elements of differing lengths. Replacing the 15 nt ITR5 spacer with that of ITR2 resulted in an ITR in which Rep5 retained the ability to replicate at a reduced level (ITR5 3 nt, SEQ ID NO:34, FIG. 3D). Additionally, the presence of the three nt spacer allowed Rep2 to function on this ITR. The addition of six nt to the ITR5 spacer (for a total spacer length of 21 nt) resulted in an ITR capable of being replicated by Rep5 at an efficient level (ITR5 21 nt, SEQ ID NO:37, FIG. 3D). Replication by Rep5 was effectively abolished only after the insertion of 15 nt into the spacer (ITR5 30 nt, SEQ ID NO:38, FIG. 3D). This panel of mutant ITR5s demonstrates the importance of a three nt spacer element for Rep2 function.

This data confirmed that the length of the ITR5 spacer was important to block Rep2 function. Even small insertions into the ITR2 spacer were not tolerated by Rep2. Meanwhile, Rep5 is flexible in regard to spacer length, demonstrating the ability to function on ITRs with spacers from 3-21 nt.

Example 5

The ITR5 Spacer Acts as a RBE for Rep5

Figure 4A:
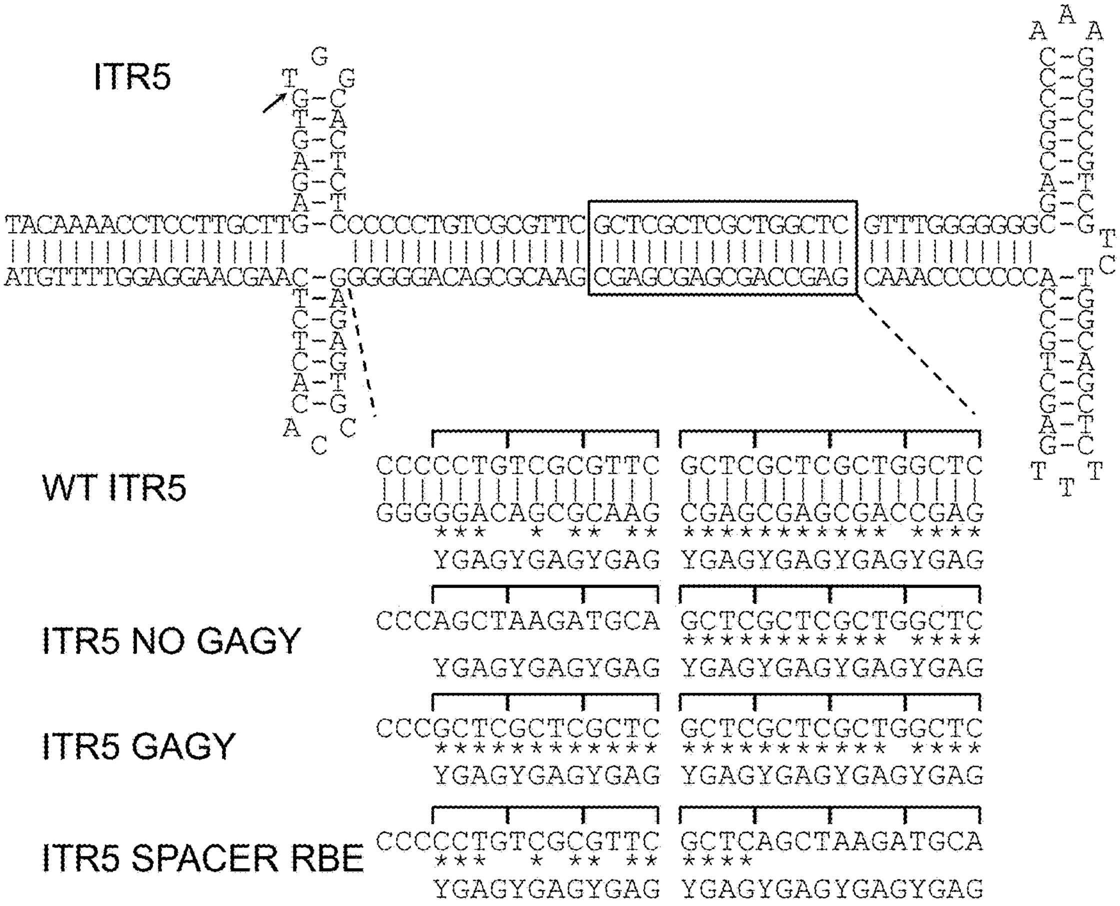
FIGS. 4A-4D demonstrate that the ITR5 spacer acts as a RBE for Rep5.

The inability of Rep2 to function on ITRs with spacers longer than three nt led to the question of why Rep5 was so flexible in this regard. It was hypothesized that Rep5 might specifically bind the ITR5 spacer just as it binds the RBE. The inability of Rep2 to bind this sequence would preclude its function on ITR5. Supporting this hypothesis was a moderately conserved GAGY Rep binding motif extending throughout the ITR5 spacer (FIG. 4A). Additionally, as Rep monomers bind every four nt, the binding of three Rep5 monomers to the 15 nt spacer element would result in a three nt spacer, similar to that of ITR2 (Hickman et al. (2004) *Mol. Cell* 13:403).

Figure 4B:
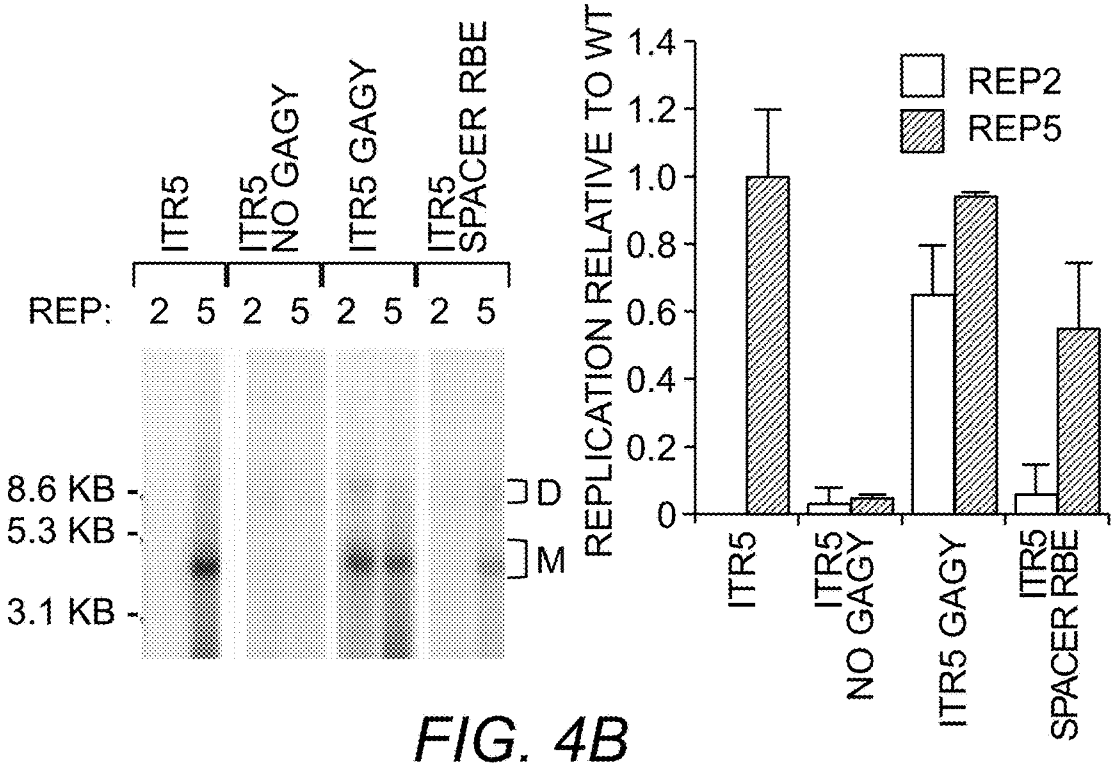

If Rep5 does bind the loosely conserved GAGY motif, the removal of that motif from the spacer should abolish Rep5 function. Indeed, the ITR5 No GAGY mutant (SEQ ID NO:40) could not be replicated by Rep2 or Rep5 (FIG. 4B). This suggested that the specific sequence of the ITR5 spacer plays an active role in the Rep5-ITR5 interaction. Conversely, a spacer with a pure GAGY repeat should not disrupt the ability of Rep5 to function on the ITR. Indeed, Rep5 was able to replicate this ITR at wt levels (ITR5 GAGY, SEQ ID NO:39, FIG. 4B). Rep2 was also able to replicate this ITR efficiently, suggesting the poorly conserved nature of the GAGY repeat within the ITR5 spacer prevents an important DNA-protein interaction with Rep2 necessary for replication.

To explore how the ITR5 spacer functioned as an RBE, we removed three GAGY repeats from the hairpin side of the RBE (ITR5 Spacer RBE, SEQ ID NO:42, FIG. 4A). This essentially shifted the 16 nt RBE 12 nt closer to the nicking stem. Rep5 replicated this ITR efficiently, confirming the ITR5 spacer acts as a RBE (FIG. 4B). The slight reduction in replication fidelity of this ITR, as compared with that of wt ITR5, may signal the inability of Rep to properly interact with the RBE' (Brister and Muzyczka (2000) *J. Virol.* 74:7762). Rep2 was again unable to replicate ITR5 Spacer RBE due to its inability to interact with the ITR5 spacer.

Figure 4C:
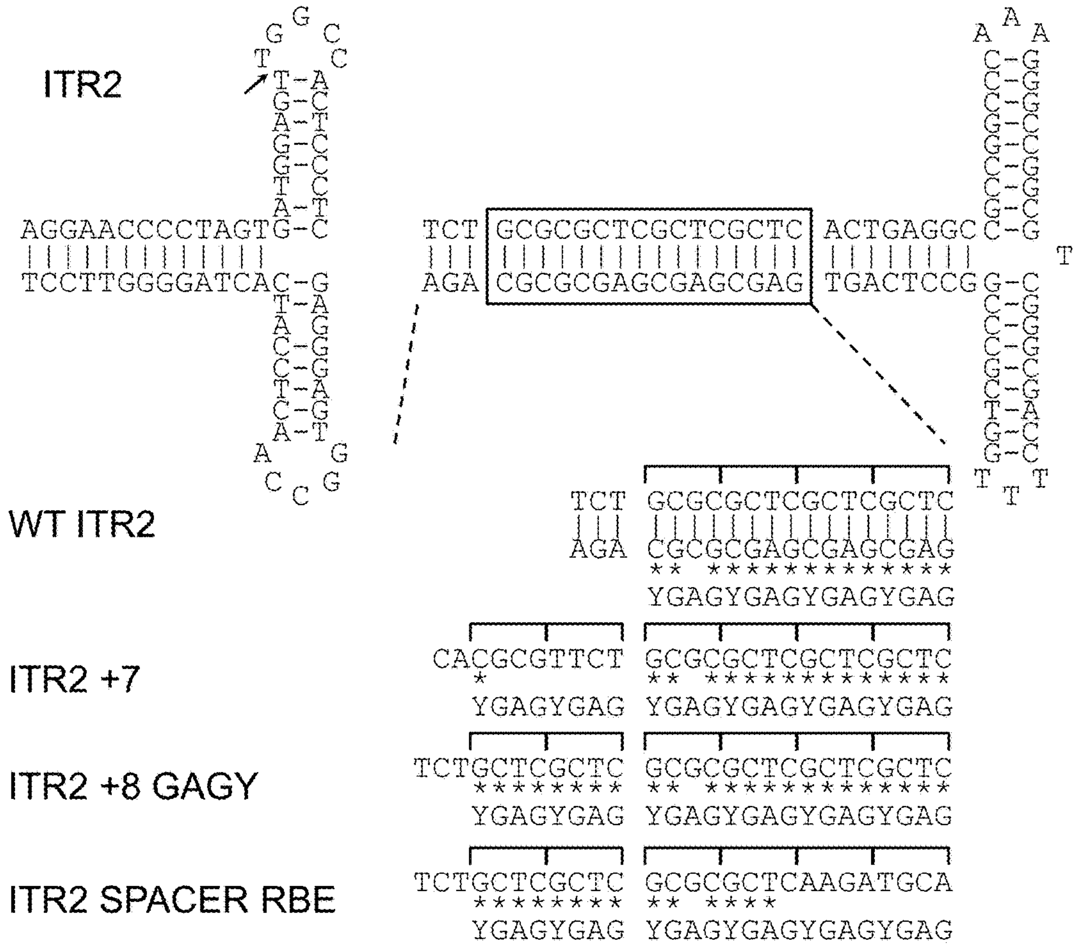
Figure 4D:
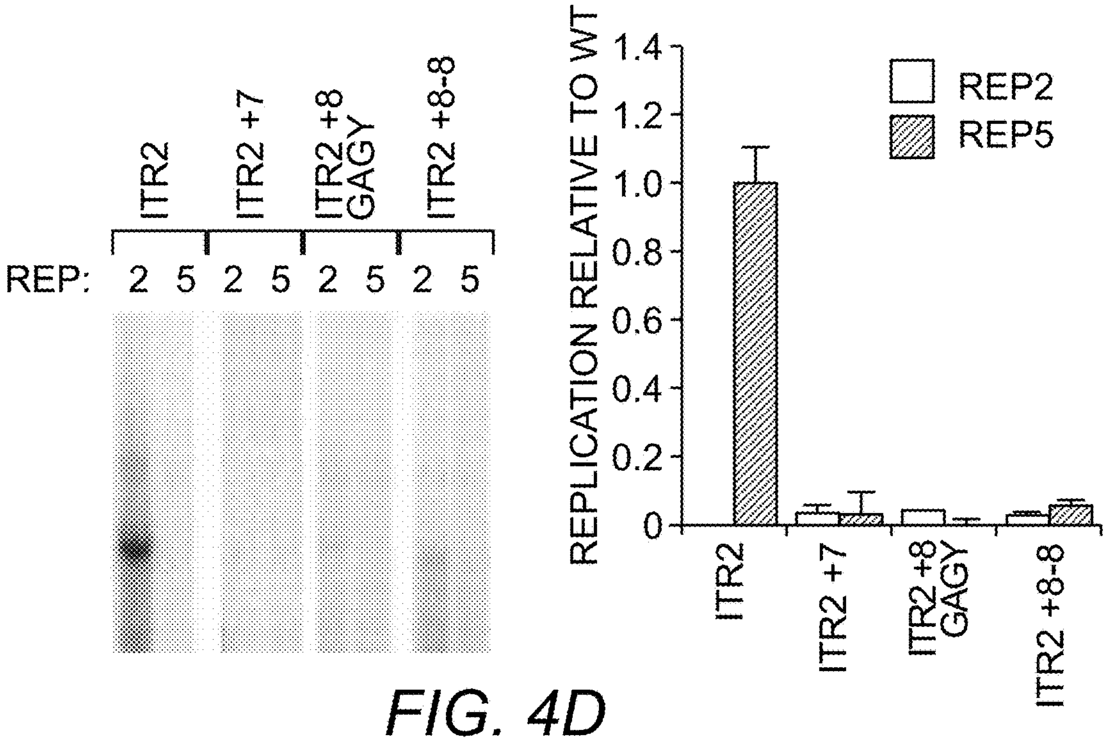

Next, we sought to extend the ITR2 spacer element to function as an extended RBE (FIG. 4C). The seven nt insertion attempted in FIG. 3A possessed essentially no GAGY homology (ITR2+7, SEQ ID NO:29, FIG. 4C). As a result, Rep2 could not replicate this ITR (FIG. 4D). Eight nt (two four nt GAGY repeats) inserted into the ITR2 spacer between the RBE and the existing spacer (ITR2+8 GAGY, SEQ ID NO:41) prevented replication by Rep2, demonstrating that the ITR2 RBE cannot be extended. This suggests that Rep2 may be dependent on RBE' binding or a specific spacer length for proper oligomerization to function on its cognate ITR. Curiously, this requirement does not apply to Rep2 function on ITR5 GAGY (FIG. 4A).

Similar to ITR5 Spacer RBE, we retained the eight nt GAGY insertion into ITR2 while removing eight nt of GAGY from the hairpin side of the RBE (ITR2+8-8 Spacer RBE, SEQ ID NO:43, FIG. 4C). This shifted the RBE eight nt closer to the nicking stem. Rep2 replicated this ITR very inefficiently at a level below the detection threshold of densitometric analysis (FIG. 4D, Southern).

Example 6

Identification of Regions in Rep Responsible for ITR Specificity

Identifying the two elements of the ITR responsible for Rep specificity allowed us to map the regions of Rep2 and Rep5 involved in ITR specificity. We focused exclusively on the N-terminal 208 aa of the large Rep proteins as this region encompasses the DNA binding and endonucleolytic activity of the protein (Yoon et al. (2001) *J. Virol.* 75:3230). This region displays approximately 60% sequence conservation evenly distributed across the protein sequence (FIG. 5A). Residues involved in the active site of the protein are 100% conserved between Rep2 and Rep5 (Hickman et al. (2002) *Mol. Cell* 10:327). Residues implicated in binding the RBE' are highly conserved (Hickman et al. (2004) *Mol. Cell* 13:403). Residues which bind the RBE display nearly perfect conservation except for two conservative substitutions near aa 140.

Figure 5C:
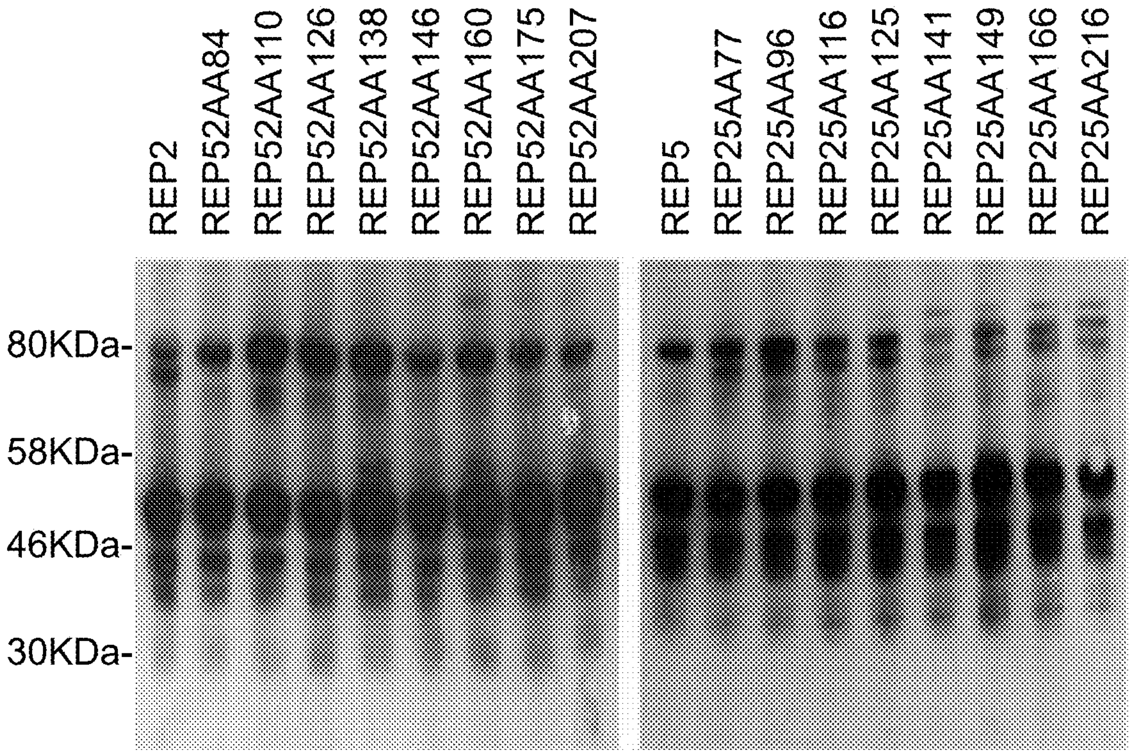
Figure 5D:
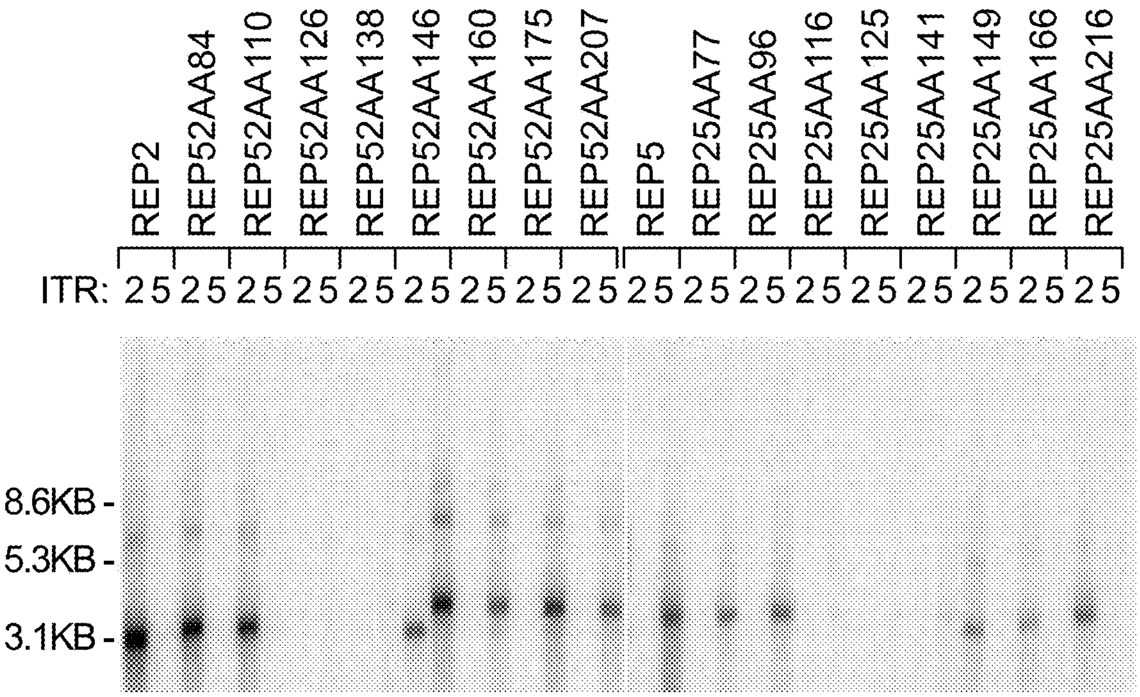
Figure 5E:
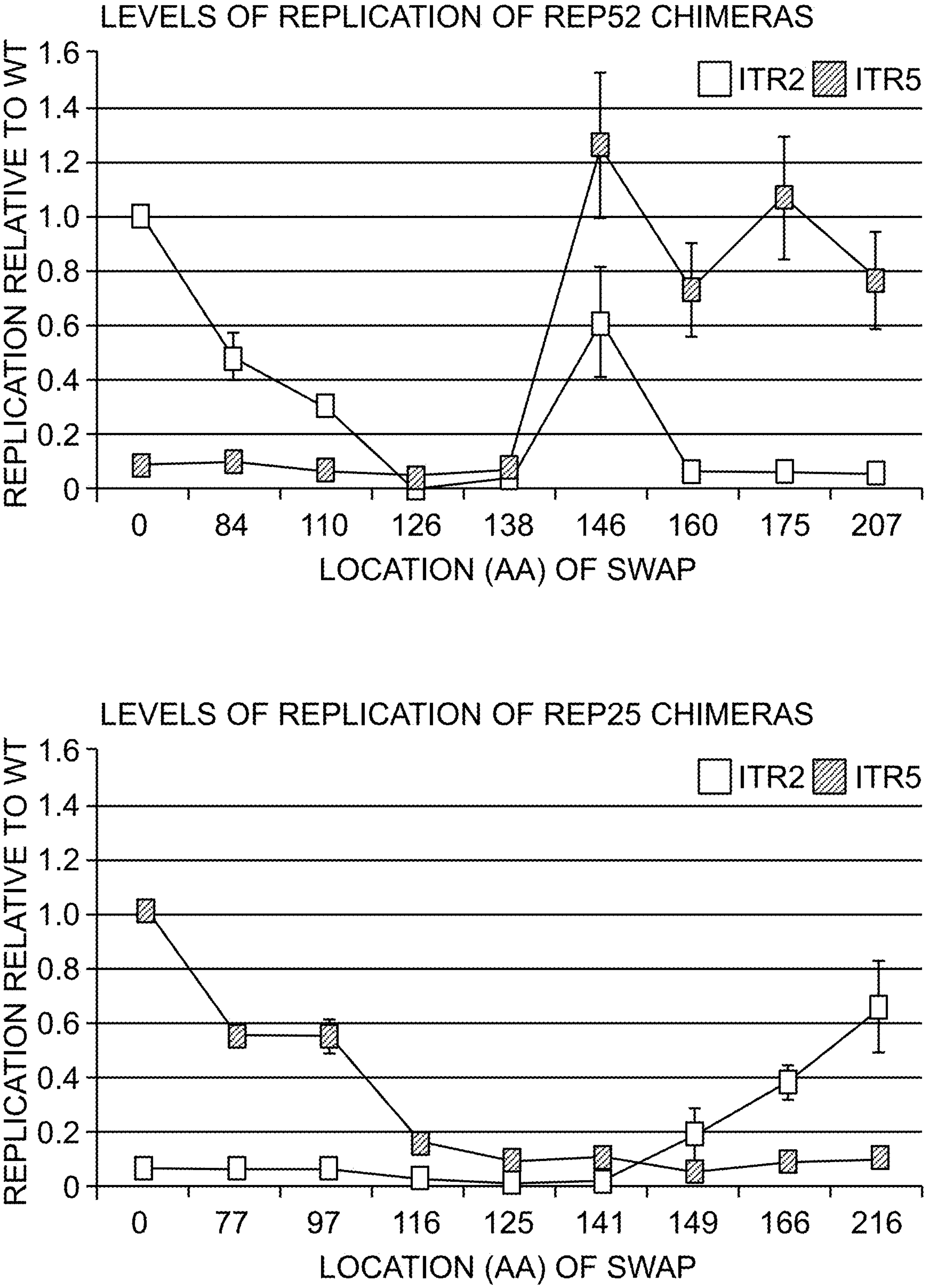

In order to map the regions of Rep involved in ITR specificity, a panel of chimeric Reps derived from Rep2 and Rep5 were generated (FIG. 5B). The ability of each chimeric Rep to replicate an ITR2- or ITR5-flanked vector in HEK 293 cells was determined by Southern blot (FIGS. 5B and 5D). Each Rep in the panel was verified by DNA sequencing and Western blot analysis (FIG. 5C). Every chimeric Rep showed similar protein expression profiles compared to wt. Densitometric analysis provided a comparison of the replication efficiency of each chimeric Rep with that of wt Rep2 or Rep5 (FIG. 5E). Chimeric Reps were named according to the aa location of the swap between serotypes; for instance, Rep25aa77 (SEQ ID NO:63) possesses the N-terminal 76 aa of Rep2 and the C-terminus of Rep5.

In the case of Rep5, replacement of the N-terminal 77 or 97 aa with Rep2 had no effect on ITR specificity nor a significant impact on replicative fidelity (FIGS. 5D and 5E). Larger pieces of Rep2 substituted onto the N-terminus of Rep5 were sufficient to prevent efficient replication of ITR5s (Rep25aa116, SEQ ID NO:65; Rep25aa125, SEQ ID NO:66; Rep25aa141, SEQ ID NO:67). This suggested that these chimeras possessed interruptions of a critical region of Rep5 for ITR5 specificity.

Rep2-based chimeras were unable to replicate ITR5s without the inclusion of the N-terminal 146 aa of Rep5 (Rep52aa146, SEQ ID NO:79, FIG. 5D). Rep52aa146 replicated ITR5 at wt levels, as did the three chimeras with larger portions of Rep5 on the N-terminus (Rep52aa160, SEQ ID NO:58; Rep52aa175, SEQ ID NO:59; Rep52aa207, SEQ ID NO:61). This mapping reveals that the critical region for ITR specificity in Rep5 lies between aa 97-146. Surprisingly, the Rep52aa146 clone also functioned efficiently on ITR2, constituting a Rep capable of replicating ITR2 and ITR5. This suggested that ITR specificity existed in two different regions of Rep.

For Rep2, the N-terminal 83 or 109 aa of Rep5 could be substituted with no effect on ITR specificity or major influence on replicative fidelity (Rep52aa84, SEQ ID NO:54; Rep52aa110, SEQ ID NO:55; FIGS. 5D and 5E). Chimeras including slightly larger portions of Rep5 were unable to replicate either ITR, again suggesting the interruption of a domain critical for ITR specificity (Rep52aa126, SEQ ID NO:56; Rep52aa138, SEQ ID NO:57).

Rep5-based chimeras were unable to replicate ITR2s without the inclusion of the N-terminal 149 aa of Rep2. However, ITR2 replication was inefficient (Rep25aa149, SEQ ID NO:68, FIGS. 5D and 5E). The inclusion of larger portions of Rep2 allowed replication of ITR2s to increase to wt levels (Rep25aa166, SEQ ID NO:69; Rep25aa216, SEQ ID NO:71). This data maps the Rep2 region involved in ITR specificity to aa 110-149. However, unlike Rep5, this was not the only region which played a role in ITR specificity. The ability of the Rep52aa146 chimera to replicate ITR2 and ITR5 vectors demonstrated a second region of Rep2 between aa 138-160 sufficient to allow replication of ITR2s even when the other critical region (aa 110-149) was Rep5. The isolation of two different Rep regions involved in ITR specificity was consistent with the discovery of two independent elements governing specificity within the ITR.

Example 7

Characterization of Rep Regions Involved in ITR Specificity

Figure 6A:
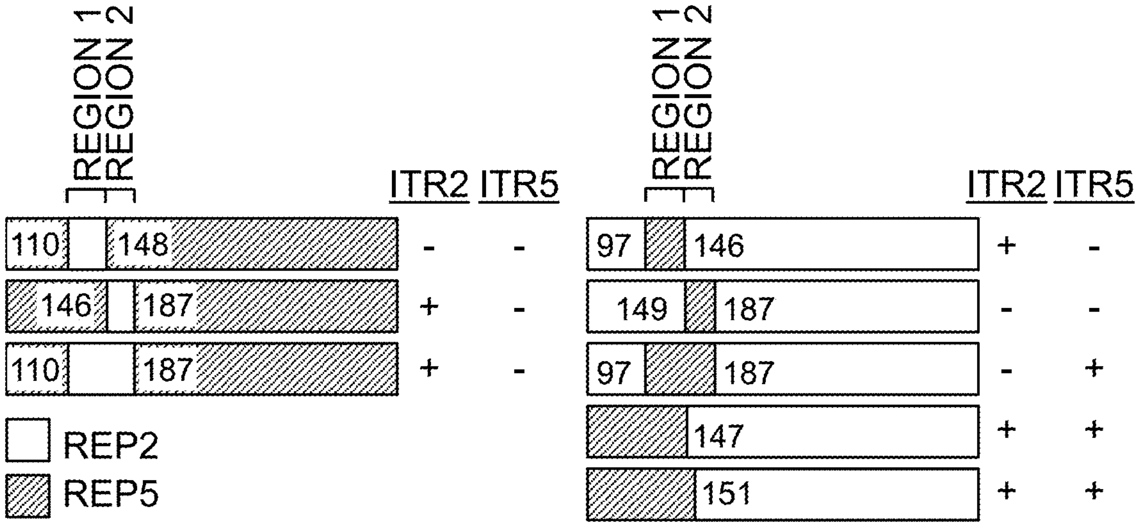
FIGS. 6A-6G show the characterization of Rep regions involved in ITR specificity.
Figure 6B:
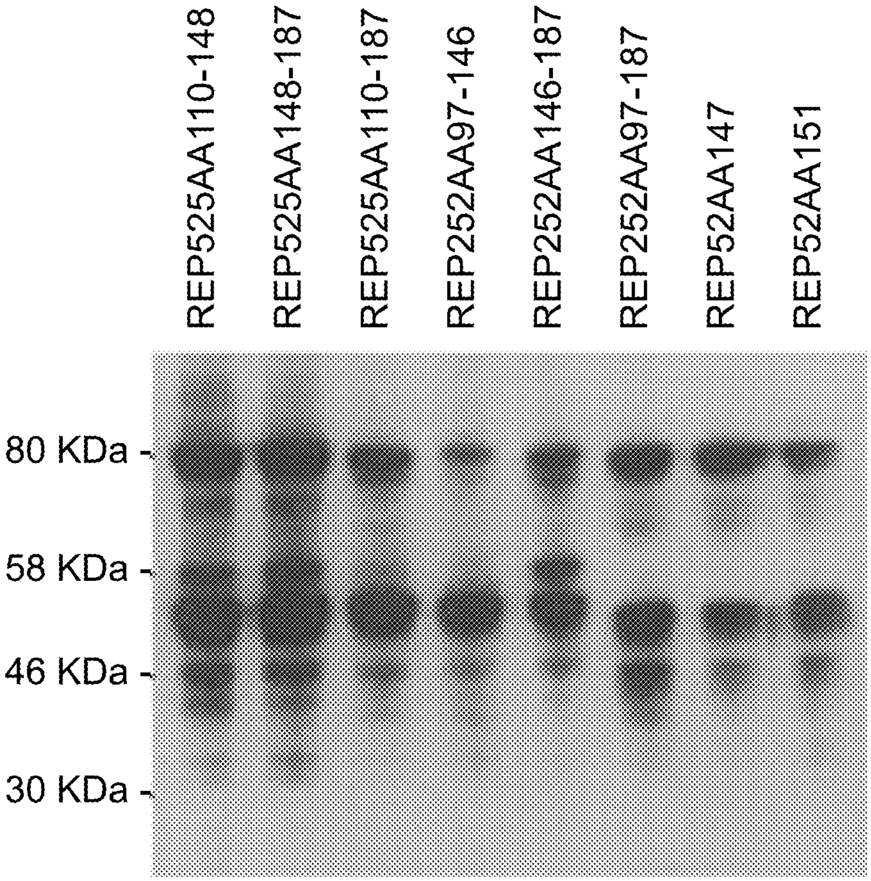

To characterize the Rep domains identified in FIGS. 5A-5E, chimeric Rep proteins which specifically exchanged the regions implicated in ITR specificity were created (FIG. 6A). Region 1 existed in Rep2 from aa 110-149 and in Rep5 from aa 97-146. Region 2 lay within Rep2 from aa 149-187 and Rep5 from aa 146-187. As in FIGS. 5A-5E, all chimeras were verified by DNA sequencing and Western blot analysis (FIG. 6B). Chimeras were then assayed for the ability to replicate ITR2- or ITR5-flanked vectors (FIG. 6C).

Figure 6C:
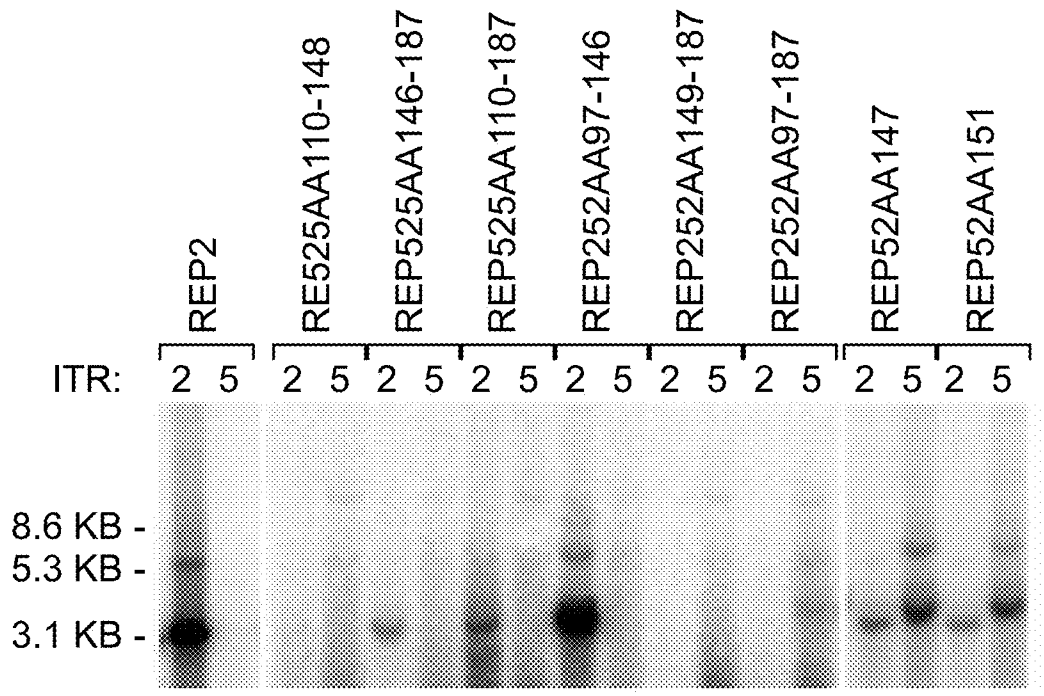

Replacing Rep5 region 1 with Rep2 yielded a clone unable to replicate either vector, suggesting the chimera lacked the ability to bind the ITR5 spacer or nick the ITR2 nicking stem (Rep525aa110-148, SEQ ID NO:72, FIG. 6C). Replacing Rep5 region 2 with that of Rep2 allowed this chimera to replicate an ITR2 vector, suggesting region 2 of Rep2 was critical to nick the ITR2 nicking stem (Rep525aa146-187, SEQ ID NO:73). The inability of this chimera to recognize ITR5 is harder to explain as Rep52aa146 could replicate ITR2 and ITR5 efficiently (FIG. 5B). This result suggests that Rep2 region 2 makes specific contacts within Rep2 aa 188-208 which are necessary in order to function on the ITR5 nicking stem. Replacing regions 1 and 2 of Rep5 with Rep2 resulted in a Rep chimera which replicated only ITR2s (Rep525aa110-187, SEQ ID NO:74).

Replacing Rep2 region 1 with Rep5 resulted in replication of only ITR2s, again demonstrating a connection between Rep2 region 2 and the ITR2 nicking stem (Rep252aa97-146, SEQ ID NO:75). The lack of ITR5 replication by Rep252aa97-146 is difficult to explain based on the Rep52aa146 chimera which replicates ITR2s and ITR5s efficiently (FIG. 5B). This result suggests that Rep5 region 1 makes specific contacts within the preceding 96 aa of Rep5 in order to replicate ITR5. Replacing Rep2 region 2 with Rep5 resulted in a chimera unable to replicate either ITR (Rep252aa149-187, SEQ ID NO:76). This chimeric Rep possesses neither Rep2 region 2 (required to nick the ITR2 nicking stem) nor Rep5 region 1 which appears to interact with the ITR5 spacer. Finally, replacing both Rep2 regions 1 and 2 with Rep5 resulted in a chimera capable of replicating only ITR5 vectors (Rep252aa97-187, SEQ ID NO:77).

Figure 6D:
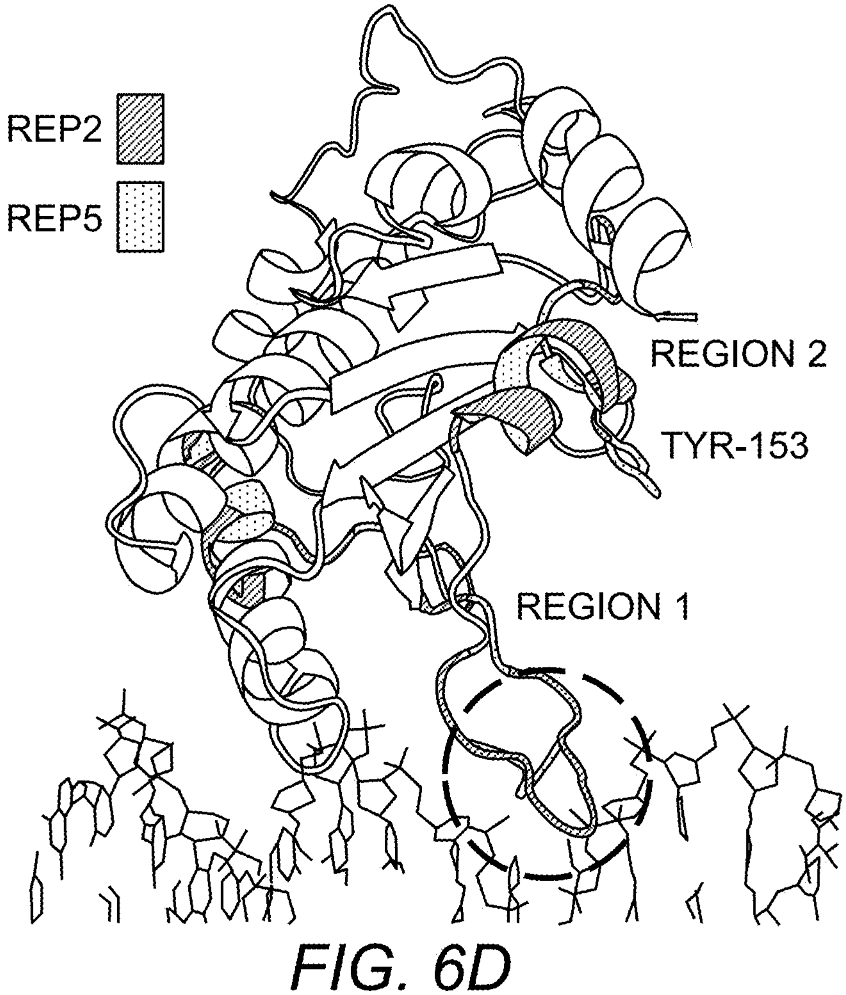

The crystal structure of the N-terminal 193 aa of Rep5 complexed to the RBE allowed the location of these two critical regions to be modeled (Hickman et al. (2004) *Mol. Cell* 13:403). The structure of the N-terminus of Rep2 was modeled with Swiss-Model software using Rep5 as a template. The location of region 1 supports its involvement with the spacer/RBE (FIG. 6D). This region interacts with the major groove of the ITR where one of the most apparent structural differences between Rep2 and Rep5 is predicted (FIG. 6D, hatched circle). Rep2 contains a two aa insertion in this loop with respect to Rep5. This insertion and other non-conservative substitutions are likely responsible for the inability of Rep2 to interact with the ITR5 spacer.

Figure 6E:
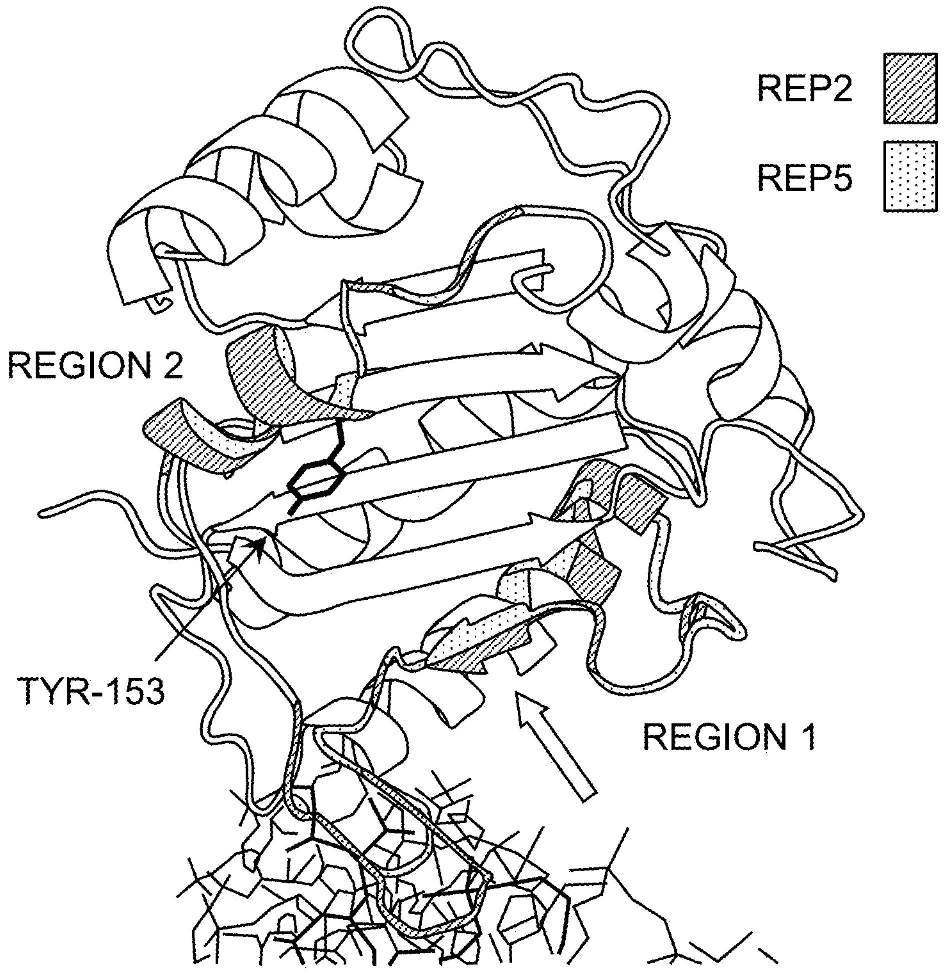
Figure 6F:
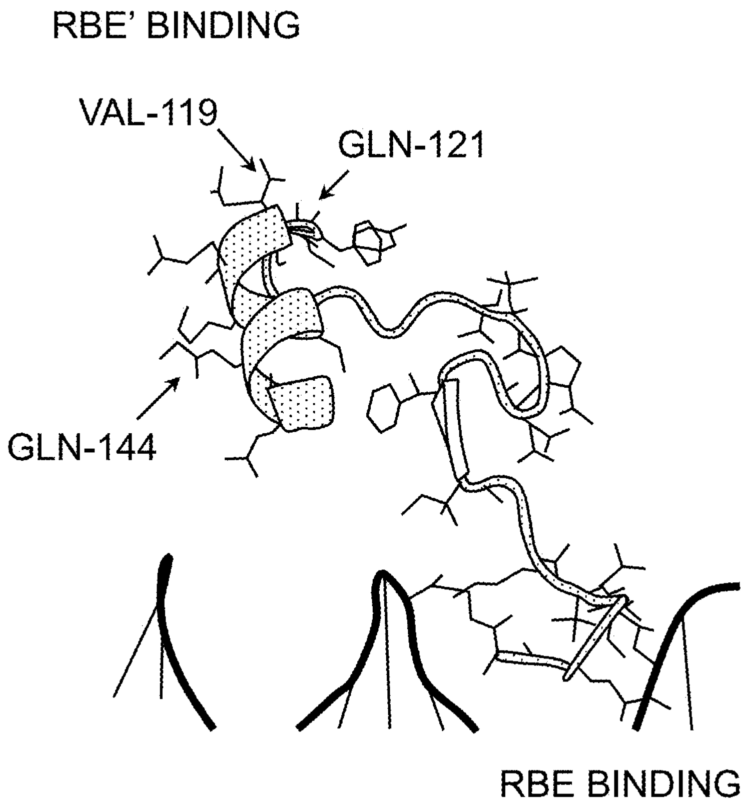

Viewing Rep along the length of the ITR illustrates that region 1 constitutes much of the base of the protein (FIG. 6E). Both Reps are predicted to participate in a β-sheet motif in the center of this region, while areas of reduced homology exist toward either side (the loop interacting with the major groove of the ITR on one side, RBE' interactions on the other). A more detailed look at region 1 reveals the greatest disparity between Rep2 and Rep5 occurs at the RBE binding interface in the major groove of the ITR (FIG. 6F).

Figure 6G:
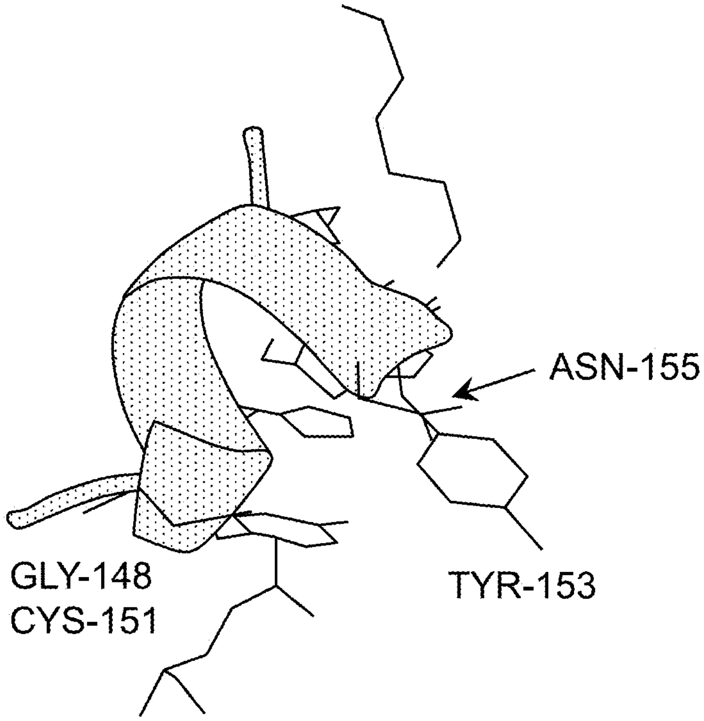

There is very little predicted structural difference between region 2 of Rep2 and Rep5 (FIGS. 6D and 6E). In an effort to dissect this region, we created two additional clones: Rep52aa147 (SEQ ID NO:81) and Rep52aa151 (SEQ ID NO:83) (FIG. 6A). Like Rep52aa146, both of these Reps were able to replicate ITR2 and ITR5 vectors (FIG. 6C). Rep52aa146 and Rep52 aa147 replicated ITR2 and ITR5 vectors with equivalent efficiency, suggesting E147 of Rep2 is not involved in ITR specificity. Rep52aa151 did display a modest reduction in ITR2 replication compared to Rep52aa146, suggesting that C151 of Rep2 plays a role in ITR2 specificity. Because Rep52aa160 cannot replicate ITR2, this leaves only two other non-conserved residues between Rep2 and Rep5 in this region (N155 and T161). Both of these residues lie near the active site and are likely to interact with the nicking stem or active site. N155 lies directly adjacent to Y156, the nucleophilic tyrosine, and may play a major role in ITR2 specificity (FIG. 6G).

Example 8

Structure-Function Model of Rep-ITR Specificity

In order to unify the ITR and Rep elements involved in specificity into a single model, the chimeric Reps separating region 1 and region 2 along with the chimeric ITRs separating the nicking stem and spacer were utilized. Rep2, Rep5, Rep52aa146 (which divides region 1 and 2 of Rep and can replicate ITR2 and ITR5), and Rep25aa149 (essentially no ITR2 or ITR5 replication) were selected. These Reps were tested for their ability to replicate ITR2, ITR5, ITR2+5NS (which is replicated by both Rep2 and Rep5), and ITR5+2NS (which is replicated by neither Rep2 nor Rep5).

Figures 7A, 7B:
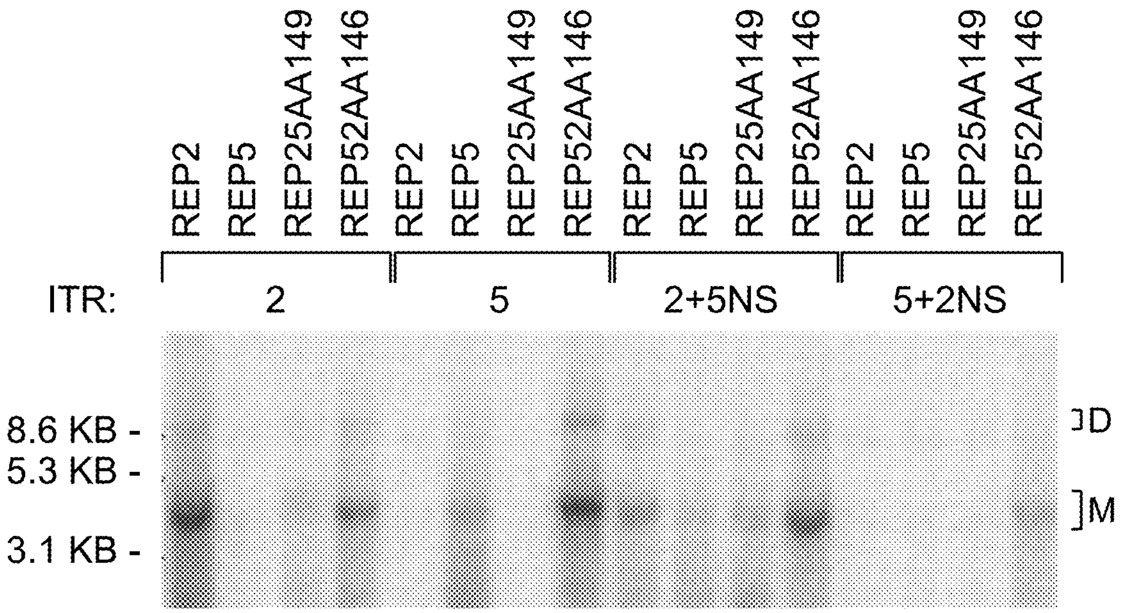
FIGS. 7A-7C show a model of Rep-ITR specificity.

Only Rep2 and Rep52aa146 efficiently replicated ITR2 (FIGS. 7A and 7B). Only Rep5 and Rep52aa146 replicated ITR5. As in FIGS. 1A and 1B, Rep2 and Rep5 replicated ITR2+5NS. Additionally, Rep25aa149 (SEQ ID NO:68) and Rep52aa146 (SEQ ID NO:79) replicated ITR2+5NS. This ITR appears to be universally replicated by every Rep in this assay due to the exclusion of DNA elements involved in protein specificity. The three nt ITR2 spacer is amenable to the DNA binding region 1 of Rep2 and Rep5. The seven bp tall ITR5 nicking stem functions with region 2 of Rep2 and Rep5. Thus, any combination of these regions constitutes a Rep protein capable of replicating ITR2+5NS.

Figure 7C:
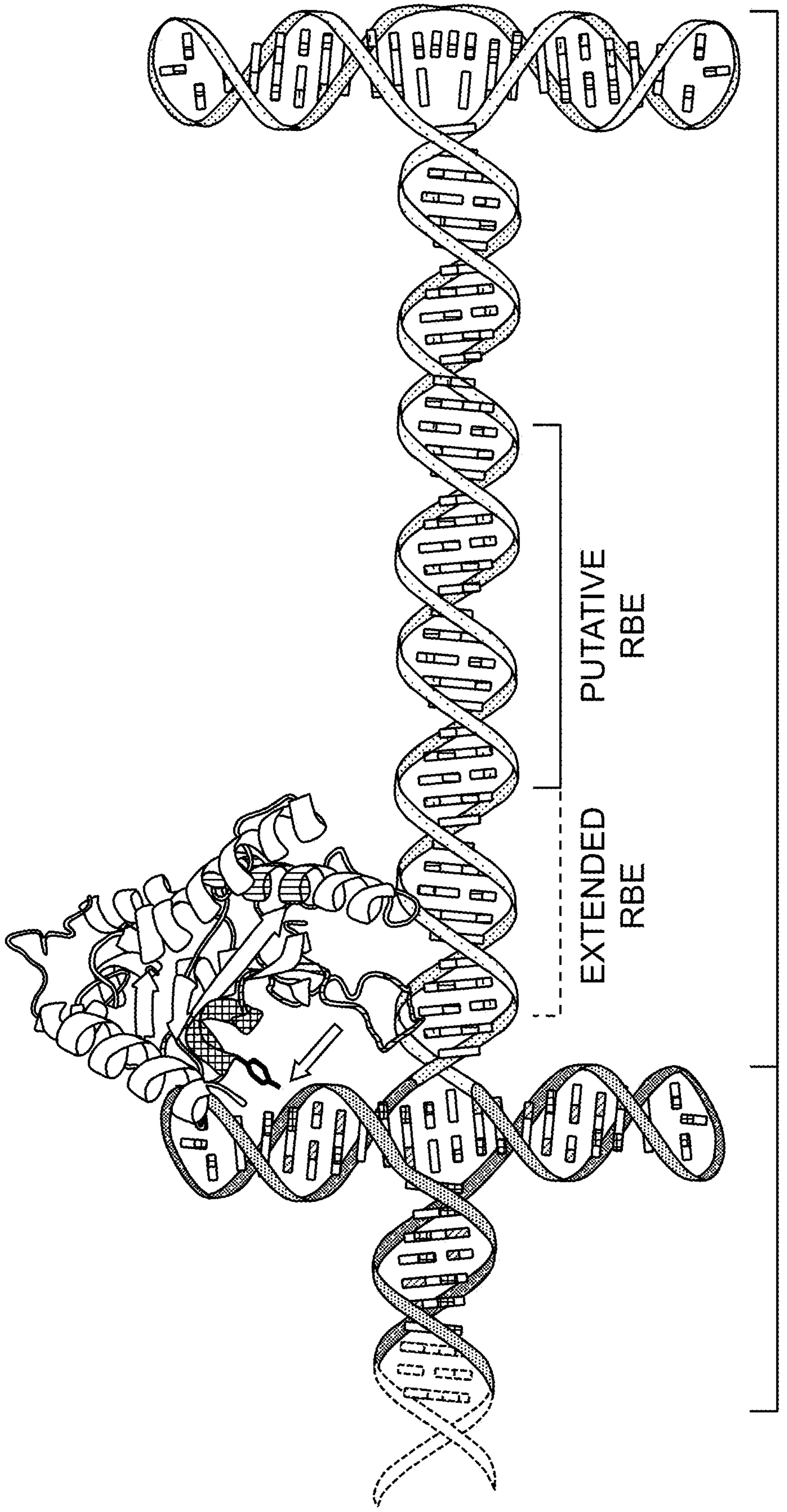

Finally, neither Rep2 nor Rep5 replicated ITR5+2NS. Rep2 is unable to interact properly with the 15 nt ITR5 spacer. Rep5 is unable to function on the ITR2 nicking stem. For these reasons, Rep25aa149 was also unable to catalyze replication. However, Rep52aa146 was able to replicate this ITR due to the proper combination of Rep regions (FIG. 7C). Rep52aa146 possesses Rep5 region 1 which interacts with the 15 nt ITR5 spacer. This chimera also possesses Rep2 region 2, which functions on the ITR2 nicking stem. This recombinant DNA-protein interaction is unique from either AAV2 or AAV5 and constitutes a novel Parvovirus origin of replication.

Taken as a whole, this work illustrates two specific mechanisms of DNA-protein specificity at the Parvovirus origin of replication. Chimeric ITRs narrowed the DNA elements involved in specificity to the spacer and nicking stem sequences (FIG. 1B). These results contradicted previous assertions that Rep-ITR specificity were driven solely by the nicking sequence as Rep2 efficiently nicked an ITR harboring the ITR5 nicking stem (Chiorini et al. (1999) *J. Virol.* 73:4293). Rep2 is highly flexible in the sequence and height of its nicking stem while Rep5 is highly specific to its cognate stem (FIGS. 2A-2D).

Three residues of Rep2 are important to cleave the ITR2 nicking stem (FIGS. 5A-5E and 6A-6G). Residues C151, N155, and T161 all lie in the active site of the protein in a predicted alpha helix along with the nucleophilic tyrosine Y156. How these residues (termed Rep region 2) grant Rep2 flexibility toward mutant nicking stems remains unclear. The corresponding Rep5 residues (G148, A152, and V158) may participate in highly specific interactions which require specific height and sequence considerations for the ITR5 nicking stem.

AAV5 Rep-ITR specificity is mediated by the ITR5 spacer. Replacement of the three nt ITR2 spacer with the 15 nt ITR5 spacer ablated replication by Rep2 (FIG. 2B). A poorly conserved Rep binding element allows Rep5 to interact with the elongated ITR5 spacer (FIG. 4B). Mutating the spacer to include a strong Rep binding element allowed Rep2 and Rep5 to replicate the ITR. However, insertion of a Rep binding element into the ITR2 spacer still largely decreased Rep2 function. While this data might suggest that additional Rep5 molecules bind to ITR5, previous in vitro experiments have not come to this conclusion, although those studies were performed in the absence of hairpins on the ITRs (Chiorini et al. (1999) *J. Virol.* 73:4293).

A 49 aa region of Rep5 interacts with the ITR5 spacer (aa 97-146, FIGS. 5A-5E and 6A-6G). The crystal structure of the N-terminus of Rep5 reveals that this region (region 1) possesses residues which specifically bind to the RBE and RBE' of the ITR. Major structural differences in the Rep5 loop which binds the major groove of the RBE likely account for the majority of ITR5 spacer specificity. While FIG. 1B predicts RBE' binding should not play a role in Rep-ITR specificity, it is possible that RBE' contacts alter the secondary structure of region 1 as it interacts with the RBE.

Because the regions of Rep conferring ITR specificity were separate (region 1 of Rep5 from aa97-146 and region 2 of Rep2 from aa151-161), a chimeric Rep possessing both regions was able to efficiently replicate ITR2 and ITR5. An ITR which could be replicated by any wt or chimeric Rep was constructed by excluding the DNA elements required for specificity; the ITR5 spacer and the ITR2 nicking stem.

Most significantly, a novel origin of replication was generated. This ITR contained both of the elements for Rep specificity; the ITR5 spacer and the ITR2 nicking stem. As a result, only a chimeric Rep protein made up of Rep5 region 1 and Rep2 region 2 was able to replicate the ITR. The creation of a unique origin of replication highlights the power of studying the DNA-protein interactions of a viral origin of replication.

The creation of a unique DNA-protein interaction was possible because of the separation of the specific Rep-ITR interactions in AAV2 and AAV5. How and why these two different DNA-protein interactions evolved is unclear. It is likely due to evolutionary divergence in the ITR sequence which may have occurred in different hosts (AAV2 is related to other primate AAVs, AAV5 is related to non-primate AAVs such as goat and bovine). This model of replicative specificity can likely be extended to other parvoviruses such as snake AAV which has a highly conserved T-shaped ITR structure but different spacer and nicking stem lengths (Farkas et al. (2004) *J. Gen. Virol.* 85:555).

These results also stand to improve the safety of future AAV therapeutic vectors. The danger of AAV vector mobilization by wt AAV could be averted if therapeutic vectors harbored ITRs which no wt Rep could replicate (Hewitt et al. (2009) *J. Virol.* 83:3919).

Example 9

Snake ITR Vector Production

HEK 293 cells were cultured in Dulbecco Modified Eagle Medium (DMEM) supplemented with 10% Fetal Bovine Serum (Sigma, St. Louis, MO) and 100 units/ml penicillin and 100 μg/ml streptomycin and grown at 37° C. with 5% $CO_2$ saturation. To produce snake (royal python) ITR vectors, 10 μg of each of the following plasmids were transfected by PEI into HEK 293 cells in a 15 cm culture dish: pXX680 (Ad helper plasmid), pSnTR-eGFP (the ITR containing plasmid, SEQ ID NO:124), pSnRepCap2 (AAV helper plasmid containing the snake Rep genes and AAV2 Cap genes, SEQ ID NO:125), and pXR2 (AAV helper plasmid containing the AAV2 Rep and Cap genes). See FIGS. 33-35. Alternately, a plasmid expressing only the small AAV2 Rep proteins (Rep52 and Rep40) could be used in place of pXR2. 48 hours post-transfection, the cells were harvested and vector was purified by CsCl gradient centrifugation as previously described for other AAV vectors.

The foregoing is illustrative of the present invention, and is not to be construed as limiting thereof. The invention is defined by the following claims, with equivalents of the claims to be included therein.

That which is claimed is:

1. A method of producing a recombinant parvovirus particle, comprising providing to a cell permissive for parvovirus replication:

A) a recombinant parvovirus template, comprising:

i) a heterologous nucleic acid; and ii) at least one parvovirus inverted terminal repeat (ITR), wherein said ITR comprises:

a) a first structural element that functionally interacts with a large Rep protein from a first adeno-associated virus (AAV) but does not functionally interact with a large Rep protein from a second AAV; and b) a second structural element that functionally interacts with the large Rep protein from the second AAV but does not functionally interact with the large Rep protein from the first AAV;

wherein the ITR functionally interacts with a synthetic AAV large Rep protein; and B) a polynucleotide encoding a synthetic large Rep protein comprising a first portion that functionally interacts with a first structural element of a parvovirus ITR and a second portion that functionally interacts with a second structural element of a parvovirus ITR, wherein said first structural element functionally interacts with a large Rep protein from a first AAV but does not functionally interact with a large Rep protein from a second AAV and said second structural element functionally interacts with a large Rep protein from a second AAV but does not functionally interact with a large Rep protein from the first AAV;

under conditions sufficient for the replication and packaging of the recombinant parvovirus template;

whereby recombinant parvovirus particles are produced in the cell.

2. The method of claim 1, wherein the at least one ITR does not functionally interact with any wild-type large Rep protein.

3. The method of claim 1, wherein the synthetic large Rep protein comprises an amino acid sequence selected from SEQ ID NOS: 79, 81, and 83.

4. The method of claim 1, wherein said structural elements are selected from the group consisting of a nicking stem, a Rep binding element (RBE), and an extended RBE.

5. The method of claim 1, wherein said first structural element is a nicking stem.

6. The method of claim 1, wherein said second structural element is a spacer, a RBE or an extended RBE.

7. The method of claim 1, wherein the at least one ITR further comprises a third structural element that functionally interacts with a large Rep protein from an AAV that is the same as or different from the first and/or second AAV.

8. The method of claim 1, wherein said parvovirus is an adeno-associated virus (AAV).

9. The method of claim 8, wherein said AAV is selected from the group consisting of AAV1, AAV2, AAV3, AAV4, AAV5, AAV6, AAV7, AAV8, AAV9, AAV10, AAV11, AAV12, and AAV13.

10. The method of claim 1, wherein said first and/or second structural element has a modified sequence as compared to the wild-type sequence of the ITR.

11. The method of claim 10, wherein said modified sequence is a wild-type sequence from a different ITR.

12. The method of claim 10, wherein said modified sequence is a synthetic sequence.

13. The method of claim 10, wherein said first structural element is a nicking stem and said nicking stem comprises a wild-type AAV2 sequence.

14. The method of claim 10, wherein said first structural element is a modified nicking stem comprising a change in height as compared to a wild-type sequence.

15. The method of claim 10, wherein said first structural element is a modified nicking stem comprising a modified sequence as compared to a wild-type sequence.

16. The method of claim 15, wherein said modified sequence is a modified terminal resolution site (trs) sequence.

17. The method of claim 10, wherein said second structural element is a RBE and said RBE comprises a wild-type AAV5 sequence.

18. The method of claim 10, wherein said second structural element is a RBE comprising a change in length relative to a wild-type sequence.

19. The method of claim 10, wherein said second structural element is a RBE comprising a change in sequence as compared to a wild-type sequence.

20. The method of claim 1, wherein said first and/or second structural element comprises a wild-type or modified sequence from snake parvovirus, shrimp parvovirus, porcine parvovirus, bovine parvovirus, goat parvovirus, equine parvovirus, canine parvovirus, avian parvovirus, or insect AAV.

21. The method of claim 1, further comprising a heterologous nucleic acid.

22. The method of claim 1, wherein the synthetic large Rep protein further comprises a third portion that functionally interacts with a third structural element that functionally interacts with a large Rep protein from an AAV that is the same as or different from the first and/or second AAV.

23. The method of claim 1, wherein said first portion comprises an amino acid sequence from about residue 97 to about residues 146-151 of a wild-type AAV5 Rep sequence.

24. The method of claim 1, wherein said second portion comprises an amino acid sequence from about residue 149 to about residue 187 of a wild-type AAV2 Rep sequence.

25. The method of claim 1, wherein said first portion comprises an amino acid sequence from about residue 97 to about residues 146-151 of a wild-type AAV5 Rep sequence and said second portion comprises an amino acid sequence from about residue 149 to about residue 187 of a wild-type AAV2 Rep sequence.

26. The method of claim 1, wherein said first portion comprises an amino acid sequence from about residue 1 to about residues 146-151 of a wild-type AAV5 Rep sequence and an amino acid sequence from about residue 149 to about residue 621 of a wild-type AAV2 Rep sequence.

27. The method of claim 1, wherein the polynucleotide further encodes a parvovirus Cap protein.

28. A method of producing a recombinant parvovirus particle, comprising providing to a cell permissive for parvovirus replication:

A) a recombinant parvovirus template, comprising:
  i) a heterologous nucleic acid; and
  ii) at least one parvovirus ITR, wherein said ITR comprises:
    a) a first structural element that functionally interacts with a large Rep protein from one or more of AAV1, AAV2, AAV3, AAV4, AAV6, AAV7, AAV8, AAV9, AAV10, AAV11, AAV12, and AAV13 but does not functionally interact with a large Rep protein from AAV5; and
    b) a second structural element that functionally interacts with the large Rep protein from AAV5 but does not functionally interact with the large Rep protein from one or more of AAV1, AAV2, AAV3, AAV4, AAV6, AAV7, AAV8, AAV9, AAV10, AAV11, AAV 12, and AAV13;

wherein the ITR functionally interacts with a synthetic AAV large Rep protein comprising an amino acid sequence selected from SEQ ID NO: 79, 81, and 83; and B) a polynucleotide encoding a synthetic large Rep protein comprising a first portion that functionally interacts with a first structural element of a parvovirus ITR and a second portion that functionally interacts with a second structural element of a parvovirus ITR, wherein said first structural element functionally interacts with a large Rep protein from a first AAV but does not functionally interact with a large Rep protein from a second AAV and said second structural element functionally interacts with a large Rep protein from a second AAV but does not functionally interact with a large Rep protein from the first AAV;

under conditions sufficient for the replication and packaging of the recombinant parvovirus template;

whereby recombinant parvovirus particles are produced in the cell.

* * * * *

UNITED STATES PATENT AND TRADEMARK OFFICE
CERTIFICATE OF CORRECTION

PATENT NO. : 11,939,597 B2
APPLICATION NO. : 18/060799
DATED : March 26, 2024
INVENTOR(S) : Hewitt et al.

It is certified that error appears in the above-identified patent and that said Letters Patent is hereby corrected as shown below:

In the Specification

Column 5, Line 67: Please correct "AG" to read --ΔG--

Column 6, Line 37: Please correct "0" to read --(')--

Column 18, Line 38, TABLE 3: Please correct "Or" to read --Orn--

Column 34, Line 12: Please correct "TRAP" to read --IRAP--

Signed and Sealed this
Thirtieth Day of July, 2024

*Katherine Kelly Vidal*

Katherine Kelly Vidal
*Director of the United States Patent and Trademark Office*